United States Patent
Blackburn et al.

(10) Patent No.: US 7,465,750 B2
(45) Date of Patent: Dec. 16, 2008

(54) USE OF GAL3 ANTAGONIST FOR TREATMENT OF DEPRESSION AND/OR ANXIETY AND COMPOUNDS USEFUL IN SUCH METHODS

(75) Inventors: Thomas P. Blackburn, Hoboken, NJ (US); Michael J. Konkel, Garfield, NJ (US); Lakmal W. Boteju, Cedar, NJ (US); Ian Jamie Talisman, New York, NY (US); John M. Wetzel, Fairlawn, NJ (US); Mathivanan Packiarajan, Saddle Brook, NJ (US); Heidi Chen, Wyckoff, NJ (US); Hermo Jimenez, Hackensack, NJ (US)

(73) Assignee: H. Lundbeck A/S, Paramus, NJ (US)

( * ) Notice: Subject to any disclaimer, the term of this patent is extended or adjusted under 35 U.S.C. 154(b) by 0 days.

(21) Appl. No.: 11/517,589

(22) Filed: Sep. 6, 2006

(65) Prior Publication Data

US 2007/0259942 A1    Nov. 8, 2007

Related U.S. Application Data

(63) Continuation of application No. 10/723,961, filed on Nov. 26, 2003, now abandoned, which is a continuation of application No. 10/066,175, filed on Jan. 31, 2002, now abandoned.

(60) Provisional application No. 60/265,586, filed on Jan. 31, 2001.

(51) Int. Cl.
*C07D 209/34* (2006.01)
*A61K 31/381* (2006.01)
*C07D 403/14* (2006.01)

(52) U.S. Cl. .................. 514/418; 548/483; 548/484
(58) Field of Classification Search .......... 548/483, 548/484; 514/418
See application file for complete search history.

(56) References Cited

U.S. PATENT DOCUMENTS

| | | | |
|---|---|---|---|
| 4,874,687 A | 10/1989 | Itabashi et al. | |
| 4,921,503 A | 5/1990 | Anderson et al. | |
| 4,946,956 A | 8/1990 | Wheeler et al. | |
| 5,017,466 A | 5/1991 | Kobayashi et al. | |
| 5,198,461 A | 3/1993 | Watjen et al. | |
| 5,547,949 A | 8/1996 | Maho et al. | |
| 5,728,704 A | 3/1998 | Mylari et al. | |
| 5,801,150 A | 9/1998 | Caillot et al. | |
| 5,840,893 A | 11/1998 | Bukrinsky et al. | |
| 6,287,788 B1 | 9/2001 | Bard et al. | |
| 6,329,197 B2 | 12/2001 | Bard et al. | |
| 6,368,812 B1 | 4/2002 | Bard et al. | |
| 7,081,470 B2 * | 7/2006 | Konkel et al. | 514/411 |
| 7,166,635 B2 * | 1/2007 | Konkel et al. | 514/418 |
| 7,220,775 B2 * | 5/2007 | Blackburn | 514/416 |
| 2003/0027254 A1 | 2/2003 | Bard et al. | |
| 2003/0118096 A1 | 6/2003 | Bard et al. | |

FOREIGN PATENT DOCUMENTS

| | | |
|---|---|---|
| EP | 0359465 | 3/1990 |
| EP | 0363002 | 4/1990 |
| EP | 0640599 | 3/1995 |
| EP | 0667340 | 8/1995 |
| EP | 0788890 | 8/1997 |
| EP | 0945442 | 9/1999 |
| EP | 0972770 | 1/2000 |
| GB | 1477349 | 6/1977 |
| JP | 11158073 | 6/1977 |
| JP | 075449 | 3/2002 |
| WO | WO9325539 | 12/1993 |
| WO | WO9815570 | 4/1998 |
| WO | WO9941253 | 8/1999 |
| WO | WO9950250 | 10/1999 |
| WO | WO9965875 | 12/1999 |
| WO | WO002865 | 1/2000 |

OTHER PUBLICATIONS

El-Ezbawy et al., Caplus Abstract 112:178540, 1990.*
Hokfelt, T. et al., "Galanin and NPY, Two Peptides with Multiple Putative Roles in the Nervous System", Horm. Metab. res. (1999);31:330-334.
Razani, H. et al., Intraventricular Galanin Produces a Time-Dependent Modulation of 5-HT1A in the Dorsal Raphe of the Rat:, Neuropharmacology and Neurotoxicology (2000) 11(18):3943-3948.
U.S. Serial No. 10/214,873 (Konkel et al.), filed Aug. 7, 2002.
U.S. Serial No. 10/066,175, filed Jan. 31, 2002.
Bionet Research Ltd., catalog #11L-312S(1-Phenyl-3-{[3-(trifluoromethyl)phenyl]imino}-1,3-dihydro-2H-indol-2-on3).

(Continued)

Primary Examiner—Deepak Rao
(74) Attorney, Agent, or Firm—Don J. Pelto; Sheppard, Mullin, Richter & Hampton LLP

(57) ABSTRACT

This invention is directed to pyrimidine and indolone derivatives which are selective antagonists for the GAL3 receptor. The invention provides a pharmaceutical composition comprising a therapeutically effective amount of a compound of the invention and a pharmaceutically acceptable carrier. This invention also provides a pharmaceutical composition made by combining a therapeutically effective amount of a compound of the invention and a pharmaceutically acceptable carrier. This invention further provides a process for making a pharmaceutical composition comprising combining a therapeutically effective amount of a compound of the invention and a pharmaceutically acceptable carrier. This invention also provides a method of treating a subject suffering from depression and/or anxiety which comprises administering to the subject an amount of a compound of the invention effective to treat the subject's depression and/or anxiety. This invention also provides a method of treating depression and/or anxiety in a subject which comprises administering to the subject a composition comprising a pharmaceutically acceptable carrier and a therapeutically effective amount of a GAL3 receptor antagonist.

16 Claims, 5 Drawing Sheets

OTHER PUBLICATIONS

U.S. Serial No. 10/006,343,, filed Dec. 3, 2001.
U.S. Serial No. 10/007,132, filed Dec. 3, 2001.
Chemical Abstracts Registry No. 61038-64-0, 2002.
Chemical Abstracts Registry No. 41230-77-7, 2002.
Chemical Abstracts Registry No. 130186-15-1, 2002.
Chemical Abstracts Registry No. 130186-16-2, 2002.
Chemical Abstracts Registry No. 130186-17-3, 2002
Chemical Abstracts Registry No. 130186-18-4, 2002.
Chemical Abstracts Registry No. 130186-21-9, 2002.
Chemical Abstracts Registry No. 130270-13-2, 2002.
Chemical Abstracts Registry No. 133939-75-0, 2002.
Chemical Abstracts Registry No. 56984-58-8, 2002.
Chemical Abstracts Registry No. 77910-42-0, 2002.
Chemical Abstracts Registry No. 70010-41-2, 2002.
Chemical Abstracts Registry No. 189264-35-5, 2002.
Chemical Abstracts Registry No. 88291-04-7, 2002.
Chemical Abstracts Registry No. 88291-07-0, 2002.
Chemical Abstracts Registry No. 154118-05-5, 2002.
Chemical Abstracts Registry No. 155717-81-0, 2002.
Chemical Abstracts Registry No. 155717-82-1, 2002.
Chemical Abstracts Registry No. 159967-24-5, 2002.
Chemical Abstracts Registry No. 138601-94-2, 2002.
Chemical Abstracts Registry No. 136647-69-3, 2002.
Chemical Abstracts Registry No. 136647-72-8, 2002.
Chemical Abstracts Registry No. 77297-28-0, 2002.
Chemical Abstracts Registry No. 43002-26-2, 2002.
Chemical Abstracts Registry No. 303984-69-2, 2002.
Chemical Abstracts Registry No. 122725-53-5, 2002.
Chemical Abstracts Registry No. 122803-89-8, 2002.
Chemical Abstracts Registry No. 303149-10-2, 2002.
Chemical Abstracts Registry No. 303149-08-8, 2002.
Chemical Abstracts Registry No. 303149-06-6, 2002.
Chemical Abstracts Registry No. 303984-47-6, 2002.
Chemical Abstracts Registry No. 303149-14-6, 2002.
Chemical Abstracts Registry No. 303149-12-4, 2002.
Chemical Abstracts Registry No. 303984-51-2, 2002.
Chemical Abstracts Registry No. 303984-49-8, 2002.
Chemical Abstracts Registry No. 303984-48-7, 2002.
Chemical Abstracts Registry No. 303984-52-3, 2002.
Chemical Abstracts Registry No. 303984-60-3, 2002.
Chemical Abstracts Registry No. 303984-61-4, 2002.
Chemical Abstracts Registry No. 303984-62-5, 2002.
Chemical Abstracts Registry No. 33984-68-1, 2002.
English Language Abstract for Japanese Patent No. JP 11158073, 1977.

* cited by examiner

USE OF GAL3 ANTAGONIST FOR TREATMENT OF DEPRESSION AND/OR ANXIETY AND COMPOUNDS USEFUL IN SUCH METHODS

RELATED APPLICATIONS

This application is a continuation of, and claims priority under 35 USC §120, to U.S. application Ser. No. 10/723,961 filed Nov. 26, 2003, now abandoned which is a continuation of, and claims priority under 35 USC §120, to U.S. application Ser. No. 10/066,175 filed Jan. 31, 2002, now abandoned, which claims the benefit of U.S. Provisional Application No. 60/265,586, filed Jan. 31, 2001, the disclosures of which are incorporated by reference into the subject application.

BACKGROUND OF THE INVENTION

Throughout this application, various publications are referenced in parentheses by author and year. Full citations for these references may be found at the end of the specification immediately preceding the claims. The disclosures of these publications in their entireties are hereby incorporated by reference into this application to describe more fully the art to which this invention pertains.

Depression is the most common of mental disorders and yet is often underdiagnosed and undertreated, inflicting substantial morbidity and psychosocial impairment on its sufferers. Depression is mainly characterized by sadness, flatness, loss of feeling, anhedonia (lack of pleasure) tearfulness, agitation or retardation, thoughts of guilt, and worthlessness; in severe cases, suicide, hallucinations and delusions.

Depression can be mainly categorized into bipolar disorders, identifying wide swings of mood; major depressive illness, marked by severe depressive symptoms but without manic swings; and less defined milder forms of bipolar and major depression that fall short of the specific diagnostic criteria e.g. dysthymic disorder (formerly called depressive neurosis). The symptomatology and diagnostic criteria for depression are set out in the DSMIV guidelines (American Psychiatric Association (1994) Diagnostic and Statistical Manual of Mental Disorders). Although many patients have single episodes of major depressive illness, the condition also can be repetitive, and this recurrent condition is frequently called unipolar depressive illness.

The key features of depressive illness are a markedly gloomy mood in which there is a loss of interest in life, and general feelings of hopelessness and worthlessness. Depressive symptoms range in severity from mild mood swings to severe delusions about self-worth, accomplishments, and the future.

The "blackness" of the presentation in the depressed patient is most often accompanied by severe motor retardation with profound sleep and appetite disturbance and suicidal ideation. Furthermore, depressive illness can also present in a highly anxious or agitated state.

The degree to which the underlying brain mechanisms in anxiety and depression differ or overlap remains unknown. The fact, however, that to some extent the same neurotransmitter systems are involved in depression and anxiety does not mean that the mechanisms are identical. However, the majority of people in an episode of either depression or anxiety also meet criteria for at least one other psychiatric disorder. But by far the strongest comorbidities in both cases are between depression and anxiety disorders. Therefore, it is now becoming common clinical practice to treat both indications with antidepressants such as SSRIs.

The key clinical features of anxiety disorders relate to various combinations of psychological and physical manifestations of anxiety, not attributable to real danger and occurring either in attacks (panic disorder—PD) or as a persisting state (generalized anxiety disorder—GAD). Other neurotic features may be present (obsessional or hysterical symptoms) but do not dominate the clinical picture.

The Pathophysiology of Depression

Theories underlying the pathophysiology of depression have developed from several lines of evidence including: 1) changes in neurotransmitter monoamine levels; 2) endocrine imbalance; and 3) electrophysiological studies on sleep functions.

Evidence implicating the role of neurotransmitters in depression, in particular the monoamines serotonin, noradrenaline and dopamine, include the success of pharmacological agents in treating depressive disorders. Many of the tricylic antidepressants (TCAs), selective serotonin re-uptake inhibitors (SSRIs) and monoamine oxidase inhibitors (MAOIs) effective in the treatment of depression increase the availability of the catecholamines (noradrenaline and dopamine) and indolamines (serotonin) in the central nervous system (CNS). The clinical efficacy of these agents has given rise to the catecholamine-indolamine hypothesis of depression. This theory postulates that a certain level of amines and/or receptor sensitivity to catecholamines functions to generate a normal mood. A receptor insensitivity, a depletion of monoamines, or a decrease in their release, synthesis or storage have been postulated to lead to depression.

Current Treatments for Depression

A variety of pharmacological agents have been employed to treat depression based on the catecholamine-indolamine hypothesis of depression. Drugs used to treat depression include MAOIs, atypical antipsychotics, lithium, TCAs, and SSRIs. In addition, a number of off-label agents such as antiepileptics are used to treat depression in treatment-resistant patients.

Tricyclic antidepressants are about equal to SSRIs in effectiveness against depression thus providing supporting evidence for the catecholamine-indolamine hypothesis of depression. However, SSRIs have largely displaced TCAs because of side effects associated with TCAs and the need to monitor EKG and plasma drug concentration. Although the SSRIs are viewed as an improvement over other antidepressants, they are not without their clinical problems. Adverse effects on sexual function, primarily anorgasmia and delayed ejaculation, have been consistently reported. Other, common side-effects include sleep disorders, yawning, weight changes, suicidal ideation and extrapyramidal-like side-effects such as dystonic reactions. Thus, there clearly remains a medical need for new treatments of depression, without the adverse side-effect profile of existing agents and with improved efficacy.

Current Treatments for Anxiety

There is now considerable direct evidence for the efficacy of the SSRIs both in depression and in anxiety disorders.

Of the current SSRIs approved for marketing in the USA all have shown sufficient efficacy to be further approved for the treatment of at least one anxiety disorder, for example; obsessive compulsive disorder (OCD) and generalized anxiety disorder (GAD). Compounds such as paroxetine and sertraline are also indicated for the treatment of panic disorder (PD).

However, it is clear from the issues raised earlier relating to the efficacy and side-effect profile of SSRIs and for that matter the more widely prescribed benzodiazapines, there still exists a real medical need for novel approaches for the treatment of anxiety and depression.

Discovery of GAL3 Receptor Subtype and its Role in Depression and Anxiety

The investigations leading to the present invention arose from the discovery that mRNA for the GAL3 receptor is localized to areas of the rat brain associated with mood and emotion (see PCT International Publication No. WO 98/15570, published Apr. 16, 1998), thus supporting the expression of GAL3 in those regions. Protein for the GAL3 receptor is also shown to localize to areas of the rat brain associated with mood and emotion (see Table 11 and discussion herein).

This discovery led to the hypothesis that the GAL3 receptor may play a role in controlling the activity of catecholamine and indolamine neurons in the CNS. Galanin is known to hyperpolarize neurons, including monoaminergic neurons (Seutin, et al., 1989) and to have inhibitory effects on 5-HT neurons (Xu, et al., 1998), and dopamine neurons (Gopalan, et al., 1993; De Weille, et al., 1989; Jansson, et al., 1989; Nordstrom, et al., 1987; Weiss, et al., 1998). In light of these reports, a is series of in vivo behavioral experiments were carried out to evaluate the antidepressant properties of a selective GAL3 receptor antagonist. The rat Forced Swim Test and the rat Social Interaction Test were employed to evaluate the use of selective GAL3 receptor antagonists to treat depression and anxiety. These models are considered by experts in the field to reflect the potential of agents to treat depression and anxiety.

Rat Forced Swim Test (FST)

The rat Forced Swim Test (FST) is a behavioral test that is used to screen compounds for antidepressant efficacy (Porsolt et al., 1977, 1978; Porsolt, 1981). This test is widely used as it is reliable across laboratories, relatively easy to perform and is sensitive to the effects of some of the major classes of antidepressant drugs, including TCAs and MAOIs, and various atypical antidepressants. Furthermore, this test is relatively selective for antidepressant drugs, as few psychoactive drugs produce similar behavioral actions in the FST.

In the rat FST, animals are placed in a cylinder of water, from which there is no escape, for an extended period of time. Typically, animals will display a range of behaviors such as immobility, climbing, swimming, and diving, with immobility being predominant after several minutes of immersion in the water. Consequently, many past studies have only measured or scored immobility after the administration of the test agent. Unfortunately, this method does not score any other active behaviors that may be produced by potential antidepressants. Thus, if a particular class of antidepressant were to have very little effect on immobility, yet produce characteristic behaviors during the FST, these behaviors would not be scored and the conclusion would be that the compound in question does not possess antidepressant action.

Recently, however, a sampling technique was developed to score active behaviors in the FST, such as swimming, climbing and diving, in addition to immobility (Detke, et al., 1995; Lucki, 1997; Page, et al., 1999; Reneric and Lucki, 1998). This modified sampling technique has indicated that SSRIs, such as fluoxetine, paroxetine and sertraline, significantly decrease immobility and increase swimming time (Detke, et al., 1995; Page, et al., 1999). In contrast, selective reuptake inhibitors of norepinephrine (NE) increase climbing behavior but do not alter swimming time (Detke, et al., 1995; Page, et al., 1999).

Rat Social Interaction Test (SIT)

There are a number of paradigms that have been used to determine whether a compound possesses anxiolytic action. A number of these tests involve food or water deprivation, punishment or measurement of consummatory behavior (see File, et al., 1980; File, 1985; Rodgers, et al., 1997; and Treit, 1985, for review). In addition, in these models, prior conditioning reduces the uncertainty or anxiety. In general, these tests lack ethological validity.

One model that is based upon an unconditioned response that does not involve punishment or deprivation is the Social Interaction Test (SIT) (File and Hyde, 1978, 1979) In this model, rats previously housed singly are placed in a familiar, dimly lit, test arena with weight-matched, novel partners. The principal anxiogenic stimulus under these conditions is the partner novelty, which involves an unconditioned response to a potential threat. After pharmacological treatments, the following behaviors are scored as active social interaction: grooming, sniffing, biting, boxing, wrestling, following, crawling over and crawling under. A wide range of psychoactive drugs have been examined in this paradigm and it has been shown that the social interaction test can distinguish anxiolytics from antidepressants, antipsychotics, analeptics and sedative agents (File, 1985; Guy and Gardner, 1985). This test can detect anxiolytic agents such as the benzodiazepines (File and Hyde, 1978; File and Hyde, 1979; File, 1980), in addition to non-benzodiazepines, including paroxetine and other SSRIs (Lightowler, et al., 1994). Finally, the social interaction test can detect anxiogenic agents, including the inverse benzodiazepine receptor agonists (File, et al., 1982; File and Pellow, 1983; File and Pellow, 1984; File, 1985).

In an embodiment of the present invention the synthesis of novel pyrimidines which bind selectively to the cloned human GAL3 receptor, compared to other cloned human G-protein coupled receptors, as measured in in vitro assays, is disclosed. In a further embodiment of the present invention the synthesis of indolones which bind selectively to the cloned human GAL3 receptor, compared to other cloned human G-protein coupled receptors, as measured in in vitro assays, is disclosed. The in vitro receptor assays described hereinafter were performed using various cultured cell lines, each transfected with and expressing only a single galanin-type receptor.

From the binding information described hereinafter, it has unexpectedly been discovered that compounds which are specific for the human GAL3 receptor with a binding affinity greater than ten-fold higher than the binding affinity with which the compounds bind to a human GAL1 receptor are effective in animal models of depression and anxiety which are predictive of efficacy in humans. Thus, we demonstrate that the GAL3 receptor antagonists, which may be classified as neutral antagonists, inverse agonists or allosteric modulators, provide a novel method to treat depressive disorders and/or anxiety.

SUMMARY OF THE INVENTION

The present invention provides a method of treating a subject suffering from depression which comprises administering to the subject an amount of compound effective to treat the subject's depression wherein the compound has the structure:

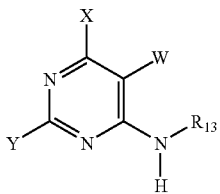

wherein W is H, —F, —Cl, —Br, —I, CN, methyl, ethyl, propyl, methoxy or ethoxy;

wherein X is; $NR_{11}R_{12}$;

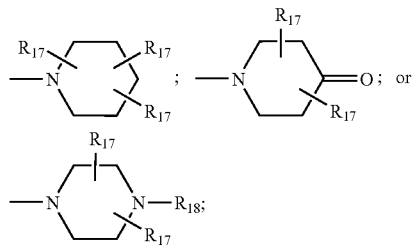

wherein $R_{11}$ is H, straight chained or branched $C_1$-$C_7$ alkyl, $(CH_2)_q$—O—$(CH_2)_m$—$CH_3$, aryl, or aryl($C_1$-$C_6$)alkyl;

wherein $R_{12}$ is straight chained or branched $C_1$-$C_7$ alkyl, $(CH_2)_q$—O—$(CH_2)_m$—$CH_3$, or —$(CH_2)_m$-Z;

wherein $R_{13}$ is a bicyclic alkyl ring system, adamantyl, noradamantyl, $C_3$-$C_{10}$ cycloalkyl, heteroaryl, aryl, aryl($C_1$-$C_6$)alkyl, $Q_1$ or $Q_2$;

wherein aryl may be substituted with one or more $C_1$-$C_{10}$ straight chained or branched alkyl, aryl, heteroaryl, or $N(R_{19})$-Z;

wherein $Q_1$ is

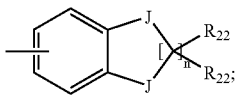

wherein $Q_2$ is

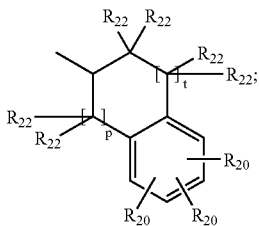

wherein each J is independently O, S, $C(R_{22})_2$ or $NR_4$;

wherein $R_4$ is H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein Y is $NR_{14}R_{15}$;

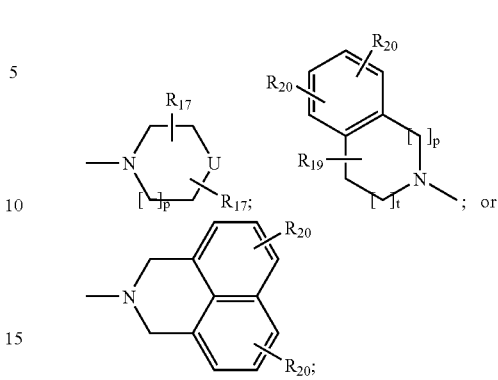

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is straight chained or branched $C_3$-$C_6$ alkyl, $(CH_2)_q$—O—$(CH_2)_m$—$CH_3$, $C_3$-$C_6$ cycloalkyl, $(C(R_{19})_2)_m N(R_{16})_2$ or $(C(R_{19})_2)_m$-Z;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein $R_{18}$ is straight chained or branched $C_1$-$C_6$ alkyl, —$(CH_2)_m$-Z, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl, or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl, or aryl($C_1$-$C_6$) alkyl;

wherein each $R_{22}$ is independently H, F, Cl or $C_1$-$C_4$ straight chained or branched alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2;

wherein U is O, —NR$_{16}$, S, C(R$_{17}$)$_2$, or —NSO$_2$R$_{16}$;

wherein Z is C$_3$-C$_{10}$ cycloalkyl, C$_4$-C$_7$ cyclic ether, C$_4$-C$_7$ cyclic thioether, aryl, or heteroaryl; or a pharmaceutically acceptable salt thereof.

The present invention provides a method of treating a subject suffering from depression which comprises administering to the subject an amount of compound effective to treat the subject's depression wherein the compound has the structure:

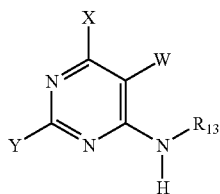

wherein W is H, —F, —Cl, —Br, —I, CN, methyl, ethyl, propyl, methoxy or ethoxy;

wherein X is NR$_{11}$R$_{12}$;

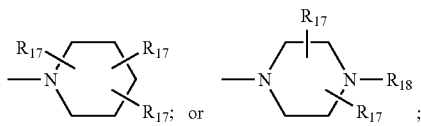

wherein R$_{11}$ is H, straight chained or branched C$_1$-C$_7$ alkyl, (CH$_2$)$_q$—O—(CH$_2$)$_m$—CH$_3$, aryl or aryl(C$_1$-C$_6$) alkyl;

wherein R$_{12}$ is straight chained or branched C$_1$-C$_7$ alkyl, (CH$_2$)$_q$—O—(CH$_2$)$_m$—CH$_3$, or —(CH$_2$)$_m$-Z;

wherein R$_{13}$ is a bicyclic alkyl ring system, aryl or aryl (C$_1$-C$_6$)alkyl;

wherein Y is NR$_{14}$R$_{15}$;

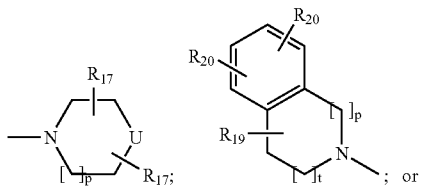

wherein R$_{14}$ is H, straight chained or branched C$_1$-C$_6$ alkyl, (CH$_2$)$_q$—O—(CH$_2$)$_m$—CH$_3$, C$_3$-C$_6$ cycloalkyl, or (C(R$_{19}$)$_2$)$_m$-Z;

wherein R$_{15}$ is straight chained or branched C$_3$-C$_6$ alkyl, (CH$_2$)$_q$—O—(CH$_2$)$_m$—CH$_3$, C$_3$-C$_6$ cycloalkyl, or (C(R$_{19}$)$_2$)$_m$-Z;

wherein U is O, —NR$_{16}$, S, C(R$_{17}$)$_2$, or —NSO$_2$R$_{16}$;

wherein Z is C$_3$-C$_{10}$ cycloalkyl, aryl, or heteroaryl;

wherein R$_{16}$ is straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_5$-C$_7$ cycloalkenyl, —(CH$_2$)$_m$-Z, or (CH$_2$)$_q$—O—(CH$_2$)$_m$—CH$_3$;

wherein each R$_{17}$ is independently H; —OR$_{21}$, —OCOR$_{21}$, —COR$_{21}$, —NCOR$_{21}$, —N(R$_{21}$)$_2$, —CON(R$_{21}$)$_2$, —COOR$_{21}$, straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_5$-C$_7$ cycloalkenyl, —(CH$_2$)$_m$-Z, or (CH$_2$)$_n$—O—(CH$_2$)$_m$—CH$_3$;

wherein R$_{18}$ is straight chained or branched C$_1$-C$_6$ alkyl, —(CH$_2$)$_m$-Z, or (CH$_2$)$_q$—O—(CH$_2$)$_m$—CH$_3$;

wherein each R$_{19}$ is independently H, or straight chained or branched C$_1$-C$_6$ alkyl;

wherein each R$_{20}$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl or C$_5$-C$_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$, —CON(R$_{21}$)$_2$, or —COOR$_{21}$; aryl or heteroaryl; or two R$_{20}$ groups present on adjacent carbon atoms can join together to form a methylenedioxy group;

wherein each R$_{21}$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, C$_5$-C$_7$ cycloalkenyl, aryl or aryl(C$_1$-C$_6$) alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2; or a pharmaceutically acceptable salt thereof.

The present invention provides a method of treating a subject suffering from depression which comprises administering to the subject an amount of compound effective to treat the subject's depression wherein the compound has the structure:

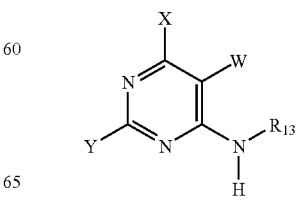

wherein W is H, —F, —Cl, —Br, —I, CN, methyl, ethyl, propyl, methoxy or ethoxy;

wherein X is N(CH$_3$)$_2$ or

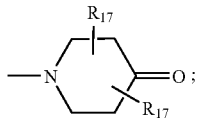

wherein R$_{13}$ is an aryl, adamantyl, noradamantyl, C$_3$-C$_{10}$ cycloalkyl, heteroaryl, Q$_1$ or Q$_2$;

wherein aryl may be substituted with one or more C$_1$-C$_{10}$ straight chained or branched alkyl, aryl, heteroaryl, or N(R$_{19}$)-Z;

wherein Q$_1$ is

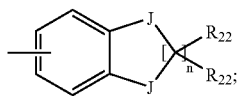

wherein Q$_2$ is

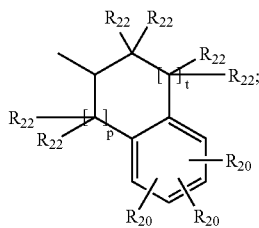

wherein each J is independently O, S, C(R$_{22}$)$_2$ or NR$_4$;

wherein R$_4$ is —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, C$_5$-C$_7$ cycloalkenyl or aryl;

wherein Y is NR$_{14}$R$_{15}$;

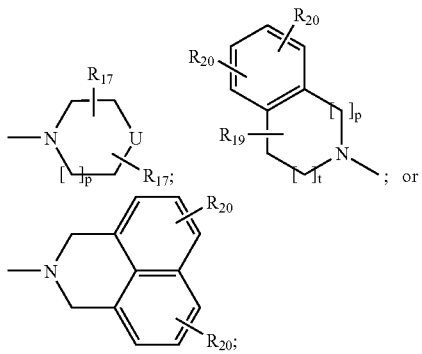

wherein R$_{14}$ is H, straight chained or branched C$_1$-C$_6$ alkyl, (CH$_2$)$_q$—O—(CH$_2$)$_m$—CH$_3$, C$_3$-C$_6$ cycloalkyl, or (C(R$_{19}$)$_2$)$_m$-Z;

wherein R$_{15}$ is straight chained or branched C$_3$-C$_6$ alkyl, (CH$_2$)$_q$—O—(CH$_2$)$_m$—CH$_3$, C$_3$-C$_6$ cycloalkyl, or (C(R$_{19}$)$_2$)$_m$-Z;

wherein U is O, —NR$_{16}$, S, C(R$_{17}$)$_2$, or —NSO$_2$R$_{16}$;

wherein Z is C$_3$-C$_{10}$ cycloalkyl, aryl, or heteroaryl;

wherein R$_{16}$ is straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_5$-C$_7$ cycloalkenyl, —(CH$_2$)$_m$-Z, or (CH$_2$)$_q$—O—(CH$_2$)$_m$—CH$_3$;

wherein each R$_{17}$ is independently H; —OR$_{21}$, —OCOR$_{21}$, —COR$_{21}$, —NCOR$_{21}$, —N(R$_{21}$)$_2$, —CON(R$_{21}$)$_2$, —COOR$_{21}$, straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_5$-C$_7$ cycloalkenyl, —(CH$_2$)$_m$-Z, or (CH$_2$)$_n$—O—(CH$_2$)$_m$—CH$_3$;

wherein R$_{18}$ is straight chained or branched C$_1$-C$_6$ alkyl, —(CH$_2$)$_m$-Z, or (CH$_2$)$_q$—O—(CH$_2$)$_m$—CH$_3$;

wherein each R$_{19}$ is independently H, or straight chained or branched C$_1$-C$_6$ alkyl;

wherein each R$_{20}$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl or C$_5$-C$_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$, —CON(R$_{21}$)$_2$, or —COOR$_{21}$; aryl or heteroaryl; or two R$_{20}$ groups present on adjacent carbon atoms can join together to form a methylenedioxy group;

wherein each R$_{21}$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, C$_5$-C$_7$ cycloalkenyl, aryl or aryl(C$_1$-C$_6$)alkyl;

wherein each R$_{22}$ is independently H, F, Cl or C$_1$-C$_4$ straight chained or branched alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2; or a pharmaceutically acceptable salt thereof.

The present invention provides a method of treating a subject suffering from depression which comprises administering to the subject an amount of compound effective to treat the subject's depression wherein the compound has the structure:

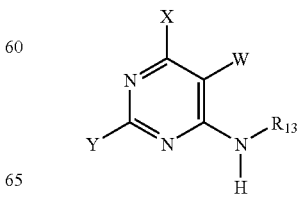

wherein W is H, —F, —Cl, —Br, —I, CN, methyl, ethyl, propyl, methoxy or ethoxy;

wherein X is N(CH$_3$)$_2$ or

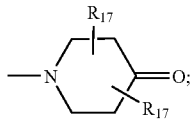

wherein R$_{13}$ is a bicyclic alkyl ring system, aryl or aryl (C$_1$-C$_6$)alkyl;

wherein Y is NR$_{14}$R$_{15}$ is;

wherein R$_{14}$ is H, straight chained or branched C$_1$-C$_6$ alkyl, (CH$_2$)$_q$—O—(CH$_2$)$_m$—CH$_3$, C$_3$-C$_6$ cycloalkyl, or (C(R$_{19}$)$_2$)$_m$-Z;

wherein R$_{15}$ is (C(R$_{19}$)$_2$)$_m$—N(R$_{16}$)$_2$;

wherein Z is C$_3$-C$_{10}$ cycloalkyl, aryl, or heteroaryl;

wherein R$_{16}$ is straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_5$-C$_7$ cycloalkenyl, —(CH$_2$)$_m$-Z, or (CH$_2$)$_q$—O—(CH$_2$)$_m$—CH$_3$;

wherein each R$_{17}$ is independently H; —OR$_{21}$, —OCOR$_{21}$, —COR$_{21}$, —NCOR$_{21}$, —N(R$_{21}$)$_2$, —CON(R$_{21}$)$_2$, —COOR$_{21}$, straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_5$-C$_7$ cycloalkenyl, —(CH$_2$)$_m$-Z, or (CH$_2$)$_n$—O—(CH$_2$)$_m$—CH$_3$;

wherein each R$_{19}$ is independently H, or straight chained or branched C$_1$-C$_6$ alkyl;

wherein each R$_{21}$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, C$_5$-C$_7$ cycloalkenyl, aryl or aryl(C$_1$-C$_6$)alkyl;

wherein each m is an integer from 0 to 4 inclusive;

wherein each n is an integer from 1 to 4 inclusive;

wherein q is an integer from 2 to 4 inclusive; or a pharmaceutically acceptable salt thereof.

The present invention also provides a method of treating a subject suffering from anxiety which comprises administering to the subject an amount of compound effective to treat the subject's anxiety wherein the compound has the structure:

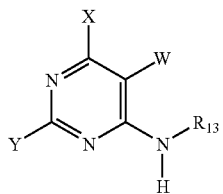

wherein W is H, —F, —Cl, —Br, —I, CN, methyl, ethyl, propyl, methoxy or ethoxy;

wherein X is; NR$_{11}$R$_{12}$;

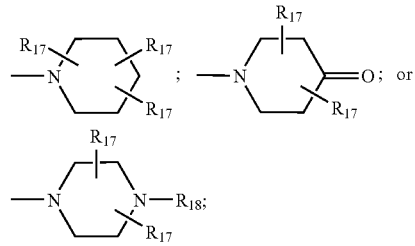

wherein R$_{11}$ is H, straight chained or branched C$_1$-C$_7$ alkyl, (CH$_2$)$_q$—O—(CH$_2$)$_m$—CH$_3$, aryl, or aryl (C$_1$-C$_6$)alkyl;

wherein R$_{12}$ is straight chained or branched C$_1$-C$_7$ alkyl, (CH$_2$)$_q$—O—(CH$_2$)$_m$—CH$_3$, or —(CH$_2$)$_m$-Z;

wherein R$_{13}$ is a bicyclic alkyl ring system, adamantyl, noradamantyl, C$_3$-C$_{10}$ cycloalkyl, heteroaryl, aryl, aryl(C$_1$-C$_6$)alkyl, Q$_1$ or Q$_2$;

wherein aryl may be substituted with one or more C$_1$-C$_{10}$ straight chained or branched alkyl, aryl, heteroaryl, or N(R$_{19}$)-Z;

wherein Q$_1$ is

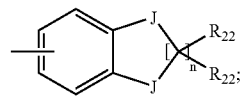

wherein Q$_2$ is

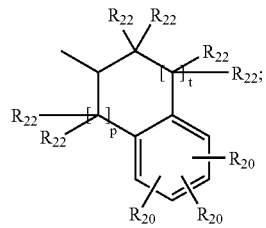

wherein each J is independently O, S, C(R$_{22}$)$_2$ or NR$_4$;

wherein R$_4$ is H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, C$_5$-C$_7$, cycloalkenyl or aryl;

wherein Y is NR$_{14}$R$_{15}$;

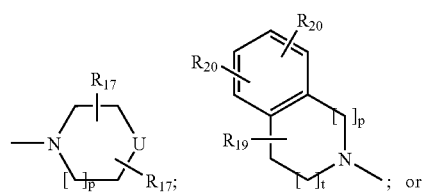

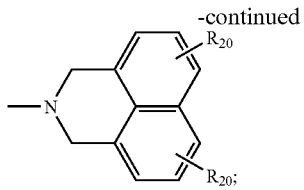

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is straight chained or branched $C_3$-$C_6$ alkyl, $(CH_2)_q$—O—$(CH_2)_m$—$CH_3$, $C_3$-$C_6$ cycloalkyl, $(C(R_{19})_2)_m$N$(R_{16})_2$ or $(C(R_{19})_2)_m$-Z;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein $R_{18}$ is straight chained or branched $C_1$-$C_6$ alkyl, —$(CH_2)_m$-Z, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl, or aryl($C_1$-$C_6$)alkyl;

wherein each $R_{22}$ is independently H, F, Cl or $C_1$-$C_4$ straight chained or branched alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2;

wherein U is O, —$NR_{16}$, S, $C(R_{17})_2$, or —$NSO_2R_{16}$;

wherein Z is $C_3$-$C_{10}$ cycloalkyl, $C_4$-$C_7$ cyclic ether, $C_4$-$C_7$ cyclic thioether, aryl, or heteroaryl; or a pharmaceutically acceptable salt thereof.

The invention provides a method of treating a subject suffering from anxiety which comprises administering to the subject an amount of compound effective to treat the subject's anxiety wherein the compound has the structure:

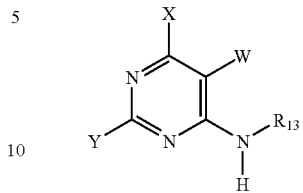

wherein W is H, —F, —Cl, —Br, —I, CN, methyl, ethyl, propyl, methoxy or ethoxy;

wherein X is $NR_{11}R_{12}$;

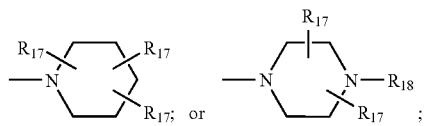

wherein $R_{11}$ is H, straight chained or branched $C_1$-$C_7$ alkyl, $(CH_2)_q$—O—$(CH_2)_m$—$CH_3$, aryl or aryl($C_1$-$C_6$)alkyl;

wherein $R_{12}$ is straight chained or branched $C_1$-$C_7$ alkyl, —$(CH_2)_q$—O—$(CH_2)_m$—$CH_3$, or —$(CH_2)_m$-Z;

wherein $R_{13}$ is a bicyclic alkyl ring system, aryl or aryl($C_1$-$C_6$) alkyl;

wherein Y is $NR_{14}R_{15}$;

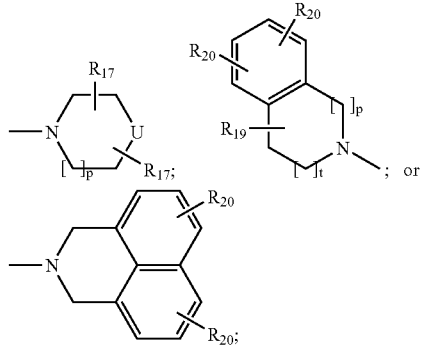

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is straight chained or branched $C_3$-$C_6$ alkyl, $(CH_2)_q$—O—$(CH_2)_m$—$CH_3$, $C_3$-$C_6$ cycloalkyl, or $(C(R_{19})_2)_m$-Z;

wherein U is O, —$NR_{16}$, S, $C(R_{17})_2$, or —$NSO_2R_{16}$;

wherein Z is $C_3$-$C_{10}$ cycloalkyl, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein $R_{18}$ is straight chained or branched $C_1$-$C_6$ alkyl, —$(CH_2)_m$-Z, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$) alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2; or a pharmaceutically acceptable salt thereof.

The invention provides a method of treating a subject suffering from anxiety which comprises administering to the subject an amount of compound effective to treat the subject's anxiety wherein the compound has the structure:

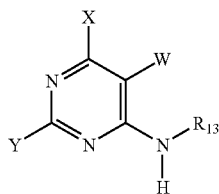

wherein W is H, —F, —Cl, —Br, —I, CN, methyl, ethyl, propyl, methoxy or ethoxy;

wherein X is $N(CH_3)_2$ or

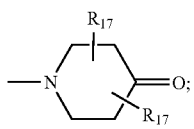

wherein $R_{13}$ is an aryl, adamantyl, noradamantyl, $C_3$-$C_{10}$ cycloalkyl, heteroaryl, $Q_1$ or $Q_2$;

wherein aryl may be substituted with one or more $C_1$-$C_{10}$ straight chained or branched alkyl, aryl, heteroaryl, or $N(R_{19})$-Z;

wherein $Q_1$ is

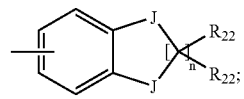

wherein $Q_2$ is

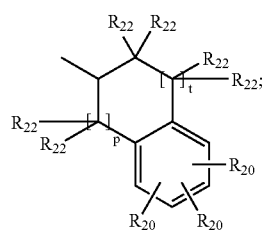

wherein each J is independently O, S, $C(R_{22})_2$ or $NR_4$;

wherein $R_4$ is —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein Y is $NR_{14}R_{15}$;

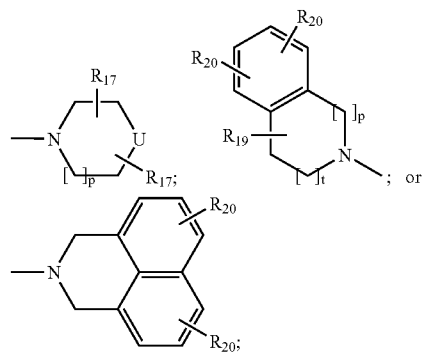

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is straight chained or branched $C_3$-$C_6$ alkyl, $(CH_2)_q$—O—$(CH_2)_m$—$CH_3$, $C_3$-$C_6$ cycloalkyl, or $(C(R_{19})_2)_m$-Z;

wherein U is O, —$NR_{16}$, S, $C(R_{17})_2$, or —$NSO_2R_{16}$;

wherein Z is $C_3$-$C_{10}$ cycloalkyl, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or —$(CH_2)_n$—O—$(CH_2)_m$—$CH_3$;

wherein $R_{18}$ is straight chained or branched $C_1$-$C_6$ alkyl, —$(CH_2)_m$-Z, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_4$) alkyl;

wherein each $R_{22}$ is independently H, F, Cl or $C_1$-$C_4$ straight chained or branched alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2; or a pharmaceutically acceptable salt thereof.

The invention provides a method of treating a subject suffering from anxiety which comprises administering to the subject an amount of compound effective to treat the subject's anxiety wherein the compound has the structure:

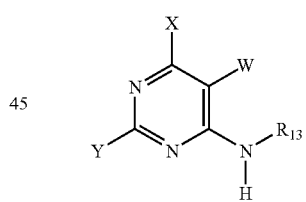

wherein W is H, —F, —Cl, —Br, —I, CN, methyl, ethyl, propyl, methoxy or ethoxy;

wherein X is $N(CH_3)_2$ or

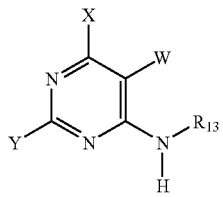

wherein $R_{13}$ is a bicyclic alkyl ring system, aryl or aryl($C_1$-$C_6$) alkyl;

wherein Y is $NR_{14}R_{15}$;

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is $(C(R_{19})_2)_m$—$N(R_{16})_2$;

wherein Z is $C_3$-$C_{10}$ cycloalkyl, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or —$(CH_2)_n$—O—$(CH_2)_m$—$CH_3$;

wherein each $R_{19}$ is independently H, or straight chained or branched $C_1$-$C_6$ alkyl;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$) alkyl;

wherein each m is an integer from 0 to 4 inclusive;

wherein each n is an integer from 1 to 4 inclusive;

wherein q is an integer from 2 to 4 inclusive; or a pharmaceutically acceptable salt thereof.

The invention also provides a pharmaceutical composition comprising a pharmaceutically acceptable carrier and a compound having the structure:

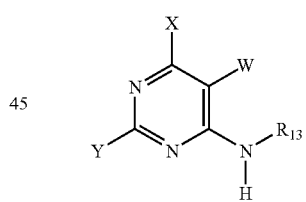

wherein W is H, —F, —Cl, —Br, —I, CN, methyl, ethyl, propyl, methoxy or ethoxy;

wherein X is; $NR_{11}R_{12}$;

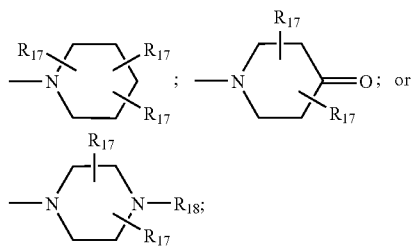

wherein $R_{11}$ is H, straight chained or branched $C_1$-$C_7$ alkyl, $(CH_2)_q$—O—$(CH_2)_m$—$CH_3$, aryl, or aryl ($C_1$-$C_6$)alkyl;

wherein $R_{12}$ is straight chained or branched $C_1$-$C_7$ alkyl, $(CH_2)_q$—O—$(CH_2)_m$—$CH_3$, or —$(CH_2)_m$-Z;

wherein $R_{13}$ is a bicyclic alkyl ring system, adamantyl, noradamantyl, $C_3$-$C_{10}$ cycloalkyl, heteroaryl, aryl, aryl($C_1$-$C_6$)alkyl, $Q_1$ or $Q_2$;

wherein aryl may be substituted with one or more $C_1$-$C_{10}$ straight chained or branched alkyl, aryl, heteroaryl, or $N(R_{19})$-Z;

wherein $Q_1$ is

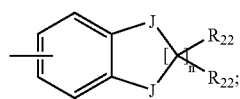

wherein $Q_2$ is

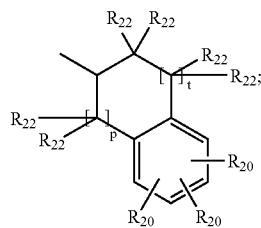

wherein each J is independently O, S, $C(R_{22})_2$ or $NR_4$;

wherein $R_4$ is H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein Y is $NR_{14}R_{15}$;

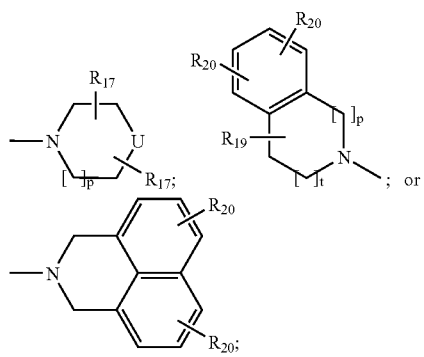

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is straight chained or branched $C_3$-$C_6$ alkyl, $(CH_2)_q$—O—$(CH_2)_m$—$CH_3$, $C_3$-$C_6$ cycloalkyl, $(C(R_{19})_2)_m N(R_{16})_2$ or $(C(R_{19})_2)_m$-Z;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein $R_{18}$ is straight chained or branched $C_1$-$C_6$ alkyl, —$(CH_2)_m$-Z, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl, or aryl ($C_1$-$C_6$) alkyl;

wherein each $R_{22}$ is independently H, F, Cl or $C_1$-$C_4$ straight chained or branched alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2;

wherein U is O, —$NR_{16}$, S, $C(R_{17})_2$, or —$NSO_2R_{16}$;

wherein Z is $C_3$-$C_{10}$ cycloalkyl, $C_4$-$C_7$ cyclic ether, $C_4$-$C_7$ cyclic thioether, aryl, or heteroaryl; or a pharmaceutically acceptable salt thereof.

The invention provides a pharmaceutical composition comprising a pharmaceutically acceptable carrier and a compound having the structure:

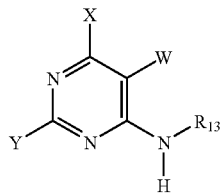

wherein W is H, —F, —Cl, —Br, —I, CN, methyl, ethyl, propyl, methoxy or ethoxy;

wherein X is $NR_{11}R_{12}$;

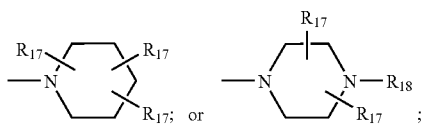

wherein R$_{11}$ is H, straight chained or branched C$_1$-C$_7$ alkyl, (CH$_2$)$_q$—O—(CH$_2$)$_m$—CH$_3$, aryl or aryl(C$_1$-C$_6$)alkyl;

wherein R$_{12}$ is straight chained or branched C$_1$-C$_7$ alkyl, (CH$_2$)$_q$—O—(CH$_2$)$_m$—CH$_3$, or —(CH$_2$)$_m$-Z;

wherein R$_{13}$ is a bicyclic alkyl ring system, aryl or aryl(C$_1$-C$_6$)alkyl;

wherein Y is NR$_{14}$R$_{15}$;

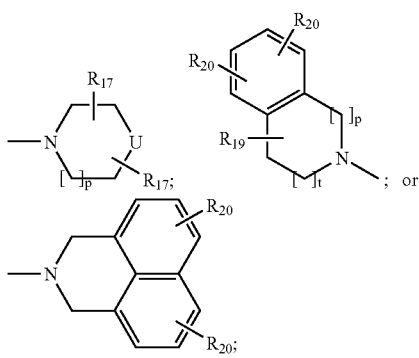

wherein R$_{14}$ is H, straight chained or branched C$_1$-C$_6$ alkyl, (CH$_2$)$_q$—O—(CH$_2$)$_m$—CH$_3$, C$_3$-C$_6$ cycloalkyl, or (C(R$_{19}$)$_2$)$_m$-Z;

wherein R$_{15}$ is straight chained or branched C$_3$-C$_6$ alkyl, (CH$_2$)$_q$—O—(CH$_2$)$_m$—CH$_3$, C$_3$-C$_6$ cycloalkyl, or (C(R$_{19}$)$_2$)$_m$-Z;

wherein U is O, —NR$_{16}$, S, C(R$_{17}$)$_2$, or —NSO$_2$R$_{16}$;

wherein Z is C$_3$-C$_{10}$ cycloalkyl, aryl, or heteroaryl;

wherein R$_{16}$ is straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_5$-C$_7$ cycloalkenyl, —(CH$_2$)$_m$-Z, or (CH$_2$)$_q$—O—(CH$_2$)$_m$—CH$_3$;

wherein each R$_{17}$ is independently H; —OR$_{21}$, —OCOR$_{21}$, —COR$_{21}$, —NCOR$_{21}$, —N(R$_{21}$)$_2$, —CON(R$_{21}$)$_2$, —COOR$_{21}$, straight chained or branched C$_1$-C$_7$ alkyl, straight chained or branched C$_1$-C$_7$ monofluoroalkyl, straight chained or branched C$_1$-C$_7$ polyfluoroalkyl; straight chained or branched C$_2$-C$_7$ alkenyl, straight chained or branched C$_2$-C$_7$ alkynyl, C$_5$-C$_7$ cycloalkenyl, —(CH$_2$)$_m$-Z, or (CH$_2$)$_n$—O—(CH$_2$)$_m$—CH$_3$;

wherein R$_{18}$ is straight chained or branched C$_1$-C$_6$ alkyl, —(CH$_2$)$_m$-Z, or (CH$_2$)$_q$—O—(CH$_2$)$_m$—CH$_3$;

wherein each R$_{19}$ is independently H, or straight chained or branched C$_1$-C$_6$ alkyl;

wherein each R$_{20}$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl or C$_5$-C$_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$, —CON(R$_{21}$)$_2$, or —COOR$_{21}$; aryl or heteroaryl; or two R$_{20}$ groups present on adjacent carbon atoms can join together to form a methylenedioxy group;

wherein each R$_{21}$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, C$_5$-C$_7$ cycloalkenyl, aryl or aryl(C$_1$-C$_6$) alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2; or a pharmaceutically acceptable salt thereof.

The invention provides a pharmaceutical composition comprising a pharmaceutically acceptable carrier and a compound having the structure:

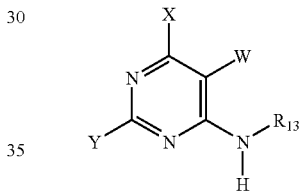

wherein W is H, —F, —Cl, —Br, —I, CN, methyl, ethyl, propyl, methoxy or ethoxy;

wherein X is N(CH$_3$)$_2$ or

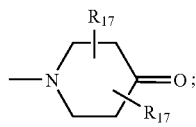

wherein R$_{13}$ is an aryl, adamantyl, noradamantyl, C$_3$-C$_{10}$ cycloalkyl, heteroaryl, Q$_1$ or Q$_2$;

wherein aryl may be substituted with one or more C$_1$-C$_{10}$ straight chained or branched alkyl, aryl, heteroaryl, or N(R$_{19}$)-Z;

wherein Q$_1$ is

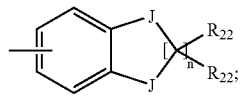

wherein $Q_2$ is

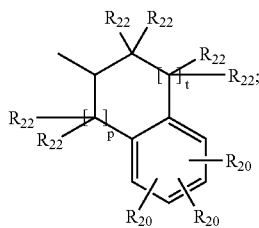

wherein each J is independently O, S, $C(R_{22})_2$ or $NR_4$;

wherein $R_4$ is —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein Y is $NR_{14}R_{15}$;

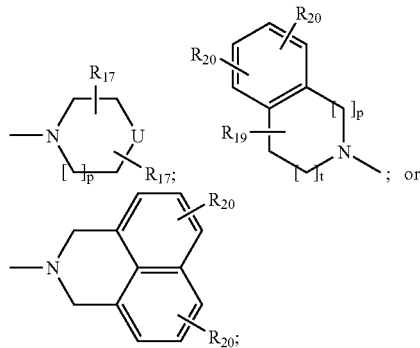

wherein $R_{14}$ is H, straight chained or branched $C_2$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is straight chained or branched $C_3$-$C_6$ alkyl, $(CH_2)_q$—O—$(CH_2)_m$—$CH_3$, $C_3$-$C_6$ cycloalkyl, or $(C(R_{19})_2)_m$-Z;

wherein U is O, —$NR_{16}$, S, $C(R_{17})_2$, or —$NSO_2R_{16}$;

wherein Z is $C_3$-$C_{10}$ cycloalkyl, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein $R_{18}$ is straight chained or branched $C_1$-$C_6$ alkyl, —$(CH_2)_m$-Z, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$) alkyl;

wherein each $R_{22}$ is independently H, F, Cl or $C_1$-$C_4$ straight chained or branched alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2; or a pharmaceutically acceptable salt thereof.

The invention provides a pharmaceutical composition comprising a pharmaceutically acceptable carrier and a compound having the structure:

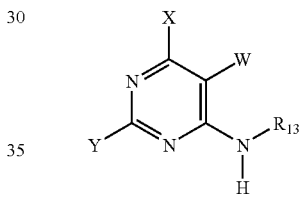

wherein W is H, —F, —Cl, —Br, —I, CN, methyl, ethyl, propyl, methoxy or ethoxy;

wherein X is $N(CH_3)_2$ or

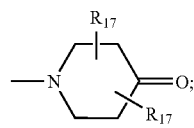

wherein $R_{13}$ is a bicyclic alkyl ring system, aryl or aryl ($C_1$-$C_6$) alkyl;

wherein Y is $NR_{14}R_{15}$;

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is $(C(R_{19})_2)_m$—$N(R_{16})_2$;

wherein Z is $C_3$-$C_{10}$ cycloalkyl, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; $—OR_{21}$, $—OCOR_{21}$, $—COR_{21}$, $—NCOR_{21}$, $—N(R_{21})_2$, $—CON(R_{21})_2$, $—COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, $—(CH_2)_m$-Z, or $(CH_2)_n$—O—$(CH_2)_m$—$CH_3$;

wherein each $R_{19}$ is independently H, or straight chained or branched $C_1$-$C_6$ alkyl;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$) alkyl;

wherein each m is an integer from 0 to 4 inclusive;

wherein each n is an integer from 1 to 4 inclusive;

wherein q is an integer from 2 to 4 inclusive; or a pharmaceutically acceptable salt thereof.

The invention provides a compound having the structure:

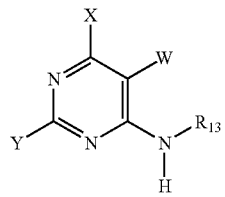

wherein W is H, —F, —Cl, —Br, —I, CN, methyl, ethyl, propyl, methoxy or ethoxy;

wherein X is; $NR_{11}R_{12}$;

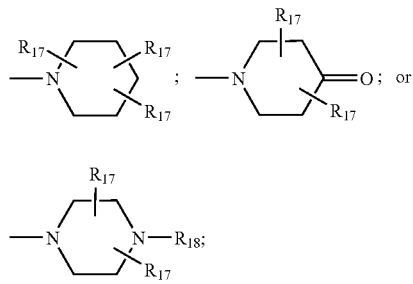

wherein $R_{11}$ is H, straight chained or branched $C_1$-$C_7$ alkyl, $(CH_2)_q$—O—$(CH_2)_m$—$CH_3$, aryl, or aryl ($C_1$-$C_6$)alkyl;

wherein $R_{12}$ is straight chained or branched $C_1$-$C_7$ alkyl, $(CH_2)_q$—O—$(CH_2)_m$—$CH_3$, or —$(CH_2)_m$-Z;

wherein $R_{13}$ is a bicyclic alkyl ring system, adamantyl, noradamantyl, $C_3$-$C_{10}$ cycloalkyl, heteroaryl, aryl, aryl($C_1$-$C_6$)alkyl, $Q_1$ or $Q_2$;

wherein aryl may be substituted with one or more $C_1$-$C_{10}$ straight chained or branched alkyl, aryl, heteroaryl, or $N(R_{19})$-Z;

wherein $Q_1$ is

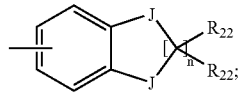

wherein $Q_2$ is

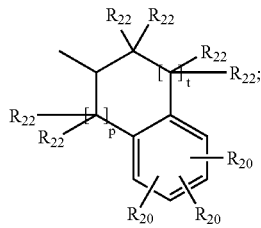

wherein each J is independently O, S, $C(R_{22})_2$ or $NR_4$;

wherein $R_4$ is H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein Y is $NR_{14}R_{15}$;

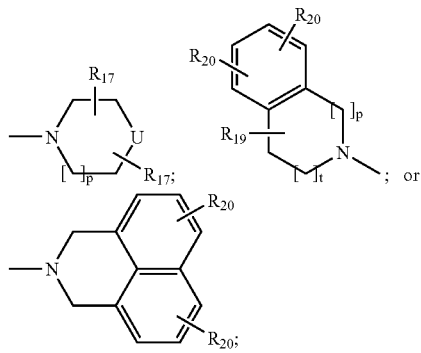

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is straight chained or branched $C_3$-$C_6$ alkyl, $(CH_2)_q$—O—$(CH_2)_m$—$CH_3$, $C_3$-$C_6$ cycloalkyl, $(C(R_{19})_2)_m(R_{16})_2$ or $(C(R_{19})_2)_m$-Z;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, $—(CH_2)_m$-Z, or $(CH_2)_q$—O—$(CH_2)_m$—$CH_3$;

wherein each $R_{17}$ is independently H; $—OR_{21}$, $—OCOR_{21}$, $—COR_{21}$, $—NCOR_{21}$, $—N(R_{21})_2$, $—CON(R_{21})_2$, $—COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, $—(CH_2)_m$-Z, or $(CH_2)_n$—O—$(CH_2)_m$—$CH_3$;

wherein $R_{18}$ is straight chained or branched $C_1$-$C_6$ alkyl, —$(CH_2)_m$-Z, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl, or aryl($C_1$-$C_6$) alkyl;

wherein each $R_{22}$ is independently H, F, Cl or $C_1$-$C_4$ straight chained or branched alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2;

wherein U is O, —$NR_{16}$, S, $C(R_{17})_2$, or —$NSO_2R_{16}$;

wherein Z is $C_3$-$C_{10}$ cycloalkyl, $C_4$-$C_7$ cyclic ether, $C_4$-$C_7$ cyclic thioether, aryl, or heteroaryl; or a pharmaceutically acceptable salt thereof.

The invention provides a compound having the structure:

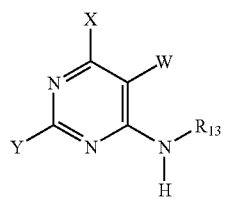

wherein W is H, —F, —Cl, —Br, —I, CN, methyl, ethyl, propyl, methoxy or ethoxy;

wherein X is $NR_{11}R_{12}$;

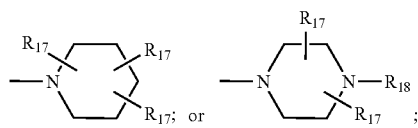

wherein $R_{11}$ is H, straight chained or branched $C_1$-$C_7$ alkyl, $(CH_2)_q$—O—$(CH_2)_m$—$CH_3$, aryl or aryl($C_1$-$C_6$)alkyl;

wherein $R_{12}$ is straight chained or branched $C_1$-$C_7$ alkyl, $(CH_2)_q$—O—$(CH_2)_m$—$CH_3$, or —$(CH_2)_m$-Z;

wherein $R_{13}$ is a bicyclic alkyl ring system, aryl or aryl ($C_1$-$C_6$) alkyl;

wherein Y is $NR_{14}R_{15}$;

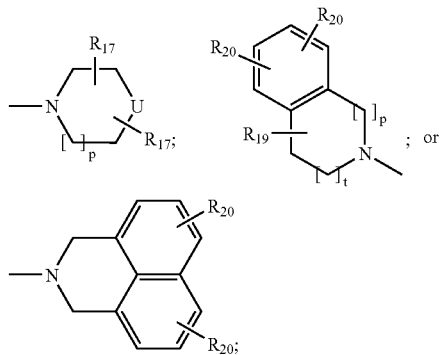

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is straight chained or branched $C_3$-$C_6$ alkyl, $(CH_2)_q$—O—$(CH_2)_m$—$CH_3$, $C_3$-$C_6$ cycloalkyl, or $(C(R_{19})_2)_m$-Z;

wherein U is O, —$NR_{16}$, S, $C(R_{17})_2$, or —$NSO_2R_{16}$;

wherein Z is $C_3$-$C_{10}$ cycloalkyl, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein $R_{18}$ is straight chained or branched $C_1$-$C_6$ alkyl, —$(CH_2)_m$-Z or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl, or aryl($C_1$-$C_6$) alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2; or a pharmaceutically acceptable salt thereof.

The invention provides a compound having the structure:

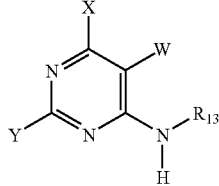

wherein W is H, —F, —Cl, —Br, —I, CN, methyl, ethyl, propyl, methoxy or ethoxy;

wherein X is $N(CH_3)_2$ or

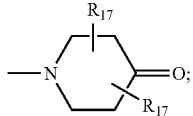

wherein $R_{13}$ is an aryl, adamantyl, noradamantyl, $C_3$-$C_{10}$ cycloalkyl, heteroaryl, $Q_1$ or $Q_2$;

wherein aryl may be substituted with one or more $C_1$-$C_{10}$ straight chained or branched alkyl, aryl, heteroaryl, or $N(R_{19})$-$Z$;

wherein $Q_1$ is

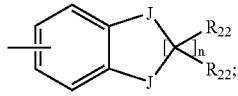

wherein $Q_2$ is

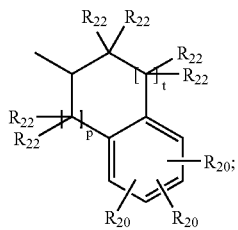

wherein each J is independently O, S, $C(R_{22})_2$ or $NR_4$;

wherein $R_4$ is —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein Y is $NR_{14}R_{15}$;

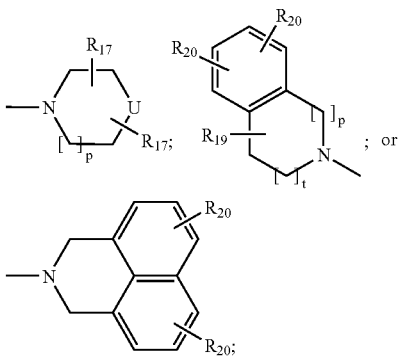

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-$Z$;

wherein $R_{15}$ is straight chained or branched $C_3$-$C_6$ alkyl, $(CH_2)_q$—O—$(CH_2)_m$—$CH_3$, $C_3$-$C_6$ cycloalkyl, or $(C(R_{19})_2)_m$-$Z$;

wherein U is O, —$NR_{16}$, S, $C(R_{17})_2$, or —$NSO_2R_{16}$;

wherein Z is $C_3$-$C_{10}$ cycloalkyl, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkyl, —$(CH_2)_m$-$Z$, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkyl, —$(CH_2)_m$-$Z$, or $(CH_2)_n$—O—$(CH_2)_m$—$CH_3$;

wherein $R_{18}$ is straight chained or branched $C_1$-$C_6$ alkyl, —$(CH_2)_m$-$Z$, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein each $R_{22}$ is independently H, F, Cl or $C_1$-$C_4$ straight chained or branched alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2; or a pharmaceutically acceptable salt thereof.

The invention provides a compound having the structure:

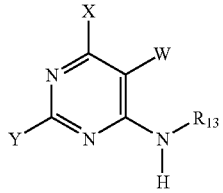

wherein W is H, —F, —Cl, —Br, —I, CN, methyl, ethyl, propyl, methoxy or ethoxy;

wherein X is N(CH$_3$)$_2$ or

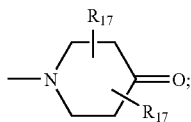

wherein $R_{13}$ is a bicyclic alkyl ring system, aryl or aryl (C$_1$-C$_6$) alkyl;

wherein Y is NR$_{14}$R$_{15}$;

wherein $R_{14}$ is H, straight chained or branched C$_1$-C$_6$ alkyl, (CH$_2$)$_q$—O—(CH$_2$)$_m$—CH$_3$, C$_3$-C$_6$ cycloalkyl, or (C(R$_{19}$)$_2$)$_m$-Z;

wherein $R_{15}$ is (C(R$_{19}$)$_2$)$_m$—N(R$_{16}$)$_2$;

wherein Z is C$_3$-C$_{10}$ cycloalkyl, aryl, or heteroaryl;

wherein $R_{16}$ is straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_5$-C$_7$ cycloalkenyl, —(CH$_2$)$_m$-Z, or (CH$_2$)$_q$—O—(CH$_2$)$_m$—CH$_3$;

wherein each $R_{17}$ is independently H; —OR$_{21}$, —OCOR$_{21}$, —COR$_{21}$, —NCOR$_{21}$, —N(R$_{21}$)$_2$, —CON(R$_{21}$)$_2$, —COOR$_{21}$, straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_5$-C$_7$ cycloalkenyl, —(CH$_2$)$_m$-Z, or (CH$_2$)$_n$—O—(CH$_2$)$_m$—CH$_3$;

wherein each $R_{19}$ is independently H, or straight chained or branched C$_1$-C$_6$ alkyl;

wherein each $R_{21}$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, C$_5$-C$_7$ cycloalkenyl, aryl or aryl(C$_1$-C$_6$) alkyl;

wherein each m is an integer from 0 to 4 inclusive;

wherein each n is an integer from 1 to 4 inclusive;

wherein q is an integer from 2 to 4 inclusive; or a pharmaceutically acceptable salt thereof.

The invention also provides a method of treating a subject suffering from depression which comprises administering to the subject an amount of compound effective to treat the subject's depression wherein the compound has the structure:

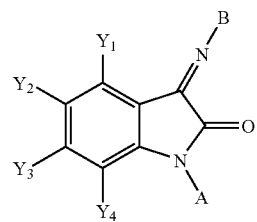

wherein each of Y$_1$, Y$_2$, Y$_3$, and Y$_4$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, or C$_5$-C$_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of Y$_1$, Y$_2$, Y$_3$ and Y$_4$ present on adjacent carbon atoms can constitute a methylenedioxy group;

wherein each R$_4$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$, cycloalkyl, C$_5$-C$_7$ cycloalkenyl, aryl or aryl(C$_1$-C$_6$)alkyl;

wherein A is A', Q$_3$, Q$_4$, Q$_5$, straight chained or branched C$_1$-C$_7$ alkyl, aryl, heteroaryl, aryl(C$_1$-C$_6$) alkyl, heteroaryl (C$_1$-C$_6$) alkyl, aryl substituted with an aryl or heteroaryl, heteroaryl substituted with an aryl or heteroaryl; or (CHR$_{17}$)—(CHR$_{17}$)$_n$-Z;

wherein A' is

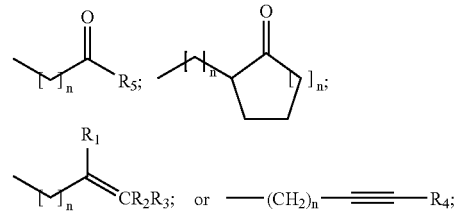

wherein Q$_3$ is

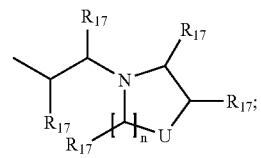

wherein $Q_4$ is

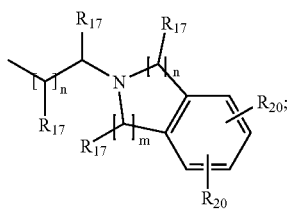

wherein $Q_5$ is

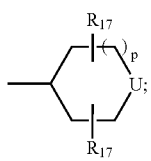

wherein $R_1$ and $R_2$ are each independently H, straight chained or branched $C_1$-$C_7$ alkyl, —F, —Cl, —Br, —I, —NO$_2$, or —CN;

wherein $R_3$ is H, straight chained or branched $C_1$-$C_7$ alkyl, —F, —Cl, —Br, —I, —NO$_2$, —CN, —OR$_6$ aryl or heteroaryl;

wherein $R_5$ is straight chained or branched $C_1$-$C_7$ alkyl, —N(R$_4$)$_2$, —OR$_6$ or aryl;

wherein $R_6$ is straight chained or branched $C_1$-$C_7$ alkyl or aryl;

wherein each $R_{17}$ is independently H; straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl; —(CH$_2$)$_m$-Z, or (CH$_2$)$_n$—O—(CH$_2$)$_m$—CH$_3$;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$, —CON(R$_{21}$)$_2$, or —COOR$_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein each m is an integer from 0 to 4 inclusive;
wherein each n is an integer from 1 to 4 inclusive;
wherein each p is an integer from 0 to 2 inclusive;
wherein U is O, —NR$_{16}$, S, C(R$_{17}$)$_2$, or —NSO$_2$R$_{16}$;
wherein Z is $C_3$-$C_{10}$ cycloalkyl, $C_4$-$C_7$ cyclic ether, $C_4$-$C_7$ cyclic thioether, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_q$—O—(CH$_2$)$_m$—CH$_3$;

wherein q is an integer from 2 to 4 inclusive;

wherein B is aryl, heteroaryl, aryl substituted with an aryl or heteroaryl, heteroaryl substituted with an aryl or heteroaryl, tricyclic heteroaryl or $Q_6$; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

wherein a tricyclic heteroaryl is a fused three member aromatic system in which one or more of the rings is heteroaryl; carbazole; or acridine;

wherein $Q_6$ is

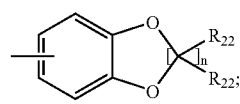

wherein each $R_{22}$ is independently H, F, Cl, or straight chained or branched $C_1$-$C_4$ alkyl;

or a pharmaceutically acceptable salt thereof.

The invention provides a method of treating a subject suffering from depression which comprises administering to the subject an amount of compound effective to treat the subject's depression wherein the compound has the structure:

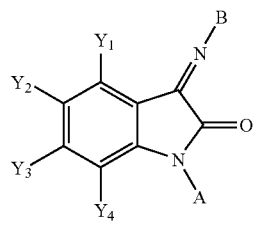

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is A', straight chained or branched $C_1$-$C_7$alkyl, aryl, heteroaryl, aryl($C_1$-$C_6$)alkyl or heteroaryl ($C_1$-$C_6$) alkyl;

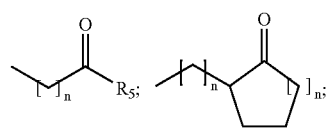

wherein A' is

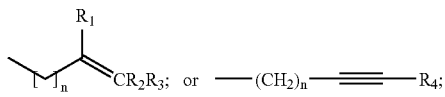

wherein $R_1$ and $R_2$ are each independently H, straight chained or branched $C_1$-$C_7$ alkyl, —F, —Cl, —Br, —I, —NO$_2$, or —CN;

wherein $R_3$ is H, straight chained or branched $C_1$-$C_7$ alkyl, —F, —Cl, —Br, —I, —NO$_2$, —CN, —OR$_6$ aryl or heteroaryl;

wherein $R_5$ is straight chained or branched $C_1$-$C_7$ alkyl, —N(R$_4$)$_2$, —OR$_6$ or aryl;

wherein $R_6$ is straight chained or branched $C_1$-$C_7$ alkyl or aryl;

wherein B is aryl, or heteroaryl; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

wherein n is an integer from 1 to 4 inclusive;

or a pharmaceutically acceptable salt thereof.

The invention provides a method of treating a subject suffering from depression which comprises administering to the subject an amount of compound effective to treat the subject's depression wherein the compound has the structure:

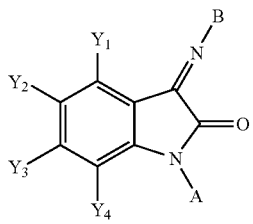

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_1$-$C_7$ alkenyl or, alkynyl; $C_3$-$C_7$ cycloalkyl, $C_5$-$C_7$ cycloalkenyl, aryl or aryl($C_1$-$C_6$)alkyl;

wherein A is A', straight chained or branched $C_1$-$C_7$ alkyl, aryl, heteroaryl, aryl($C_1$-$C_6$)alkyl or heteroaryl ($C_1$-$C_6$) alkyl;

wherein A' is

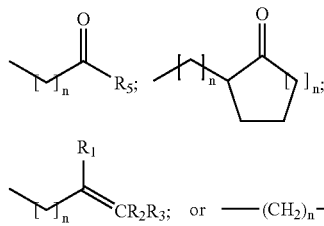

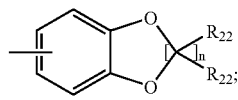

wherein B is aryl substituted with an aryl or, heteroaryl, heteroaryl substituted with an aryl or heteroaryl, tricyclic heteroaryl or $Q_6$;

wherein a tricyclic heteroaryl is a fused three ring aromatic system in which one or more of the rings is heteroaryl; carbazole; or acridine;

wherein $Q_6$ is

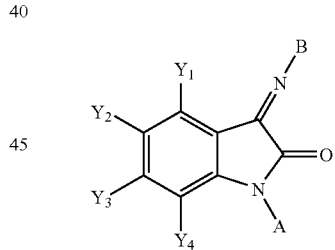

wherein n is an integer from 1 to 4 inclusive;

wherein each $R_{22}$ is independently H, F, Cl, or straight chained or branched $C_1$-$C_4$ alkyl;

or a pharmaceutically acceptable salt thereof.

The invention provides a method of treating a subject suffering from depression which comprises administering to the subject an amount of compound effective to treat the subject's depression wherein the compound has the structure:

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —NC(R$_4$)$_2$, —CON(R$_4$)$_2$, or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is $Q_3$, $Q_4$, $Q_5$, aryl substituted with an aryl or heteroaryl, heteroaryl substituted with an aryl or heteroaryl, or $(CHR_{17})\text{—}(CHR_{17})_n\text{-}Z$;

wherein $Q_3$ is

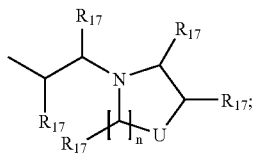

wherein $Q_4$ is

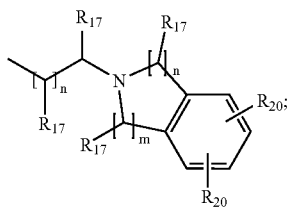

wherein $Q_5$ is

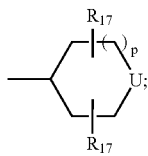

wherein each $R_{17}$ is independently H; straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, $\text{—}(CH_2)_m\text{-}Z$, or $(CH_2)_n\text{—}O\text{—}(CH_2)_m\text{—}CH_3$;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein each $R_{22}$ is independently H, F, Cl, or straight chained or branched $C_1$-$C_4$ alkyl;

wherein each m is an integer from 0 to 4 inclusive;

wherein each n is an integer from 1 to 4 inclusive;

wherein each p is an integer from 0 to 2 inclusive;

wherein U is O, —$NR_{16}$, S, $C(R_{17})_2$, or —$NSO_2R_{16}$;

wherein Z is $C_3$-$C_{10}$ cycloalkyl, $C_4$-$C_7$ cyclic ether, $C_4$-$C_7$ cyclic thioether, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_1$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein q is an integer from 2 to 4 inclusive;

wherein B is aryl, or heteroaryl; provided however, if B is aryl or hetetoaryl the carbon atom or carbon atoms ortho to the nitrogen atom of the imine bond may only be substituted with one or more of the following —F, —Cl, —Br, —I, —CN, methyl, ethyl or methoxy;

or a pharmaceutically acceptable salt thereof.

The invention provides a method of treating a subject suffering from anxiety which comprises administering to the subject an amount of compound effective to treat the subject's anxiety wherein the compound has the structure:

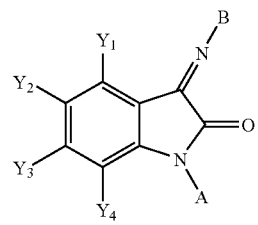

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —$NO_2$; —$N_3$; —CN; —$OR_4$, —$SR_4$, —$OCOR_4$, —$COR_4$, —$NCOR_4$, —$N(R_4)_2$, —$CON(R_4)_2$, or —$COOR_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is A', $Q_3$, $Q_4$, $Q_5$ straight chained or branched $C_1$-$C_7$ alkyl, aryl, heteroaryl, aryl($C_1$-$C_6$)alkyl, heteroaryl($C_1$-$C_6$)alkyl, aryl substituted with an aryl or heteroaryl, heteroaryl substituted with an aryl or heteroaryl; or $(CHR_{17})\text{—}(CHR_{17})_n\text{-}Z$;

wherein A' is

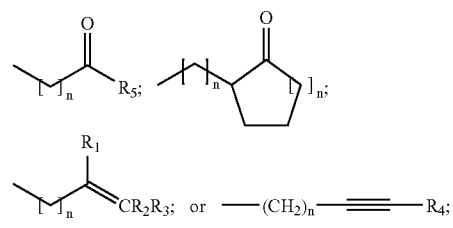

wherein $Q_3$ is

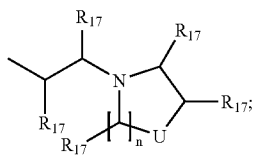

wherein $Q_4$ is

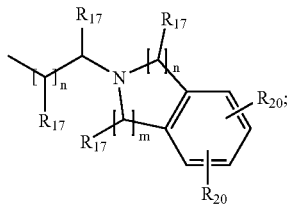

wherein $Q_5$ is

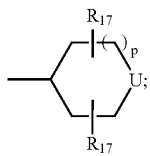

wherein $R_1$ and $R_2$ are each independently H, straight chained or branched $C_1$-$C_7$ alkyl, —F, —Cl, —Br, —I, —NO$_2$, or —CN;

wherein $R_3$ is H, straight chained or branched $C_1$-$C_7$ alkyl, —F, —Cl, —Br, —I, —NO$_2$, —CN, —OR$_6$, aryl or heteroaryl;

wherein $R_5$ is straight chained or branched $C_1$-$C_7$ alkyl, —N(R$_4$)$_2$, —OR$_6$ or aryl;

wherein $R_6$ is straight chained or branched $C_1$-$C_7$ alkyl or aryl;

wherein each $R_{17}$ is independently H; straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_n$—O—(CH$_2$)$_m$—CH$_3$;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$, —CON(R$_{21}$)$_2$, or —COOR$_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein each m is an integer from 0 to 4 inclusive;
wherein each n is an integer from 1 to 4 inclusive;
wherein each p is an integer from 0 to 2 inclusive;

wherein U is O, —NR$_{16}$, S, C(R$_{17}$)$_2$, or —NSO$_2$R$_{16}$;

wherein Z is $C_3$-$C_{10}$ cycloalkyl, $C_4$-$C_7$ cyclic ether, $C_4$-$C_7$ cyclic thioether, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_q$—O—(CH$_2$)$_m$—CH$_3$;

wherein q is an integer from 2 to 4 inclusive;

wherein B is aryl, heteroaryl, aryl substituted with an aryl or heteroaryl, heteroaryl substituted with an aryl or heteroaryl, tricyclic heteroaryl or $Q_6$; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

wherein a tricyclic heteroaryl is a fused three member aromatic system in which one or more of the rings is heteroaryl; carbazole; or acridine;

wherein $Q_6$ is

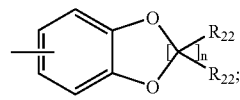

wherein each $R_{22}$ is independently H, F, Cl, or straight chained or branched $C_1$-$C_4$ alkyl;

or a pharmaceutically acceptable salt thereof.

The invention provides a method of treating a subject suffering from anxiety which comprises administering to the subject an amount of compound effective to treat the subject's anxiety wherein the compound has the structure:

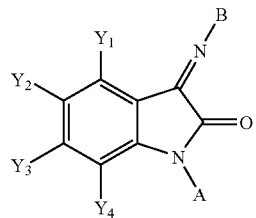

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, N(R$_4$)$_2$, —CON(R$_4$)$_2$, or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is A', straight chained or branched $C_1$-$C_7$ alkyl, aryl, heteroaryl, aryl($C_2$-$C_6$)alkyl or heteroaryl ($C_1$-$C_6$) alkyl;

wherein A' is

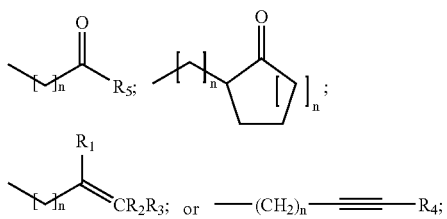

wherein $R_1$ and $R_2$ are each independently H, straight chained or branched $C_1$-$C_7$ alkyl, —F, —Cl, —Br, —I, —$NO_2$, or —CN;
wherein $R_3$ is H, straight chained or branched $C_1$-$C_7$ alkyl, —F, —Cl, —Br, —I, —$NO_2$, —CN, —$OR_6$ aryl or heteroaryl;
wherein $R_5$ is straight chained or branched $C_1$-$C_7$ alkyl, —$N(R_4)_2$, —$OR_6$ or aryl;
wherein $R_6$ is straight chained or branched $C_1$-$C_7$ alkyl or aryl;
wherein B is aryl, or heteroaryl; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;
wherein n is an integer from 1 to 4 inclusive;
or a pharmaceutically acceptable salt thereof.

The invention provides a method of treating a subject suffering from anxiety which comprises administering to the subject an amount of compound effective to treat the subject's anxiety wherein the compound has the structure:

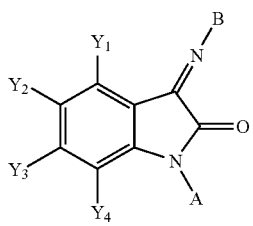

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —$NO_2$; —$N_3$; —CN; —$OR_4$, —$SR_4$, —$OCOR_4$, —$COR_4$, —$NCOR_4$, —$N(R_4)_2$, —$CON(R_4)_2$, or —$COOR_4$; aryl or heteroaryl; or any two of $Y_1$, $Y_2$, $Y_3$ and $Y_4$ present on adjacent carbon atoms can constitute a methylenedioxy group;
wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;
wherein A is A', straight chained or branched $C_1$-$C_7$ alkyl, aryl, heteroaryl, aryl($C_1$-$C_6$)alkyl or heteroaryl ($C_1$-$C_6$) alkyl;

wherein A' is

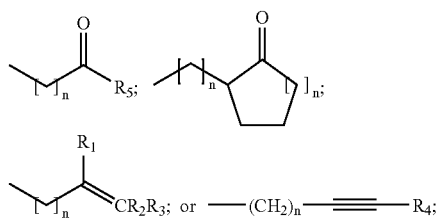

wherein B is aryl substituted with an aryl or heteroaryl, heteroaryl substituted with an aryl or heteroaryl, tricyclic heteroaryl or $Q_6$;
wherein a tricyclic heteroaryl is a fused three ring aromatic system in which one or more of the rings is heteroaryl; carbazole; or acridine;
wherein $Q_6$ is

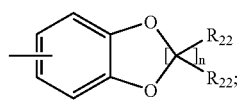

wherein n is an integer from 1 to 4 inclusive;
wherein each $R_{22}$ is independently H, F, Cl, or straight chained or branched $C_1$-$C_4$ alkyl;
or a pharmaceutically acceptable salt thereof.

The invention provides a method of treating a subject suffering from anxiety which comprises administering to the subject an amount of compound effective to treat the subject's anxiety wherein the compound has the structure:

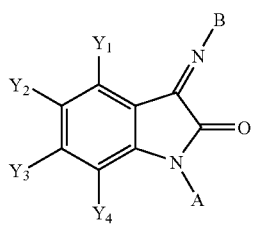

wherein each of $Y_1$, $Y_2$, $Y_3$, and $Y_4$ is independently —H; straight chained or branched $C_1$-$C_7$ alkyl, is monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —$NO_2$; —$N_3$; —CN; —$OR_4$, —$SR_4$, —$OCOR_4$, —$COR_4$, —$NCOR_4$, —$N(R_4)_2$, —$CON(R_4)_2$, or —$COOR_4$; aryl or heteroaryl; or any two of $Y_1$, $Y_2$, $Y_3$ and $Y_4$ present on adjacent carbon atoms can constitute a methylenedioxy group;
wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;
wherein A is $Q_3$, $Q_4$, $Q_5$, aryl substituted with an aryl or heteroaryl, heteroaryl substituted with an aryl or heteroaryl, or $(CHR_{17})$—$(CHR_{17})_n$-Z;

wherein $Q_3$ is

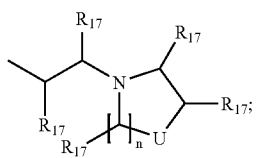

wherein $Q_4$ is

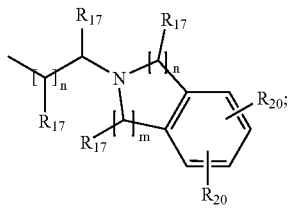

wherein $Q_5$ is

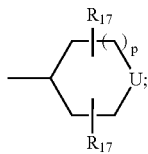

wherein each $R_{17}$ is independently —H; straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_n$—O—(CH$_2$)$_m$—CH$_3$;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$, —CON (R$_{21}$)$_2$, or —COOR$_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein each $R_{22}$ is independently H, F, Cl, or straight chained or branched $C_1$-$C_4$ alkyl;

wherein q is an integer from 2 to 4 inclusive;

wherein each m is an integer from 0 to 4 inclusive;

wherein each n is an integer from 1 to 4 inclusive;

wherein each p is an integer from 0 to 2 inclusive;

wherein U is O, —NR$_{16}$, S, C(R$_{17}$)$_2$, or —NSO$_2$R$_{16}$;

wherein Z is $C_3$-$C_{10}$ cycloalkyl, $C_4$-$C_7$ cyclic ether, $C_4$-$C_7$ cyclic thioether, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_q$—O—(CH$_2$)$_m$—CH$_3$;

wherein B is aryl, or heteroaryl; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

or a pharmaceutically acceptable salt thereof.

The invention provides a pharmaceutical composition comprising a pharmaceutically acceptable carrier and a compound having the structure:

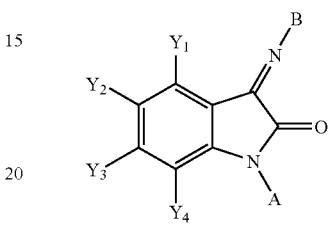

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is A', $Q_3$, $Q_4$, $Q_5$ straight chained or branched $C_1$-$C_7$ alkyl, aryl, heteroaryl, aryl($C_1$-$C_6$)alkyl, heteroaryl($C_1$-$C_6$)alkyl, aryl substituted with an aryl or heteroaryl, heteroaryl substituted with an aryl or heteroaryl; or (CHR$_{17}$)—(CHR$_{17}$)$_n$-Z;

wherein A' is

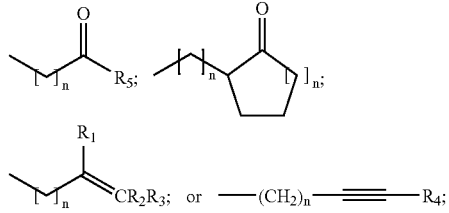

wherein $Q_3$ is

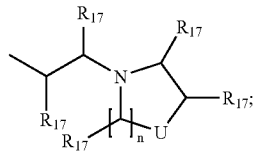

wherein $Q_4$ is

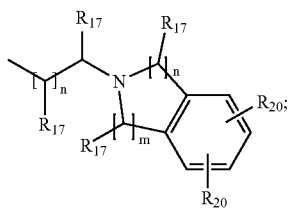

wherein $Q_5$ is

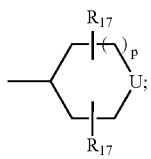

wherein $R_1$ and $R_2$ are each independently H, straight chained or branched $C_1$-$C_7$ alkyl, —F, —Cl, —Br, —I, —NO$_2$, or —CN;

wherein $R_3$ is H, straight chained or branched $C_1$-$C_7$ alkyl, —F, —Cl, —Br, —I, —NO$_2$, —CN, —OR$_6$, aryl or heteroaryl;

wherein $R_5$ is straight chained or branched $C_1$-$C_7$ alkyl, —N(R$_4$)$_2$, —OR$_6$ or aryl;

wherein $R_6$ is straight chained or branched $C_1$-$C_7$ alkyl or aryl;

wherein each $R_{17}$ is independently H; straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_n$—O—(CH$_2$)$_m$—CH$_3$;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or, $C_5$-$C_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$, —CON(R$_{21}$)$_2$, or —COOR$_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein each m is an integer from 0 to 4 inclusive;
wherein each n is an integer from 1 to 4 inclusive;
wherein each p is an integer from 0 to 2 inclusive;
wherein U is O, —NR$_{16}$, S, C(R$_{17}$)$_2$, or —NSO$_2$R$_{16}$;
wherein Z is $C_3$-$C_{10}$ cycloalkyl, $C_4$-$C_7$ cyclic ether, $C_4$-$C_7$ cyclic thioether, aryl, or heteroaryl;
wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_q$—O—(CH$_2$)$_m$—CH$_3$;
wherein q is an integer from 2 to 4 inclusive;

wherein B is aryl, heteroaryl, aryl substituted with an aryl or heteroaryl, heteroaryl substituted with an aryl or heteroaryl, tricyclic heteroaryl or $Q_6$; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

wherein a tricyclic heteroaryl is a fused three member aromatic system in which one or more of the rings is heteroaryl; carbazole; or acridine;

wherein $Q_6$ is

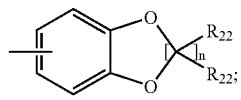

wherein each $R_{22}$ is independently H, F, Cl, or straight chained or branched $C_1$-$C_4$ alkyl;
or a pharmaceutically acceptable salt thereof.

The invention provides a pharmaceutical composition comprising a pharmaceutically acceptable carrier and a compound having the structure:

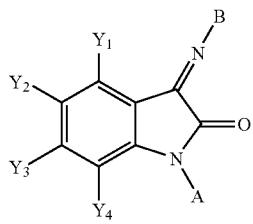

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is A', straight chained or branched $C_1$-$C_7$ alkyl, aryl, heteroaryl, aryl($C_1$-$C_6$)alkyl or heteroaryl ($C_1$-$C_6$) alkyl;

wherein A' is

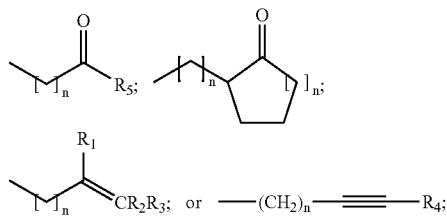

wherein $R_1$ and $R_2$ are each independently H, straight chained or branched $C_1$-$C_7$ alkyl, —F, —Cl, —Br, —I, —NO$_2$, or —CN;

wherein $R_3$ is H, straight chained or branched $C_1$-$C_7$ alkyl, —F, —Cl, —Br, —I, —NO$_2$, —CN, —OR$_6$ aryl or heteroaryl;

wherein $R_5$ is straight chained or branched $C_1$-$C_7$ alkyl, —N($R_4$)$_2$, —OR$_6$ or aryl;

wherein $R_6$ is straight chained or branched $C_1$-$C_7$ alkyl or aryl;

wherein B is aryl, or heteroaryl; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

wherein n is an integer from 1 to 4 inclusive;

or a pharmaceutically acceptable salt thereof.

The invention provides a pharmaceutical composition comprising a pharmaceutically acceptable carrier and a compound having the structure:

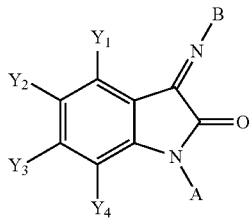

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N($R_4$)$_2$, —CON($R_4$)$_2$, or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_3$-$C_6$)alkyl;

wherein A is A', straight chained or branched $C_1$-$C_7$ alkyl, aryl, heteroaryl, aryl($C_1$-$C_6$)alkyl or heteroaryl ($C_1$-$C_6$) alkyl;

wherein A' is

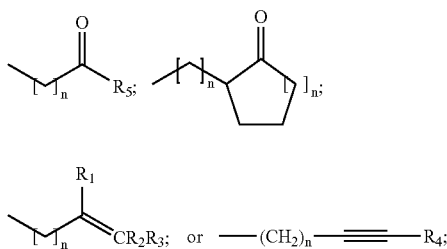

wherein B is aryl substituted with an aryl or heteroaryl, heteroaryl substituted with an aryl or heteroaryl, tricyclic heteroaryl or $Q_6$;

wherein a tricyclic heteroaryl is a fused three ring aromatic system in which one or more of the rings is heteroaryl; carbazole; or acridine;

wherein $Q_6$ is

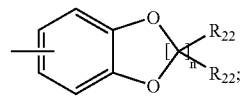

wherein n is an integer from 1 to 4 inclusive;

wherein each $R_{22}$ is independently H, F, Cl, or straight chained or branched $C_1$-$C_4$ alkyl;

or a pharmaceutically acceptable salt thereof.

The invention provides a pharmaceutical composition comprising a pharmaceutically acceptable carrier and a compound having the structure:

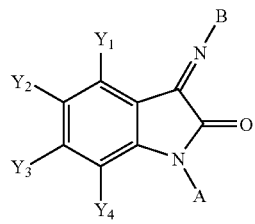

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N($R_4$)$_2$, —CON($R_4$)$_2$, or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl ($C_1$-$C_6$) alkyl;

wherein A is $Q_3$, $Q_4$, $Q_5$, aryl substituted with an aryl or heteroaryl, heteroaryl substituted with an aryl or heteroaryl, or (CHR$_{17}$)—(CHR$_{17}$)$_n$-Z;

wherein $Q_3$ is

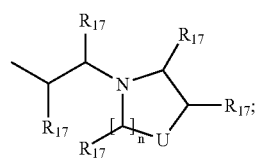

wherein $Q_4$ is

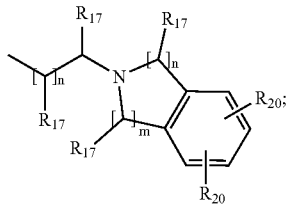

wherein $Q_5$ is

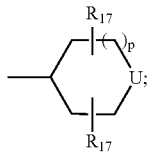

wherein each $R_{17}$ is independently H; straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_n$—O—(CH$_2$)$_m$—CH$_3$;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$, —CON(R$_{21}$)$_2$, or —COOR$_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein each $R_{22}$ is independently H, F, Cl, or straight chained or branched $C_1$-$C_4$ alkyl;

wherein q is an integer from 2 to 4 inclusive;

wherein each m is an integer from 0 to 4 inclusive;

wherein each n is an integer from 1 to 4 inclusive;

wherein each p is an integer from 0 to 2 inclusive;

wherein U is O, —NR$_{16}$, S, C(R$_{17}$)$_2$, or —NSO$_2$R$_{16}$;

wherein Z is $C_3$-$C_{10}$ cycloalkyl, $C_4$-$C_7$ cyclic ether, $C_4$-$C_7$ cyclic thioether, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_q$—O—(CH$_2$)$_m$—CH$_3$;

wherein B is aryl, or heteroaryl; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

or a pharmaceutically acceptable salt thereof.

The invention provides a compound having the structure:

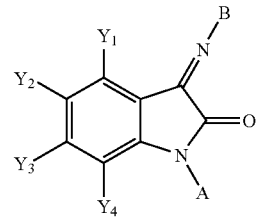

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$; or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl ($C_1$-$C_6$) alkyl;

wherein A is A', $Q_3$, $Q_4$, $Q_5$, straight chained or branched $C_1$-$C_7$ alkyl, aryl, heteroaryl, aryl($C_1$-$C_6$)alkyl, heteroaryl($C_1$-$C_6$)alkyl, aryl substituted with an aryl or heteroaryl, heteroaryl substituted with an aryl or heteroaryl; or (CHR$_{17}$)—(CHR$_{17}$)$_n$-Z;

wherein A' is

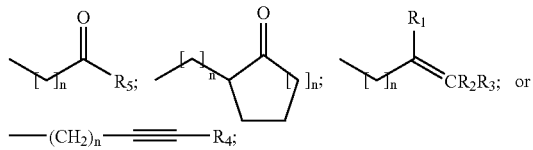

wherein $Q_3$ is

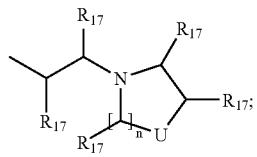

wherein $Q_4$ is

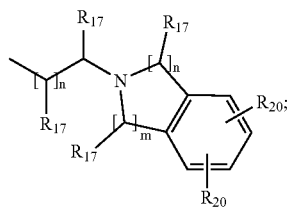

wherein $Q_5$ is

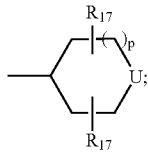

wherein $R_1$ and $R_2$ are each independently H, straight chained or branched $C_1$-$C_7$ alkyl, —F, —Cl, —Br, —I, —NO$_2$, or —CN;
wherein $R_3$ is H, straight chained or branched $C_1$-$C_7$ alkyl, —F, —Cl, —Br, —I, —NO$_2$, —CN, —OR$_6$, aryl or heteroaryl;
wherein $R_5$ is straight chained or branched $C_1$-$C_7$ alkyl, —N(R$_4$)$_2$, —OR$_6$ or aryl;
wherein $R_6$ is straight chained or branched $C_1$-$C_7$ alkyl or aryl;
wherein each $R_{17}$ is independently H; straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_n$—O—(CH$_2$)$_m$—CH$_3$;
wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$, —CON(R$_{21}$)$_2$, or —COOR$_{21}$; aryl or heteroaryl; or two $R_{20}$ groups present on adjacent carbon atoms can join together to form a methylenedioxy group;
wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;
wherein each m is an integer from 0 to 4 inclusive;
wherein each n is an integer from 1 to 4 inclusive;
wherein each p is an integer from 0 to 2 inclusive;
wherein U is O, —NR$_{16}$, S, C(R$_{17}$)$_2$, or —NSO$_2$R$_{16}$;
wherein Z is $C_3$-$C_{10}$ cycloalkyl, $C_4$-$C_7$ cyclic ether, $C_4$-$C_7$ cyclic thioether, aryl, or heteroaryl;
wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_q$—O—(CH$_2$)$_m$—CH$_3$;
wherein q is an integer from 2 to 4 inclusive;
wherein B is aryl, heteroaryl, aryl substituted with an aryl or heteroaryl, heteroaryl substituted with an aryl or heteroaryl, tricyclic heteroaryl or $Q_6$; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;
wherein a tricyclic heteroaryl is a fused three member aromatic system in which one or more of the rings is heteroaryl; carbazole; or acridine;

wherein $Q_6$ is

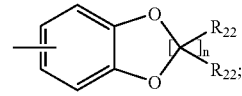

wherein each $R_{22}$ is independently H, F, Cl, or straight chained or branched $C_1$-$C_4$ alkyl;
or a pharmaceutically acceptable salt thereof.
The invention provides a compound having the structure:

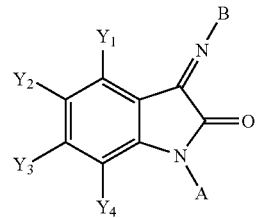

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of $Y_1$, $Y_2$, $Y_3$ and $Y_4$ present on adjacent carbon atoms can constitute a methylenedioxy group;
wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;
wherein A is A', straight chained or branched $C_1$-$C_7$ alkyl, aryl, heteroaryl, aryl($C_1$-$C_6$)alkyl or heteroaryl ($C_1$-$C_6$) alkyl;
wherein A' is

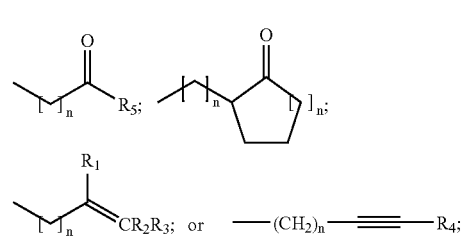

wherein $R_1$ and $R_2$ are each independently H, straight chained or branched $C_1$-$C_7$ alkyl, —F, —Cl, —Br, —I, —NO$_2$, or —CN;
wherein $R_3$ is H, straight chained or branched $C_1$-$C_7$ alkyl, —F, —Cl, —Br, —I, —NO$_2$, —CN, —OR$_6$ aryl or heteroaryl;
wherein $R_5$ is straight chained or branched $C_1$-$C_7$ alkyl, —N(R$_4$)$_2$, —OR$_6$ or aryl;
wherein $R_6$ is straight chained or branched $C_1$-$C_7$ alkyl or aryl;
wherein B is aryl, or heteroaryl; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;
wherein n is an integer from 1 to 4 inclusive;
or a pharmaceutically acceptable salt thereof.
The invention provides a compound having the structure:

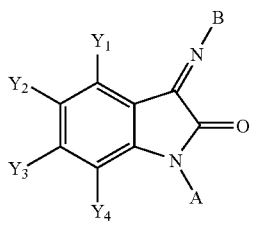

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —$NO_2$; —$N_3$; —CN; —$OR_4$, —$SR_4$, —$OCOR_4$, —$COR_4$, —$NCOR_4$, —$N(R_4)_2$, —$CON(R_4)_2$, or —$COOR_4$; aryl or heteroaryl; or any two of $Y_1$, $Y_2$, $Y_3$ and $Y_4$ present on adjacent carbon atoms can constitute a methylenedioxy group;
wherein each $R_4$ is independently —H; straight chained or branched $C_1$-$C_7$ alkyl, monofluoroalkyl or is polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;
wherein A is A', straight chained or branched $C_1$-$C_7$ alkyl, aryl, heteroaryl, aryl($C_3$-$C_6$)alkyl or heteroaryl ($C_1$-$C_6$) alkyl;
wherein A' is

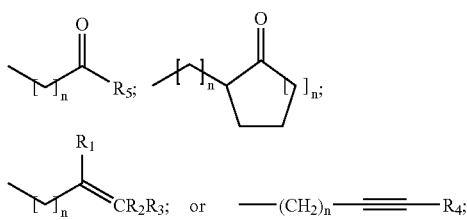

wherein B is aryl substituted with an aryl or heteroaryl, heteroaryl substituted with an aryl or heteroaryl, tricyclic heteroaryl or $Q_6$;
wherein a tricyclic heteroaryl is a fused three ring aromatic system in which one or more of the rings is heteroaryl; carbazole; or acridine;
wherein $Q_6$ is

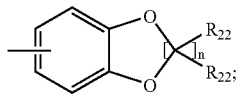

wherein n is an integer from 1 to 4 inclusive;
wherein each $R_{22}$ is independently H, F, Cl, or straight chained or branched $C_1$-$C_4$ alkyl;
or a pharmaceutically acceptable salt thereof.

The invention provides a compound having the structure:

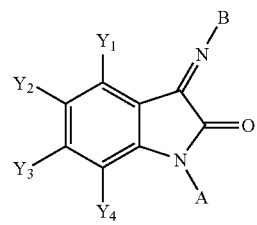

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —$NO_2$; —$N_3$; —CN; —$OR_4$, —$SR_4$, —$OCOR_4$, —$COR_4$, —$NCOR_4$, —$N(R_4)_2$, —$CON(R_4)_2$, or —$COOR_4$; aryl or heteroaryl; or any two of $Y_1$, $Y_2$, $Y_3$ and $Y_4$ present on adjacent carbon atoms can constitute a methylenedioxy group;
wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;
wherein A is $Q_3$, $Q_4$, $Q_5$, aryl substituted with an aryl or heteroaryl, heteroaryl substituted with an aryl or heteroaryl, or $(CHR_{17})$—$(CHR_{17})_n$-Z;
wherein $Q_3$ is

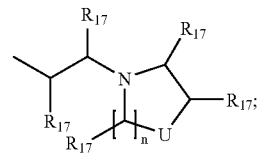

wherein $Q_4$ is

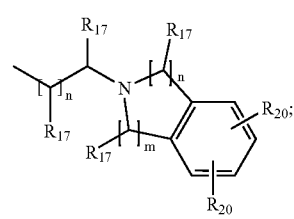

wherein $Q_5$ is

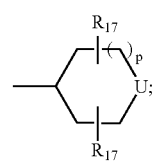

wherein each $R_{17}$ is independently H; straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein each $R_{22}$ is independently H, F, Cl, or straight chained or branched $C_1$-$C_4$ alkyl;

wherein q is an integer from 2 to 4 inclusive;

wherein each m is an integer from 0 to 4 inclusive;

wherein each n is an integer from 1 to 4 inclusive;

wherein each p is an integer from 0 to 2 inclusive;

wherein U is O, —$NR_{16}$, S, $C(R_{17})_2$, or —$NSO_2R_{16}$;

wherein Z is $C_3$-$C_{10}$ cycloalkyl, $C_4$-$C_7$ cyclic ether, $C_4$-$C_7$ cyclic thioether, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein B is aryl, or heteroaryl; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

or a pharmaceutically acceptable salt thereof.

The invention provides a method of treating depression in a subject which comprises administering to the subject a composition comprising a pharmaceutically acceptable carrier and a therapeutically effective amount of a GAL3 receptor antagonist, wherein:

(a) the GAL3 receptor antagonist binds to the human GAL3 receptor with a binding affinity at least ten-fold higher than the binding affinity with which it binds to the human GAL1 receptor;

(b) (1) the GAL3 receptor antagonist does not inhibit the activity of central monoamine oxidase A greater than 50 percent, at a concentration of 10 μM; and (2) the GAL3 receptor antagonist does not inhibit the activity of central monoamine oxidase B greater than 50 percent, at a concentration of 10 μM; and (c) the GAL3 receptor antagonist binds to the human GAL3 receptor with a binding affinity at least ten-fold higher than the binding affinity with which it binds to each of the following transporters: serotonin transporter, norepinephrine transporter, and dopamine transporter.

The invention provides a method of treating anxiety in a subject which comprises administering to the subject a composition comprising a pharmaceutically acceptable carrier and a therapeutically effective amount of a GAL3 receptor antagonist, wherein:

(a) the GAL3 receptor antagonist binds to the human GAL3 receptor with a binding affinity at least ten-fold higher than the binding affinity with which it binds to the human GAL1 receptor; and (b) the GAL3 receptor antagonist binds to the human GAL3 receptor with a binding affinity at least ten-fold higher than the binding affinity with which it binds to each of the following transporters: serotonin transporter, norepinephrine transporter, and dopamine transporter.

Vehicle (V) and test compounds (F10=fluoxetine at 10 mg/kg ip; C1, C3, C10 or C30=Example 92 at 1, 3, 10 or 30 mg/kg ip) were injected into normal rats by intraperitonal administration (n=5 for each treatment condition). One hour later, rats were examined in a 5 minute forced swim test. For each treatment condition, the number of 5-sec intervals culminating with a display of immobility was derived and plotted as the average+/−S.E.M. A significant decrease in immobility was observed for rats injected with fluoxetine at 10 mg/kg, or with Example 92 at 3 and 10 mg/kg, relative to vehicle injected controls (p<0.01, ANOVA and Student-Nerman-Keuls).

Figure 2:
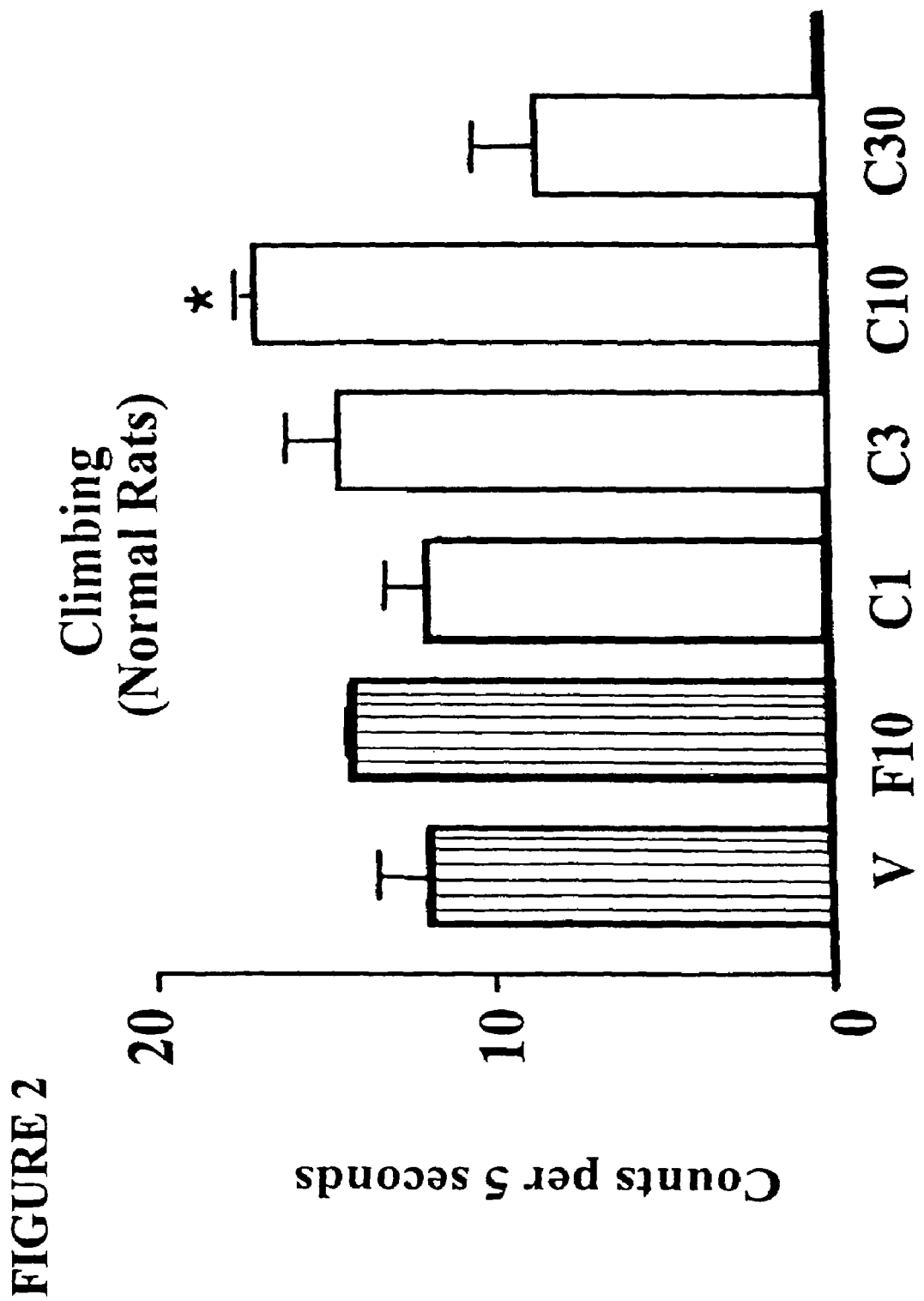

FIG. 2: Rat Forced Swim Test Results (Climbing: Normal Rats)

Vehicle (V) and test compounds (F10=fluoxetine at 10 mg/kg ip; C1, C3, C10 or C30=Example 92 at 1, 3, 10 or 30 mg/kg ip) were injected into normal rats by intraperitonal administration (n=5 for each treatment condition). One hour later, rats were examined in a 5 minute forced swim test. For each treatment condition, the number of 5-sec intervals culminating with a display of climbing was derived and plotted as the average+/−S.E.M. A significant increase in climbing was observed for rats injected with Example 92 at 10 mg/kg, relative to vehicle injected controls (p<0.01, ANOVA and Student-Nerman-Keuls), but not in rats dosed with Example 92 at 30 mg/kg ip.

Figure 3:
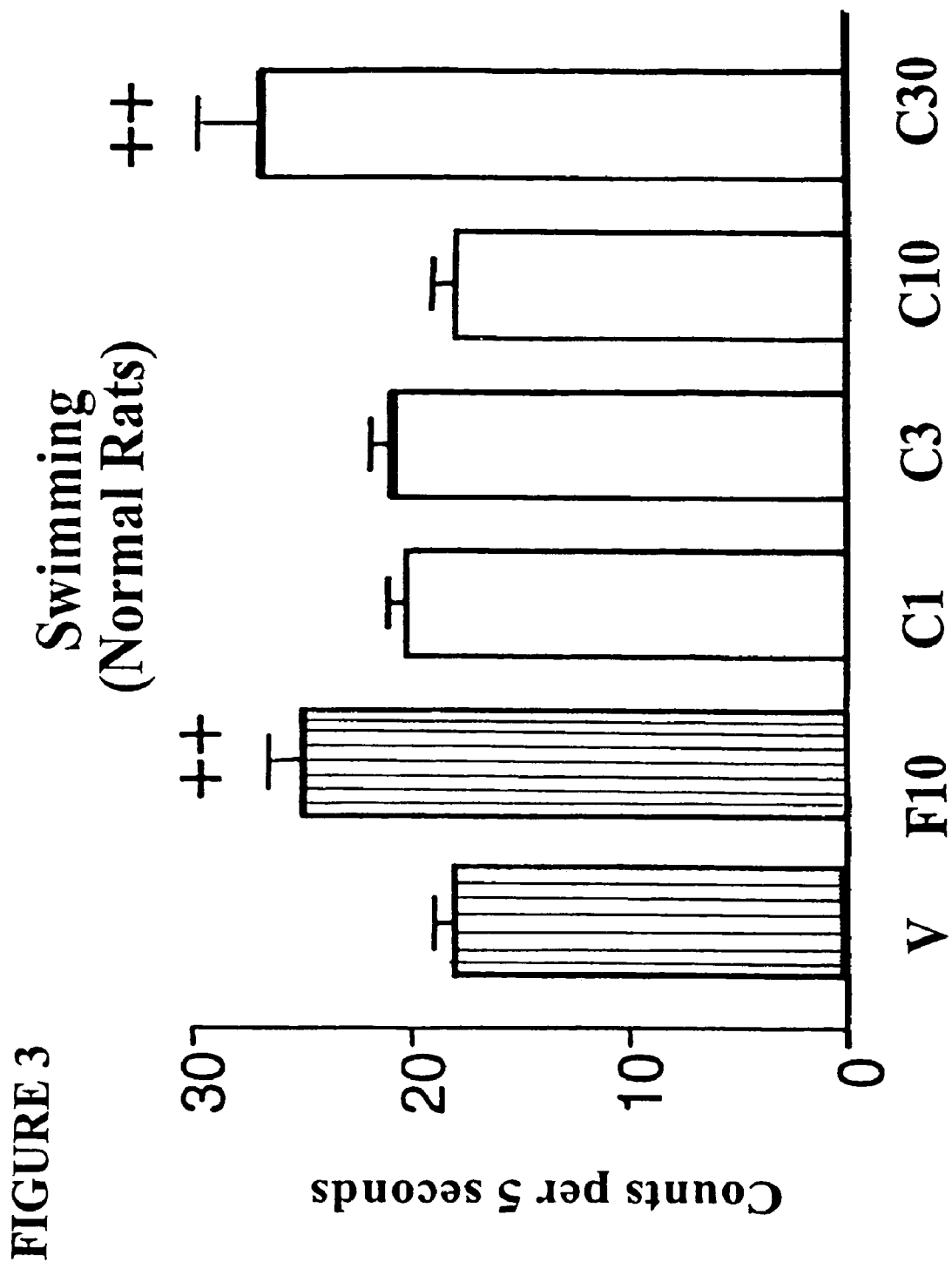

FIG. 3: Rat Forced Swim Test Results (Swimming: Normal Rats)

Vehicle (V) and test compounds (F10=fluoxetine at 10 mg/kg ip; C1, C3, C10 or C30=Example 92 at 1, 3, 10 or 30 mg/kg ip) were injected into normal rats by intraperitonal administration (n=5 for each treatment condition). One hour later, rats were examined in a 5 minute forced swim test. For each treatment condition, the number of 5-sec intervals culminating with a display of swimming was derived and plotted as the average+/−S.E.M. A significant increase in swimming was observed for rats injected with fluoxetine at 10 mg/kg ip or with Example 92 at 30 mg/kg, relative to vehicle injected controls (p<0.01, ANOVA and Student-Nerman-Keuls).

Figure 4:
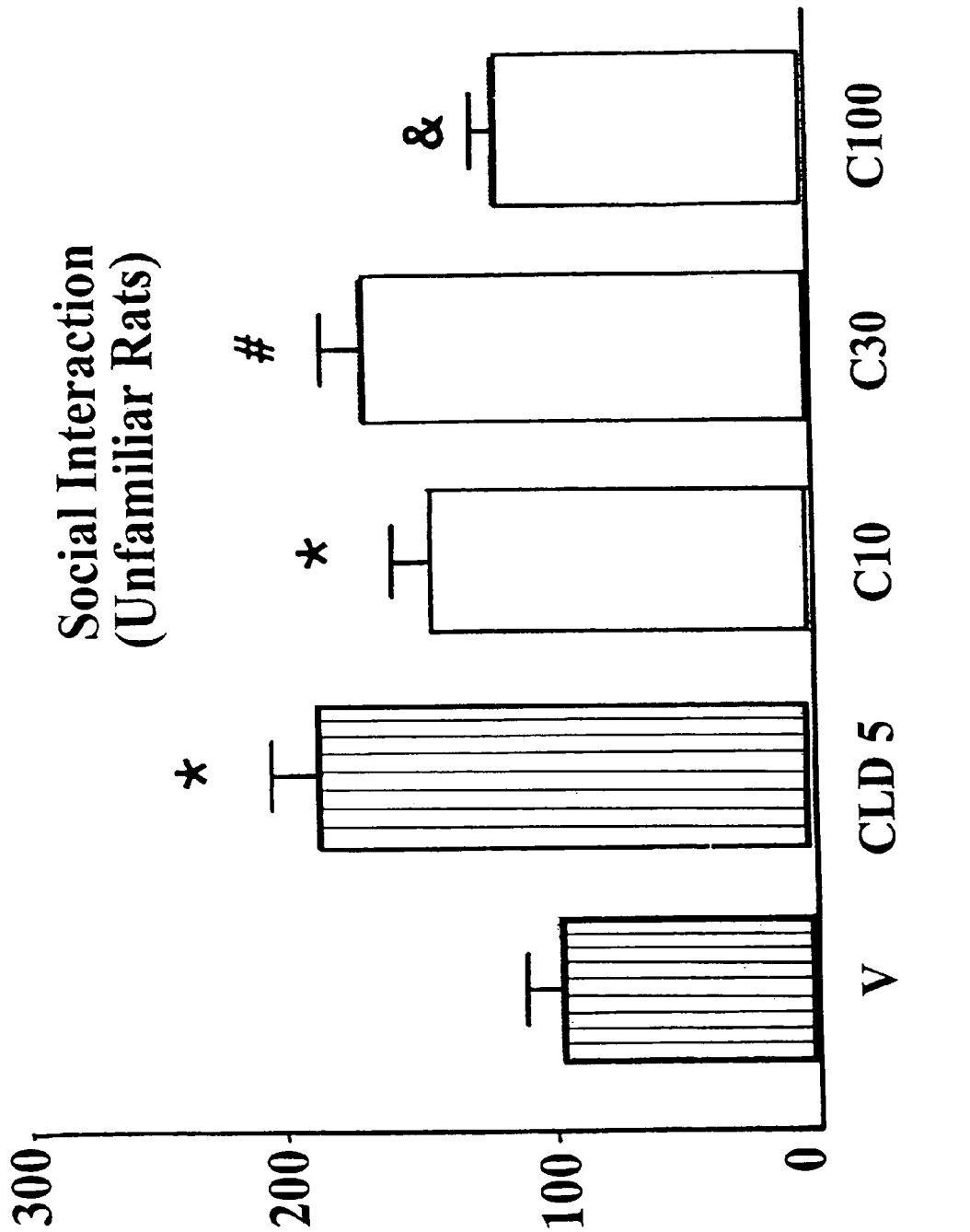

FIG. 4: Social Interaction Test Results (Social Interaction: Unfamiliar Rats)

Vehicle (V) and test compounds (CLD 5=chlordiazepoxide at 5 mg/kg ip; C10, C30 or C100=Example 92 at 10, 30 or 100 mg/kg ip) were injected into normal rats by intraperitonal administration (n=5 for each treatment condition). One hour later, unfamiliar rats were examined in a 15 minute social interaction test. For each treatment condition, the amount of time spent in social interaction was derived and plotted as the average+/−S.E.M. A significant increase in social interaction was observed for rats injected with chlordiazepoxide at 5 mg/kg i.p. or with Example 92 at 10 mg/kg ip (p<0.05) as well as 30 mg/kg (p<0.01). When the dose of Example 92 was increased to 100 mg/kg, the amount of social interaction time was significantly less than measured after chlordiazepoxide at 5 mg/kg ip or Example 92 at 30 mg/kg ip (p<0.01). Significance in all cases was determined by ANOVA and Student-Nerman-Keuls.

Figure 5:
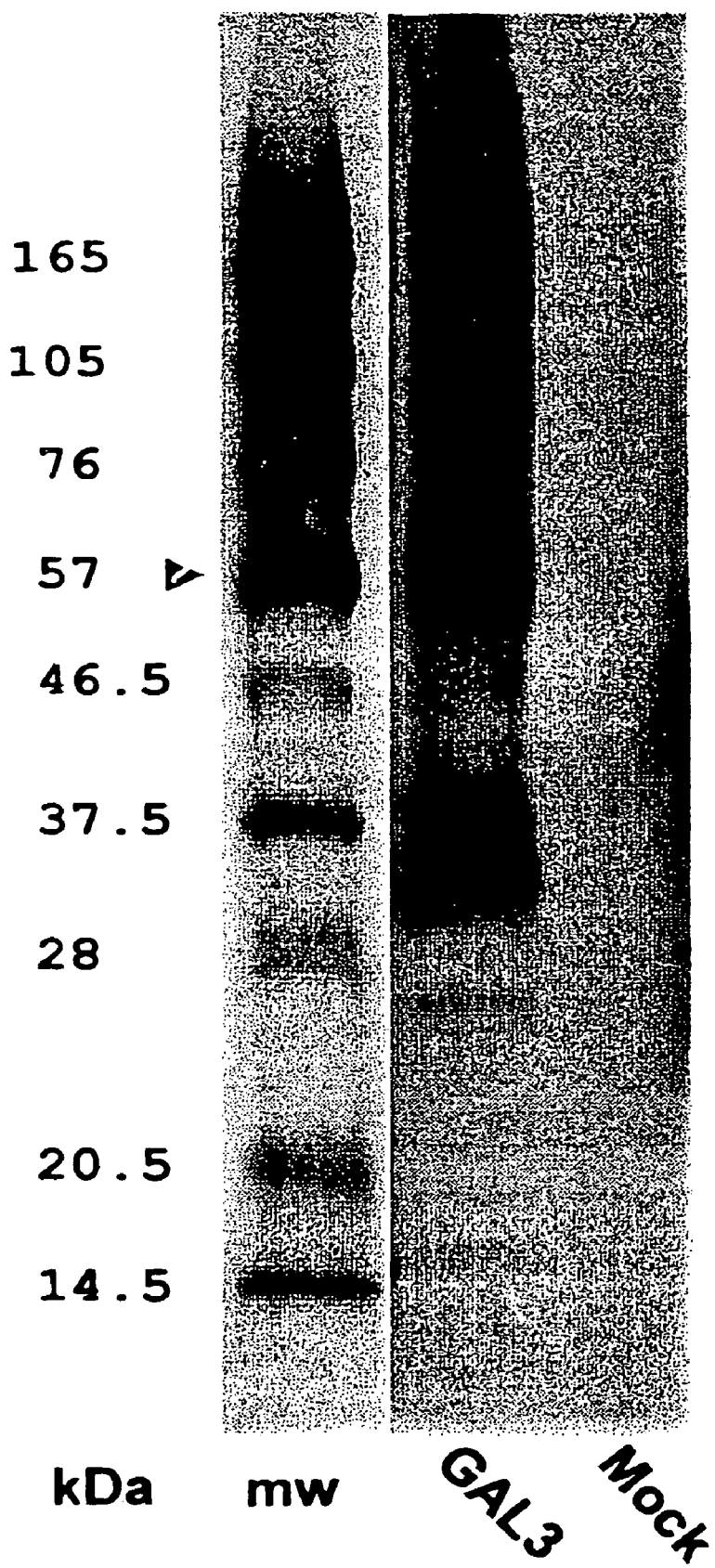

FIG. 5: Western Blot Results

In order to establish the specificity of the anti-GAL3 antiserum, membranes prepared from COS-7 cells transiently transfected with the rat recombinant GAL3 (Borowsky et al., 1999) (Lane 2) or mock-transfected (vector only) (Lane 3) were applied to an SDS-PAGE gel and blotted using the GAL3 receptor polyclonal antibody. Lane 1 corresponds to molecular weight marker. The anti-GAL3 antiserum labeled proteins in membranes only from rat GAL3-transfected cells (Lane 2); a predominant band was evident with an apparent molecular weight of approximately 56 kDa, (somewhat higher than the amino acid-derived value of 40.4 kDa). The apparently high molecular weight observed for rat GAL3 very likely reflects post-translational processing such as glycosylation; note that rat GAL3 contains multiple N-terminal glycosylation sites (Smith et al., 1998). Relative to the predominant band, additional species of higher molecular weight as well as lower molecular weight were labeled by the GAL3 antiserum. These are interpreted as protein aggregates of C-terminal fragments, as they are absent in mock-transfected cells.

DETAILED DESCRIPTION OF THE INVENTION

The present invention provides a method of treating a subject suffering from depression which comprises administering to the subject an amount of compound effective to treat the subject's depression wherein the compound has the structure:

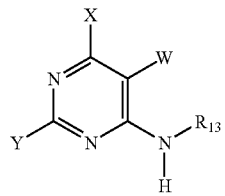

wherein W is H, —F, —Cl, —Br, —I, CN, methyl, ethyl, propyl, methoxy or ethoxy;

wherein X is; $NR_{11}R_{12}$;

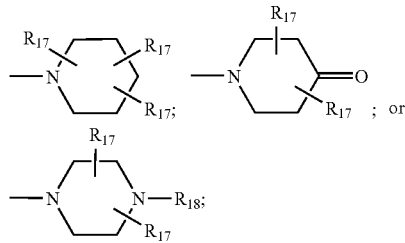

wherein $R_{11}$ is H, straight chained or branched $C_1$-$C_7$ alkyl, $(CH_2)_q$—O—$(CH_2)_m$—$CH_3$, aryl, or aryl $(C_1$-$C_6)$alkyl;

wherein $R_{12}$ is straight chained or branched $C_1$-$C_7$ alkyl, $(CH_2)_q$—O—$(CH_2)_m$—$CH_3$, or —$(CH_2)_m$-Z;

wherein $R_{13}$ is a bicyclic alkyl ring system, adamantyl, noradamantyl, $C_3$-$C_{10}$ cycloalkyl, heteroaryl, aryl, aryl($C_1$-$C_6$)alkyl, $Q_1$ or $Q_2$;

wherein aryl may be substituted with one or more $C_1$-$C_{10}$ straight chained or branched alkyl, aryl, heteroaryl, or $N(R_{19})$-Z;

wherein $Q_1$ is

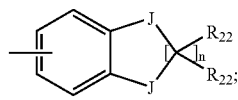

wherein $Q_2$ is

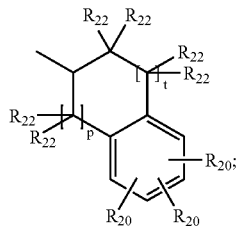

wherein each J is independently O, S, $C(R_{22})_2$ or $NR_4$;

wherein $R_4$ is H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein Y is $NR_{14}R_{15}$;

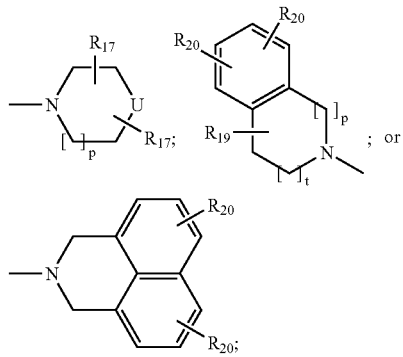

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is straight chained or branched $C_3$-$C_6$ alkyl, $(CH_2)_q$—O—$(CH_2)_m$—$CH_3$, $C_3$-$C_6$ cycloalkyl, $(C(R_{19})_2)_m N(R_{16})_2$ or $(C(R_{19})_2)_m$-Z;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein $R_{18}$ is straight chained or branched $C_1$-$C_6$ alkyl, —$(CH_2)_m$-Z, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl, or aryl($C_3$-$C_6$) alkyl;

wherein each $R_{22}$ is independently H, F, Cl or $C_1$-$C_4$ straight chained or branched alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2;

wherein U is O, —$NR_{16}$, S, $C(R_{17})_2$, or —$NSO_2R_{16}$;

wherein Z is $C_3$-$C_{10}$ cycloalkyl, $C_4$-$C_7$ cyclic ether, $C_4$-$C_7$ cyclic thioether, aryl, or heteroaryl; or a pharmaceutically acceptable salt thereof.

The invention provides a method of treating a subject suffering from depression which comprises administering to the subject an amount of compound effective to treat the subject's depression wherein the compound has the structure:

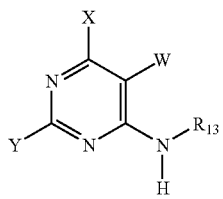

wherein W is H, —F, —Cl, —Br, —I, CN, methyl, ethyl, propyl, methoxy or ethoxy;

wherein X is $NR_{11}R_{12}$;

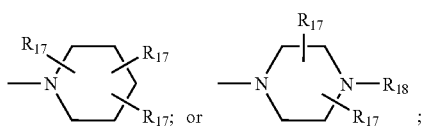

wherein $R_{11}$ is H, straight chained or branched $C_1$-$C_7$ alkyl, $(CH_2)_q$—O—$(CH_2)_m$—$CH_3$, aryl or aryl($C_1$-$C_6$)alkyl;

wherein $R_{12}$ is straight chained or branched $C_1$-$C_7$ alkyl, $(CH_2)_q$—O—$(CH_2)_m$—$CH_3$, or —$(CH_2)_m$-Z;

wherein $R_{13}$ is a bicyclic alkyl ring system, aryl or aryl ($C_1$-$C_6$) alkyl;

wherein Y is $NR_{14}R_{15}$;

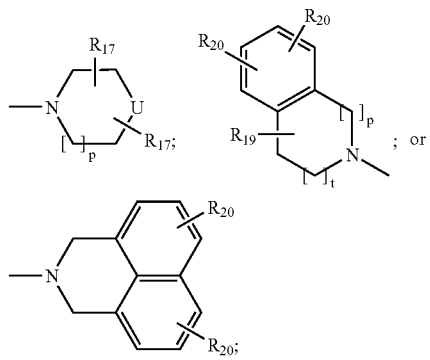

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is straight chained or branched $C_3$-$C_6$ alkyl, $(CH_2)_q$—O—$(CH_2)_m$—$CH_3$, $C_3$-$C_6$ cycloalkyl, or $(C(R_{19})_2)_m$-Z;

wherein U is O, —$NR_{16}$, S, $C(R_{17})_2$, or —$NSO_2R_{16}$;

wherein. Z is $C_3$-$C_{10}$ cycloalkyl, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein $R_{18}$ is straight chained or branched $C_1$-$C_6$ alkyl, —$(CH_2)_m$-Z, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$) alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2; or a pharmaceutically acceptable salt thereof.

The invention provides a method of treating a subject suffering from depression which comprises administering to the subject an amount of compound effective to treat the subject's depression wherein the compound has the structure:

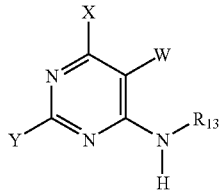

wherein W is H, —F, —Cl, —Br, —I, CN, methyl, ethyl, propyl, methoxy or ethoxy;

wherein X is N(CH$_3$)$_2$ or

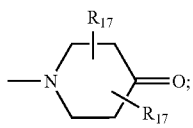

wherein R$_{13}$ is an aryl, adamantyl, noradamantyl, C$_3$-C$_{10}$ cycloalkyl, heteroaryl, Q$_1$ or Q$_2$;

wherein aryl may be substituted with one or more C$_1$-C$_{10}$ straight chained or branched alkyl, aryl, heteroaryl, or N(R$_{19}$)-Z;

wherein Q$_1$ is

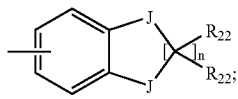

wherein Q$_2$ is

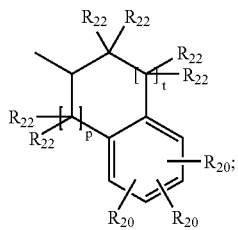

wherein each J is independently O, S, C(R$_{22}$)$_2$ or NR$_4$;

wherein R$_4$ is —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, C$_5$-C$_7$ cycloalkenyl or aryl;

wherein Y is NR$_{14}$R$_{15}$;

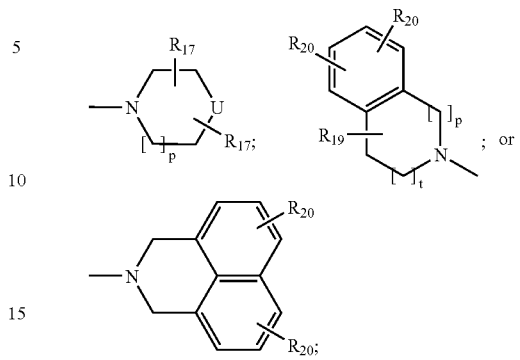

wherein R$_{14}$ is H, straight chained or branched C$_1$-C$_6$ alkyl, (CH$_2$)$_q$—O—(CH$_2$)$_m$—CH$_3$, C$_3$-C$_6$ cycloalkyl, or (C(R$_{19}$)$_2$)$_m$-Z;

wherein R$_{15}$ is straight chained or branched C$_3$-C$_6$ alkyl, (CH$_2$)$_q$—O—(CH$_2$)$_m$—CH$_3$, C$_3$-C$_6$ cycloalkyl, or (C(R$_{19}$)$_2$)$_m$-Z;

wherein U is O, —NR$_{16}$, S, C(R$_{17}$)$_2$, or —NSO$_2$R$_{16}$;

wherein Z is C$_3$-C$_{10}$ cycloalkyl, aryl, or heteroaryl;

wherein R$_{16}$ is straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_5$-C$_7$ cycloalkyl, —(CH$_2$)$_m$-Z, or (CH$_2$)$_q$—O—(CH$_2$)$_m$—CH$_3$;

wherein each R$_{17}$ is independently H; —OR$_{21}$, —OCOR$_{21}$, —COR$_{21}$, —NCOR$_{21}$, —N(R$_{21}$)$_2$, —CON(R$_{21}$)$_2$, —COOR$_{21}$, straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_5$-C$_7$ cycloalkyl, —(CH$_2$)$_m$-Z, or (CH$_2$)$_n$—O—(CH$_2$)$_m$—CH$_3$;

wherein R$_{18}$ is straight chained or branched C$_1$-C$_6$ alkyl, —(CH$_2$)$_m$-Z, or (CH$_2$)$_q$—O—(CH$_2$)$_m$—CH$_3$;

wherein each R$_{19}$ is independently H, or straight chained or branched C$_1$-C$_6$ alkyl;

wherein each R$_{20}$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl or C$_5$-C$_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$, —CON(R$_{21}$)$_2$, or —COOR$_{21}$; aryl or heteroaryl; or two R$_{20}$ groups present on adjacent carbon atoms can join together to form a methylenedioxy group;

wherein each R$_{21}$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, C$_5$-C$_7$ cycloalkenyl, aryl or aryl(C$_1$-C$_6$) alkyl;

wherein each R$_{22}$ is independently H, F, Cl or C$_1$-C$_4$ straight chained or branched alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2; or a pharmaceutically acceptable salt thereof.

The invention provides a method of treating a subject suffering from depression which comprises administering to the subject an amount of compound effective to treat the subject's depression wherein the compound has the structure:

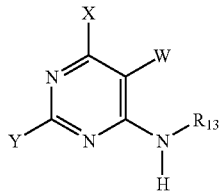

wherein W is H, —F, —Cl, —Br, —I, CN, methyl, ethyl, propyl, methoxy or ethoxy;

wherein X is $N(CH_3)_2$ or

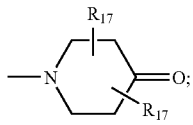

wherein $R_{13}$ is a bicyclic alkyl ring system, aryl or aryl ($C_1$-$C_6$) alkyl;

wherein Y is $NR_{14}R_{15}$;

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is $(C(R_{19})_2)_m$—$N(R_{16})_2$;

wherein Z is $C_3$-$C_{10}$ cycloalkyl, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein each $R_{19}$ is independently H, or straight chained or branched $C_1$-$C_6$ alkyl;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein each m is an integer from 0 to 4 inclusive;

wherein each n is an integer from 1 to 4 inclusive;

wherein q is an integer from 2 to 4 inclusive; or a pharmaceutically acceptable salt thereof.

As used in the present invention, the term "bicyclic alkyl ring systems" includes, but is not limited to, bicyclo[2.2.1]heptane, bicyclo[3.1.1]heptane and bicyclo[2.2.2]octane. In addition, the bicyclic alkyl ring systems may be substituted with one or more of the following: —F, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_5$-$C_7$ cycloalkenyl, —$N(R_{21})_2$, —$OR_{21}$, —$COR_{21}$, —$CO_2R_{21}$, —$CON(R_{21})_2$ or $(CH_2)_n$—O—$(CH_2)_m$—$CH_3$.

As used in the present invention, the term "cycloalkyl" includes, $C_3$-$C_7$ cycloalkyl moieties which may be substituted with one or more of the following: —F, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, $OR_4$, —$COR_4$, —$NCOR_4$, —$CO_2R_4$, $CON(R_4)_2$ or $(CH_2)_n$—O—$(CH_2)_m$—$CH_3$.

As used in the present invention, the term "cyclohexyl" includes, cyclohexyl groups which may be substituted with one or more of the following: —F, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

As used in the present invention, the term "cycloalkenyl" includes, $C_5$-$C_7$ cycloalkenyl moieties which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

In the present invention, the term "heteroaryl" is used to include five and six membered unsaturated rings that may contain one or more oxygen, sulfur, or nitrogen atoms. Examples of heteroaryl groups include, but are not limited to, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl.

In addition the term "heteroaryl" is used to include fused bicyclic ring systems that may contain one or more heteroatoms such as oxygen, sulfur and nitrogen. Examples of such heteroaryl groups include, but are not limited to, indolizinyl, indolyl, isoindolyl, benzo[b]furanyl, benzo[b]thiophenyl, indazolyl, benzimidazolyl, purinyl, benzoxazolyl, benzisoxazolyl, benzo[b]thiazolyl, imidazo[2,1-b]thiazolyl, cinnolinyl, quinazolinyl, quinoxalinyl, 1,8-naphthyridinyl, pteridinyl, quinolinyl, isoquinolinyl, phthalimidyl and 2,1,3-benzothiazolyl.

The term "heteroaryl" also includes those chemical moieties recited above which may be substituted with one or more of the following: —F, —Cl, —Br, —I, —NO$_2$, —CN, straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_3$-C$_7$ cycloalkyl, C$_3$-C$_7$ monofluorocycloalkyl, C$_3$-C$_7$ polyfluorocycloalkyl, C$_5$-C$_7$ cycloalkenyl, —N(R$_4$)$_2$, —OR$_4$, COR$_4$, —NCOR$_4$, —CO$_2$R$_4$, —CON(R$_4$)$_2$ or (CH$_2$)$_n$—O—(CH$_2$)$_m$—CH$_3$.

The term "heteroaryl" further includes the N-oxides of those chemical moieties recited above which include at least one nitrogen atom.

In the present invention the term "aryl" is phenyl or naphthyl. The term "aryl" also includes phenyl and naphthyl which may be substituted with one or more of the following: —F, —Cl, —Br, —I, —NO$_2$, —CN, straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_3$-C$_7$ cycloalkyl, C$_3$-C$_7$ monofluorocycloalkyl, C$_3$-C$_7$ polyfluorocycloalkyl, C$_5$-C$_7$ cycloalkenyl, —N(R$_4$)$_2$, —OR$_4$, —SR$_4$—OCOR$_4$, —COR$_4$, —NCOR$_4$—CO$_2$R$_4$, —CON(R$_4$)$_2$ or (CH$_2$)$_n$—O—(CH$_2$)$_m$—CH$_3$.

In one embodiment of any of the methods described herein, the compound is enantiomerically and diasteriomerically pure. In one embodiment, the compound is enantiomerically or diasteriomerically pure.

In one embodiment of any of the methods described herein, the compound can be administered orally.

In one embodiment, X is:

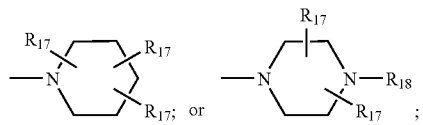

In one embodiment, X is NR$_{11}$R$_{12}$ and R$_{11}$ is H or straight chained or branched C$_1$-C$_7$ alkyl.

In one embodiment, the compound has the structure:

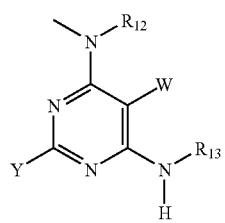

In one embodiment, R$_{13}$ is a bicyclic alkyl ring system, cyclohexyl or aryl.

In one embodiment, R$_{14}$ is H, straight chained or branched C$_1$-C$_6$ alkyl or (CH$_2$)$_q$—O—(CH$_2$)$_m$—CH$_3$ In one embodiment, R$_{14}$ is H, straight chained or branched C$_1$-C$_6$ alkyl or (CH$_2$)$_q$—O—(CH$_2$)$_m$—CH$_3$.

In one embodiment, the compound is selected from the group consisting of:

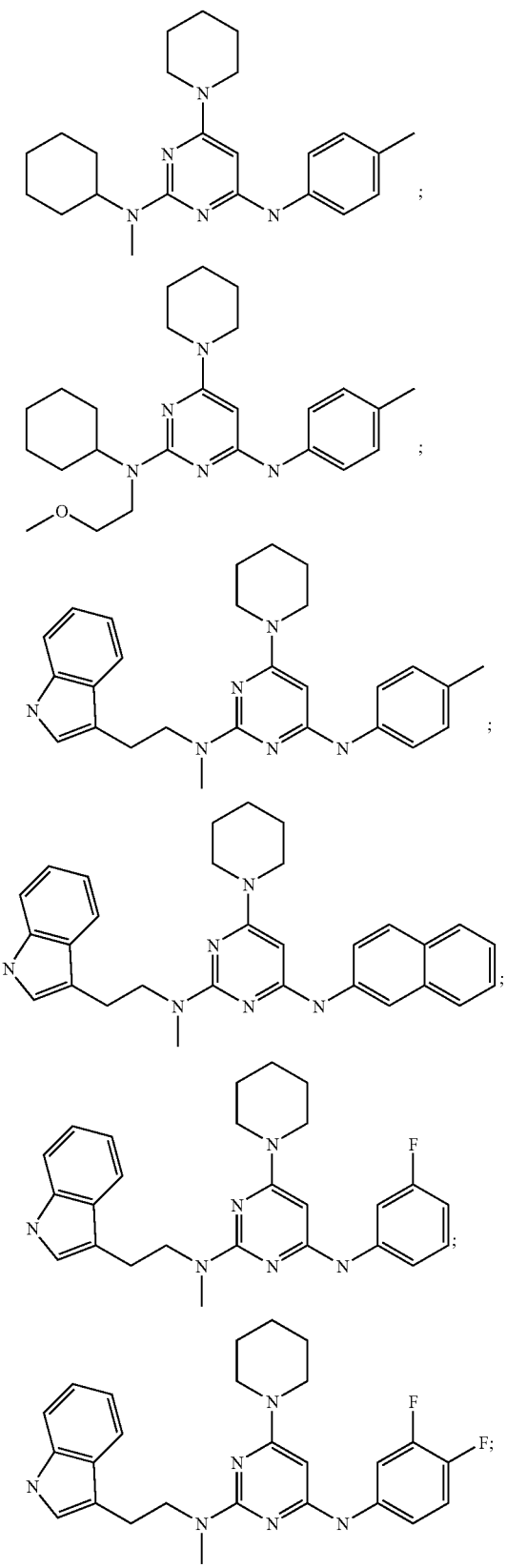

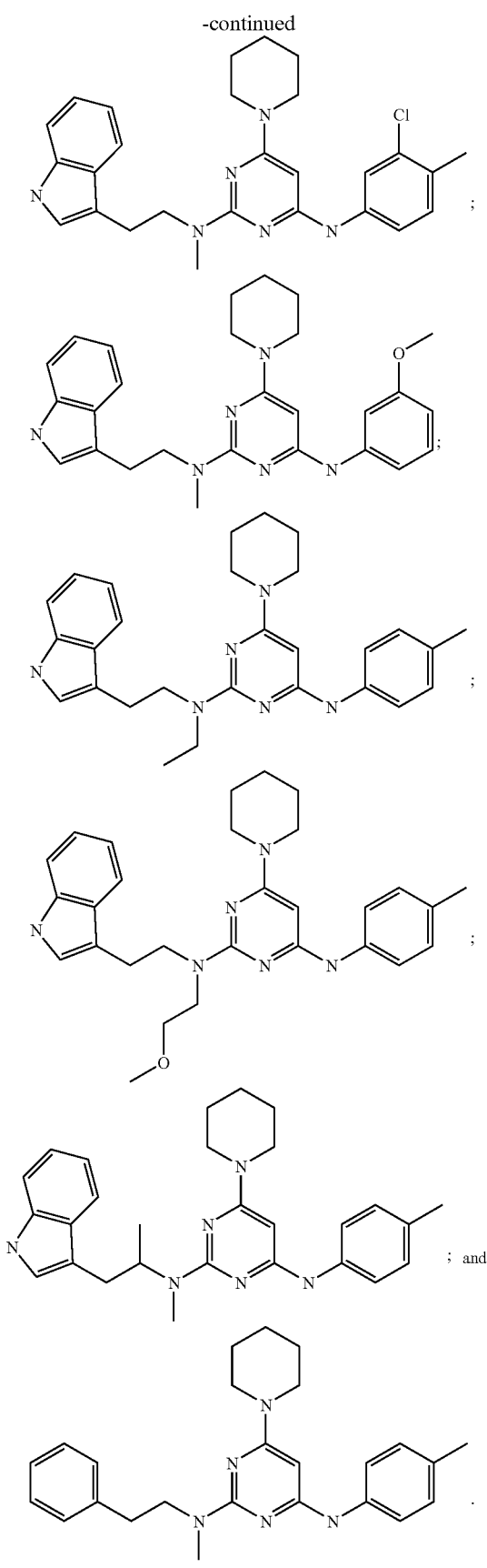
In one embodiment, Y is
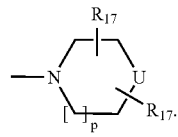
In one embodiment, U is $NR_{16}$.
In one embodiment, $R_{16}$ is $(CH_2)_m$-Z.
In one embodiment, Z is aryl or heteroaryl.
In one embodiment, the compound is selected from the group consisting of:
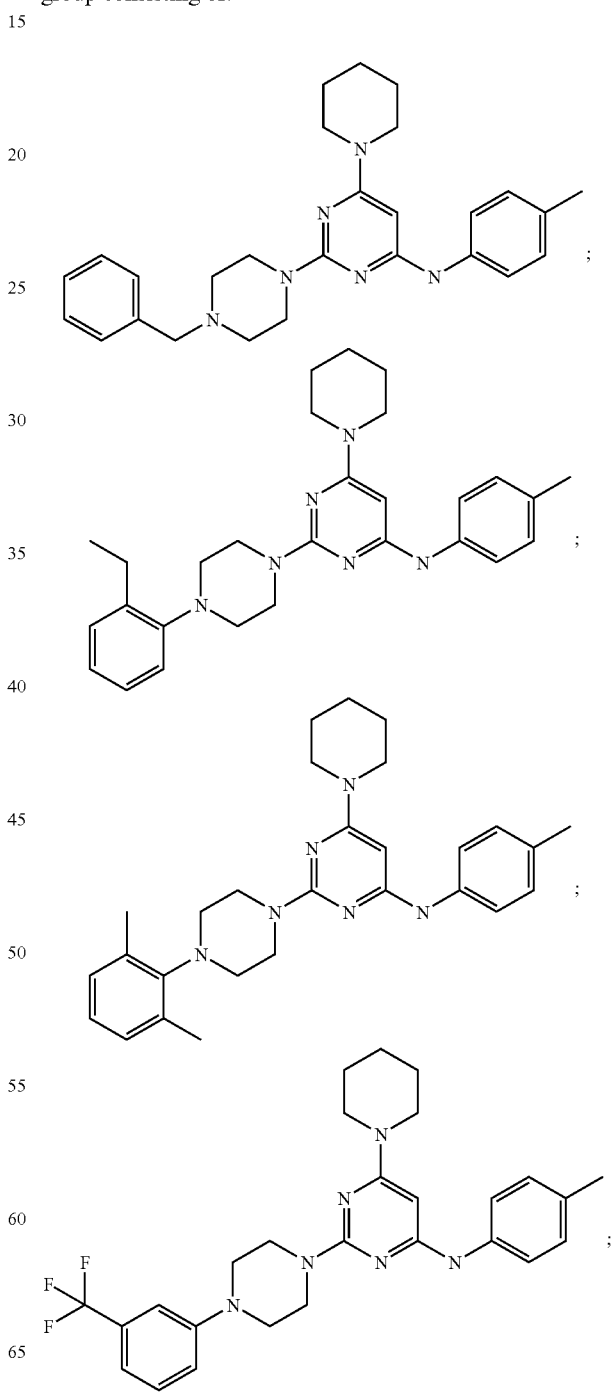

-continued
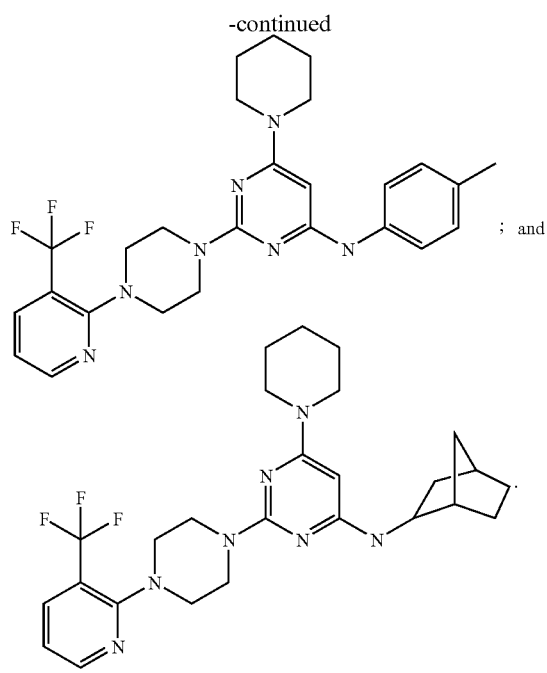
; and
In one embodiment, the compound is selected from the group consisting of:
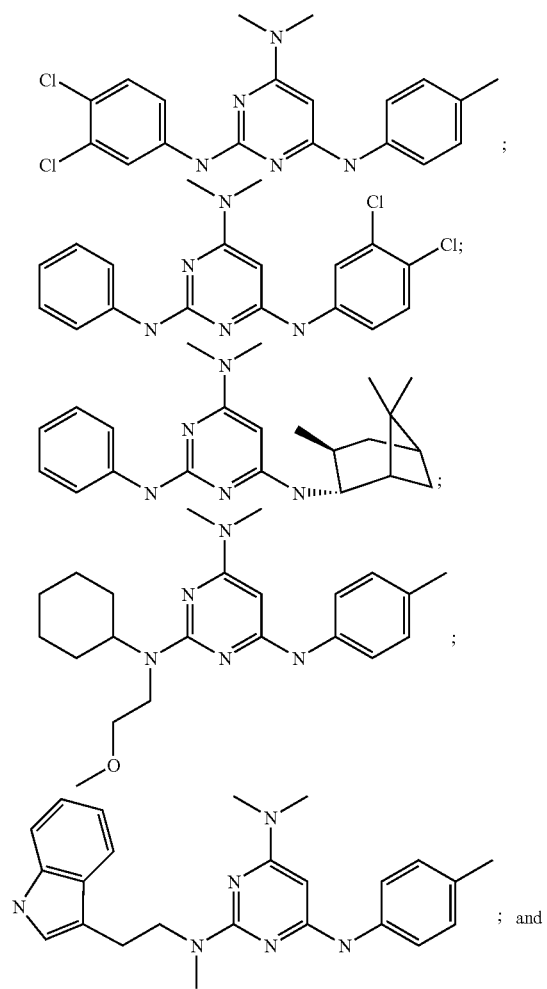
; and
-continued
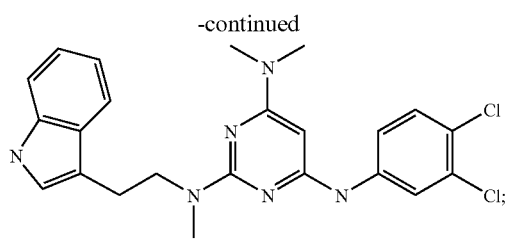
In one embodiment, Y is
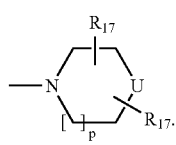
In one embodiment, U is $NR_{16}$.
In one embodiment, the compound is
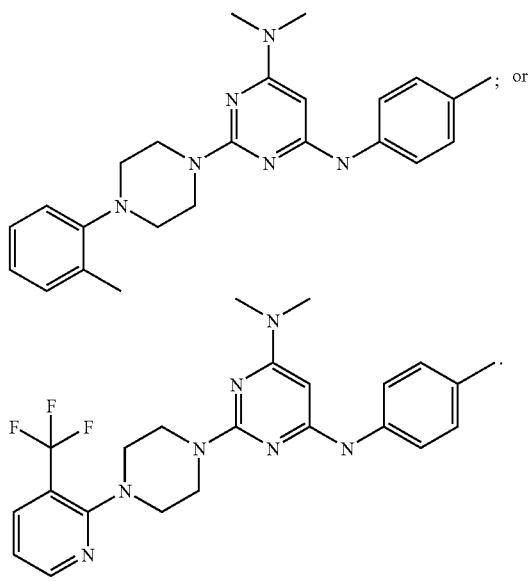
; or
In one embodiment, the compound is
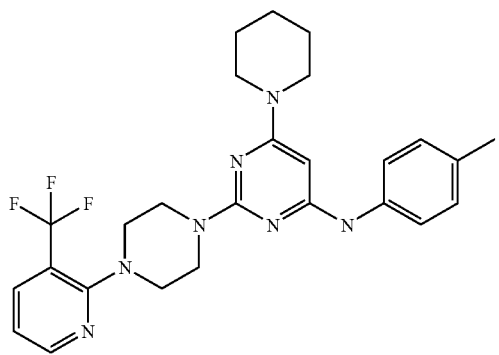

In one embodiment, the compound is selected from the group consisting of:
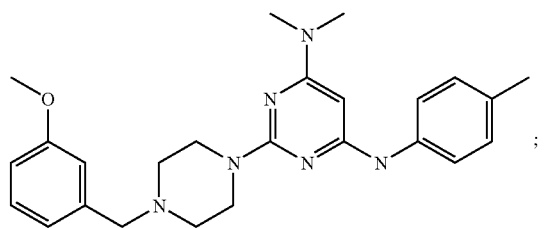
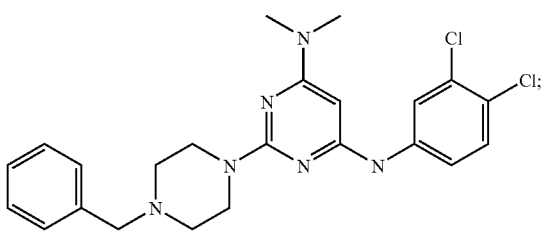
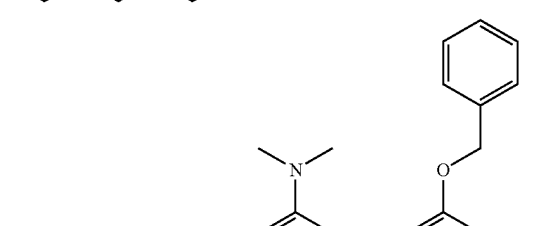
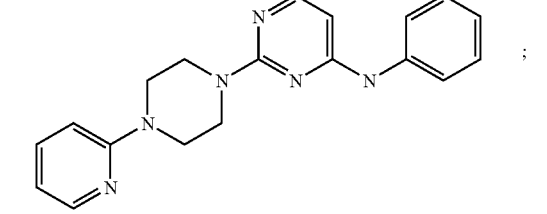
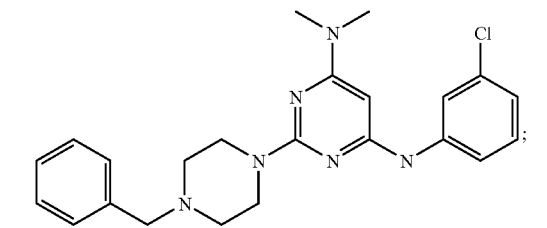
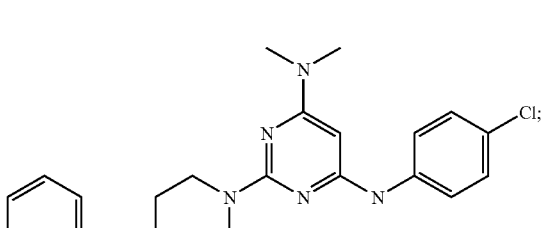
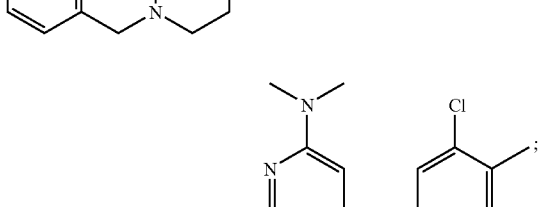
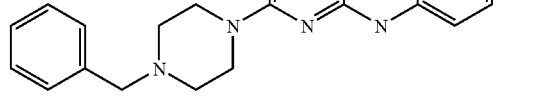
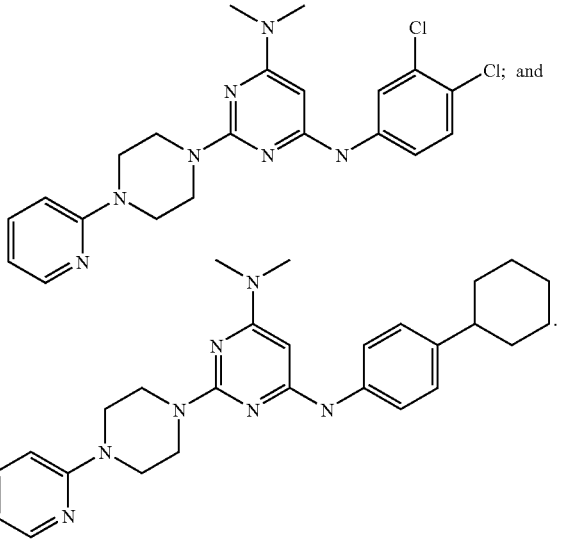
In one embodiment, the compound is selected from the group consisting of:
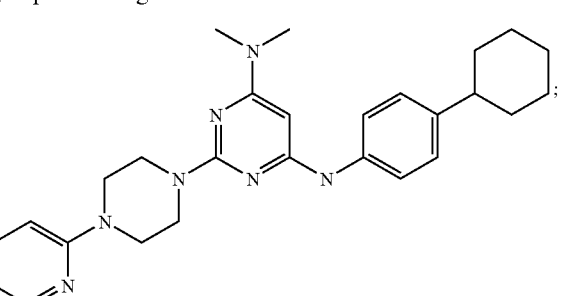
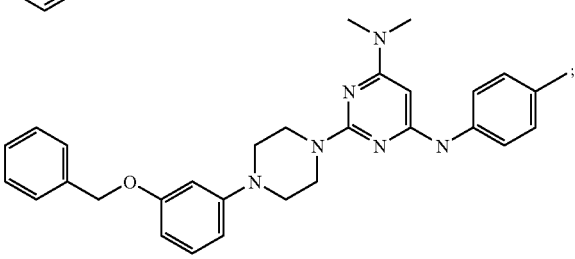
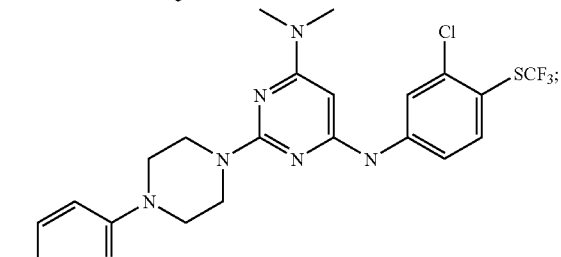
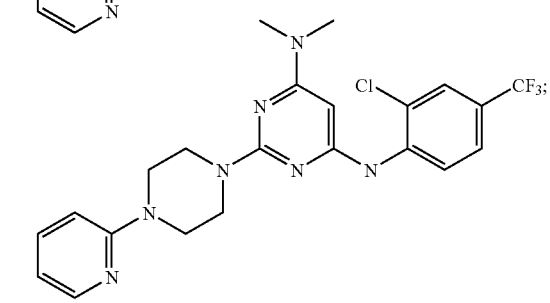

-continued

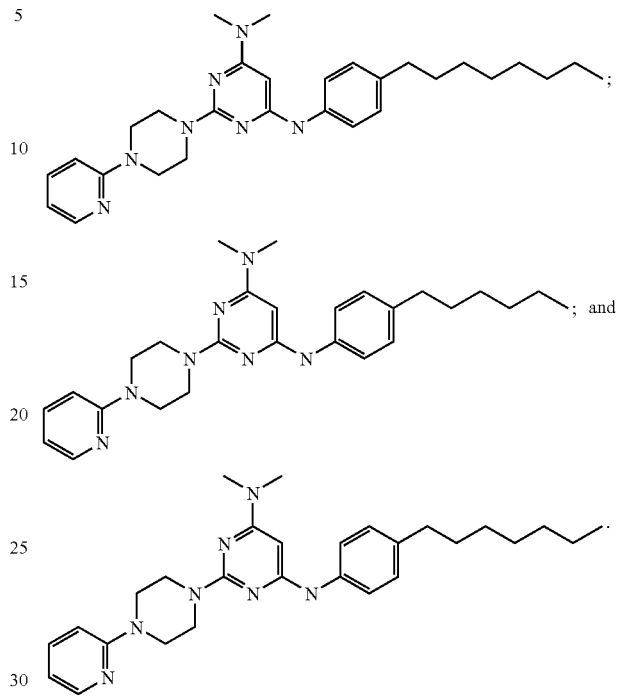

In one embodiment, X is N(CH₃)₂.
In one embodiment, Y is

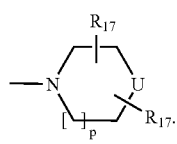

In one embodiment, R₁₃ is an aryl substituted with a $C_1$-$C_{10}$ straight chained alkyl.

In one embodiment, the compound is selected from a group consisting of:

The invention provides a method of treating a subject suffering from anxiety which comprises administering to the subject an amount of compound effective to treat the subject's anxiety wherein the compound has the structure:

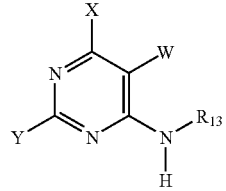

wherein W is H, —F, —Cl, —Br, —I, CN, methyl, ethyl, propyl, methoxy or ethoxy;

wherein X is; NR₁₁R₁₂;

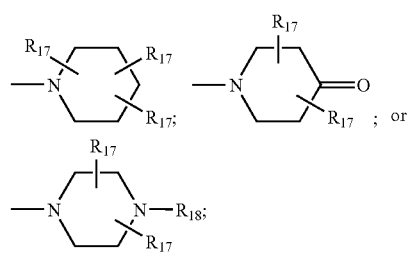

wherein R₁₁ is H, straight chained or branched $C_1$-$C_7$ alkyl, (CH₂)_q—O—(CH₂)_m—CH₃, aryl, or aryl ($C_1$-$C_6$)alkyl;

wherein $R_{12}$ is straight chained or branched $C_1$-$C_7$ alkyl, $(CH_2)_q$—O—$(CH_2)_m$—$CH_3$, or —$(CH_2)_m$-Z;

wherein $R_{13}$ is a bicyclic alkyl ring system, adamantyl, noradamantyl, $C_3$-$C_{10}$ cycloalkyl, heteroaryl, aryl, aryl($C_1$-$C_6$)alkyl, $Q_1$ or $Q_2$;

wherein aryl may be substituted with one or more $C_1$-$C_{10}$ straight chained or branched alkyl, aryl, heteroaryl, or $N(R_{19})$-Z;

wherein $Q_1$ is

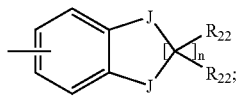

wherein $Q_2$ is

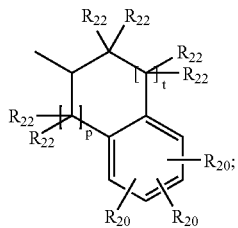

wherein each J is independently O, S, $C(R_{22})_2$ or $NR_4$;

wherein $R_4$ is H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein Y is $NR_{14}R_{15}$;

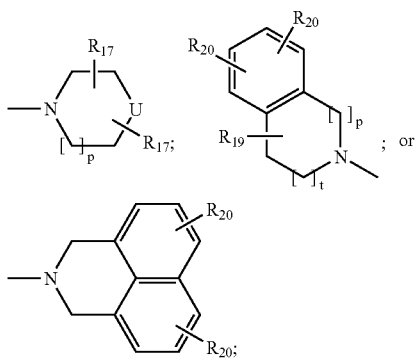

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is straight chained or branched $C_3$-$C_6$ alkyl, $(CH_2)_q$—O—$(CH_2)_m$—$CH_3$, $C_3$-$C_6$ cycloalkyl, $(C(R_{19})_2)_mN(R_{16})_2$ or $(C(R_{19})_2)_m$-Z;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_2$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein $R_{18}$ is straight chained or branched $C_1$-$C_6$ alkyl, —$(CH_2)_m$-Z, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl, or aryl($C_1$-$C_6$) alkyl;

wherein each $R_{22}$ is independently H, F, Cl or $C_1$-$C_4$ straight chained or branched alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2;

wherein U is O, —$NR_{16}$, S, $C(R_{17})_2$, or —$NSO_2R_{16}$;

wherein Z is $C_3$-$C_{10}$ cycloalkyl, $C_4$-$C_7$ cyclic ether, $C_4$-$C_7$ cyclic thioether, aryl, or heteroaryl; or a pharmaceutically acceptable salt thereof.

The invention provides a method of treating a subject suffering from anxiety which comprises administering to the subject an amount of compound effective to treat the subject's anxiety wherein the compound has the structure:

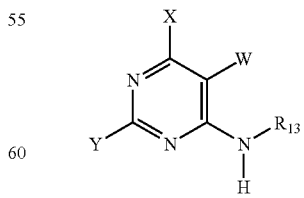

wherein W is H, —F, —Cl, —Br, —I, CN, methyl, ethyl, propyl, methoxy or ethoxy;

wherein X is $NR_{11}R_{12}$;

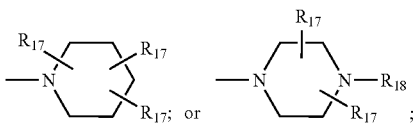

wherein R$_{11}$ is H, straight chained or branched C$_1$-C$_7$ alkyl, (CH$_2$)$_q$—O—(CH$_2$)$_m$—CH$_3$, aryl or aryl(C$_1$-C$_6$)alkyl;

wherein R$_{12}$ is straight chained or branched C$_1$-C$_7$ alkyl, (CH$_2$)$_q$—O—(CH$_2$)$_m$—CH$_3$, or —(CH$_2$)$_m$-Z;

wherein R$_{13}$ is a bicyclic alkyl ring system, aryl or aryl (C$_1$-C$_6$) alkyl;

wherein Y is NR$_{14}$R$_{15}$;

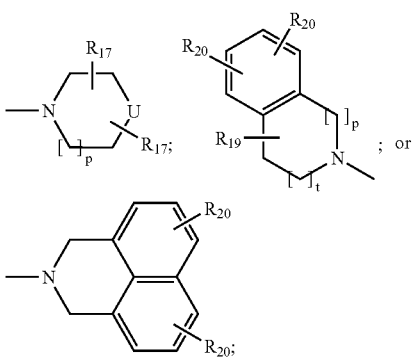

wherein R$_{14}$ is H, straight chained or branched C$_1$-C$_6$ alkyl, (CH$_2$)$_q$—O—(CH$_2$)$_m$—CH$_3$, C$_3$-C$_6$ cycloalkyl, or (C(R$_{19}$)$_2$)$_m$-Z;

wherein R$_{15}$ is straight chained or branched C$_3$-C$_6$ alkyl, (CH$_2$)$_q$—O—(CH$_2$)$_m$—CH$_3$, C$_3$-C$_6$ cycloalkyl, or (C(R$_{19}$)$_2$)$_m$-Z;

wherein U is O, —NR$_{16}$, S, C(R$_{17}$)$_2$, or —NSO$_2$R$_{16}$;

wherein Z is C$_3$-C$_{10}$ cycloalkyl, aryl, or heteroaryl;

wherein R$_{16}$ is straight chained or branched C$_2$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_5$-C$_7$ cycloalkenyl, —(CH$_2$)$_m$-Z, or (CH$_2$)$_q$—O—(CH$_2$)$_m$—CH$_3$;

wherein each R$_{17}$ is independently H; —OR$_{21}$, —OCOR$_{21}$, —COR$_{21}$, —NCOR$_{21}$, —N(R$_{21}$)$_2$, —CON(R$_{21}$)$_2$, —COOR$_{21}$, straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_5$-C$_7$ cycloalkenyl, —(CH$_2$)$_m$-Z, or (CH$_2$)$_n$—O—(CH$_2$)$_m$—CH$_3$;

wherein R$_{18}$ is straight chained or branched C$_1$-C$_6$ alkyl, —(CH$_2$)$_m$-Z, or (CH$_2$)$_q$—O—(CH$_2$)$_m$—CH$_3$;

wherein each R$_{19}$ is independently H, or straight chained or branched C$_1$-C$_6$ alkyl;

wherein each R$_{20}$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl or C$_5$-C$_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$, —CON(R$_{21}$)$_2$, or —COOR$_{21}$; aryl or heteroaryl; or two R$_{20}$ groups present on adjacent carbon atoms can join together to form a methylenedioxy group;

wherein each R$_{21}$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, C$_5$-C$_7$ cycloalkenyl, aryl or aryl(C$_2$-C$_6$) alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2; or a pharmaceutically acceptable salt thereof.

The invention provides a method of treating a subject suffering from anxiety which comprises administering to the subject an amount of compound effective to treat the subject's anxiety wherein the compound has the structure:

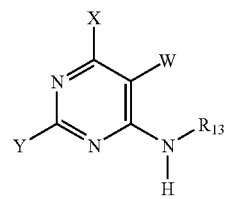

wherein W is H, —F, —Cl, —Br, —I, CN, methyl, ethyl, propyl, methoxy or ethoxy;

wherein X is N(CH$_3$)$_2$ or

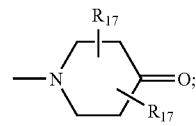

wherein R$_{13}$ is an aryl, adamantyl, noradamantyl, C$_3$-C$_{10}$ cycloalkyl, heteroaryl, Q$_1$ or Q$_2$;

wherein aryl may be substituted with one or more C$_1$-C$_{10}$ straight chained or branched alkyl, aryl, heteroaryl, or N(R$_{19}$)-Z;

wherein Q$_1$ is

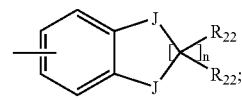

wherein $Q_2$ is

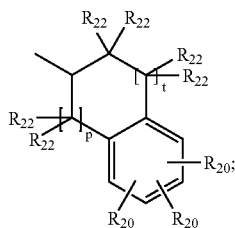

wherein each J is independently O, S, $C(R_{22})_2$ or $NR_4$;

wherein $R_4$ is —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein Y is $NR_{14}R_{15}$;

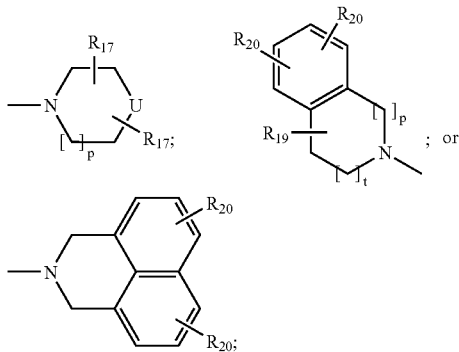

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is straight chained or branched $C_3$-$C_6$ alkyl, $(CH_2)_q$—O—$(CH_2)_m$—$CH_3$, $C_3$-$C_6$ cycloalkyl, or $(C(R_{19})_2)_m$-Z;

wherein U is O, —$NR_{16}$, S, $C(R_{17})_2$, or —$NSO_2R_{16}$;

wherein Z is $C_3$-$C_{10}$ cycloalkyl, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkyl, —$(CH_2)_m$-Z, or $(CH_2)_n$—O—$(CH_2)_m$—$CH_3$;

wherein $R_{18}$ is straight chained or branched $C_1$-$C_6$ alkyl, —$(CH_2)_m$-Z, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$) alkyl;

wherein each $R_{22}$ is independently H, F, Cl or $C_1$-$C_4$ straight chained or branched alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2; or a pharmaceutically acceptable salt thereof.

The invention provides a method of treating a subject suffering from anxiety which comprises administering to the subject an amount of compound effective to treat the subject's anxiety wherein the compound has the structure:

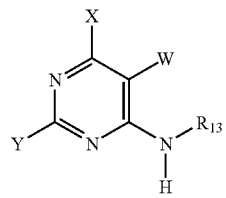

wherein W is H, —F, —Cl, —Br, —I, CN, methyl, ethyl, propyl, methoxy or ethoxy;

wherein X is $N(CH_3)_2$ or

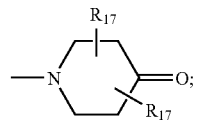

wherein $R_{13}$ is a bicyclic alkyl ring system, aryl or aryl ($C_1$-$C_6$) alkyl;

wherein Y is $NR_{14}R_{15}$;

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is $(C(R_{19})_2)_m$—$N(R_{16})_2$;

wherein Z is $C_3$-$C_{10}$ cycloalkyl, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein each $R_{19}$ is independently H, or straight chained or branched $C_1$-$C_6$ alkyl;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_3$-$C_6$)alkyl;

wherein each m is an integer from 0 to 4 inclusive;

wherein each n is an integer from 1 to 4 inclusive;

wherein q is an integer from 2 to 4 inclusive; or a pharmaceutically acceptable salt thereof.

As used in the present invention, the term "bicyclic alkyl ring systems" includes, but is not limited to, bicyclo[2.2.1]heptane, bicyclo[3.1.1]heptane and bicyclo[2.2.2]octane. In addition, the bicyclic alkyl ring systems may be substituted with one or more of the following: —F, —$NO_2$, —CN, straight chained or branched $C_1$-$C_7$ alkyl, straight chained, or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_5$-$C_7$ cycloalkenyl, —$N(R_{21})_2$, —$OR_{21}$, —$COR_{21}$, —$CO_2R_{21}$, —$CON(R_{21})_2$ or $(CH_2)_n$—O—$(CH_2)_m$—$CH_3$.

As used in the present invention, the term "cycloalkyl" includes, $C_3$-$C_7$ cycloalkyl moieties which may be substituted with one or more of the following: —F, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

As used in the present invention, the term "cyclohexyl" includes, cyclohexyl groups which may be substituted with one or more of the following: —F, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$—$COR_4$, —$NCOR_4$, —$CO_2R_4$, —$CON(R_4)_2$ or $(CH_2)_n$—O—$(CH_2)_m$—$CH_3$.

As used in the present invention, the term "cycloalkenyl" includes, $C_5$-$C_7$ cycloalkenyl moieties which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

In the present invention, the term "heteroaryl" is used to include five and six membered unsaturated rings that may contain one or more oxygen, sulfur, or nitrogen atoms. Examples of heteroaryl groups include, but are not limited to, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl.

In addition the term "heteroaryl" is used to include fused bicyclic ring systems that may contain one or more heteroatoms such as oxygen, sulfur and nitrogen. Examples of such heteroaryl groups include, but are not limited to, indolizinyl, indolyl, isoindolyl, benzo[b]furanyl, benzo[b]thiophenyl, indazolyl, benzimidazolyl, purinyl, benzoxazolyl, benzisoxazolyl, benzo[b]thiazolyl, imidazo[2,1-b]thiazolyl, cinnolinyl, quinazolinyl, quinoxalinyl, 1,8-naphthyridinyl, pteridinyl, quinolinyl, isoquinolinyl, phthalimidyl and 2,1,3-benzothiazolyl.

The term "heteroaryl" also includes those chemical moieties recited above which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

The term "heteroaryl" further includes the N-oxides of those chemical moieties recited above which include at least one nitrogen atom.

In the present invention the term "aryl" is phenyl or naphthyl. The term "aryl" also includes phenyl and naphthyl which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_3$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$SR_4$, —$OCOR_4$, —$COR_4$, —$NCOR_4$, —$CO_2R_4$, —$CON(R_4)_2$ or $(CH_2)_n$—O—$(CH_2)_m$—$CH_3$.

In one embodiment of any of the methods described herein, the compound is enantiomerically and diasteriomerically pure. In one embodiment, the compound is enantiomerically or diasteriomerically pure.

In one embodiment, the compound can be administered orally.

In one embodiment, X is:

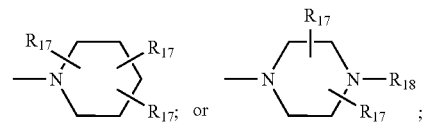

In one embodiment, X is $NR_{11}R_{12}$ and $R_{11}$ is H or straight chained or branched $C_1$-$C_7$ alkyl.

In one embodiment, the compound has the structure:
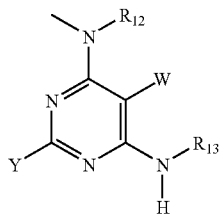
In one embodiment, R$_{13}$ is a bicyclic alkyl ring system, cyclohexyl or aryl.
In one embodiment, R$_{14}$ is H; straight chained or branched C$_1$-C$_6$ alkyl or (CH$_2$)$_q$—O—(CH$_2$)$_m$—CH$_3$.
In one embodiment, the compound is selected from the group consisting of:
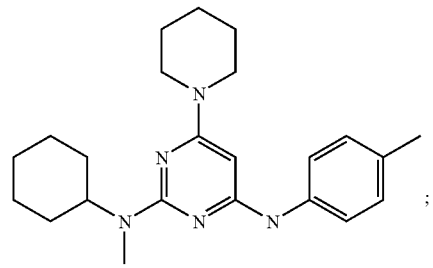
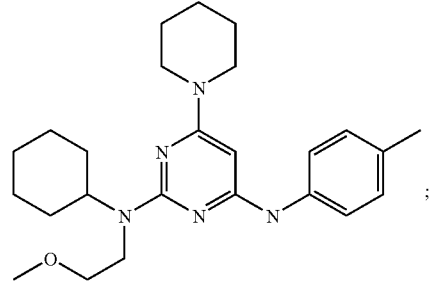
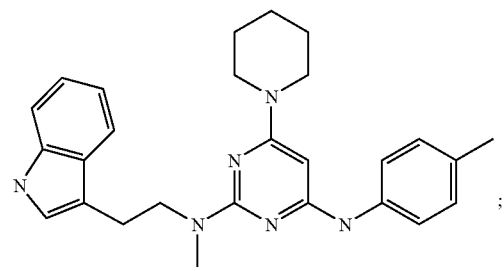
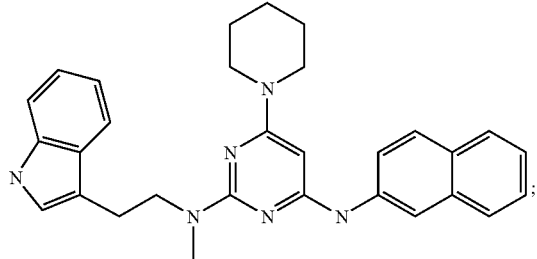
-continued
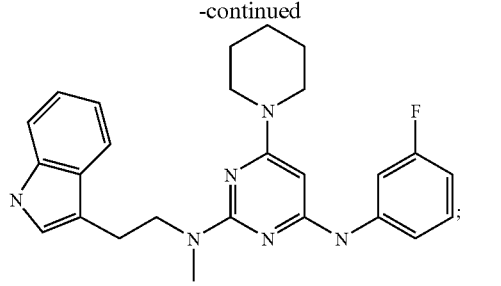
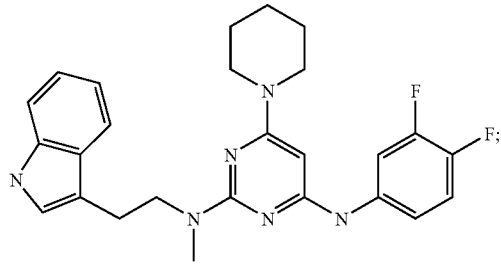
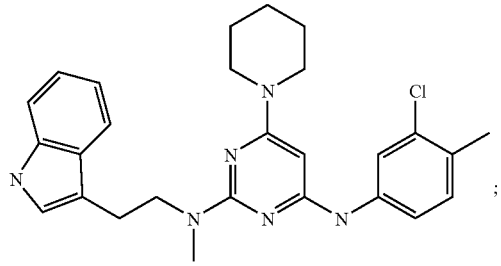
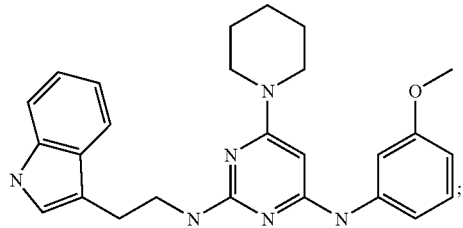
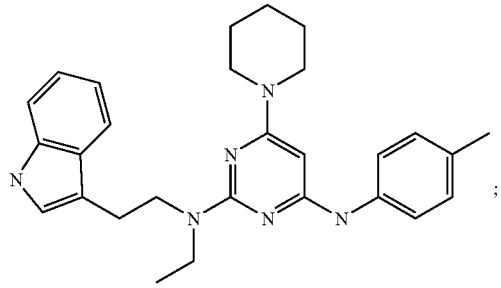
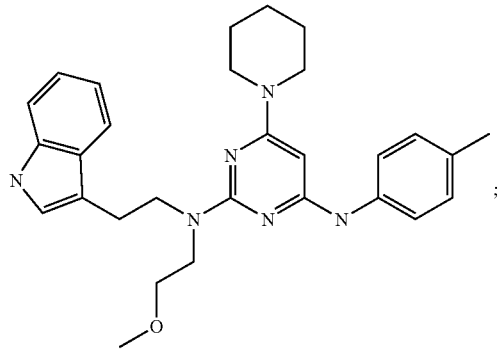

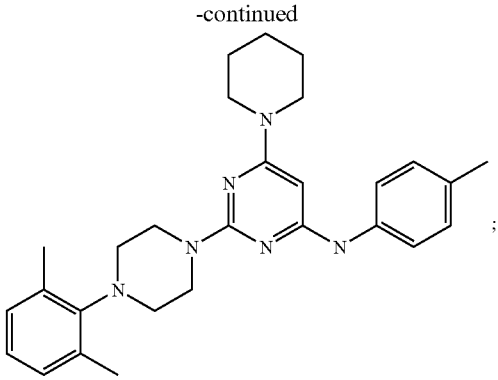; and
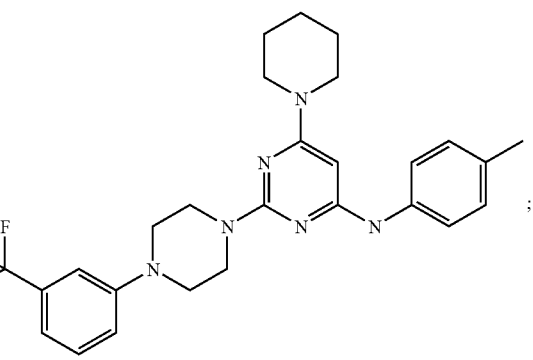
In one embodiment, Y is
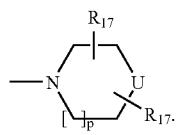
In one embodiment, U is $NR_{16}$.
In one embodiment, $R_{16}$ is $(CH_2)_m$-Z.
In one embodiment, Z is aryl or heteroaryl.
In one embodiment, the compound is selected from the group consisting of:
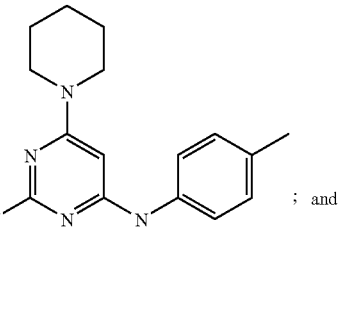;
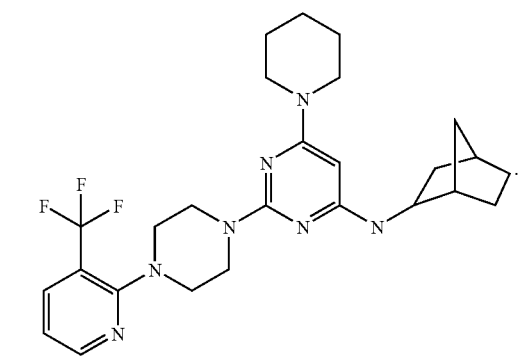

In one embodiment, the compound is selected from the group consisting of:
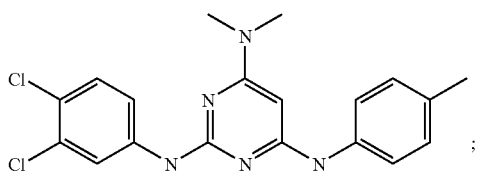
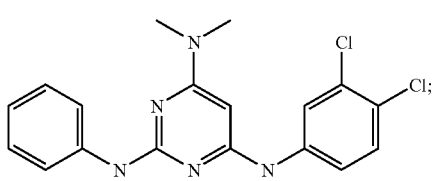
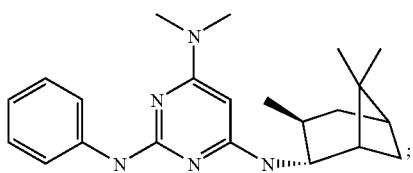
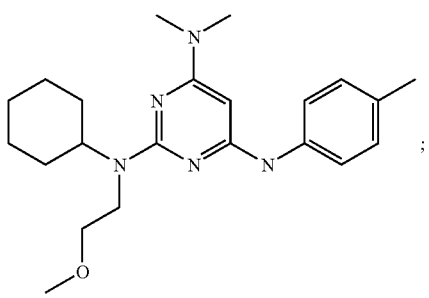
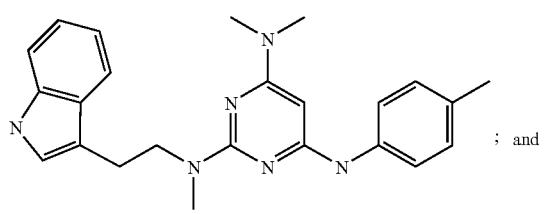
; and
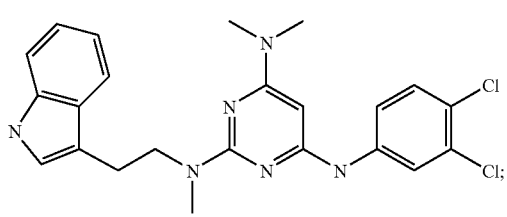
In one embodiment, Y is
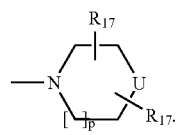
In one embodiment, U is $NR_{16}$.
In one embodiment, the compound is
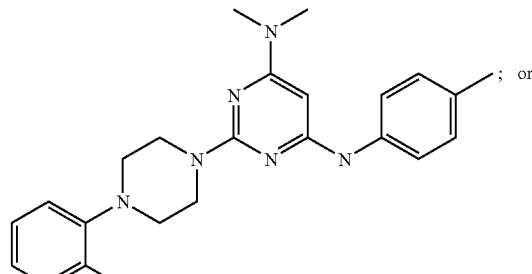
; or
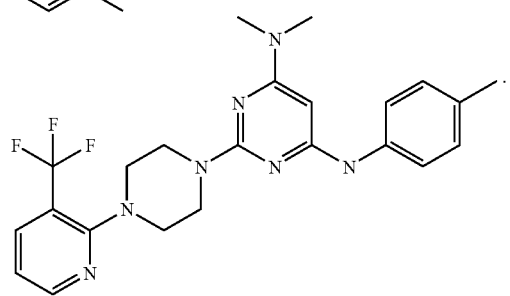
In one embodiment, the compound is
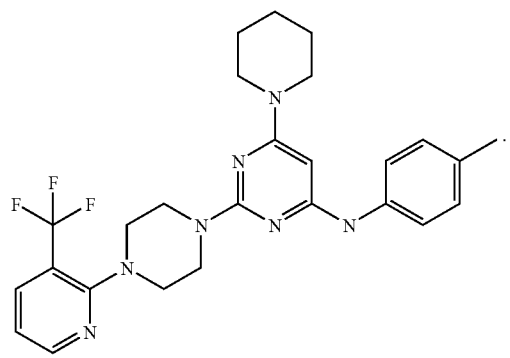
In one embodiment, the compound is selected from the group consisting of:
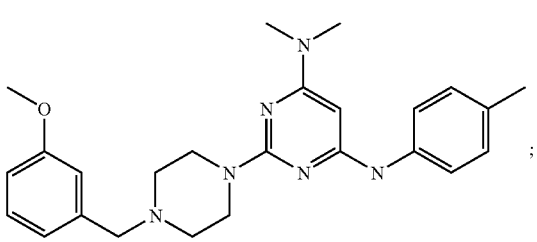
;

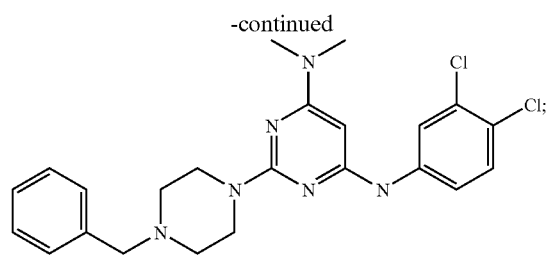
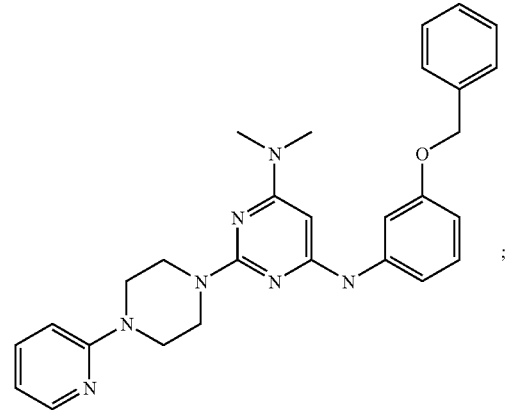
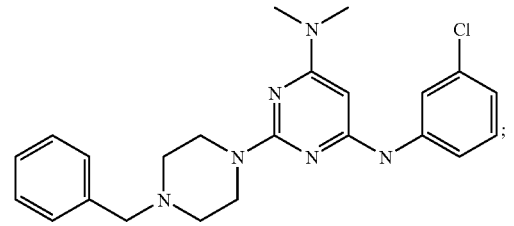
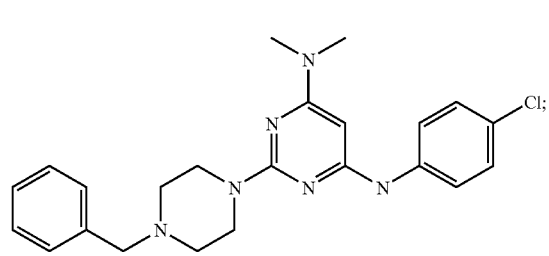
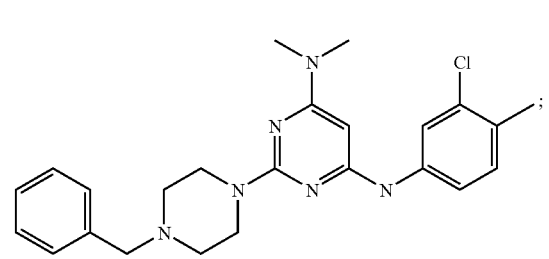
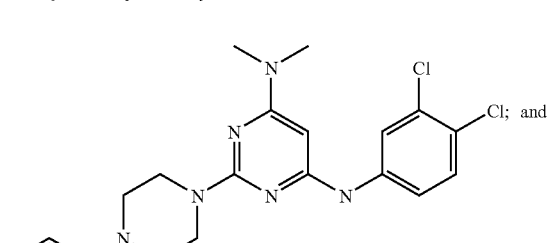
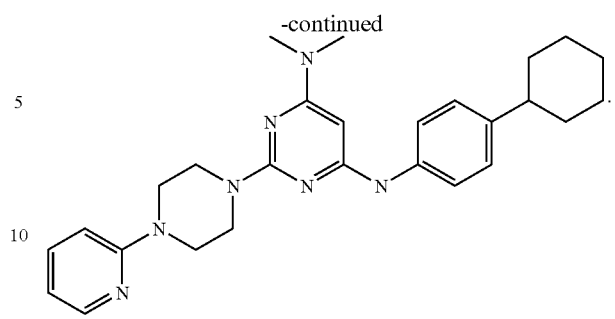
In one embodiment, the compound is selected from the group consisting of:
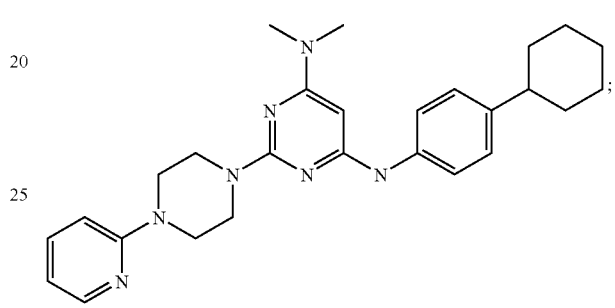
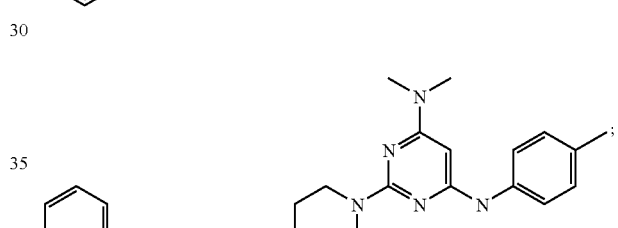
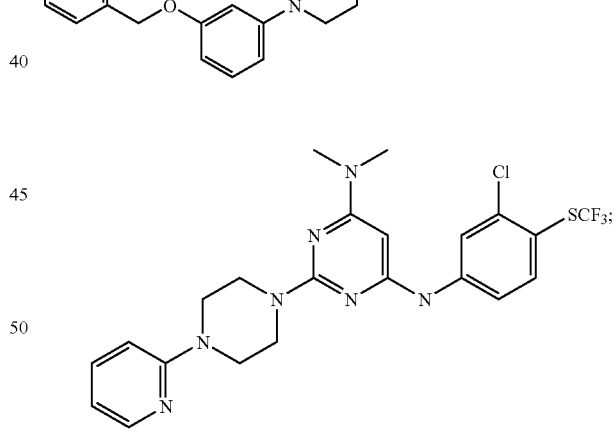
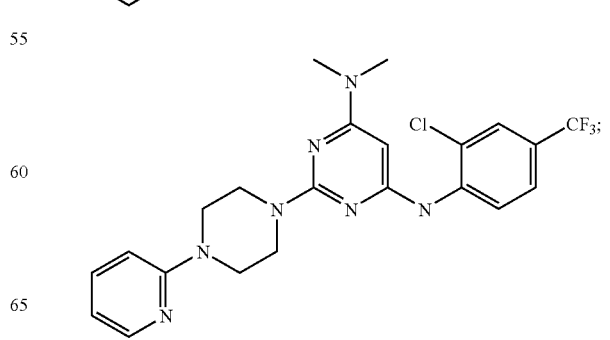

-continued

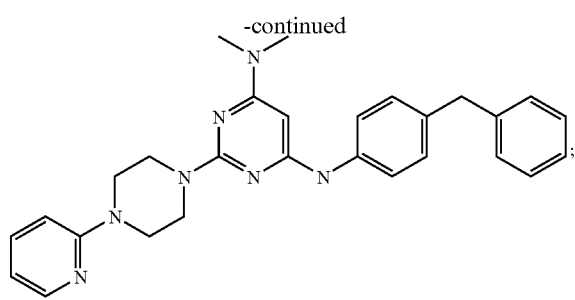

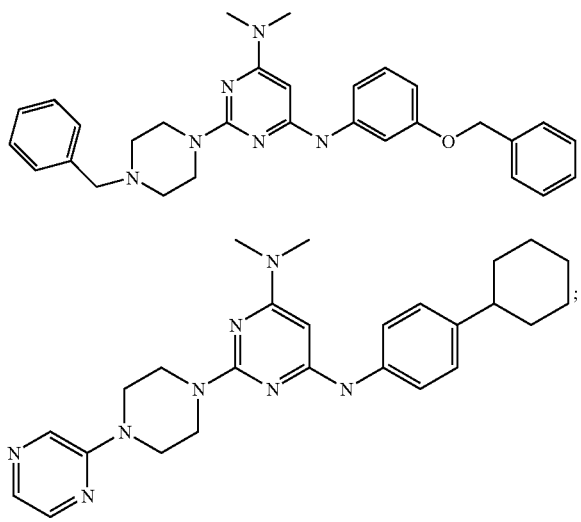

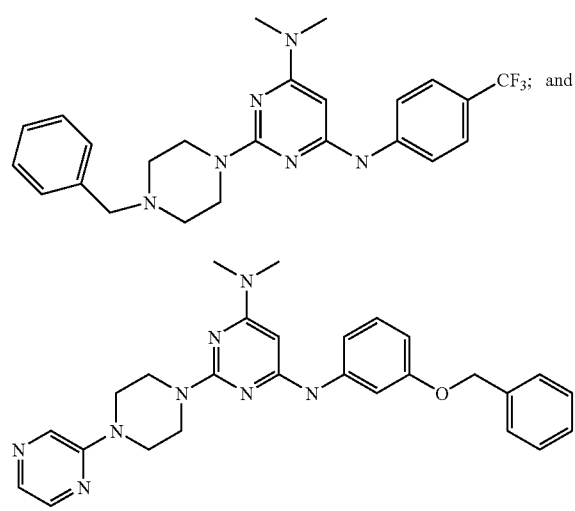

In one embodiment, X is N(CH$_3$)$_2$.
In one embodiment, Y is

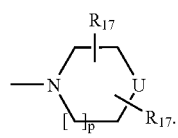

In one embodiment, R$_{13}$ is an aryl substituted with a C$_1$-C$_{10}$ straight chained alkyl.

In one embodiment, the compound is selected from a group consisting of:

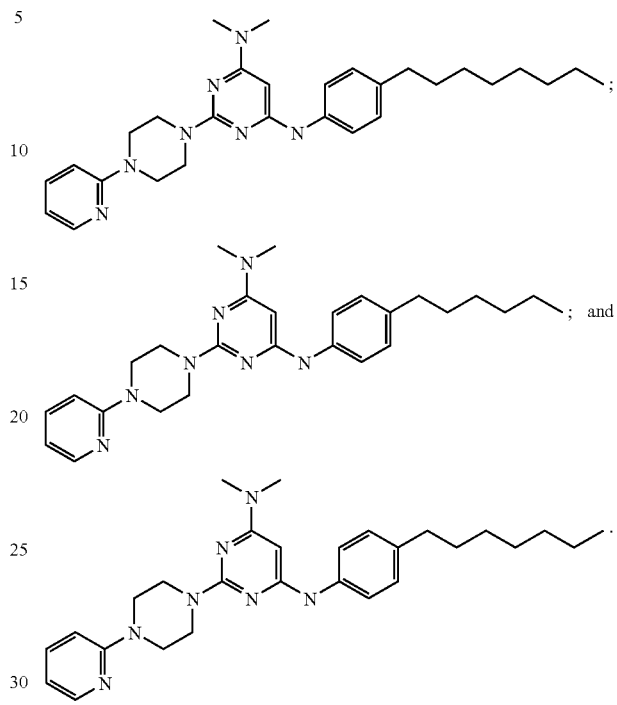

The invention provides a pharmaceutical composition comprising a pharmaceutically acceptable carrier and a compound having the structure:

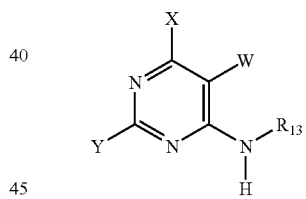

wherein W is H, —F, —Cl, —Br, —I, CN, methyl, ethyl, propyl, methoxy or ethoxy;

wherein X is; NR$_{11}$R$_{12}$;

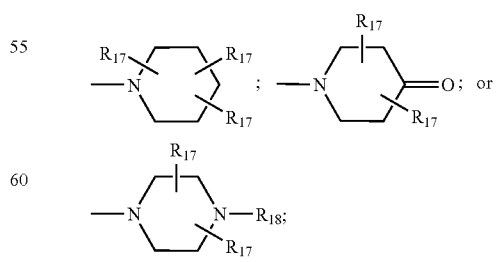

wherein R$_{11}$ is H, straight chained or branched C$_1$-C$_7$ alkyl, (CH$_2$)$_q$—O—(CH$_2$)$_m$—CH$_3$, aryl, or aryl (C$_1$-C$_6$)alkyl;

wherein $R_{12}$ is straight chained or branched $C_1$-$C_7$ alkyl, $(CH_2)_q$—O—$(CH_2)_m$—$CH_3$, or —$(CH_2)_m$-Z;

wherein $R_{13}$ is a bicyclic alkyl ring system, adamantyl, noradamantyl, $C_3$-$C_{10}$ cycloalkyl, heteroaryl, aryl, aryl($C_1$-$C_6$)alkyl, $Q_1$ or $Q_2$;

wherein aryl may be substituted with one or more $C_1$-$C_{10}$ straight chained or branched alkyl, aryl, heteroaryl, or N($R_{19}$)-Z;

wherein $Q_1$ is

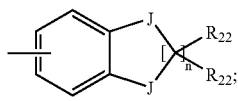

wherein $Q_2$ is

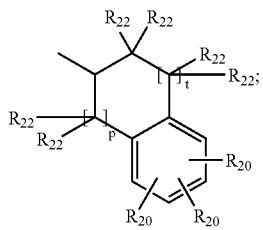

wherein each J is independently O, S, $C(R_{22})_2$ or $NR_4$;

wherein $R_4$ is H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein Y is $NR_{14}R_{15}$;

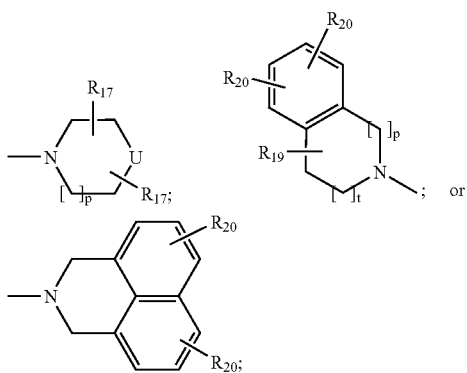

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is straight chained or branched $C_3$-$C_6$ alkyl, $(CH_2)_q$—O—$(CH_2)_m$—$CH_3$, $C_3$-$C_6$ cycloalkyl, $(C(R_{19})_2)_m N(R_{16})_2$ or $(C(R_{19})_2)_m$-Z;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein $R_{18}$ is straight chained or branched $C_1$-$C_6$ alkyl, —$(CH_2)_m$-Z, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl, or aryl($C_1$-$C_6$) alkyl;

wherein each $R_{22}$ is independently H, F, Cl or $C_1$-$C_4$ straight chained or branched alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2;

wherein U is O, —$NR_{16}$, S, $C(R_{17})_2$, or —$NSO_2R_{16}$;

wherein Z is $C_3$-$C_{10}$ cycloalkyl, $C_4$-$C_7$ cyclic ether, $C_4$-$C_7$ cyclic thioether, aryl, or heteroaryl; or a pharmaceutically acceptable salt thereof.

The invention provides a pharmaceutical composition comprising a pharmaceutically acceptable carrier and a compound having the structure:

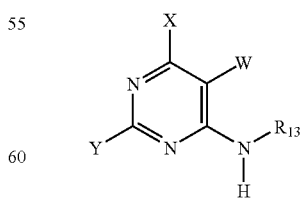

wherein W is H, —F, —Cl, —Br, —I, CN, methyl, ethyl, propyl, methoxy or ethoxy;

wherein X is $NR_{11}R_{12}$;

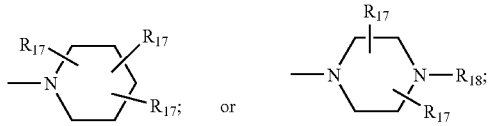

wherein $R_{11}$ is H, straight chained or branched $C_1$-$C_7$ alkyl, $(CH_2)_q$—O—$(CH_2)_m$—$CH_3$, aryl or aryl($C_1$-$C_6$)alkyl;

wherein $R_{12}$ is straight chained or branched $C_1$-$C_7$ alkyl, $(CH_2)_q$—O—$(CH_2)_m$—$CH_3$, or —$(CH_2)_m$-Z;

wherein $R_{13}$ is a bicyclic alkyl ring system, aryl or aryl ($C_3$-$C_6$) alkyl;

wherein Y is $NR_{14}R_{15}$;

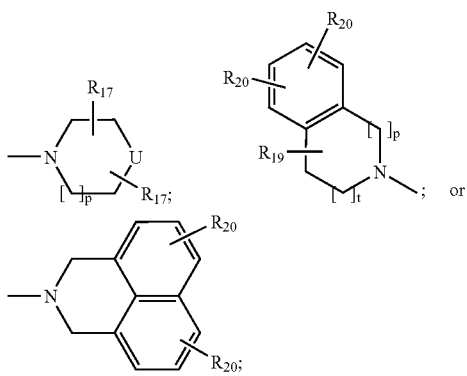

wherein $R_{14}$ is H, straight chained or branched $C_2$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is straight chained or branched $C_3$-$C_6$ alkyl, $(CH_2)_q$—O—$(CH_2)_m$—$CH_3$, $C_3$-$C_6$ cycloalkyl, or $(C(R_{19})_2)_m$-Z;

wherein U is O, —$NR_{16}$, S, $C(R_{17})_2$, or —$NSO_2R_{16}$;

wherein Z is $C_3$-$C_{10}$ cycloalkyl, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein $R_{18}$ is straight chained or branched $C_1$-$C_6$ alkyl, —$(CH_2)_m$-Z, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$) alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2; or a pharmaceutically acceptable salt thereof.

The invention provides a pharmaceutical composition comprising a pharmaceutically acceptable carrier and a compound having the structure:

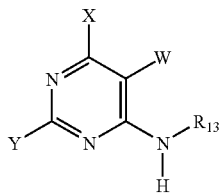

wherein W is H, —F, —Cl, —Br, —I, CN, methyl, ethyl, propyl, methoxy or ethoxy;

wherein. X is $N(CH_3)_2$ or

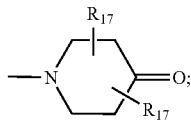

wherein $R_{13}$ is an aryl, adamantyl, noradamantyl, $C_3$-$C_{10}$ cycloalkyl, heteroaryl, $Q_1$ or $Q_2$;

wherein aryl may be substituted with one or more $C_1$-$C_{10}$ straight chained or branched alkyl, aryl, heteroaryl, or $N(R_{19})$-Z;

wherein $Q_1$ is

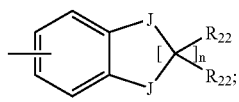

wherein $Q_2$ is

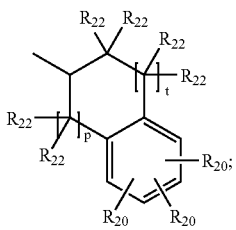

wherein each J is independently O, S, $C(R_{22})_2$ or $NR_4$;

wherein $R_4$ is —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein Y is $NR_{14}R_{15}$;

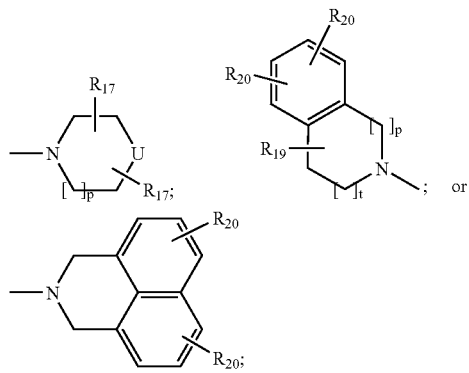

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is straight chained or branched $C_3$-$C_6$ alkyl, $(CH_2)_q$—O—$(CH_2)_m$—$CH_3$, $C_3$-$C_6$ cycloalkyl, or $(C(R_{19})_2)_m$-Z;

wherein U is O, —$NR_{16}$, S, $C(R_{17})_2$, or —$NSO_2R_{16}$;

wherein Z is $C_3$-$C_{10}$ cycloalkyl, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z or $(CH_2)_n$—O—$(CH_2)_m$—$CH_3$;

wherein $R_{18}$ is straight chained or branched $C_1$-$C_6$ alkyl, —$(CH_2)_m$-Z, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein each $R_{22}$ is independently H, F, Cl or $C_1$-$C_4$ straight chained or branched alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2; or a pharmaceutically acceptable salt thereof.

The invention provides a pharmaceutical composition comprising a pharmaceutically acceptable carrier and a compound having the structure:

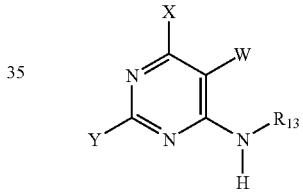

wherein W is H, —F, —Cl, —Br, —I, CN, methyl, ethyl, propyl, methoxy or ethoxy;

wherein X is $N(CH_3)_2$ or

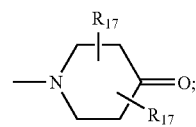

wherein $R_{13}$ is a bicyclic alkyl ring system, aryl or aryl ($C_2$-$C_6$) alkyl;

wherein Y is $NR_{14}R_{15}$;

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is $(C(R_{19})_2)_m$—$N(R_{16})_2$;

wherein Z is $C_3$-$C_{10}$ cycloalkyl, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein each $R_{19}$ is independently H, or straight chained or branched $C_1$-$C_6$ alkyl;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$) alkyl;

wherein each m is an integer from 0 to 4 inclusive;

wherein each n is an integer from 1 to 4 inclusive;

wherein q is an integer from 2 to 4 inclusive; or a pharmaceutically acceptable salt thereof.

As used in the present invention, the term "bicyclic alkyl ring systems" includes, but is not limited to, bicyclo[2.2.1]heptane, bicyclo[3.1.1]heptane and bicyclo[2.2.2]octane. In addition, the bicyclic alkyl ring systems may be substituted with one or more of the following: —F, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_5$-$C_7$ cycloalkenyl, —$N(R_{21})_2$, —$OR_{21}$, —$COR_{21}$, $CO_2R_{21}$, —$CON(R_{21})_2$ or $(CH_2)_n$—O—$(CH_2)_m$—$CH_3$.

As used in the present invention, the term "cycloalkyl" includes, $C_3$-$C_7$ cycloalkyl moieties which may be substituted with one or more of the following: —F, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

As used in the present invention, the term "cyclohexyl" includes, cyclohexyl groups which may be substituted with one or more of the following: —F, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

As used in the present invention, the term "cycloalkenyl" includes, $C_5$-$C_7$ cycloalkenyl moieties which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

In the present invention, the term "heteroaryl" is used to include five and six membered unsaturated rings that may contain one or more oxygen, sulfur, or nitrogen atoms. Examples of heteroaryl groups include, but are not limited to, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl.

In addition the term "heteroaryl" is used to include fused bicyclic ring systems that may contain one or more heteroatoms such as oxygen, sulfur and nitrogen. Examples of such heteroaryl groups include, but are not limited to, indolizinyl, indolyl, isoindolyl, benzo[b]furanyl, benzo[b]thiophenyl, indazolyl, benzimidazolyl, purinyl, benzoxazolyl, benzisoxazolyl, benzo[b]thiazolyl, imidazo[2,1-b]thiazolyl, cinnolinyl, quinazolinyl, quinoxalinyl, 1,8-naphthyridinyl, pteridinyl, quinolinyl, isoquinolinyl, phthalimidyl and 2,1,3-benzothiazolyl.

The term "heteroaryl" also includes those chemical moieties recited above which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, $COR_4$, —$NCOR_4$, —$CO_2R_4$, —$CON(R_4)_2$ or $(CH_2)_n$—O—$(CH_2)_m$—$CH_3$.

The term "heteroaryl" further includes the N-oxides of those chemical moieties recited above which include at least one nitrogen atom.

In the present invention the term "aryl" is phenyl or naphthyl. The term "aryl" also includes phenyl and naphthyl which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, $SR_4$, —$OCOR_4$, —$COR_4$, —$NCOR_4$, —$CO_2R_4$, —$CON(R_4)_2$ or $(CH_2)_n$—O—$(CH_2)_m$—$CH_3$.

In one embodiment of any of the pharmaceutical compositions described herein, the compound is enantiomerically and diasteriomerically pure. In one embodiment the compound is enantiomerically or diasteriomerically pure.

In one embodiment of any of the pharmaceutical compositions described herein, the compound can be administered orally.

In one embodiment, X is:

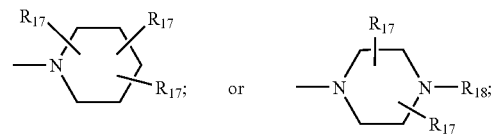

In one embodiment, X is $NR_{11}R_{12}$ and $R_{11}$ is H or straight chained or branched $C_1$-$C_7$ alkyl.

In one embodiment, the compound has the structure:

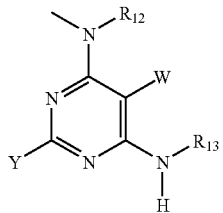

In one embodiment, $R_{13}$ is a bicyclic alkyl ring system, cyclohexyl or aryl.

In one embodiment, $R_{14}$ is H, straight chained or branched $C_1$-$C_6$ alkyl or $(CH_2)_q$—O—$(CH_2)_m$—$CH_3$.

In one embodiment, Y is

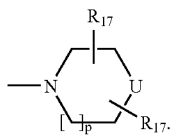

In one embodiment, U is $NR_{16}$.
In one embodiment, $R_{16}$ is $(CH_2)_m$-Z.
In one embodiment, Z is aryl or heteroaryl.
In one embodiment, Y is

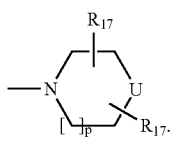

In one embodiment, U is $NR_{16}$.
In one embodiment, the compound is selected from the group consisting of:

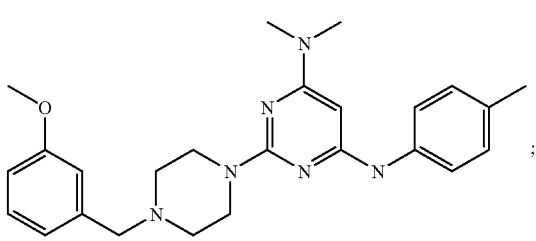

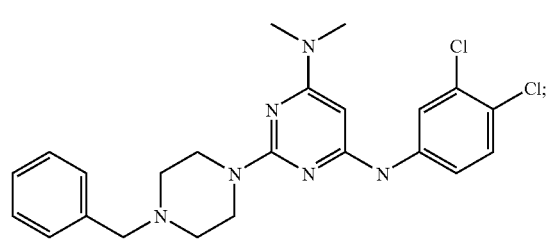

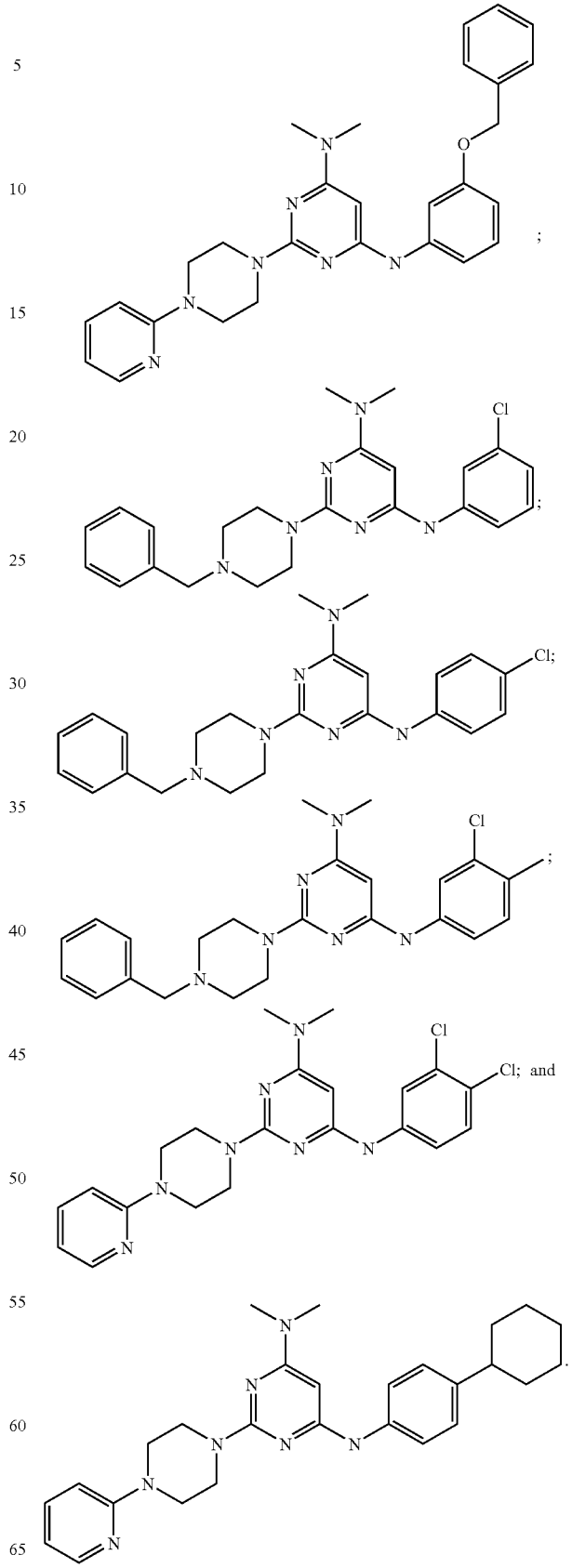

In one embodiment, compound is selected from the group consisting of:
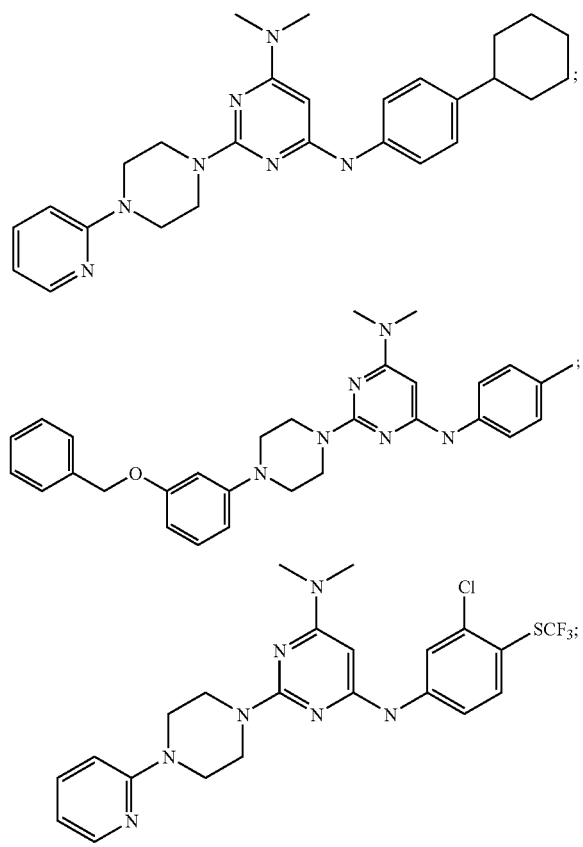
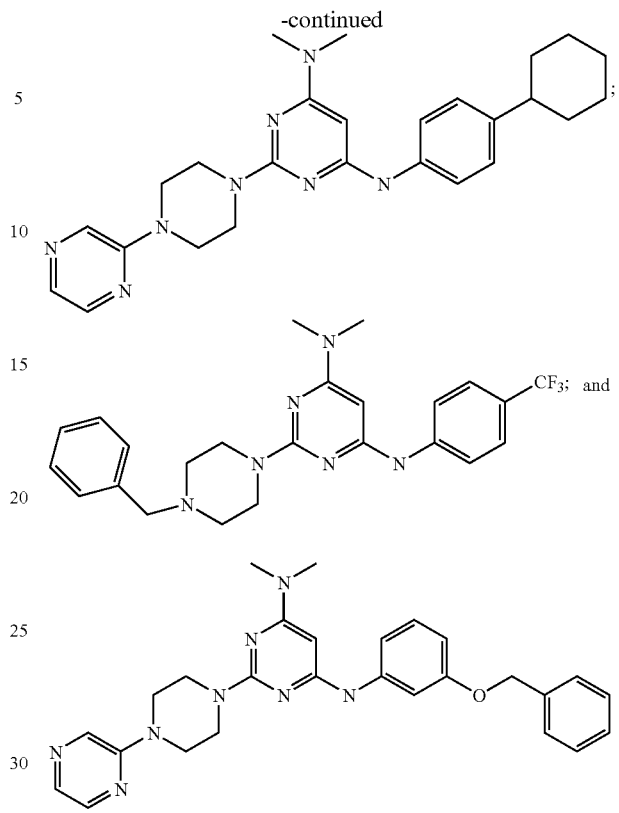
In one embodiment, X is N(CH$_3$)$_2$.
In one embodiment, Y is
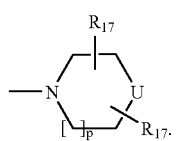
In one embodiment, R$_{13}$ is an aryl substituted with a C$_1$-C$_{10}$ straight chained alkyl.
In one embodiment, the compound is selected from a group consisting of:
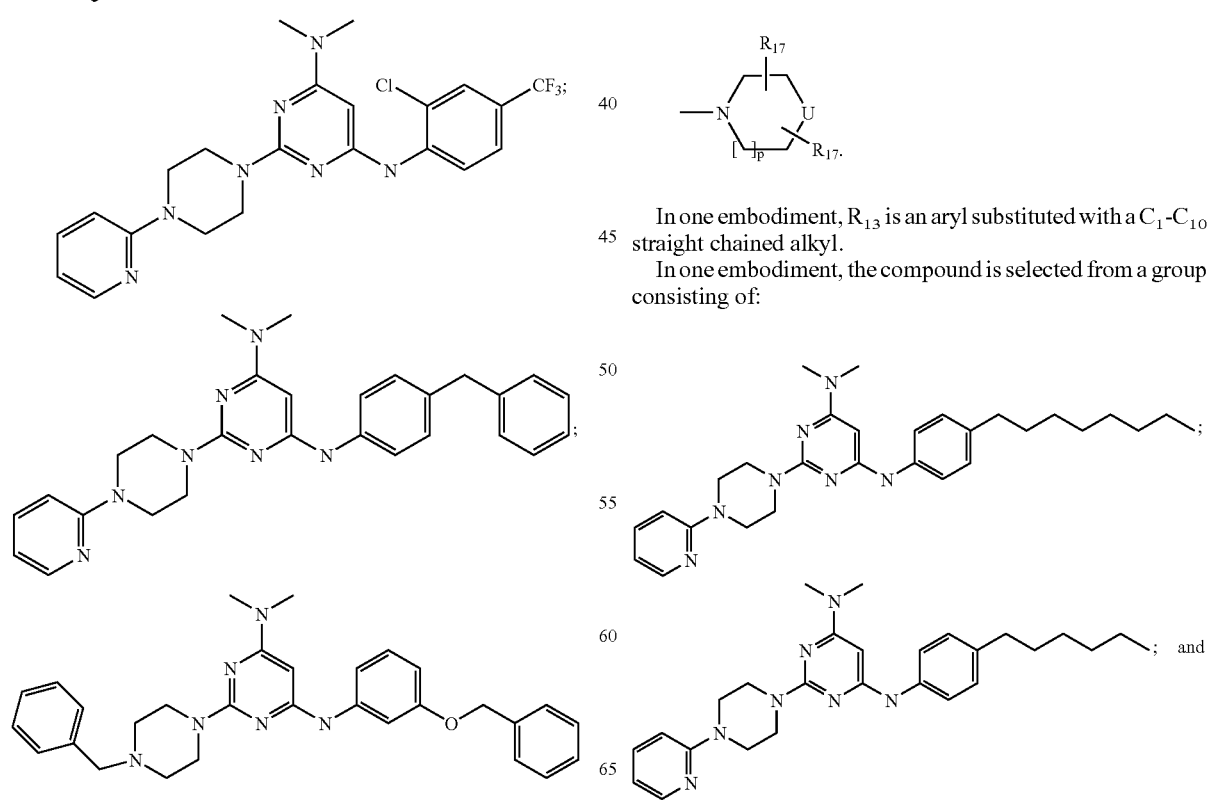

-continued

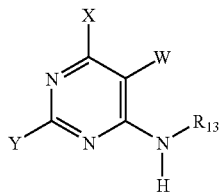

The invention provides a compound having the structure:

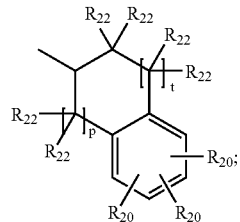

wherein W is H; —F, —Cl, —Br, —I, CN, methyl, ethyl, propyl, methoxy or ethoxy;

wherein X is; $NR_{11}R_{12}$;

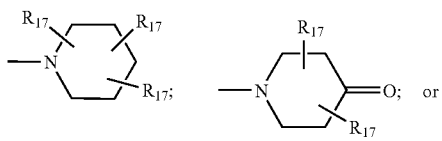

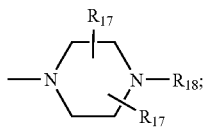

wherein $R_{11}$ is H, straight chained or branched $C_1$-$C_7$ alkyl, $(CH_2)_q$—O—$(CH_2)_m$—$CH_3$, aryl, or aryl ($C_1$-$C_6$)alkyl;

wherein $R_{12}$ is straight chained or branched $C_1$-$C_7$ alkyl, $(CH_2)_q$—O—$(CH_2)_m$—$CH_3$, or —$(CH_2)_m$-Z;

wherein $R_{13}$ is a bicyclic alkyl ring system, adamantyl, noradamantyl, $C_3$-$C_{10}$ cycloalkyl, heteroaryl, aryl, aryl($C_1$-$C_6$)alkyl, $Q_1$ or $Q_2$;

wherein aryl may be substituted with one or more $C_1$-$C_{10}$ straight chained or branched alkyl, aryl, heteroaryl, or $N(R_{19})$-Z;

wherein $Q_1$ is

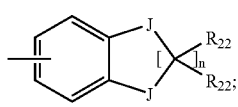

wherein $Q_2$ is

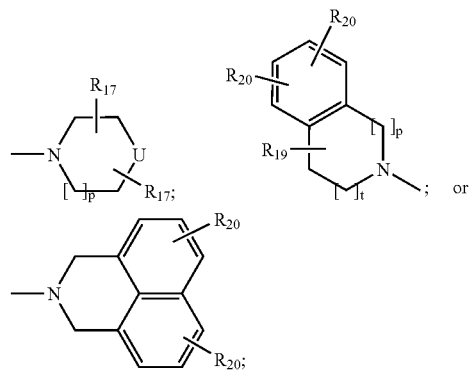

wherein each J is independently O, S, $C(R_{22})_2$ or $NR_4$;

wherein $R_4$ is H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein Y is $NR_{14}R_{15}$;

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is straight chained or branched $C_3$-$C_6$ alkyl, $(CH_2)_q$—O—$(CH_2)_m$—$CH_3$, $C_3$-$C_6$ cycloalkyl, $(C(R_{19})_2)_m N(R_{16})_2$ or $(C(R_{19})_2)_m$-Z;

wherein $R_{16}$ is straight chained or branched $C_1$-$C_7$ alkyl, straight chained or branched $C_1$-$C_7$ monofluoroalkyl, straight chained or branched $C_2$-$C_7$ polyfluoroalkyl, straight chained or branched $C_2$-$C_7$ alkenyl, straight chained or branched $C_2$-$C_7$ alkynyl, $C_5$-$C_7$ cycloalkyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkyl, —$(CH_2)_m$-Z, or $(CH_2)_n$—O—$(CH_2)_m$—$CH_3$;

wherein $R_{18}$ is straight chained or branched $C_1$-$C_6$ alkyl, —$(CH_2)_m$-Z, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$, —CON(R$_{21}$)$_2$, or —COOR$_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl, or aryl($C_1$-$C_6$) alkyl;

wherein each $R_{22}$ is independently H, F, Cl or $C_1$-$C_4$ straight chained or branched alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2;

wherein U is O, —NR$_{16}$, S, C(R$_{17}$)$_2$, or —NSO$_2$R$_{16}$;

wherein Z is $C_3$-$C_{10}$ cycloalkyl, $C_4$-$C_7$ cyclic ether, $C_4$-$C_7$ cyclic thioether, aryl, or heteroaryl; or a pharmaceutically acceptable salt thereof.

The invention provides a compound having the structure:

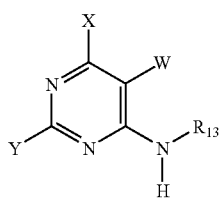

wherein W is H, —F, —Cl, —Br, —I, CN, methyl, ethyl, propyl, methoxy or ethoxy;

wherein X is NR$_{11}$R$_{12}$;

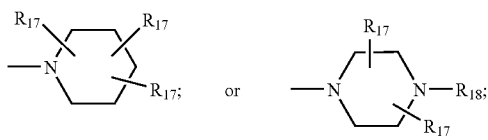

wherein $R_{11}$ is H, straight chained or branched $C_1$-$C_7$ alkyl, (CH$_2$)$_q$—O—(CH$_2$)$_m$—CH$_3$, aryl or aryl($C_1$-$C_6$)alkyl;

wherein $R_{12}$ is straight chained or branched $C_1$-$C_7$ alkyl, (CH$_2$)$_q$—O—(CH$_2$)$_m$—CH$_3$, or —(CH$_2$)$_m$-Z;

wherein $R_{13}$ is a bicyclic alkyl ring system, aryl or aryl($C_1$-$C_6$)alkyl;

wherein Y is NR$_{14}$R$_{15}$;

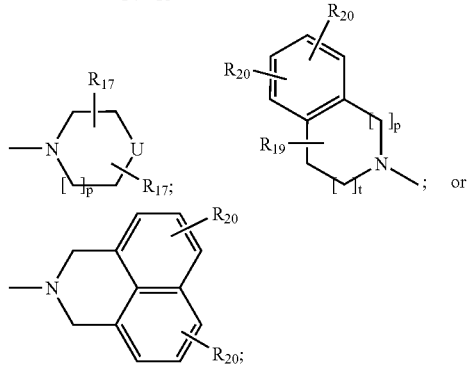

wherein $R_{14}$ is H, straight chained or branched $C_1$-$C_6$ alkyl, (CH$_2$)$_q$—O—(CH$_2$)$_m$—CH$_3$, $C_3$-$C_6$ cycloalkyl, or (C(R$_{19}$)$_2$)$_m$-Z;

wherein $R_{15}$ is straight chained or branched $C_3$-$C_6$ alkyl, (CH$_2$)$_q$—O—(CH$_2$)$_m$—CH$_3$, $C_3$-$C_6$ cycloalkyl, or (C(R$_{19}$)$_2$)$_m$-Z;

wherein U is O, —NR$_{16}$, S, C(R$_{17}$)$_2$, or —NSO$_2$R$_{16}$;

wherein Z is $C_3$-$C_{10}$ cycloalkyl, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_q$—O—(CH$_2$)$_m$—CH$_3$;

wherein each $R_{17}$ is independently H; —OR$_{21}$, —OCOR$_{21}$, —COR$_{21}$, —NCOR$_{21}$, —N(R$_{21}$)$_2$, —CON(R$_{21}$)$_2$, —COOR$_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_n$—O—(CH$_2$)$_m$—CH$_3$;

wherein $R_{18}$ is straight chained or branched $C_1$-$C_6$ alkyl, —(CH$_2$)$_m$-Z, or (CH$_2$)$_q$—O—(CH$_2$)$_m$—CH$_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$, —CON(R$_{21}$)$_2$, or —COOR$_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$) alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2; or a pharmaceutically acceptable salt thereof.

The invention provides a compound having the structure:

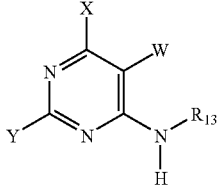

wherein W is H, —F, —Cl, —Br, —I, CN, methyl, ethyl, propyl, methoxy or ethoxy;

wherein X is N(CH$_3$)$_2$ or

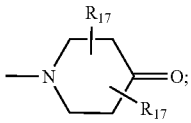

wherein R$_{13}$ is an aryl, adamantyl, noradamantyl, C$_3$-C$_{10}$ cycloalkyl, heteroaryl, Q$_1$ or Q$_2$;

wherein aryl may be substituted with one or more C$_1$-C$_{30}$ straight chained or branched alkyl, aryl, heteroaryl, or N(R$_{19}$)-Z;

wherein Q$_1$ is

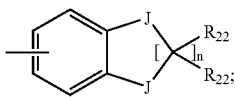

wherein Q$_2$ is

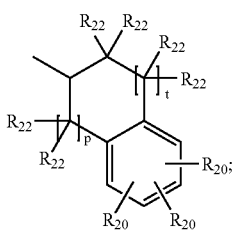

wherein each J is independently O, S, C(R$_{22}$)$_2$ or NR$_4$;

wherein R$_4$ is —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, C$_5$-C$_7$ cycloalkenyl or aryl;

wherein Y is NR$_{14}$R$_{15}$;

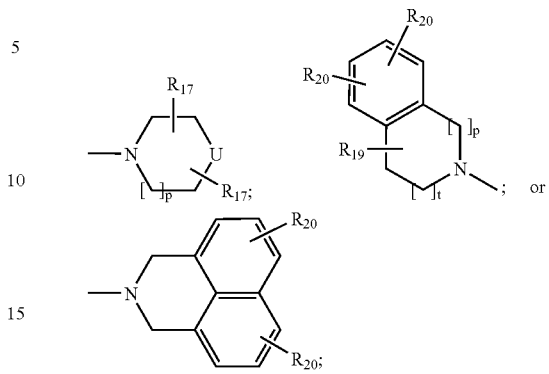

wherein R$_{14}$ is H, straight chained or branched C$_1$-C$_6$ alkyl, (CH$_2$)$_q$—O—(CH$_2$)$_m$—CH$_3$, C$_3$-C$_6$ cycloalkyl, or (C(R$_{19}$)$_2$)$_m$-Z;

wherein R$_{15}$ is straight chained or branched C$_3$-C$_6$ alkyl, (CH$_2$)$_q$—O—(CH$_2$)$_m$—CH$_3$, C$_3$-C$_6$ cycloalkyl, or (C(R$_{19}$)$_2$)$_m$-Z;

wherein U is O, —NR$_{16}$, S, C(R$_{17}$)$_2$, or —NSO$_2$R$_{16}$;

wherein Z is C$_3$-C$_{10}$ cycloalkyl, aryl, or heteroaryl;

wherein R$_{16}$ is straight chained or branched C$_1$-C$_7$ alkyl, straight chained or branched C$_1$-C$_7$ monofluoroalkyl, straight chained or branched C$_2$-C$_7$ polyfluoroalkyl, straight chained or branched C$_2$-C$_7$ alkenyl, straight chained or branched C$_2$-C$_7$ alkynyl, C$_5$-C$_7$ cycloalkenyl, —(CH$_2$)$_m$-Z, or (CH$_2$)$_q$—O—(CH$_2$)$_m$—CH$_3$;

wherein each R$_{17}$ is independently H; —OR$_{21}$, —OCOR$_{21}$, —COR$_{21}$, —NCOR$_{21}$, —N(R$_{21}$)$_2$, —CON(R$_{21}$)$_2$, —COOR$_{21}$, straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_5$-C$_7$ cycloalkenyl, —(CH$_2$)$_m$-Z, or (CH$_2$)$_n$—O—(CH$_2$)$_m$—CH$_3$;

wherein R$_{18}$ is straight chained or branched C$_1$-C$_6$ alkyl, —(CH$_2$)$_m$-Z, or (CH$_2$)$_q$—O—(CH$_2$)$_m$—CH$_3$;

wherein each R$_{19}$ is independently H, or straight chained or branched C$_1$-C$_6$ alkyl;

wherein each R$_{20}$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl or C$_5$-C$_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$—. CON(R$_{21}$)$_2$, or —COOR$_{21}$; aryl or heteroaryl; or two R$_{20}$ groups present on adjacent carbon atoms can join together to form a methylenedioxy group;

wherein each R$_{21}$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, C$_5$-C$_7$ cycloalkenyl, aryl or aryl(C$_1$-C$_6$) alkyl; straight chained or branched C$_2$-C$_7$ alkenyl or alkynyl; C$_3$-C$_7$ cycloalkyl, C$_5$-C$_7$ cycloalkenyl, aryl or aryl(C$_1$-C$_6$) alkyl;

wherein each $R_{22}$ is independently H; F, Cl or $C_1$-$C_4$ straight chained or branched alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2; or a pharmaceutically acceptable salt thereof.

The invention provides a compound having the structure:

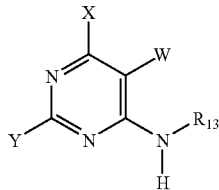

wherein W is H, —F, —Cl, —Br, —I, CN, methyl, ethyl, propyl, methoxy or ethoxy;

wherein X is $N(CH_3)_2$ or

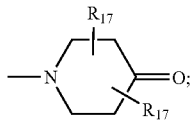

wherein $R_{13}$ is a bicyclic alkyl ring system, aryl or aryl ($C_1$-$C_6$) alkyl;

wherein Y is $NR_{14}R_{15}$;

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is $(C(R_{19})_2)_m$—$N(R_{16})_2$;

wherein Z is $C_3$-$C_{10}$ cycloalkyl, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein each $R_{19}$ is independently H, or straight chained or branched $C_1$-$C_6$ alkyl;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein each m is an integer from 0 to 4 inclusive;

wherein each n is an integer from 1 to 4 inclusive;

wherein q is an integer from 2 to 4 inclusive; or a pharmaceutically acceptable salt thereof.

As used in the present invention, the term "bicyclic alkyl ring systems" includes, but is not limited to, bicyclo[2.2.1]heptane, bicyclo[3.1.1]heptane and bicyclo[2.2.2]octane. In addition, the bicyclic alkyl ring systems may be substituted with one or more of the following: —F, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_5$-$C_7$ cycloalkenyl, —$N(R_{21})_2$, —$OR_{21}$, —$COR_{21}$, —$CO_2R_{21}$, —$CON(R_{21})_2$ or $(CH_2)_n$—O—$(CH_2)_m$—$CH_3$.

As used in the present invention, the term "cycloalkyl" includes, $C_3$-$C_7$ cycloalkyl moieties which may be substituted with one or more of the following: —F, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R)_2$, —$OR_4$, —$COR_4$, —$NCOR_4$, —$CO_2R_4$, —$CON(R_4)_2$ or $(CH_2)_n$—O—$(CH_2)_m$—$CH_3$ As used in the present invention, the term "cyclohexyl" includes, cyclohexyl groups which may be substituted with one or more of the following: —F, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

As used in the present invention, the term "cycloalkenyl" includes, $C_5$-$C_7$ cycloalkenyl moieties which may be substituted with one or more of the following: —F, —Cl, —Br, —I, —$NO_2$, —CN, straight chained or branched $C_1$-$C_7$ alkyl, straight chained or branched $C_2$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

In the present invention, the term "heteroaryl" is used to include five and six membered unsaturated rings that may contain one or more oxygen, sulfur, or nitrogen atoms. Examples of heteroaryl groups include, but are not limited to, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl.

In addition the term "heteroaryl" is used to include fused bicyclic ring systems that may contain one or more heteroatoms such as oxygen, sulfur and nitrogen. Examples of such heteroaryl groups include, but are not limited to, indolizinyl, indolyl, isoindolyl, benzo[b]furanyl, benzo[b]thiophenyl, indazolyl, benzimidazolyl, purinyl; benzoxazolyl, benzisoxazolyl, benzo[b]thiazolyl, imidazo[2,1-b]thiazolyl, cinnolinyl, quinazolinyl, quinoxalinyl, 1,8-naphthyridinyl, pteridinyl, quinolinyl, isoquinolinyl, phthalimidyl and 2,1,3-benzothiazolyl.

The term "heteroaryl" also includes those chemical moieties recited above which may be substituted with one or more of the following: —F, —Cl, —Br, —I, —NO$_2$, —CN, straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_3$-C$_7$ cycloalkyl, C$_3$-C$_7$ monofluorocycloalkyl, C$_3$-C$_7$ polyfluorocycloalkyl, C$_5$-C$_7$ cycloalkenyl, —N(R)$_2$, —OR$_4$, —COR$_4$, —NCOR$_4$, —CO$_2$R$_4$, —CON(R$_4$)$_2$ or (CH$_2$)$_n$—O—(CH$_2$)$_m$—CH$_3$.

The term "heteroaryl" further includes the N-oxides of those chemical moieties recited above which include at least one nitrogen atom.

In the present invention the term "aryl" is phenyl or naphthyl. The term "aryl" also includes phenyl and naphthyl which may be substituted with one or more of the following: —F, —Cl, —Br, —I, —NO$_2$, —CN, straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_3$-C$_7$ cycloalkyl, C$_3$-C$_7$ monofluorocycloalkyl, C$_3$-C$_7$ polyfluorocycloalkyl, C$_5$-C$_7$ cycloalkenyl, —N(R$_4$)$_2$, —OR$_4$, —SR$_4$, —OCOR$_4$, —COR$_4$, —NCOR$_4$, —CO$_2$R$_4$, —CON(R$_4$)$_2$ or (CH$_2$)$_n$—O—(CH$_2$)$_m$—CH$_3$.

In one embodiment of any of the compounds described herein, the compound is enantiomerically or diasteriomerically pure. In one embodiment of any of the compounds described herein, the compound is enantiomerically and diasteriomerically pure.

In one embodiment, X is:

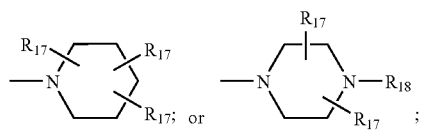

In one embodiment, X is NR$_{11}$R$_{12}$ and R$_{11}$ is H or straight chained or branched C$_1$-C$_7$ alkyl.

In one embodiment, the compound has the structure:

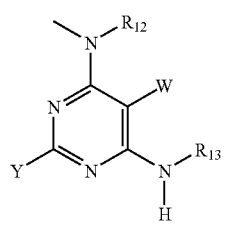

In one embodiment, R$_{13}$ is a bicyclic alkyl ring system, cyclohexyl or aryl.

In one embodiment, R$_{14}$ is H, straight chained or branched C$_1$-C$_6$ alkyl or (CH$_2$)$_q$—O—(CH$_2$)$_m$—CH$_3$.

In one embodiment, Y is

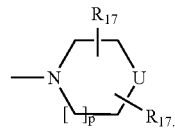

In one embodiment, U is NR$_{16}$.
In one embodiment, R$_{16}$ is (CH$_2$)$_m$-Z.
In one embodiment Z is aryl or heteroaryl.
In one embodiment, Y is

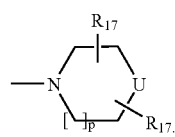

In one embodiment, U is NR$_{16}$.
In one embodiment, the compound is selected from the group consisting of:

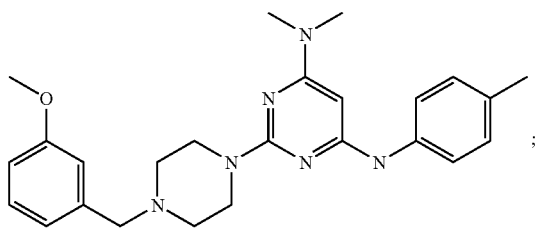

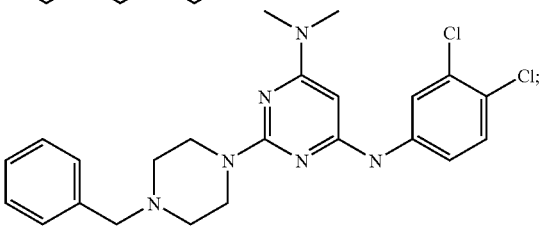

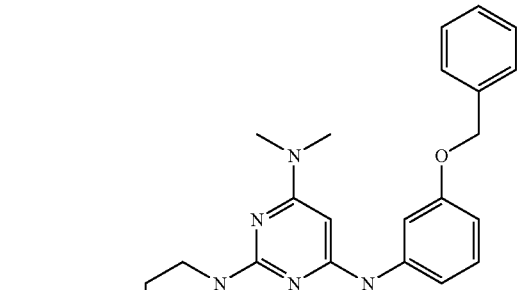

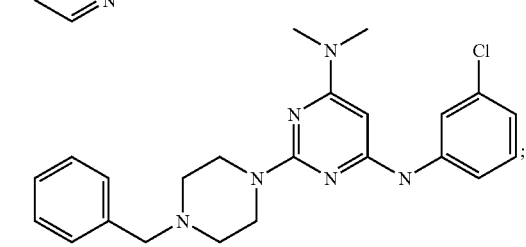

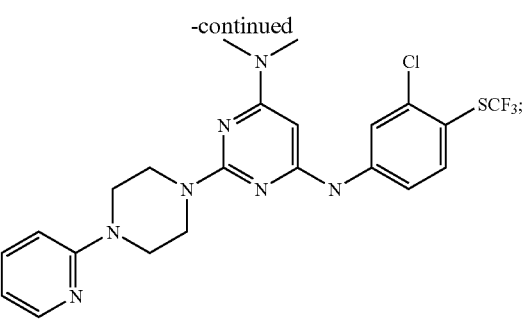
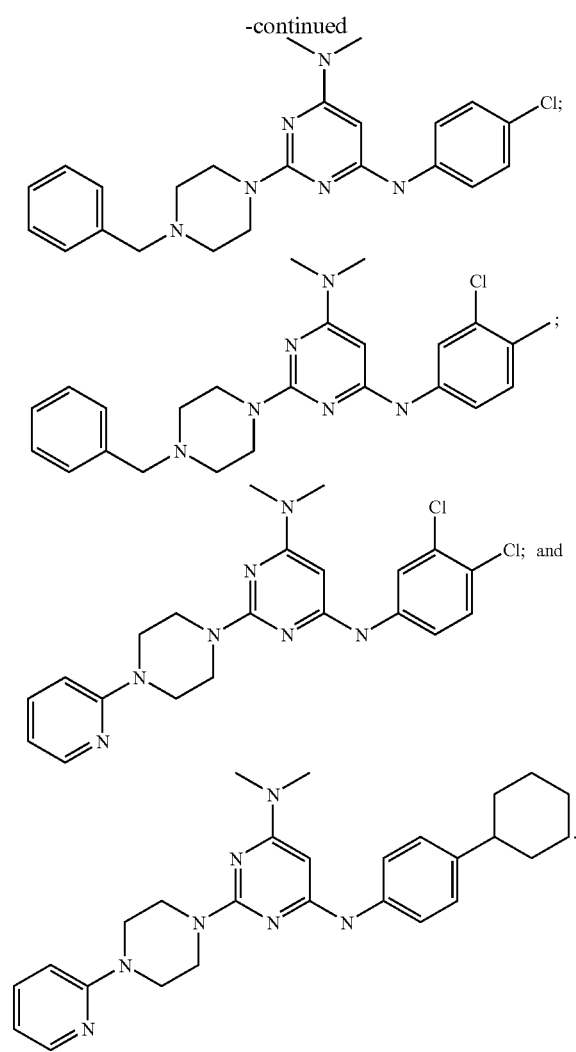
In one embodiment, the compound is selected from the group consisting of:

117

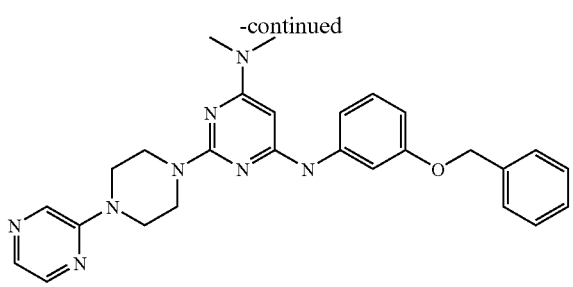

In one embodiment, X is N(CH$_3$)$_2$.
In one embodiment, Y is

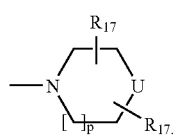

In one embodiment, R$_{13}$ is an aryl substituted with a C$_1$-C$_{10}$ straight chained alkyl.

In one embodiment, the compound is selected from a group consisting of:

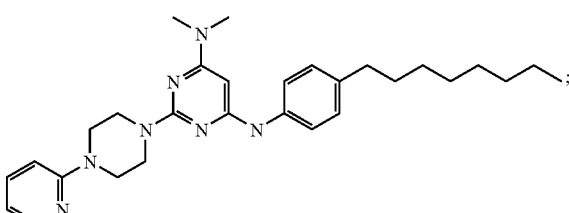

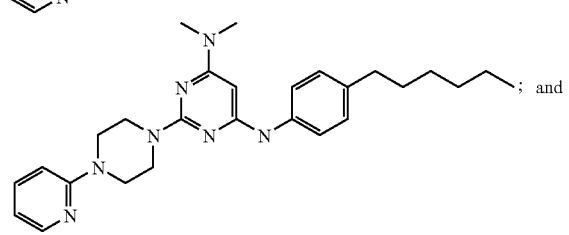

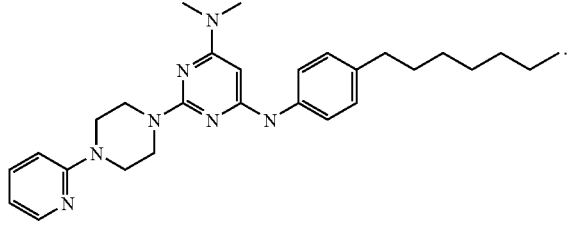

The invention provides a pharmaceutical composition comprising a therapeutically effective amount of any of the compounds described herein and a pharmaceutically acceptable carrier.

The invention provides a pharmaceutical composition made by combining a therapeutically effective amount of any of the compounds described herein and a pharmaceutically acceptable carrier.

The invention provides a process for making a pharmaceutical composition comprising combining a therapeutically effective amount of any of the compounds described herein and a pharmaceutically acceptable carrier.

The invention provides a method of treating a subject suffering from depression which comprises administering to the subject an amount of any of the compounds described herein effective to treat the subject's depression.

The invention provides a method of treating a subject suffering from anxiety which comprises administering to the subject an amount of any of the compounds described herein effective to treat the subject's anxiety.

The invention provides a method of treating a subject suffering from depression and anxiety which comprises administering to the subject an amount of any of the compounds described herein effective to treat the subject's depression and anxiety.

The invention provides a method of treating a subject suffering from depression which comprises administering to the subject an amount of compound effective to treat the subject's depression wherein the compound has the structure:

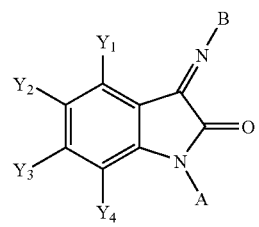

wherein each of Y$_1$, Y$_2$, Y$_3$, and Y$_4$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, or C$_5$-C$_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of Y$_1$, Y$_2$, Y$_3$ and Y$_4$ present on adjacent carbon atoms can constitute a methylenedioxy group;

wherein each R$_4$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, C$_5$-C$_7$ cycloalkenyl, aryl or aryl(C$_1$-C$_6$)alkyl;

wherein A is A', Q$_3$, Q$_4$, Q$_5$, straight chained or branched C$_1$-C$_7$ alkyl, aryl, heteroaryl, aryl(C$_1$-C$_6$)alkyl, heteroaryl(C$_1$-C$_6$)alkyl, aryl substituted with an aryl or heteroaryl, heteroaryl substituted with an aryl or heteroaryl; or (CHR$_{17}$)—(CHR$_{17}$)$_n$-Z;

wherein A' is

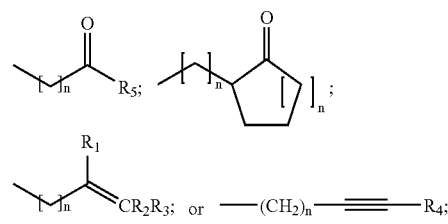

wherein $Q_3$ is

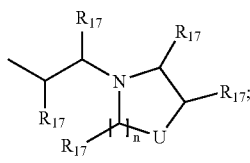

wherein $Q_4$ is

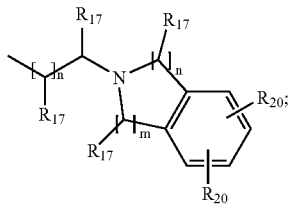

wherein $Q_5$ is

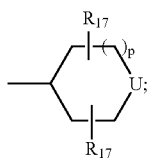

wherein $R_1$ and $R_2$ are each independently H, straight chained or branched $C_1$-$C_7$ alkyl, —F, —Cl, —Br, —I, —NO$_2$, or —CN;
wherein $R_3$ is H, straight chained or branched $C_1$-$C_7$ alkyl, —F, —Cl, —Br, —I, —NO$_2$, —CN, —OR$_6$, aryl or heteroaryl;
wherein $R_5$ is straight chained or branched $C_1$-$C_7$ alkyl, —N(R$_4$)$_2$, —OR$_6$ or aryl;
wherein $R_6$ is straight chained or branched $C_1$-$C_7$ alkyl or aryl;
wherein each $R_{17}$ is independently H; straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_n$—O—(CH$_2$)$_m$—CH$_3$;
wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —NO$_2$; —N$_3$; —CN; —OR$_{21}$, —OCOR$_{21}$—COR$_{21}$, —NCOR$_{21}$, —N(R$_{21}$)$_2$, —CON(R$_{21}$)$_2$, or —COOR$_{21}$; aryl or heteroaryl; or two $R_{20}$ groups present on adjacent carbon atoms can join together to form a methylenedioxy group;
wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl ($C_1$-$C_6$) alkyl;
wherein each m is an integer from 0 to 4 inclusive;
wherein each n is an integer from 1 to 4 inclusive;
wherein each p is an integer from 0 to 2 inclusive;

wherein U is O, —NR$_{16}$, S, C(R$_{17}$)$_2$, or —NSO$_2$R$_{16}$;
wherein Z is $C_3$-$C_{10}$ cycloalkyl, $C_4$-$C_7$ cyclic ether, $C_4$-$C_7$ cyclic thioether, aryl, or heteroaryl;
wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, (CH$_2$)$_m$-Z, or (CH$_2$)$_q$—O—(CH$_2$)$_m$—CH$_3$;
wherein q is an integer from 2 to 4 inclusive;
wherein B is aryl, heteroaryl, aryl substituted with an aryl or heteroaryl, heteroaryl substituted with an aryl or heteroaryl, tricyclic heteroaryl or $Q_6$; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;
wherein a tricyclic heteroaryl is a fused three member aromatic system in which one or more of the rings is heteroaryl; carbazole; or acridine;
wherein $Q_6$ is

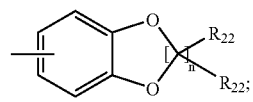

wherein each $R_{22}$ is independently H, F, Cl, or straight chained or branched $C_1$-$C_4$ alkyl;
or a pharmaceutically acceptable salt thereof.

The invention provides a method of treating a subject suffering from depression which comprises administering to the subject an amount of compound effective to treat the subject's depression wherein the compound has the structure:

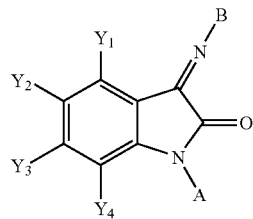

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of $Y_1$, $Y_2$, $Y_3$ and $Y_4$ present on adjacent carbon atoms can constitute a methylenedioxy group;
wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;
wherein A is A', straight chained or branched $C_1$-$C_7$ alkyl, aryl, heteroaryl, aryl($C_1$-$C_6$)alkyl or heteroaryl ($C_1$-$C_6$) alkyl;

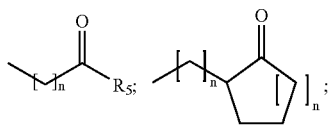

wherein A' is

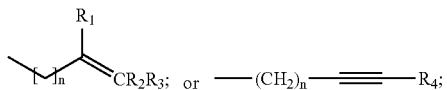

wherein $R_1$ and $R_2$ are each independently H, straight chained or branched $C_1$-$C_7$ alkyl, —F, —Cl, —Br, —I, —$NO_2$, or —CN;

wherein $R_3$ is H, straight chained or branched $C_1$-$C_7$ alkyl, —F, —Cl, —Br, —I, —$NO_2$, —CN, —$OR_6$ aryl or heteroaryl;

wherein $R_5$ is straight chained or branched $C_1$-$C_7$ alkyl, —$N(R_4)_2$, —$OR_6$ or aryl;

wherein $R_6$ is straight chained or branched $C_1$-$C_7$ alkyl or aryl;

wherein B is aryl, or heteroaryl; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

wherein n is an integer from 1 to 4 inclusive;

or a pharmaceutically acceptable salt thereof.

The invention provides a method of treating a subject suffering from depression which comprises administering to the subject an amount of compound effective to treat the subject's depression wherein the compound has the structure:

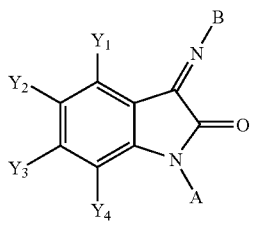

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —$NO_2$; —$N_3$; —CN; —$OR_4$, —$SR_4$, —$OCOR_4$, —$COR_4$, —$NCOR_4$, —$N(R_4)_2$, —$CON(R_4)_2$, or —$COOR_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is A', straight chained or branched $C_1$-$C_7$ alkyl, aryl, heteroaryl, aryl($C_1$-$C_6$)alkyl or heteroaryl ($C_1$-$C_6$) alkyl;

wherein A' is

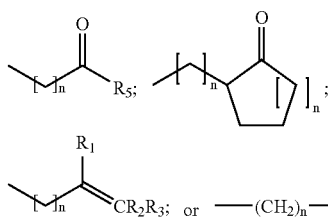

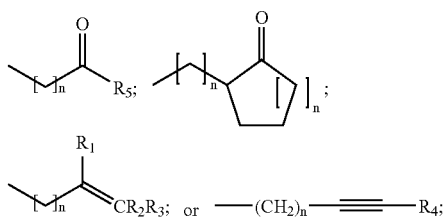

wherein B is aryl substituted with an aryl or heteroaryl, heteroaryl substituted with an aryl or heteroaryl, tricyclic heteroaryl or $Q_6$;

wherein a tricyclic heteroaryl is a fused three ring aromatic system in which one or more of the rings is heteroaryl; carbazole; or acridine;

wherein $Q_6$ is

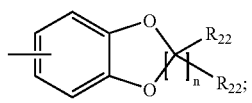

wherein n is an integer from 1 to 4 inclusive;

wherein each $R_{22}$ is independently H, F, Cl, or straight chained or branched $C_1$-$C_4$ alkyl;

or a pharmaceutically acceptable salt thereof.

The invention provides a method of treating a subject suffering from depression which comprises administering to the subject an amount of compound effective to treat the subject's depression wherein the compound has the structure:

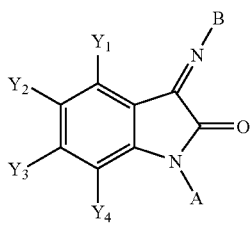

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —$NO_2$; —$N_3$; —CN; —$OR_4$, —$SR_4$, —$OCOR_4$, —$COR_4$, —$NCOR_4$, —$N(R_4)_2$, —$CON(R_4)_2$, or —$COOR_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is $Q_3$, $Q_4$, $Q_5$, aryl substituted with an aryl or heteroaryl, heteroaryl substituted with an aryl or heteroaryl, or $(CHR_{17})$—$(CHR_{17})_n$-Z;

wherein $Q_3$ is

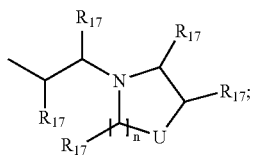

wherein $Q_4$ is

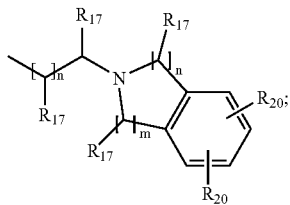

wherein $Q_5$ is

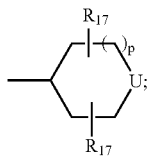

wherein each $R_{17}$ is independently H; straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein each $R_{22}$ is independently H, F, Cl, or straight chained or branched $C_1$-$C_4$ alkyl;

wherein q is an integer from 2 to 4 inclusive;

wherein each m is an integer from 0 to 4 inclusive;

wherein each n is an integer from 1 to 4 inclusive;

wherein each p is an integer from 0 to 2 inclusive;

wherein U is O, —$NR_{16}$, S, $C(R_{17})_2$, or —$NSO_2R_{16}$;

wherein Z is $C_3$-$C_{10}$ cycloalkyl, $C_4$-$C_7$ cyclic ether, $C_4$-$C_7$ cyclic thioether, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein B is aryl, or heteroaryl; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

or a pharmaceutically acceptable salt thereof.

As used in the present invention, the term cycloalkyl includes $C_3$-$C_7$ cycloalkyl moieties which may be substituted with one or more of the following: —F, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

As used in the present invention, the term "cycloalkenyl" includes $C_5$-$C_7$ cycloalkenyl moieties which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R)_2$, —$OR_4$, —$COR_4$, —$NCOR_4$, —$CO_2R_4$, —$CON(R_4)_2$ or $(CH_2)_n$—O—$(CH_2)_m$—$CH_3$.

In the present invention, the term "heteroaryl" is used to include five and six membered unsaturated rings that may contain one or more oxygen, sulfur, or nitrogen atoms. Examples of heteroaryl groups include, but are not limited to, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl.

In addition the term "heteroaryl" is used to include fused bicyclic ring systems that may contain one or more heteroatoms such as oxygen, sulfur and nitrogen. Examples of such heteroaryl groups include, but are not limited to, indolizinyl, indolyl, isoindolyl, benzo[b]furanyl, benzo[b]thiophenyl, indazolyl, benzimidazolyl, purinyl, benzoxazolyl, benzisoxazolyl, benzo[b]thiazolyl, imidazo[2,1-b]thiazolyl, cinnolinyl, quinazolinyl, quinoxalinyl, 1,8-naphthyridinyl, pteridinyl, quinolinyl, isoquinolinyl, phthalimidyl and 2,1,3-benzothiazolyl.

The term "heteroaryl" also includes those chemical moieties recited above which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

The term "heteroaryl" further includes the N-oxides of those chemical moieties recited above which include at least one nitrogen atom.

In the present invention the term "aryl" is phenyl or naphthyl. The term "aryl" also includes phenyl and naphthyl which may be substituted with one or more of the following: —F, —Cl, —Br, —I, —NO$_2$, —CN, straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_3$-C$_7$ cycloalkyl, C$_3$-C$_7$ monofluorocycloalkyl, C$_3$-C$_7$ polyfluorocycloalkyl, C$_5$-C$_7$ cycloalkenyl, —N(R$_4$)$_2$, —OR$_4$, —SR$_4$, —OCOR$_4$, —COR$_4$, —NCOR$_4$, —CO$_2$R$_4$, —CON(R$_4$)$_2$ or (CH$_2$)$_n$—O—(CH$_2$)$_m$—CH$_3$.

The present invention also provides a method of treating a subject suffering from depression which compromises administering to the subject an amount of compound effective to treat the subject's depression, wherein the compound has the structure:

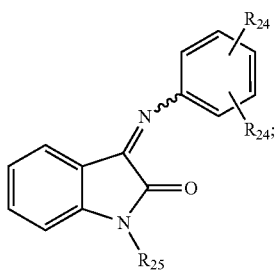

wherein each R$_{24}$ is independently one or more of the following: H, F, Cl, Br, I, CF$_3$, OCH$_3$ or NO$_2$;
wherein R$_{25}$ is methyl; ethyl, allyl, phenyl and the phenyl is optionally substituted with a F, Cl, Br, CF$_3$, NO$_2$.

In one embodiment of any one of the methods described herein, the compound is enantiomerically or diastereomerically pure. In one embodiment of any of the methods described herein, the compound is enantiomerically and diastereomerically pure.

In one embodiment, the compound is a pure Z imine isomer or a pure Z alkene isomer. In one embodiment, the compound is a pure E imine isomer or a pure E alkene isomer.

In one embodiment, the compound is administered orally.
In one embodiment, the compound has the structure:

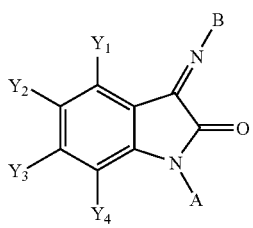

wherein each of Y$_1$, Y$_2$, Y$_3$, and Y$_4$ is independently —H;straight chained or branched C$_1$-C$_7$ alkyl, —CF$_3$, —F, —Cl, —Br, —I, —OR$_4$, —N(R$_4$)$_2$, or —CON(R$_4$)$_2$;
wherein each R$_4$ is independently —H; straight chained or branched C$_1$-C$_7$ alkyl, —CF$_3$, or phenyl;

wherein A is A', straight chained or branched C$_1$-C$_7$ alkyl, aryl, heteroaryl, aryl(C$_1$-C$_6$)alkyl or heteroaryl(C$_1$-C$_6$) alkyl; and
wherein A' is

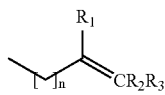

In one embodiment, B is heteroaryl. In one embodiment, B is aryl.

In one embodiment, B is phenyl and the phenyl is optionally substituted with one or more of the following: —F, —Cl, —Br, —CF$_3$, straight chained or branched C$_1$-C$_7$ alkyl, —N(R$_4$)$_2$, —OR$_4$, —COR$_4$, —NCOR$_4$, —CO$_2$R$_4$, or —CON(R$_4$)$_2$.

In one embodiment, A is aryl. In one embodiment, A is heteroaryl.

In one embodiment, the compound is selected from the group consisting of:

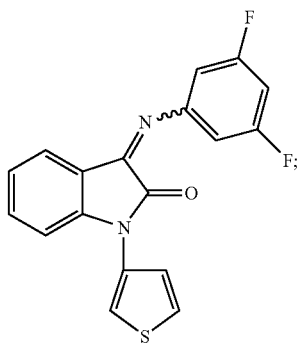

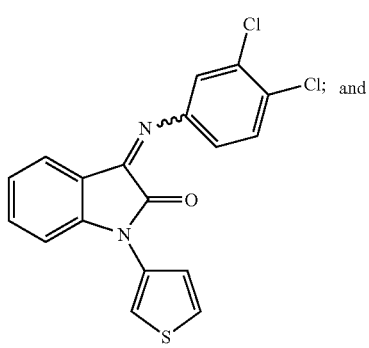

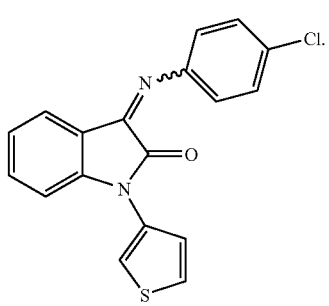

In one embodiment, the compound is selected from the group consisting of:
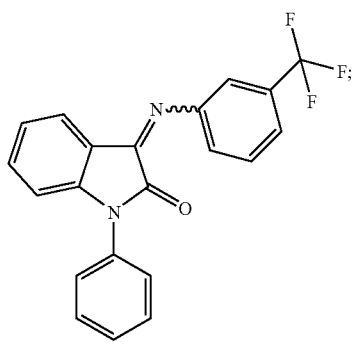
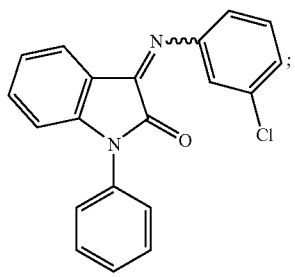
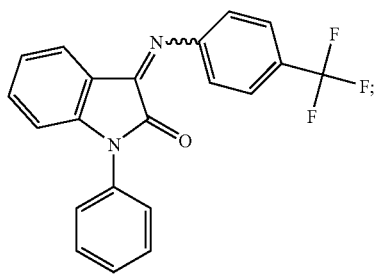
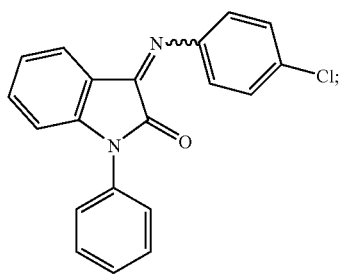
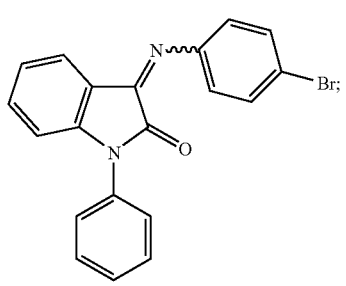
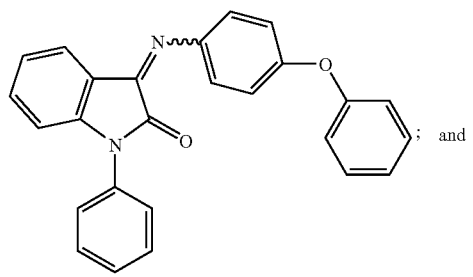
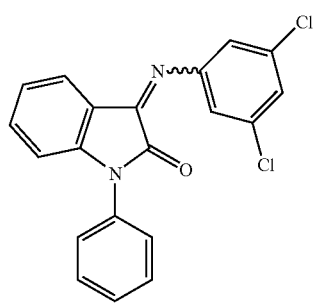
In one embodiment, A is A' and A' is
In one embodiment, the compound is:
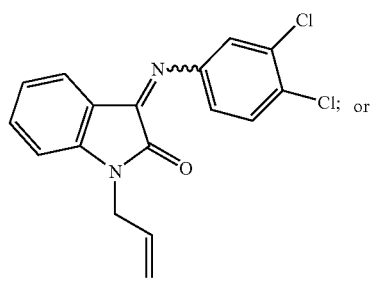
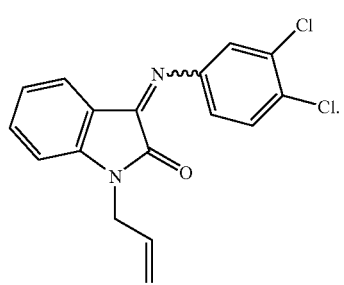
In one embodiment, B is $Q_6$.

In one embodiment, A is aryl.
In one embodiment, the compound has the structure:

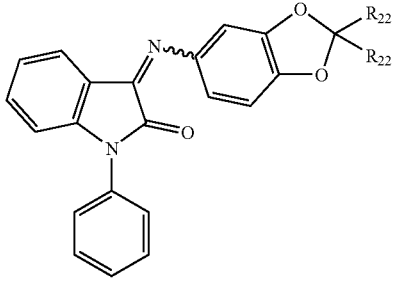

In one embodiment, the compound is:

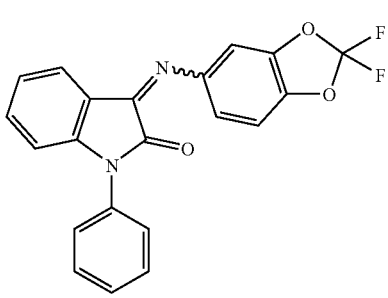

In one embodiment, B is aryl.
In one embodiment, A is (CHR$_{17}$)—(CHR$_{17}$)$_n$-Z.
In one embodiment, the compound is:

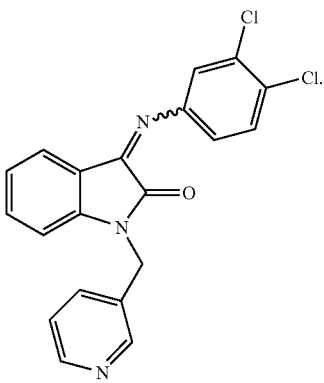

The invention provides a method of treating a subject suffering from anxiety which comprises administering to the subject an amount of compound effective to treat the subject's anxiety wherein the compound has the structure:

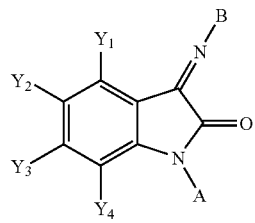

wherein each of Y$_1$, Y$_2$, Y$_3$, and Y$_4$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, or C$_5$-C$_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of Y$_1$, Y$_2$, Y$_3$ and Y$_4$ present on adjacent carbon atoms can constitute a methylenedioxy group;

wherein each R$_4$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, C$_5$-C$_7$ cycloalkenyl, aryl or aryl(C$_1$-C$_6$)alkyl;

wherein A is A', Q$_3$, Q$_4$, Q$_5$, straight chained or branched C$_1$-C$_7$ alkyl, aryl, heteroaryl, aryl(C$_1$-C$_6$)alkyl, heteroaryl (C$_1$-C$_6$)alkyl, aryl substituted with an aryl or heteroaryl, heteroaryl substituted with an aryl or heteroaryl; or (CHR$_{17}$)—(CHR$_{17}$)$_n$-Z;

wherein A' is

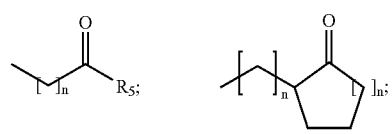

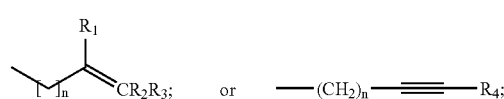

wherein Q$_3$ is

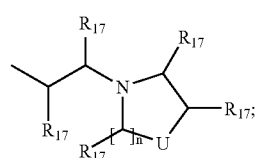

wherein Q$_4$ is

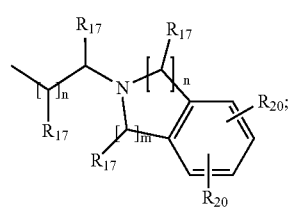

wherein $Q_5$ is

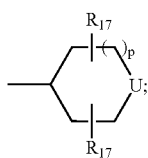

wherein $R_1$ and $R_2$ are each independently H, straight chained or branched $C_1$-$C_7$ alkyl, —F, —Cl, —Br, —I, —NO$_2$, or —CN;

wherein $R_3$ is H, straight chained or branched $C_1$-$C_7$ alkyl, —F, —Cl, —Br, —I, —NO$_2$, —CN, —OR$_6$, aryl or heteroaryl;

wherein $R_5$ is straight chained or branched $C_1$-$C_7$ alkyl, —N(R$_4$)$_2$, —OR$_6$ or aryl;

wherein $R_6$ is straight chained or branched $C_1$-$C_7$ alkyl or aryl;

wherein each $R_{17}$ is independently H; straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_n$—O—(CH$_2$)$_m$—CH$_3$;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$, —CON(R$_{21}$)$_2$, or —COOR$_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein each m is an integer from 0 to 4 inclusive;

wherein each n is an integer from 1 to 4 inclusive;

wherein each p is an integer from 0 to 2 inclusive;

wherein U is O, —NR$_{16}$, S, C(R$_{17}$)$_2$, or —NSO$_2$R$_{16}$;

wherein Z is $C_3$-$C_{10}$ cycloalkyl, $C_4$-$C_7$ cyclic ether, $C_4$-$C_7$ cyclic thioether, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_q$—O—(CH$_2$)$_m$—CH$_3$;

wherein q is an integer from 2 to 4 inclusive;

wherein B is aryl, heteroaryl, aryl substituted with an aryl or heteroaryl, heteroaryl substituted with an aryl or heteroaryl, tricyclic heteroaryl or $Q_6$; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

wherein a tricyclic heteroaryl is a fused three member aromatic system in which one or more of the rings is heteroaryl; carbazole; or acridine;

wherein $Q_6$ is

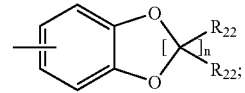

wherein each $R_{22}$ is independently H, F, Cl, or straight chained or branched $C_1$-$C_4$ alkyl;

or a pharmaceutically acceptable salt thereof.

The invention provides a method of treating a subject suffering from anxiety which comprises administering to the subject an amount of compound effective to treat the subject's anxiety wherein the compound has the structure:

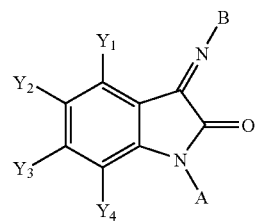

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is A', straight chained or branched $C_1$-$C_7$ alkyl, aryl, heteroaryl, aryl($C_1$-$C_6$)alkyl or heteroaryl ($C_1$-$C_6$) alkyl;

wherein A' is

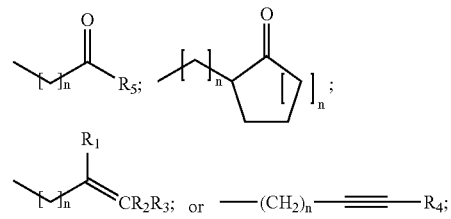

wherein $R_1$ and $R_2$ are each independently H, straight chained or branched $C_1$-$C_7$ alkyl, —F, —Cl, —Br, —I, —NO$_2$, or —CN;

wherein $R_3$ is H, straight chained or branched $C_1$-$C_7$ alkyl, —F, —Cl, —Br, —I, —NO$_2$, —CN, —OR$_6$ aryl or heteroaryl;

wherein $R_5$ is straight chained or branched $C_1$-$C_7$ alkyl, —N(R$_4$)$_2$, —OR$_6$ or aryl;

wherein $R_6$ is straight chained or branched $C_1$-$C_7$ alkyl or aryl;

wherein B is aryl, or heteroaryl; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

wherein n is an integer from 1 to 4 inclusive;

or a pharmaceutically acceptable salt thereof.

The invention provides a method of treating a subject suffering from anxiety which comprises administering to the subject an amount of compound effective to treat the subject's anxiety wherein the compound has the structure:

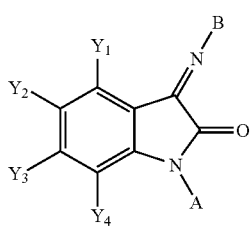

wherein each of $Y_1, Y_2, Y_3,$ and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —$NO_2$; —$N_3$; —CN; —$OR_4$, —$SR_4$, —$OCOR_4$, —$COR_4$, —$NCOR_4$, —$N(R_4)_2$, —$CON(R_4)_2$, or —$COOR_4$; aryl or heteroaryl; or any two of $Y_1, Y_2, Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is A', straight chained or branched $C_1$-$C_7$ alkyl, aryl, heteroaryl, aryl($C_1$-$C_6$)alkyl or heteroaryl ($C_1$-$C_6$) alkyl;

wherein A' is

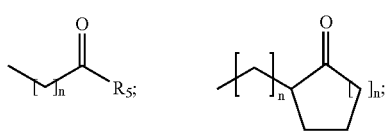

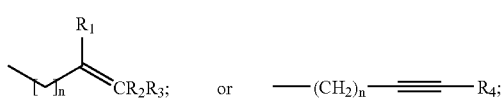

wherein B is aryl substituted with an aryl or heteroaryl, heteroaryl substituted with an aryl or heteroaryl, tricyclic heteroaryl or $Q_6$.

wherein a tricyclic heteroaryl is a fused three ring aromatic system in which one or more of the rings is heteroaryl; carbazole; or acridine;

wherein $Q_6$ is

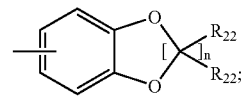

wherein n is an integer from 1 to 4 inclusive;

wherein each $R_{22}$ is independently H, F, Cl, or straight chained or branched $C_1$-$C_4$ alkyl;

or a pharmaceutically acceptable salt thereof.

The invention provides a method of treating a subject suffering from anxiety which comprises administering to the subject an amount of compound effective to treat the subject's anxiety wherein the compound has the structure:

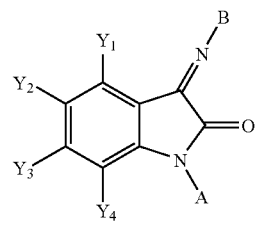

wherein each of $Y_1, Y_2, Y_3,$ and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —$NO_2$; —$N_3$; —CN; —$OR_4$, —$SR_4$, —$OCOR_4$, —$COR_4$, —$NCOR_4$, —$N(R_4)_2$, —$CON(R_4)_2$, or —$COOR_4$; aryl or heteroaryl; or any two of $Y_1, Y_2, Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is $Q_3, Q_4, Q_5$, aryl substituted with an aryl or heteroaryl, heteroaryl substituted with an aryl or heteroaryl, or $(CHR_{17})$—$(CHR_{17})_n$-Z;

wherein $Q_3$ is

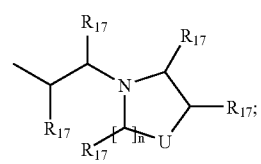

wherein $Q_4$ is

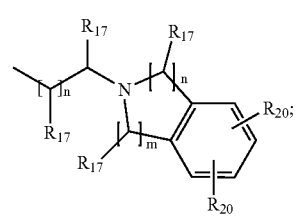

wherein $Q_5$ is

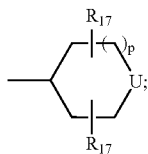

wherein each $R_{17}$ is independently H; straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein each $R_{22}$ is independently H, F, Cl, or straight chained or branched $C_1$-$C_4$ alkyl;

wherein q is an integer from 2 to 4 inclusive;

wherein each m is an integer from 0 to 4 inclusive;

wherein each n is an integer from 1 to 4 inclusive;

wherein each p is an integer from 0 to 2 inclusive;

wherein U is O, —$NR_{16}$, S, $C(R_{17})_2$, or —$NSO_2R_{16}$;

wherein Z is $C_3$-$C_{10}$ cycloalkyl, $C_4$-$C_7$ cyclic ether, $C_4$-$C_7$ cyclic thioether, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein B is aryl, or heteroaryl; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

or a pharmaceutically acceptable salt thereof.

As used in the present invention, the term "cycloalkyl" includes $C_3$-$C_7$ cycloalkyl moieties which may be substituted with one or more of the following: —F, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

As used in the present invention, the term "cycloalkenyl" includes $C_5$-$C_7$ cycloalkenyl moieties which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

In the present invention, the term "heteroaryl" is used to include five and six membered unsaturated rings that may contain one or more oxygen, sulfur, or nitrogen atoms. Examples of heteroaryl groups include, but are not limited to, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl.

In addition the term "heteroaryl" is used to include fused bicyclic ring systems that may contain one or more heteroatoms such as oxygen, sulfur and nitrogen. Examples of such heteroaryl groups include, but are not limited to, indolizinyl, indolyl, isoindolyl, benzo[b]furanyl, benzo[b]thiophenyl, indazolyl, benzimidazolyl, purinyl, benzoxazolyl, benzisoxazolyl, benzo[b]thiazolyl, imidazo[2,1-b]thiazolyl, cinnolinyl, quinazolinyl, quinoxalinyl, 1,8-naphthyridinyl, pteridinyl, quinolinyl, isoquinolinyl, phthalimidyl and 2,1,3-benzothiazolyl.

The term "heteroaryl" also includes those chemical moieties recited above which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

The term "heteroaryl" further includes the N-oxides of those chemical moieties recited above which include at least one nitrogen atom.

In the present invention the term "aryl" is phenyl or naphthyl. The term "aryl" also includes phenyl and naphthyl which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$SR_4$, —$OCOR_4$, —$COR_4$, —$NCOR_4$, —$CO_2R_4$, —$CON(R_4)_2$ or $(CH_2)_n$—O—$(CH_2)_m$—$CH_3$.

The present invention also provides a method of treating a subject suffering from anxiety which compromises administering to the subject an amount of compound effective to treat the subject's anxiety where in the compound has the structure:

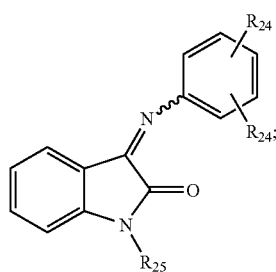

wherein each $R_{24}$ is independently one or more of the following: H, F, Cl, Br, I, $CF_3$, $OCH_3$ or $NO_2$;

wherein $R_{25}$ is methyl, ethyl, allyl, phenyl and the phenyl is optionally substituted with a F, Cl, Br, $CF_3$, $NO_2$.

In one embodiment of any of the methods described herein, the compound is enantiomerically and diastereomerically pure. In one embodiment of any of the methods described herein, the compound is enantiomerically or diastereomerically pure.

In one embodiment of any of the methods described herein, the compound is a pure Z imine isomer or a pure Z alkene isomer. In one embodiment, the compound is a pure. E imine isomer or a pure E alkene isomer.

In one embodiment, the compound has the structure:

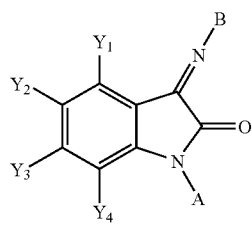

wherein each of $Y_1$, $Y_2$, $Y_3$, and $Y_4$ is independently —H; straight chained or branched $C_1$-$C_7$ alkyl, —$CF_3$, —F, —Cl, —Br, —I, —$OR_4$, —$N(R_4)_2$, or —$CON(R_4)_2$;

wherein each $R_4$ is independently —H; straight chained or branched $C_1$-$C_7$ alkyl, —$CF_3$, or phenyl;

wherein A is A', straight chained or branched $C_1$-$C_7$ alkyl, aryl, heteroaryl, aryl($C_1$-$C_6$)alkyl or heteroaryl($C_1$-$C_6$) alkyl; and wherein A' is

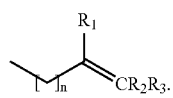

In one embodiment, B is heteroaryl. In one embodiment, B is aryl.

In one embodiment, B is phenyl and the phenyl is optionally substituted with one or more of the following: —F, —Cl, —Br, —$CF_3$, straight chained or branched $C_1$-$C_7$ alkyl, —$N(R_4)_2$, —$OR_4$, —$COR_4$, —$NCOR_4$, —$CO_2R_4$, or —$CON(R_4)_2$.

In one embodiment, A is aryl. In one embodiment, A is heteroaryl.

In one embodiment, the compound is selected from the group consisting of:

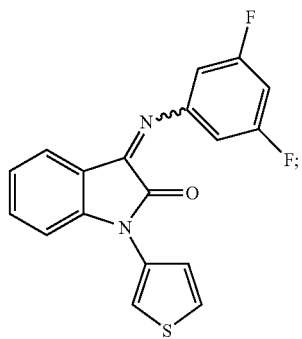

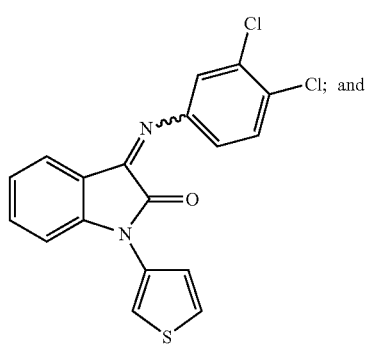

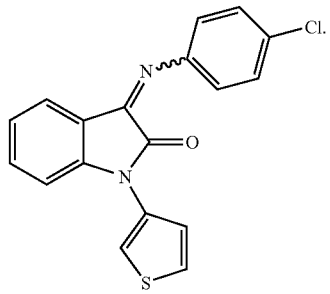

In one embodiment, the compound is selected from the group consisting of:

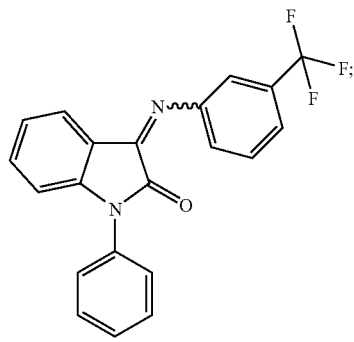

-continued
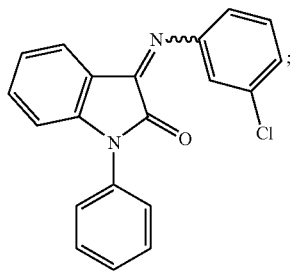
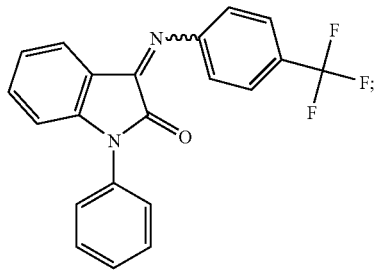
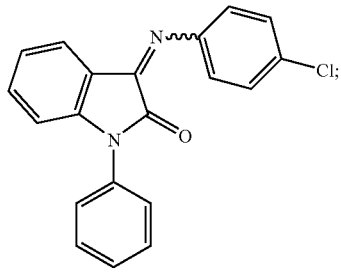
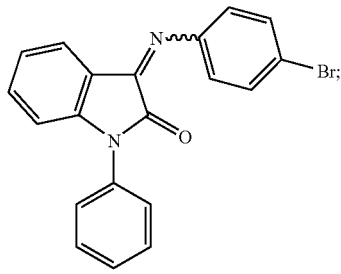
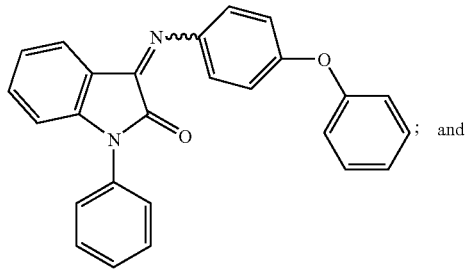; and
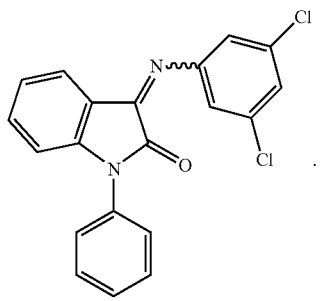.
In one embodiment, A is A' and A' is
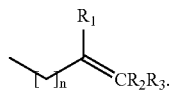
In one embodiment, the compound is:
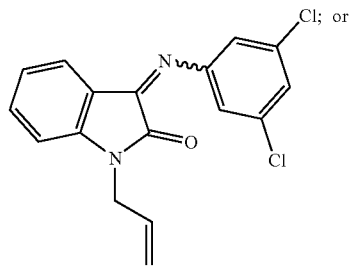; or
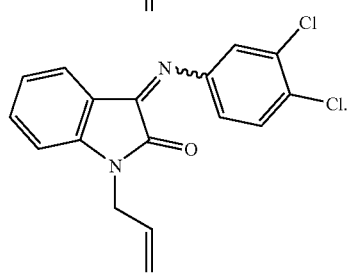.
In one embodiment, B is $Q_6$.
In one embodiment, A is aryl.
In one embodiment, the compound has the structure:
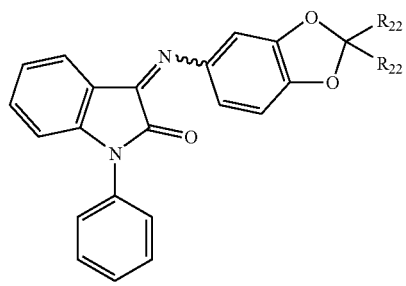
In one embodiment, the compound is:
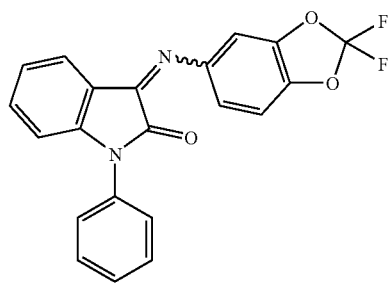
In one embodiment, B is aryl.
In one embodiment, A is $(CHR_{17})-(CHR_{17})_n-Z$.

In one embodiment, the compound is:

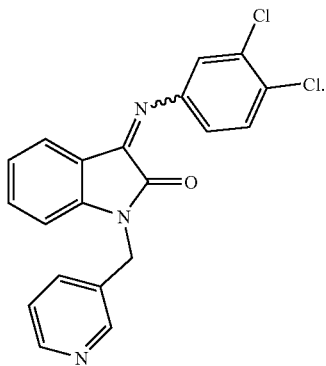

The invention provides a pharmaceutical composition comprising a pharmaceutically acceptable carrier and a compound having the structure:

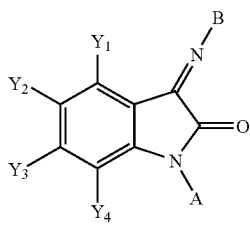

wherein each of $Y_1, Y_2, Y_3,$ and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of $Y_1, Y_2, Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl ($C_1$-$C_6$) alkyl;

wherein A is A', $Q_3$, $Q_4$, $Q_5$ straight chained or branched $C_1$-$C_7$ alkyl, aryl, heteroaryl, aryl($C_1$-$C_6$)alkyl, heteroaryl($C_1$-$C_6$)alkyl, aryl substituted with an aryl or heteroaryl, heteroaryl substituted with an aryl or heteroaryl; or (CHR$_{17}$)—(CHR$_{17}$)$_n$-Z;

wherein A' is

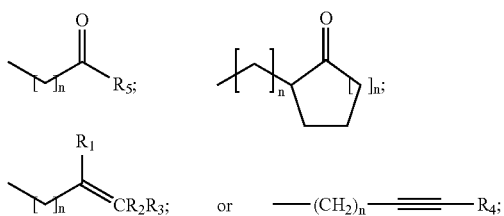

wherein $Q_3$ is

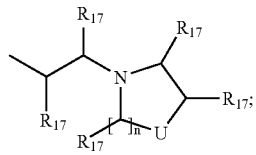

wherein $Q_4$ is

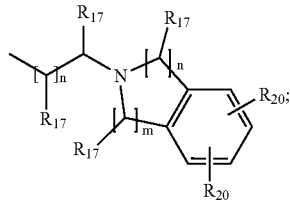

wherein $Q_5$ is

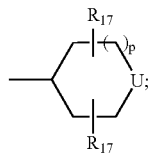

wherein $R_1$ and $R_2$ are each independently H, straight chained or branched $C_1$-$C_7$ alkyl, —F, —Cl, —Br, —I, —NO$_2$, or —CN;

wherein $R_3$ is H, straight chained or branched $C_1$-$C_7$ alkyl, —F, —Cl, —Br, —I, —NO$_2$, —CN, —OR$_6$, aryl or heteroaryl;

wherein $R_5$ is straight chained or branched $C_1$-$C_7$ alkyl, —N(R$_4$)$_2$, —OR$_6$ or aryl;

wherein $R_6$ is straight chained or branched $C_1$-$C_7$ alkyl or aryl;

wherein each $R_{17}$ is independently H; straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_n$—O—(CH$_2$)$_m$—CH$_3$;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$, —CON(R$_{21}$)$_2$, or —COOR$_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein each m is an integer from 0 to 4 inclusive;
wherein each n is an integer from 1 to 4 inclusive;
wherein each p is an integer from 0 to 2 inclusive;

wherein U is O, —NR$_{16}$, S, C(R$_{17}$)$_2$, or —NSO$_2$R$_{16}$;

wherein Z is C$_3$-C$_{10}$ cycloalkyl, C$_4$-C$_7$ cyclic ether, C$_4$-C$_7$ cyclic thioether, aryl, or heteroaryl;

wherein R$_{16}$ is straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_5$-C$_7$ cycloalkenyl, —(CH$_2$)$_m$-Z, or (CH$_2$)$_q$—O—(CH$_2$)$_m$—CH$_3$;

wherein q is an integer from 2 to 4 inclusive;

wherein B is aryl, heteroaryl, aryl substituted with an aryl or heteroaryl, heteroaryl substituted with an aryl or heteroaryl, tricyclic heteroaryl or Q$_6$; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

wherein a tricyclic heteroaryl is a fused three member aromatic system in which one or more of the rings is heteroaryl; carbazole; or acridine;

wherein Q$_6$ is

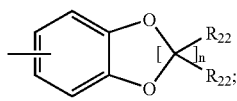

wherein each R$_{22}$ is independently H, F, Cl, or straight chained or branched C$_1$-C$_4$ alkyl;

or a pharmaceutically acceptable salt thereof.

The invention provides a pharmaceutical composition comprising a pharmaceutically acceptable carrier and a compound having the structure:

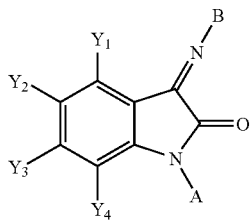

wherein each of Y$_1$, Y$_2$, Y$_3$, and Y$_4$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, or C$_5$-C$_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of Y$_1$, Y$_2$, Y$_3$ and Y$_4$ present on adjacent carbon atoms can constitute a methylenedioxy group;

wherein each R$_4$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, C$_5$-C$_7$ cycloalkenyl, aryl or aryl(C$_1$-C$_6$)alkyl;

wherein A is A', straight chained or branched C$_1$-C$_7$ alkyl, aryl, heteroaryl, aryl(C$_1$-C$_6$)alkyl or heteroaryl(C$_1$-C$_6$) alkyl;

wherein A' is

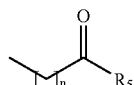  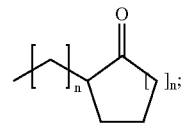

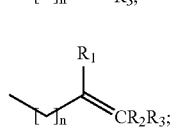  or  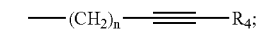

wherein R$_1$ and R$_2$ are each independently H, straight chained or branched C$_1$-C$_7$ alkyl, —F, —Cl, —Br, —I, —NO$_2$, or —CN;

wherein R$_3$ is H, straight chained or branched C$_1$-C$_7$ alkyl, —F, —Cl, —Br, —I, —NO$_2$, —CN, —OR$_6$ aryl or heteroaryl;

wherein R$_5$ is straight chained or branched C$_1$-C$_7$ alkyl, —N(R$_4$)$_2$, —OR$_6$ or aryl;

wherein R$_6$ is straight chained or branched C$_1$-C$_7$ alkyl or aryl;

wherein B is aryl, or heteroaryl; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

wherein n is an integer from 1 to 4 inclusive;

or a pharmaceutically acceptable salt thereof.

The invention provides a pharmaceutical composition comprising a pharmaceutically acceptable carrier and a compound having the structure:

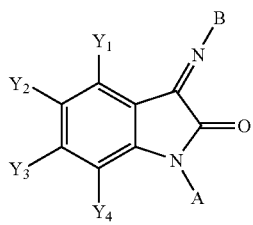

wherein each of Y$_1$, Y$_2$, Y$_3$, and Y$_4$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, or C$_5$-C$_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of Y$_1$, Y$_2$, Y$_3$ and Y$_4$ present on adjacent carbon atoms can constitute a methylenedioxy group;

wherein each R$_4$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, C$_3$-C$_7$ cycloalkenyl, aryl or aryl(C$_1$-C$_6$)alkyl;

wherein A is A', straight chained or branched C$_1$-C$_7$ alkyl, aryl, heteroaryl, aryl(C$_1$-C$_6$)alkyl or heteroaryl (C$_1$-C$_6$) alkyl;

wherein A' is

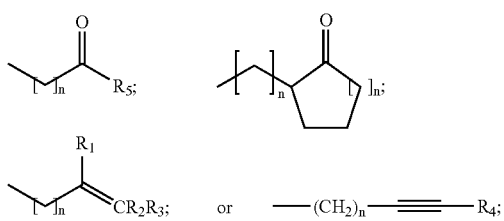

wherein B is aryl substituted with an aryl or heteroaryl, heteroaryl substituted with an aryl or heteroaryl, tricyclic heteroaryl or $Q_6$;

wherein a tricyclic heteroaryl is a fused three ring aromatic system in which one or more of the rings is heteroaryl; carbazole; or acridine;

wherein $Q_6$ is

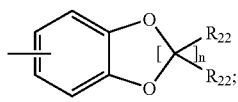

wherein n is an integer from 1 to 4 inclusive;

wherein each $R_{22}$ is independently H, F, Cl, or straight chained or branched $C_1$-$C_4$ alkyl;

or a pharmaceutically acceptable salt thereof.

The invention provides a pharmaceutical composition comprising a pharmaceutically acceptable carrier and a compound having the structure:

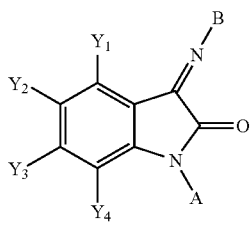

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is $Q_3$, $Q_4$, $Q_5$, aryl substituted with an aryl or heteroaryl, heteroaryl substituted with an aryl or heteroaryl, or (CHR$_{17}$)—(CHR$_{17}$)$_n$-Z;

wherein $Q_3$ is

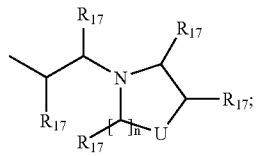

wherein $Q_4$ is

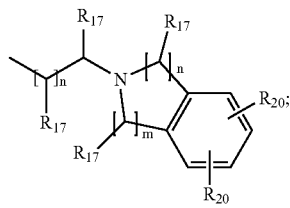

wherein $Q_5$ is

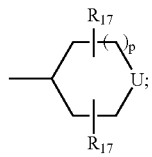

wherein each $R_{17}$ is independently H; straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_n$—O—(CH$_2$)$_m$—CH$_3$;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$—, —CON(R$_{21}$)$_2$, or —COOR$_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein each $R_{22}$ is independently H, F, Cl, or straight chained or branched $C_1$-$C_4$ alkyl;

wherein q is an integer from 2 to 4 inclusive;

wherein each m is an integer from 0 to 4 inclusive;

wherein each n is an integer from 1 to 4 inclusive;

wherein each p is an integer from 0 to 2 inclusive;

wherein U is O, —NR$_{16}$, S, C(R$_{17}$)$_2$, or —NSO$_2$R$_{16}$;

wherein Z is $C_3$-$C_{10}$ cycloalkyl, $C_4$-$C_7$ cyclic ether, $C_4$-$C_7$ cyclic thioether, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_q$—O—(CH$_2$)$_m$—CH$_3$;

wherein B is aryl, or heteroaryl; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

or a pharmaceutically acceptable salt thereof.

As used in the present invention, the term "cycloalkyl" includes $C_3$-$C_7$ cycloalkyl moieties which may be substituted with one or more of the following: —F, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

As used in the present invention, the term "cycloalkenyl" includes $C_5$-$C_7$ cycloalkenyl moieties which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, $CO_2R_4$, —$CON(R_4)_2$ or $(CH_2)_n$—O—$(CH_2)_m$—$CH_3$.

In the present invention, the term "heteroaryl" is used to include five and six membered unsaturated rings that may contain one or more oxygen, sulfur, or nitrogen atoms. Examples of heteroaryl groups include, but are not limited to, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl.

In addition the term "heteroaryl" is used to include fused bicyclic ring systems that may contain one or more heteroatoms such as oxygen, sulfur and nitrogen. Examples of such heteroaryl groups include, but are not limited to, indolizinyl, indolyl, isoindolyl, benzo[b]furanyl, benzo[b]thiophenyl, indazolyl, benzimidazolyl, purinyl, benzoxazolyl, benzisoxazolyl, benzo[b]thiazolyl, imidazo[2,1-b]thiazolyl, cinnolinyl, quinazolinyl, quinoxalinyl, 1,8-naphthyridinyl, pteridinyl, quinolinyl, isoquinolinyl, phthalimidyl and 2,1,3-benzothiazolyl.

The term "heteroaryl" also includes those chemical moieties recited above which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, $OR_4$, —$COR_4$, —$NCOR_4$, —$CO_2R_4$, —$CON(R_4)_2$ or $(CH_2)_n$—O—$(CH_2)_m$—$CH_3$.

The term "heteroaryl" further includes the N-oxides of those chemical moieties recited above which include at least one nitrogen atom.

In the present invention the term "aryl" is phenyl or naphthyl. The term "aryl" also includes phenyl and naphthyl which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$SR_4$, —$OCOR_4$, —$COR_4$, —$NCOR_4$, —$CO_2R_4$, —$CON(R_4)_2$ or $(CH_2)_n$—O—$(CH_2)_m$—$CH_3$.

In one embodiment of any of the pharmaceutical compositions described herein, the compound is enantiomerically and diastereomerically pure. In one embodiment, the compound is enantiomerically or diastereomerically pure.

In one embodiment, the compound is a pure Z imine isomer or a pure Z alkene isomer.

In one embodiment, the compound is a pure E imine isomer or a pure E alkene isomer.

In one embodiment, the composition can be administered orally.

In one embodiment of the pharmaceutical composition, the compound has the structure:

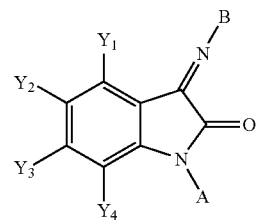

wherein each of $Y_1$, $Y_2$, $Y_3$, and $Y_4$ is independently —H; straight chained or branched $C_1$-$C_7$ alkyl, —$CF_3$, —F, —Cl, —Br, —I, —$OR_4$, —$N(R_4)_2$, or —$CON(R_4)_2$;

wherein each $R_4$ is independently —H; straight chained or branched $C_1$-$C_7$ alkyl, —$CF_3$, or phenyl;

wherein A is A', straight chained or branched $C_1$-$C_7$ alkyl, aryl, heteroaryl, aryl($C_1$-$C_6$)alkyl or heteroaryl ($C_1$-$C_6$) alkyl; and wherein A' is

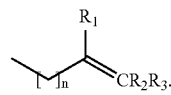

In one embodiment, B is heteroaryl.

In one embodiment, B is aryl.

In one embodiment, B is phenyl and the phenyl is optionally substituted with one or more of the following: —F, —Cl, —Br, —$CF_3$, straight chained or branched $C_1$-$C_7$ alkyl, —$N(R_4)_2$, —$OR_4$, —$COR_4$, —$NCOR_4$, —$CO_2R_4$, or —$CON(R_4)_2$.

In one embodiment, A is aryl. In one embodiment, A is heteroaryl.

In one embodiment, the compound is selected from the group consisting of:

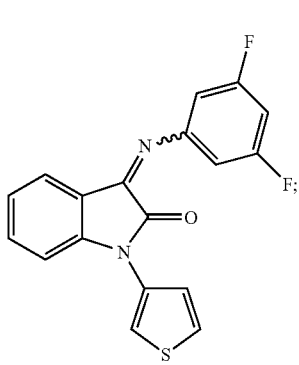

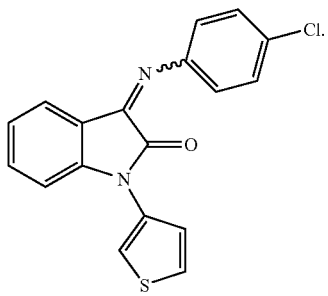

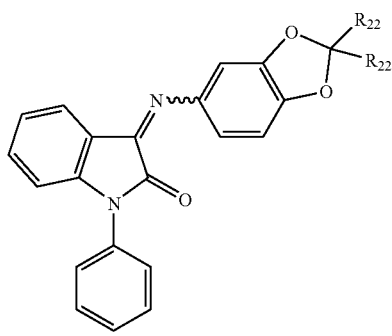

In one embodiment, B is $Q_6$.
In one embodiment, A is aryl.
In one embodiment, the compound has the structure:

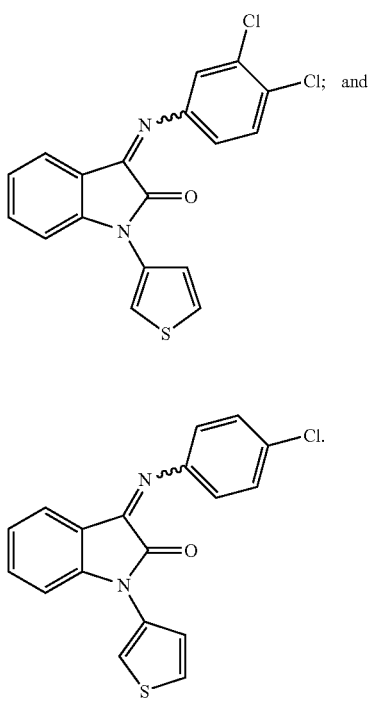

In one embodiment, the compound is:

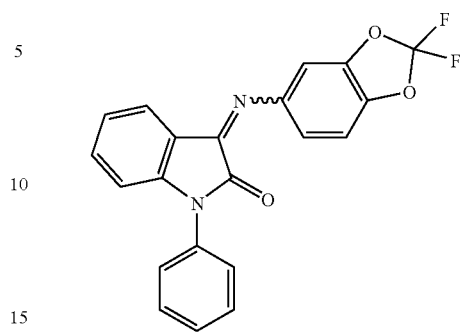

In one embodiment, B is aryl.
In one embodiment, A is $(CHR_{17})-(CHR_{17})_n$-Z.
In one embodiment, the compound is:

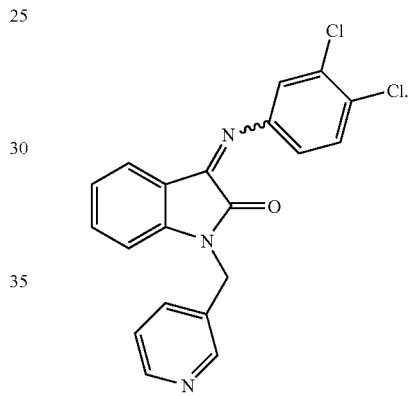

The invention provides a compound having the structure:

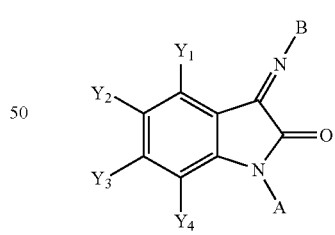

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO₂; —N₃; —CN; —OR₄, —SR₄, —OCOR₄, —COR₄, —NCOR₄, —N(R₄)₂, —CON(R₄)₂, or —COOR₄; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is A', $Q_3$, $Q_4$, $Q_5$, straight chained or branched $C_1$-$C_7$ alkyl, aryl, heteroaryl, aryl($C_1$-$C_6$)alkyl, heteroaryl ($C_1$-$C_6$)alkyl, aryl substituted with an aryl or heteroaryl, heteroaryl substituted with an aryl or heteroaryl; or $(CHR_{17})$—$(CHR_{17})_n$-Z;

wherein A' is

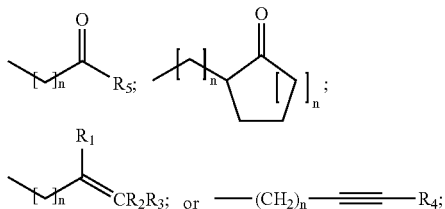

wherein $Q_3$ is

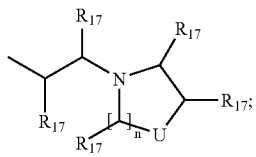

wherein $Q_4$ is

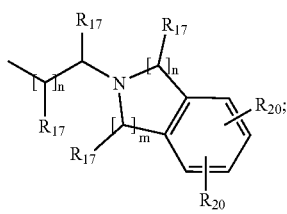

wherein $Q_5$ is

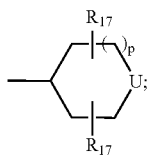

wherein $R_1$ and $R_2$ are each independently H, straight chained or branched $C_1$-$C_7$ alkyl, —F, —Cl, —Br, —I, —NO$_2$, or —CN;

wherein $R_3$ is H, straight chained or branched $C_1$-$C_7$ alkyl, —F, —Cl, —Br, —I, —NO$_2$, —CN, —OR$_6$ aryl or heteroaryl;

wherein $R_5$ is straight chained or branched $C_1$-$C_7$ alkyl, —N(R$_4$)$_2$, —OR$_6$ or aryl;

wherein $R_6$ is straight chained or branched $C_1$-$C_7$ alkyl or aryl;

wherein each $R_{17}$ is independently H; straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_n$—O—(CH$_2$)$_m$—CH$_3$;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$, —CON(R$_{21}$)$_2$, or —COOR$_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein each m is an integer from 0 to 4 inclusive;
wherein each n is an integer from 1 to 4 inclusive;
wherein each p is an integer from 0 to 2 inclusive;
wherein U is O, —NR$_{16}$, S, C(R$_{17}$)$_2$, or —NSO$_2$R$_{16}$;
wherein Z is $C_3$-$C_{10}$ cycloalkyl, $C_4$-$C_7$ cyclic ether, $C_4$-$C_7$ cyclic thioether, aryl, or heteroaryl;
wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_q$—O—(CH$_2$)$_m$—CH$_3$;
wherein q is an integer from 2 to 4 inclusive,
wherein B is aryl, heteroaryl, aryl substituted with an aryl or heteroaryl, heteroaryl substituted with an aryl or heteroaryl, tricyclic heteroaryl or $Q_6$; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;
wherein a tricyclic heteroaryl is a fused three member aromatic system in which one or more of the rings is heteroaryl; carbazole; or acridine;
wherein $Q_6$ is

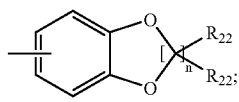

wherein each $R_{22}$ is independently H, F, Cl, or straight chained or branched $C_1$-$C_4$ alkyl;

or a pharmaceutically acceptable salt thereof.

The invention provides a compound having the structure:

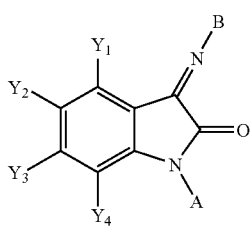

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is A', straight chained or branched $C_1$-$C_7$ alkyl, aryl, heteroaryl, aryl($C_1$-$C_6$)alkyl or heteroaryl($C_1$-$C_6$)alkyl;

wherein A' is

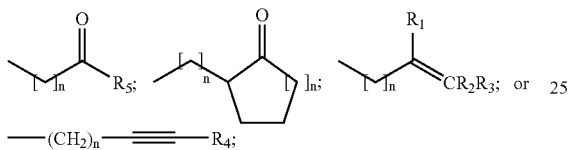

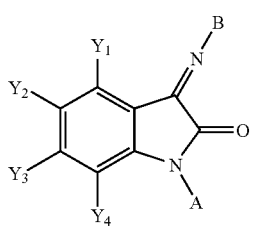

wherein $R_1$ and $R_2$ are each independently H, straight chained or branched $C_1$-$C_7$ alkyl, —F, —Cl, —Br, —I, —NO$_2$, or —CN;

wherein $R_3$ is H, straight chained or branched $C_1$-$C_7$ alkyl, —F, —Cl, —Br, —I, —NO$_2$, —CN, —OR$_6$ aryl or heteroaryl;

wherein $R_5$ is straight chained or branched $C_1$-$C_7$ alkyl, —N(R$_4$)$_2$, —OR$_6$ or aryl;

wherein $R_6$ is straight chained or branched $C_1$-$C_7$ alkyl or aryl;

wherein B is aryl, or heteroaryl; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

wherein n is an integer from 1 to 4 inclusive;

or a pharmaceutically acceptable salt thereof.

The invention provides a compound having the structure:

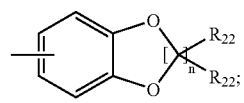

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is A', straight chained or branched $C_1$-$C_7$ alkyl, aryl, heteroaryl, aryl($C_1$-$C_6$)alkyl or heteroaryl ($C_1$-$C_6$) alkyl;

wherein A' is

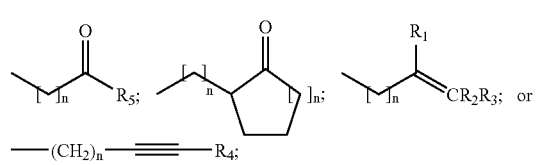

wherein B is aryl substituted with an aryl or heteroaryl, heteroaryl substituted with an aryl or heteroaryl, tricyclic heteroaryl or $Q_6$;

wherein a tricyclic heteroaryl is a fused three ring aromatic system in which one or more of the rings is heteroaryl; carbazole; or acridine;

wherein $Q_6$ is

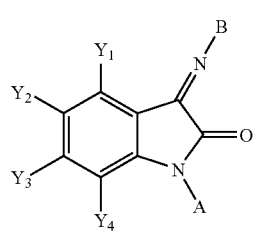

wherein n is an integer from 1 to 4 inclusive;

wherein each $R_{22}$ is independently H, F, Cl, or straight chained or branched $C_1$-$C_4$ alkyl;

or a pharmaceutically acceptable salt thereof.

The invention provides a compound having the structure:

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is $Q_3$, $Q_4$, $Q_5$, aryl substituted with an aryl or heteroaryl, heteroaryl substituted with an aryl or heteroaryl, or $(CHR_{17})$—$(CHR_{17})_n$-Z;

wherein $Q_3$ is

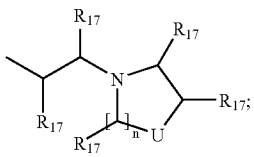

wherein $Q_4$ is

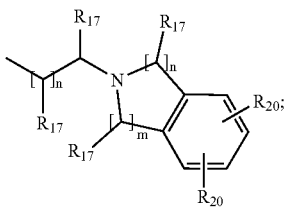

wherein $Q_5$ is

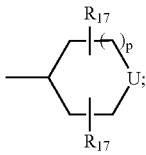

wherein each $R_{17}$ is independently H; straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; $OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein each $R_{22}$ is independently H, F, Cl, or straight chained or branched $C_1$-$C_4$ alkyl;

wherein q is an integer from 2 to 4 inclusive;

wherein each m is an integer from 0 to 4 inclusive;

wherein each n is an integer from 1 to 4 inclusive;

wherein each p is an integer from 0 to 2 inclusive;

wherein U is O, —$NR_{16}$, S, $C(R_{17})_2$, or —$NSO_2R_{16}$;

wherein Z is $C_3$-$C_{10}$ cycloalkyl, $C_4$-$C_7$ cyclic ether, $C_4$-$C_7$ cyclic thioether, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein B is aryl, or heteroaryl; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

or a pharmaceutically acceptable salt thereof.

As used in the present invention, the term "cycloalkyl" includes $C_3$-$C_7$ cycloalkyl moieties which may be substituted with one or more of the following: —F, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

As used in the present invention, the term "cycloalkenyl" includes $C_5$-$C_7$ cycloalkenyl moieties which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

In the present invention, the term "heteroaryl" is used to include five and six membered unsaturated rings that may contain one or more oxygen, sulfur, or nitrogen atoms. Examples of heteroaryl groups include, but are not limited to, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl.

In addition the term "heteroaryl" is used to include fused bicyclic ring systems that may contain one or more heteroatoms such as oxygen, sulfur and nitrogen. Examples of such heteroaryl groups include, but are not limited to, indolizinyl, indolyl, isoindolyl, benzo[b]furanyl, benzo[b]thiophenyl, indazolyl, benzimidazolyl, purinyl, benzoxazolyl, benzisoxazolyl, benzo[b]thiazolyl, imidazo[2,1-b]thiazolyl, cinnolinyl, quinazolinyl, quinoxalinyl, 1,8-naphthyridinyl, pteridinyl, quinolinyl, isoquinolinyl, phthalimidyl and 2,1,3-benzothiazolyl.

The term "heteroaryl" also includes those chemical moieties recited above which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

The term "heteroaryl" further includes the N-oxides of those chemical moieties recited above which include at least one nitrogen atom.

In the present invention the term "aryl" is phenyl or naphthyl. The term "aryl" also includes phenyl and naphthyl which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$SR_4$, —$OCOR_4$, —$COR_4$, —$NCOR_4$, —$CO_2R_4$, —$CON(R_4)_2$ or $(CH_2)_n$—O—$(CH_2)_m$—$CH_3$.

In one embodiment of any of the compounds described herein, the compound is enantiomerically and diastereomerically pure. In one embodiment, the compound is enantiomerically or diastereomerically pure.

In one embodiment, the compound is a pure Z imine isomer or a pure Z alkene isomer.

In one embodiment, the compound is a pure E imine isomer or a pure E alkene isomer.

In one embodiment, the compound can be administered orally.

In one embodiment, the compound has the structure:

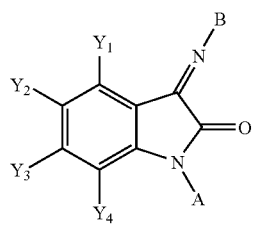

wherein each of $Y_1$, $Y_2$, $Y_3$, and $Y_4$ is independently —H; straight chained or branched $C_1$-$C_7$ alkyl, —$CF_3$, —F, —Cl, —Br, —I, —$OR_4$, —$N(R_4)_2$, or —$CON(R_4)_2$;

wherein each $R_4$ is independently —H; straight chained or branched $C_1$-$C_7$ alkyl, —$CF_3$, or phenyl;

wherein A is A', straight chained or branched $C_1$-$C_7$ alkyl, aryl, heteroaryl, aryl($C_1$-$C_6$)alkyl or heteroaryl($C_1$-$C_6$) alkyl; and wherein A' is

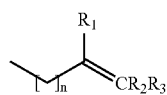

In one embodiment, B is heteroaryl.
In one embodiment, B is aryl.
In one embodiment, B is phenyl and the phenyl is optionally substituted with one or more of the following: —F, —Cl, —Br, —$CF_3$, straight chained or branched $C_1$-$C_7$ alkyl, —$N(R_4)_2$, —$OR_4$, —$COR_4$, —$NCOR_4$, —$CO_2R_4$, or —$CON(R_4)_2$.

In one embodiment, A is aryl.
In one embodiment, A is heteroaryl.
In one embodiment, the compound is selected from the group consisting of:

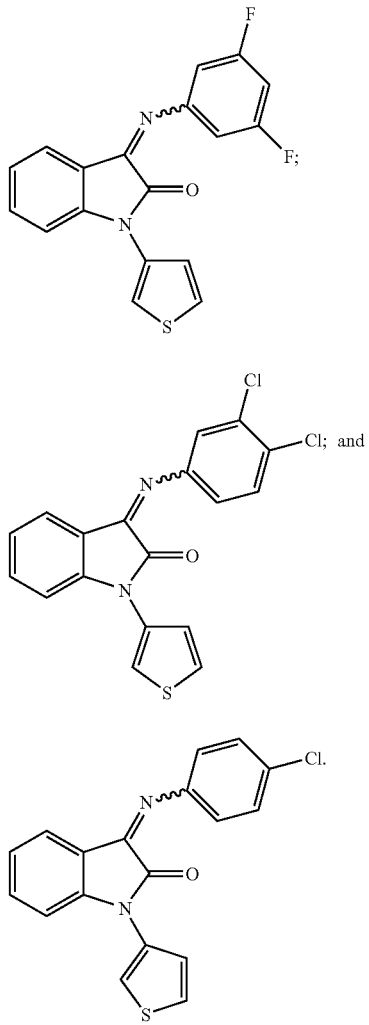

In one embodiment, B is $Q_6$.
In one embodiment, A is aryl.
In one embodiment, the compound has the structure:

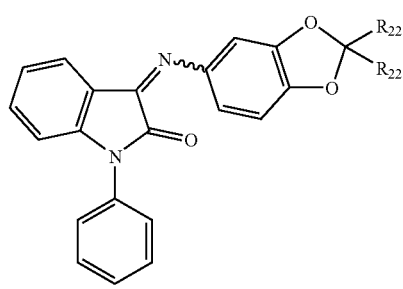

In one embodiment, the compound is:

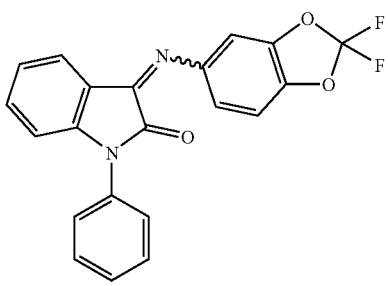

In one embodiment, B is aryl.
In one embodiment, A is $(CHR_{17})-(CHR_{17})_n-Z$.
In one embodiment, the compound is:

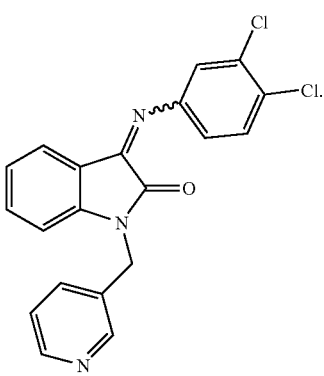

In one embodiment, the compound is a pure Z imine isomer.

In one embodiment, the compound is a pure E imine isomer.

The invention provides a pharmaceutical composition comprising a therapeutically effective amount of any of the compounds described herein and a pharmaceutically acceptable carrier.

The invention provides a pharmaceutical composition made by combining a therapeutically effective amount of any of the compounds described herein and a pharmaceutically acceptable carrier.

The invention provides a process for making a pharmaceutical composition comprising combining a therapeutically effective amount of any of the compounds described herein and a pharmaceutically acceptable carrier.

The invention provides a method of treating a subject suffering from depression which comprises administering to the subject an amount of any of the compounds described herein effective to treat the subject's depression.

The invention provides a method of treating a subject suffering from anxiety which comprises administering to the subject an amount of any of the compounds described herein effective to treat the subject's anxiety.

The invention provides a method of treating a subject suffering from depression and anxiety which comprises administering to the subject an amount of any of the compounds described herein effective to treat the subject's depression and anxiety.

The invention provides for each pure stereoisomer of any of the compounds described herein. Such stereoisomers may include enantiomers, diastereomers, or E or Z alkene or imine isomers. The invention also provides for stereoisomeric mixtures, including racemic mixtures, diastereomeric mixtures, or E/Z isomeric mixtures. Stereoisomers can be synthesized in pure form (Nógrádi, M.; Stereoselective Synthesis, (1987) VCH Editor Ebel, H. and Asymmetric Synthesis, Volumes 3-5, (1983) Academic Press, Editor Morrison, J.) or they can be resolved by a variety of methods such as crystallization and chromatographic techniques (Jaques, J.; Collet, A.; Wilen, S.; Enantiomer, Racemates, and Resolutions, 1981, John Wiley and Sons and Asymmetric Synthesis, Vol. 2, 1983, Academic Press, Editor Morrison, J).

In addition the compounds of the present invention may be present as enantiomers, diastereomers, isomers or two or more of the compounds may be present to form a racemic or diastereomeric mixture.

The compounds of the present invention are preferably 80% pure, more preferably 90% pure, and most preferably 95% pure.

Included in this invention are pharmaceutically acceptable salts and complexes of all of the compounds described herein. The acids and bases from which these salts are prepared include but are not limited to the acids and bases listed herein. The acids include, but are not limited to, the following inorganic acids: hydrochloric acid, hydrobromic acid, hydroiodic acid, sulfuric acid and boric acid. The acids include, but are not limited to, the following organic acids: acetic acid, malonic acid, succinic acid, fumaric acid, tartaric acid, maleic acid, citric acid, methanesulfonic acid, benzoic acid, glycolic acid, lactic acid and mandelic acid. The bases include, but are not limited to ammonia, methylamine, ethylamine, propylamine, dimethylamine, diethylamine, trimethylamine, triethylamine, ethylenediamine, hydroxyethylamine, morpholine, piperazine and guanidine. This invention further provides for the hydrates and polymorphs of all of the compounds described herein.

The present invention includes within its scope prodrugs of the compounds of the invention. In general, such prodrugs will be functional derivatives of the compounds of the invention which are readily convertible in vivo into the required compound. Thus, in the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in Design of Prodrugs, ed. H. Bundgaard, Elsevier, 1985.

The present invention further includes metabolites of the compounds of the present invention. Metabolites include active species produced upon introduction of compounds of this invention into the biological milieu.

Throughout the invention, the term "binding affinity" describes the concentration of a compound required to occupy one-half of the binding sites in a receptor population, as detectable by radioligand binding. Binding affinity concentration can be represented as $K_i$, inhibition constant, or $K_D$, dissociation constant.

The term "selectivity of binding affinity" refers to the ability of a chemical compound to discriminate one receptor from another. For example, a compound showing selectivity for receptor A versus receptor B will bind receptor A at lower concentrations than those required to bind receptor B.

Therefore, the statements of the form "binds to the GAL3 receptor with a binding affinity at least ten-fold higher than" a named receptor, indicates that the binding affinity at the GAL3 receptor is at least ten-fold greater than that for a named receptor, and binding affinity measurements (i.e. $K_i$ or $K_D$) for the compound are at least ten-fold lower in numerical value.

The present invention provides a method of treating depression in a subject which comprises administering to the subject a composition comprising a pharmaceutically acceptable carrier and a therapeutically effective amount of a GAL3 receptor antagonist, wherein:
(a) the GAL3 receptor antagonist binds to the human GAL3 receptor with a binding affinity at least ten-fold higher than the binding affinity with which it binds to the human GAL1 receptor;
(b) (1) the GAL3 receptor antagonist does not inhibit the activity of central monoamine oxidase A greater than 50 percent, at a concentration of 10 µM; and
   (2) the GAL3 receptor antagonist does not inhibit the activity of central monoamine oxidase B greater than 50 percent, at a concentration of 10 µM; and
(c) the GAL3 receptor antagonist binds to the human GAL3 receptor with a binding affinity at least ten-fold higher than the binding affinity with which it binds to each of the following transporters: serotonin transporter, norepinephrine transporter, and dopamine transporter.

The present invention provides a method of treating anxiety in a subject which comprises administering to the subject a composition comprising a pharmaceutically acceptable carrier and a therapeutically effective amount of a GAL3 receptor antagonist, wherein:
(a) the GAL3 receptor antagonist binds to the human GAL3 receptor with a binding affinity at least ten-fold higher than the binding affinity with which it binds to the human GAL1 receptor; and
(b) the GAL3 receptor antagonist binds to the human GAL3 receptor with a binding affinity at least ten-fold higher than the binding affinity with which it binds to each of the following transporters: serotonin transporter, norepinephrine transporter, and dopamine transporter.

In some embodiments of this invention, the GAL3 receptor antagonist binds to the human GAL3 receptor with a binding affinity at least 30-fold higher than the binding affinity with which it binds to the human GAL1 receptor.

In further embodiments of the invention, the GAL3 receptor antagonist binds to the human GAL3 receptor with a binding affinity at least 50-fold higher than the binding affinity with which it binds to the human GAL1 receptor.

In other embodiments of the invention, the GAL3 receptor antagonist binds to the human GAL3 receptor with a binding affinity at least 100-fold higher than the binding affinity with which it binds to the human GAL1 receptor.

In still other embodiments of the invention, the GAL3 receptor antagonist binds to the human GAL3 receptor with a binding affinity at least 200-fold higher than the binding affinity with which it binds to the human GAL1 receptor.

For the purposes of this invention the term "pharmaceutically acceptable carrier" has been defined herein.

The term "antagonist" refers to a compound which binds to, and decreases the activity of, a receptor in the presence of an agonist. In the case of a G-protein coupled receptor, activation may be measured using an appropriate second messenger system which is coupled to the receptor in a cell or tissue in which the receptor is expressed. Some specific but by no means limiting examples of well-known second messenger systems are adenylate cyclase, intracellular calcium mobilization, ion channel activation, guanylate cyclase, inositol phospholipid hydrolysis, and MAP kinase activation. Conversely, the term "agonist" refers to a compound which binds to, and increases the activity of, a receptor as compared with the activity of the receptor in the absence of any agonist. Methods to perform second messenger assays are described in PCT International Publication No. 97/46250 and in PCT International Publication No. 98/15570, the contents of which are hereby incorporated by reference.

In the case that a receptor has activity in the absence of an agonist (constitutive receptor activity) the antagonist may act as an inverse agonist or an allosteric modulator, as opposed to a neutral antagonist, and suppress receptor signaling independent of the agonist (Lutz and Kenakin, 1999). The categories of "antagonist compounds" are therefore seen to include 1) neutral antagonists (which block agonist actions but do not affect constitutive activity); 2) inverse agonists (which block agonist actions as well as constitutive activity by stabilizing an inactive receptor conformation); 3) and allosteric modulators (which block agonist actions to a limited extent and which may also block constitutive activity through allosteric regulation). The probability that an antagonist is neutral and therefore of "zero efficacy" is relatively low, given that this would require identical affinities for different tertiary conformations of the receptor. Thus, Kenakin proposed in 1996 that, "with the development of sensitive test systems for the detection of inverse agonism will come a reclassification of many drugs. It might be observed that numerous previously classified neutral antagonists may be inverse agonists" (Kenakin, 1996). Indeed, there is now evidence from studies with known pharmacological agents to support the existence of inverse agonists for numerous receptors, including histamine, $5HT_{1A}$, $5HT_{2C}$, cannabinoid, dopamine, calcitonin and human formyl peptide receptors, among others (de Ligt, et al, 2000; Herrick-Davis, et al, 2000; Bakker, et al, 2000). In the case of the $5HT_{2C}$ receptor, clinically effective atypical antipsychotics drugs such as sertindole, clozapine, olanzapine, ziprasidone, risperidone, zotepine, tiospirone, fluperlapine and tenilapine displayed potent inverse activity whereas typical antipsychotic drugs such as chlorpromazine, thioridazine, spiperone and thiothixene were classified as neutral antagonists (Herrick-Davis et al, 2000). In the case of the histamine $H_1$ receptor, the therapeutically used anti-allergics cetirizine, loratadine and epinastine were found to be inverse agonists. These findings further extend the idea that many compounds previously thought of as neutral antagonists will be reclassified as inverse agonists when tested in a constitutively active receptor system (de Ligt et al, 2000).

For the purpose of the claimed invention, a GAL3 antagonist useful in the treatment of depression is one which a) selectively binds to the GAL3 receptor, and b) displays antidepressant activity in the rat Forced Swim Test. Furthermore, a GAL3 antagonist useful in the treatment of anxiety is one which a) selectively binds to the GAL3 receptor, and b) displays anxiolytic activity in the rat Social Interaction. Also for the purpose in the present invention, a GAL3 antagonist useful in the treatment of depression and anxiety, is one which a) selectively binds to the GAL3 receptor, b) displays antidepressant activity in the rat Forced Swim Test, and c) displays anxiolytic activity in the rat Social Interaction Test.

In order to test compounds for selective binding to the human GAL3 receptor the cloned cDNAs encoding both the human and rat GALL and GAL2 receptors have been used. The cloning and assay methods for the human and rat GAL1 receptors may be found in PCT International Publication No. WO 95/22608, the contents of which are hereby incorporated by reference. The cloning and assay methods for the human and rat GAL2 receptors may be found in PCT International Publication No. WO 97/26853, the contents of which are hereby incorporated by reference.

The present invention provides for a method of determining the binding affinity of a GAL3 antagonist, wherein the GAL3 antagonist is dissolved in a "suitable solvent". A "suitable solvent" means one which permits the measurement of binding affinity of the GAL3 antagonist to the human GAL3 receptor at concentrations less than 1 µM, preferably less than 100 nM. Examples of solvents include, but are not limited to, DMSO, ethanol, N,N-dimethylacetamide, or water. For indolones, the preferred solvent is 3% DMSO (final concentration in the assay). For pyrimidines, the preferred solvent is 1% ethanol/0.09% polypuronic acid F-127 (final concentration in the assay). For any other type of compounds, the preferred solvent is the solvent which permits the measurement of binding affinity of a GAL3 antagonist at the lowest concentration. Once a suitable solvent is ascertained for the binding assay of the human GAL3 receptor, the same solvent is used in assays to determine the binding affinity at the GAL1 receptor, the serotonin transporter, the norepinephrine transporter, and the dopamine transporter. A solvent of 0.4% DMSO is used in the central monoamine oxidase enzyme assay.

In certain embodiments, the aforementioned GAL3 receptor antagonist additionally binds to the human GAL3 receptor with a binding affinity at least ten-fold higher than the binding affinity with which it binds to the human GAL2 receptor.

In other embodiments, the GAL3 receptor antagonist additionally binds to the human GAL3 receptor with a binding affinity at least 30-fold higher than the binding affinity with which it binds to the human GAL2 receptor.

In still other embodiments, the GAL3 receptor antagonist additionally binds to the human GAL3 receptor with a binding affinity at least 50-fold higher than the binding affinity with which it binds to the human GAL2 receptor.

In some embodiments, the GAL3 receptor antagonist additionally binds to the human GAL3 receptor with a binding affinity at least 100-fold higher than the binding affinity with which it binds to the human GAL2 receptor.

In further embodiments, the GAL3 receptor antagonist, additionally binds to the human GAL3 receptor with a binding affinity at least 200-fold higher than the binding affinity with which it binds to the human GAL2 receptor.

In other embodiments, the receptor antagonist also binds to the human GAL3 receptor with a binding affinity at least ten-fold higher than the binding affinity with which it binds to each of the human $5HT_{1B}$, human $5HT_{1D}$, human $5HT_{1E}$, human $5HT_{1F}$, human $5HT_{2A}$, rat $5HT_{2C}$, human $5HT_6$ and human $5HT_7$ receptors.

In still another embodiment, the receptor antagonist also binds to the human GAL3 receptor with a binding affinity at least ten-fold higher than the binding affinity with which it binds to the human histamine $H_1$ receptor.

In still another embodiment, the receptor antagonist also binds to the human GAL3 receptor with a binding affinity at least ten-fold higher than the binding affinity with which it binds to the human dopamine $D_1$, $D_2$, $D_3$, $D_4$ and $D_5$ receptors.

In a further embodiment, the receptor antagonist also binds to the human GAL3 receptor with a binding affinity at least ten-fold higher than the binding affinity with which it binds to the human $\alpha_{1A}$ adrenoceptor, the human $\alpha_{1B}$ adrenoceptor and the human $\alpha_{1D}$ adrenoceptor.

In another embodiment, the receptor antagonist also binds to the human GAL3 receptor with a binding affinity at least ten-fold higher than the binding affinity with which it binds to the human $\alpha_{2A}$ adrenoceptor, the human $\alpha_{2B}$ adrenoceptor and the human $\alpha_{2C}$ adrenoceptor.

In certain embodiments, the GAL3 receptor antagonist also binds to the human GAL3 receptor with a binding affinity less than ten-fold higher than the binding affinity with which it binds to the human $5HT_4$ receptor.

In further embodiments, the GAL3 receptor antagonist also binds to the human GAL3 receptor with a binding affinity less than ten-fold higher than the binding affinity with which it binds to the human $5HT_{1A}$ receptor.

In some embodiments the receptor antagonist does not inhibit the activity of central monoamine oxidase A greater than 30 percent. In further embodiments the receptor antagonist does not inhibit the activity of central monoamine oxidase B greater than 30 percent. In other embodiments the receptor antagonist does not inhibit the activity of central monoamine oxidase A greater than 15 percent. In still other embodiments the receptor antagonist does not inhibit the activity of central monoamine oxidase B greater, than 15 percent. In still other embodiments the receptor antagonist does not inhibit the activity of central monoamine oxidase A and/or central monoamine oxidase B greater than 10 percent.

The binding properties of compounds at different receptors were determined using cultured cell lines that selectively express the receptor of interest. Cell lines were prepared by transfecting the cloned cDNA or cloned genomic DNA or constructs containing both genomic DNA and cDNA encoding the receptors as further described in the Experimental Details herein below. Furthermore, the binding interactions of compounds at different transporters and enzymes were determined using tissue preparations and specific assays as further described in the Experimental Details herein below.

In connection with this invention, a number of cloned receptors discussed herein, as stably transfected cell lines, have been made pursuant to, and in satisfaction of, the Budapest Treaty on the International Recognition of the Deposit of Microorganisms for the Purpose of Patent Procedure, and are made with the American Type Culture Collection, 10801 University Blvd., Manassas, Va. 20110-2209. Specifically, these deposits have been accorded ATCC Accession Numbers as follows:

| Designation | Receptor | ATCC Accession No. | Date of Deposit |
|---|---|---|---|
| | human GAL1 | CRL-1650 | |
| (CHO)hGalR2-264 | human GAL2 | CRL 12379 | Jul. 22, 1997 |
| L-hGalR3-228 | human GAL3 | CRL-12373 | Jul. 01, 1997 |
| 5HT1A-3 | human 5-$HT_{1A}$ | CRL 11889 | May 11, 1995 |
| Ltk-11 | human 5-$HT_{1B}$ (formerly human 5-HT1D2) | CRL 10422 | Apr. 17, 1990 |
| Ltk-8-30-84 | human 5-$HT_{1D}$ (formerly human 5-HT1D1) | CRL 10421 | Apr. 17, 1990 |
| $5HT_{1E}$-7 | human 5-$HT_{1E}$ | CRL 10913 | Nov. 06, 1991 |
| L-5-$HT_{1F}$ | human 5-$HT_{1F}$ | CRL 10957 | Dec. 27, 1991 |
| L-NGC-5$HT_2$ | human 5-$HT_{2A}$ (formerly human 5-HT2) | CRL 10287 | Oct. 31, 1989 |
| pSr-1c | rat 5-$HT_{2C}$ (formerly rat 5HT1C) | 67636 | |
| pBluescript-hS10 | human 5-$HT_4$ | 75392 | Dec. 22, 1992 |
| L-5HT-4B | human 5-$HT_7$ (formerly human 5-HT4B) | CRL 11166 | Oct. 20, 1992 |
| L-$\alpha_{1C}$ | human $\alpha_{1A}$ (formerly human α1C) | CRL11140 | Sep. 25, 1992 |
| L-$\alpha_{1B}$ | human $\alpha_{1B}$ | CRL11139 | Sep. 25, 1992 |

-continued

ATCC Deposits:

| Designation | Receptor | ATCC Accession No. | Date of Deposit |
|---|---|---|---|
| L-$\alpha_{1A}$ | human $\alpha_{1D}$ (formerly hum $\alpha$1A) | CRL11138 | Sep. 25, 1992 |
| L-$\alpha_{2A}$ | human $\alpha_{2A}$ | CRL11180 | Nov. 06, 1992 |
| L-NGC-$\alpha_{2B}$ | human $\alpha_{2B}$ | CRL10275 | Oct. 25, 1989 |
| L-$\alpha_{2C}$ | human $\alpha_{2C}$ | CRL11181 | Nov. 06, 1992 |
| pDopD$_1$-GL-30 | human D$_5$ (formerly hum D1$\beta$) | 40839 | Jul. 10, 1990 |
| pCEXV-H$_1$ | human H$_1$ | 75346 | Nov. 06, 1992 |

The "5-HT$_{1C}$", "5-HT$_{1D1}$", "5-HT$_{1D2}$", "5-HT$_{4B}$", and "5-HT$_7$" receptors were renamed the "5-HT$_{2C}$", "5-HT$_{1D}$", "5-HT$_{1B}$", "5-HT$_7$", and "5-HT$_{2A}$" receptors, respectively, by the Serotonin Receptor Nomenclature Committee of the IUPHAR.
The "human $\alpha_{1C}$", "human $\alpha_{1A}$", and "human D$_{1\beta}$" were renamed the "human $\alpha_{1A}$", "human $\alpha_{1D}$", and "human D$_5$" respectively.

The following receptor sequences have been deposited with the GenBank DNA database, which is managed by the National Center for Biotechnology (Bethesda, Md.).

GENBANK DEPOSITS

| DESIGNATION | RECEPTOR | GENBANK No. |
|---|---|---|
| human mRNA for D-1 receptor | human D$_1$ (formerly human D$_{1\alpha}$) | X58987 |
| human dopamine D2 receptor (DRD2) mRNA complete cds | human D$_2$ | M29066 |
| Rat mRNA for dopamine D3 receptor | rat D$_3$ | X53944 |
| *Homo sapiens* dopamine D4 receptor (DRD4) gene (D4.4) sequence | human D$_4$ | L12397 |

*The "human D$_{1\alpha}$" receptor was renamed the "human D$_1$" receptor.

This invention further provides a pharmaceutical composition comprising a therapeutically effective amount of the compound of the invention and a pharmaceutically acceptable carrier. In one embodiment, the amount of the compound is an amount from about 0.01 mg to about 800 mg. In another embodiment, the amount of the compound is an amount from about 0.01 mg to about 500 mg. In another embodiment, the amount of the compound is an amount from about 0.01 mg to about 250 mg. In another embodiment, the amount of the compound is an amount from about 0.1 mg to about 60 mg. In another embodiment, the amount of the compound is an amount from about 1 mg to about 20 mg. In a further embodiment, the carrier is a liquid and the composition is a solution. In another embodiment, the carrier is a solid and the composition is a powder or tablet. In a further embodiment, the carrier is a gel and the composition is a capsule or suppository.

This invention provides a pharmaceutical composition made by combining a therapeutically effective amount of the compound of this invention and a pharmaceutically acceptable carrier.

This invention provides a process for making a pharmaceutical composition comprising combining a therapeutically effective amount of the compound of this invention and a pharmaceutically acceptable carrier.

In the subject invention a "therapeutically effective amount" is any amount of a compound which, when administered to a subject suffering from a disease against which the compounds are effective, causes reduction, remission, or regression of the disease. In the subject application, a "subject" is a vertebrate, a mammal, or a human.

The present invention provides for a method of treating a subject suffering from depression which comprises administering to the subject an amount of a compound provided in the present invention effective to treat the subject's depression. The present invention also provides for a method of treating a subject suffering from anxiety which comprises administering to the subject an amount of a compound provided in the present invention effective to treat the subject's anxiety. The present invention further provides for a method of treating a subject suffering from depression and anxiety which comprises administering to the subject an amount of a compound described in the present invention effective to treat the subject's depression and anxiety.

The present invention provides for the use of any of the chemical compounds disclosed herein for the preparation of a pharmaceutical composition for treating an abnormality. The invention also provides for the use of a chemical compound for the preparation of a pharmaceutical composition for treating an abnormality, wherein the abnormality is alleviated by decreasing the activity of a human GAL3 receptor. In one embodiment, the abnormality is depression. In one embodiment, the abnormality is anxiety. In one embodiment, the abnormality is depression and anxiety.

In one embodiment, the chemical compound is a GAL3 receptor antagonist, wherein:
  (a) the GAL3 receptor antagonist binds to the human GAL3 receptor with a binding affinity at least ten-fold higher than the binding affinity with which it binds to the human GAL1 receptor;
  (b) (1) the GAL3 receptor antagonist does not inhibit the activity of central monoamine oxidase A greater than 50 percent, at a concentration of 10 µM; and
  (2) the GAL3 receptor antagonist does not inhibit the activity of central monoamine oxidase B greater than 50 percent, at a concentration of 10 µM; and
  (c) the GAL3 receptor antagonist binds to the human GAL3 receptor with a binding affinity at least ten-fold higher than the binding affinity with which it binds to each of the following transporters: serotonin transporter, norepinephrine transporter, and dopamine transporter.

In one embodiment, the chemical compound is a GAL3 receptor antagonist, wherein:
  (a) the GAL3 receptor antagonist binds to the human GAL3 receptor with a binding affinity at least ten-fold higher than the binding affinity with which it binds to the human GAL1 receptor; and
  (b) the GAL3 receptor antagonist binds to the human GAL3 receptor with a binding affinity at least ten-fold higher than the binding affinity with which it binds to each of the following transporters: serotonin transporter, norepinephrine transporter, and dopamine transporter.

In the present invention the term "pharmaceutically acceptable carrier" is any pharmaceutical carrier known to those of ordinary skill in the art as useful in formulating pharmaceutical compositions. On Dec. 24, 1997 the Food and Drug Administration of the United States Department of Health and Human Services published a guidance entitled "Q3C Impurities: Residual Solvent". The guidance recommends acceptable amounts of residual solvents in pharmaceuticals for the safety of the patient, and recommends the use of less toxic solvents in the manufacture of drug substances and dosage forms. Table 1 of the guidance lists "Class 1 Solvents". The guidance then states that the use of Class 1 Solvents should be avoided in the production of drug substances, excipients, or drug products unless their use can be strongly justified in a risk-benefit assessment. The guidance further states that Class 2 Solvents should be limited in order to protect patients from potentially adverse effects. The guidance characterized the following solvents as Class 1 Solvents: benzene, carbon tetrachloride, 1,2-dichloroethane, 1,1-dichloroethene, and 1,1,1-trichloroethane. The guidance characterized the following solvents as Class 2 Solvents: acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidone, nitromethane, pyridine, sulfolane, tetralin, toluene, 1,1,2-trichloroethene and xylene. As used in this invention the term "pharmaceutically acceptable carrier" shall not include Class 1 or Class 2 Solvents.

In an embodiment of the present invention, the pharmaceutical carrier may be a liquid and the pharmaceutical composition would be in the form of a solution. In another embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch. In yet a further embodiment, the compound may be delivered to the subject by means of a spray or inhalant.

A solid carrier can include one or more substances which may also act as endogenous carriers (e.g. nutrient or micronutrient carriers), flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmoregulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate or isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The compound can be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms, such as pills, capsules, granules; tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

I. Synthesis of Chemical Compounds

The following examples are for the purpose of illustrating methods useful for making compounds of this invention.

General Methods: All reactions were performed under an Argon atmosphere and the reagents, neat or in appropriate solvents, were transferred to the reaction vessel via syringe and cannula techniques. Anhydrous solvents were purchased from the Aldrich Chemical Company and used as received. The examples described in the patent were named using the ACD/Name Program (version 4.01, Advanced Chemistry Development Inc., Toronto, Ontario, M5H2L3, Canada). The $^1$H NMR and $^{13}$C NMR spectra were recorded at either 300 MHz (GEQE Plus) or 400 MHz (Bruker Avance) in CDCl$_3$ as solvent and tetramethylsilane as the internal standard unless otherwise noted. Chemical shifts ($\delta$) are expressed in ppm, coupling constants (J) are expressed in Hz, and splitting patterns are described as follows: s=singlet; d=doublet; t=triplet; q=quartet; quintet; sextet; septet; br=broad; m=mutiplet; dd=doublet of doublets; dt=doublet of triplets. Elemental analyses were performed by Robertson Microlit Laboratories, Inc. Unless otherwise, mass spectra were obtained using electrospray ionization (ESI, Micromass Platform II) and MH$^+$ is reported. Thin-layer Chromatography (TLC) was carried out on glass plates pre-coated with silica gel 60 F$_{254}$ (0.25 mm, EM Separations Tech.). Preparative TLC was carried out on glass sheets pre-coated with silica gel GF (2 mm, Analtech). Flash column chromatography was performed on Merck silica gel 60 (230-400 mesh). Melting points (mp) were determined in open capillary tubes on a Mel-Temp apparatus and are uncorrected.

The following additional abbreviations are used: HOAc, acetic acid; DIPEA, diisopropylethylamine; DMF, N,N-dimethylformamide; EtOAc, ethyl acetate; MeOH, methanol; TEA, triethylamine; THF, tetrahydrofuran; All solvent ratios are volume/volume unless stated otherwise.

A. General Procedures for Preparing Pyrimidines

The compounds of this invention were prepared by successively displacing the three chlorine atoms of a 2,4,6-trichloropyrimidine with amines. It was found that some amines (i.e. anilines) selectively displace the 2-position chlorine of 2,4,6-trichloropyrimidine, whereas other amines (e.g. piperidine) selectively displace the 4- or 6-position chlorine first (note that the 4- and 6-positions are chemically equivalent). Some amines react non-selectively at both the 2- and 4-positions of 2,4,6-trichloropyrimidine. It was also found that if the pyrimidine is substituted at the 4- or 6-position with an amine (mono- or di-substituted, or unsubstituted), then the next amine (mono- or di-substituted) undergoes substitution at the 2-position of the pyrimidine. Thus, several different Procedures were used to obtain the compounds described by this invention. The following Procedures are representative of the methods that are useful for making compounds of this invention.

Procedure A:

4,6-DICHLORO-N-PHENYL-2-PYRIMIDINAMINE: A solution of 2,4,6-trichloropyrimidine (5.5 g, 30 mmol) in tetrahydrofuran (15 mL) was added dropwise to a solution of aniline (2.8 mL, 1 equivalent) in tetrahydrofuran (25 mL). N,N-diisopropylethylamine (5.2 mL) was added and the solution was stirred at room temperature overnight. The solvent was removed and the crude material was purified by flash chromatography on silica gel. The column was eluted with 3% ethyl acetate in hexane, followed by 15% ethyl acetate in hexane. The eluent was removed, giving 4,6-dichloro-N-phenyl-2-pyrimidinamine (1.11 g, 4.6 mmol, 15%, $R_f$=0.4 in 3% ethyl acetate in hexane).

Procedure B:

4,6-DICHLORO-N-(3,4-DICHLOROPHENYL)-2-PYRIMIDINAMINE: A solution of 2,4,6-trichloropyrimidine (5.00 g), 3,4-dichloroaniline (4.45 g, 1 equivalent) in 1,4-dioxane (20 mL) and N,N-diisopropylethylamine (10 mL) was heated at reflux with stirring for 3 hours. The solvent was removed and the crude material was purified by flash chromatography on silica gel. The column was eluted with a gradient of cyclohexane to ethyl acetate/cyclohexane (1:9). The eluent was removed, giving 4,6-dichloro-N-(3,4-dichlorophenyl)-2-pyrimidinamine (1.83 g, 58%, $R_f$=0.39 in ethyl acetate/cyclohexane, 2:3).

Procedure C:

6-CHLORO-$N^4$,$N^4$-DIMETHYL-$N^2$-PHENYL-2,4-PYRIMIDINEDIAMINE: Dimethylamine in tetrahydrofuran (2M, 15 mL) was added to a solution of 4,6-dichloro-N-phenyl-2-pyrimidinamine (0.715 g, 2.97 mmol) in tetrahydrofuran (30 mL) and N,N-diisopropylethylamine (0.52 mL). The resulting mixture was stirred at room temperature overnight. The solvent was removed and the crude material was purified by flash chromatography on silica gel, eluting with ethyl acetate/hexane (1:9). The eluent was removed, giving 6-chloro-$N^4$, $N^4$-dimethyl-1-phenyl-2,4-pyrimidinediamine (0.592 g, 2.39 mmol, 80%, $R_f$=0.3).

Procedure D:

2,4-DICHLORO-6-(1-PIPERIDINYL)PYRIMIDINE: A mixture of 2,4,6-trichloropyrimidine (5.0 g, 27 mmol) and piperidine (2.3 g, 27 mmol) in tetrahydrofuran (50 mL) and N,N-diisopropylethylamine (3.5 g, 27 mmol) was stirred at room temperature for 24 hours. The solvent was removed and the crude material was purified by flash chromatography on silica gel. The column was eluted with a gradient of hexane to yield ethyl acetate/hexane (1:4). The eluent was removed, giving 2,4-dichloro-6-(1-piperidinyl)pyrimidine (3.67 g, 15.8 mmol, 59%, $R_f$=0.58 in ethyl acetate/hexane, 1:4).

Procedure E:

4-CHLORO-6-(1-PIPERIDINYL)-2-{4-[3-(TRIFLUOROMETHYL)-2-PYRIDINYL]-1-PIPERAZINYL}PYRIMIDINE: A mixture of 2,4-dichloro-6-(1-piperidinyl)pyrimidine (100 mg, 0.43 mmol) and 1-[3-(trifluoromethyl)pyrid-2-yl]piperazine (119 mg, 0.52 mmol) in chlorobenzene (1 mL) was heated at 140° C. in a sealed tube for 24 hours. The solvent was removed and the crude material was purified by preparative TLC, eluting with hexane/ethyl acetate (9:1). 4-chloro-6-(1-piperidinyl)-2-{4-[3-(trifluoromethyl)-2-pyridinyl]-1-piperazinyl}pyrimidine was obtained as a solid (79 mg, 0.19 mmol, 44%).

Procedure F:

N-(4-METHYLPHENYL)-6-(1-PIPERIDINYL)-2-{4-[3-(TRIFLUOROMETHYL)-2-PYRIDINYL]-1-PIPERAZINYL}-4-PYRIMIDINAMINE: A mixture of 4-chloro-6-(1-piperidinyl)-2-{4-[3-(trifluoromethyl)-2-pyridinyl]-1-piperazinyl}pyrimidine (75.0 mg, 0.176 mmol), p-toluidine (23.1 mg, 0.216 mmol), 1,1'-(bisdiphenylphosphino)-1,1'-binaphthol (8.4 mg), tris(dibenzylidene acetone)dipalladium (0) (8.2 mg), and sodium tert-butoxide (86.4 mg) in dry toluene (1 mL) was heated at 90° C. in a sealed tube for 90 minutes. The solvent was removed and the crude material was purified by preparative TLC, eluting with hexane/ethyl acetate (4:1). N-(4-Methylphenyl)-6-(1-piperidinyl)-2-{4-[3-(trifluoromethyl)-2-pyridinyl]-1-piperazinyl}-4-pyrimidinamine was obtained, from the band at $R_f$=0.4, as a solid (59.5 mg, 0.119 mmol, 68%).

Procedure G:

$N^2$-ETHYL-$N^2$-[2-(1H-3-INDOLYL)ETHYL]-$N^4$-(4-METHYLPHENYL)-6-PIPERIDINO-2,4-PYRIMIDINEDIAMINE: A mixture of N-[4-chloro-6-(1-piperidinyl)-2-pyrimidinyl]-N-ethyl-N-[2-(1H-indol-3-yl)ethyl] amine (33.4 mg, 0.087 mmol) and p-toluidine (47 mg, 0.43 mmol) was heated neat under argon at 160° C. in a sealed tube for 12 hours. The crude material was purified by preparative TLC, eluting with hexane/ethyl acetate (4:1). $N^2$-Ethyl-$N^2$-[2-(1H-3-indolyl)ethyl]-$N^4$-(4-methylphenyl)-6-piperidino-2,4-pyrimidinediamine was obtained, from a band at $R_f$=0.37, as a solid (15 mg, 0.033 mmol, 38%).

Procedure H:

2,6-DICHLORO-N,N-DIMETHYL-4-PYRIMIDINAMINE: Sodium hydride (0.13 g, 0.79 mmol) was added to a solution of 2,6-dichloro-4-pyrimidinamine (0.40 g, 0.95 mmol) in dry tetrahydrofuran (5 mL) and stirred for 10 minutes, at which point gas evolution had ceased. Methyl iodide (0.06 mL, 0.95 mmol) was added and the resulting solution was stirred for 3 hours at room temperature. The solution was quenched with aqueous ammonium chloride/ammonium carbonate. The solution was extracted with ethyl acetate and the extracts were dried over sodium sulfate. The solvent was removed and the resulting crude product was purified by flash chromatography over silica gel, eluting with hexane/ethyl acetate (2:1). The desired product ($R_f$=0.55) was obtained as a white powder (70 mg, 0.36 mmol, 46%).

Procedure I:

N-ETHYL-2-(1H-INDOL-3-YL)ETHANAMINE: Step 1. Acetic anhydride (1.02 g) was added dropwise to a stirring solution of tryptamine (1.60 g) in tetrahydrofuran (5 mL) at 0° C. and then brought to room temperature. After 2 hours, the solvent was removed and the residue was taken up into ethyl acetate. The solution was filtered through a plug of silica gel and the solvent removed, giving N-[2-(1H-indol-3-yl)ethylacetyltryptamineacetamide (1.65 g, 100%).

Step 2. Lithium aluminum hydride in tetrahydrofuran (1M, 30 mL) was added dropwise to a stirring solution of N-[2-(1H-indol-3-yl)ethylacetyltryptamineacetamide (2.02 g) in tetrahydrofuran (10 mL) at 0° C. The solution was then heated at reflux overnight. The solution was cooled to 0° C. and water was very carefully added dropwise. The white solid was filtered and rinsed with ether/methanol (9:1, 2×25 mL). The solvent was removed from the filtrate, giving N-ethyl-2-(1H-indol-3-yl)ethanamine as a viscous-pale yellow oil (1.75 g, 93%).

Procedure J:

4-CHLORO-N-[2-(1H-INDOL-3-YL)-1-METHYL-ETHYL]-6-(1-PIPERIDINYL)-2-PYRIMIDINAMINE: A mixture of 2,4-dichloro-6-(1-piperidinyl)pyrimidine (80 mg, 0.34 mmol), α-methyltryptamine (59 mg, 0.34 mmol), and potassium carbonate (47 mg, 0.34 mmol) in chlorobenzene (1 mL) was heated at 150° C. in a sealed tube for 16 hours. The solvent was removed and the crude material was purified by preparative TLC, eluting with cyclohexane/ethyl acetate (4:1). 4-Chloro-N-[2-(1H-indol-3-yl)-1-methylethyl]-6-(1-piperidinyl)-2-pyrimidinamine ($R_f$=0.19) was obtained as a solid (64.5 mg, 51%). $^1$H NMR (300 MHz, CDCl$_3$) δ 8.29 (br s, 1H), 7.68 (br d, 1H, J=7.5), 7.32 (d, 1H, J=7.8), 7.16 (t, 1H, J=7.8), 7.12 (t, 1H, J=7.8), 6.95 (d, 1H, J=2.1), 5.87 (s, 1H), 4.89 (br d, 1H, J=8.1), 4.36 (sextet, 1H, J=6.6), 3.58-3.50 (m, 4H), 3.07 (dd, 1H, J=14.4, 5.1), 2.83 (dd, 1H, J=14.1, 7.2), 1.70-1.55 (m, 6H), 1.16 (d, 3H, J=6.6).

Procedure K:

N-(4-METHYLPHENYL)-2-(1-PIPERAZINYL)-6-(1-PIPERIDINYL)-4-PYRIMIDINAMINE: A solution of 2-(4-benzyl-1-piperazinyl)-N-(4-methylphenyl)-6-(1-piperidinyl)-4-pyrimidinamine (0.40 g, 0.90 mmol) and ammonium formate (0.28 g, 4.5 mmol) in methanol over 10% palladium/charcoal was stirred at 70° C. for 3 hours. The solution was cooled and passed through celite. The solvent was removed, giving the desired product as a solid (0.21 g, 0.60 mmol, 66%).

Procedure L:

N-(4-METHYLPHENYL)-2-[4-(3-METHYL-2-PYRIDINYL)-1-PIPERAZINYL]-6-(1-PIPERIDINYL)-4-PYRIMIDINAMINE: A mixture of N-(4-methylphenyl)-2-(1-piperazinyl)-6-(1-piperidinyl)-4-pyrimidinamine (100 mg, 0.284 mmol), 2-bromo-3-methylpyridine (54 mg, 0.312 mmol), 1,1'-(bisdiphenylphosphino)-1,1'-binaphthol (13 mg), tris(dibenzylidene acetone)dipalladium(0) (13 mg), and sodium tert-butoxide (136 mg) in dry toluene (4 mL) was heated at 90° C. in a sealed tube for 2 hours. The reaction was quenched with water and the solution was extracted three times with ethyl acetate. The solvent was dried and removed. The crude material was purified by preparative. TLC, eluting with hexane/ethyl acetate (2:1). N-(4-methylphenyl)-2-[4-(3-methyl-2-pyridinyl)-1-piperazinyl]-6-(1-piperidinyl)-4-pyrimidinamine was obtained, from the band at $R_f$=0.46, as a solid (17.1 mg, 0.0385 mmol, 14%).

Procedure M:

4,6-DICHLORO-2-{4-[3-(TRIFLUOROMETHYL)-2-PYRIDINYL]-1-PIPERAZINYL}PYRIMIDINE and 2,4-DICHLORO-6-{4-[3-(TRIFLUOROMETHYL)-2-PYRIDINYL]-1-PIPERAZINYL }PYRIMIDINE: A solution of 4-[3-(trifluoromethyl)-2-pyridinyl]-1-piperazine (127 mg, 0.66 mmol), 2,4,6-trichloropyrimidine (100 mg, 0.55 mmol) and N,N-diisopropylethylamine (95 µL) in tetrahydrofuran (1 mL) was stirred at 0° C. for 15 minutes. At this time, the starting material could no longer be detected by TLC. The solvent was removed and the crude material was purified by preparative TLC, eluting with ethyl acetate/hexane (1:4). Two bands were removed giving 4,6-dichloro-2-{4-[3-(trifluoromethyl)-2-pyridinyl]-1-piperazinyl}pyrimidine (41.7 mg, 0.110 mmol, 17%, $R_f$=0.41), and 2,4-dichloro-6-{4-[3-(trifluoromethyl)-2-pyridinyl]-1-piperazinyl}pyrimidine (162 mg, 0.429 mmol, 65%, $R_f$=0.10).

Procedure N:

4-{4-[4-CHLORO-6-(DIMETHYLAMINO)-2-PYRIMIDINYL]-1-PIPERAZINYL}PHENOL: DIPEA (4.535 g, 0.0260 mol) was added to a stirred solution of 4-N,N-dimethylamino-2,6-dichloropyrimidine (2.00 g, 0.0104 mol) and 4-(1-piperazinyl)phenol (2.23 g, 0.0125 mol) in THF (50 mL) at room temperature under argon. The resulting mixture was refluxed for 48 h, cooled to room temperature, quenched with water (100 mL), concentrated under reduced pressure and the crude product was redissolved in EtOAc. The organic layer was separated and washed with water (2×100 mL), brine (2×100 mL) and purified by column chromatography on silica using EtOAc/Hexane (1:9), giving the desired product (2.77 g, 80%).

Procedure O:

A solution of p-toludine (0.2 g, 1.87 mmol) in THF (2 mL) was added to a stirred suspension of NaH (0.11 g, 2.79 mmol) in anhydrous THF (2 mL) at room temperature. The resulting mixture was heated at 40° C. for 15 minutes under argon and cooled to room temperature. 6-Chloropyrimidine (0.34 g, 1.03 mmol) in THF (25 mL) was added to the above mixture and the resulting mixture was heated at refluxed for 15 h. The reaction mixture was then cooled to room temperature and quenched with saturated. NH$_4$Cl (2 drops). The crude product was concentrated under reduced pressure and redissolved in EtOAc. The organic layer was separated and washed with aqueous citric acid (2×100 mL), water (2×100 mL) and brine (2×100 mL). The crude product was purified by column chromatography on silica using EtOAc/hexanes (1:4), giving the desired product (0.23 g, 55%).

Procedure P:

2-(4-BENZYL-1-PIPERAZINYL)-N$^4$-(3,4-DICHLOROPHENYL)-N$^6$,N$^6$-DIMETHYL-4,6-PYRIMIDINEDIAMINE: Potassium tert-butoxide (1.6 mmol, 1 M in 2-methyl 2-propanol) was added to a solution of N-[2-(4-benzyl-1-piperazinyl)-6-chloro-4-pyrimidinyl]-N,N-dimethylamine (0.331 g, 0.997 mmol) and 3,4 dichloroaniline (0.178 g, 1.10 mmol) in dioxane (2 mL). Subsequently, tris(dibenzylidineacetone)dipalladium (40 mg, 0.04 mmol) and 2,2'-Bis (diphenylphosphino)-1,1'-binapthyl (44 mg, 0.070 mmol) were added and the mixture was stirred for 7 h at 110° C. The resulting mixture was cooled to room temperature and concentrated under reduced pressure. The residue was treated with saturated NaHCO$_3$ (50 mL) and extracted with CH$_2$Cl$_2$ (3×50 mL). The organic layer washed with brine (2×100 mL), dried over Na$_2$SO$_4$, concentrated in vacuo, and purified by preparative TLC using hexane/EtOAc to give the desired product (300 mg, 65%).

Procedure Q:

N-[2-(4-BENZYL-1-PIPERAZINYL)-6-CHLORO-4-PYRIMIDINYL]-N,N—: DIPEA (5.00 g, 40.0 mmol) was added dropwise to a solution of the N-(2,6-dichloro-4-pyrimidinyl)-N,N-dimethylamine (5.70 g, 29.6 mmol) and benzyl piperazine (6.00 g, 34.0 mmol) in m-xylene (15 mL). The mixture was stirred overnight at 130° C., cooled to room temperature, treated with saturated NaHCO$_3$ (50 mL) and then extracted with CH$_2$Cl$_2$ (3×50 mL). The organic layer washed with brine (2×100 mL), dried over Na$_2$SO$_4$, and concentrated in vacuo. The crude product was purified by chromatography on silica using EtOAc/hexane (1:3), giving the desired product (6.8 g, 20 mmol, 67%).

Procedure R:

$N^4,N^4$-DIMETHYL-$N^6$-(4-METHYLPHENYL)-$N^2$-(2-PHENYLETHYL)-2,4,6-PYRIMIDINETRIAMINE: A mixture of N-[4-(dimethylamino)-6-(4-toluidino)-2-pyrimidinyl]-2-phenylacetamide (60 mg, 0.166 mmol), and LAH (1 mL, 1M in THF) in THF (10 mL) was refluxed for 3 h.

The crude product was concentrated in vacuo and treated with saturated NaHCO$_3$ (50 mL) and extracted with CH$_2$Cl$_2$ (3×50 mL). The organic layer washed with brine (2×100 mL), dried over Na$_2$SO$_4$, filtered, and concentrated in vacuo. The crude product was purified by preparative TLC using hexane/EtOAc (1:3), giving the desired product (30 mg, 52%).

Procedure S:

N-[4-(DIMETHYLAMINO)-6-(4-TOLUIDINO)-2-PYRIMIDINYL]-2-PHENYLACETAMIDE: A mixture of $N^4,N^4$-dimethyl-$N^6$-(4-methylphenyl)-2,4,6-pyrimidinetriamine (122 mg, 0.50 mmol), phenylacetyl chloride (84 mg, 0.55 mmol), and triethylamine (100 mg, 1.00 mmol) in CH$_2$Cl$_2$ was stirred at room temperature for 16 h. The crude product was concentrated in vacuo and treated with saturated NaHCO$_3$ (50 mL) and extracted with CH$_2$Cl$_2$ (3×50 mL). The organic layer washed with brine (2×100 mL), dried over Na$_2$SO$_4$, filtered, and concentrated in vacuo. The crude product was purified by preparative TLC using hexane/EtOAc (1:3), giving the desired product (60 mg, 33%).

Procedure T:

A mixture of $N^4$-(3-methoxyphenyl)-$N^6,N^6$-dimethyl-2-[4-(2-thienylcarbonyl)-1-piperazinyl]-4,6-pyrimidinediamine (28 mg, 0.06 mmol) and LAH (300 uL 1M, 0.3 mmol) in THF (10 mL) was refluxed for 16 h. The crude product was concentrated in vacuo and treated with saturated NaHCO$_3$ (50 mL) and extracted with EtOAc (3×50 mL). The organic layer washed with brine (2×100 mL), dried over Na$_2$SO$_4$, filtered, and concentrated in vacuo. The crude product was purified by preparative TLC using hexane/EtOAc (1:3), giving the desired product (20 mg, 39%).

Procedure U:

2-[4-(3-METHOXYBENZYL)-1-PIPERAZINYL]-$N^4$-(3-METHOXYPHENYL)-$N^6,N^6$-DIMETHYL-4,6-PYRIMIDINEDIAMINE: A solution of $N^4$-(3-methoxyphenyl)-$N^6,N^6$-dimethyl-2-(1-piperazinyl)-4,6-pyrimidinediamine (36 mg, 0.1 mmol), DIPEA (52 mg, 0.4 mmol), and 1-(chloromethyl)-3-methoxybenzene (20 mg, 0.13 mmol) in 5 mL of dioxane was stirred at 100° C. for 16 h. The crude product was concentrated in vacuo and treated with saturated NaHCO$_3$ (50 mL) and extracted with CH$_2$Cl$_2$ (3×50 mL). The organic layer washed with brine (2×100 mL), dried over Na$_2$SO$_4$, and concentrated in vacuo. The crude product was purified by chromatography on silica using hexane/EtOAc (1:3), giving the desired product (32 mg, 70%).

Procedure V:

6-CHLORO-$N^4$-(4-METHYLPHENYL)-2,4-PYRIMIDINEDIAMINE: A mixture of 4,6-dichloro-2-pyrimidinamine (1.64 g, 0.01 mol), p-toluidine (1.07 g, 0.01 mol) in dioxane (2 mL) was heated in a sealed tube for 30 minutes at 140° C. The crude product was treated with NaOH (50 ml, 2M) and extracted with CH$_2$Cl$_2$ (3×50 mL). The organic layer was washed with brine (2×100 mL), dried over Na$_2$SO$_4$, filtered, and concentrated in vacuo. The crude product was purified by chromatography on silica using hexane/EtOAc (1:3), giving the desired product (2 g, 78%).

Procedure W:

$N^4$-(3-METHOXYPHENYL)-$N^6,N^6$-DIMETHYL-2-[4-(2-THIENYLCARBONYL)-1-PIPERAZINYL]-4,6-PYRIMIDINEDIAMINE: A mixture of 2-thiophenecarboxylic acid (15 mg, 0.12 mmol), DIPEA (129 mg, 1.00 mmol) and O-(7-azabenzotriazol-1-yl)N,N,N',N'-tetramethyluronium hexafluorophosphate (44 mg, 0.12 mmol) in DMF (5 mL) was stirred at room temperature for 30 minutes. $N^4$-(3-methoxyphenyl)-$N^6,N^6$-dimethyl-2-(1-piperazinyl)-4,6-pyrimidinediamine (36 mg, 0.10 mmol) was added to the above mixture and stirred at room temperature for 16 h. The crude product was treated with saturated NaHCO$_3$ (50 mL) and extracted with EtOAC (3×50 mL). The organic layer washed with brine (2×100 mL), dried over Na$_2$SO$_4$, filtered and concentrated in vacuo. The crude product was purified by chromatography on silica using hexane/EtOAc (1:3), giving the desired product (25 mg, 57%).

Procedure X:

2-(4-BENZYL-1-PIPERAZINYL)-$N^4$-(3-METHOXYPHENYL)-$N^6,N^6$-DIMETHYL-4,6-PYRIMIDINEDIAMINE: A mixture of $N^4$-(3-methoxyphenyl)-$N^6,N^6$-dimethyl-2-(1-piperazinyl)-4,6-pyrimidinediamine (36 mg, 0.10 mmol) and benzaldehyde (11 mg, 0.1 mmol) in a solution of methanol (5 mL) and acetic acid (0.5 mL) was stirred at room temperature for 1 h. Sodium cyanoborohydride (7 mg, 0.1 mmol) was added to the above solution and stirred at room temperature for 16 h. The crude product was treated with saturated NaHCO$_3$ (50 mL) and extracted with EtOAC (3×50 mL). The organic layer washed with brine (2×50 mL), dried over Na$_2$SO$_4$, filtered, and concentrated in vacuo. The crude product was purified by chromatography on silica using hexane/EtOAc (1:3), giving the desired product (8 mg, 40%).

Procedure Y:

2-[4-(4-BROMOPHENYL)-1-PIPERAZINYL]-$N^4$-(3-METHOXYPHENYL)-$N^6,N^6$-DIMETHYL-4,6-PYRIMIDINEDIAMINE: A mixture of $N^4$-(3-methoxyphenyl)-$N^6$,$N^6$-dimethyl-2-(1-piperazinyl)-4,6-pyrimidinediamine (36 mg, 0.1 mmol), 1-bromo-4-fluorobenzene (20 mg, 0.13 mmol) was heated at 100° C. for 1 h. The crude product was dissolved in CH$_2$Cl$_2$ (0.5 mL) and purified by preparative TLC using 5% methanol in EtOAc, giving the desired product (20 mg, 40%).

Procedure Z:

2-[4-(2-METHOXYBENZYL)-1-PIPERAZINYL]-$N^4$,$N^4$-DIMETHYL-$N^6$-(4-METHYLPHENYL)-4,6-PYRIMIDINEDIAMINE: A mixture of $N^4,N^4$-dimethyl-$N^6$-(4-methylphenyl)-2-(1-piperazinyl)-4,6-pyrimidinediamine (30 mg, 0.086 mmol), 1-(chloromethyl)-2-methoxybenzene (17 mg, 0.1 mmol) and triethylamine (200 mg, 2 mmol) in 1 DMF (1 mL) heated by microwave at 200° C. for 12 minutes. The crude product was treated with saturated NaHCO$_3$ (50 mL)

and extracted with EtOAC (3×50 mL). The organic layer washed with brine (2×100 mL), dried over Na$_2$SO$_4$, filtered, and concentrated in vacuo. The crude product was purified by chromatography on silica using hexane/EtOAc (1:3), giving the desired product (10 mg, 27%).

Procedure AA:

N$^4$-(3-METHOXYPHENYL)-N$^6$,N$^6$-DIMETHYL-2-[4-(2-THIENYLCARBONYL)-1-PIPERAZINYL]-4,6-PYRIMIDINEDIAMINE: A solution of N$^4$-(3-methoxyphenyl)-N$^6$,N$^6$-dimethyl-2-(1-piperazinyl)-4,6-pyrimidinediamine (33 mg, 0.1 mmol), 2-thiophenecarbonyl chloride (20 mg, 0.14 mmol), and triethylamine (40 mg, 0.4 mmol) in CH$_2$Cl$_2$ (5 mL) was stirred at room temperature for 16 h. The crude product was concentrated in vacuo and treated with saturated NaHCO$_3$ (50 mL) and extracted with CH$_2$Cl$_2$ (3×50 mL). The organic layer washed with brine (2×100 mL), dried over Na$_2$SO$_4$, filtered, and concentrated in vacuo. The crude product was purified by chromatography on silica using hexane/EtOAc (1:3), giving the desired product as a pale red oil (35 mg, 80%).

Procedure BB:

N$^4$,N$^4$-DIMETHYL-N$^6$-(4-METHYLPHENYL)-2,4,6-PYRIMIDINETRIAMINE: A mixture of 6-chloro-N$^4$-(4-methylphenyl)-2,4-pyrimidinediamine (1.5 g, 6.4 mmol), and N,N-dimethylamine hydrochloride (0.56 g, 7 mmol) and triethylamine (1.4 g, 14 mmol) in DMF (2 mL), was heated at 170° C. for 16 h. The product was filtered out and the organic layer was treated with saturated NaHCO$_3$ (50 mL) and extracted with EtOAC (3×50 mL). The organic layer washed with brine (2×100 mL), dried over Na$_2$SO$_4$, filtered, and concentrated in vacuo. The crude product was purified by chromatography on silica using hexane/EtOAc (1:3), giving the desired product (0.6 g, 40%).

Procedure CC:

N-(4-METHYLPHENYL)-2-[4-(1-OXIDO-2-PYRIDINYL)-1-PIPERAZINYL]-6-(1-PIPERIDINYL)-4-PYRIMIDINAMINE: A solution of 3-cholorperbenzoic acid (450 mg, 2.6 mmol), and 30% H$_2$O$_2$ (0.1 mL) in CH$_2$Cl$_2$ (2 mL) was added to a solution of N-(4-methylphenyl)-6-(1-piperidinyl)-2-[4-(2-pyridinyl)-1-piperazinyl]-4-pyrimidinamine (150 mg, 0.300 mmol) in CH$_2$Cl$_2$ at 0° C. The resulting mixture was gradually warmed to room temperature and stirred for 24 h, crude product was treated with saturated NaHCO$_3$ (50 mL) and extracted with EtOAC (3×50 mL). Combined organic layers were washed with brine (2×50 mL), dried over Na$_2$SO$_4$, filtered, concentrated in vacuo, and purified by chromatography on silica using hexane/EtOAc (1:3) to give the desired product.

Piperazines that were not commercially available were synthesized according to the method previously described (Ennis and Ghazal, 1992).

The following are examples to illustrate the compounds of this invention. Procedures A-BB as described above, were used and any modifications are noted in parentheses.

Example 1

N$^2$-Cyclohexyl-N$^2$-methyl-N$^4$-(4-methylphenyl)-6-(1-piperidinyl)-2,4-pyrimidinediamine Prepared by Procedures D, G (for substitution with cyclohexylamine); and G. $^1$H NMR (300 MHz, CDCl$_3$) δ 7.22 (d, 2H, J=7.8), 7.12 (d, 2H, J=7.8), 5.29 (s, 1H), 4.43 (br s, 1H), 3.55-3.44 (m, 5H), 3.01 (s, 3H), 2.33 (s, 3H), 2.00-1.05 (m, 16H).

Example 2

N$^2$-Cyclohexyl-N$^2$-(2-methoxyethyl)-N$^4$-(4-methylphenyl)-6-(1-piperidinyl)-2,4-pyrimidinediamine Prepared by Procedures D, J (130° C.), and F (2 hours). $^1$H NMR (300 MHz, CDCl$_3$) δ 7.25 (d, 2H, J=8.1), 7.10 (d, 2H, J=8.1), 6.17 (br s, 1H), 5.31 (s, 1H), 4.58-4.43 (m, 1H), 3.61-3.57 (m, 4H), 3.52-3.48 (m, 4H), 3.39 (s, 3H), 2.31 (s, 3H), 1.83-1.75 (m, 4H), 1.70-1.50 (m, 7H), 1.43-1.37 (m, 4H), 1.19-1.05 (m, 1H); ESI-MS m/z 424 (MH$^+$).

Example 3

N$^4$-(4-Methylphenyl)-N$^2$-phenyl-6-(1-piperidinyl)-2,4-pyrimidinediamine

Prepared by Procedures A, B (for substitution with aniline), and E (100° C., for substitution with piperidine). $^1$H NMR (300 MHz, CDCl$_3$) δ 7.58 (d, 2H, J=8.7), 7.26 (t, 2H, J=7.8), 7.19 (d, 2H, J=8.7), 7.15 (d, 2H, J=7.8), 6.95 (t, 1H, J=7.8), 6.82 (br s, 1H), 6.48 (br s, 1H), 5.49 (s, 1H), 3.56-3.46 (m, 4H), 2.34 (9, 3H), 1.67-1.52 (m, 6H); ESI-MS m/z 360 (MH$^+$).

Example 4

N$^4$,N$^4$-Di(4-methylphenyl)-6-piperidino-2,4-pyrimidinediamine

Prepared by Procedures D and G (100° C., 12 hours, for substitution of p-toludine at C2 and C4 of the pyrimidine). $^1$H NMR (300 MHz, CDCl$_3$) δ 7.47 (d, 2H, J=8.3), 7.20 (d, 2H, J=7.8), 7.15 (d, 2H, J=8.3), 7.10 (d, 2H, J=8.3), 6.79 (br s, 1H), 6.46 (br s, 1H), 5.52 (s, 1H), 3.51 (t, 4H, J=4.6), 2.36 (s, 3H), 2.31 (s, 3H), 1.69-1.53 (m, 6H); ESI-MS m/z 374 (MH$^+$).

Example 5

N$^2$-(4-Chlorophenyl)-N$^4$-(4-methylphenyl)-6-(1-piperidinyl)-2,4-pyrimidinediamine Prepared by Procedures D, G (for substitution with 4-chloroaniline), and G (3.5 hours). $^1$H NMR (300 MHz, CDCl$_3$) δ 8.79 (br s, 1H), 7.72 (br s, 1H), 7.54 (d, 2H, J=8.3), 7.28-7.17 (m, 6H), 5.36 (s, 1H), 3.61-3.46 (m, 4H), 2.36 (s, 3H), 1.76-1.53 (m, 6H); ESI-MS m/z 393 (MH$^+$ with $^{35}$Cl), 395 (MH$^+$ with $^{37}$Cl).

Example 6

N$^2$-Methyl-N$^4$-(4-methylphenyl)-N$^2$-phenyl-6-(1-piperidinyl)-2,4-pyrimidinediamine Prepared by Procedures D, G (140° C., 90 minutes, for substitution with aniline), and G (3.5 hours). $^1$H NMR (300 MHz, CDCl$_3$) δ 7.42-7.33 (m, 4H), 7.18-7.14 (overlapping t at 7.16 & d at 7.15, 3H), 7.07 (d, 2H, J=7.8), 6.25 (br s, 1H), 5.41 (s, 1H), 3.54 (s, 3H), 3.50-3.42 (m, 4H), 2.33 (s, 3H), 1.68-1.50 (m, 6H); ESI-MS m/z 374 (MH$^+$).

Example 7

N²-Methyl-N²,N⁴-di(4-methylphenyl)-6-(1-piperidinyl)-2,4-pyrimidinediamine

Prepared by Procedures D, G (180° C., 10 hours, for substitution with N-methyl-p-toluidine), and G (140° C.). $^1$H NMR (300 MHz, CDCl$_3$) δ 7.27-7.04 (m, 8H), 6.19 (br s, 1H), 5.38 (s, 1H), 3.52 (s, 3H), 3.48-3.41 (m, 4H), 2.38 (s, 3H), 2.31 (s, 3H), 1.67-1.49 (m, 6H); ESI-MS m/z 388 (MH⁺).

Example 8

N²-[2-(5-Methyl-1H-3-indolyl)ethyl]-N⁴-(4-methylphenyl)-6-(1-piperidinyl)-2,4-pyrimidinediamine Prepared by Procedures D, J, and G (160° C., 12 hours). $^1$H NMR (300 MHz, CDCl$_3$) δ 8.05 (br s, 1H), 7.43 (s, 1H), 7.23 (d, 1H, J=8.4), 7.15 (d, 2H, J=8.4), 7.10 (d, 2H, J=8.4), 7.00 (d, 1H, J=8.4), 6.98 (s, 1H), 6.43 (br s, 1H), 5.37 (s, 1H), 4.86 (br t, 1H, J=7.1), 3.70 (q, 2H, J=7.1), 3.52-3.43 (m, 4H), 3.02 (t, 2H, J=7.1), 2.46 (s, 3H), 2.32 (s, 3H), 1.67-1.49 (m, 6H); ESI-MS m/z 441 (MH⁺).

Example 9

N²-[2-(5-Methoxy-1H-3-indolyl)ethyl]-N⁴-(4-methylphenyl)-6-(1-piperidinyl)-2,4-pyrimidinediamine Prepared by Procedures D, E (160° C., 36 hours), and G. $^1$H NMR (300 MHz, CDCl$_3$) δ 8.00 (br s, 1H), 7.15 (d, 2H, J=8.4), 7.12 (d, 2H, J=8.4), 7.08-7.04 (m, 3H), 6.85 (dd, 1H, J=8.8, 2.6), 6.48 (br s, 1H), 5.36 (s, 1H), 4.96 (br s, 1H), 3.85 (s, 3), 3.72-3.67 (m, 2H), 3.55-3.45 (m, 4H), 3.02 (t, 2H, J=6.9), 2.32 (s, 3H), 1.68-1.49 (m, 6H); ESI-MS m/z 457 (MH⁺).

Example 10

N²-[2-(1H-3-Indolyl)ethyl]-N⁴-(4-methylphenyl)-6-(1-piperidinyl)-2,4-pyrimidinediamine Prepared by Procedures D, E (100° C.), and G (150° C.). $^1$H NMR (300 MHz, CDCl$_3$) δ 8.34 (br s, 1H), 7.63 (d, 1H, J=7.8), 7.31 (d, 1H, J=7.8), 7.23-7.09 (m, 6H), 6.94 (s, 1H), 6.60 (br s, 1H), 5.36 (s, 1H), 4.95 (t, 1H, J=6.3), 3.68 (dt, 2H, J=6.3, 6.9), 3.48-3.44 (m, 4H), 3.01 (t, 2H, J=6.9), 2.31 (s, 3H), 1.65-1.48 (m, 6H); ESI-MS m/z 427 (MH⁺).

Example 11

N²-[2-(1H-3-Indolyl)ethyl]-N²-methyl-N⁴-(4-methylphenyl)-6-(1-piperidinyl)-2,4-pyrimidinediamine Prepared by Procedures D, E (160° C., 4 hours), and F (12 hours). $^1$H NMR (300 MHz, CDCl$_3$) δ 8.02 (br s, 1H), 7.71 (d, 1H, J=7.8), 7.36 (d, 1H, J=7.8), 7.22 (d, 2H, J=7.8), 7.20 (t, 1H, J=7.8), 7.17-7.09 (m, 3H), 7.03 (s, 1H), 6.40 (br s, 1H), 5.35 (s, 1H), 3.91 (t, 2H, J=7.8), 3.56-3.46 (m, 4H), 3.16 (s, 3H), 3.09 (t, 2H, J=7.8), 2.33 (S, 3H), 1.70-1.52 (m, 6H); ESI-MS m/z 441 (MH⁺).

Example 12

N²-[2-(1H-Indol-3-YL)ethyl]-N²-methyl-N⁴-phenethyl-6-(1-piperidinyl)-2,4-pyrimidinediamine Prepared by Procedures D, E (160° C., 12 hours), and G. $^1$H NMR (300 MHz, CDCl$_3$) δ 8.00 (br, s, 1H), 7.71 (d, 1H, J=7.8), 7.34 (t, 2H, J=7.8), 7.24-7.15 (m, 5H), 7.08 (t, 1H, J=7.8), 6.98 (s, 1H), 4.95 (s, 1H), 4.39 (br, s, 1H), 3.88 (t, 2H, J=7.8), 3.57-3.48 (m, 6H), 3.12 (s, 3H), 3.05 (t, 2H, J=7.8), 2.89 (t, 2H, J=7.8), 1.68-1.53 (m, 6H); ESI-MS m/z 455 (MH⁺).

Example 13

N²-[2-(1H-Indol-3-YL)ethyl]-N²-methyl-N⁴-(2-naphthyl)-6-(1-piperidinyl)-2,4-pyrimidinediamine Prepared by Procedures D, E (160° C., 12 hours, for substitution with N-methyltryptamine), and E (160° C., 12 hours). $^1$H NMR (300 MHz, CDCl$_3$) δ 7.95 (br s, 1H), 7.92 (s, 1H), 7.78-7.75 (m, 3H), 7.72 (d, 1H, J=8.1), 7.46-7.41 (m, 2H), 7.37 (d, 2H, J=8.4), 7.20 (t, 1H, J=7.8), 7.11 (t, 1H, J=7.8), 7.01 (s, 1H), 6.42 (br s, 1H), 5.45 (s, 1H), 3.95 (t, 2H, J=7.8), 3.56-3.49 (m, 4H), 3.19 (s, 3H), 3.11 (t, 2H, J=7.8), 1.62-1.59 (m, 6H); ESI-MS m/z 477 (MH⁺).

Example 14

N⁴-(3-Fluorophenyl)-N²-[2-(1H-indol-3-YL)ethyl]-N²-methyl-6-(1-piperidinyl)-2,4-pyrimidinediamine Prepared by Procedures D, E (160° C., 12 hours, for substitution with N-methyltryptamine), and G.
$^1$H NMR (300 MHz, CDCl$_3$) δ 7.97 (br s, 1H), 7.71 (d, 1H, J=7.8), 7.41 (dt, 1H, J=9.5, 1.0), 7.34 (d, 1H, J=7.8), 7.22-7.06 (m, 4H), 7.02-7.00 (s at 7.02 & d at 7.01 overlapping, 2H), 7.01 (s, 1H), 6.33 (br s, 1H), 5.34 (s, 1H), 3.90 (t, 2H, J=7.8), 3.58-3.50 (m, 4H), 3.16 (s, 3H), 3.08 (t, 2H, J=7.8), 1.70-1.54 (m, 6H); ESI-MS m/z 445 (MH⁺).

Example 15

N⁴-(3,4-Difluorophenyl)-N²-[2-(1H-indol-3-YL)ethyl]-N²-methyl-6-(1-piperidinyl)-2,4-pyrimidinediamine Prepared by Procedures D, E (160° C., 12 hours, for substitution with N-methyltryptamine), and G.
$^1$H NMR (300 MHz, CDCl$_3$) δ 7.99 (br s, 1H), 7.68 (d, 1H, J=7.8), 7.51 (ddd, 1H, J=9.5, 7.8, 2.3), 7.35 (d, 1H, J=7.8), 7.19 (t, 1H, J=7.8), 7.11 (t, 1H, J=7.8), 7.07-6.90 (m, 3H), 7.01 (s, 1H), 6.22 (br s, 1H), 5.23 (s, 1H), 3.89 (t, 2H, J=7.8), 3.57-3.49 (m, 4H), 3.15 (s, 3H), 3.07 (t, 2H, J=7.8), 1.68-1.53 (m, 6H); ESI-MS m/z 463 (MH⁺).

Example 16

N⁴-(3-Chloro-4-methylphenyl)-N²-[2-(1H-indol-3-yl)ethyl]-N²-methyl-6-(1-piperidinyl)-2,4-pyrimidinediamine Prepared by Procedures D, E (160° C., 12 hours, for substitution with N-methyltryptamine), and G.
$^1$H NMR (300 MHz, CDCl$_3$) δ 7.96 (br s, 1H), 7.69 (d, 1H, J=7.5), 7.51 (s, 1H), 7.36 (d, 1H, J=7.8), 7.19 (t, 1H, J=7.8), 7.14-7.06 (m, 3H), 7.01 (s, 1H), 6.18 (br s, 1H), 5.29 (s, 1H), 3.89 (t, 2H, J=7.8), 3.53-3.48 (m, 4H), 3.13 (s, 3H), 3.07 (t, 2H, J=7.8), 2.31 (s, 3H), 1.70-1.55 (m, 6H); ESI-MS m/z 475 (MH⁺).

Example 17

N$^2$-[2-(1H-Indol-3-YL)ethyl]-N$^4$-(3-methoxyphenyl)-N$^2$-methyl-6-(1-piperidinyl)-2,4-pyrimidinediamine Prepared by Procedures D, E (160° C., 12 hours, for substitution with N-methyltryptamine), and G.

$^1$H NMR (300 MHz, CDCl$_3$) δ 8.02 (br s, 1H), 7.71 (d, 1H, J=7.8), 7.34 (d, 1H, J=8.3), 7.25-7.04 (m, 4H), 7.01 (s, 1H), 6.89 (d, 1H, J=7.8), 6.57 (dd, 1H, J=8.3, 2.4), 6.30 (br s, 1H), 5.42 (s, 1H), 3.91 (t, 2H, J=7.7), 3.76 (s, 3H), 3.57-3.49 (m, 4H), 3.16 (s, 3H), 3.08 (t, 2H, J=7.7), 1.70-1.53 (m, 6H); ESI-MS m/z 457 (MH$^+$).

Example 18

N$^2$-Ethyl-N$^2$-[2-(1H-indol-3-yl)ethyl]-N$^4$-(4-methylphenyl)-6-(1-piperidinyl)-2,4-pyrimidinediamine Prepared by Procedures D, E (160° C., 12 hours, for substitution with N-ethyltryptamine), and G. $^1$H NMR (300 MHz, CDCl$_3$) δ 7.97 (br s, 1H), 7.71 (d, 1H, J=7.8), 7.35 (d, 1H, J=7.8), 7.25-7.16 (overlapping d at 7.23 & t at 7.22, 3H), 7.14 (t, 1H, J=7.8), 7.08 (d, 2H, J=7.8), 7.02 (s, 1H), 6.19 (br s, 1H), 5.34 (s, 1H), 3.82 (t, 2H, J=7.9), 3.61 (q, 2H, J=7.1), 3.55-3.45 (m, 4H), 3.08 (t, 2H, J=7.9), 2.30 (s, 6H), 1.68-1.50 (m, 6H), 1.18 (t, 3H, J=7.1); ESI-MS m/z 455 (MH$^+$).

Example 19

N$^2$-[2-(1H-Indol-3-yl)ethyl]-N$^2$-(2-methoxyethyl)-N$^4$-(4-methylphenyl)-6-(1-piperidinyl)-2,4-pyrimidinediamine Prepared by Procedures D, E (160° C., 12 hours, for substitution with N-methoxyethyltryptamine), and G. $^1$H NMR (300 MHz, CDCl$_3$ δ 7.96 (br s, 1H), 7.72 (d, 1H, J=7.5), 7.35 (d, 1H, J=7.8), 7.27-7.07 (m, 6H), 7.02 (s, 1H), 6.19 (br s, 1H), 5.35 (s, 1H), 3.88 (dd, 2H, J=9.9, 5.4), 3.74 (t, 2H, J=6.0), 3.60 (dd, 2H, J=10.5, 4.8), 3.57-3.46 (m, 4H), 3.34 (s, 3H), 3.12-3.07 (m, 2H), 2.32 (s, 6H), 1.70-1.58 (m, 6H); ESI-MS m/z 485 (MH$^+$).

Example 20

N$^2$-[2-(1H-3-Indolyl)-1-methylethyl]-N$^4$-(4-methylphenyl)-6-(1-piperidinyl)-2,4-pyrimidinediamine Prepared by Procedures D, J, and G. $^1$H NMR (300 MHz, CDCl$_3$) δ 8.10 (br s, 1H) 7.70 (d, 1H, J=7.8), 7.36 (d, 1H, J=8.1), 7.19-6.98 (m, 7H), 6.60 (br s, 1H), 5.35 (s, 1H), 4.89 (br s, 1H), 4.44-4.36 (m, 1H), 3.55-3.45 (m, 4H), 3.14 (dd 1H, J=14.1, 5.1), 2.84 (dd, 1H, J=14.1, 7.5), 2.33 (s, 3H), 1.62-1.50 (m, 6H), 1.18 (d, 3H, J=6.6); ESI-MS m/z 441 (MH$^+$).

Example 21

N$^2$-[2-(1H-Indol-3-yl)-1-methylethyl]-N$^2$-methyl-N$^4$-(4-methylphenyl)-6-(1-piperidinyl)-2,4-pyrimidinediamine Prepared by Procedures D, E (160° C., 12 hours, for substitution with N,α-dimethyltryptamine), and G. $^1$H NMR (300 MHz, CDCl$_3$) δ 7.92 (br s, 1H) 7.73 (d, 1H, J=7.8), 7.34 (d, 1H, J=7.8), 7.19-7.09 (m, 4H), 7.03 (s, 1H), 6.17 (br s, 1H), 5.34 (s, 1H), 3.51-3.44 (m, 5H), 3.11-3.05 (m, 1H), 3.02 (s, 2H), 2.90 (dd, 1H, J=14.7, 7.5), 2.32 (s, 3H), 1.65-1.49 (m, 6H), 1.18 (d, 3H, J=6.6); ESI-MS m/z 455 (MH$^+$).

Example 22

N$^2$-Methyl-N$^4$-(4-methylphenyl)-N$^2$-phenethyl-6-(1-piperidinyl)-2,4-pyrimidinediamine Prepared by Procedures D, E (160° C., 12 hours, for substitution at C2 of the pyrimidine), and G. ESI-MS m/z 402 (MH$^+$).

Example 23

2-(4-Benzyl-1-peperazinyl)-N-(4-methylphenyl)-6-(1-piperidinyl)-4-pyrimidinamine Prepared by Procedures D, I (140° C., overnight, for substitution with N-benzylpiperazine), and F (2 hours).

$^1$H NMR (300 MHz, CDCl$_3$) δ 7.38-7.26 (m, 5H) 7.18 (d, 1H, J=7.8), 7.12 (d, 1H, J=7.8) 6.18 (br s, 1H), 5.34 (s, 1H), 3.93-3.87 (m, 4H), 3.77 (t, 4H, J=5.0), 3.55 (s, 2H), 3.48-3.42 (m, 4H), 2.49 (t, 4H, J=5.0), 2.31 (s, 3H), 1.66-1.49 (m, 6H); ESI-MS m/z 443 (MH$^+$).

Example 24

N-(4-Methylphenyl)-2-(4-phenyl-1-piperidinyl)-6-(1-piperidinyl)-4-pyrimidinamine Prepared by Procedures D, E (16 hours, for substitution with 4-phenylpiperidine), and F (1 hour). $^1$H NMR (300. MHz, CDCl$_3$) δ 7.34-7.24 (m, 5H), 7.19 (d, 2H, J=7.8), 7.12 (d, 2H, J=7.8), 6.22 (br s, 1H), 5.36 (s, 1H), 4.89 (d with fine splitting, 2H, J=13.0), 3.52-3.42 (m, 4H), 2.86 (dt, 2H, J=1.0, 13.0), 2.73 (tt, 1H, J=11.6, 1.5), 2.32 (s, 3H), 1.89 (d with fine splitting, 2H, J=12.0), 1.74 (ddd, 2H, J=13.0, 12.0, 1.5), 1.67-1.52 (m, 6H); ESI-MS m/z 428 (MH$^+$).

Example 25

N-(4-Methylphenyl)-2-(4-phenylpiperazinyl)-6-(1-piperidinyl)-4-pyrimidinamine

Prepared by Procedures D, G (180° C., 2.5 hours, for substitution with N-phenylpiperazine), and G (140° C., overnight). $^1$H NMR (300 MHz, CDCl$_3$) δ 7.28 (t, 2H, J=7.8), 7.19 (d, 2H, J=7.8), 7.13 (d, 2H, J=7.8), 6.99 (d, 2H, J=7.8), 6.89 (t, 1H, J=7.8), 6.23 (br s, 1H), 5.38 (s, 1H), 3.91 (t, 2H, J=4.6), 3.54-3.44 (m, 4H), 3.23 (t, 2H, J=4.6), 2.34 (s, 3H), 1.71-1.51 (m, 6H); ESI-MS m/z 429 (MH$^+$).

Example 26

2-[4-(2-Ethylphenyl)-1-piperazinyl]-N-(4-methylphenyl)-6-(1-piperidinyl)-4-pyrimidinamine Prepared by Procedures D, E (120° C.), and F. $^1$H NMR (300 MHz, CDCl$_3$) δ 7.28 (d, 1H, J=7.8), 7.24-7.08 (m, 7H), 6.37 (br s, 1H), 5.41 (s, 1H), 3.98-3.90 (m, 4H), 3.53-3.47 (m, 4H), 2.99-2.92 (m, 4H), 2.80 (q, 2H, J=8.3), 2.35 (s, 3H), 1.69-1.54 (m, 6H), 1.31 (t, 3H, J=8.3); ESI-MS m/z 457 (MH$^+$).

Example 27

2-[4-(2,6-Dimethylphenyl)-1-piperazinyl]-N-(4-methylphenyl)-6-(1-piperidinyl)-4-pyrimidinamine Prepared by Procedures D, E (120° C.), and F. $^1$H NMR (300 MHz, CDCl$_3$) δ 7.22 (d, 2H, J=7.8), 7.15 (d, 2H, J=7.8), 7.05-7.95 (m, 3H), 6.30 (br s, 1H), 5.39 (s, 1H), 3.88 (t, 4H, J=4.6), 3.53-3.47 (m, 4H), 3.15 (t, 4H, J=4.6), 2.37 (s, 6H), 2.34 (s, 3H), 1.68-1.53 (m, 6H); ESI-MS m/z 457 (MH$^+$).

Example 28

N-{2-(4-[2,4-Dimethoxyphenyl)piperazinyl]-6-(1-piperidinyl)-4-pyrimidinyl}-N-(4-methylphenyl) amine Prepared by Procedures D, E (150° C., 16 hours), and F (5 hours). $^1$H NMR (300 MHz, CDCl$_3$) δ 7.18 (d, 2H, J=8.1), 7.12 (d, 2H, J=8.1), 6.88 (d, 1H, J=9.0), 6.50 (d, 1H, J=2.4), 6.43 (dd, 1H, J=8.7, 2.4), 6.23 (br 6, 1H), 5.36 (s, 1H), 3.94 (t, 4H, J=7.5), 3.87 (s, 3H), 3.79 (s, 3H), 3.52-3.44 (m, 4H), 3.03 (t, 4H, J=7.5), 2.33 (s, 3H), 1.65-1.52 (m, 6H); ESI-MS m/z 488 (MH$^+$).

Example 29

N-(4-Methylphenyl)-6-(1-piperidinyl)-2-{4-[3-(trifluoromethyl)phenyl]-1-piperazinyl}-4-pyrimidinamine Prepared by Procedures D, E (120° C., 16 hours), and F. $^1$H NMR (300 MHz, CDCl$_3$) δ 7.36 (t, 1H, J=7.8), 7.20-7.09 (m, 7H), 6.25 (br s, 1H), 5.37 (s, 1H), 4.93 (t, 4H, J=4.6), 3.52-3.45 (m, 4H), 3.26 (t, 4H, J=4.6), 2.34 (s, 3H), 1.66-1.52 (m, 6H); ESI-MS m/z 497 (MH$^+$).

Example 30

N-(4-methylphenyl)-6-(1-piperidinyl)-2-[4-(2-pyridyl)-1-piperazinyl]-4-pyrimidinamine Prepared by Procedures D, G (120° C., 12 hours, for substitution with N-pyrid-2-ylpiperazine), and G (140° C.). $^1$H NMR (300 MHz, CDCl$_3$) δ 8.22 (dd, 1H, J=4.4, 1.5), 7.50 (dd, 1H, J=7.8, 1.5), 7.20 (d, 2H, J=8.1), 7.13 (d, 2H, J=8.1), 6.69 (d, 1H, J=7.08) 6.63 (t, 1H, J=7.08), 6.26 (br s, 1H), 5.38 (s, 1H), 3.89 (t, 4H, J=4.8), 3.62 (t, 4H, J=4.8), 3.55-3.45 (m, 4H), 2.33 (s, 3H), 1.70-1.52 (m, 6H); ESI-MS m/z 430 (MH$^+$).

Example 31

N-(4-Methylphenyl)-2-[4-(3-methyl-2-pyridinyl)-1-piperazinyl]-6-(1-piperidinyl)-4-pyrimidinamine Prepared from 2-(4-benzyl-1-piperazinyl)-N-(4-methylphenyl)-6-(1-piperidinyl)-4-pyrimidinamine by Procedures K and L. $^1$H NMR (300 MHz, CDCl$_3$). δ 8.19 (dd, 1H, J=4.4, 2.2), 7.42 (dd, 1H, J=7.8, 2.2), 7.19 (d, 2H, J=8.1), 7.12 (d, 2H, J=8.1), 6.85 (dd, 1H, J=7.8, 4.4), 6.20 (br s, 1H), 5.38 (s, 1H), 3.93-3.87 (m, 4H), 3.53-3.48 (m, 4H), 3.24-3.18 (m, 4H), 2.33 (s, 3H), 1.67-1.53 (m, 6H); ESI-MS m/z 444 (MH$^+$).

Example 32

N-(4-Methylphenyl)-6-(1-piperidinyl)-2-{4-[4-(trifluoromethyl)-2-pyridinyl]-1-piperazinyl}-4-pyrimidinamine Prepared by Procedures D, E (16 hours), and F. ESI-MS m/z 498 (MH$^+$).

Example 33

N-(4-Methylphenyl)-6-(1-piperidinyl)-2-{4-[6-(trifluoromethyl)-2-pyridinyl]-1-piperazinyl}-4-pyrimidinamine Prepared by Procedures D, E (16 hours), and F. $^1$H NMR (300 MHz, CDCl$_3$) δ 7.56 (d, 1H, J=8.1), 7.19 (d, 2H, J=8.4), 7.14 (d, 2H, J=8.4), 6.94 (d, 1H, J=7.2), 6.80 (d, 1H, J=8.7), 6.23 (br s, 1H), 5.37 (s, 1H), 3.90-3.87 (m, 4H), 3.69-3.66 (m, 4H), 3.50-4.46 (m, 4H), 2.34 (s, 3H), 1.67-1.53 (m, 6H); ESI-MS m/z 498 (MH$^+$).

Example 34

N-(4-Methylphenyl)-6-(1-piperidinyl)-2-{4-[3-(trifluoromethyl)-2-pyridinyl]-1-piperazinyl}-4-pyrimidinamine Prepared by Procedures D, E (16 hours), and F. $^1$H NMR (300 MHz, CDCl$_3$) δ 8.43 (dd, 1H, J=4.4, 2.2), 7.87 (dd, 1H, J=7.8, 2.2), 7.19 (d, 2H, J=8.1), 7.13 (d, 2H, J=8.1), 6.99 (dd, 1H, J=7.8 4.4), 6.23 (br s, 1H), 5.37 (s, 1H), 3.89 (t, 4H, J=4.8), 3.53-3.48 (m, 4H), 3.36 (t, 4H, J=4.8), 2.33 (s, 3H), 1.67-1.53 (m, 6H); ESI-MS m/z 498 (MH$^+$).

Example 35

N-Cyclohexyl-6-(1-piperidinyl)-2-{4-[3-(trifluoromethyl)-2-pyridinyl]-1-piperazinyl}-4-pyrimidinamine Prepared by Procedures M, E (120° C., for addition of piperidine), and F (3 hours). $^1$H NMR (300 MHz, CDCl$_3$) δ 8.43 (d, 1H, J=5.6), 7.84 (d, 1H, J=7.4), 6.95 (dd, 1H, J=7.4, 5.6), 4.95 (s, 1H), 4.34 (br s, 1H), 3.84 (t, 4H, J=5.1), 3.55-3.38 (m, 5H), 3.34 (t, 4H, J=5.1), 2.02 (dd, 2H, J=12.0, 1.4), 1.79-1.71 (m, 2H), 1.69-1.52 (m, 6H), 1.44-1.10 (m, 6H); ESI-MS m/z 490 (MH$^+$).

Example 36

N-Bicylco[2.2.1]HEPT-2-yl-6-(1-piperidinyl)-2-{4-[3-(Trifluoromethyl)-2-pyridinyl]-1-piperazinyl}-4-pyrimidinamine Prepared by Procedures M, E (120° C., for addition of piperidine), and F (3 hours). $^1$H NMR (300 MHz, CDCl$_3$) δ 8.42 (d, 1H, J=5.6), 7.86 (d, 1H, J=7.4), 6.95 (dd, 1H, J=7.4, 5.6), 4.95 (s, 1H), 4.37 (br s, 1H), 3.84 (t, 4H, J=5.1), 3.57-3.47 (m, 4H), 3.40-3.31 (m, 5H), 2.25 (br s, 2H), 1.78 (ddd, 2H, J=13.0, 4.6, 1.4), 1.67-1.42 (m, 9H), 1.25-1.12 (m, 4H); ESI-MS m/z 502 (MH$^+$).

Example 37

N-(4-Methylphenyl)-6-(1-piperidinyl)-2-[4-(2-pyrimidinyl)-1-piperazinyl]-4-pyrimidinamine Prepared by Procedures D, G (120° C., 12 hours, for substitution with N-pyrimid-2-ylpiperazine), and G (150° C., 24 hours). $^1$H NMR (300 MHz, CDCl$_3$) δ 8.33 (d, 2H, J=4.9), 7.19 (d, 2H, J=7.8), 7.13 (d, 2H, J=7.8), 6.50 (t, 1H, J=7.8), 6.23 (br s, 1H), 5.37 (s, 1H), 3.97-3.82 (m, 8H), 3.56-3.44 (m, 4H), 2.34 (s, 3H), 1.70-1.53 (m, 6H); ESI-MS m/z 431 (MH$^+$).

Example 38

N-(4-Methylphenyl)-6-(1-piperidinyl)-2-(1-pyrrolidinyl)-4-pyrimidinamine

Prepared by Procedures D, G (120° C., 3 hours, for substitution with pyrrolidine), and G (140° C., 12 hours). $^1$H NMR (300 MHz, CDCl$_3$) δ 7.20 (d, 2H, J=7.8), 7.11 (d, 2H, J=7.8), 6.39 (br s, 1H), 5.34 (s, 1H), 3.56 (t, 4H, J=5.6), 3.53-3.44 (m, 4H), 2.33 (s, 3H), 1.91 (quintet, 4H, J=5.6), 1.67-1.50 (m, 6H); ESI-MS m/z 338 (MH$^+$).

Example 39

N-[2-(2,3-Dihydro-1H-indol-1-yl)-6-(1-piperidinyl)-4-pyrimidinyl]-N-(4-methylphenyl)amine Prepared by Procedures D, E (16 hours), and F. $^1$H NMR (300 MHz, CDCl$_3$) δ 8.31 (d, 1H, J=7.8), 7.26-7.15 (m, 6H), 6.86 (t, 1H, J=7.8), 6.31 (br s, 1H), 5.49 (s, 1H), 4.22 (t, 4H, J=8.3), 3.59-3.53 (m, 4H), 3.13 (t, 4H, J=8.3), 2.35 (s, 3H), 1.70-1.55 (m, 6H); ESI-MS m/z 386 (MH$^+$).

Example 40

N-(4-METHYLPHENYL)-N-[6-(1-PIPERIDINYL)-2-(1,2,3,4-TETRAHYDRO-1-QUINOLINYL)-4-PYRIMIDINYL]AMINE

Prepared by Procedures D, G (180° C., 3 hours, for substitution with 1,2,3,4-tetrahydroquinoline), and G (140° C., 12 hours). $^1$H NMR (300 MHz, CDCl$_3$) δ 7.87 (d, 1H, J=7.8), 7.19 (d, 2H, J=7.8), 7.15-7.07 (m, 4H), 6.93 (t, 1H, J=7.8), 6.33 (br s, 1H), 5.49 (s, 1H), 4.04 (t, 2H, J=6.0), 3.54-3.44 (m, 4H), 2.79 (t, 2H, J=6.0), 2.34 (s, 3H), 1.98 (pentet, 2H, J=6.0), 1.69-1.52 (m, 6H); ESI-MS m/z 400 (MH$^+$).

Example 41

N-(4-METHYLPHENYL)-N-[6-(1-PIPERIDINYL)-2-(1,2,3,4-TETRAHYDRO-2-ISOQUINOLINYL)-4-PYRIMIDINYL]AMINE

Prepared by Procedures D, G (180° C., 3 hours, for substitution with 1,2,3,4-tetrahydroisoquinoline), and G (140° C., 12 hours). $^1$H NMR (300 MHz, CDCl$_3$) δ 7.56 (d, 1H, J=7.8), 7.26-7.06 (m, 7H), 6.37 (br. s, 1H), 5.35 (s, 1H), 4.89 (s, 2H), 4.00 (t, 2H, J=6.0), 3.58-3.44 (m, 4H), 2.91 (t, 2H, J=6.0), 2.32 (s, 3H), 1.68-1.47 (m, 6H); ESI-MS m/z 400 (MH$^+$).

Example 42

N-[2-(6,7-DIMETHOXY-3,4-DIHYDRO-2(1H)-ISOQUINOLINYL)-6-(1-PIPERIDINYL)-4-PYRIMIDINYL]-N-(4-METHYLPHENYL)AMINE

Prepared by Procedures D, E (160° C., 12 hours), and F (5 hours). $^1$H NMR (300 MHz, CDCl$_3$) δ 7.19 (d, 2H, J=7.8), 7.13 (d, 2H, J=7.8), 6.70 (s, 1H), 6.64 (s, 1H), 6.25 (br s, 1H), 5.36 (s, 1H), 4.82 (s, 2H), 4.01 (t, 2H, J=5.9), 3.89 (s, 3H), 3.87 (s, 3H), 3.58-3.44 (m, 4H), 2.84 (t, 2H, J=5.9), 2.33 (s, 3H), 1.68-1.52 (m, 6H); ESI-MS m/z 460 (MH$^+$).

Example 43

N-[2-(2,3-DIHYDRO-1H-BENZO[DE]ISOQUINOLIN-2-YL)-6-(1-PIPERIDINYL)-4-PYRIMIDINYL]-N-(4-METHYLPHENYL)AMINE

Prepared by Procedures D, E (160° C., 12 hours), and G. ESI-MS m/z 436 (MH$^+$).

Example 44

4-PHENYL-1-[4-(1-PIPERIDINYL)-6-(4-TOLUIDINO)-2-PYRIMIDINYL]-4-PIPERIDINOL

Prepared by Procedures D, E (23 hours), and F. $^1$H NMR (300 MHz, CDCl$_3$) δ 7.51 (d, 2H, J=7.5), 7.36 (t, 2H, J=7.8), 7.26 (t, 1H+CHCl$_3$, J=7.8), 7.19 (d, 2H, J=8.4), 7.12 (d, 2H, J=8.4), 6.20 (br s, 1H), 5.36 (s, 1H), 4.67 (br d, 2H, J=13.5), 3.50-3.45 (m, 4H), 4.67 (br t, 2H, J=13.1), 2.33 (s, 3H), 2.10 (dt, 2H, J=4.2, 12.6), 1.78 (br d, 2H, J=13.5), 1.65-1.53 (m, 6H); ESI-MS m/z 444 (MH$^+$).

Example 45

N$^2$,N$^2$-BIS(2-METHOXYETHYL)-N$^4$-(4-METHYLPHENYL)-6-(1-PIPERIDINYL)-2,4-PYRIMIDINEDIAMINE

Prepared by Procedures D, G [140° C., 2 hours, for substitution with bis(methoxyethyl)amine], and G (140° C., 1.5 hours). $^1$H NMR (300 MHz, CDCl$_3$) δ 7.20 (d, 2H, J=7.8), 7.10 (d, 2H, J=7.8), 6.20 (br s, 1H), 5.33 (s, 1H), 3.77 (t, 4H, J=6.2), 3.59 (t, 4H, J=6.3), 3.47-3.40 (m, 4H), 3.36 (s, 6H), 1.64-1.49 (m, 6H); ESI-MS m/z 400 (MH$^+$).

Example 46

N-(4-METHYLPHENYL)-2-(3-PHENYL-4-MORPHOLINYL)-6-(1-PIPERIDINYL)-4-PYRIMIDINAMINE

Prepared by Procedures D, E (16 hours), and F (1 hour). $^1$H NMR (300 MHz, CDCl$_3$) δ 7.51 (d, 2H, J=7.8), 7.31 (t, 2H, J=7.8), 7.23 (t, 1H, J=7.8), 7.15 (d, 2H, J=7.8), 7.10 (d, 2H, J=7.8), 6.22 (br s, 1H), 5.84 (d, 1H, J=1.0), 5.36 (s, 1H), 4.51-4.42 (m, 2H), 3.94 (m, 2H), 3.66 (dt, 1H, J=1.0, 11.5), 3.49-3.43 (m, 4H), 3.24 (dt, 1H, J=1.5, 11.5), 2.32 (s, 3H), 1.64-1.47 (m, 6H); ESI-MS m/z 430 (MH$^+$).

Example 47

N-(4-METHYLPHENYL)-2-(2-PHENYL-4-MORPHOLINYL)-6-(1-PIPERIDINYL)-4-PYRIMIDINAMINE

Prepared by Procedures D, E (14 hours), and F (100° C., 2 hours). $^1$H NMR (300 MHz, CDCl$_3$) $^1$H NMR (300 MHz, CDCl$_3$) δ 7.46 (d, 2H, J=7.8), 7.386 (t, 2H, J=7.8), 7.34 (t, 1H, J=7.8), 7.18 (d, 2H, J=8.7), 7.13 (d, 2H, J=8.4), 6.19 (br s, 1H), 5.38 (s, 1H), 4.70 (br d, 1H, J=12.6), 4.58-4.51 (m, 1H), 4.11 (dd, 1H, J=10.2, 2.4), 3.80 (dt, 1H, J=2.7, 11.7), 3.50-3.43 (m, 4H), 3.10 (dt, 1H, J=2.1, 12.8), 2.89 (dd, 1H, J=13.2, 10.2), 2.33 (s, 3H), 1.66-1.50 (m, 6H); ESI-MS-m/z 430 (MH$^+$).

Example 48

N-(4-METHYLPHENYL)-2-[(2S,3R)-3-METHYL-2-PHENYLMORPHOLINYL]-6-(1-PIPERIDINYL)-4-PYRIMIDINAMINE

Prepared by Procedures D, E (120° C.), and F (1 hour). $^1$H NMR (300 MHz, CDCl$_3$) δ 7.42 (d, 2H, J=7.8), 7.39 (t, 2H, J=7.8), 7.27 (t, 1H, J=7.8), 7.20 (d, 2H, J=7.8), 7.14 (d, 2H, J=7.8), 6.25 (br s, 1H), 5.39 (s, 1H), 4.99-4.90 (m, 1H), 4.77 (d, 1H, J=1.5), 4.39 (dd, 1H, J=13.0, 1.5), 4.15 (dd, 1H, J=8.3, 1.5), 3.80 (dt, 1H, J=3.7, 11.6), 3.53-3.45 (m, 4H), 3.26 (dt, 1H, J=3.7, 13.0), 2.3.3 (s, 3H), 1.68-1.52 (m, 6H), 0.90 (d, 3H, J=8.3); ESI-MS m/z 444 (MH$^+$).

Example 49

2-[(2R,3R)-3-(METHOXYMETHYL)-2-PHENYLMORPHOLINYL]-N-(4-METHYLPHENYL)-6-(1-PIPERIDINYL)-4-PYRIMIDINAMINE

Prepared by Procedures D, E, and F (3 hours). $^1$H NMR (300 MHz, CDCl$_3$) δ 7.56 (d, 2H, J=7.8), 7.31 (t, 2H, J=7.8), 7.27-7.20 (m, 3H), 7.13 (d, 2H, J=7.8), 6.31 (br s, 1H), 5.84 (d, 1H, J=1.0), 5.35 (dd, 1H, J=9.3, 2.7), 5.11 (s, 1H), 4.28 (d with splitting, 1H, J=13.0), 4.01 (t, 1H, J=9.0), 3.58-3.46 (m, 6H), 3.40 (s, 3H), 3.27-3.15 (m, 1H), 2.31 (s, 3H), 1.69-1.50 (m, 6H); ESI-MS m/z 473 (MH$^+$).

Example 50

N$^4$,N$^4$-DIMETHYL-N$^2$,N$^6$-DIPHENYL-2,4,6-PYRIMIDINETRIAMINE

Prepared by Procedures A, C, and G (140° C., overnight). $^1$H NMR (300 MHz, CDCl$_3$) δ 7.68 (d, 2H, J=7.8), 7.38-7.27 (m, 6H), 7.11-7.04 (m, 1H), 6.95 (t, 1H, J=7.8), 6.75 (br s, 1H), 6.38 (br s, 1H), 5.45 (s, 1H), 3.06 (s, 6H); ESI-MS m/z 306 (MH$^+$).

Example 51

N$^4$,N$^4$-DIMETHYL-N$^6$-(2-METHYLPHENYL)-N$^2$-PHENYL-2,4,6-PYRIMIDINETRIAMINE

Prepared by Procedures A, C, and G (140° C., overnight). $^1$H NMR (300 MHz, CDCl$_3$) δ 7.63 (d, 2H, J=7.5), 7.43 (d, 1H, J=7.5), 7.31-7.24 (m, 3H), 7.21 (d, 1H, J=7.8), 7.11 (t, 1H, J=7.4), 6.96 (t, 1H, J=7.7), 6.73 (br s, 1H), 6.12 (br s, 1H), 5.16 (s, 1H), 3.01 (s, 6H), 2.29 (s, 3H); ESI-MS m/z 320 (MH$^+$).

Example 52

N$^4$,N$^4$-DIMETHYL-N$^6$-(3-METHYLPHENYL)-N$^2$-PHENYL-2,4,6-PYRIMIDINETRIAMINE

Prepared by Procedures A, C, and G (140° C., overnight). $^1$H NMR (300 MHz, CDCl$_3$) δ 7.63 (d, 2H, J=7.8), 7.29 (t, 2H, J=7.8), 7.21 (d, 1H, J=8.1), 7.16-7.11 (m, 2H), 6.97 (d, 1H, J=8.1), 6.91 (d, 1H, J=7.5), 6.78 (br s, 1H), 6.38 (br s, 1H), 5.44 (s, 1H), 3.05 (s, 6H), 2.35 (s, 3H); ESI-MS m/z 320 (MH$^+$).

Example 53

N$^4$,N$^4$-DIMETHYL-N$^6$-(3-METHYLPHENYL)-N$^2$-(4-METHYLPHENYL)-2,4,6-PYRIMIDINETRIAMINE

Prepared by Procedures A, C, and G (overnight). $^1$H NMR (300 MHz, CDCl$_3$) δ 7.50 (d, 2H, J=7.8), 7.25-7.08 (m, 5H), 6.90 (d, 1H, J=7.5), 6.86 (br s, 1H), 6.54 (br s, 1H), 5.44 (s, 1H), 3.05 (s, 6H), 2.34 (s, 3H), 2.31 (s, 3H); ESI-MS m/z 334 (MH$^+$).

Example 54

N$^4$,N$^4$-DIMETHYL-N$^6$-(4-METHYLPHENYL)-N$^2$-PHENYL-2,4,6-PYRIMIDINETRIAMINE

Prepared by Procedures A, C, and G (140° C., overnight). $^1$H NMR (300 MHz, CDCl$_3$) δ 7.63 (d, 2H, J=7.8), 7.28 (t, 2H, J=, 7.5), 7.21 (d, 2H, J=7.8), 7.15 (d, 2H, J=8.1), 6.96 (t, 1H, J=7.5), 6.71 (br s, 1H), 6.29 (br s, 1H), 5.39 (s, 1H), 3.04 (s, 6H), 2.34 (s, 3H); ESI-MS m/z 320 (MH$^+$).

Example 55

N$^2$-(3,4-DICHLOROPHENYL)-N$^4$,N$^4$-DIMETHYL-N$^6$-(4-METHYLPHENYL)-2,4,6-PYRIMIDINETRIAMINE

Prepared by Procedures B, C, and G (180° C., 3 hours). $^1$H NMR (300 MHz, CDCl$_3$) δ 8.04 (d, 1H, J=2.1), 7.27 (d, 1H, J=7.8), 7.24 (dd, 1H, J=7.8, 2.1), 7.19 (d, 2H, J=8.7), 7.15 (d, 2H, J=8.7), 7.01 (br s, 1H), 6.59 (br s, 1H), 5.39 (s, 1H), 3.04 (s, 6H), 2.35 (s, 3H); ESI-MS m/z 388 (MH$^+$ with $^{35}$Cl, $^{35}$Cl), 390 (MH$^+$ with $^{35}$Cl, $^{37}$Cl), 392 (MH$^+$ with $^{37}$Cl, $^{37}$Cl).

Example 56

N$^4$,N$^4$-DIMETHYL-N$^2$,N$^6$-BIS(4-METHYLPHENYL)-2,4,6-PYRIMIDINETRIAMINE

Prepared by Procedures B, C, and G (180° C., 3 hours). $^1$H NMR (300 MHz, CDCl$_3$) δ 7.49 (d, 2H, J=8.7), 7.19 (d, 2H, J=8.4), 7.14 (d, 2H, J=8.4), 7.08 (d, 2H, J=8.4), 6.73 (br s, 1H), 6.39 (br s, 1H), 5.37 (s, 1H), 3.02 (s, 6H); ESI-MS m/z 334 (MH$^+$).

Example 57

N$^4$-(3-FLUOROPHENYL)-N$^6$,N$^6$-DIMETHYL-N$^2$-PHENYL-2,4,6-PYRIMIDINETRIAMINE

Prepared by Procedures. A, C, and G (140° C., overnight). $^1$H NMR (300 MHz, CDCl$_3$) δ 7.62 (d, 2H, J=7.8), 7.34-7.23

(m, 5H), 7.01 (t, 1H, J=7.4), 6.77 (br s, 1H), 6.38 (br s, 1H), 5.43 (s, 1H), 3.07 (s, 6H); ESI-MS m/z 324 (MH$^+$).

Example 58

$N^2$-(4-CHLOROPHENYL)-$N^6$,$N^6$-DIMETHYL-$N^2$-PHENYL-2,4,6-PYRIMIDINETRIAMINE

Prepared by Procedures A, C, and G (150° C., overnight). $^1$H NMR (300 MHz, CDCl$_3$) δ 7.60 (d, 2H, J=7.5), 7.32-7.26 (m, 6H), 6.96 (t, 1H, J=7.5), 6.77 (br s, 1H), 6.34 (br s, 1H), 5.34 (s, 1H), 3.04 (s, 6H); ESI-MS m/z 340 (MH$^+$ with $^{35}$Cl), 342 (MH$^+$ with $^{37}$Cl).

Example 59

$N^4$-(4-BROMOPHENYL)-$N^6$,$N^6$-DIMETHYL-$N^2$-PHENYL-2,4,6-PYRIMIDINETRIAMINE

Prepared by Procedures A, C, and G (150° C., overnight). $^1$H NMR (300 MHz, CDCl$_3$) δ 7.59 (d, 2H, J=8.5), 7.42 (d, 2H, J=8.5), 7.31-7.22 (m, 4H), 6.98 (t, 1H, J=7.2), 6.92 (br s, 1H), 6.48 (br s, 1H), 5.35 (s, 1H), 3.05 (s, 6H), ESI-MS m/z 384 (MH$^+$ with $^{79}$Br), 386 (MH$^+$ with $^{81}$Br).

Example 60

$N^4$-(3,4-DICHLOROPHENYL)-$N^6$,$N^6$-DIMETHYL-$N^2$-PHENYL-2,4,6-PYRIMIDINETRIAMINE

Prepared by Procedures A, C, and G (0.5 mL diisopropylethylamine added, 150° C., overnight). $^1$H NMR (300 MHz, CDCl$_3$) δ 7.61 (d with s at the center, 3H, J=7.8), 7.34 (d, 2H, J=7.8), 7.29 (d, 1H, J=8.7), 7.17 (dd, 1H, J=8.7, 2.6), 6.98 (t, 1H, J=7.8), 6.80 (br s, 1H), 6.33 (br s, 1H), 5.33 (s, 1H), 3.07 (s, 6H); ESI-MS m/z 373 (MH$^+$).

Example 61

$N^4$-(4-CHLORO-3-METHYLPHENYL)-$N^6$,$N^6$-DIMETHYL-$N^2$-PHENYL-2,4,6-PYRIMIDINETRIAMINE

Prepared by Procedures A, C, and G (150° C., 1 hour). $^1$H NMR (300 MHz, CDCl$_3$) δ 7.61 (dd, 2H, J=7.4, 0.9), 7.30-7.25 (m, 3H), 7.19 (d, 1H, J=2.4); 7.12 (dd, 1H, J=8.5, 2.4), 6.97 (t, 1H, J=7.4), 6.88 (br s, 1H), 6.44 (br s, 1H), 5.35 (s, 1H), 3.05 (s, 6H), 2.35 (s, 3H); ESI-MS m/z 454 (MH$^+$ with $^{35}$Cl), 456 (MH$^+$ with $^{37}$Cl).

Example 62

$N^4$-(3-CHLORO-4-METHYLPHENYL)-$N^6$,$N^6$-DIMETHYL-$N^2$-PHENYL-2,4,6-PYRIMIDINETRIAMINE

Prepared by Procedures A, C, and F (100° C., 3 hours). $^1$H NMR (300 MHz, CDCl$_3$) δ 7.63 (d, 2H, J=7.8), 7.41 (d, 1H, J=1.8), 7.30 (t, 2H, J=7.8), 7.18 (d, 1H, J=7.8), 7.09 (dd, 1H, J=7.8, 1.8), 6.98 (t, 1H, J=7.8), 6.67 (br s, 2H), 5.35 (s, 1H), 3.07 (s, 6H), 2.37 (s, 3H); ESI-MS m/z 454 (MH$^+$ with $^{35}$Cl), 456 (MH$^+$ with $^{37}$Cl).

Example 63

$N^4$-(4-tert-BUTYLPHENYL)-$N^6$,$N^6$-DIMETHYL-$N^2$-PHENYL-2,4,6-PYRIMIDINETRIAMINE Prepared by Procedures A, C, and G (150° C., 5 hours). $^1$H NMR (300 MHz, CDCl$_3$) δ 7.62 (d, 2H, J=7.5), 7.36 (d, 2H, J=8.7), 7.29 (d, 2H, J=7.5), 7.25 (t, 2H, J=8.7), 6.95 (t, 1H, J=7.4), 6.69 (br s, 1H), 6.30 (br B, 1H), 5.44 (s, 1H), 3.05 (s, 6H), 1.33 (s, 9H); ESI-MS m/z 362 (MH$^+$).

Example 64

$N^4$,$N^4$-DIMETHYL-$N^6$-(4-PHENOXYPHENYL)-$N^2$-PHENYL-2,4,6-PYRIMIDINETRIAMINE

Prepared by Procedures A, C, and G (150° C., 2 hours). $^1$H NMR (300 MHz, CDCl$_3$) δ 7.61 (d, 2H, J=7.8), 7.35 (t, 2H, J=7.8), 7.31-7.24 (m, 3H), 7.12 (t, 2H, J=7.8), 7.08-7.04 (m, 3H), 6.98 (t, 1H, J=8.1), 6.74 (br s, 1H), 6.71 (dd, 1H, J=7.8, 2.0), 6.43 (br s, 1H), 5.41 (s, 1H), 3.03 (9, 6H); ESI-MS m/z 398 (MH$^+$).

Example 65

$N^4$,$N^4$-DIMETHYL-$N^6$-(2-NAPHTHYL)-$N^2$-PHENYL-2,4,6-PYRIMIDINETRIAMINE

Prepared by Procedures A, C, and G (150° C., 2 hours). $^1$H NMR (300 MHz, CDCl$_3$) δ 7.81 (s, 1H), 7.80 (d, 1H, J=7.5), 7.75 (d, 2H, J=7.8), 7.65 (d, 2H, J=7.5), 7.49-7.37 (m, 3H), 7.29 (t, 2H, J=7.5), 6.98 (t, 1H, J=8.1), 6.85 (br s, 1H), 6.59 (br s, 1H), 5.51 (s, 1H), 3.06 (s, 6H); ESI-MS m/z 356 (MH$^+$).

Example 66

$N^4$-CYCLOHEXYL-$N^6$,$N^6$-DIMETHYL-$N^2$-PHENYL-2,4,6-PYRIMIDINETRIAMINE

Prepared by Procedures A, C, and G (140° C., 2 days). $^1$H NMR (300 MHz, CDCl$_3$) δ 7.62 (d, 2H, J=8.1), 7.26 (t, 2H, J=8.1), 6.92 (t, 1H, J=8.1), 6.64 (br s, 1H), 4.96 (s, 1H), 4.39 (br d, 1H, J=8.1), 3.53-3.44 (m, 1H), 3.05 (s, 6H), 2.09-1.99 (m, 2H), 1.80-1.55 (m, 4H), 1.44-1.11 (m, 4H); ESI-MS m/z 312 (MH$^+$).

Example 67

$N^4$,$N^4$-DIMETHYL-$N^6$-(4-METHYLCYCLOHEXYL)-$N^2$-PHENYL-2,4,6-PYRIMIDINETRIAMINE

Prepared by Procedures A, C, and G (150° C., overnight). ESI-MS m/z 326 (MH$^+$).

Example 68

$N^4$-(4-tert-BUTYLCYCLOHEXYL)-$N^6$,$N^6$-DIMETHYL-$N^2$-PHENYL-2,4,6-PYRIMIDINETRIAMINE Prepared by Procedures A, C, and G (150° C., overnight). $^1$H NMR (300 MHz, CDCl$_3$) δ 7.62 (d, 2H, J=8.4), 7.26 (t, 2H, J=7.7), 6.92 (t, 1H, J=7.1), 6.61 (br s, 1H), 4.96 (s, 1H), 4.32 (br d, 1H, J=8.4), 3.46-3.37 (m, 1H), 3.06 (s, 6H), 1.88-1.80 (m, 2H), 1.29-1.20 (m, 1H), 1.19-0.97 (m, 4H), 0.87 (s, 9H); ESI-MS m/z 368 (MH$^+$).

Example 69

N$^4$-BICYCLO[2.2.1]HEPT-2-YL-N$^6$,N$^6$-DIMETHYL-N$^2$-PHENYL-2,4,6-PYRIMIDINETRIAMINE

Prepared by Procedures A, C, and G (140° C.). $^1$H NMR (300 MHz, CDCl$_3$) δ 7.62 (d, 2H, J=7.8), 7.26 (t, 2H, J=8.0), 6.92 (t, 1H, J=7.2), 6.62 (br s, 1H), 4.94 (s, 1H), 4.42 (br d, 1H, J=5.4), 3.45-3.37 (m, 1H), 3.06 (s, 6H), 2.33-2.27 (m, 1H), 1.82 (dd, 1H, J=12.3, 6.0), 1.56-1.42 (m, 2H), 1.30-1.14 (m, 5H), 0.91-0.85 (m, 1H); ESI-MS m/z 324 (MH$^+$).

Example 70

N$^4$,N$^4$-DIMETHYL-N$^2$-PHENYL-N$^6$-(1,7,7-TRIMETHYLBICYCLO[2.2.1]HEPT-2-YL)-2,4,6-PYRIMIDINETRIAMINE

Prepared by Procedures A, C, and G (overnight). $^1$H NMR (300 MHz, CDCl$_3$) δ 7.62 (d, 2H, J=7.8), 7.26 (t, 2H, J=7.8), 6.93 (t, 1H, J=7.7), 6.87 (br s, 1H), 4.95 (s, 1H), 4.80 (br d, 1H, J=6.9), 3.94-3.84 (m, 1H), 3.06 (s, 6H), 2.45-2.34 (m, 1H), 1.82-1.62 (m, 3H), 1.46-1.32 (m, 1H), 1.29-1.16 (m, 2H), 0.99 (s, 3H), 0.90 (s, 3H), 0.89 (s, 3H); ESI-MS m/z 366 (MH$^+$).

Example 71

N$^4$,N$^4$-DIMETHYL-N$^2$-PHENYL-N$^6$-[(2R,3S)-3,6,6-TRIMETHYLBICYCLO[3.1.1]HEPT-2-YL]-2,4,6-PYRIMIDINETRIAMINE

Prepared by Procedures A, C, and G (5 hours). $^1$H NMR (300 MHz, CDCl$_3$) δ 7.64 (d, 2H, J=8.1), 7.26 (t, 2H, J=8.1), 6.92 (t, 1H, J=7.4), 6.72 (br s, 1H), 4.99 (s, 1H), 4.47 (br d, 1H, J=8.4), 4.05-3.91 (m, 1H), 3.06 (s, 6H), 2.72-2.62 (m, 1H), 2.46-2.36 (m, 1H), 2.00-1.45 (m, 5H), 1.25 (s, 3H), 1.16 (d, 3H, J=7.8), 1.10 (s, 3H); ESI-MS m/z 366 (MH$^+$).

Example 72

N$^2$,N$^4$,N$^4$-TRIMETHYL-N$^2$,N$^6$-BIS(4-METHYLPHENYL)-2,4,6-PYRIMIDINETRIAMINE

Prepared by Procedures D, E (150° C., 16 hours), and F (5 hours). $^1$H NMR (300 MHz, CDCl$_3$) δ 7.26 (d, 2H, J=8.1), 7.15 (br d, 4H, J=8), 7.04 (d, 2H, J=8.1), 6.19 (br s, 1H), 5.29 (s, 1H), 3.50 (s, 3H), 2.94 (s, 6H), 2.36 (s, 3H), 2.29 (s, 3H); ESI-MS m/z 348 (MH$^+$).

Example 73

N$^2$-CYCLOHEXYL-N$^2$,N$^4$,N$^4$-TRIMETHYL-N$^6$-(4-METHYLPHENYL)-2,4,6-PYRIMIDINETRIAMINE

Prepared by Procedures D, E (150° C., 12 hours), and F (5 hours). $^1$H NMR (300 MHz, CDCl$_3$) δ 7.25 (d, 2H, J=8.4), 7.10 (d, 2H, J=8.1), 6.26 (br s, 1H), 5.22 (s, 1H), 4.66-4.52 (m, 1H), 3.01 (s, 3H), 2.99 (s, 6H), 2.32 (s, 3H), 1.87-1.64 (m, 5H), 1.52-1.35 (m, 4H), 1.22-1.06 (m, 1H); ESI-MS m/z 340 (MH$^+$).

Example 74

N$^2$-CYCLOHEXYL-N$^2$-(2-METHOXYETHYL)-N$^4$,N$^4$-DIMETHYL-N$^6$-(4-METHYLPHENYL)-2,4,6-PYRIMIDINETRIAMINE

Prepared by Procedures H, J (overnight), and F (2 hours). $^1$H NMR (300 MHz, CDCl$_3$) δ 7.28 (d, 2H, J=8.1), 7.11 (d, 2H, J=8.1), 6.19 (br s, 1H), 5.22 (s, 1H), 4.60-4.50 (m, 1H), 3.64-3.55 (m, 4H), 3.39 (s, 3H), 2.99 (s, 6H), 2.31 (s, 3H), 1.83-1.75 (m, 4H), 1.73-1.63 (m, 1H), 1.52-1.38 (m, 4H), 1.19-1.05 (m, 1H); ESI-MS m/z 384 (MH$^+$).

Example 75

2-(2,3-DIHYDRO-1H-INDOL-1-YL)-N$^4$,N$^4$-DIMETHYL-N$^6$-(4-METHYLPHENYL)-4,6-PYRIMIDINEDIAMINE

Prepared by Procedures H, E (150° C., 16 hours), and F (2 hours). $^1$H NMR (300 MHz, CDCl$_3$) δ 8.37 (d, 1H, J=7.8), 7.26 (d, 2H, J=7.8), 7.20-7.11 (m, 4H), 6.86 (t, 1H, J=7.8), 6.31 (br s, 1H), 5.39 (s, 1H), 4.24 (t, 4H, J=8.3), 3.13 (t, 4H, J=8.3), 3.07 (s, 6H), 2.35 (s, 3H); ESI-MS m/z 346 (MH$^+$).

Example 76

N$^2$-[2-(1H-3-INDOLYL)ETHYL]-N$^4$,N$^4$-DIMETHYL-N$^6$-(4-METHYLPHENYL)-2,4,6-PYRIMIDINETRIAMINE

Prepared by Procedures H, J, and G. $^1$H NMR (300 MHz, CDCl$_3$) δ 8.19 (br s, 1H), 7.65 (d 1H, J=7.8), 7.36 (d, 1H, J=7.8), 7.21-7.09 (m, 6H), 7.04 (s, 1H) 6.52 (br s, 1H), 5.28 (s, 1H), 4.95 (br d, 1H, J=7.2), 3.72 (q, 2H, J=7.2), 3.06 (t, 2H, J=7.8), 2.99 (s, 6H), 2.32 (s, 3H); ESI-MS m/z 387 (MH$^+$).

Example 77

N$^2$-[2-(1H-INDOL-3-YL)ETHYL]-N$^2$,N$^4$,N$^4$-TRIMETHYL-N$^6$-(4-METHYLPHENYL)-2,4,6-PYRIMIDINETRIAMINE

Prepared by Procedures H, J, and G or F. $^1$H NMR (300 MHz, CDCl$_3$) δ 8.14 (br s, 1H), 7.70 (d 1H, J=7.8), 7.32 (d, 1H, J=7.8), 7.22 (d, 2H, J=7.8), 7.17 (t, 1H, J=7.2), 7.12 (t, 1H, J=7.2), 7.08 (d, 2H, J=7.8), 6.98 (s, 1H), 6.36 (br s, 1H), 5.25 (s, 1H), 3.90 (t, 2H, J=7.8), 3.14 (s, 3H), 3.07 (t, 2H, J=7.8), 2.99 (s, 6H), 2.30 (s, 3H); ESI-MS m/z 401 (MH$^+$).

Example 78

N$^4$-(3,4-DICHLOROPHENYL)-N$^2$-[2-(1H-3-INDOLYL)ETHYL]-N$^2$,N$^6$,N$^6$-TRIMETHYL-2,4,6-PYRIMIDINETRIAMINE

Prepared by Procedures H, J, and G.
$^1$H NMR (300 MHz, CDCl$_3$) δ 8.00 (br s, 1H), 7.75 (s, 1H), 7.68 (d 1H, J=7.8), 7.35 (d, 1H, J=7.8), 7.24-7.15 (m, 3H), 7.10 (t, 1H, J=7.2), 7.00 (s, 1H) 6.23 (br s, 1H), 5.15 (s, 1H), 3.90 (t, 2H, J=7.8), 3.14 (s, 3H), 3.08 (t, 2H, J=7.8), 3.03 (s, 6H); ESI-MS m/z 455 (MH$^+$ with $^{35}$Cl), 457 (MH$^+$ with $^{37}$Cl).

Example 79

N²-[2-(1H-INDOL-3-YL)ETHYL)]-N²,N⁴,N⁴-TRI-METHYL-(2-NAPHTHYL)-6-(1-PIPERIDINYL)-2,4,6-PYRIMIDINETRIAMINE

Prepared by Procedures D, E (160° C., 28 hours), and G. $^1$H NMR (300 MHz, CDCl$_3$) δ 8.18 (br s, 1H), 7.92 (s, 1H), 7.90-7.03 (m, 10H), 6.95 (s, 1H) 6.84 (br s, 1H), 5.34 (s, 1H), 3.90 (t, 2H, J=7.8), 3.17 (s, 3H), 3.07 (t, 2H, J=7.8), 2.96 (s, 6H); ESI-MS m/z 437 (MH⁺).

Example 80

1-[4-(DIMETHYLAMINO)-6-(4-TOLUIDINO)-2-PYRIMIDINYL]-4-PHENYL-4-PIPERIDINOL

Prepared by Procedures H, E (150° C., 10 hours), and F (3 hours); $^1$H NMR (300 MHz, CDCl$_3$) δ 7.43 (d, 2H, J=7.8), 7.35 (t, 2H, J=7.8), 7.27-7.21 (m, 3H), 7.14 (d, 2H, J=7.8), 6.24 (br s, 1H), 6.18 (br s, 1H), 5.28 (s, 1H), 4.43-4.37 (m, 2H), 4.03 (t, 2H, J=5.6), 3.06-2.97 (m with s at 3.03, 8H), 2.66-2.58 (m, 2H), 2.34 (s, 3H).

Example 81

N⁴N⁴-DIMETHYL-N⁶-(4-METHYLPHENYL)-2-(4-PHENYL-1-PIPERIDINYL)-4,6-PYRIMIDINEDIAMINE

Prepared by Procedures H, E (150° C., 16 hours), and F (4 hours). $^1$H NMR (300 MHz, CDCl$_3$) δ 7.34-7.18 (m, 7H), 7.13 (d, 2H, J=7.8), 6.25 (br s, 1H), 5.28 (s, 1H), 4.94 (d with fine splitting, 2H, J=13.0), 3.01 (s, 6H), 2.87 (dt, 2H, J=1.0, 13.0), 2.74 (tt, 1H, J=11.6, 1.5), 2.32 (s, 3H), 1.90 (d with fine splitting, 2H, J=12.0), 1.72 (ddd, 2H, J=13.0, 12.0, 1.5); ESI-MS m/z 388 (MH⁺).

Example 82

N⁴,N⁴-DIMETHYL-N⁶-(4-METHYLPHENYL)-2-(3-PHENYL-4-MORPHOLINYL)-4,6-PYRIMIDINEDIAMINE

Prepared by Procedures H, E (150° C., 20 hours), and F (3 hours). $^1$H NMR (300 MHz, CDCl$_3$) δ 7.51 (d, 2H, J=7.8), 7.32 (t, 2H, J=7.8), 7.23 (t, 1H, J=7.8), 7.17 (d, 2H, J=7.8), 7.09 (d, 2H, J=7.8), 6.25 (br s, 1H), 5.88 (d, 1H, J=1.0), 5.27 (s, 1H), 4.49 (t, 2H, J=13.2), 3.94 (m, 2H), 3.66 (dt, 1H, J=1.0, 11.5), 3.24 (dt, 1H, J=1.5, 11.5), 2.97 (s, 6H), 2.32 (s, 3H); ESI-MS m/z 390 (MH⁺).

Example 83

N⁴,N⁴-DIMETHYL-N⁶-(4-METHYLPHENYL)-2-(2-PHENYL-4-MORPHOLINYL)-4,6-PYRIMIDINEDIAMINE

Prepared by Procedures H, E (150° C., 20 hours), and F (3 hours). $^1$H NMR (300 MHz, CDCl$_3$) δ 7.47 (d, 2H, J=7.8), 7.38 (t, 2H, J=7.8), 7.33 (t, 1H, J=7.8), 7.19 (d, 2H, J=7.8), 7.11 (d, 2H, J=7.8), 6.22 (br s, 1H), 5.29 (s, 1H), 4.74 (dd, 1H, J=13.2, 1.0), 4.59-4.51 (m, 2H), 4.16-4.08 (m, 1H), 3.80 (dt, 1H, J=1.0, 11.9), 3.11 (dt, 1H, J=1.5, 12.4), 2.98 (s, 6H), 2.90 (dd, 1H, J=10.6, 11.9), 2.33 (s, 3H); ESI-MS m/z 390 (MH⁺).

Example 84

N⁴,N⁴-DIMETHYL-N⁶-(4-METHYLPHENYL)-2-{4-[(4-METHYLPHENYL)SULFONYL]-1-PIPERAZINYL}-4,6-PYRIMIDINEDIAMINE

Prepared by Procedures H, E (150° C., overnight), and F (3 hours). $^1$H NMR (300 MHz, CDCl$_3$) δ 7.65 (d, 2H, J=8.3), 7.31 (d, 2H, J=8.3), 7.15 (d, 2H, J=8.4), 7.11 (d, 2H, J=7.2), 6.20 (br s, 1H), 5.22 (s, 1H), 3.87 (t, 4H, J=4.2), 3.02 (t, 4H, J=4.2), 2.95 (s, 6H), 2.43 (s, 3H), 2.33 (s, 3H); ESI-MS m/z 467 (MH⁺).

Example 85

N⁴,N⁴-DIMETHYL-N⁶-(4-METHYLPHENYL)-2-[4-(2-METHYLPHENYL)-1-PIPERAZINYL]-4,6-PYRIMIDINEDIAMINE

Prepared by Procedures D, E (160° C., 12 hours), and F (12 hours). $^1$H NMR (300 MHz, CDCl$_3$) δ 7.23-7.10 (m, 6H), 7.02-6.96 (m, 2H), 6.28 (br s, 1H), 5.28 (s, 1H), 3.95-3.86 (m, 4H), 2.99 (s, 6H), 2.96-2.92 (m, 4H), 2.36 (s, 3H), 2.32 (s, 3H); ESI-MS m/z 403 (MH⁺).

Example 86

N⁴,N⁴-DIMETHYL-N⁶-(4-METHYLPHENYL)-2-[4-(3-METHYLPHENYL)-1-PIPERAZINYL]-4,6-PYRIMIDINEDIAMINE

Prepared by Procedures D, E (160° C., 12 hours), and F (12 hours). $^1$H NMR (300 MHz, CDCl$_3$) δ 7.19 (d, 2H, J=7.8), 7.17 (t, 1H, J=7.8), 7.11 (d, 2H, J=7.8), 6.91 (s, 1H), 6.89 (d, 1H, J=7.8), 6.69 (d, 1H, J=7.8), 6.33 (br s, 1H), 5.29 (s, 1H), 3.93 (t, 4H, J=5.1), 3.22 (t, 4H, J=5.1), 3.01 (s, 6H), 2.33 (s, 6H); ESI-MS m/z 403 (MH⁺).

Example 87

N⁴,N⁴-DIMETHYL-N⁶-(4-METHYLPHENYL)-2-[4-(4-METHYLPHENYL)-1-PIPERAZINYL]-4,6-PYRIMIDINEDIAMINE

Prepared by Procedures D, E (160° C., 36 hours), and F (8 hours). $^1$H NMR (300 MHz, CDCl$_3$) δ 7.19 (d, 2H, J=9.0), 7.16 (d, 2H, J=8.7), 7.10 (d, 2H, J=9.0), 6.90 (d, 2H, J=8.4), 6.24 (br s, 1H), 5.27 (s, 1H), 3.93 (t, 4H, J=4.8), 3.18 (t, 4H, J=5.1), 3.00 (s, 6H), 2.33 (s, 3H), 2.28 (s, 3H); ESI-MS m/z 403 (MH⁺).

Example 88

N⁴,N⁴-DIMETHYL-N⁶-(4-METHYLPHENYL)-2-{4-[3-(TRIFLUOROMETHYL)-2-PYRIDINYL]-1-PIPERAZINYL}-4,6-PYRIMIDINEDIAMINE

Prepared by Procedures H, E (16 hours), and F. $^1$H NMR (300 MHz, CDCl$_3$) δ 8.57 (dd, 1H, J=4.4, 2.2), 7.87 (dd, 1H, J=7.8, 2.2), 7.20 (d, 2H, J=8.1), 7.13 (d, 2H, J=8.1), 6.98 (dd, 1H, J=7.8, 4.4), 6.24 (br s, 1H), 5.28 (s, 1H), 3.90 (t, 4H, J=4.8), 3.36 (t, 4H, J=4.8), 3.00 (s, 6H), 2.32 (s, 3H); ESI-MS m/z 458 (MH⁺).

Example 89

N-(4-METHYLPHENYL)-2-(1-PIPERIDINYL)-6-{4-[3-(TRIFLUOROMETHYL)-2-PYRIDINYL]-1-PIPERAZINYL}-4-PYRIMIDINAMINE

Prepared by Procedures M, E (120° C., for addition of piperidine), and F. $^1$H NMR (300 MHz, CDCl$_3$) δ 8.43 (dd, 1H, J=4.4, 2.2), 7.87 (dd, 1H, J=7.8, 2.2), 7.19 (d, 2H, J=8.1), 7.12 (d, 2H, J=8.1), 6.99 (dd, 1H, J=7.8, 4.4), 6.28 (br s, 1H), 5.35 (s, 1H), 3.77-3.72 (m, 4H), 3.62 (t, 4H, J=4.8), 3.33 (t, 4H, J=4.8), 2.33 (s, 3H), 1.69-1.52 (m, 6H); ESI-MS m/z 498 (MH$^+$).

Example 90

6-[2-(METHOXYMETHYL)-1-PIPERIDINYL]-N-(4-METHYLPHENYL)-2-{4-[3-(TRIFLUOROMETHYL)-2-PYRIDINYL]-1-PIPERAZINYL}-4-PYRIMIDINAMINE

Prepared by Procedures D, J (90° C., overnight), and F (2 hours). $^1$H NMR (300 MHz, CDCl$_3$) δ 8.44 (dd, 1H, J=4.4, 2.2), 7.88 (dd, 1H, J=7.8, 2.2), 7.20 (d, 2H, J=8.1), 7.12 (d, 2H, J=8.1), 6.99 (dd, 1H, J=7.8, 4.4), 6.23 (br s, 1H), 5.38 (s, 1H), 4.68-4.54 (m, 1H), 4.15-4.03 (m, 1H), 3.90 (t, 4H, J=4.8), 3.57 (t, 1H, J=9.7), 3.44-3.35 (m, 5H), 3.34 (s, 3H), 2.81 (t, 1H, J=12.0), 2.33 (s, 3H), 1.93-1.86 (m, 1H), 1.72-1.41 (m, 3H), 1.29-1.25 (m, 1H), 0.91-0.86 (m, 1H); ESI-MS m/z 542 (MH$^+$).

Example 115

N-4-[3-(BENZYLOXY)PHENYL]-N-6-,N-6-DIMETHYL-2-[4-(2-PYRIDINYL)-1-PIPERAZINYL]-4,6-PYRIMIDINEDIAMINE

Prepared by Procedures A (CH$_2$Cl$_2$, Et$_3$N, Me$_2$NHHCl, stirred 3.5 h at −78° C., warmed to 0° C. and stirred 3 h), N, and O. $^1$H NMR (400 MHz, CDCl$_3$) δ 8.23-8.19 (m, 1H), 7.52 (dt, 1H, J=1.9, 7.2), 7.43-7.20 (m, 7H), 6.96 (s, 1H), 6.88 (d, 1H, J=8.0), 6.80 (d, 1H, J=8.1), 6.69-6.63 (m, 2H), 5.34 (s, 1H), 5.03 (s, 2H), 4.03-3.97 (m, 4H), 3.66 (t, 4H, J=5.2), 3.02 (s, 6H); ESI-MS m/z 482 (MH$^+$).

Example 116

4-{4-[4-(DIMETHYLAMINO)-6-(4-TOLUIDINO)-2-PYRIMIDINYL]-1-PIPERAZINYL}PHENOL

Prepared by Procedures A (CH$_2$Cl$_2$, Et$_3$N, Me$_2$NHHCl, stirred 3.5 h at −78° C., warmed to 0° C. and stirred 3 h), N, and O. $^1$H NMR (400 MHz, CDCl$_3$) δ 10.04 (s, 1H), 7.19-7.14 (m, 4H), 6.85-6.79 (m, 4H), 5.31 (s, 1H), 5.22 (s, 1H), 3.96 (t, 4H, J=5.1), 3.05 (t, 4H, J=5.0), 3.03 (s, 6H), 2.34 (s, 3H); FIAMS m/z 405 (MH$^+$).

Example 117

N$^4$-[4-(BENZYLOXY)PHENYL]-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, Et$_3$N, Me$_2$NHHCl, stirred 3.5 h at −78° C., warmed to 0° C. and stirred 3 h), N, and O. $^1$H NMR (400 MHz, CDCl$_3$) δ 8.21 (dd, 1H, J=1.9, 5.6), 7.55-7.27 (m, 7H), 7.24-7.16 (m, 2H), 7.04-6.91 (m, 2H), 6.69-6.64 (m, 2H), 5.06 (s, 2H), 5.05 (s, 1H), 4.08-3.97 (m, 4H), 3.69 (t, 4H, J=5.1), 3.03 (s, 6H); ESI-MS m/z 482 (MH$^+$).

Example 118

N$^4$-(1,3-BENZODIOXOL-5-YL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, Et$_3$N, Me$_2$NHHCl, stirred 3.5 h at −78° C., warmed to 0° C. and stirred 3 h), N, and O. $^1$H NMR (400 MHz, CDCl$_3$) δ 8.24-8.18 (m, 1H), 7.48 (dt, 1H, J=1.9, 8.1), 6.92 (d, 1H, J=1.9), 6.75 (d, 1H, J=8.2), 6.74-6.54 (m, 3H), 6.41 (br s, 1H), 5.95 (s, 2H), 5.16 (s, 1H), 3.89 (t, 4H, J=5.1), 3.60 (t, 4H, J=5.3), 2.99 (s, 6H); ESI-MS m/z 420 (MH$^+$).

Example 119

N$^4$-(2,3-DIHYDRO-1,4-BENZODIOXIN-6-YL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, Et$_3$N, Me$_2$NHHCl, stirred 3.5 h at −78° C., warmed to 0° C. and stirred 3 h), N, and O. $^1$H NMR (400 MHz, CDCl$_3$) δ 8.24-8.18 (m, 1H), 7.49 (dt, 1H, J=2.1, 7.1), 6.89 (d, 1H, J=2.2), 6.81 (d, 1H, J=8.6), 6.76 (d, 1H, J=2.4), 6.68 (d, 1H, J=8.5), 6.62 (dd, 1H, J=4.6, 7.0), 6.18 (br s, 1H), 5.21 (s, 1H), 4.33-4.15 (m, 4H), 3.89 (t, 4H, J=5.1), 3.61 (t, 4H, J=5.1), 3.00 (s, 6H), ESI-MS m/z 434 (MH$^+$).

Example 120

N$^4$-(4-ISOQUINOLINYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, Et$_3$N, Me$_2$NHHCl, stirred 3.5 h at −78° C., warmed to 0° C. and stirred 3 h), N, and O. $^1$H NMR (400 MHz, CDCl$_3$) δ 8.93 (d, 1H, J=1.5), 8.31 (d, 1H, J=2.6), 8.27-8.19 (m, 1H), 8.01 (d, 1H, J=8.2), 7.70 (d, 1H, J=7.8), 7.59-7.52 (m, 1H), 7.51-7.45 (m, 2H), 6.78 (br s, 1H), 6.68 (d, 1H, J=8.6), 6.63 (dd, 1H, J=5.0, 7.1), 5.29 (s, 1H), 3.94 (t, 4H, J=5.0), 3.63 (t, 4H, J=5.3), 3.01 (s, 6H); ESI-MS m/z 427 (MH$^+$).

Example 121

N$^4$-(4-CYCLOHEXYLPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, Et$_3$N, Me$_2$NHHCl, stirred 3.5 h at −78° C., warmed to 0° C. and stirred 3 h), N, and O. $^1$H NMR (400 MHz, CDCl$_3$) δ 8.25-8.19 (m, 1H), 7.49 (dt, 1H, J=2.0, 6.9), 7.22 (d, 2H, J=6.4), 7.16 (d, 2H, J=8.2), 6.68 (d, 1H, J=8.6), 6.66-6.60 (m, 1H), 6.21 (br s, 1H), 5.30 (s, 1H), 3.99-3.91 (m, 4H), 3.63 (t, 4H, J=5.2), 3.02 (s, 6H), 2.53-2.42 (m, 1H), 1.92-1.79 (m, 4H), 1.48-1.32 (m, 4H), 1.31-1.19 (m, 2H); ESI-MS m/z 458 (MH$^+$).

Example 122

N$^4$,N$^4$-DIMETHYL-2-[4-(2-PYRIDINYL)-1-PIPERAZINYL]-N$^6$-(5,6,7,8-TETRAHYDRO-1-NAPHTHALENYL)-4,6-PYRIMIDINEDIAMINE

Prepared by Procedures A (CH$_2$Cl$_2$, Et$_3$N, Me$_2$NHHCl, stirred 3.5 h at −78° C., warmed to 0° C. and stirred 3 h), N, and O. $^1$H NMR (400 MHz, CDCl$_3$) δ 8.20 (dd, 1H, J=1.3, 4.9), 7.50 (dt, 1H, J=2.2, 6.8), 7.17 (d, 1H, J=7.5), 7.09 (t, 1H, JT 7.6), 6.94 (d, 1H, J=7.7), 6.73-6.62 (m, 2H), 5.06 (s, 1H), 4.08-3.93 (m, 4H), 3.66 (t, 4H, J=5.3), 3.00 (s, 6H), 2.79 (t, 2H, J=6.0), 2.72 (t, 2H, J=5.9), 1.88-1.67 (m, 4H), NH (1H, unobserved); ESI-MS m/z 430 (MH$^+$).

Example 123

N$^4$-(2,3-DIHYDRO-1H-INDEN-5-YL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, Et$_3$N, Me$_2$NHHCl, stirred 3.5 h at −78° C., warmed to 0° C. and stirred 3 h), N, and O. $^1$H NMR (400 MHz, CDCl$_3$) δ 8.20 (d, 1H, J=4.8), 7.51 (dt, 1H, J=1.8, 6.9), 7.19 (d, 1H, J=7.6), 7.14 (s, 1H), 7.04 (dd, 1H, J=1.7, 7.7), 6.73-6.61 (m, 2H), 5.23 (s, 1H), 4.09-3.94 (m, 4H), 3.68 (t, 4H, J=5.9), 3.04 (s, 6H), 2.89 (t, 4H, J=7.8), 2.16-2.01 (m, 2H), NH (1H, unobserved); ESI-MS m/z 416 (MH$^+$).

Example 124

N$^4$-(3,4-DICHLOROPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, Et$_3$N, Me$_2$NHHCl, stirred 3.5 h at −78° C., warmed to 0° C. and stirred 3 h), N, and O. $^1$H NMR (400 MHz, CDCl$_3$) δ 8.31-6.20 (m, 1H), 7.79-7.69 (m, 1H), 7.61-7.44 (m, 1H), 7.42-7.28 (m, 1H), 7.25-7.11 (m, 1H), 6.79-6.61 (m, 2H), 6.42 (br s, 1H), 5.22 (s, 1H), 3.98-3.82 (m, 4H), 3.65-3.56 (m, 4H), 3.02 (s, 6H); ESI-MS m/z 444 (MH$^+$ with $^{35}$Cl, $^{35}$Cl), 446 (MH$^+$ with $^{35}$Cl, $^{37}$Cl), 448 (MH$^+$ with $^{37}$Cl, $^{37}$Cl).

Example 125

N$^4$,N$^4$-DIMETHYL-2-[4-(2-PYRIDINYL)-1-PIPERAZINYL]-N$^6$-[3-(TRIFLUOROMETHYL)PHENYL]-4,6-PYRIMIDINEDIAMINE

Prepared by Procedures A (CH$_2$Cl$_2$, Et$_3$N, Me$_2$NHHCl, stirred 3.5 h at −78° C., warmed to 0° C. and stirred 3 h), N, and O. $^1$H NMR (400 MHz, CDCl$_3$) δ 8.59 (br s, 1H), 8.24-8.18 (m, 1H), 7.86 (s, 1H) 7.78-7.22 (m, 4H), 6.65 (t, 2H, J=5.0), 5.29 (s, 1H), 3.96 (t, 4H, J=5.5), 3.64 (t, 4H, J=5.2), 3.03 (s, 6H); ESI-MS m/z 444 (MH$^+$).

Example 126

2-(4-BENZYL-1-PIPERAZINYL)-N$^4$-[3-(DIMETHYLAMINO)PHENYL]-N$^6$,N$^6$-DIMETHYL-4,6-PYRIMIDINEDIAMINE

Prepared by Procedures P (toluene, 95° C., 16 h), Q (dioxane, 120° C.), and A. $^1$H NMR (400 MHz, CDCl$_3$) δ 7.52-7.37 (m, 7H), 7.25 (t, 1H, J=2.0), 7.14 (dd, 1H, J=1.5, 8.2), 7.05 (dd, 1H, J=2.5, 8.2), 4.36 (s, 2H), 3.98 (br s, 4H), 3.36 (s, 4H), 3.11 (s, 6H), 3.05 (s, 6H), 2.60 (s, 1H); ESI-MS m/z 432 (MH$^+$).

Example 127

2-(4-BENZYL-1-PIPERAZINYL)-N$^4$,N$^4$-DIMETHYL-N$^6$-(2-METHYL-1,3-BENZOTHIAZOL-5-YL)-4,6-PYRIMIDINEDIAMINE

Prepared by Procedures P (130° C. 13 h), Q, and A. $^1$H NMR (400 MHz, CDCl$_3$) δ 8.12 (s, 1H), 7.87 (d, 1H, J=8.8), 7.52-7.38 (m, 6H), 5.58 (s, 1H), 4.5.8 (s, 1H), 4.30 (s, 2H), 3.79-3.42 (m, 4H), 3.22-2.91 (m, 4H), 3.09 (s, 6H), 2.98 (s, 3H); ESI-MS m/z 460 (MH$^+$).

Example 128

2-(4-BENZYL-1-PIPERAZINYL)-N$^4$-CYCLOHEPTYL-N$^6$,N$^6$-DIMETHYL-4,6-PYRIMIDINEDIAMINE

Prepared by Procedures P (140° C., toluene, 6 h), Q, and A. $^1$H NMR (400 MHz, CDCl$_3$) δ 7.20-7.09 (m, 5H), 4.78 (s, 1H), 4.18 (br s, 1H), 3.74 (t, 4H, J=5.2), 3.52 (s, 2H), 2.99 (s, 6H), 2.46 (t, 4H, J=5.1), 2.03-1.92 (m, 2H), 1.87-1.68 (m, 11H); ESI-MS m/z 409 (MH$^+$).

Example 129

4-{[2-(4-BENZYL-1-PIPERAZINYL)-6-(DIMETHYLAMINO)-4-PYRIMIDINYL]AMINO}-2-CHLOROBENZONITRILE

Prepared by Procedures P (toluene, 95° C., 16 h), Q (dioxane, 120° C.), and A. $^1$H NMR (400 MHz, CDCl$_3$) δ 7.88 (d, 1H, J=3.1), 7.48 (d, 1H, J=8.5), 7.42-7.22 (m, 6H), 6.45 (s, 1H), 5.20 (s, 1H), 3.79 (t, 4H, J=5.2), 3.55 (s, 2H), 3.02 (s, 6H), 2.51 (t, 4H, J=5.0); ESI-MS m/z 448 (MH$^+$ with $^{35}$Cl), 450 (MH$^+$ with $^{37}$Cl).

Example 130

2-(4-BENZYL-1-PIPERAZINYL)-N$^4$,N$^4$-DIMETHYL-N$^6$-(1,3,3-TRIMETHYLBICYCLO[2.2.1]HEPT-2-YL)-4,6-PYRIMIDINEDIAMINE

Prepared by procedures P (toluene, 95° C., 16 h), Q (dioxane, 120° C.), and A. $^1$H NMR (400 MHz, CDCl$_3$) δ 7.38-7.21 (m, 6H), 4.87 (s, 1H), 3.79-3.69 (m, 4H), 3.53 (s, 2H), 3.46 (s, 1H), 2.98 (s, 6H), 2.46 (t, 4H, J=5.1), 1.71 (s, 1H), 1.69-1.62 (m, 2H), 1.48-1.35 (m, 2H), 1.20 (d, 1H, J=10.2), 1.19-1.02 (m, 1H), 1.14 (s, 3H), 1.07 (s, 3H), 0.79 (s, 3H); ESI-MS m/z 449 (MH$^+$).

Example 131

2-{4-[3-(BENZYLOXY)PHENYL]-1-PIPERAZINYL}-N$^4$,N$^4$-DIMETHYL-N$^6$-(4-METHYLPHENYL)-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 7.44 (d, 2H, J=7.1), 7.36 (t, 2H, J=7.0), 7.29 (d, 1H, J=7.1), 7.22-7.04 (m, 5H), 6.58-6.52 (m, 2H), 6.48 (d, 1H, J=7.2), 5-29 (s, 1H), 5.21 (s, 1H), 5.03 (s, 2H), 3.89-3.80 (m, 4H), 3.28-3.15 (m, 4H), 3.00 (s, 6H), 2.30 (s, 3H); ESI-MS m/z 495 (MH$^+$).

Example 132

N$^4$,N$^4$-DIMETHYL-2-[4-(2-PYRIDINYL)-1-PIPERAZINYL]-N$^6$-(3-QUINOLINYL)-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.93 (d, 1H, J=2.6), 8.31 (d, 1H, J=2.5), 8.26-8.18 (m, 1H), 8.02 (d, 1H; J=8.2), 7.71 (d, 1H, J=7.7), 7.57 (dt, 1H, J=1.5, 5.3), 7.53-7.46 (m, 2H), 6.68 (d, 1H, J=8.6), 6.64 (dd, 1H, J=4.9, 7.1), 5.30 (d, 2H, J=3.7), 3.94 (t, 4H, J=4.9), 3.64 (t, 4H, J=5.4), 3.03 (s, 6H); ESI-MS m/z 427 (MH$^+$).

Example 133

N$^4$-[4-BROMO-3-(TRIFLUOROMETHYL)PHENYL]-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.23-8.19 (m, 1H), 8.17 (d, 1H, J=2.3), 7.57 (d, 1H, J=8.7), 7.53-7.47 (m, 1H), 7.39 (d, 1H, J=5.2), 6.69 (d, 1H, J=8.7), 6.64 (t, 1H, J=5.0), 6.27 (s, 1H), 5.19 (s, 1H), 3.94-3.87 (m, 4H), 3.65-3.59 (m, 4H), 3.04 (s, 6H); ESI-MS m/z 522 (MH$^+$ with $^{79}$Br), 524 (MH$^+$ with $^{81}$Br).

Example 134

N$^4$-{3-CHLORO-4-[(TRIFLUOROMETHYL)SULFANYL]PHENYL}-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.23-8.19 (m, 1H), 7.91 (d, 1H, J=2.3), 7.61 (d, 1H, J=8.5), 7.50 (dt, 1H, J=2.1, 8.5), 7.30-7.20 (m, 1H), 6.70 (d, 1H, J=9.1), 6.64 (dd, 1H, J=4.7, 7.1), 6.35 (br s, 1H), 5.26 (s, 1H), 3.92 (t, 4H, J=5.6), 3.64 (t, 4H, J=5.0), 3.06 (s, 6H); ESI-MS m/z 510 (MH$^+$ with $^{35}$Cl), 512 (MH$^+$ with $^{37}$Cl).

Example 135

N$^4$-(3-ETHOXYPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.28-8.19 (m, 1H), 7.50 (dt, 1H, J=2.1, 6.9), 7.19 (t, 1H, J=8.1), 6.96 (t, 1H, J=2.1), 6.85 (d, 1H, J=8.2), 6.68 (d, 1H, J=8.6), 6.63-6.56 (m, 1H), 6.35 (br s, 1H), 5.36 (s, 1H), 4.09-3.98 (m, 2H), 3.91 (t, 4H, J=5.3), 3.61 (t, 4H, J=5.1), 3.02 (s, 6H), 1.39 (t, 3H, J=5.7); ESI-MS m/z 420 (MH$^+$).

Example 136

N$^4$-[2-CHLORO-4-(TRIFLUOROMETHYL)PHENYL]-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O.
$^1$H NMR (400 MHz, CDCl$_3$) δ 8.23-8.15 (m, 1H), 8.15 (d, 1H, J=2.1), 7.50 (dt, 1H, J=2.0, 8.8), 7.42-7.33 (m, 2H), 6.69 (d, 1H, J=8.6), 6.64 (dd, 1H, J=4.8, 6.3), 6.28 (s, 1H), 5.18 (s, 1H), 3.91 (t, 4H, J=5.0), 3.62 (t, 4H, J=5.1), 3.04 (s, 6H); ESI-MS m/z 478 (MH$^+$ with $^{35}$Cl), 480 (MH$^+$ with $^{37}$Cl).

Example 137

N-4-(2-ADAMANTYL)-2-(4-BENZYL-1-PIPERAZINYL)-N-6-N-6-DIMETHYL-4,6-PYRIMIDINEDIAMINE

Prepared by Procedures P (toluene, 90° C.), Q, and A. $^1$H NMR (400 MHz, CDCl$_3$) δ 7.39-7.21 (m, 5H), 4.83 (s, 1H), 4.72 (br s, 1H), 3.74 (m, 3H), 3.52 (s, 2H), 2.98 (s, 6H), 2.46 (t, 4H, J=5.3), 2.05-1.53 (m, 13H); ESI-MS m/z: 433 (MH$^+$).

Example 138

N-4-(1-NORADAMANTYL)-2-(4-BENZYL-1-PIPERAZINYL)-N-6-N-6-DIMETHYL-4,6-PYRIMIDINEDIAMINE

Prepared by Procedures P (toluene, 90° C.), Q, and A. $^1$H NMR (400 MHz, CDCl$_3$) δ 7.38-7.20 (m, 5H), 4.97 (s, 1H), 4.67 (br s, 1H), 3.74 (s, 4H), 3.52 (s, 2H), 2.99 (s, 6H), 2.46 (t, 4H, J=5.2), 2.32-1.51 (m, 15H); ESI-MS m/z: 447 (MH$^+$).

Example 139

2-(4-BENZYL-1-PIPERAZINYL)-N$^4$,N$^4$-DIMETHYL-N$^6$-[(1S,2R,3R,5S)-2,6,6-TRIMETHYLBICYCLO[3.1.1]HEPT-3-YL]-4,6-PYRIMIDINEDIAMINE

Prepared by Procedures P (toluene, 150° C., 4 h), Q (neat, 130° C.), and A. $^1$H NMR (400 MHz, CDCl$_3$) δ 7.38-7.21 (m, 5H), 4.86 (s, 1H), 4.35 (br s, 1H), 3.75 (t, 4H, J=4.6), 3.53 (s, 2H), 2.99 (s, 6H), 2.66-2.56 (m, 1H), 2.47 (t, 4H, J=4.5), 2.41-2.33 (m, 1H), 1.98-1.92 (m, 1H), 1.83 (t, 1H, J=5.8), 1.68-1.60 (m, 2H), 1.23 (s, 3H), 1.14 (d, 3H, J=7.3), 1.05 (s, 3H), 0.92 (d, 2H); ESI-MS m/z: 449 (MH$^+$).

Example 140

2-[4-(5-BROMO-2-PYRIDINYL)-1-PIPERAZINYL]-N$^4$,N$^4$-DIMETHYL-N$^6$-(4-METHYLPHENYL)-4,6-PYRIMIDINEDIAMINE

Prepared using Procedure Y (DMF). $^1$H NMR (400 MHz, CDCl$_3$) δ 8.21 (d, 1H, J=2.6), 7.53 (dd, 1H, J=2.6, 8.8), 7.19 (d, 2H, J=8.5), 7.12 (d, 2H, J=8.5), 6.21 (s, 1H), 5.28 (s, 1H), 3.88 (t, 4H, J=5.0), 3.58 (t, 4H, J=5.2), 3.00 (s, 6H), 2.33 (s, 3H); ESI-MS m/z: 468 (MH$^+$ with $^{79}$Br), 470 (MH$^+$ with $^{81}$Br).

Example 141

6-{4-[4-(DIMETHYLAMINO)-6-(4-TOLUDINO)-2-PYRIMIDINYL]-1-PIPERAZINYL}NICOTINAMIDE

Prepared by Procedure Y (DMF). $^1$H NMR (400 MHz, CDCl$_3$) δ 8.13 (s, 1H), 7.30-7.25 (m, 4H), 7.17 (d, 2H, J=8.5), 7.13 (d, 2H, J=8.6), 6.18 (br s, 1H), 5.28 (s, 1H), 3.82 (t, 2H, J=5.1), 3.79 (t, 2H, J=5.3), 3.60 (t, 2H, J=5.1), 3.41 (t, 2H, J=5.3), 2.99 (s, 6H), 2.33 (s, 3H); ESI-MS m/z: 433 (MH$^+$).

Example 142

2-[4-(3-METHOXYBENZYL)-1-PIPERAZINYL]-$N^4$,$N^4$-DIMETHYL-$N^6$-(4-METHYLPHENYL)-4,6-PYRIMIDINEDIAMINE

Prepared by Procedure Z (DIEA). $^1$H NMR (400 MHz, CDCl$_3$) δ 7.22 (d, 1H, J=6.8), 7.17 (d, 2H, J=8.3), 7.10 (d, 2H, J=8.2), 6.93 (d, 1H, J=2.3), 6.92 (d, 1H, J=2.4), 6.80 (dd, 1H, J=2.0, 7.6), 6.18 (br s, 1H), 5.25 (s, 1H), 3.82 (s, 3H), 3.78 (t, 4H, J=5.1), 3.52 (s, 2H), 2.97 (s, 6H), 2.49 (t, 4H, J=5.1), 2.31 (s, 3H); ESI-MS m/z: 433 (MH$^+$).

Example 143

2-[4-(5-BROMO-2-PYRIDINYL)-1-PIPERAZINYL]-$N^4$-(3-METHOXYPHENYL)-$N^6$,$N^6$-DIMETHYL-4,6-PYRIMIDINEDIAMINE

Prepared by Procedure Y. $^1$H NMR (400 MHz, CDCl$_3$) δ 8.21 (d, 1H, J=2.4), 7.53 (dd, 1H, J=2.5, 9.2), 7.20 (t, 1H, J=8.1), 7.00 (t, 1H, J=2.0), 6.85 (dd, 1H, J=2.0, 8.0), 6.62-6.54 (m, 2H), 6.29 (s, 1H), 5.36 (s, 1H), 3.89 (t, 4H, J=5.1), 3.80 (s, 3H), 3.58 (t, 4H, J=4.9), 3.02 (s, 6H); ESI-MS m/z: 484 (MH$^+$ with $^{79}$Br), 486 (MH$^+$ with $^{81}$Br).

Example 144

$N^4$-(3-METHOXYPHENYL)-$N^6$,$N^6$-DIMETHYL-2-[4-(2-PYRIDINYLMETHYL)-1-PIPERAZINYL]-4,6-PYRIMIDINEDIAMINE

Prepared by Procedure X. $^1$H NMR (400 MHz, CDCl$_3$) δ 8.61-8.54 (m, 1H), 7.66 (dt, 1H, J=1.8, 7.8), 7.45 (d, 1H, J=7.8), 7.23-7.14 (m, 2H), 7.00 (t, 1H, J=2.5), 6.87-6.78 (m, 1H), 6.61-6.54 (m, 1H), 6.26 (br s, 1H), 5.33 (s, 1H), 3.82 (t, 4H, J=5.0), 3.78 (s, 3H), 3.70 (s, 2H), 2.99 (s, 6H), 2.56 (t, 4H, J=5.0); ESI-MS m/z: 420 (MH$^+$).

Example 145

2-[4-(CYCLOHEXYLMETHYL)-1-PIPERAZINYL]-$N^4$-(3-METHOXYPHENYL)-$N^6$,$N^6$-DIMETHYL-4,6-PYRIMIDINEDIAMINE

Prepared by Procedure T. $^1$H NMR (400 MHz, CDCl$_3$) δ 7.21 (t, 1H, J=8.2), 7.00-6.95 (m, 1H), 6.85 (d, 1H, J=8.2), 6.59 (d, 1H, J=7.7), 6.32 (s, 1H), 5.36 (s, 1H), 3.82-3.71 (m, 4H), 3.79 (s, 3H), 3.69-3.62 (m, 2H), 3.58-3.50 (m, 2H), 3.01 (s, 6H), 2.54-2.45 (m, 1H), 1.87-1.48 (m, 8H), 1.45-1.29 (m, 4H); ESI-MS m/z: 425 (MH$^+$).

Example 146

$N^4$-(3-METHOXYPHENYL)-$N^6$,$N^6$-DIMETHYL-2-[4-(3-THIENYLMETHYL)-1-PIPERAZINYL]-4,6-PYRIMIDINEDIAMINE

Prepared by Procedures T (reduction 4 h) and W. $^1$H NMR (400 MHz, CDCl$_3$) δ 7.27 (dd, 1H, J=3.2, 5.1), 7.19 (t, 1H, J=8.0), 7.16-7.11 (m, 1H), 7.08 (dd, 1H, J=1.3, 4.9), 7.00 (t, 1H, J=2.3), 6.82 (dd, 1H, J=2.0, 8.3), 6.57 (dd, 1H, J=2.5, 8.2), 6.25 (s, 1H), 5.33 (s, 1H), 3.79 (t, 4H, J=5.5), 3.78 (s, 3H), 3.57 (s, 2H), 2.99 (s, 6H), 2.48 (t, 4H, J=5.2) ESI-MS m/z: 425 (MH$^+$).

Example 147

$N^4$-(3-METHOXYPHENYL)-$N^6$,$N^6$-DIMETHYL-2-[4-(4-PYRIDINYLMETHYL)-1-PIPERAZINYL]-4,6-PYRIMIDINEDIAMINE

Prepared by Procedure T (acylation with DIPEA). $^1$H NMR (400 MHz, CDCl$_3$) δ 8.55 (dd, 2H, J=1.5, 5.8), 7.31 (d, 2H, J=6.0), 7.1.9 (t, 1H, J=8.3), 6.99 (t, 1H, J=2.1), 6.83 (dd, 1H, J=1.5, 7.8), 6.58 (dd, 1H, J=2.0, 7.8), 6.28 (br s, 1H), 5.34 (s, 1H), 3.80 (t, 4H, J=5.2), 3.78 (s, 3H), 3.54 (s, 2H), 3.00 (s, 6H), 2.49 (t, 4H, J=5.3; ESI-MS m/z: 420 (MH$^+$).

Example 148

2-[4-(3-METHOXYBENZYL)-1-PIPERAZINYL]-$N^4$-(3-METHOXYPHENYL)-$N^6$,$N^6$-DIMETHYL-4,6-PYRIMIDINEDIAMINE

Prepared by Procedure S. $^1$H NMR (400 MHz, CDCl$_3$) δ 7.22 (d, 1H, J=7.9), 7.17 (t, 1H, J=8.2), 6.99 (t, 1H, J=2.1), 6.95-6.84 (m, 2H), 6.86-6.78 (m, 2H), 6.59-6.55 (m, 1H), 6.29 (br s, 1H), 5.32 (s, 1H), 3.82 (s, 3H), 3.79 (t, 4H, J=5.1), 3.77 (s, 3H), 3.52 (s, 2H) 2.99 (s, 6H), 2.49 (t, 4H, J=5.1); ESI-MS m/z: 449 (MH$^+$).

Example 149

$N^2$-[2-(3-METHOXYPHENYL)ETHYL]-$N^4$,$N^4$-DIMETHYL-$N^6$-(4-METHYLPHENYL)-2,4,6-PYRIMIDINETRIAMINE

Prepared by Procedure F (dioxane, potassium tert-butoxide, 120° C., 16 h), Q (toluene, TEA, 120° C.), A (CH$_2$Cl$_2$, Δ, TEA). $^1$H NMR (400 MHz, CDCl$_3$) δ 7.22 (t, 1H, J=7.9), 7.18 (d, 2H, J=8.4), 7.12 (d, 2H, J=8.3), 6.84 (d, 1H, J=7.6), 6.82-6.74 (m, 2H), 6.28 (br s, 1H), 5.28 (s, 1H), 4.77 (s, 1H), 3.80 (s, 3H), 3.63 (q, 2H, J=6.7), 2.99 (s, 6H), 2.89 (t, 2H, J=7.4), 2.32 (s, 3H); ESI-MS m/z: 378 (MH$^+$).

Example 150

$N^2$-[2-(2-METHOXYPHENYL)ETHYL]-$N^4$,$N^4$-DIMETHYL-$N^6$-(4-METHYLPHENYL)-2,4,6-PYRIMIDINETRIAMINE

Prepared by Procedures F (dioxane, potassium tert-butoxide, 140° C., 16 h), Q (toluene), and A (CH$_2$Cl$_2$, Δ, TEA). $^1$H NMR (400 MHz, CDCl$_3$) δ 7.23-7.12 (m, 4H), 7.12 (d, 2H, J=8.1), 6.89 (d, 1H, J=7.8), 6.86 (d, 1H, J=7.6), 6.61 (d, 1H, J=8.0), 6.50 (br s, 1H), 5.25 (s, 1H), 3.84 (s, 3H), 3.60 (q, 2H, J=7.1), 3.00 (s, 6H), 2.93 (t, 2H, J=7.6), 2.33 (s, 3H); ESI-MS m/z: 378 (MH$^+$).

Example 151

2-(4-BENZYL-1-PIPERAZINYL)-$N^4$-(3,4-DICHLOROPHENYL)-$N^6$,$N^6$-DIMETHYL-4,6-PYRIMIDINEDIAMINE

Prepared by Procedures P (toluene, 140° C., 6 h), Q (dioxane, 120° C.), and A. $^1$H NMR (400 MHz, CDCl$_3$) δ 7.65 (d, 1H, J=2.5), 7.35-7.30 (m, 4H), 7.29-7.22 (m, 2H), 7.13 (dd, 1H, J=1.5, 8.5), 6.19 (br s, 1H), 5.21 (s, 1H), 3.78 (t, 4H, J=5.0), 3.55 (s, 2H), 3.00 (s, 6H), 2.49 (t, 4H, J=5.0); ESI-MS m/z: 457 (MH$^+$ with $^{35}$Cl, $^{35}$Cl), 459 (MH$^+$ with $^{35}$Cl, $^{37}$Cl), 461 (MH$^+$ with $^{37}$Cl, $^{37}$Cl).

Example 152

N⁴-[4-(BENZYLOXY)CYCLOHEXYL]-2-(4-BENZYL-1-PIPERAZINYL)-N⁶,N⁶-DIMETHYL-4,6-PYRIMIDINEDIAMINE

Prepared by Procedures P (16 h), Q, and A. ¹H NMR (400 MHz, CDCl₃) δ 7.42-7.18 (m, 10H), 4.94 (s, 1H), 4.61 (d, 1H, J=11.8), 4.51 (d, 1H, J=11.8), 4.39 (br s, 1H), 3.75 (t, 4H, J=5.0), 3.53 (s, 2H), 3.31 (dt, 1H, J=5.3, 8.3), 2.95 (s, 6H), 2.46 (t, 4H, J=5.0), 2.19-2.11 (m, 1H), 2.07-1.98 (m, 1H), 1.79-1.56 (m, 3H), 1.53-1.41 (m, 1H), 1.40-1.21 (m, 3H); ESI-MS m/z: 501 (MH⁺).

Example 153

2-(4-BENZYL-1-PIPERAZINYL)-N⁴,N⁴-DIMETHYL-N⁶-[(1R,2R,4R)-1,7,7-TRIMETHYLBICYCLO[2.2.1]HEPT-2-YL]-4,6-PYRIMIDINEDIAMINE

Prepared by Procedures P (90° C., 16 h), Q, and A. ¹H NMR (400 MHz, CDCl₃) δ 7.44-7.22 (m, 6H), 4.81 (s, 1H), 4.36 (d, 1H, J=7.0), 3.74 (s, 4H), 3.53 (s, 2H), 2.98 (s, 6H), 2.46 (t, 4H, J=5.1), 1.84 (dd, 1H, J=8.9, 12.9), 1.78-1.52 (m, 4H), 1.29-1.11 (m, 2H), 0.97 (s, 3H), 0.89 (s, 3H), 0.83 (s, 3H); ESI-MS m/z: 449 (MH⁺).

Example 154

N⁴,N⁴-DIMETHYL-N⁶-(4-METHYLPHENYL)-2-[4-(TETRAHYDRO-2-FURANYLMETHYL)-1-PIPERAZINYL]-4,6-PYRIMIDINEDIAMINE

Prepared by Procedures A, P (16 h), and Q (dioxane, 120° C.). ¹H NMR (400 MHz, CDCl₃) δ 7.17 (d, 2H, J=8.4), 7.11 (d, 2H, J=8.0), 6.22 (br s, 1H), 5.29 (s, 1H), 4.12-4.03 (m, 1H), 3.91 (q, 1H, J=6.7), 3.80 (t, 4H, J=5.1), 3.76 (q, 1H, J=7.5), 2.98 (s, 6H), 2.57 (t, 4H, J=5.0), 2.56-2.40 (m, 2H), 2.32 (s, 3H), 2.05-1.96 (m, 1H), 1.94-1.80 (m, 2H), 1.57-1.45 (m, 1H); ESI-MS m/z: 397 (MH⁺).

Example 155

3-{[2-(4-BENZYL-1-PIPERAZINYL)-6-(DIMETHYLAMINO)-4-PYRIMIDINYL]AMINO}PHENOL

Prepared By Procedures P (Toluene, 120° C., 40H), Q (dioxane, 120° C.), AND A. ¹H NMR (400 MHz, CDCl₃) δ 7.38-7.29 (m, 4H), 7.28-7.26 (m, 1H), 7.13 (t, 1H, J=8.0), 6.84 (t, 1H, J=2.8), 6.80 (ddd, 1H, J=0.7, 2.0, 7.9), 6.48 (ddd, 1H, J=0.7, 2.1, 8.0), 6.32 (br s, 1H), 5.32 (s, 1H), 3.79 (t, 4H, J=5.0), 3.55 (s, 2H), 3.49 (s, 1H), 2.99 (s, 6H), 2.50 (t, 4H, J=5.0); ESI-MS m/z: 405 (MH⁺).

Example 156

2-(4-BENZYL-1-PIPERAZINYL)-N⁴-(4-FLUOROPHENYL)-N⁶,N⁶-DIMETHYL-4,6-PYRIMIDINEDIAMINE

Prepared by Procedures P (toluene, sodium tert-butoxide, 120° C., 16 h), Q (dioxane, 120° C.), and A. ¹H NMR (400 MHz, CDCl₃) δ 7.37-7.30 (m, 4H), 7.29-7.21 (m, 3H), 6.99 (t, 2H, J=8.6), 6.14 (br s, 1H), 5.13 (s, 1H), 3.77 (t, 4H, J=4.9), 3.54 (s, 2H), 2.97 (s, 6H), 2.48 (t, 4H, J=4.9); ESI-MS m/z: 407 (MH⁺).

Example 157

2-(4-BENZYL-1-PIPERAZINYL)-N⁴,N⁴-DIMETHYL-N⁶-(4-METHYLCYCLOHEXYL)-4,6-PYRIMIDINEDIAMINE

Prepared by Procedures P (sodium tert-butoxide, toluene, 120° C., 16 h), Q (dioxane, 120° C.), and A. ¹H NMR (400 MHz, CDCl₃) δ 7.35-7.10 (m, 6H), 4.82 (d, 1H, J=4.9), 3.81-3.61 (m, 5H), 3.53 (s, 2H), 2.99 (s, 6H), 2.46 (t, 4H, J=4.5), 1.79-1.46 (m, 7H), 1.29-0.98 (m, 2H), 0.90 (d, 3H, J=6.6); ESI-MS m/z: 409 (MH⁺).

Example 158

2-(4-BENZYL-1-PIPERAZINYL)-N⁴-[4-(DIMETHYLAMINO)PHENYL]-N⁶,N⁶-DIMETHYL-4,6-PYRIMIDINEDIAMINE

Prepared by Procedures P (sodium tert-butoxide, toluene, 120° C., 16 h); Q (neat, 130° C.), and A. ¹H NMR (400 MHz, CDCl₃) δ 7.39-7.22 (m, 5H), 7.14 (d, 2H, J=8.4), 6.71 (d, 2H, J=8.8), 6.04 (br s, 1H) 5.08 (s, 1H), 3.85-3.74 (m, 4H), 3.54 (s, 2H), 2.94 (s, 6H), 2.93 (s, 6H), 2.48 (t, 4H, J=5.1); ESI-MS m/z: 432 (MH⁺).

Example 159

N⁴,N⁴-DIMETHYL-N⁶-(4-METHYLPHENYL)-2-[4-(2-PHENYLETHYL)-1-PIPERAZINYL]-4,6-PYRIMIDINEDIAMINE

Prepared by Procedure S (toluene, 120° C.). ¹H NMR (400 MHz, CDCl₃) δ 7.34-7.20 (m, 5H), 7.18 (d, 2H, J=8.5), 7.12 (d, 2H, J=8.5), 6.21 (br s, 1H), 5.26 (s, 1H), 3.88-3.79 (m, 4H), 2.99 (s, 6H), 2.90-2.83 (m, 2H), 2.68-2.63 (m, 2H), 2.60 (t, 4H, J=4.4), 2.32 (s, 3H); ESI-MS m/z: 417 (MH⁺).

Example 160

2-(4-BENZYL-1-PIPERAZINYL)-N⁴-(3-CHLOROPHENYL)-N⁶,N⁶-DIMETHYL-4,6-PYRIMIDINEDIAMINE

Prepared by Procedures P (toluene, sodium tert-butoxide, 120° C., 40 h), Q (dioxane, 120° C.), and A. ¹H NMR (400 MHz, CDCl₃) δ 7.48 (t, 1H, J=1.9), 7.38-7.23 (m, 5H), 7.20-7.11 (m, 2H), 6.95 (ddd, 1H, J=1.2, 1.9, 7.6), 6.28 (br s, 1H), 5.24 (s, 1H), 3.79 (t, 4H, J=5.0), 3.54 (s, 2H), 3.00 (s, 6H), 2.49 (t, 4H, J=5.0); ESI-MS m/z: 423 (MH⁺ with ³⁵Cl), 425 (MH⁺ with ³⁷Cl).

Example 161

N²,N⁴,N⁴-TRIMETHYL-N⁶-(4-METHYLPHENYL)-N²-[2-(2-PYRIDINYL)ETHYL]-2,4,6-PYRIMIDINETRIAMINE

Prepared by Procedures F (dioxane, potassium tert-butoxide, 140° C., 16 h), Q, and A (CH₂Cl₂, Δ, TEA). ¹H NMR (400 MHz, CDCl₃) δ 8.54 (ddd, 1H, J=1.2, 2.1, 5.3), 7.57 (dt, 1H, J=1.7, 7.6), 7.23 (d, 2H, J=8.6), 7.18 (d, 1H, J=7.7), 7.14-7.09 (m, 1H), 7.10 (d, 2H, J=7.7), 6.29 (br s, 1H), 5.24 (s, 1H), 3.93 (dd, 2H, J=5.9, 7.8), 3.11 (dd, 2H, J=6.0, 7.7), 3.08 (s, 3H), 3.00 (s, 6H), 2.32 (s, 3H); ESI-MS m/z: 363 (MH⁺).

Example 162

N$^4$,N$^4$-DIMETHYL-N$^6$-(4-METHYLPHENYL)-N$^2$-(3-PHENYLPROPYL)-2,4,6-PYRIMIDINETRIAMINE

Prepared using Procedures R, S, and V. $^1$H NMR (400 MHz, CDCl$_3$) δ 7.25 (d, 2H, J=7.7), 7.22-7.14 (m, 5H), 7.11 (d, 2H, J=8.1), 6.41 (br s, 1H), 5.27 (s, 1H), 4.76 (t, 1H, J=5.7), 3.41 (dd, 2H, J=7.0, 12.9), 2.96 (s, 6H), 2.70 (t, 2H, J=7.7), 2.31 (s, 3H), 1.91 (t, 2H, J=7.5); ESI-MS m/z: 362 (MH$^+$).

Example 163

2-(4-CYCLOHEXYL-1-PIPERAZINYL)-N$^4$-(3-METHOXYPHENYL)-N$^6$,N$^6$-DIMETHYL-4,6-PYRIMIDINEDIAMINE

Prepared using Procedures P (16 h), Q (dioxane, 120° C.), and A. $^1$H NMR (400 MHz, CDCl$_3$) δ 7.11 (t, 1H, J=8.3), 6.92 (t, 1H, J=2.4), 6.78-6.73 (m, 1H), 6.53-6.48 (m, 1H), 6.39 (br s, 1H), 5.27 (s, 1H), 3.72 (t, 4H, J=5.0), 3.71 (s, 3H), 2.92 (s, 6H), 2.55 (t, 4H, J=5.1), 2.28-2.18 (m, 1H), 1.87-1.79 (m, 2H), 1.77-1.68 (m, 2H), 1.56 (d, 1H, J=12.4), 1.24-1.08 (m, 4H), 1.08-0.97 (m, 1H); ESI-MS m/z: 411 (MH$^+$).

Example 164

2-(4-BENZYL-1-PIPERAZINYL)-N$^4$-(3-FLUOROPHENYL)-N$^6$,N$^6$-DIMETHYL-4,6-PYRIMIDINEDIAMINE

Prepared by Procedures P (140° C., 4 h), Q (neat, 130° C.), and A. $^1$H NMR (400 MHz, CDCl$_3$) δ 7.37-7.31 (m, 5H), 7.28-7.17 (m, 2H), 6.98 (ddd, 1H, J=0.7, 2.0, 8.1), 6.67 (ddt, 1H, J=0.9, 2.0, 8.3), 6.30 (br s, 1H), 5.27 (s, 1H), 3.79 (t, 4H, J=5.1), 3.55 (s, 2H), 3.00 (s, 6H), 2.50 (t, 4H, J=5.0); ESI-MS m/z: 407 (MH$^+$).

Example 165

N$^4$-(3-METHOXYPHENYL)-N$^6$,N$^6$-DIMETHYL-2-[4-(2-THIENYLMETHYL)-1-PIPERAZINYL]-4,6-PYRIMIDINEDIAMINE

Prepared by Procedure T. $^1$H NMR (400 MHz, CDCl$_3$) δ 7.24 (dd, 1H, J=1.2, 5.2), 7.19 (t, 1H, J=8.1), 6.99 (t, 1H, J=2.0), 6.96-6.91 (m, 2H), 6.83 (ddd, 1H, J=0.8, 1.7, 7.9), 6.57 (dd, 1H, J=2.0, 8.2), 6.25 (br s, 1H), 5.33 (s, 1H), 3.81 (t, 4H, J=5.2), 3.78 (s, 3H), 3.76 (s, 2H), 2.99 (s, 6H), 2.53 (t, 4H, J=5.1); ESI-MS m/z: 425 (MH$^+$).

Example 166

2-[4-(2-METHOXYBENZYL)-1-PIPERAZINYL]-N$^4$-(3-METHOXYPHENYL)-N$^6$,N$^6$-DIMETHYL-4,6-PYRIMIDINEDIAMINE

Prepared by Procedure T (reduction 3 h). $^1$H NMR (400 MHz, CDCl$_3$) δ 7.40 (dd, 1H, J=1.6, 7.6), 7.23 (dd, 1H, J=1.2, 7.6), 7.19 (t, 1H, J=8.3), 7.01 (t, 1H, J=1.9), 6.95 (dt, 1H, J=1.0, 7.3), 6.87 (dd, 1H, J=1.1, 8.3), 6.82 (dd, 1H, J=1.0, 2.0, 8.2), 6.57 (ddd, 1H, J=0.7, 2.5, 8.2), 6.26 (br s, 1H), 5.32 (s, 1H), 3.82 (s, 3H), 3.81 (t, 4H, J=5.1), 3.78 (s, 3H), 3.62 (s, 2H), 2.99 (s, 6H), 2.55 (t, 4H, J=5.0); ESI-MS m/z: 449 (MH$^+$).

Example 167

2-(4-BENZYL-1-PIPERAZINYL)-N$^4$,N$^4$-DIMETHYL-N$^6$-[(1R,2S)-1,7,7-TRIMETHYLBICYCLO[2.2.1]HEPT-2-YL]-4,6-PYRIMIDINEDIAMINE

Prepared by Procedures P (toluene, 120° C., 16 h) Q (neat, 130° C.), and A. $^1$H NMR (400 MHz, CDCl$_3$) δ 7.37-7.22 (m, 5H), 4.82 (s, 1H), 4.51 (br s, 1H), 3.74 (m, 4H), 3.53 (s, 2H), 2.97 (s, 6H), 2.47 (t, 4H, J=4.7), 2.39-2.30 (m, 1H), 1.76-1.68 (m, 4H), 1.66 (t, 1H, J=4.7), 1.41-1.31 (m, 2H) 0.96 (s, 3H), 0.88 (s, 3H), 0.86 (s, 3H); ESI-MS m/z: 449 (MH$^+$).

Example 168

N$^4$-(2-ADAMANTYL)-2-(4-BENZYL-1-PIPERAZINYL)-N$^6$,N$^6$-DIMETHYL-4,6-PYRIMIDINEDIAMINE

Prepared by Procedures P (90° C. toluene), Q, and A. $^1$H NMR (400 MHz, CDCl$_3$) δ 7.39-7.21 (m, 5H), 4.83 (s, 1H), 4.72 (br s, 1H), 3.74 (m, 5H), 3.52 (s, 2H), 2.98 (s, 6H), 2.46 (t, 4H, J=5.3), 2.05-1.53 (m, 14H); ESI-MS m/z: 447 (MH$^+$).

Example 169

2-(4-BENZYL-1-PIPERAZINYL)-N$^4$-(4-TERT-BUTYLCYCLOHEXYL)-N$^6$,N$^6$-DIMETHYL-4,6-PYRIMIDINEDIAMINE

Prepared by, Procedures P (toluene, 16 h), Q (neat, 130° C.), and A. $^1$H NMR (400 MHz, CDCl$_3$) δ 7.36-7.22 (m, 5H), 4.82 (s, 1H), 3.74 (t, 4H, J=4.7), 3.53 (s, 2H), 3.33 (s, 1H), 2.98 (s, 6H), 2.46 (t, 4H, J=4.7), 1.15-0.91 (m, 9H), 0.86 (s, 9H); ESI-MS m/z: 451 (MH$^+$).

Example 170

2-(4-BENZYL-1-PIPERAZINYL)-N$^4$-CYCLOOCTYL-N$^6$,N$^6$-DIMETHYL-4,6-PYRIMIDINEDIAMINE

Prepared by Procedures P (16 h), Q, and A. $^1$H NMR (400 MHz; CDCl$_3$) δ 7.39-7.21 (m, 5H), 4.79 (s, 1H), 4.34 (s, 1H), 3.74 (t, 4H, J=4.7), 3.53 (s, 2H), 2.99 (s, 6H), 2.40 (t, 4H, J=4.6), 1.93-1.49 (m, 15H); ESI-MS m/z: 423 (MH$^+$).

Example 171

2-(4-BENZYL-1-PIPERAZINYL)-N$^4$-(4-CHLOROPHENYL)-N$^6$,N$^6$-DIMETHYL-4,6-PYRIMIDINEDIAMINE

Prepared by Procedures P (140° C., Q (neat, 130° C.), and A. $^1$H NMR (400 MHz, CDCl$_3$) δ 7.38-7.22 (m, 9H), 6.31 (br s, 1H), 5.21 (s, 1H), 3.78 (t, 4H, J=5.1 Hz), 3.55 (s, 2H), 2.99 (s, 6H), 2.49 (t, 4H, J=5.1); ESI-MS m/z: 423 (MH$^+$ with $^{35}$Cl), 425 (MH$^+$ with $^{37}$Cl).

Example 172

2-(4-BENZYL-1-PIPERAZINYL)-N$^4$-(3-CHLORO-4-METHYLPHENYL)-N$^6$,N$^6$-DIMETHYL-4,6-PYRIMIDINEDIAMINE

Prepared by Procedures P (toluene, 120° C., 16 h), Q (neat, 130° C.), and A. $^1$H NMR (400 MHz, CDCl$_3$) δ 7.43 (d, 1H, J=2.1), 7.38-7.09 (m, 5H), 7.07 (d, 1H, J=2.1), 7.05 (d, 1H, J=2.6), 6.02 (s, 1H), 5.21 (s, 1H), 3.78 (t, 4H, J=5.6), 3.54 (s, 2H), 2.99 (s, 6H), 2.49 (t, 4H, J=5.0), 2.31 (s, 3H); ESI-MS m/z: 437 (MH$^+$ with $^{35}$Cl), 439 (MH$^+$ with $^{37}$Cl).

Example 173

2-(4-BENZYL-1-PIPERAZINYL)-N$^4$,N$^4$-DIMETHYL-N$^6$-(1,2,3,4-TETRAHYDRO-2-NAPHTHALENYL)-4,6-PYRIMIDINEDIAMINE

Prepared by Procedures P (16 h), Q, and A. $^1$H NMR (400 MHz, CDCl$_3$) δ 7.41-7.04 (m, 9H), 4.99 (s, 1H), 4.91 (s, 1H), 3.74 (m, 4H), 3.53 (s, 2H), 3.47 (m, 1H), 2.99 (s, 6H), 2.90-2.69 (m, 2H), 2.49 (m, 4H), 2.09-1.71 (m, 4H); ESI-MS m/z: 443 (MH$^+$).

Example 174

N$^4$,N$^4$-DIMETHYL-N$^6$-(4-METHYLPHENYL)-2-[4-(2-THIENYLMETHYL)-1-PIPERAZINYL]-4,6-PYRIMIDINEDIAMINE

Prepared by Procedure X (NaBH(OAc)$_3$, CH$_2$Cl$_2$, molecular sieves). $^1$H NMR (400 MHz, CDCl$_3$) δ 7.17 (d, 2H, J=8.3), 7.15-7.09 (m, 2H), 7.03-6.94 (m, 3H), 5.22 (br s, 1H), 4.85 (s, 1H), 3.86-3.79 (m, 4H), 3.7.7 (s, 2H), 2.98 (s, 6H), 2.62-2.53 (m, 4H), 2.32 (s, 3H); ESI-MS m/z: 409 (MH$^+$).

Example 175

2-[4-(2-METHOXYBENZYL)-1-PIPERAZINYL]-N$^4$,N$^4$-DIMETHYL-N$^6$-(4-METHYLPHENYL)-4,6-PYRIMIDINEDIAMINE

Prepared by Procedure Z. $^1$H NMR (400 MHz, CDCl$_3$) δ 7.40 (dd, 1H, J=1.6, 7.5), 7.23 (dt, 1H, J=1.4, 7.6), 7.17 (d, 2H, J=8.4), 7.10 (d, 2H, J=8.3), 6.94 (t, 1H, J=7.5), 6.87 (d, 1H, J=7.6), 6.17 (br s, 1H), 5.24 (s, 1H), 3.82 (s, 3H), 3.79 (t, 4H, J=5.0), 3.62 (s, 2H), 2.97 (s, 6H), 2.55 (t, 4H, J=5.0), 2.31 (s, 3H); ESI-MS m/z: 433 (MH$^+$).

Example 176

N$^2$-(2-ANILINOETHYL)-N$^4$,N$^4$-DIMETHYL-N$^6$-(4-METHYLPHENYL)-2,4,6-PYRIMIDINETRIAMINE

Prepared by Procedures A, Q (toluene, 100° C.), and F (potassium tert-butoxide, 110° C., 16 h). $^1$H NMR (400 MHz, CDCl$_3$) δ 7.19-7.10 (m, 6H), 6.67 (dt, 1H, J=0.8, 7.3), 6.59 (dd, 2H, J=0.8, 8.4), 6.31 (br s, 1H), 5.28 (s, 1H), 4.99 (s, 1H), 3.66 (q, 2H, J=6.0), 3.49 (s, 1H), 3.37 (t, 2H, J=6.0), 3.00 (s, 6H), 2.33 (s, 3H); ESI-MS m/z: 363 (MH$^+$).

Example 177

N$^4$-(3-METHOXYPHENYL)-N$^2$,N$^6$,N$^6$-TRIMETHYL-N$^2$-[2-(2-PYRIDINYL)ETHYL]-2,4,6-PYRIMIDINETRIAMINE

Prepared by Procedures F (dioxane, 140° C., 15 h), A (CH$_2$Cl$_2$, Δ, TEA), and Q (toluene, TEA, Δ, 40 h). $^1$H NMR (400 MHz, CDCl$_3$) δ 8.55 (d, 1H, J=4.7), 7.58 (t, 1H, J=7.4), 7.25-7.16 (m, 2H), 7.15-7.06 (m, 2H), 6.89 (d, 1H, J=8.1), 6.57 (d, 1H, J=6.7), 6.30 (br s, 1H), 5.31 (s, 1H), 3.95 (t, 2H, J=6.4), 3.78 (s, 3H), 3.18-3.06 (m, 5H), 3.02 (s, 6H); ESI-MS m/z: 379 (MH$^+$).

Example 178

N$^4$-(4-CYCLOHEXYLPHENYL)-N$^6$,N$^6$-DIMETHYL-2-[4-(2-PYRAZINYL)-1-PIPERAZINYL]-4,6-PYRIMIDINEDIAMINE

Prepared by Procedures A (CH$_2$Cl$_2$, Et$_3$N, Me$_2$NHHCl, −78° C. for 3.5 h, warmed from −78° C. to 0° C. and stirred for 3 h), N, and O. $^1$H NMR (400 MHz, CDCl$_3$) δ 9.90 (br s, 1H), 8.19-8.16 (m, 1H), 8.09-8.06 (m, 1H), 7.89-7.85 (m, 1H), 7.20-7.18 (m, 4H), 5.28 (s, 1H), 3.99 (t, 4H, J=5.3), 3.73 (t, 4H, J=5.3), 3.04 (s, 6H), 2.53-2.44 (m, 1H), 1.91-1.71 (m, 4H), 1.46-1.71 (m, 6H); ESI-MS m/z: 459 (MH$^+$).

Example 179

N$^4$-[3-(BENZYLOXY)PHENYL]-N$^6$,N$^6$-DIMETHYL-2-[4-(2-PYRAZINYL)-1-PIPERAZINYL]-4,6-PYRIMIDINEDIAMINE

Prepared by Procedures A (CH$_2$Cl$_2$, Et$_3$N, Me$_2$NHHCl, −78° C. for 3.5 h, warmed from −78° C. to 0° C. and stirred for 3 h), N, and O. $^1$H NMR (400 MHz, CDCl$_3$) δ 9.82 (br s, 1H), 8.17-8.15 (m, 1H), 8.09-8.06 (m, 1H), 7.89 (d, 1H, J=2.8), 7.45-7.29 (m, 9H), 5.32 (s, 1H), 5.05 (s, 2H), 4.03 (t, 4H, J=5.6), 3.74 (t, 4H, J=5.0), 3.05 (s, 6H); ESI-MS m/z: 483 (MH$^+$).

Example 180

N$^4$-(2,3-DIHYDRO-1H-INDEN-5-YL)-N$^6$,N$^6$-DIMETHYL-2-[4-(2-PYRAZINYL)-1-PIPERAZINYL]-4,6-PYRIMIDINEDIAMINE

Prepared by Procedures A (CH$_2$Cl$_2$, Et$_3$N, Me$_2$NHHCl, −78° C. for 3.5 h, warmed from −78° C. to 0° C. and stirred for 3 h), N, and O. $^1$H NMR (400 MHz, CDCl$_3$) δ 10.01 (br s, 1H), 8.16 (s, 1H), 8.10-8.97 (m, 1H), 7.91-7.87 (m, 1H), 7.19 (d, 1H, J=6.3), 7.13 (s, 1H), 7.04 (d, 1H, J=7.6), 5.23 (s, 1H), 4.03 (t, 4H, J=5.2), 3.74 (t, 4H, J=5.1), 3.05 (s, 6H), 2.89 (t, 2H, J=6.9), 2.14-2.04 (m, 4H); ESI-MS m/z: 417 (MH$^+$).

Example 181

N$^4$,N$^4$-DIMETHYL-N$^6$-(4-METHYLPHENYL)-2-[4-(2-PYRAZINYL)-1-PIPERAZINYL]-4,6-PYRIMIDINEDIAMINE

Prepared by Procedures A (CH$_2$Cl$_2$, Et$_3$N, Me$_2$NHHCl, −78° C. for 3.5 h, warmed from −78° C. to 0° C. and stirred for 3 h), N, and O. $^1$H NMR (400 MHz, CDCl$_3$) δ 10.01 (s, 1H), 8.17 (s, 1H), 8.12-8.09 (m, 1H), 7.90 (d, 1H, J=2.6), 7.18 (d, 2H, J=8.6), 7.16 (d, 2H, J=8.1), 5.19 (s, 1H), 4.18-4.02 (m, 4H), 3.77 (t, 4H, J=5.1), 3.20 (br s, 3H), 2.99 (br s, 3H), 2.35 (s, 3H); ESI-MS m/z: 391 (MH$^+$).

Example 183

N⁴-(3,4-DIMETHYLPHENYL)-N⁶,N⁶-DIMETHYL-2-[4-(2-PYRAZINYL)-1-PIPERAZINYL]-4,6-PYRIMIDINEDIAMINE

Prepared by Procedures A (CH$_2$Cl$_2$, Et$_3$N, Me$_2$NHHCl, –78° C. for 3.5 h, warmed from –78° C. to 0° C. and stirred for 3 h), N, and O. $^1$H NMR (400 MHz, CDCl$_3$) δ 8.75 (br s, 1H), 8.16 (d, 1H, J=1.3), 8.08 (dd, 1H, J=1.5, 2.8), 7.88 (d, 1H, J=2.5), 7.10 (d, 1H, J=7.8), 7.08-7.00 (m, 2H), 5.26 (s, 1H), 4.00 (t, 4H, J=5.1), 3.72 (t, 4H, J=5.0), 3.03 (s, 6H), 2.24 (s, 6H); ESI-MS m/z: 405 (MH⁺).

Example 184

1-[2-(4-BENZYL-1-PIPERAZINYL)-6-(4-TOLUIDINO)-4-PYRIMIDINYL]-4-PIPERIDINONE

Prepared by Procedures a (Ch$_2$Cl$_2$, –78° C., 4H), N (24H), and O. $^1$H NMR (400 MHz, CDCl$_3$) δ 7.38-7.30 (m, 5H), 7.19-7.10 (m, 4H), 6.24 (s, 1H), 5.40 (s, 1H), 3.84-3.75 (m, 8H), 3.56 (s, 2H), 2.54-2.43 (m, 8H), 2.32 (s, 3H); ESI-MS m/z: 457 (MH⁺).

Example 185

N⁴,N⁴-dimethyl-N⁶-(2-propylphenyl)-2-[4-(2-pyridinyl)-1-piperazinyl]-4,6-pyrimidinediamine Prepared by Procedures A (Ch$_2$Cl$_2$, Tea, 3-4H at –78° C., then 3-4H at 0° C.), N, and O. $^1$H NMR (400 MHz, CDCl$_3$) δ 8.22-8.18 (m, 1H), 7.56-7.40 (m, 2H), 7.25-7.07 (m, 3H), 6.75-6.60 (m, 2H), 6.04 (s, 1H), 5.04 (s, 1H), 3.91 (m, 4H), 3.62 (m, 4H), 2.96 (s, 6H), 2.60 (t, 2H, J=7.5), 1.62 (m, 2H), 0.96 (t, 3H, J=8.8); ESI-MS M/Z: 418 (MH⁺).

Example 186

N⁴-(2-BENZYLPHENYL)-N⁶,N⁶-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4H at –78° C., then 3-4H at 0° C.), N, AND O. $^1$H NMR (400 MHZ, CDCl$_3$) δ 8.20-8.18 (M, 1H), 7.54-7.45 (M, 1H), 7.34-7.04 (M, 9H), 6.73-6.59 (M, 2H), 5.99 (BR S, 1H), 5.01 (S, 1H), 3.99 (S, 2H), 3.93-3.83 (M, 4H), 3.66-3.57 (M, 4H), 2.96 (S, 6H); ESI-MS M/Z: 466 (MH⁺).

Example 187

N⁴-(4-HEXYLPHENYL)-N⁶,N⁶-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at –78° C., then 3-4 h at 0° C.), N, and O. ESI-MS m/z: 460 (MH⁺).

Example 188

N⁴-(4-BENZYLPHENYL)-N⁶,N⁶-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at –78° C., then 3-4 h at 0° C.), N, and O. $^1$H NMR (400 MHz, CDCl$_3$) δ 8.22-8.18 (m, 1H), 7.52-7.45 (m, 1H), 7.32-7.09 (m, 9H), 6.78 (d, 1H, J=9.2), 6.65-6.59 (m, 1H), 6.24 (br s, 1H), 5.29 (s, 1H), 3.96 (s, 2H), 3.91-3.83 (m, 4H), 3.63-3.55 (m, 4H), 3.00 (s, 6H); ESI-MS m/z: 466 (MH⁺).

Example 189

N⁴-(4-HEPTYLPHENYL)-N⁶,N⁶-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at –78° C., then 3-4 h at 0° C.), N, and O. $^1$H NMR (400 MHz, CDCl$_3$) δ 8.25-8.18 (m, 1H), 7.57-7.44 (m, 1H), 7.38-7.08 (m, 4H), 6.75-6.57 (m, 2H), 6.26 (br s, 1H), 5.29 (s, 1H), 3.95-3.85 (m, 4H), 3.71-3.56 (m, 4H), 3.00 (s, 6H), 2.57 (t, 2H, J=5.2), 1.84-1.51 (m, 4H), 1.40-1.16 (m, 6H), 0.93-0.82 (m, 3H); ESI-MS m/z: 474 (MH⁺).

Example 190

N⁴-(3,4-DIMETHYLPHENYL)-N⁶,N⁶-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at –78° C., then 3-4 h at 0° C.), N, and O. $^1$H NMR (400 MHz, CDCl$_3$) δ 8.25-8.19 (m, 1H), 7.55-7.44 (m, 1H), 7.31-7.23 (m, 1H), 7.14-7.02 (m, 2H), 6.73-6.59 (m, 2H), 6.18 (br s, 1H), 5.29 (s, 1H), 3.95-3.85 (m, 4H), 3.67-3.55 (m, 4H), 3.00 (s, 6H), 2.24 (s, 3H), 2.23 (s, 3H), ESI-MS m/z: 404 (MH⁺).

Example 191

N⁴-(3-ISOPROPYLPHENYL)-N⁶,N⁶-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at –78° C., then 3-4 h at 0° C.), N, and O. $^1$H NMR (400 MHz, CDCl$_3$) δ 8.25-8.19 (m, 1H), 7.54-7.45 (m, 1H), 7.31-7.21 (m, 2H), 7.13-7.08 (m, 1H), 6.95-6.88 (m, 1H), 6.74-6.60 (m, 2H), 6.29 (br s, 1H), 5.37-5.34 (m, 1H), 3.96-3.87 (m, 4H), 3.68-3.57 (m, 4H), 3.00 (s, 6H), 2.95-2.85 (m, 1H), 1.36-1.19 (m, 6H); ESI-MS m/z: 418 (MH⁺).

Example 192

N⁴,N⁴-DIMETHYL-N⁶-(4-OCTYLPHENYL)-2-[4-(2-PYRIDINYL)-1-PIPERAZINYL]-4,6-PYRIMIDINEDIAMINE

Prepared by Procedures A (CH$_2$Cl$_2$, TEA, 3-4 h at –78° C., then 3-4 h at 0° C.), N, and O. $^1$H NMR (400 MHz, CDCl$_3$) δ 8.22 (s, 1H), 7.55-7.44 (m, 1H), 7.37-7.07 (m, 4H), 6.76-6.59 (m, 2H), 6.28 (br s, 1H), 5.29 (s, 1H), 3.96-3.86 (m, 4H), 3.69-3.56 (m, 4H), 3.00 (s, 6H), 2.57 (t, 2H, J=5.1), 1.74-1.51 (m, 4H), 1.41-1.08 (m, 8H), 0.93-0.82 (m, 3H); ESI-MS m/z: 488 (MH⁺).

Example 193

N⁴-(3-IODOPHENYL)-N⁶,N⁶-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.29-8.18 (m, 1H), 8.01-7.93 (m, 1H), 7.56-7.45 (m, 1H), 7.39-7.29 (m, 1H), 7.11-6.95 (m, 2H), 6.78-6.56) (m, 2H), 6.42-6.25 (m, 1H), 5.34 (s, 1H), 3.95-3.85 (m, 4H), 3.65-3.56 (m, 4H), 3.00 (s, 6H); ESI-MS m/z: 502 (MH$^+$).

Example 194

N⁴-(4-CHLOROPHENYL)-N⁶,N⁶-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.28 (s, 1H), 7.53-7.42 (m, 1H), 7.35-7.24 (m, 2H), 7.11-6.95 (m, 2H), 6.76-6.57 (m, 2H), 6.21 (s, 1H), 5.29 (s, 1H), 3.97-3.86 (m, 4H), 3.67-3.57 (m, 4H), 3.00 (s, 6H); ESI-MS m/z: 410 (MH$^+$).

Example 195

N⁵-(2-CHLOROPHENYL)-N⁴,N⁴-DIMETHYL-2-[4-(2-PYRIDINYL)-1-PIPERAZINYL]-4,5-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.50-8.10 (m, 2H), 7.55-7.12 (m, 4H), 7.05-6.90 (m, 2H), 6.61 (s, 1H), 5.31 (s, 1H), 3.95-3.85 (m, 4H), 3.65-3.54 (m, 4H), 3.00 (s, 6H); ESI-MS m/z: 410 (MH$^+$).

Example 196

N⁴-(3,4-DIFLUOROPHENYL)-N⁶,N⁶-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.31 (s, 1H), 7.59-6.95 (m, 4H), 6.68-6.54 (m, 2H), 6.29 (s, 1H), 5.27 (s, 1H), 3.94-3.82 (m, 4H), 3.63-3.51 (m, 4H), 3.01 (s, 6H); ESI-MS m/z: 412 (MH$^+$).

Example 197

N⁴-[3-METHOXY-5-(TRIFLUOROMETHYL)PHENYL]-N⁶,N⁶-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.26-8.18 (m, 1H), 7.58-7.11 (m, 3H), 6.77-6.38 (m, 3H), 6.34 (s, 1H), 5.25 (s, 1H), 3.96-3.88 (m, 4H), 3.85 (s, 3H), 3.69-3.55 (m, 4H), 3.00 (s, 6H); ESI-MS m/z: 474 (MH$^+$).

Example 198

N⁴,N⁴-DIMETHYL-2-[4-(2-PYRIDINYL)-1-PIPERAZINYL]-N⁶-(2,3,4-TRIFLUOROPHENYL)-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.26-8.18 (m, 1H), 7.58-7.11 (m, 3H), 6.77-6.38 (m, 2H), 6.34 (s, 1H), 5.25 (so 1H), 3.96-3.88 (m, 4H), 3.85 (s, 3H), 3.69-3.55 (m, 4H), 3.00 (s, 6H); ESI-MS m/z: 430 (MH$^+$).

Example 199

N⁴-(4-BROMO-2-FLUOROPHENYL)-N⁶,N⁶-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.27-8.17 (m, 1H), 7.61-7.01 (m, 4H), 6.75-6.57 (m, 2H), 6.34 (br s, 1H), 5.23 (s, 1H), 3.95-3.85 (m, 4H), 3.68-3.59 (m, 4H), 3.00 (s, 6H); ESI-MS m/z: 472 (MH$^+$).

Example 200

N⁴-(4-FLUORO-3-METHYLPHENYL)-N⁶,N⁶-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.27-8.17 (m, 1H), 7.56-7.47 (m, 1H), 7.21-6.89 (m, 3H), 6.75-6.58 (m, 2H), 6.24 (br s, 1H), 5.18 (s, 1H), 3.95-3.84 (m, 4H), 3.69-3.55 (m, 4H), 3.00 (s, 6H), 2.25 (s, 3H); ESI-MS m/z: 408 (MH$^+$).

Example 201

N⁴-(2,5-DIMETHOXYPHENYL)-N⁶,N⁶-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.27-8.16 (m, 1H), 7.96-7.86 (m, 1H), 7.56-7.43 (m, 1H), 6.93-6.42 (m, 5H), 5.31 (s, 1H), 4.01-3.90 (m, 4H), 3.84 (s, 3H), 3.79 (s, 3H), 3.70-3.54 (m, 4H), 3.04 (s, 6H); ESI-MS m/z: 436 (MH$^+$).

Example 202

N⁴-(3,5-DIMETHOXYPHENYL)-N⁶,N⁶-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.26-8.17 (m, 1H), 7.55-7.44 (m, 1H), 6.73-6.58 (m, 2H), 6.59-6.53 (m, 2H), 6.23 (br s, 1H) 5.37 (s, 1H), 3.98-3.88 (m, 4H), 3.77 (s, 6H), 3.62-3.58 (m, 4H), 3.01 (s, 6H); ESI-MS m/z: 436 (MH$^+$).

Example 203

N$^4$-[3-(BENZYLOXY)PHENYL]-2-[4-(3-BROMOPHENYL)-1-PIPERAZINYL]-N$^6$,N$^6$-DIMETHYL-4,6-PYRIMIDINEDIAMINE

Prepared by Procedures A (CH$_2$Cl$_2$, TEA, 3-4 h at −78° C., then 3-4 h at 0° C.), N (TEA), and O.
$^1$H NMR (400 MHz, CDCl$_3$) δ 7.55-6.26 (m, 14H), 5.29 (s, 1H), 5.06 (s, 2H), 3.97-3.82 (m, 4H), 3.21-3.14 (m, 4H), 3.01 (s, 6H); ESI-MS m/z: 560 (MH$^+$).

Example 204

N$^4$-(2-BROMO-4-METHYLPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.26-8.16 (m, 1H), 7.81 (d, 1H, J=8.8), 7.52-7.44 (m, 1H), 7.38 (d, 1H, J=8.5), 7.08 (d, 1H, J=8.5), 6.72 (m, 2H), 6.47 (br s, 1H), 5.24 (s, 1H), 3.90 (t, 4H, J=6.3), 3.61 (t, 4H, J=6.4), 3.01 (s, 6H), 2.28 (s, 3H); ESI-MS m/z: 468 (MH$^+$).

Example 205

N$^4$-(2,4-DICHLOROPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.25-8.17 (m, 1H), 8.21 (d, 1H, J=9.2), 7.49 (t, 1H, J=9.0), 7.38-7.16 (m, 2H), 6.71-6.59 (m, 2H), 6.57 (br s, 1H), 5.25 (s, 1H), 3.93-3.85 (m, 4H), 3.65-3.55 (m, 4H), 3.03 (s, 6H); ESI-MS m/z: 444 (MH$^+$).

Example 206

N$^4$-(3-FLUOROPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.25-6.39 (m, 9H), 5.30 (s, 1H), 3.97-3.85 (m, 4H), 3.74-3.58 (m, 4H), 3.01 (s, 6H); ESI-MS m/z: 394 (MH$^+$).

Example 207

N$^4$,N$^4$-DIMETHYL-2-[4-(2-PYRIDINYL)-1-PIPERAZINYL]-N$^6$-[3-(TRIFLUOROMETHOXY)PHENYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 460 (MH$^+$).

Example 208

N$^4$-(2,5-DICHLOROPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 445 (MH$^+$).

Example 209

N$^4$,N$^4$-DIMETHYL-N$^6$-(4-PROPYLPHENYL)-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 418 (MH$^+$).

Example 210

N$^4$,N$^4$-DIMETHYL-N$^6$-(4-PENTYLPHENYL)-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 446 (MH$^+$).

Example 211

N$^4$-(4-SEC-BUTYLPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 432 (MH$^+$).

Example 212

N$^4$-(2-TERT-BUTYLPHENYL)-1,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 432 (MH$^+$).

Example 213

N$^4$-(2,5-DIMETHYLPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 404 (MH$^+$).

Example 214

N$^4$-(3,5-DIMETHYLPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C., N, and O. ESI-MS m/z: 404 (MH$^+$).

Example 215

N$^4$-(2,3-DIMETHYLPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 404 (MH$^+$).

Example 216

N$^4$-(3-BENZYLPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 466 (MH$^+$).

Example 217

N$^4$-(4-BROMO-2-CHLOROPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3.4 h at 0° C.), N, and O. ESI-MS m/z: 489 (MH$^+$).

Example 218

N$^4$-(2,3-DICHLOROPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 445 (MH$^+$).

Example 219

N$^4$,N$^4$-DIMETHYL-2-[4-(2-PYRIDINYL)-1-PIPERAZINYL]-N$^6$-(2,4,5-TRIFLUOROPHENYL)-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 430 (MH$^+$).

Example 220

N$^4$-(5-CHLORO-2-METHOXYPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 440 (MH$^+$).

Example 221

N$^4$,N$^4$-DIMETHYL-2-[4-(2-PYRIDINYL)-1-PIPERAZINYL]-N$^6$-(3,4,5-TRIFLUOROPHENYL)-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 430 (MH$^+$).

Example 222

N$^4$-(2-CHLORO-5-FLUOROPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 428 (MH$^+$).

Example 223

N$^2$-(2-CHLORO-4-METHYLPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 424 (MH$^+$).

Example 224

N$^4$-(3-CHLOROPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 410 (MH$^+$).

Example 225

2-(4-BENZYL-1-PIPERAZINYL)-N$^4$-[3-METHOXY-5-(TRIFLUOROMETHYL)PHENYL]-N$^6$,N$^6$-DIMETHYL-4,6-PYRIMIDINEDIAMINE

Prepared by Procedures O (toluene, 75° C.), Q (toluene, 120° C.), and A. ESI-MS m/z: 487 (MH$^+$).

Example 226

2-(4-BENZYL-1-PIPERAZINYL)-N$^4$-[2-METHOXY-5-(TRIFLUOROMETHYL)PHENYL]-N$^6$,N$^6$-DIMETHYL-4,6-PYRIMIDINEDIAMINE

Prepared by Procedures O, Q (dioxane, 120° C.), and A. ESI-MS m/z: 487 (MH$^+$).

Example 227

2-(4-BENZYL-1-PIPERAZINYL)-N$^4$-(2,5-DIMETHOXYPHENYL)-N$^6$,N$^6$-DIMETHYL-4,6-PYRIMIDINEDIAMINE

Prepared by Procedures O, Q (dioxane, 120° C.), and A. ESI-MS m/z: 449 (MH$^+$).

Example 228

N$^4$-[3-(BENZYLOXY)PHENYL]-2-(4-BENZYL-1-PIPERAZINYL)-N$^6$,N$^6$-DIMETHYL-4,6-PYRIMIDINEDIAMINE

Prepared by Procedures O, Q (toluene, 120° C.), and A. ESI-MS m/z: 495 (MH$^+$).

Example 229

2-(4-BENZYL-1-PIPERAZINYL)-N$^4$,N$^4$-DIMETHYL-N$^6$-[4-(TRIFLUOROMETHYL)PHENYL]-4,6-PYRIMIDINEDIAMINE

Prepared by Procedures P (toluene, 105° C.), Q (toluene, 120° C.), and A. ESI-MS m/z: 457 (MH$^+$).

Example 230

2-(4-BENZYL-1-PIPERAZINYL)-$N^4,N^4$-DIMETHYL-$N^6$-(2,3,4-TRICHLOROPHENYL)-4,6-PYRIMIDINEDIAMINE

Prepared by Procedures O (60° C.), Q (toluene, 120° C., and A. ESI-MS m/z: 492 (MH$^+$).

Example 231

2-[4-(2-FURYLMETHYL)-1-PIPERAZINYL]-$N^4$,$N^4$-DIMETHYL-$N^6$-(4-METHYLPHENYL)-4,6-PYRIMIDINEDIAMINE

Prepared by Procedures R (16 h), P (sodium tert-butoxide, toluene, 120° C.), N (TEA, toluene reflux), and A. ESI-MS m/z: 393 (MH$^+$).

Example 232

$N^2$-[2-(4-METHOXYPHENYL)ETHYL]-$N^4,N^4$-DIMETHYL-$N^6$-(4-METHYLPHENYL)-2,4,6-PYRIMIDINETRIAMINE

Prepared by Procedures V, R, and S (DIEA, DMAP). ESI-MS m/z: 378 (MH$^+$).

Example 233

$N^4$-(3-METHOXYPHENYL)-$N^6,N^6$-DIMETHYL-2-[4-(TETRAHYDRO-2-FURANYLMETHYL)-1-PIPERAZINYL]-4,6-PYRIMIDINEDIAMINE

Prepared by Procedures A, P (16 h), and Q (dioxane, 120° C.). ESI-MS m/z: 413 (MH$^+$).

Example 235

2-[4-(4-METHOXYBENZYL)-1-PIPERAZINYL]-$N^4,N^4$-DIMETHYL-$N^6$-(4-METHYLPHENYL)-4,6-PYRIMIDINEDIAMINE

Prepared by Procedure Z. ESI-MS m/z: 433 (MH$^+$).

Example 237

$N^4,N^4$-DIMETHYL-$N^6$-(4-METHYLPHENYL)-$N^2$-[2-(2-THIENYL)ETHYL]-2,4,6-PYRIMIDINETRIAMINE

Prepared by Procedures R, S, and V. ESI-MS m/z: 354 (MH$^+$).

Example 238

$N^4,N^4$-DIMETHYL-$N^6$-(4-METHYLPHENYL)-2-[4-(3-THIENYLMETHYL)-1-PIPERAZINYL]-4,6-PYRIMIDINEDIAMINE

Prepared by Procedures AA, T (2 h), and W. ESI-MS m/z: 409 (MH$^+$).

Example 239

2-(4-BENZYL-1-PIPERAZINYL)-$N^4$-[4-CHLORO-2-(TRIFLUOROMETHYL)PHENYL]-$N^6,N^6$-DIMETHYL-4,6-PYRIMIDINEDIAMINE

Prepared by Procedures O (100° C., 40 h), Q (toluene, 120° C.), and A. ESI-MS m/z: 491 (MH$^+$).

Example 240

$N^4$-(3-BROMO-4-METHYLPHENYL)-$N^6,N^6$-DIMETHYL-2-[4-(2-PYRIDINYL)-1-PIPERAZINYL]-4,6-PYRIMIDINEDIAMINE

Prepared by Procedures O (80° C.), Q (toluene, 120° C.), and A. ESI-MS m/z: 469 (MH$^+$).

Example 241

2-{4-[4-(DIMETHYLAMINO)-6-(4-TOLUIDINO)-2-PYRIMIDINYL]-1-PIPERAZINYL}NICOTINONITRILE

Prepared by Procedures O, Q (toluene, 120° C.) and A. ESI-MS m/z: 415 (MH$^+$).

Example 242

$N^4,N^4$-DIMETHYL-$N^6$-[4-METHYL-3-(2-PYRIDINYLAMINO)PHENYL]-2-[4-(2-PYRIDINYL)-1-PIPERAZINYL]-4,6-PYRIMIDINEDIAMINE

Prepared by Procedures P (toluene), Q (toluene, 120° C.), and A. ESI-MS m/z: 482 (MH$^+$).

Example 243

$N^4$-(3-BROMOPHENYL)-$N^6,N^6$-DIMETHYL-2-[4-(2-PYRIDINYL)-1-PIPERAZINYL]-4,6-PYRIMIDINEDIAMINE

Prepared by Procedures O (85° C.), Q (toluene, 120° C.), and A. ESI-MS m/z: 455 (MH$^+$).

Example 244

2-(4-BENZYL-1-PIPERAZINYL)-$N^4$-[2-CHLORO-4-(TRIFLUOROMETHYL)PHENYL]-$N^6,N^6$-DIMETHYL-4,6-PYRIMIDINEDIAMINE

Prepared by Procedures P (16 h, toluene), Q (toluene, 120° C.), and A. ESI-MS m/z: 491 (MH$^+$).

Example 245

$N^4$-(3-METHOXYPHENYL)-$N^6,N^6$-DIMETHYL-2-[4-(2-PYRIDINYL)-1-PIPERAZINYL]-4,6-PYRIMIDINEDIAMINE

Prepared by Procedures A, N, and P. ESI-MS m/z: 406 (MH$^+$).

Example 246

N⁴-(3-METHOXYPHENYL)-N⁶,N⁶-DIMETHYL-2-{4-[2-(TRIFLUOROMETHYL)PHENYL]-1-PIPERAZINYL}-4,6-PYRIMIDINEDIAMINE

Prepared by Procedures A, N, and P. ESI-MS m/z: 473 (MH⁺).

Example 247

N⁴-(3-METHOXYPHENYL)-N⁶,N⁶-DIMETHYL-N²-(2-PHENYLETHYL)-2,4,6-PYRIMIDINETRIAMINE

Prepared by Procedures A, N, and P. ESI-MS m/z: 364 (MH⁺).

Example 248

N²,N⁴,N⁴-TRIMETHYL-N⁶-(4-METHYLPHENYL)-N²-(2-PHENYLETHYL)-2,4,6-PYRIMIDINETRIAMINE

Prepared by Procedures A, N, and P. ESI-MS m/z: 362 (MH⁺).

Example 249

N-(4-METHYLPHENYL)-2-{4-[1-OXIDO-3-(TRIFLUOROMETHYL)-2-PYRIDINYL]-1-PIPERAZINYL}-6-(1-PIPERIDINYL)-4-PYRIMIDINAMINE

Prepared by Procedure CC. ESI-MS m/z: 514 (MH⁺).

Example 250

N⁴,N⁴-DIMETHYL-N⁶-(4-METHYLPHENYL)-N²-(2-PHENYLETHYL)-2,4,6-PYRIMIDINETRIAMINE

Prepared by Procedures R and S. ESI-MS m/z: 348 (MH⁺).

Example 251

N⁴-(3-METHOXYPHENYL)-N²,N⁶,N⁶-TRIMETHYL-N²-(2-PHENYLETHYL)-2,4,6-PYRIMIDINETRIAMINE

Prepared by Procedures A, N, and P. ESI-MS m/z: 378 (MH⁺).

Example 252

2-(4-BENZYL-1-PIPERAZINYL)-N⁴-(3-METHOXYPHENYL)-N⁶,N⁶-DIMETHYL-4,6-PYRIMIDINEDIAMINE

Prepared by Procedures A, N, and P. ESI-MS m/z: 419 (MH⁺).

Example 253

2-(4-BENZYL-1-PIPERAZINYL)-N⁴,N⁴-DIMETHYL-N⁶-(4-METHYLPHENYL)-4,6-PYRIMIDINEDIAMINE

Prepared by Procedures A, N, and P. ESI-MS m/z: 403 (MH⁺).

Examples 1-90 and 115-253 as described above are merely illustrative of the methods used to synthesize pyrimidine derivatives. Further derivatives may be obtained utilizing methods shown in Schemes 1-5b. The substituents in Schemes 1-5b are described in the Detailed Description.

It may be necessary to incorporate protection and deprotection strategies for substituents such as amino, amido, carboxylic acid, and hydroxyl groups in the synthetic methods described above to form pyrimidine derivatives. Methods for protection and deprotection of such groups are well-known in the art, and may be found, for example in Green, T. W. and Wuts, P. G. M. (1991) Protection Groups in Organic Synthesis, 2nd Edition John Wiley & Sons, New York.

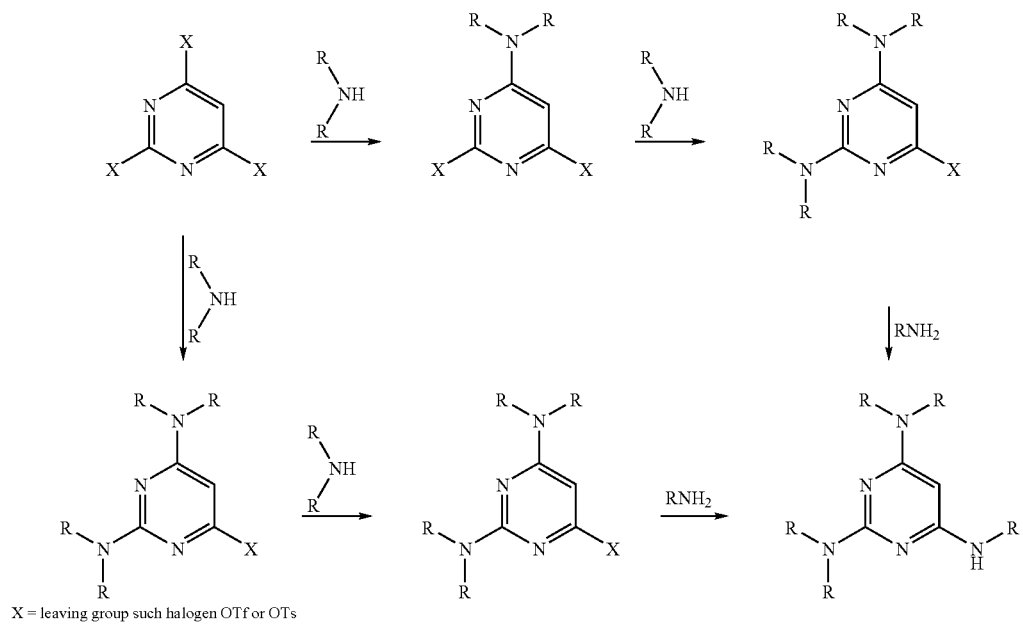

Scheme 1. Synthesis of Substituted Triaminopyrimidines

X = leaving group such halogen OTf or OTs

Scheme 2. Alternate Synthesis of Substituted Triaminopyrimidines

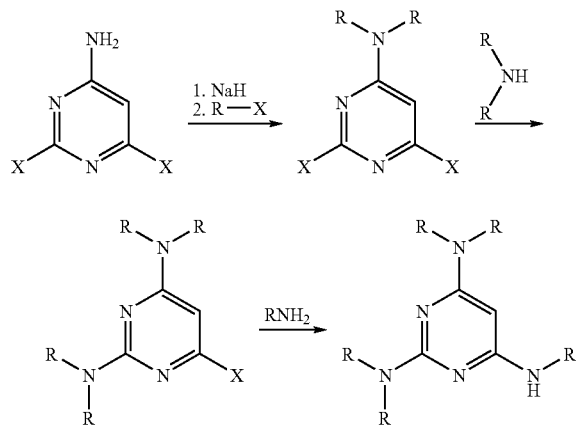

X = leaving group such halogen OTf or OTs

Scheme 3. Alternate Synthesis of Substituted Triaminopyrimidines

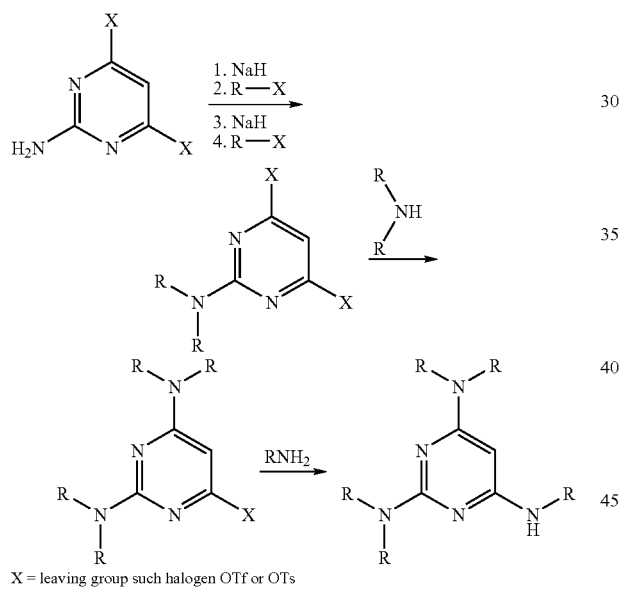

X = leaving group such halogen OTf or OTs

Alternatively,

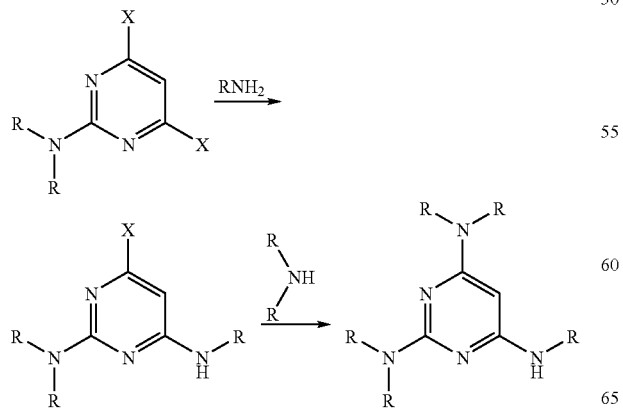

Scheme 4. Synthesis of Morpholine Intermediates

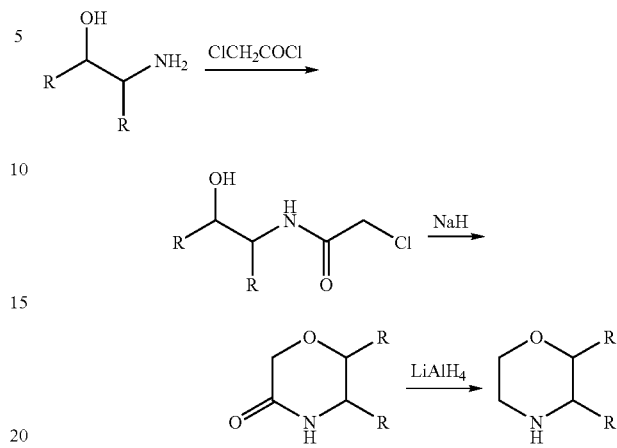

Scheme 5. Synthesis of N-Alkylamine Intermediates

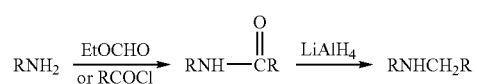

Scheme 5a. Synthesis of Triaminopyrimidines from 2-Amidopyrimidines

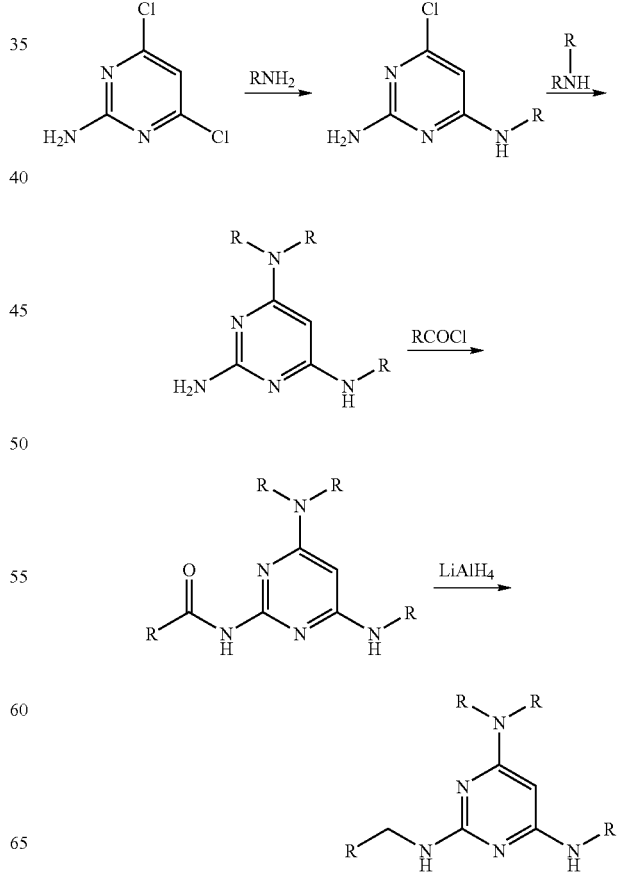

Scheme 5b. Substitution on the Piperazin Moiety of 2-(Piperazin-1-yl)pyrimidines

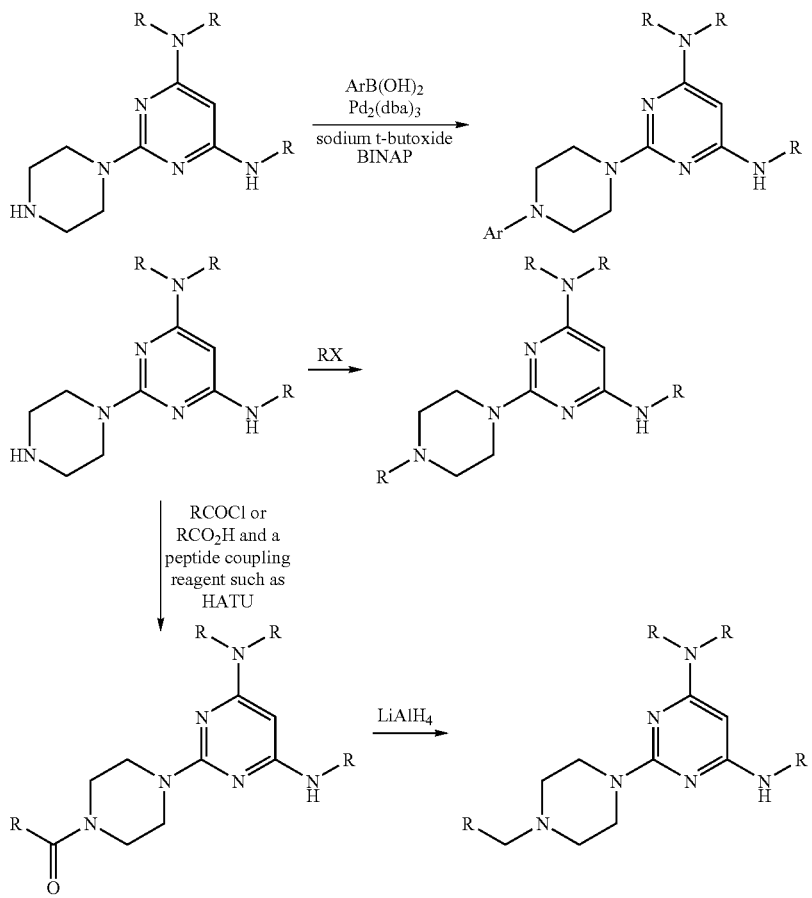

X is a leaving group such as a halogen or tosylate; HATU is O-(7-azabenzenzotriazol-1-yl)-N,N,N',N'–tetramethyluronium hexafluorophosphate; dba is dibenzylideneacetone; BINAP is 2,2'-bis(diphenylphosphino)-1,1'-binaphthyl.

Radioligand Binding of Pyrimidines at Cloned Galanin Receptors

The binding properties of the pyrimidines of the present invention were evaluated at the cloned human galanin receptors, GAL1, GAL2, and GAL3, using protocols described herein.

Radioligand Binding Assay Results

The pyrimidines described in Examples 1-90 and 115-253 were assayed using cloned human galanin receptors. The compounds were found to be selective for the GAL3 receptor. The binding affinities of the compounds of Examples 1-90 and 115-253 are illustrated in Tables 1-3a.

TABLE 1

| Example | substitution R1 | R2 | Ki (nM) GalR1 | GalR2 | GalR3 |
|---|---|---|---|---|---|
| 1 | cyclohexyl-N(CH3)- | 4-methylphenyl-NH- | 668 | 188 | 35 |

TABLE 1-continued
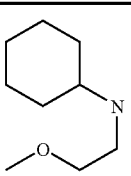
| | substitution | | Ki (nM) | | |
|---|---|---|---|---|---|
| Example | R1 | R2 | GalR1 | GalR2 | GalR3 |
| 2 | 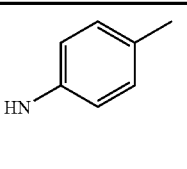 | 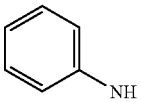 | 2818 | 562 | 26 |
| 3 | 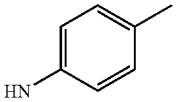 | 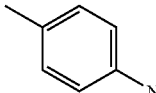 | >5000 | >5000 | 163 |
| 4 | 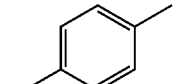 | 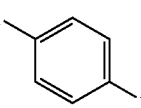 | >5000 | >5000 | 627 |
| 5 | 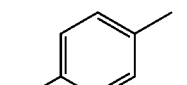 | 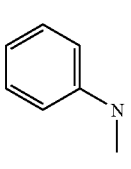 | >5000 | >5000 | 345 |
| 6 | 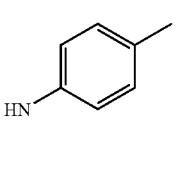 | 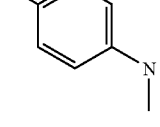 | >5000 | 2157 | 248 |
| 7 | 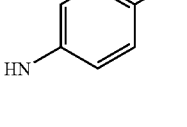 | 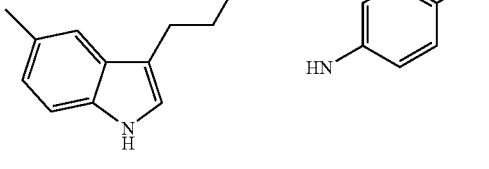 | 1107 | 775 | 177 |
| 8 | 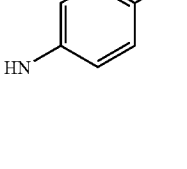 | 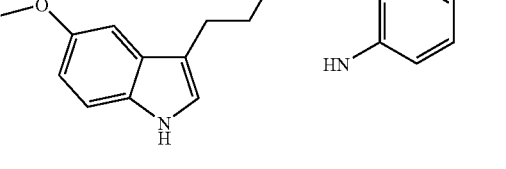 | >5000 | 795 | 264 |
| 9 | 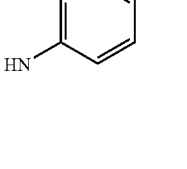 | | >5000 | 2110 | 568 |

TABLE 1-continued
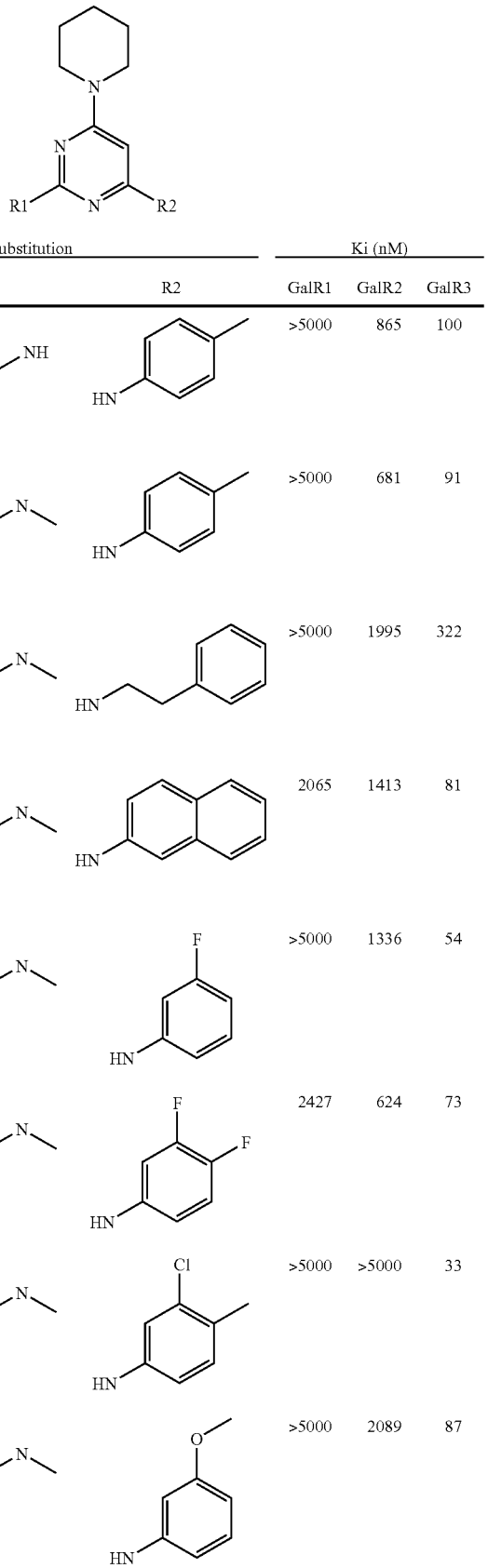
| Example | substitution R1 | R2 | Ki (nM) GalR1 | GalR2 | GalR3 |
|---|---|---|---|---|---|
| 10 | tryptamine-NH | p-tolyl-NH | >5000 | 865 | 100 |
| 11 | N-methyl tryptamine | p-tolyl-NH | >5000 | 681 | 91 |
| 12 | N-methyl tryptamine | phenethyl-NH | >5000 | 1995 | 322 |
| 13 | N-methyl tryptamine | 2-naphthyl-NH | 2065 | 1413 | 81 |
| 14 | N-methyl tryptamine | 3-fluorophenyl-NH | >5000 | 1336 | 54 |
| 15 | N-methyl tryptamine | 3,4-difluorophenyl-NH | 2427 | 624 | 73 |
| 16 | N-methyl tryptamine | 3-chloro-4-methylphenyl-NH | >5000 | >5000 | 33 |
| 17 | N-methyl tryptamine | 3-methoxyphenyl-NH | >5000 | 2089 | 87 |

TABLE 1-continued
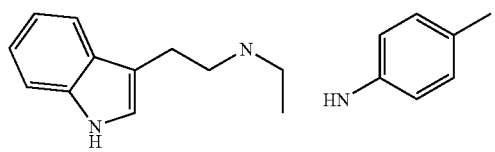
| | substitution | | Ki (nM) | | |
|---|---|---|---|---|---|
| Example | R1 | R2 | GalR1 | GalR2 | GalR3 |
| 18 | 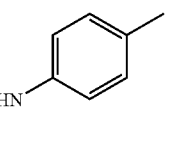 | 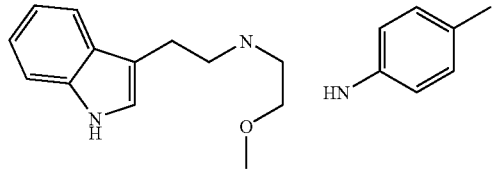 | 3589 | 543 | 40 |
| 19 | 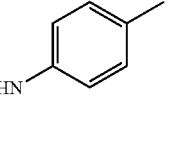 | 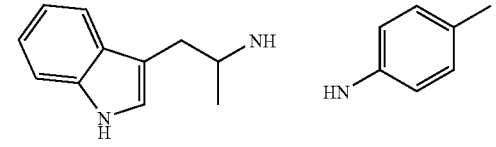 | >5000 | 1771 | 79 |
| 20 | 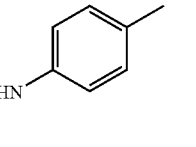 | 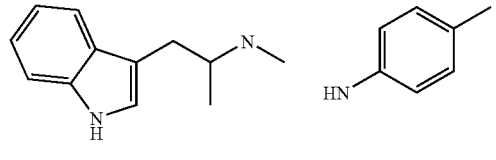 | >5000 | >5000 | 164 |
| 21 | 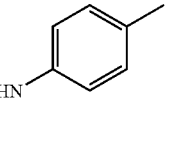 | 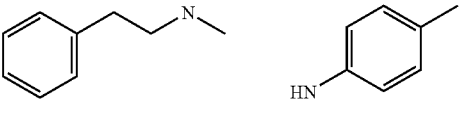 | 4786 | 1096 | 49 |
| 22 | 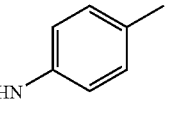 | 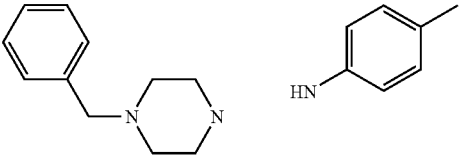 | 442 | 176 | 28 |
| 23 | 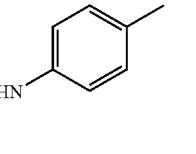 | 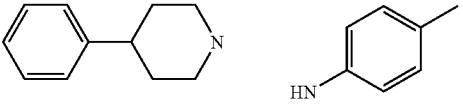 | >5000 | >5000 | 60 |
| 24 | 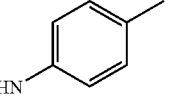 | 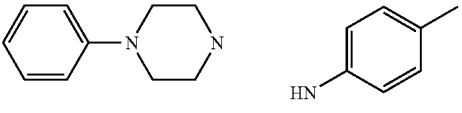 | >5000 | 3961 | 210 |
| 25 | 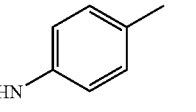 | | >5000 | 1497 | 548 |

TABLE 1-continued
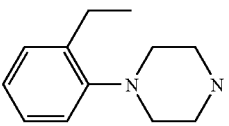
| Example | substitution | | Ki (nM) | | |
|---|---|---|---|---|---|
| | R1 | R2 | GalR1 | GalR2 | GalR3 |
| 26 | 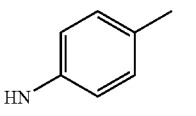 | 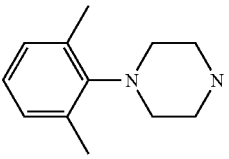 | >5000 | 4049 | 85 |
| 27 | 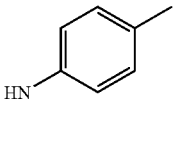 | 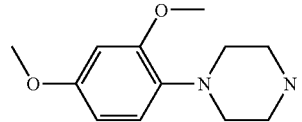 | 2692 | 272 | 63 |
| 28 | 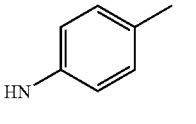 | 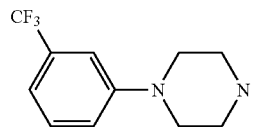 | >5000 | >5000 | 270 |
| 29 | 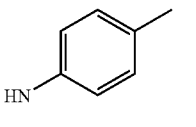 | 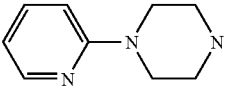 | 716 | 359 | 46 |
| 30 | 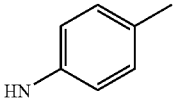 | 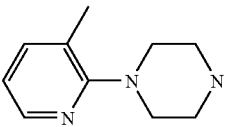 | >5000 | 2613 | 197 |
| 31 | 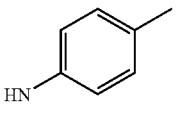 | 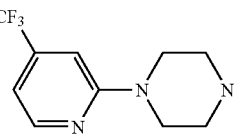 | >5000 | 3402 | 174 |
| 32 | 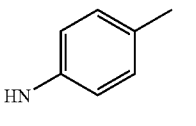 | 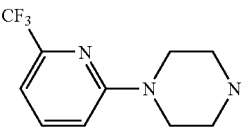 | >5000 | 1860 | 145 |
| 33 | 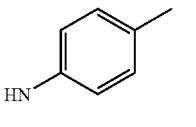 | 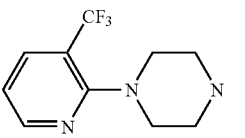 | >5000 | >5000 | 181 |
| 34 | 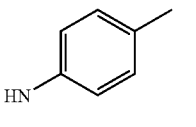 | | 912 | 168 | 23 |

TABLE 1-continued
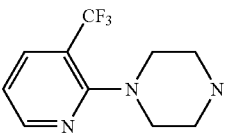
| | substitution | | Ki (nM) | | |
|---|---|---|---|---|---|
| Example | R1 | R2 | GalR1 | GalR2 | GalR3 |
| 35 | 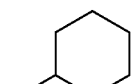 | 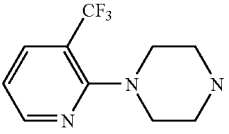 | | | 111 |
| 36 | 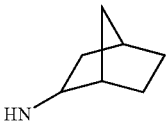 | 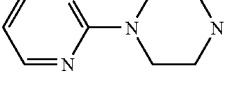 | 442 | 90 | 93 |
| 37 | 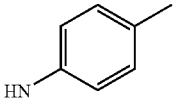 |  | >5000 | 903 | 343 |
| 38 | 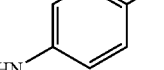 | 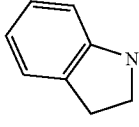 | 2901 | 516 | 320 |
| 39 | 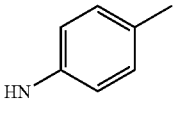 | 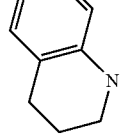 | >5000 | >5000 | 128 |
| 40 | 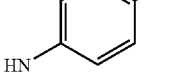 | 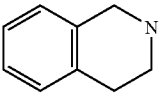 | >5000 | 2623 | 164 |
| 41 | 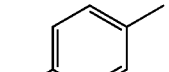 | 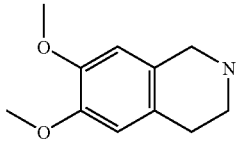 | 2131 | 840 | 151 |
| 42 | 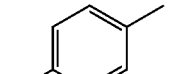 | 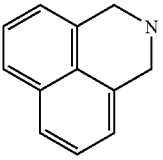 | >5000 | 1137 | 275 |
| 43 | 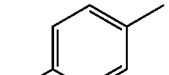 | | >5000 | >5000 | 107 |

TABLE 1-continued
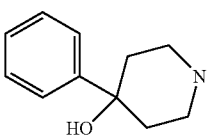
| Example | substitution R1 | R2 | Ki (nM) GalR1 | GalR2 | GalR3 |
|---|---|---|---|---|---|
| 44 | 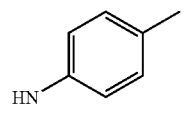 | 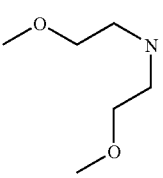 | >5000 | 1023 | 133 |
| 45 | 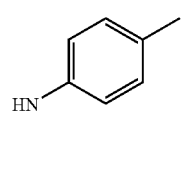 | 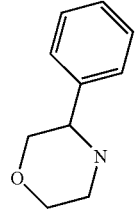 | >5000 | >5000 | 505 |
| 46 | 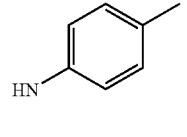 | 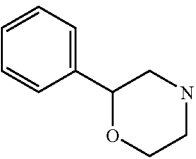 | >5000 | >5000 | 577 |
| 47 | 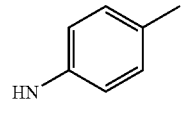 | 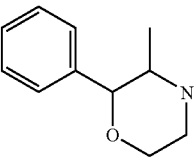 | >5000 | 3012 | 115 |
| 48 | 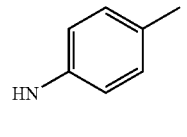 | 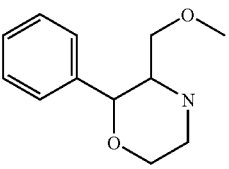 | >5000 | 4233 | 120 |
| 49 | 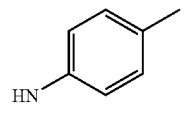 | | >5000 | 3273 | 211 |

TABLE 2
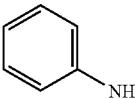
| | substitution | | Ki (nM) | | |
|---|---|---|---|---|---|
| Example | R1 | R2 | GalR1 | GalR2 | GalR3 |
| 50 | 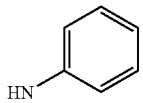 | 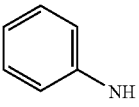 | >5000 | >5000 | 699 |
| 51 | 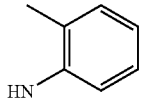 | 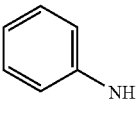 | >5000 | >5000 | 987 |
| 52 | 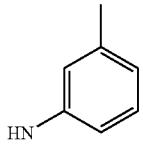 | 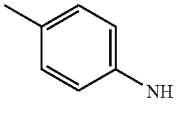 | >5000 | >5000 | 570 |
| 53 | 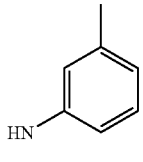 | 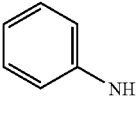 | >5000 | >5000 | 980 |
| 54 | 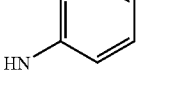 | 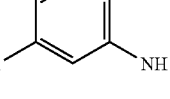 | >5000 | >5000 | 132 |
| 55 | 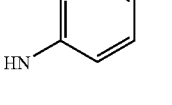 | 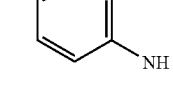 | >5000 | >5000 | 48 |
| 56 | 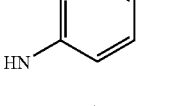 | 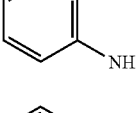 | >5000 | >5000 | 794 |
| 57 | 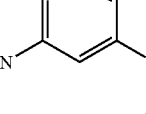 | 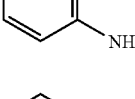 | >5000 | >5000 | 360 |
| 58 | 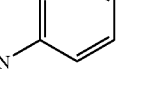 | 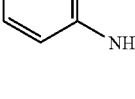 | >5000 | >5000 | 783 |
| 59 | 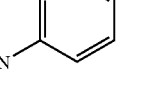 | | >5000 | >5000 | 566 |

TABLE 2-continued
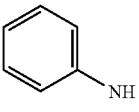
| Example | substitution | | Ki (nM) | | |
| --- | --- | --- | --- | --- | --- |
| | R1 | R2 | GalR1 | GalR2 | GalR3 |
| 60 | 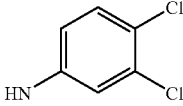 | 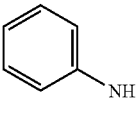 | >5000 | >5000 | 86 |
| 61 | 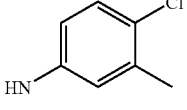 | 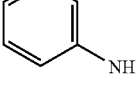 | >5000 | >5000 | 753 |
| 62 | 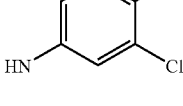 | 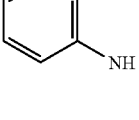 | >5000 | >5000 | 736 |
| 63 | 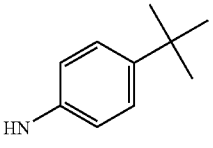 | 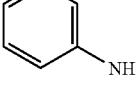 | >5000 | >5000 | 731 |
| 64 | 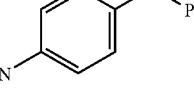 | 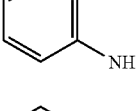 | >5000 | >5000 | 572 |
| 65 | 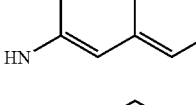 | 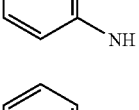 | >5000 | >5000 | 329 |
| 66 | 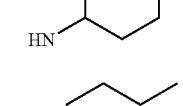 | 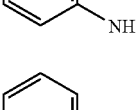 | >5000 | >5000 | 699 |
| 67 | 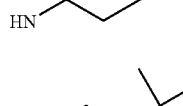 | 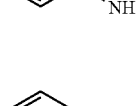 | >5000 | >5000 | 752 |
| 68 | 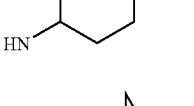 | 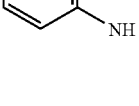 | >5000 | 2155 | 164 |
| 69 | 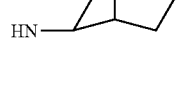 |  | >5000 | >5000 | 417 |

TABLE 2-continued

| | substitution | | Ki (nM) | | |
|---|---|---|---|---|---|
| Example | R1 | R2 | GalR1 | GalR2 | GalR3 |
| 70 | phenyl-NH | bornyl-HN | >5000 | 944 | 476 |
| 71 | phenyl-NH | pinanyl-HN | >5000 | 944 | 72 |
| 72 | 4-methylphenyl-N(CH3) | 4-methylphenyl-HN | >5000 | 2083 | 132 |
| 73 | cyclohexyl-N(CH3) | 4-methylphenyl-HN | >5000 | 1550 | 124 |
| 74 | cyclohexyl-N(CH2CH2OCH3) | 4-methylphenyl-HN | 2291 | 468 | 47 |
| 75 | indolin-1-yl | 4-methylphenyl-HN | 1462 | 2458 | 144 |
| 76 | tryptaminyl-NH | 4-methylphenyl-HN | 3802 | 1657 | 392 |
| 77 | N-methyl-tryptaminyl | 4-methylphenyl-HN | 3802 | 709 | 79 |

TABLE 2-continued
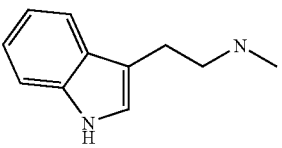
| | substitution | | Ki (nM) | | |
|---|---|---|---|---|---|
| Example | R1 | R2 | GalR1 | GalR2 | GalR3 |
| 78 | 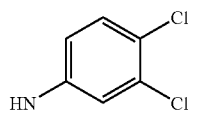 | 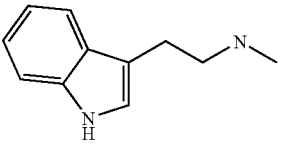 | 4942 | 1862 | 41 |
| 79 | 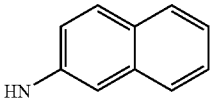 | 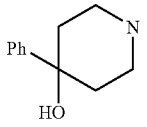 | 3802 | 1656 | 190 |
| 80 | 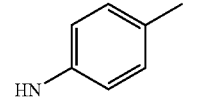 | 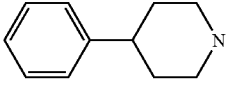 | >5000 | 2478 | 615 |
| 81 | 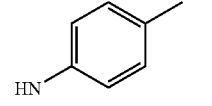 | 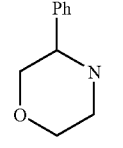 | >5000 | 4789 | 160 |
| 82 | 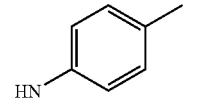 | 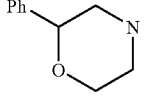 | >5000 | >5000 | 232 |
| 83 | 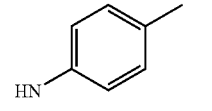 | 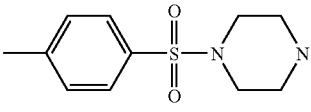 | >5000 | >5000 | 160 |
| 84 | 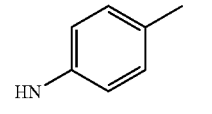 | 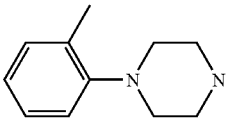 | >5000 | >5000 | 261 |
| 85 | 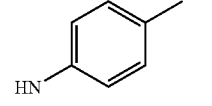 | 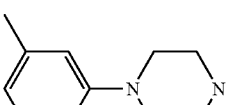 | >5000 | 4228 | 72 |
| 86 | 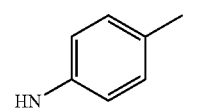 | 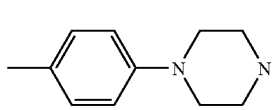 | >5000 | >5000 | 227 |
| 87 | 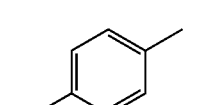 | | >5000 | 4617 | 157 |

TABLE 2-continued
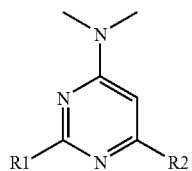
| | substitution | | Ki (nM) | | |
|---|---|---|---|---|---|
| Example | R1 | R2 | GalR1 | GalR2 | GalR3 |
| 88 | (3-CF₃-pyridin-2-yl)piperazinyl | 4-methylphenylamino | 2188 | 355 | 39 |
Key: Ph = Phenyl
TABLE 3
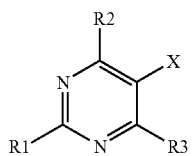
| | | substitution | | | Ki (nM) | | |
|---|---|---|---|---|---|---|---|
| Example | X | R1 | R2 | R3 | GalR1 | GalR2 | GalR3 |
| 89 | H | piperidinyl | (3-CF₃-pyridin-2-yl)piperazinyl | 4-methylphenylamino | 1122 | 1274 | 105 |
| 90 | H | (3-CF₃-pyridin-2-yl)piperazinyl | (piperidin-2-yl)methoxy | 4-methylphenylamino | >5000 | 2460 | 105 |

TABLE 3a

| Example | Structure | Ki (nM) Gal3 |
|---|---|---|
| 115 | 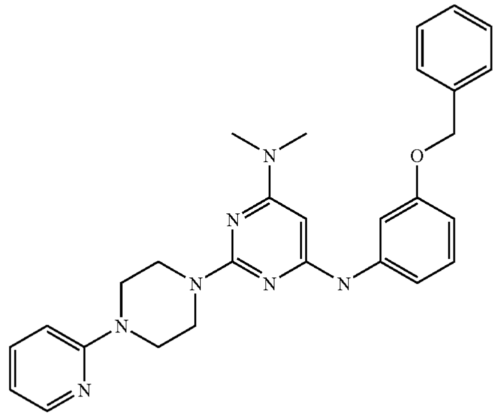 | 13 |
| 116 | 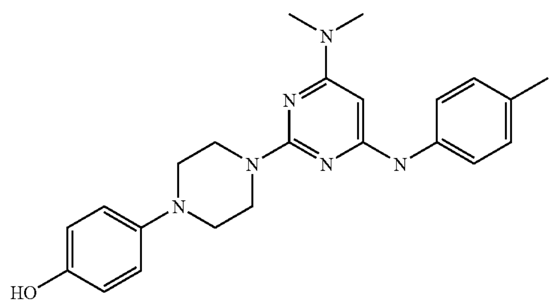 | 479 |
| 117 | 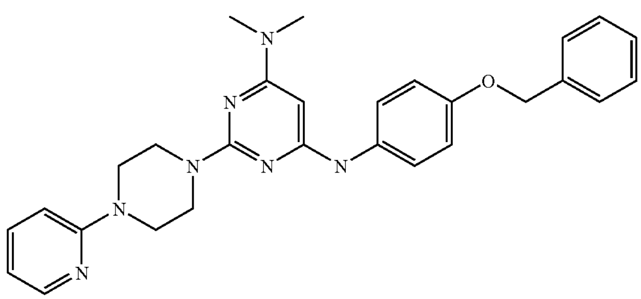 | 61 |
| 118 | 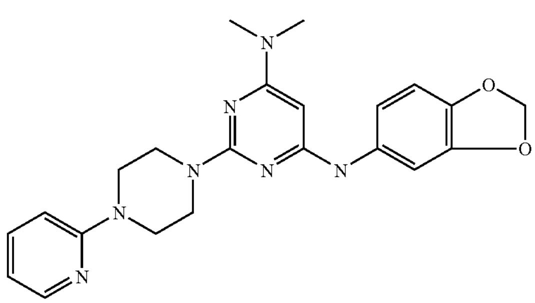 | 508 |

TABLE 3a-continued
| Example | Structure | Ki (nM) Gal3 |
|---|---|---|
| 119 | 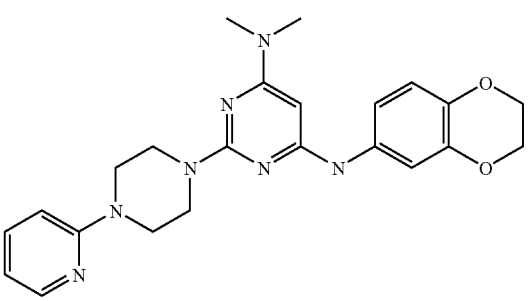 | 540 |
| 120 | 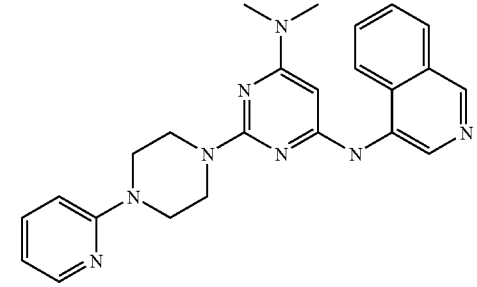 | 664 |
| 121 | 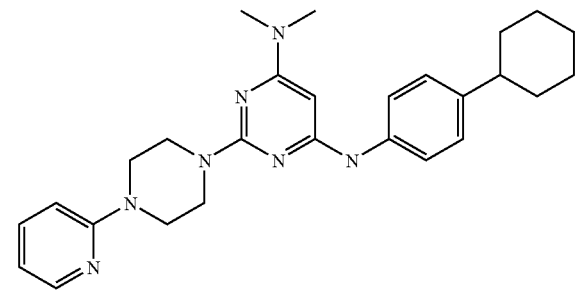 | 21 |
| 122 | 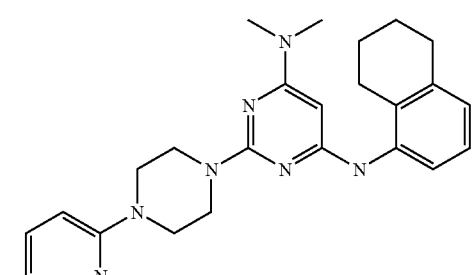 | 65 |
| 123 | 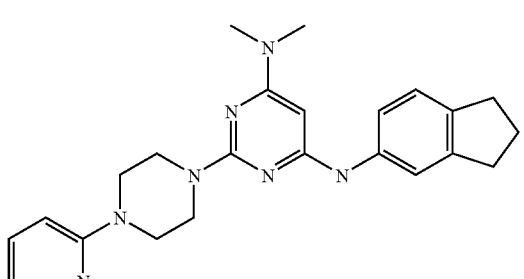 | 61 |

TABLE 3a-continued

| Example | Structure | Ki (nM) Gal3 |
|---|---|---|
| 124 | 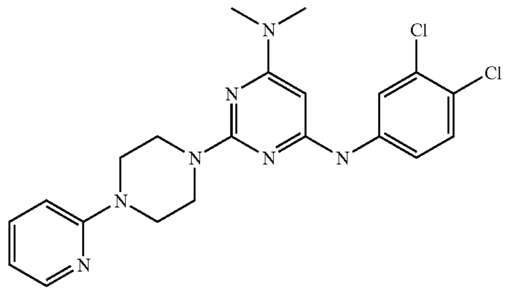 | 36 |
| 125 | 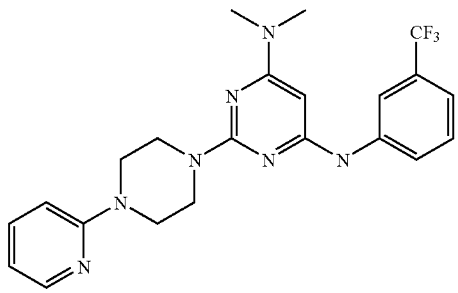 | 75 |
| 126 | 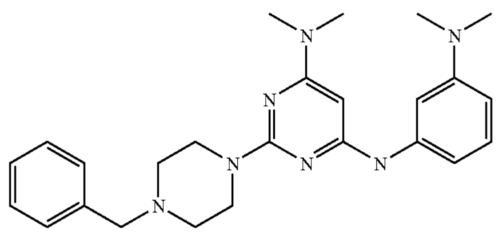 | 99 |
| 127 | 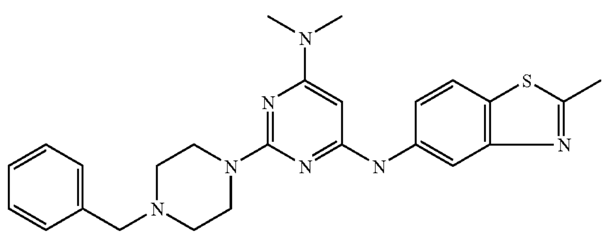 | 255 |
| 128 | 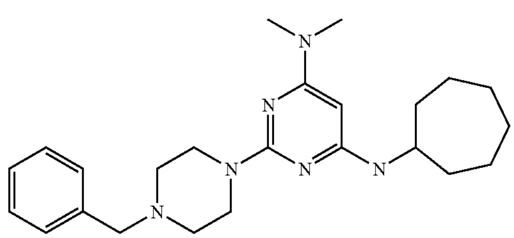 | 249 |
| 129 | 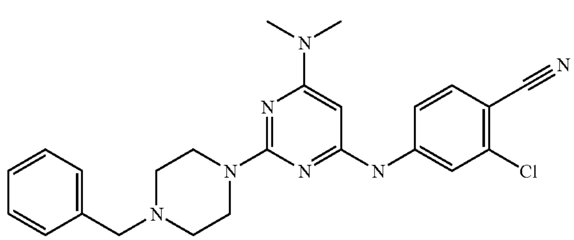 | 405 |

TABLE 3a-continued

| Example | Structure | Ki (nM) Gal3 |
|---|---|---|
| 130 | 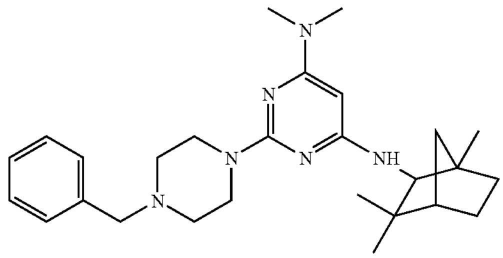 | 100 |
| 131 | 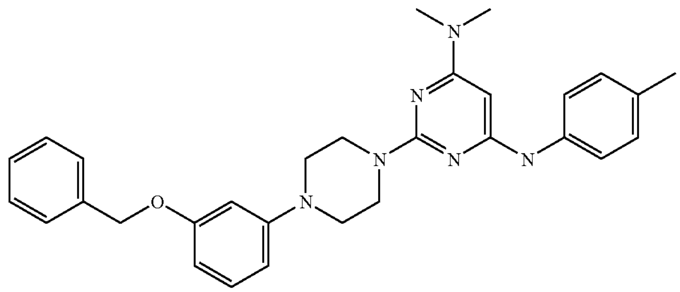 | 20 |
| 132 | 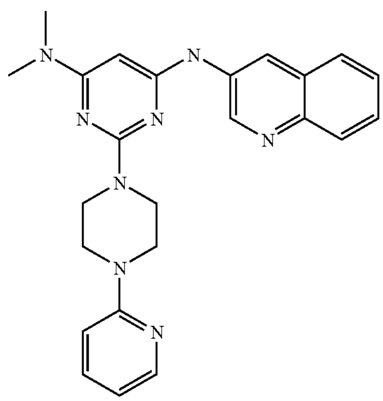 | 618 |
| 133 | 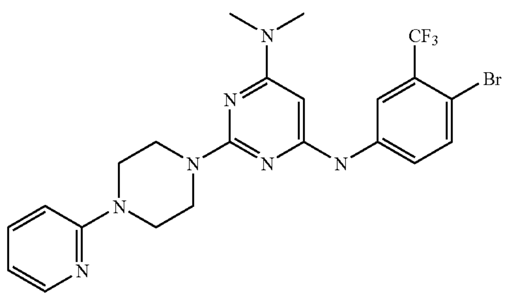 | 60 |
| 134 | 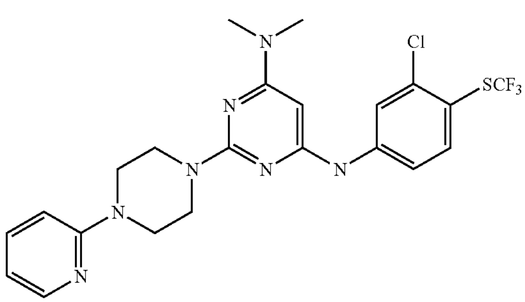 | 25 |

TABLE 3a-continued
| Example | Structure | Ki (nM) Gal3 |
|---|---|---|
| 135 | 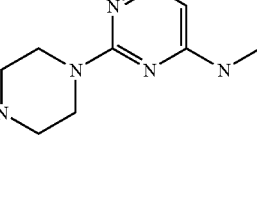 | 100 |
| 136 | 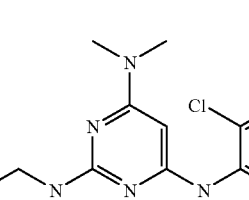 | 25 |
| 137 | 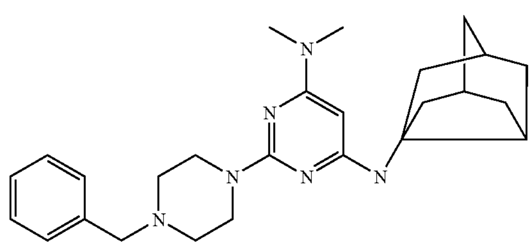 | 124 |
| 138 | 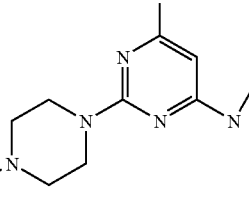 | 52 |
| 139 | 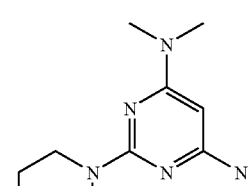 | 47 |

TABLE 3a-continued

| Example | Structure | Ki (nM) Gal3 |
|---|---|---|
| 140 | 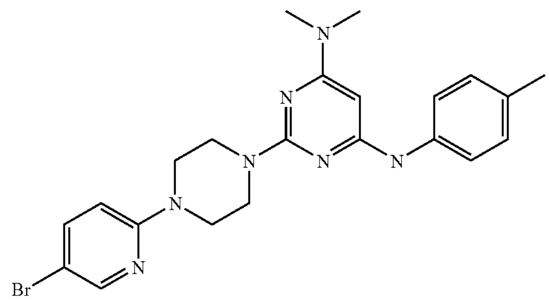 | 169 |
| 141 | 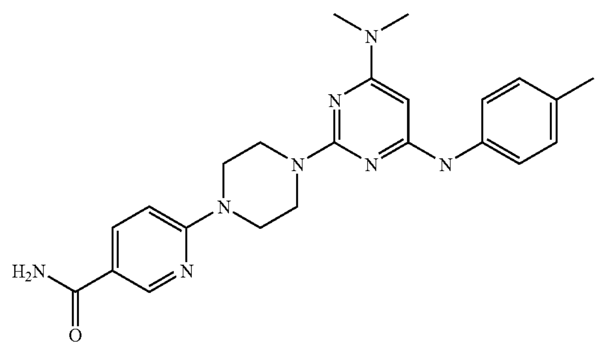 | 509 |
| 142 | 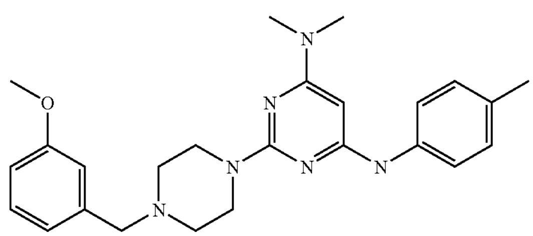 | 28 |
| 143 | 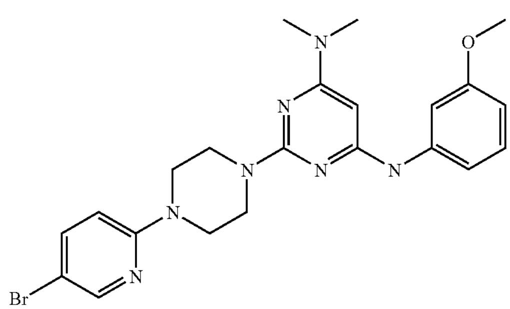 | 144 |
| 144 | 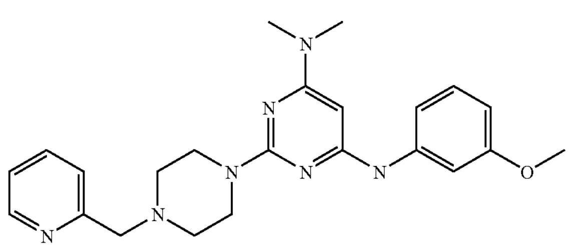 | 529 |

TABLE 3a-continued
| Example | Structure | Ki (nM) Gal3 |
|---|---|---|
| 145 | 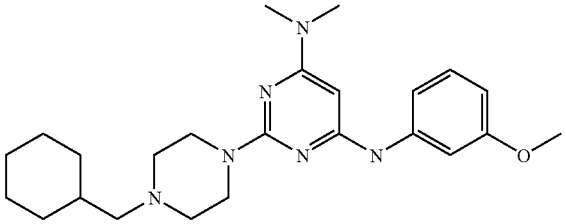 | 155 |
| 146 | 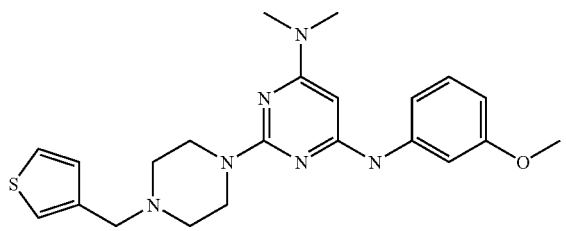 | 72 |
| 147 | 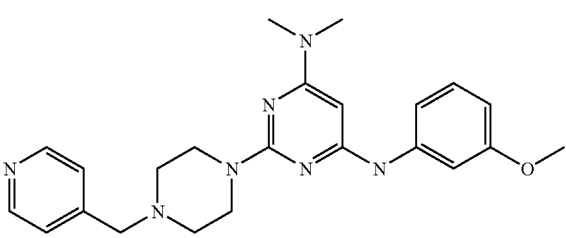 | 640 |
| 148 | 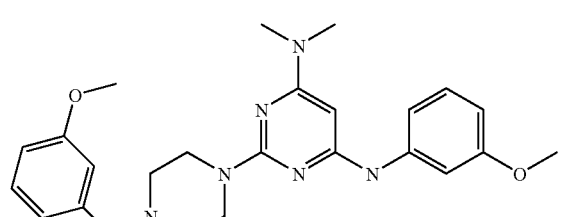 | 276 |
| 149 | 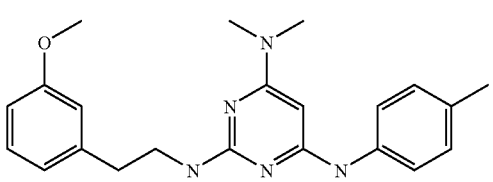 | 138* |
| 150 | 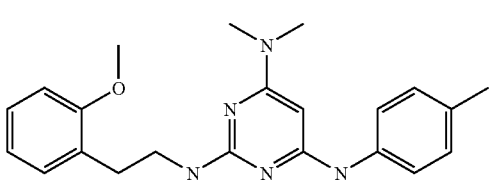 | 180 |
| 151 | 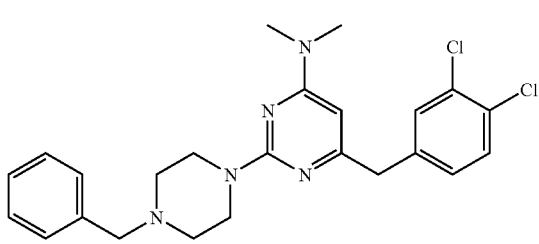 | 11 |

TABLE 3a-continued

| Example | Structure | Ki (nM) Gal3 |
|---|---|---|
| 152 | 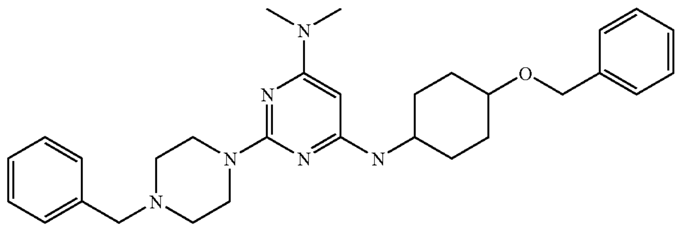 | 172 |
| 153 | 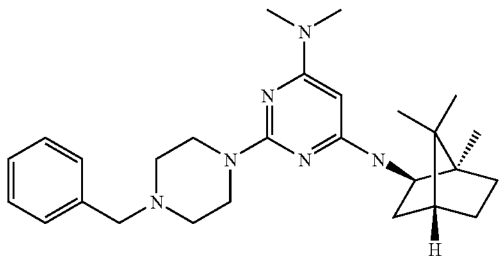 | 55 |
| 154 | 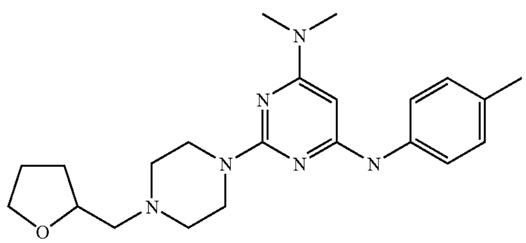 | 441 |
| 155 | 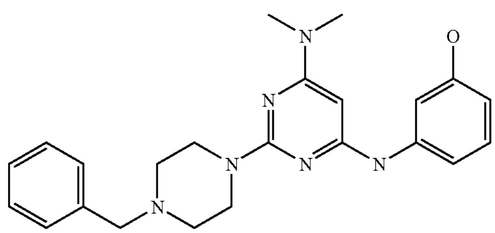 | 316 |
| 156 | 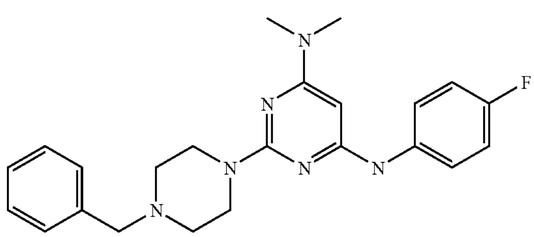 | 61 |
| 157 | 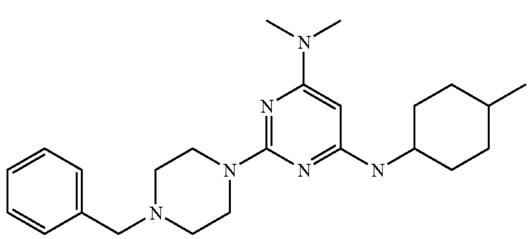 | 273 |

TABLE 3a-continued
| Example | Structure | Ki (nM) Gal3 |
|---|---|---|
| 158 | 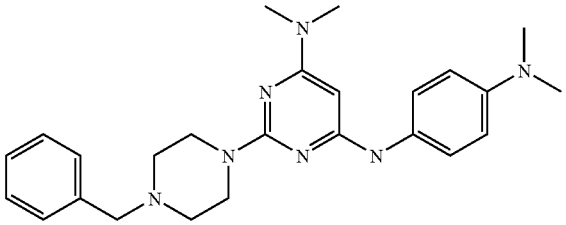 | 941 |
| 159 | 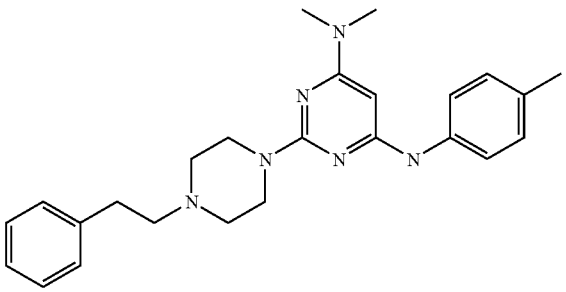 | 180 |
| 160 | 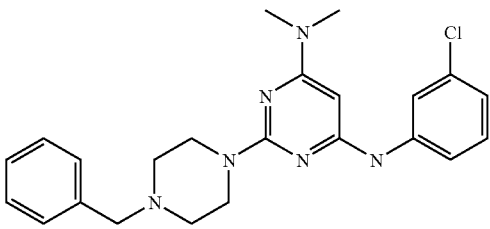 | 26 |
| 161 | 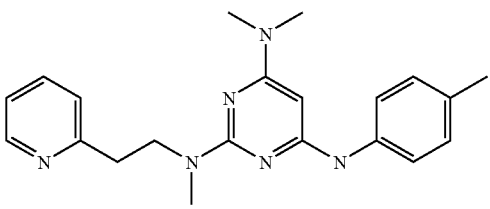 | 114 |
| 162 | 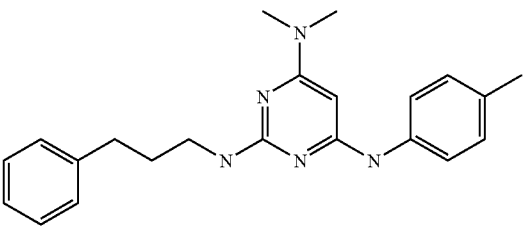 | 42 |
| 163 | 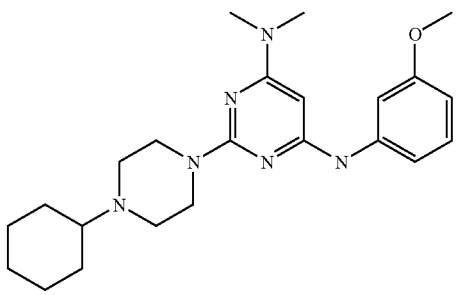 | 500 |

TABLE 3a-continued

| Example | Structure | Ki (nM) Gal3 |
|---|---|---|
| 164 | 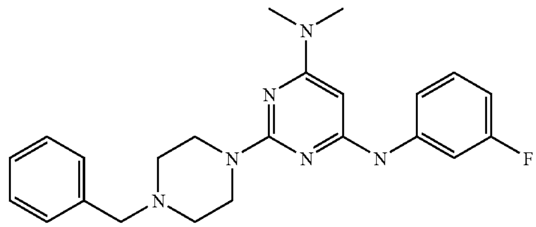 | 60 |
| 165 | 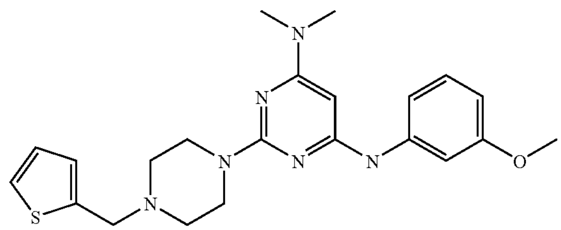 | 139* |
| 166 | 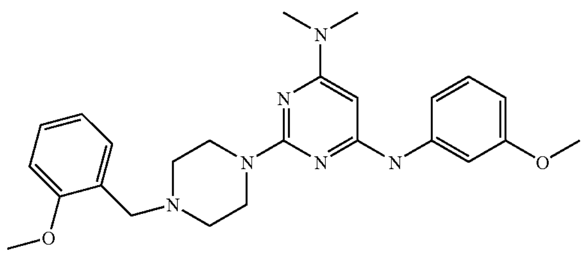 | 263 |
| 167 | 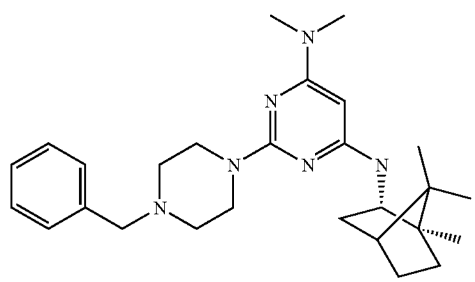 | 50 |
| 168 | 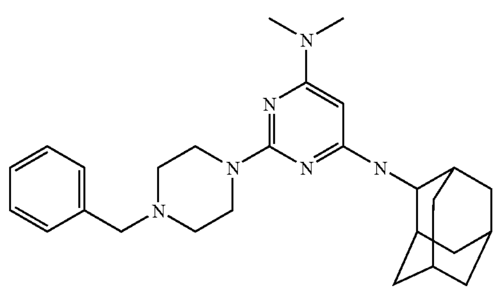 | 50 |
| 169 | 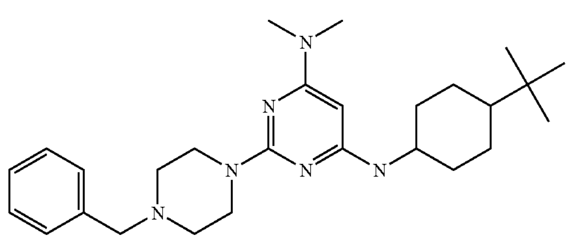 | 77 |

TABLE 3a-continued

| Example | Structure | Ki (nM) Gal3 |
|---|---|---|
| 170 | 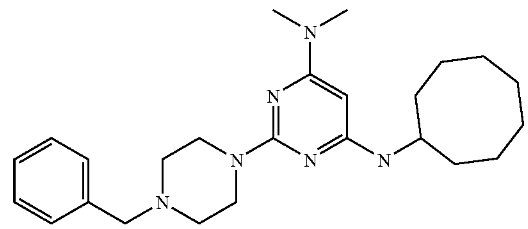 | 91 |
| 171 | 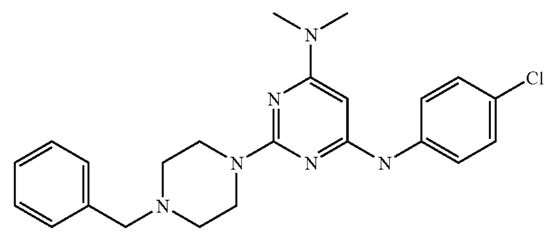 | 25 |
| 172 | 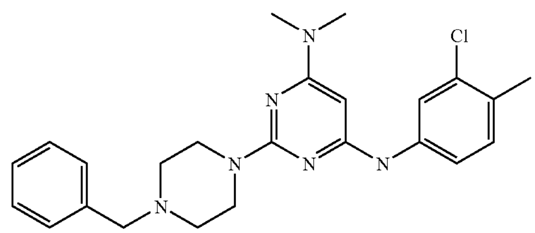 | 20 |
| 173 | 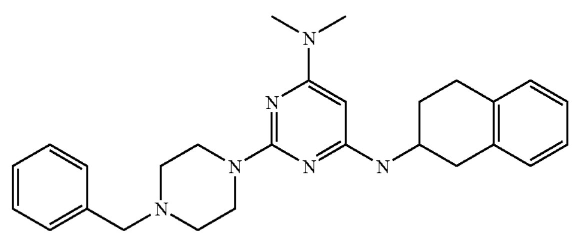 | 117 |
| 174 | 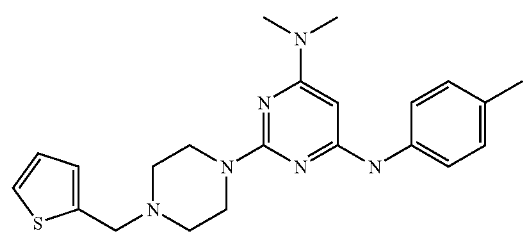 | 325* |
| 175 | 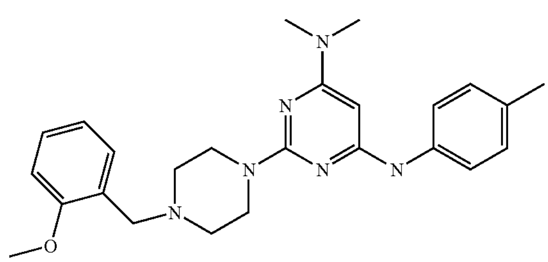 | 56 |

TABLE 3a-continued

| Example | Structure | Ki (nM) Gal3 |
|---|---|---|
| 176 | 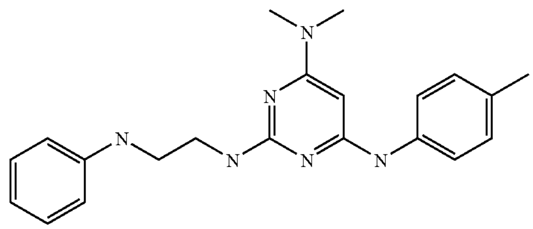 | 608 |
| 177 | 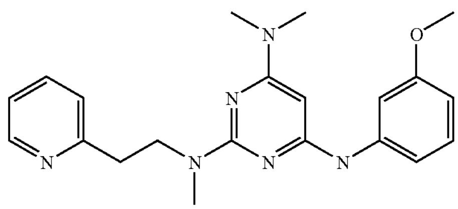 | 142 |
| 178 | 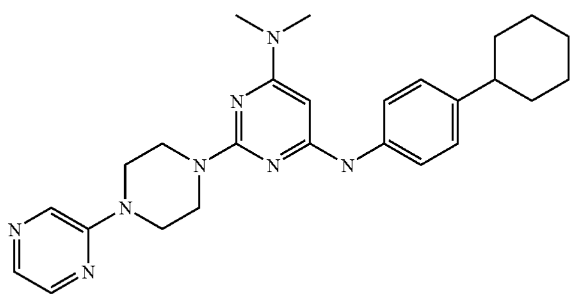 | 26 |
| 179 | 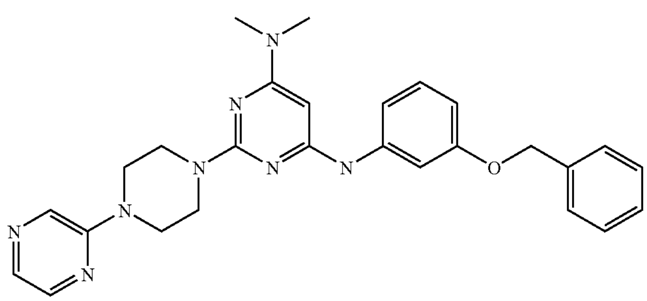 | 15 |
| 180 | 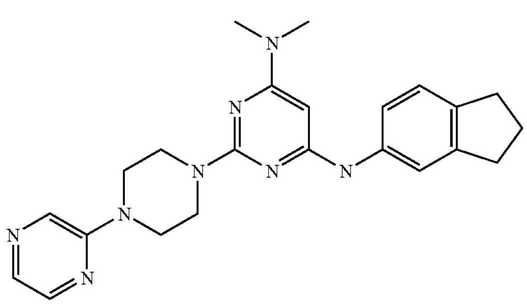 | 151 |

TABLE 3a-continued

| Example | Structure | Ki (nM) Gal3 |
|---|---|---|
| 181 | 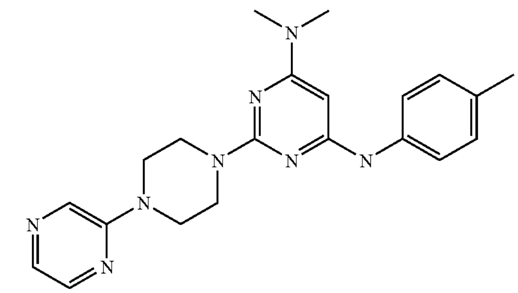 | 750 |
| 183 | 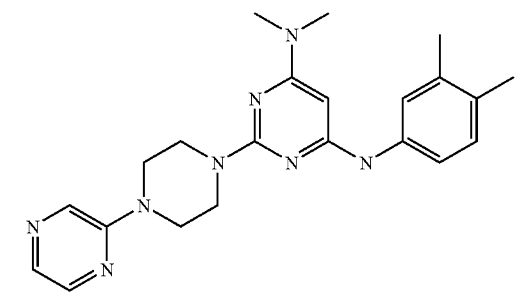 | 66 |
| 184 | 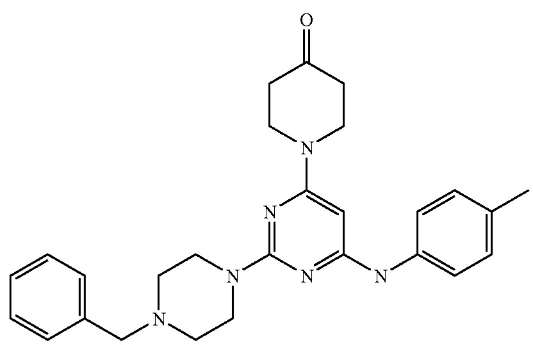 | 163 |
| 185 | 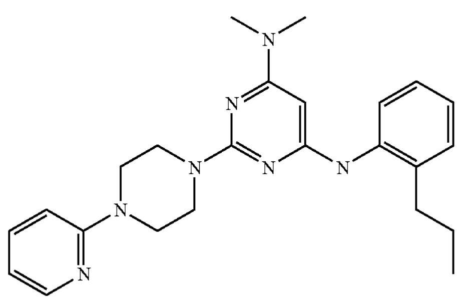 | 365 |
| 186 | 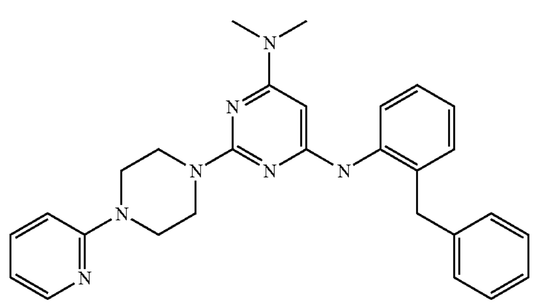 | 69 |

TABLE 3a-continued
| Example | Structure | Ki (nM) Gal3 |
|---|---|---|
| 187 | 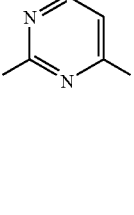 | 19 |
| 188 | 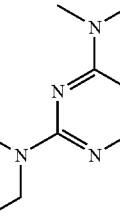 | 27 |
| 189 | 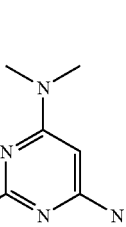 | 26 |
| 190 | 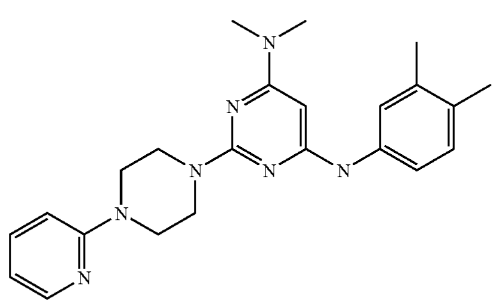 | 153 |
| 191 | 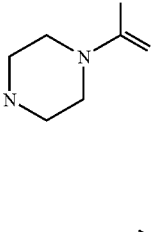 | 75 |

TABLE 3a-continued

| Example | Structure | Ki (nM) Gal3 |
|---|---|---|
| 192 | 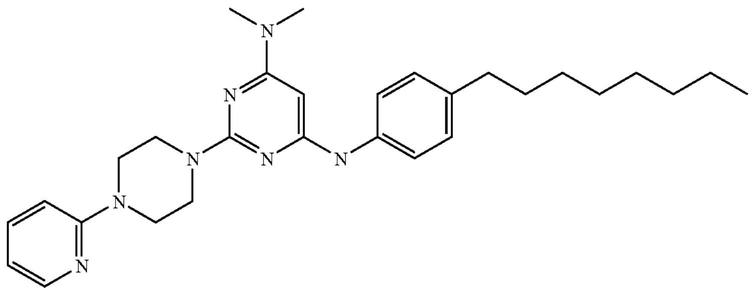 | 18 |
| 193 | 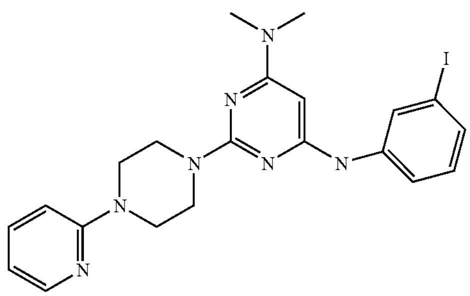 | 244 |
| 194 | 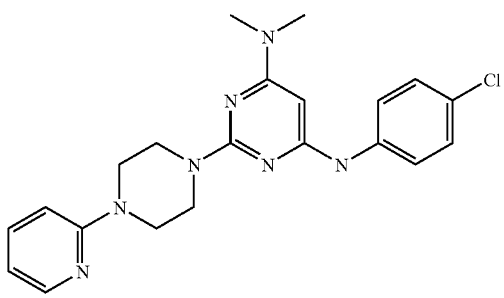 | 248 |
| 195 | 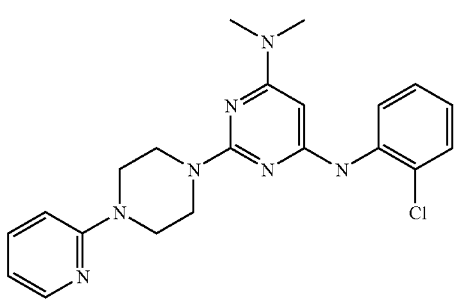 | 388 |
| 196 | 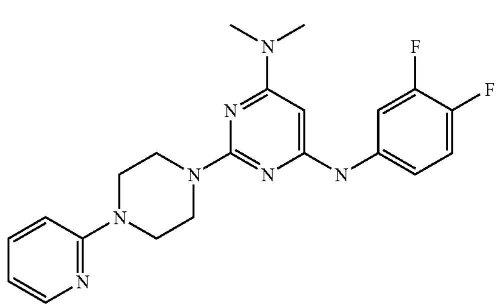 | 443 |

TABLE 3a-continued

| Example | Structure | Ki (nM) Gal3 |
|---|---|---|
| 197 | 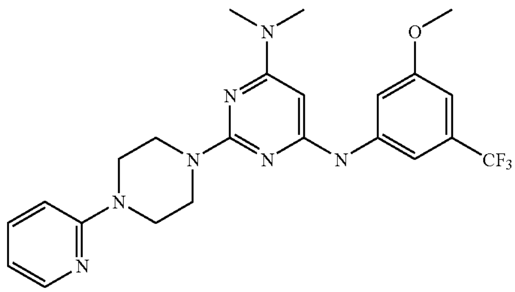 | 666 |
| 198 | 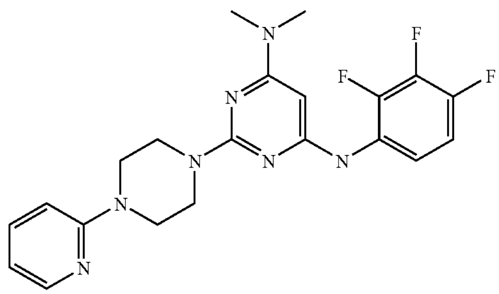 | 560 |
| 199 | 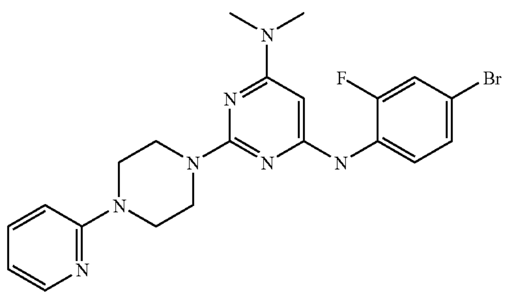 | 199 |
| 200 | 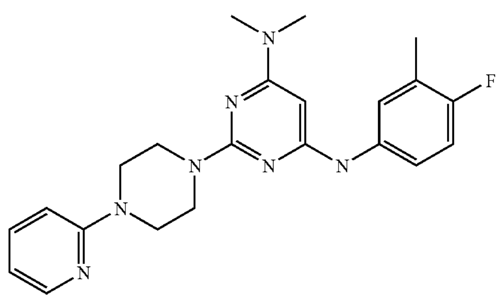 | 311 |
| 201 | 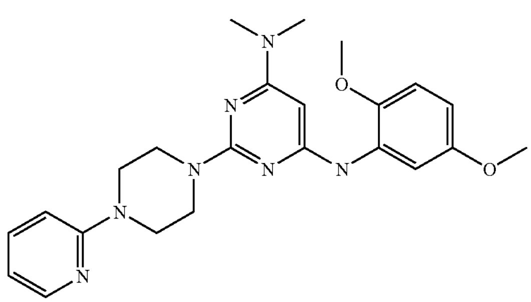 | 566 |

TABLE 3a-continued

| Example | Structure | Ki (nM) Gal3 |
|---|---|---|
| 202 | 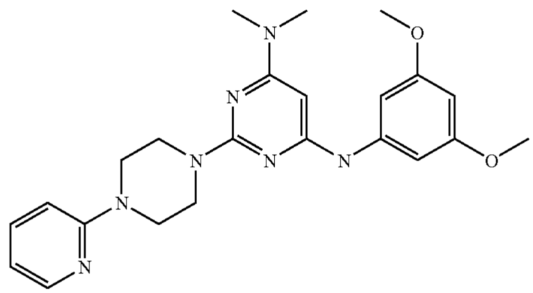 | 740 |
| 203 | 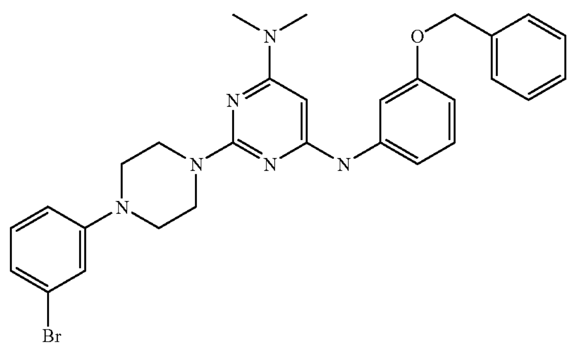 | 52 |
| 204 | 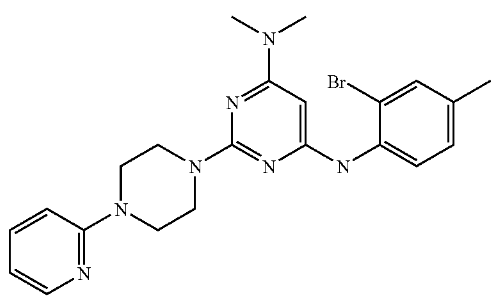 | 269 |
| 205 | 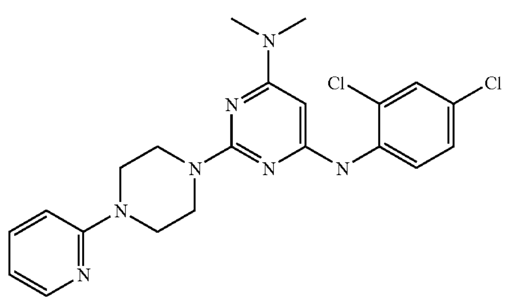 | 193 |
| 206 | 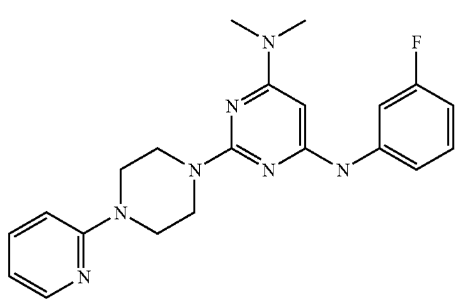 | 454 |

TABLE 3a-continued
| Example | Structure | Ki (nM) Gal3 |
|---|---|---|
| 207 | 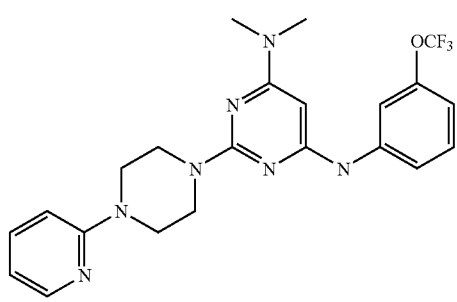 | 58 |
| 208 | 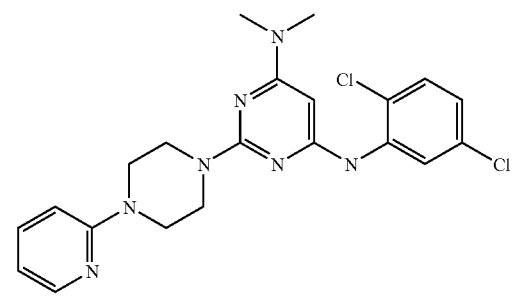 | 120 |
| 209 | 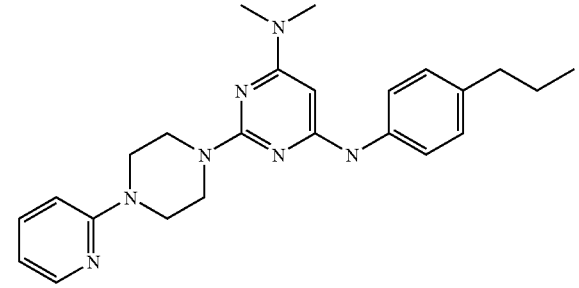 | 205 |
| 210 | 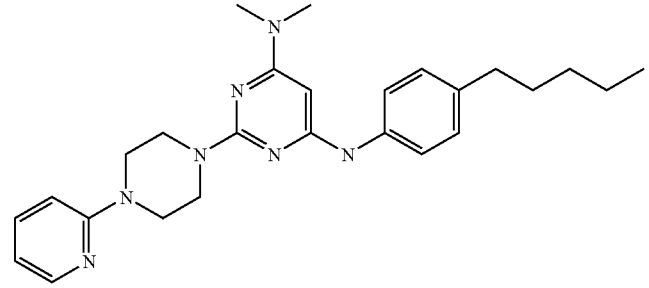 | 58 |
| 211 | 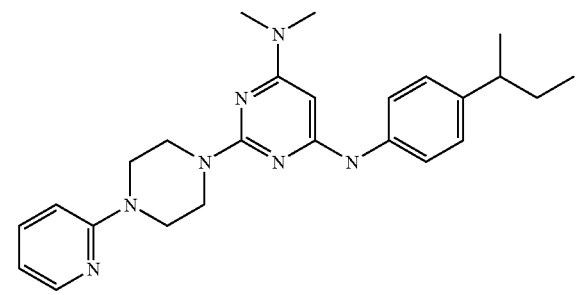 | 58 |

TABLE 3a-continued

| Example | Structure | Ki (nM) Gal3 |
|---|---|---|
| 212 | 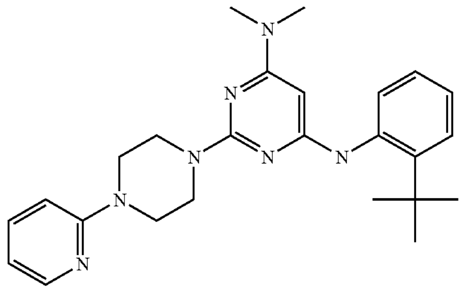 | 231 |
| 213 | 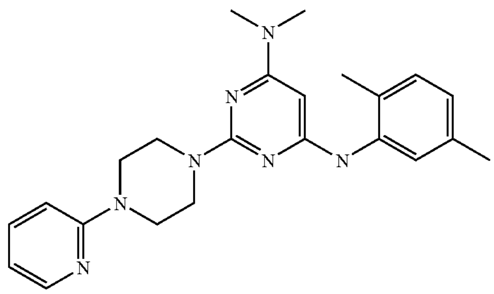 | 165 |
| 214 | 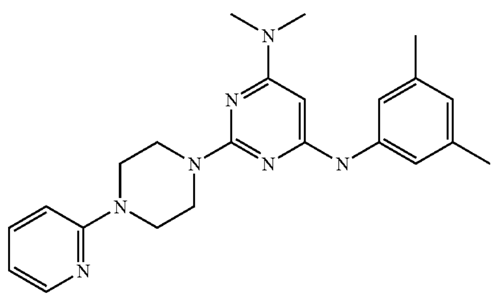 | 676 |
| 215 | 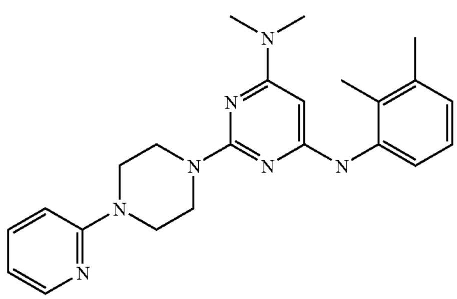 | 450 |
| 216 | 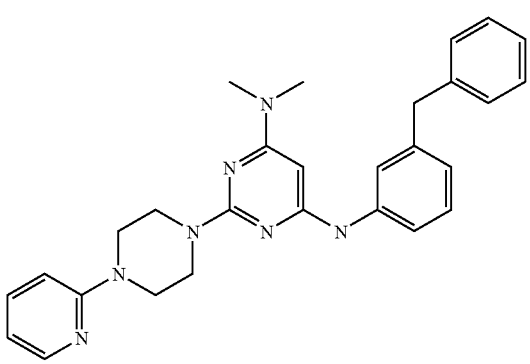 | 50 |

TABLE 3a-continued

| Example | Structure | Ki (nM) Gal3 |
|---|---|---|
| 217 | 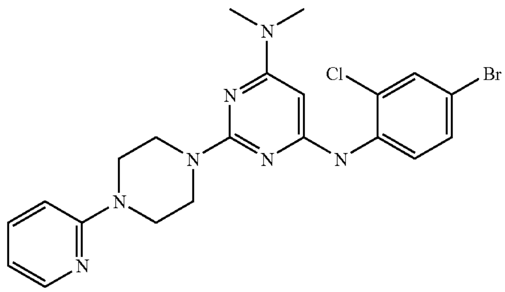 | 190 |
| 218 | 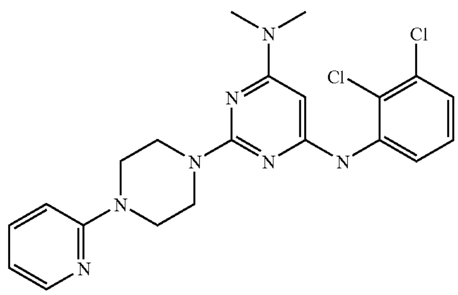 | 616 |
| 219 | 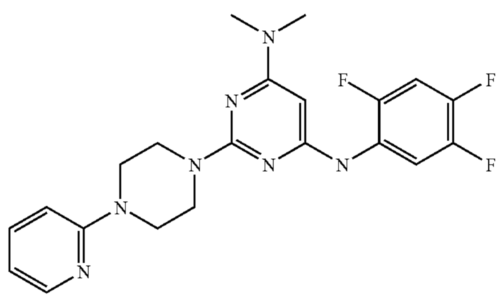 | 558 |
| 220 | 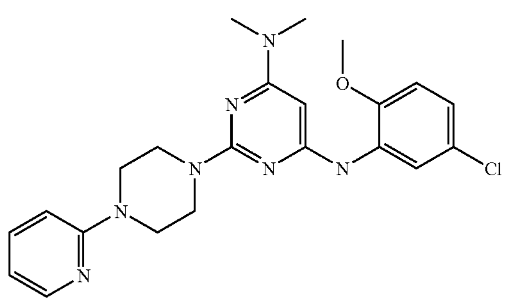 | 708 |
| 221 | 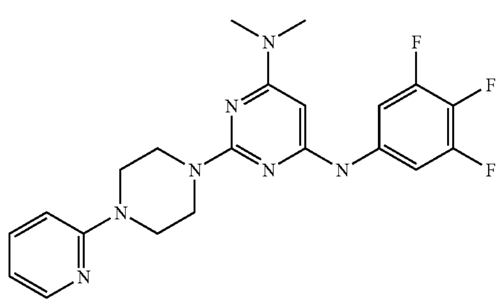 | 213 |

TABLE 3a-continued

| Example | Structure | Ki (nM) Gal3 |
|---|---|---|
| 222 | 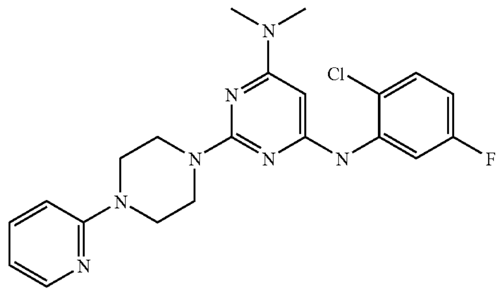 | 847 |
| 223 | 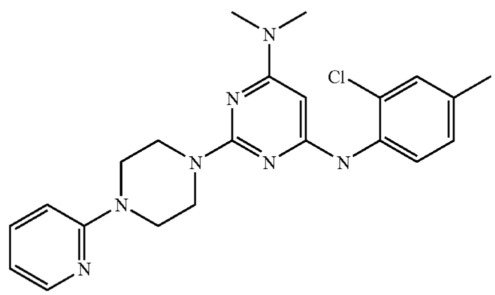 | 559 |
| 224 | 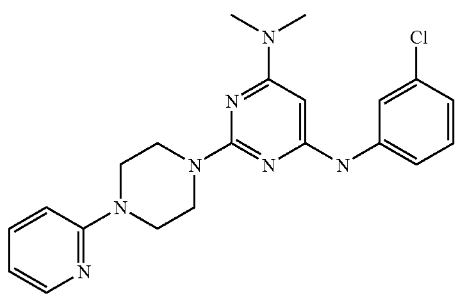 | 218 |
| 225 | 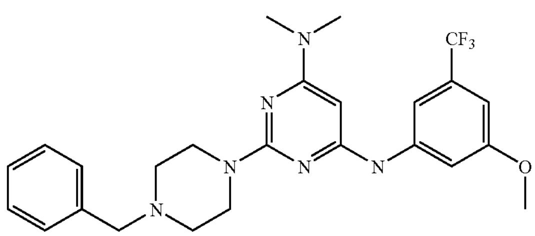 | 66 |
| 226 | 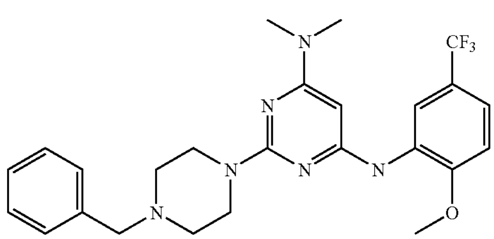 | 72 |

TABLE 3a-continued
| Example | Structure | Ki (nM) Gal3 |
|---|---|---|
| 227 | 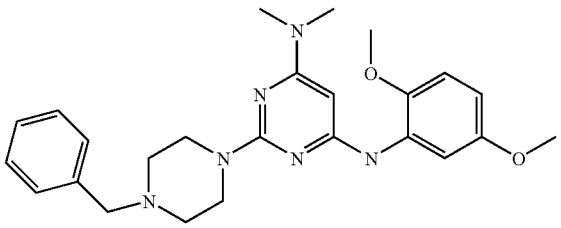 | 600 |
| 228 | 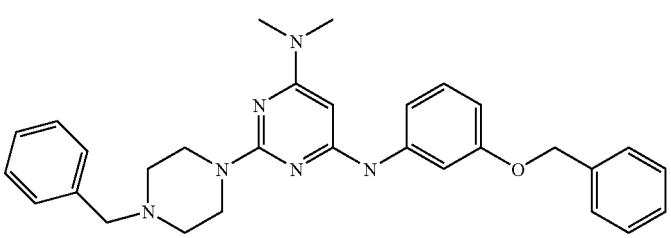 | 32 |
| 229 | 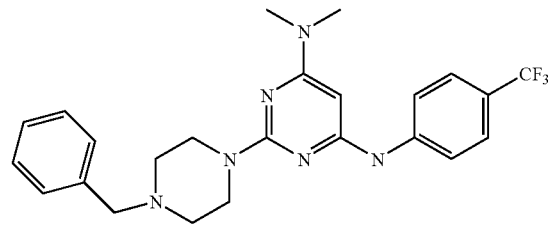 | 37 |
| 230 | 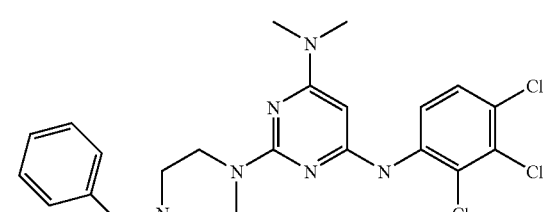 | 52 |
| 231 | 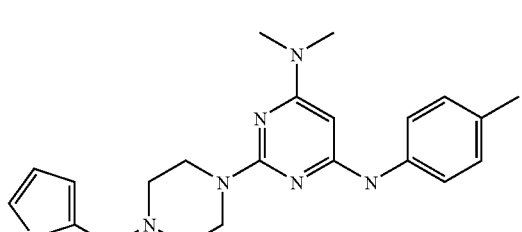 | 136 |
| 232 | 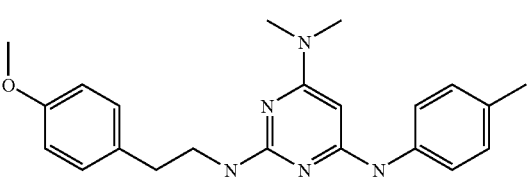 | 155* |

TABLE 3a-continued

| Example | Structure | Ki (nM) Gal3 |
|---|---|---|
| 233 | 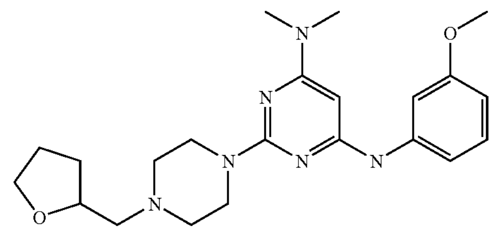 | 869 |
| 235 | 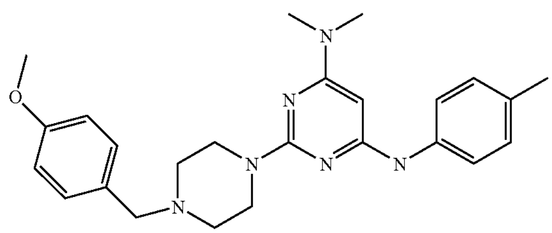 | 114* |
| 237 | 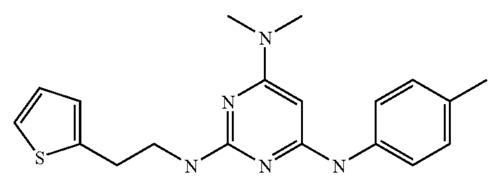 | 404* |
| 238 | 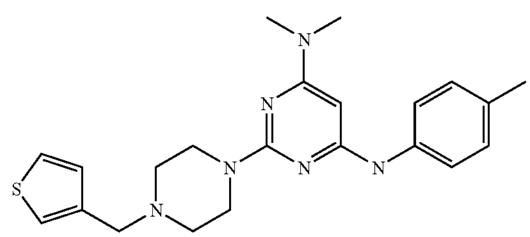 | 331* |
| 39 | 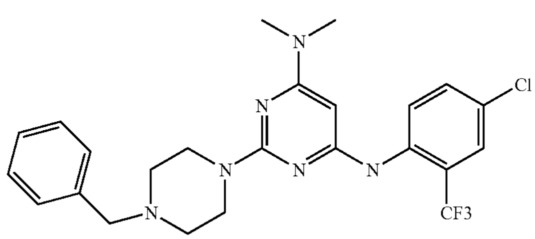 | 59 |
| 240 | 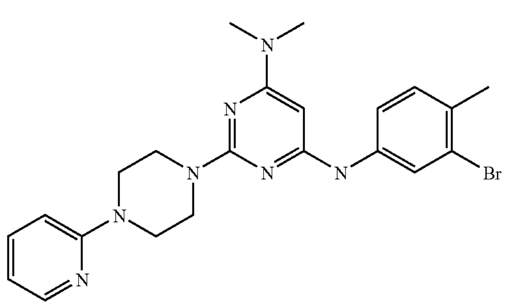 | 77 |

TABLE 3a-continued

| Example | Structure | Ki (nM) Gal3 |
|---|---|---|
| 241 | 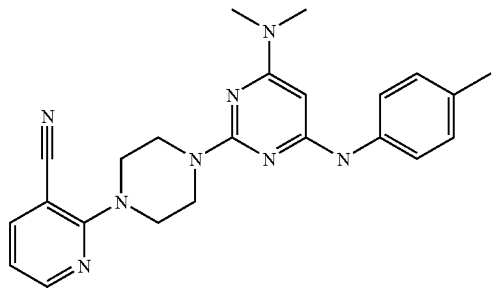 | 261 |
| 242 | 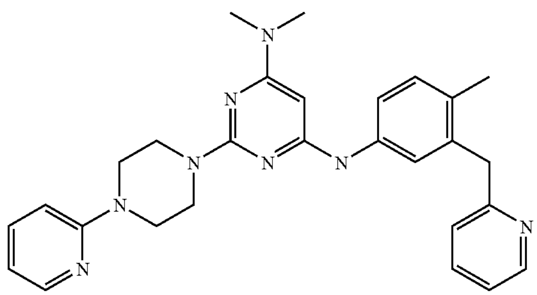 | 166 |
| 243 | 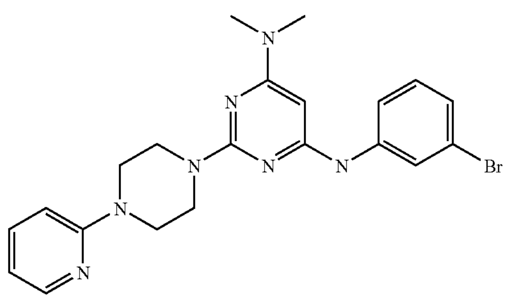 | 46 |
| 244 | 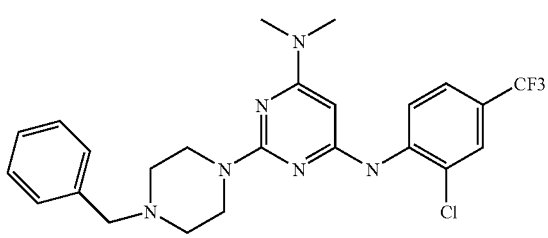 | 55 |
| 245 | 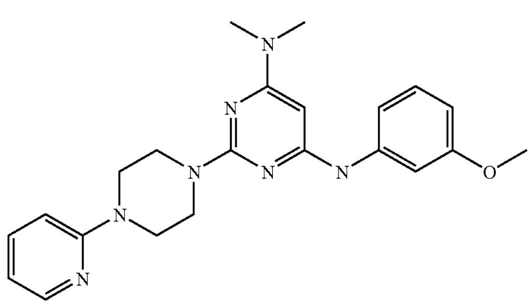 | 537 |

TABLE 3a-continued

| Example | Structure | Ki (nM) Gal3 |
|---|---|---|
| 246 | 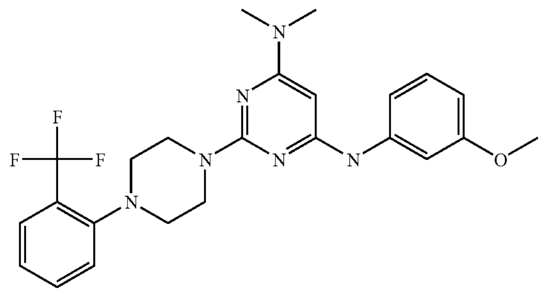 | 270 |
| 247 | 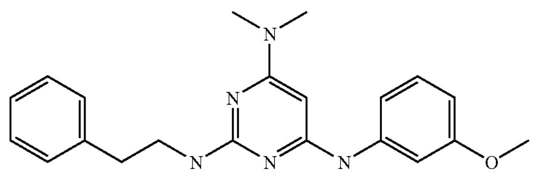 | 195 |
| 248 | 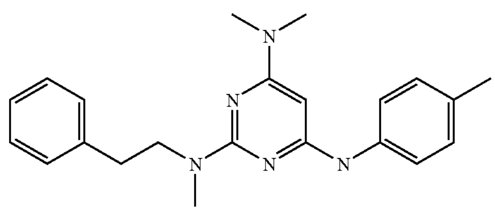 | 33 |
| 249 | 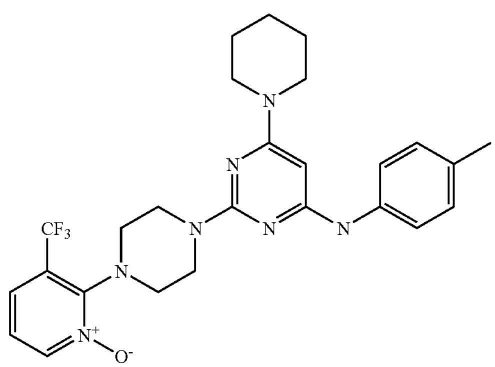 | 386 |
| 250 | 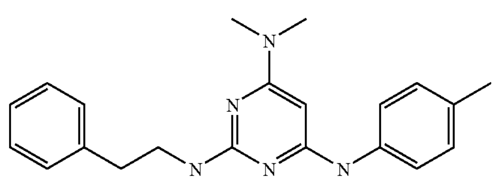 | 119 |
| 251 | 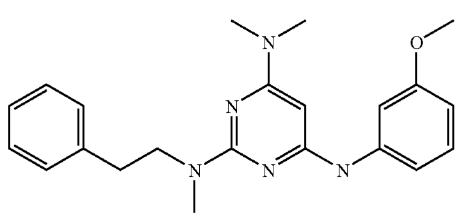 | 54 |

TABLE 3a-continued

| Example | Structure | Ki (nM) Gal3 |
|---|---|---|
| 252 | 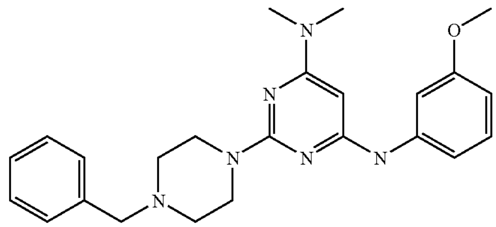 | 88 |
| 253 | 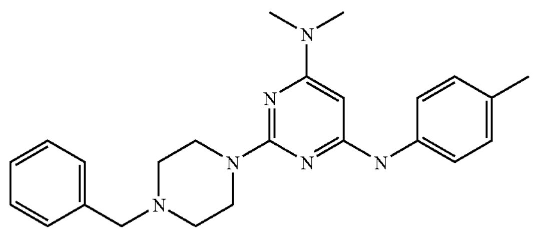 | 49 |

*The binding assay normally used for the indolone compounds was used to test this compound.

B. General Procedure for Preparing Indolones

General Procedure for Synthesis of Iminoisatins. The appropriately substituted isatin (10 mg-10 g) was placed in a flask and the appropriate aniline (1.0-1.1 equivalents) was added and the mixture was stirred to homogeneity. The mixture was then heated to 110° C. for 2-7 hours and then cooled. Solids were crystallized from hot methanol and filtered, giving the desired products (usually as an inseparable interconverting mixture of E/Z isomers).

Procedure A:

1-(3-THIENYL)-1H-INDOLE-2,3-DIONE: Triethylamine (56.9 mL, 0.408 mol), was added to a mixture of 1H-indole-2,3-dione (15.0 g, 0.102 mol), copper (II) acetate (46.0 g, 0.255 mol), and 3-thienylboronic acid (19.6 g, 0.153 mol) in $CH_2Cl_2$ (500 mL). The reaction mixture was stirred overnight, filtered through Celite, rinsed with EtOAc/hexane (1:1, 300 mL), and concentrated in vacuo. The crude product was purified by column chromatography on silica using Hexane/EtOAc (1:1), giving the desired product (1.1 g, 50%).

Procedure B:

(3E)-3-[(4-METHYLPHENYL)IMINO]-1-(3-THIENYL)-1,3-DIHYDRO-2H-INDOL-2-ONE: A solution of 1-(3-Thienyl)-1H-indole-2,3-dione (20 mg, 0.087 mmol) in 1% HOAc/MeOH (8 mL) was added to a solution of p-toluidine (19 mg, 0.18 mmol) in 1% HOAc/MeOH (8 mL). The reaction mixture was stirred for 12 h at room temperature, heated at 50° C. for 1 h, and concentrated in vacuo. The residue was purified by preparative TLC on silica using EtOAc/hexanes (3:7, 0.1% TEA) giving the desired product (14 mg, 50%).

Procedure C:

(3Z)-1-PHENYL-3-{[4-(3-THIENYL)PHENYL]IMINO}-1,3-DIHYDRO-2H-INDOL-2-ONE: A mixture of (3Z)-3-[(4-bromophenyl)imino]-1-phenyl-1,3-dihydro-2H-indol-2-one (50.0 mg, 0.133 mmol), thiophene-3-boronic acid (26.0 mg, 0.199 mmol), tetrakis(triphenylphosphine)palladium(0) (31.0 mg, 0.0268 mmol in THF (5 mL), and aqueous $Na_2CO_3$ (2M, 100 μL) was heated at 67° C. for 24 h. The crude product was concentrated in vacuo and the residue was extracted with $CH_2Cl_2$ (3×1 ml), and concentrated. The crude product was purified by preparative TLC using 10% methanol in $CHCl_3$, giving the desired product (18 mg, 35%).

Procedure D:

(3Z)-5-BROMO-3-{[3-(TRIFLUOROMETHYL)PHENYL]IMINO}-1,3-DIHYDRO-2H-INDOL-2-ONE: A mixture of 5-bromo-1H-indole-2,3-dione (1.0 g, 0.442 mmol) and 3-trifluoromethylaniline (0.993 g, 6.2 mmol) in a solution of 1% acetic acid in methanol was stirred at 50° C. for 12 h. The crude product was concentrated in vacuo, giving the desired crude product (640 mg, 40%).

Procedure E:

(3Z)-5-BROMO-1-PHENYL-3-{[3-(TRIFLUOROMETHYL)PHENYL]IMINO}-1,3-DIHYDRO-2H-INDOL-2-ONE: A mixture of (3z)-5-bromo-3-{[3-(trifluoromethyl)phenyl]imino}-1,3-dihydro-2h-indol-2-one (100 mg, 0.272 mmol), copper (II) acetate (54 mg, 0.33 mmol), triethylamine (82.8 mg, 0.817 mmol), and benzene boronic acid (40 mg, 0.325 mmol) in 5 mL of $CH_2Cl_2$ was stirred at room temperature for 12 h. The crude mixture was concentrated in vacuo and purified by preparative TLC using EtOAc:hexane (3:7, 1% triethylamine), giving the desired product (22 mg, 20%).

Procedure F:

(3Z)-1,5-DIPHENYL-3-{[3-(TRIFLUOROMETHYL)PHENYL]IMINO}-1,3-DIHYDRO-2H-INDOL-2-ONE: A mixture of (3z)-5-bromo-1-phenyl-3-{[3-(trifluoromethyl)phenyl]imino}-1,3-dihydro-2H-indol-2-one (22 mg, 0.05 mmol), tetrakis(triphenylphosphine)palladium(0) (12.0 mg, 0.01 mmol), benzene boronic acid (10 mg, 0.08 mmol) in THF (5 mL), and aqueous $Na_2CO_3$ (2M, 100 μL) was heated at 67° C. for 24 h. The crude product was concentrated in vacuo and the residue was extracted with $CH_2Cl_2$ (3×1 ml), concentrated, and purified by preparative TLC using 10% methanol in $CHCl_3$, giving the desired product (4 mg, 18%).

Procedure G:

ETHYL 5-[(2,3-DIOXO-2,3-DIHYDRO-1H-INDOL-1-YL)METHYL]-2-FUROATE: A mixture of ethyl 5-(chloromethyl)-2-furoate (148 mg, 1.01 mmol) in dioxane (15 ml) was added to a mixture of NaH (48 mg, 1.20 mmol) in dioxane (10 mL) under argon at 0° C. The mixture was stirred for 1 h at room temperature, refluxed under argon for 16 h, cooled to room temperature, and then concentrated in vacuo. The residue was purified by preparative TLC using EtOAc/hexane (3:7), giving the desired product (56 mg, 19%).

Procedure H:

ETHYL 5-[((3Z)-2-OXO-3-{[3-(TRIFLUOROM-ETHYL)PHENYL]IMINO}-2,3-DIHYDRO-1H-INDOL-1-YL)METHYL]-2-FUROATE: A mixture of ethyl 5-[(2,3-dioxo-2,3-dihydro-1H-indol-1-yl)methyl]-2-furoate (60 mg, 0.200 mmol) and 3-trifluoromethylaniline (32 mg, 0.200 mmol) was heated at 140° C. for 2 h. The residue was dissolved in $CHCl_3$ (1 mL) and purified by preparative TLC using EtOAc/hexane (6:4), giving the desired product (20 mg, 23%).

Procedure I:

6-METHOXY-1-PHENYL-1H-INDOLE-2,3-DIONE: A solution of N-(3-methoxyphenyl)-N-phenylamine (1.14 g, 5.72 in ether (3 mL) was added to a solution of oxylyl chloride (728 g, 5.75 mmol) and heated at reflux for 1 h. The resulting mixture was cooled to room temperature, concentrated to dryness, and redissolved in nitrobenzene (35 mL). The solution was added to a solution of $AlCl_3$ in nitrobenzene (0.762 g, 5.72 mmol), and the resulting mixture was heated at 70° C. for 16 h. The crude product was concentrated in vacuo and purified by column chromatography using EtOAc/hexane (1:1), giving the desired product 60, mg, 50%).

Procedure J:

(3Z)-1-(4-BROMOPHENYL)-3-{[3-(TRIFLUOROM-ETHYL)PHENYL]IMINO}-1,3-DIHYDRO-2H-INDOL-2-ONE: A solution of (3Z)-3-{[3-(trifluoromethyl)phenyl]imino}-1,3-dihydro-2H-indol-2-one (100 mg, 0.344 mmol), copper (II) acetate (93 mg, 0.516 mmol), triethylamine (105 mg, 1.03 mmol), and 4-bromobenzene boronic acid (104 mg, 0.516 mmol) in 5 mL of $CH_2Cl_2$ was stirred at room temperature for 12 h. The crude mixture was concentrated in vacuo and purified by preparative TLC using EtOAc:hexane (3:7, 1% triethylamine), giving the desired product (65 mg, 42%).

Procedure K:

A solution of (3Z)-1-(4-bromophenyl)-3-{[3-(trifluoromethyl)phenyl]imino}-1,3-dihydro-2H-indol-2-one (30 mg, 0.068), tetrakis(triphenylphosphine)palladium(0) (16.0 mg, 0.014 mmol), benzene boronic acid (13 mg, 0.101 mmol) in THF (5 mL), and aqueous $Na_2CO_3$ (0.45 M, 300 µL) was heated at 67° C. for 40 h. The crude product was concentrated in vacuo and the residue was extracted with $CH_2Cl_2$ (3×1 ml) concentrated, and purified by preparative TLC using 10% methanol in $CHCl_3$, giving the desired product (5 mg, 16%).

The compounds of Examples 92-107, inclusive, were purchased from Bionet Research Ltd., 3 Highfield Industrial Estate, Camelford, Cornwall PL32 9QZ, UK. These compounds can also be synthesized using the procedure described above.

Example 91

3-[(2-METHOXYPHENYL) IMINO]-1-PHENYL-1,3-DIHYDRO-2H-INDOL-2-ONE

Example 92

1-PHENYL-3-[[3-(TRIFLUOROMETHYL)PHE-NYL]IMINO]-1,3-DIHYDRO-2H-INDOL-2-ONE

Example 93

3-[(3-METHYLPHENYL)IMINO]-1-PHENYL-1,3-DIHYDRO-2H-INDOL-2-ONE

Example 94

3-[(3-CHLOROPHENYL)IMINO]-1-PHENYL-1,3-DIHYDRO-2H-INDOL-2-ONE

Example 95

1-PHENYL-3-[[4-(TRIFLUOROMETHYL)PHE-NYL]IMINO]-1,3-DIHYDRO-2H-INDOL-2-ONE

Example 96

3-[(4-METHYLPHENYL) IMINO]-1-PHENYL-1,3-DIHYDRO-2H-INDOL-2-ONE

Example 97

3-[(4-CHLOROPHENYL) IMINO]-1-PHENYL-1,3-DIHYDRO-2H-INDOL-2-ONE

Example 98

3-[(4-BROMOPHENYL)IMINO]-1-PHENYL-1,3-DIHYDRO-2H-INDOL-2-ONE

Example 99

3-[(4-FLUOROPHENYL)IMINO]-1-PHENYL-1,3-DIHYDRO-2H-INDOL-2-ONE

Example 100

3-[(4-PHENOXYPHENYL)IMINO]-1-PHENYL-1,3-DIHYDRO-2H-INDOL-2-ONE

Example 101

3-[(4-ETHOXYPHENYL)IMINO]-1-PHENYL-1,3-DIHYDRO-2H-INDOL-2-ONE

Example 102

3-[(4-METHOXYPHENYL)IMINO]-1-PHENYL-1,3-DIHYDRO-2H-INDOL-2-ONE

Example 103

3-[(3,5-DICHLOROPHENYL)IMINO]-1-PHENYL-1,3-DIHYDRO-2H-INDOL-2-ONE

Example 104

3-[(3,5-DIMETHYLPHENYL)IMINO]-1-PHE-NYL-1,3-DIHYDRO-2H-INDOL-2-ONE

Example 105

1-ALLYL-3-[(3,4-DICHLOROPHENYL)IMINO]-1,3-DIHYDRO-2H-INDOL-2-ONE

Example 106

1-ALLYL-3-[(3,5-DICHLOROPHENYL)IMINO]-1,3-DIHYDRO-2H-INDOL-2-ONE

Example 107

3-[(4-BROMOPHENYL)IMINO]-1-ISOPROPYL-1,3-DIHYDRO-2H-INDOL-2-ONE

The methods that follow demonstrate procedures useful for synthesizing compounds of this invention (illustrated in Schemes 6 and 7). Substituted isatins useful for synthesizing compounds of this invention can alternatively be obtained using the procedures described in the following references:

Garden, S. J.; Da Silva, L. E.; Pinto, A. C.; *Synthetic Communications,* 1998, 28, 1679-1689.

Coppola, G. M.; *Journal of Heterocyclic Chemistry,* 1987, 24, 1249.

Hess, B. A. Jr; Corbino, S.; *Journal of Heterocyclic Chemistry,* 1971, 8, 161.

Bryant, W. M. III; Huhn, G. F.; Jensen, J. H.; Pierce, M. E.; Stammbach, C.; *Synthetic Communications,* 1993, 23, 1617-1625.

Example 108

1-[(5-CHLORO-2-THIENYL)METHYL]-3-{[3-(TRIFLUOROMETHYL)PHENYL]IMINO}-1,3-DIHYDRO-2H-INDOL-2-ONE

A mixture of 1-[(5-chloro-2-thienyl)methyl]-2H-indole-2,3-dione (25 mg, 0.09 mmol) (prepared as described below) and 3-trifluoromethylaniline (11.3 μL, 0.09 mmol) was heated neat at 140° C. for 2 h. The crude material was purified by preparative TLC using a mixture of 3:7 ethyl acetate in hexane as the eluent, giving the desired product (23 mg 0.05 mmol, 61%). $^1$H NMR (400 MHz): δ (major isomer) 7.57 (t, J=7.7, 1H), 7.53 (t, J=7.8, 1H), 7.33 (t, J=7.8, 1H), 7.28 (s, 1H), 7.19 (d, J=7.6, 2H), 6.94-6.72 (m, 4H), 6.56 (d, J=7.7, 1H), 5.02 (s, 2H); ESI-MS m/z found 421 (MH$^+$).

1-[(5-CHLORO-2-THIENYL)METHYL]-2H-INDOLE-2,3-DIONE

A solution of isatin (125 mg, 0.85 mmol) in anhydrous dioxane (10 mL) was added dropwise to a solution of sodium hydride (60% dispersion in mineral oil, 24 mg, 0.62 mmol) in anhydrous dioxane (10 mL) at 0° C. under argon. The mixture was allowed to stir for 5 minutes and then 2-chloro-5-(chloromethyl)thiophene (0.12 mL, 1.02 mmol) in dioxane (10 mL) was added dropwise to the resulting mixture. The reaction mixture was heated at reflux under argon for 16 h and concentrated in vacuo. The crude material was purified preparative TLC using 1:24 methanol in chloroform as the eluent, giving the desired product as a yellow solid (53 mg, 0.19 mmol, 22%). $^1$H NMR (400 MHz): δ 7.62 (d, J=7.4, 1H), 7.56 (t, J=7.8, 1H), 7.14 (t, J=7.7, 1H), 6.94 (d, J=8.0, 1H), 6.90 (d, J=3.2, 1H), 6.78 (d, J=3.7, 1H), 4.90 (s, 2H).

Example 109

1-(3-THIENYL)-3-{[3-(TRIFLUOROMETHYL)PHENYL]IMINO}-1,3-DIHYDRO-2H-INDOL-2-ONE

A mixture of 1-(3-thienyl)-2H-indole-2,3-dione (25 mg, 0.11 mmol) (prepared as described below) and 3-trifluoromethylaniline (14 uL, 0.11 mmol) was heated neat at 140° C. for 2 h. The crude material was purified by preparative TLC using a mixture of 3:7 ethyl acetate and hexane as the eluent, giving the desired product as a yellow solid (7.3 mg, 0.02 mmol, 22%). $^1$H NMR (400 MHz) δ 7.62-7.19 (m, 9H), 6.94 (d, J=8.0, 1H), 6.76 (t, J=7.6, 1H); ESI-MS m/z found 373 (MH$^+$).

1-(3-THIENYL)-2H-INDOLE-2,3-DIONE

Copper(II) acetate monohydrate (4.25 g, 23.4 mmol) was heated at reflux in acetic anhydride (30 mL) for 2 h. The mixture was filtered and washed with anhydrous ether (500 mL). The solid was dried in vacuo at 55° C. for 16 h. Dichloromethane (1 mL) was added to a mixture of copper(II) acetate (62 mg, 0.34 mmol), isatin (50 mg, 0.34 mmol), and thiophene-3-boronic acid (87 mg, 0.68 mmol), followed by triethylamine (0.10 mL, 0.68 mmol) under argon. The resulting solution was stirred for 16 h at room temperature. The reaction mixture was then recharged with 0.10 mmol copper (II) acetate, 0.10 mmol of 3-thiophene boronic acid, and 1 drop of triethylamine, and the mixture was heated at 50° C. for 6 h. The crude material was purified by preparative TLC using 3:97 methanol in chloroform as the eluent, giving the desired product as a yellow solid (25 mg, 0.11 mmol, 33%). $^1$H NMR (400 MHz): δ 7.70 (d, J=7.5, 1H), 7.58 (t, J=7.8, 1H), 7.50 (d, J=5.1, 1H), 7.48 (s, 1H), 7.24 (d, J=5.1, 1H), 7.18 (t, J=7.51, 1H), 7.05 (d, J=8.0, 1H).

Example 110

2-METHYL-5-[(2-OXO-1-PHENYL-1,2-DIHYDRO-3H-INDOL-3-YLIDENE)AMINO]-2H-ISOINDOLE-1,3(2H)-DIONE

A mixture of 1-phenylisatin (50 mg, 0.22 mmol) and 4-amino-N-methylpthalimide (40 mg, 0.22 mmol) was heated neat at 215° C. for 2 h. The crude material was purified by preparative TLC using a mixture of 3:7 ethyl acetate and hexane as the eluent, giving the desired product as a yellow solid (8 mg, 0.02 mmol, 10%). $^1$H NMR (400 MHz): δ 7.88 (d, J=7.8, 1H), 7.83-7.80 (m, 1H), 7.51 (t, J=7.5, 1H), 7.47-7.18 (m, 6H), 7.02 (t, J=8.0, 1H), 6.91-6.79 (m, 2H), 6.58 (d, J=7.5, 1H), 3.22 (s, 3H); ESI-MS m/z found 382 (MH$^+$).

Example 111

1-[(5-CHLORO-1-BENZOTHIEN-3-YL)METHYL]-3-{[3-(TRIFLUOROMETHYL)PHENYL]IMINO}-1,3-DIHYDRO-2H-INDOL-2-ONE

A mixture of 1-[(5-chloro-1-benzothien-3-yl)methyl]-2H-indole-2,3-dione (50 mg, 0.15 mmol) (prepared as described below) and 3-trifluoromethylaniline (0.020 mL, 0.15 mmol) was heated neat at 140° C. for 2 h. The crude material was purified by preparative TLC using a mixture of 1:3 ethyl acetate and hexane as the eluent giving the desired product as a yellow solid (13 mg, 0.030 mmol, 18%). $^1$H NMR (400 MHz): δ 7.98 (d, J=2.0, 1H), 7.80 (d, J=8.6, 1H), 7.58 (t, J=7.7, 1H), 7.52 (d, J=8.1, 1H), 7.43 (s, 1H), 7.38 (dd, J=8.6, 1.9, 1H), 7.31 (overlapping singlet and dt, J=1.2, 7.8, 2H), 7.24 (d, J=7.8, 1H), 6.87 (d, J=7.9, 1H), 6.77 (t, J=7.7, 1H), 6.59 (d, J=7.7, 1H), 5.20 (s, 2H). ESI-MS m/z found 471 (MH$^+$ with $^{35}$Cl), 473 (MH$^+$ with $^{37}$Cl).

1-[(5-CHLORO-1-BENZOTHIEN-3-YL)METHYL]-2H-INDOLE-2,3-dione

A solution of isatin (125 mg, 0.85 mmol) in anhydrous dioxane (10 mL) was added dropwise to a solution of sodium hydride (60% dispersion in mineral oil, 25 mg, 0.62 mmol) in anhydrous dioxane (10 mL) at 0° C. under argon. The mixture was allowed to stir for 5 minutes and then a solution of 3-(bromomethyl)-5-chlorobenzo[b]thiophene (267 mg, 1.02 mmol) in dioxane (10 mL) was added dropwise to the reaction mixture. The reaction mixture was heated at reflux under argon for 16 h and concentrated in vacuo. The crude material was purified by preparative TLC using 1:24 methanol in chloroform as the eluent, giving the desired product as a yellow solid (125 mg, 0.38 mmol, 45%). $^1$H NMR (400 MHz): δ 7.89 (s, 1H), 7.79 (d, J=8.5, 1H), 7.65 (d, J=7.5, 1H), 7.54 (t, J=8.0, 1H), 7.42 (s, 1H), 7.38 (d, J=8.5, 1H), 7.14 (t, J=7.5, 1H), 6.88 (d, J=7.8, 1H), 5.13 (s, 2H).

Example 112

3-(1H-INDOL-5-YLIMINO)-1-PHENYL-1,3-DIHYDRO-2H-INDOL-2-ONE 1-phenylisatin (51.8 mg, 0.23 mmol) and 5-aminoindole (31 mg, 0.23 mmol) were mixed and heated at 140° C. for 2 h. The resulting crude product was purified by preparative TLC using ethyl acetate/hexane (6:4) as the eluent, giving the desired product as a yellow solid (10.8 mg, 14%). $^1$H NMR (400 MHz): δ 8.28 (s, 1H), 7.57 (t, J=7.7, 2H), 7.49-7.40 (m, 6H), 7.29-7.23 (m, 1H), 7.03 (dd, J=8.5, 1.7, 1H), 6.98 (d, J=7.6, 1H), 61.83 (d, J=8.0, 1H), 6.74, J=7.6, 1H), 6.59 (s, 1H); ESI-MS m/z found 338 (MH$^+$).

Example 113

3-[(6-CHLORO-3-PYRIDINYL)IMINO]-1-PHENYL-1,3-DIHYDRO-2H-INDOL-2-ONE 1-phenylisatin (23.0 mg, 0.10 mmol) and 5-amino-2-chloropyridine (12.8 mg, 0.10 mmol) were mixed and heated at 140° C. for 7 h. The resulting crude product was purified by preparative TLC using hexane/ethyl acetate (8:2) as the eluent, giving the desired product as a yellow-solid (19.7 mg, 59%). $^1$H NMR (400 MHz) δ 8.15 (d, J=8, 1H), 7.6-7.2 (m, 9H), 6.85-6.75 (m, 2H); ESI-MS m/z found 334 (MH$^+$).

Example 114

3-[(2-METHYL-1,3-BENZOTHIAZOL-5-YL)IMINO]-1-PHENYL-1,3-DIHYDRO-2H-INDOL-2-ONE 5-amino-2-methylbenzothiazole (52.2 mg, 0.31 mmol) was mixed with 1-phenylisatin (69.7 mg, 0.31 mmol) and heated at 140° C. for 3 h. The resulting crude product was purified by preparative TLC using ethyl acetate/hexane (6:4) as the eluent to give the desired product as a yellow solid (36.9 mg, 32.3%). $^1$H NMR Data: δ 7.9-6,7 (m, 12H), 2.9 (s, 3H). ESI-MS m/z found 370 (MH$^+$).

Example 254

(3Z)-3-[(3,4-DICHLOROPHENYL)IMINO]-1-(2-PYRIDINYLMETHYL)-1,3-DIHYDRO-2H-INDOL-2-ONE

Prepared by Procedures H and K (for substitution of 2-picolyl chloride). $^1$H NMR (400 MHz, CDCl$_3$) δ 8.51-8.46 (m, 1H), 7.87-7.78 (m, 1H) 7.64 (d, 1H, J=7.1), 7.53-7.31 (m, 5H), 7.28 (d, 1H, J=4.1), 7.12 (d, 1H, J=8.1), 6.58-6.53 (m, 1H), 5.51 (s, 2H); ESI-MS m/z 381 (MH$^+$).

Example 255

(3Z)-3-[(3,4-DICHLOROPHENYL)IMINO]-1-[(3,5-DIMETHYL-4-ISOXAZOLYL)METHYL]-1,3-DIHYDRO-2H-INDOL-2-ONE

Prepared by Procedure B (microwave heating). $^1$H NMR (400 MHz, CDCl$_3$) δ 7.63 (d, 1H, J=9.1), 7.46 (dt, 1H, J=8.1, 2.0), 7.28 (d, 1H, J=2.1), 7.02 (d, 1H, J=2.0), 6.88 (dt, 1H, J=8.0, 2.1), 6.74-6.72 (m, 1H), 6.72-6.70 (m, 1H), 5.53 (s, 2H), 2.50 (s, 3H), 2.24 (s, 3H); ESI-MS m/z 399 (MH$^+$).

Example 256

(3Z)-3-[(3,4-DICHLOROPHENYL)IMINO]-1-[3-(TRIFLUOROMETHYL)PHENYL]-1,3-DIHYDRO-2H-INDOL-2-ONE

Prepared by Procedures A and B. $^1$H NMR (400 MHz, CDCl$_3$) δ 7.90-7.87 (m, 1H), 7.83-7.79 (m, 1H), 7.67 (d, 1H, J=8), 7.46-7.40 (m, 1H), 7.33 (d, 1H, J=2), 7.08-7.05 (m, 1H), 6.96-6.80 (m, 5H); ESI-MS m/z 435 (MH$^+$).

Example 257

(3Z)-1-(3,5-DICHLOROPHENYL)-3-[(3,4-DICHLOROPHENYL)IMINO]-1,3-DIHYDRO-2H-INDOL-2-ONE

Prepared by Procedures A and B. $^1$H NMR (400 MHz, CDCl$_3$) δ 7.93 (d, 1H, J=8.1), 7.79 (d, 1H, J=6.0), 7.72-7.68 (m, 1H), 7.59-7.45 (m, 1H), 7.46 (d, 1H, J=8.1), 7.32 (dt, 1H, J=8.0, 2.1), 7.23 (d, 1H, J=2.5), 6.97 (dd, 1H, J=8.0, 2.1), 6.92-6.87 (m, 1H), 6.85-6.81 (m, 1H); ESI-MS m/z 435 (MH$^+$).

Example 258

(3Z)-3-[(3,4-DICHLOROPHENYL)IMINO]-6-METHOXY-1-PHENYL-1,3-DIHYDRO-2H-INDOL-2-ONE

Prepared by Procedures K, L, and B. $^1$H NMR (400 MHz, CDCl$_3$) δ 7.69-7.54 (m, 1H), 7.53-7.38 (m, 3H), 7.29 (d, 1H, J=2.0), 7.17 (d, 1H, J=8.1), 7.12 (d, 1H, J=8.0), 6.84 (d, 1H, J=2.5), 6.78 (d, 1H, J=8), 6.6 (dd, 2H, J=8.0, 2.0), 6.55 (dd, 2H, J=8.1, 2.5); ESI-MS m/z (398 MH$^+$).

Example 259

(3Z)-3-[(4-CHLORO-3-METHYLPHENYL)IMINO]-1-(3-THIENYL)-1,3-DIHYDRO-2H-INDOL-2-ONE

Prepared by Procedures A and B (80° C.). $^1$H NMR (400 MHz, CDCl$_3$) δ 7.69-7.62 (m, 2H), 7.49 (s, 1H), 7.47 (s, 1H), 7.41 (dt, 1H, J=7.1, 1.6), 7.3 (dd, 1H, J=5.0, 1.6), 7.05-6.97 (m, 1H, 6.93-6.86 (m, 1H), 6.77 (m, 1H), 6.56 (m, 1H), 2.53 (s, 3H); ESI-MS m/z 353 (MH$^+$).

Example 260

(3Z)-3-(2-NAPHTHYLIMINO)-1-(3-THIENYL)-1,3-DIHYDRO-2H-INDOL-2-ONE

Prepared by Procedures A and B (80° C.). $^1$H NMR (400 MHz, CDCl$_3$) δ 6.15 (d, 1H, J=9.1), 8.06-7.99 (m, 1H), 7.89-7.80 (m, 1H), 7.78-7.71 (m, 1H), 7.71-7.47 (m, 4H), 7.41-7.35 (m, 1H), 7.33 (d, 1H, J=5.2), 7.28 (d, 1H, J=6.8.1), 7.00 (d, 1H, J=8.0), 6.76 (t, 1H, J=7.8), 6.67 (d, 1H, J=7.9); ESI-MS m/z 355 (MH$^+$).

Example 261

(3Z)-3-[(4-CHLOROPHENYL)IMINO]-1-(3-THIENYL)-1,3-DIHYDRO-2H-INDOL-2-ONE

Prepared by Procedures A and B (80° C.). $^1$H NMR (400 MHz, CDCl$_3$) δ 7.69-7.56 (m, 2H), 7.54-7.48° (m, 1H), 7.41 (dt, 1H, J=8, 2), 7.32-7.28 (m, 1H), 7.11-6.99 (m, 3H), 6.89 (dt, 1H, J=8), 6.77-6.73 (m. 1H), 6.66-6.33 (m, 1H); ESI-MS m/z 339 (MH$^+$).

Example 262

(3Z)-3-[(4-IODOPHENYL)IMINO]-1-(3-THIENYL)-1,3-DIHYDRO-2H-INDOL-2-ONE

Prepared by Procedures A and B (1% HOAC in MeOH). $^1$H NMR (400 MHz, CDCl$_3$) δ 7.79-7.74 (m, 2H), 7.53-7.48 (m, 2H), 7.35 (dt, 1H, J=8.0, 1.2), 7.29-7.24 (m, 1H), 6.98 (d, 1H, J=8.0), 6.69-6.75 (m, 4H); ESI-MS m/z 431 (MH$^+$).

Example 263

(3Z)-3-[(4-METHYLPHENYL)IMINO]-1-(3-THIENYL)-1,3-DIHYDRO-2H-INDOL-2-ONE

Prepared by Procedures A and B (1% HOAC in MeOH). $^1$H NMR (400 MHz, CDCl$_3$) δ 7.52-7.44 (m, 2H), 7.35-7.22 (m, 4H), 6.99-6.93 (m, 3H), 6.87-6.78 (m, 2H), 2.42 (s, 3H); ESI-MS m/z 319 (MH$^+$).

Example 264

(3Z)-3-[(3,5-DIFLUOROPHENYL)IMINO]-1-(3-THIENYL)-1,3-DIHYDRO-2H-INDOL-2-ONE

Prepared by Procedures A and B (1% HOAC in MeOH). $^1$H NMR (400 MHz, CDCl$_3$) δ 7.54-7.16 (m, 4H), 6.99 (dt, 1H, J=8.2, 0.8), 6.89 (dt, 1H, J=7.7, 1.1), 6.76 (d, 1H, J=7.5), 6.71 (tt, 1H, J=9.3, 2.3), 6.64-6.57 (m, 2H); ESI-MS m/z 341 (MH$^+$).

Example 265

(3Z)-3-([1,1'-BIPHENYL]-4-YLIMINO)-1-(3-THIENYL)-1,3-DIHYDRO-2H-INDOL-2-ONE

Prepared by Procedures A and B (1% HOAC in MeOH). $^1$H NMR (400 MHz, CDCl$_3$) δ 7.73-7.12 (m, 13H), 6.99 (d, 1H, J=8.0), 6.89 (d, 1H, J=8.0), 6.82 (dt, 1H, J=7.6, 1.0); ESI-MS m/z 381 (MH$^+$).

Example 266

ETHYL 3-{[(3Z)-2-OXO-1-(3-THIENYL)-1,2-DIHYDRO-3H-INDOL-3-YLIDENE]AMINO}BENZOATE

Prepared by Procedures A and B (1% HOAC in MeOH). $^1$H NMR (400 MHz, CDCl$_3$) δ 7.96 (d, 1H, J=7.4), 7.75-7.17 (m, 6H), 6.98 (d, 1H, J=8.0), 6.87-6.78 (m, 2H), 6.63 (d, 1H, J=7.8), 4.45-4.32 (m, 2H), 1.43-1.33 (m, 3H); ESI-MS m/z 377 (MH$^+$).

Example 267

(3Z)-3-[(6-CHLORO-3-PYRIDINYL)IMINO]-1-(3-THIENYL)-1,3-DIHYDRO-2H-INDOL-2-ONE

Prepared by Procedures A and B (1% HOAC in MeOH). $^1$H NMR (400 MHz, CDCl$_3$) δ 8.21-6.81 (m, 10H); ESI-MS m/z 340.13 (MH$^+$).

Example 268

3Z)-3-[(4-PHENOXYPHENYL)IMINO]-1-(3-THIENYL)-1,3-DIHYDRO-2H-INDOL-2-ONE

Prepared by Procedures A and B (1% HOAC in MeOH). $^1$H NMR (400 MHz, CDCl$_3$) δ 7.85-6.70 (m, 16H); ESI-MS m/z 397 (MH$^+$).

Example 269

(3Z)-3-[(4-BROMOPHENYL)IMINO]-1-(3-THIENYL)-1,3-DIHYDRO-2H-INDOL-2-ONE

Prepared by Procedures A and H. $^1$H NMR (400 MHz, CDCl$_3$) δ 7.82-6.55 (m, 11H); ESI-MS m/z 383 (MH$^+$).

Example 270

(3Z)-3-[(3-CHLOROPHENYL)IMINO]-1-(3-THIENYL)-1,3-DIHYDRO-2H-INDOL-2-ONE

Prepared by Procedures A and H. $^1$H NMR (400 MHz, CDCl$_3$) δ 7.55-6.50 (m, 11H); ESI-MS m/z 339 (MH$^+$).

Example 271

(3Z)-3-[(3-METHYLPHENYL)IMINO]-1-(3-THIENYL)-1,3-DIHYDRO-2H-INDOL-2-ONE

Prepared by Procedures A and B (1% HOAc in MeOH). $^1$H NMR (400 MHz, CDCl$_3$) δ 7.67-6.78 (m, 11H), 2.39 (s, 3H); ESI-MS m/z 319 (MH$^+$).

Example 272

(3Z)-3-[(3,4-DICHLOROPHENYL)IMINO]-1-(3-THIENYL)-1,3-DIHYDRO-2H-INDOL-2-ONE

Prepared by Procedures A and B (1% HOAC in MeOH). $^1$H NMR (400 MHz, CDCl$_3$) δ 7.82-6.80 (m, 10H); ESI-MS m/z 373 (MH$^+$).

Example 273

(3Z)-1-(2-PYRIDINYLMETHYL)-3-{[3-(TRIFLUOROMETHYL)PHENYL]IMINO}-1,3-DIHYDRO-2H-INDOL-2-ONE

Prepared by Procedure B. ESI-MS m/z 382 (MH$^+$).

Example 274

(3Z)-3-[(3,5-DICHLOROPHENYL)IMINO]-1-(2-PYRIDINYLMETHYL)-1,3-DIHYDRO-2H-INDOL-2-ONE

Prepared by Procedure B. ESI-MS m/z 382 (MH$^+$).

Example 275

(3Z)-1-[(3,5-DIMETHYL-4-ISOXAZOLYL)METHYL]-3-{[3-(TRIFLUOROMETHYL)PHENYL]IMINO}-1,3-DIHYDRO-2H-INDOL-2-ONE

Prepared by Procedure B. ESI-MS m/z 400 (MH$^+$).

Example 276

(3Z)-3-[(3,4-DIFLUOROPHENYL)IMINO]-1-(3-PYRIDINYLMETHYL)-1,3-DIHYDRO-2H-INDOL-2-ONE

Prepared by Procedure B. ESI-MS m/z 350 (MH$^+$).

Example 277

(3Z)-1-(3-PYRIDINYLMETHYL)-3-{[3-(TRIFLUOROMETHYL)PHENYL]IMINO}-1,3-DIHYDRO-2H-INDOL-2-ONE

Prepared by Procedure B. ESI-MS m/z 382 (MH$^+$).

Example 278

(3Z)-3-[(3,4-DIFLUOROPHENYL)IMINO]-1-(2-PYRIDINYLMETHYL)-1,3-DIHYDRO-2H-INDOL-2-ONE

Prepared by Procedure B. ESI-MS m/z 350 (MH$^+$).

Example 279

(3Z)-3-[(3,5-DICHLOROPHENYL)IMINO]-1-(3-PYRIDINYLMETHYL)-1,3-DIHYDRO-2H-INDOL-2-ONE

Prepared by Procedure B. ESI-MS m/z 384 (MH$^+$).

Example 280

(3Z)-3-[(3,5-DICHLOROPHENYL)IMINO]-1-[(3,5-DIMETHYL-4-ISOXAZOLYL)METHYL]-1,3-DIHYDRO-2H-INDOL-2-ONE

Prepared by Procedure B. ESI-MS m/z 402 (MH$^+$).

Example 281

(3Z)-3-[(9-ETHYL-9H-CARBAZOL-3-YL)IMINO]-1-PHENYL-1,3-DIHYDRO-2H-INDOL-2-ONE

Prepared by Procedure H. $^1$H NMR (400 MHz, CDCl$_3$) δ 8.28-6.66 (m, 16H), 4.47-4.35 (m, 2H), 1.55-1.44 (m, 3H); ESI-MS m/z 416 (MH$^+$).

Example 282

(3Z)-1-PHENYL-3-(5-QUINOLINYLIMINO)-1,3-DIHYDRO-2H-INDOL-2-ONE

Prepared by Procedure H. $^1$H NMR (400 MHz, CDCl$_3$) δ 9.38-9.32 (m, 1H), 8.55-8.50 (m, 1H), 8.01-6.62 (m, 12H) 6.43-6.35 (m, 1H); ESI-MS m/z 350 (MH$^+$).

Example 283

(3Z)-3-[(4-IODOPHENYL)IMINO]-1-PHENYL-1,3-DIHYDRO-2H-INDOL-2-ONE

Prepared by Procedure B (0.1% HOAc, 80° C., 92 h, 4 eq RNH$_2$, 3 Å molecular sieves). ESI-MS m/z 425 (MH$^+$).

Example 285

(3Z)-3-[(3,4-DIFLUOROPHENYL)IMINO]-1-PHENYL-1,3-DIHYDRO-2H-INDOL-2-ONE

Prepared by Procedure B (0.1% HOAc, 80° C., 92 h, 4 eq RNH$_2$, 3 Å molecular sieves). ESI-MS m/z 335 (MH$^+$).

Example 286

(3Z)-3-[(2-CHLORO-4-METHYLPHENYL)IMINO]-1-PHENYL-1,3-DIHYDRO-2H-INDOL-2-ONE

Prepared by Procedure B (0.1% HOAc, 80° C., 92 h, 4 eq RNH$_2$, 3 Å molecular sieves). ESI-MS m/z 347 (MH$^+$ with $^{35}$Cl), 349 (MH$^+$ with $^{37}$Cl).

Example 287

(3Z)-3-[(2,4-DIMETHOXYPHENYL)IMINO]-1-PHENYL-1,3-DIHYDRO-2H-INDOL-2-ONE

Prepared by Procedure B (0.1% HOAc, 80° C., 92 h, 4 eq RNH$_2$, 3 Å molecular sieves). ESI-MS m/z 359 (MH$^+$).

Example 288

3-{[(3Z)-2-OXO-1-PHENYL-1,2-DIHYDRO-3H-INDOL-3-YLIDENE]AMINO}BENZONITRILE

Prepared by Procedure B (0.1% HOAc, 80° C., 92 h, 4 eq RNH$_2$, 3 Å molecular sieves). ESI-MS m/z 324 (MH$^+$).

Example 289

(3Z)-3-{[2-METHYL-5-(TRIFLUOROMETHYL)PHENYL]IMINO}-1-PHENYL-1,3-DIHYDRO-2H-INDOL-2-ONE

Prepared by Procedure B (0.1% HOAc, 80° C., 92 h, 4 eq RNH$_2$, 3 Å molecular sieves). ESI-MS m/z 381 (MH$^+$).

Example 290

(3Z)-3-[(4-CHLORO-3-METHYLPHENYL)IMINO]-1-(3-THIENYL)-1,3-DIHYDRO-2H-INDOL-2-ONE

Prepared by Procedures A and B (80° C.). ESI-MS m/z 353 (MH$^+$).

Example 291

(3Z)-3-(6-QUINOLINYLIMINO)-1-(3-THIENYL)-1,3-DIHYDRO-2H-INDOL-2-ONE

Prepared by Procedures A and B (80° C.). ESI-MS m/z 356 (MH$^+$).

Example 292

(3Z)-3-[(4-CHLOROPHENYL)IMINO]-1-(3-THIENYL)-1,3-DIHYDRO-2H-INDOL-2-ONE

Prepared by Procedures A and B (80° C.). ESI-MS m/z 339 (MH$^+$).

Example 295

(3Z)-3-[(3-ISOPROPYLPHENYL)IMINO]-1-(3-THIENYL)-1,3-DIHYDRO-2H-INDOL-2-ONE

Prepared by Procedures A and B (80° C.). ESI-MS m/z 347 (MH$^+$).

Example 296

(3Z)-3-[(4-CYCLOHEXYLPHENYL)IMINO]-1-(3-THIENYL)-1,3-DIHYDRO-2H-INDOL-2-ONE

Prepared by Procedures A and B (80° C.). ESI-MS m/z 387 (MH$^+$).

Example 297

(4-{[(3Z)-2-OXO-1-PHENYL-1,2-DIHYDRO-3H-INDOL-3-YLIDENE]AMINO}PHENYL)ACETONITRILE

Prepared by Procedure B (0.1% HOAc, 80° C., 92 h, 4 eq RNH$_2$, 3 Å molecular sieves). ESI-MS m/z 339 (MH$^+$).

Example 298

(3Z)-3-[(2,2-DIFLUORO-1,3-BENZODIOXOL-5-YL)IMINO]-1-PHENYL-1,3-DIHYDRO-2H-INDOL-2-ONE

Prepared by Procedure B (0.1% HOAc, 80° C., 92 h, 4 eq RNH$_2$, 3 Å molecular sieves). ESI-MS m/z 379 (MH$^+$).

Example 299

(3Z)-3-(1,3-BENZOTHIAZOL-6-YLIMINO)-1-PHENYL-1,3-DIHYDRO-2H-INDOL-2-ONE

Prepared by Procedure H. ESI-MS m/z 356 (MH$^+$).

Example 300

(3Z)-1-TETRAHYDRO-2H-PYRAN-4-YL-3-{[3-(TRIFLUOROMETHYL)PHENYL]IMINO}-1,3-DIHYDRO-2H-INDOL-2-ONE

Prepared by Procedures G and H. ESI-MS m/z 375 (MH$^+$).

Example 301

(3Z)-3-(1-H-INDAZOL-6-YLIMINO)-1-PHENYL-1,3-DIHYDRO-2H-INDOL-2-ONE

Prepared by Procedure H. ESI-MS m/z 339 (MH$^+$).

Example 302

(3Z)-3-[(3-CHLOROPHENYL)IMINO]-6-METHOXY-1-PHENYL-1,3-DIHYDRO-2H-INDOL-2-ONE

Prepared by Procedures I and H. ESI-MS m/z 363 (MH$^+$).

Example 303

(3Z)-6-METHOXY-1-PHENYL-3-{[3-(TRIFLUOROMETHYL)PHENYL]IMINO}-1,3-DIHYDRO-2H-INDOL-2-ONE

Prepared by Procedures I and H. ESI-MS m/z 397 (MH$^+$).

Example 304

(3Z)-1-PHENYL-3-{[4-(3-THIENYL)PHENYL]IMINO}-1,3-DIHYDRO-2H-INDOL-2-ONE

Prepared by Procedures H and C. ESI-MS m/z 381 (MH$^+$).

Example 305

(3Z)-1-PHENYL-3-{[3'-(TRIFLUOROMETHYL)[1,1'-BIPHENYL]-4-YL]IMINO}-1,3-DIHYDRO-2H-INDOL-2-ONE

Prepared by Procedures H and C. ESI-MS m/z 443 (MH$^+$).

Example 306

(3Z)-1-PHENYL-3-{[4-(3-PYRIDINYL)PHENYL]IMINO}-1,3-DIHYDRO-2H-INDOL-2-ONE

Prepared by Procedures H and C. ESI-MS m/z 376 (MH⁺).

Example 307

(3Z)-3-[(3-BROMOPHENYL)IMINO]-1-PHENYL-1,3-DIHYDRO-2H-INDOL-2-ONE

Prepared by Procedure B. ESI-MS m/z 378 (MH⁺).

Example 308

(3Z)-1,5-DIPHENYL-3-{[3-(TRIFLUOROMETHYL)PHENYL]IMINO}-1,3-DIHYDRO-2H-INDOL-2-ONE

Prepared by Procedures D, E, and F. ESI-MS m/z 443 (MH⁺).

Example 309

(3Z)-1-[1,1'-BIPHENYL]-4-YL-3-{[3-(TRIFLUOROMETHYL)PHENYL]IMINO}-1,3-DIHYDRO-2H-INDOL-2-ONE

Prepared by Procedures H (6 eq of aniline), J, and K. ESI-MS m/z 443 (MH⁺).

Example 310

(3Z)-1-(4-HYDROXYPHENYL)-3-{[3-(TRIFLUOROMETHYL)PHENYL]IMINO}-1,3-DIHYDRO-2H-INDOL-2-ONE

Prepared by Procedures H (6 eq of aniline) and E. ESI-MS m/z 383 (MH⁺).

Example 311

(3Z)-3-[(3,4-DICHLOROPHENYL)IMINO]-1-(3-PYRIDINYLMETHYL)-1,3-DIHYDRO-2H-INDOL-2-ONE

Prepared by Procedures H (75° C., 2 h), K (3-picolyl chloride), and B. ESI-MS m/z 383 (MH Examples 91-114 and 254-311 as described above are merely illustrative of the methods used to synthesize indolone derivatives. Further derivatives may be obtained utilizing methods shown in Schemes 6a, 7a and 8-10. The substituents in Schemes 6a, 7a and 8-10 are described in the Detailed Description.

It may be necessary to incorporate protection and deprotection strategies for substituents such as amino, amido, carboxylic acid, and hydroxyl groups in the synthetic methods described above to form indolone derivatives. Methods for protection and deprotection of such groups are well-known in the art, and may be found, for example in Green, T. W. and Wuts, P. G. M. (1991) Protection Groups in Organic Synthesis, 2nd Edition John Wiley & Sons, New York.

Scheme 6ᵃ

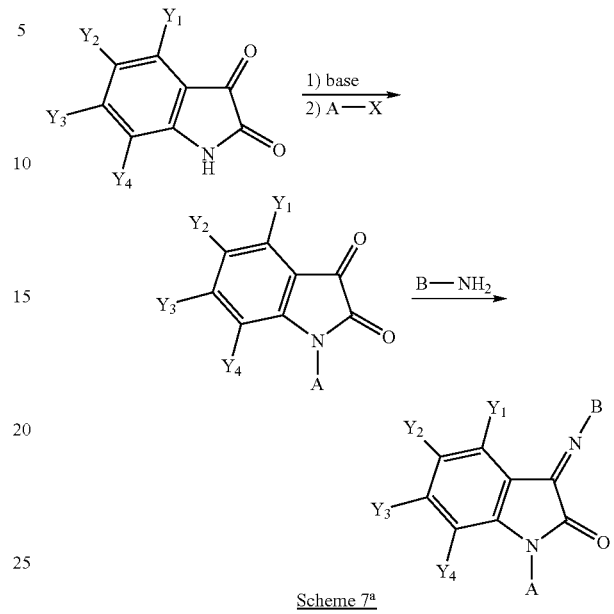

Scheme 7ᵃ

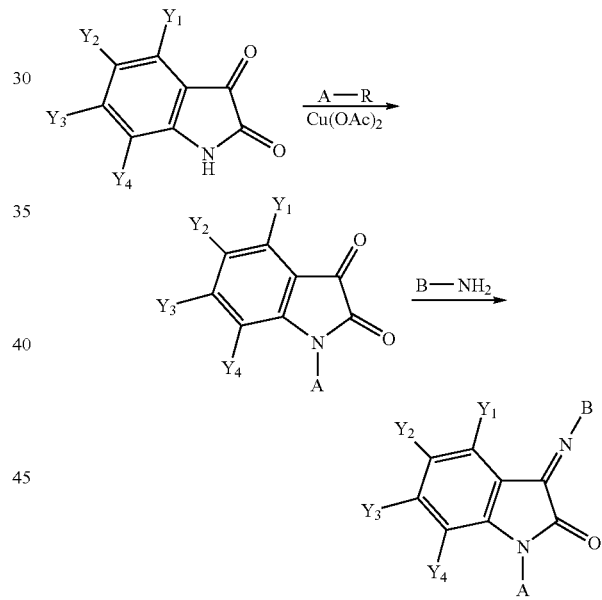

ᵃY₁, Y₂, Y₃, Y₄, A, and B are defined as described in the specification. X is a leaving group such as Cl, Br, I, or OTs. R is boric acid or a dialkylborate group.

Scheme 8ᵃ. Synthesis of Isatins

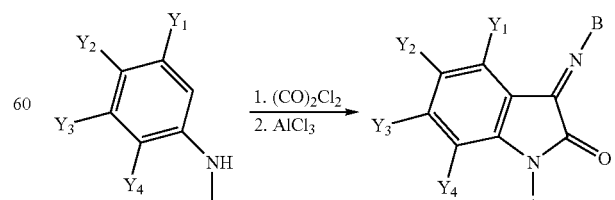

ᵃY₁, Y₂, Y₃, Y₄, A, and B are defined as described in the specification. X is a leaving group such as Cl, Br, I, or OTs. R is boric acid or a dialkylborate group.

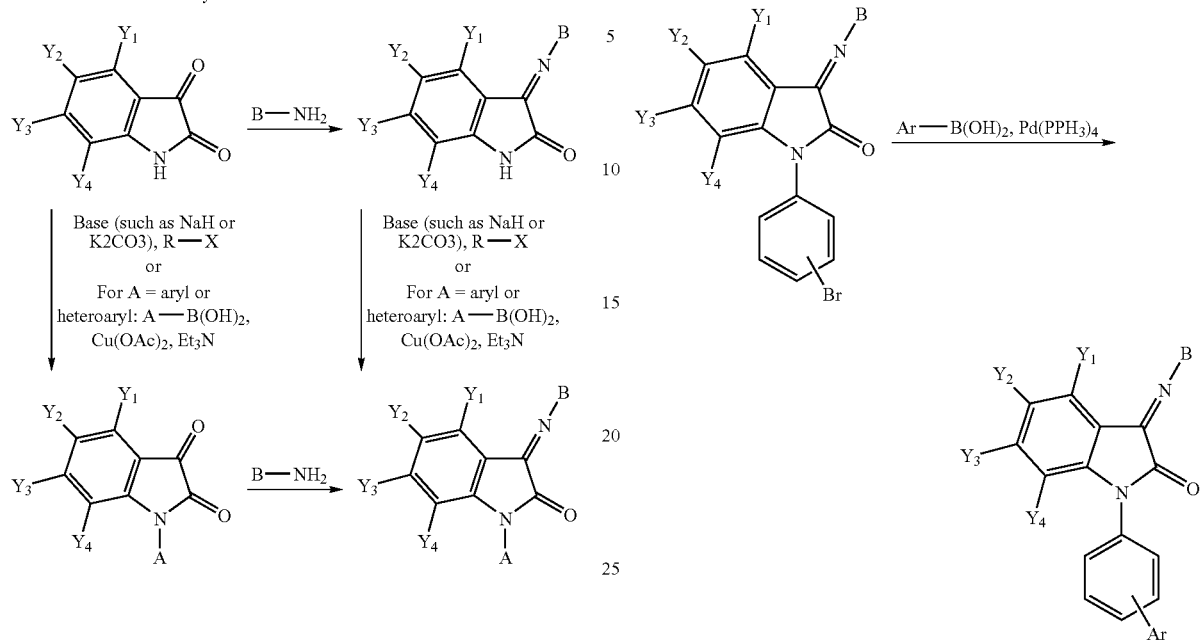

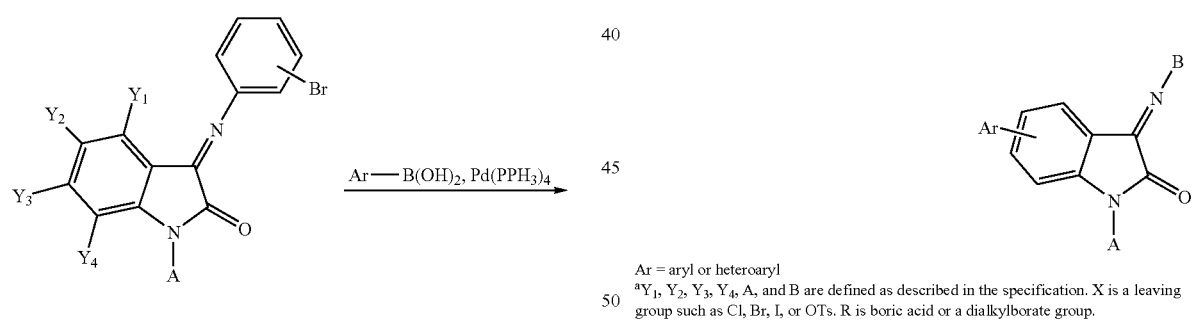

Ar = aryl or heteroaryl
[a]$Y_1$, $Y_2$, $Y_3$, $Y_4$, A, and B are defined as described in the specification. X is a leaving group such as Cl, Br, I, or OTs. R is boric acid or a dialkylborate group.

Radioligand Binding of Indolones at Cloned Galanin Receptors

The binding properties of the indolones of the present invention were evaluated at the cloned human galanin receptors, GAL1, GAL2, and GAL3, using protocols described herein.

Radioligand Binding Assay Results

The indolones described in Examples 91-114 and 254-311 were assayed using cloned human galanin receptors. The compounds were found to be selective for the GAL3 receptor. The binding affinities of the compounds of Examples 91-114 and 254-311 are illustrated in Tables 4 and 4a.

TABLE 4

Binding Affinities of Indolones at Galanin Receptors.

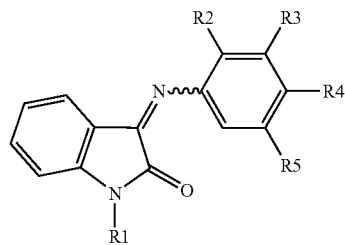

| | substitution | | | | | Ki (nM) | | |
|---|---|---|---|---|---|---|---|---|
| Example | R1 | R2 | R3 | R4 | R5 | GalR1 | GalR2 | GalR3 |
| 91 | Ph | OMe | H | H | H | >10000 | >10000 | 527 |
| 92 | Ph | H | CF$_3$ | H | H | >10000 | >10000 | 38 |
| 93 | Ph | H | Me | H | H | >10000 | >10000 | 171 |
| 94 | Ph | H | Cl | H | H | >10000 | >10000 | 49 |
| 95 | Ph | H | H | CF$_3$ | H | >10000 | >10000 | 29 |
| 96 | Ph | H | H | Me | H | >10000 | >10000 | 111 |
| 97 | Ph | H | H | Cl | H | >10000 | >10000 | 51 |
| 98 | Ph | H | H | Br | H | >10000 | >10000 | 38 |
| 99 | Ph | H | H | F | H | >10000 | >10000 | 229 |
| 100 | Ph | H | H | OPh | H | >10000 | >10000 | 90 |
| 101 | Ph | H | H | OEt | H | >10000 | >10000 | 305 |
| 102 | Ph | H | H | OMe | H | >10000 | >10000 | 429 |
| 103 | Ph | H | Cl | H | Cl | >10000 | >10000 | 68 |
| 104 | Ph | H | Me | H | Me | >10000 | >10000 | 143 |
| 105 | allyl | H | Cl | Cl | H | >10000 | >10000 | 97 |
| 106 | allyl | H | Cl | H | Cl | >10000 | >10000 | 62 |
| 107 | isopropyl | H | H | Br | H | >10000 | >10000 | 126 |

Key:
Ph = Phenyl
OMe = Methoxy
OEt = Ethoxy
Me = Methyl
OPh = Phenoxy

| Example | Structure | Ki (nM) Gal3 |
|---|---|---|
| 108 | (3-CF$_3$-phenyl)imino indolone with N-(5-chlorothiophen-2-ylmethyl) | 84 |
| 109 | (3-CF$_3$-phenyl)imino indolone with N-(thiophen-3-yl) | 103 |

TABLE 4a-continued

| Example | Structure | Ki (nM) Gal3 |
|---|---|---|
| 110 | 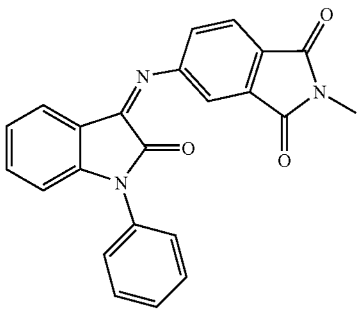 | 138 |
| 111 | 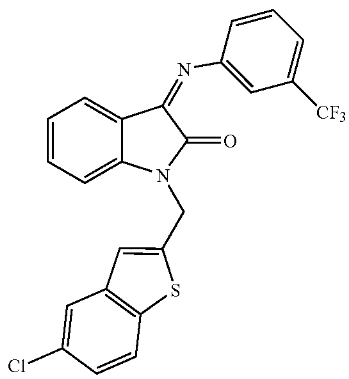 | 1178 |
| 112 | 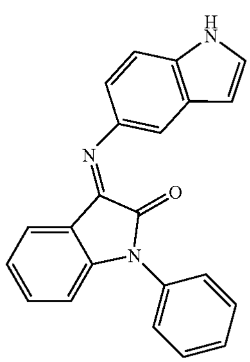 | 2324 |
| 113 | 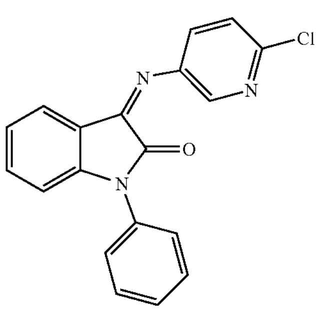 | 136 |

TABLE 4a-continued

| Example | Structure | Ki (nM) Gal3 |
|---|---|---|
| 114 | | 569 |
| 254 | | 64 |
| 255 | | 49 |
| 256 | | 18 |

TABLE 4a-continued

| Example | Structure | Ki (nM) Gal3 |
|---|---|---|
| 257 | (3,4-dichlorophenyl)imino indolinone, N-(3,5-dichlorophenyl) | 33 |
| 258 | (3,4-dichlorophenyl)imino, 6-methoxy indolinone, N-phenyl | 67 |
| 259 | (4-chloro-3-methylphenyl)imino indolinone, N-(3-thienyl) | 55 |
| 260 | (2-naphthyl)imino indolinone, N-(3-thienyl) | 60 |

TABLE 4a-continued

| Example | Structure | Ki (nM) Gal3 |
|---|---|---|
| 261 | (4-chlorophenyl)imino indolinone, N-(3-thienyl) | 34 |
| 262 | (4-iodophenyl)imino indolinone, N-(3-thienyl) | 46 |
| 263 | (4-methylphenyl)imino indolinone, N-(3-thienyl) | 136 |
| 264 | (3,5-difluorophenyl)imino indolinone, N-(3-thienyl) | 27 |

TABLE 4a-continued

| Example | Structure | Ki (nM) Gal3 |
|---|---|---|
| 265 | 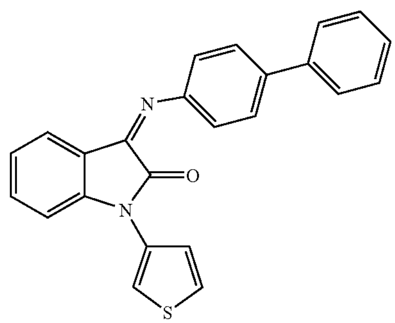 | 80 |
| 266 | 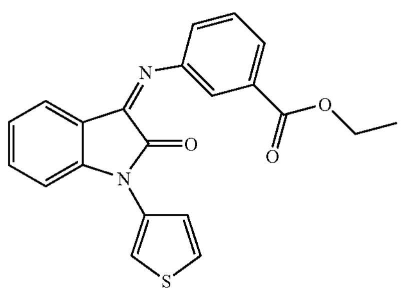 | 236 |
| 267 | 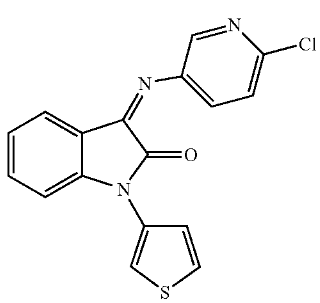 | 234 |
| 268 | 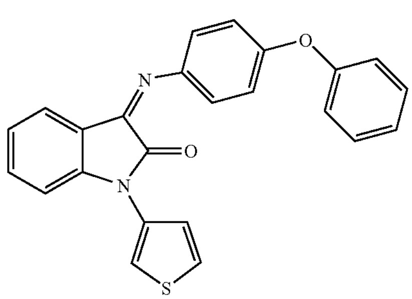 | 57 |
| 269 | | 46 |
| 270 | | 42 |
| 271 | | 114 |
| 272 | | 26 |

TABLE 4a-continued
| Example | Structure | Ki (nM) Gal3 |
|---|---|---|
| 273 | 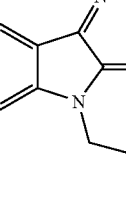 | 202 |
| 274 | 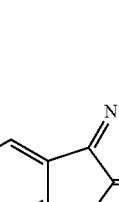 | 174 |
| 275 | 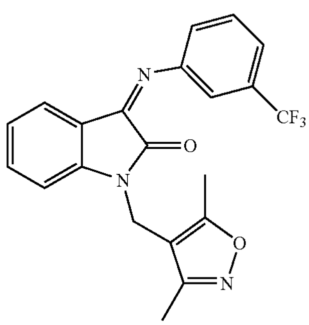 | 595 |
| 276 | 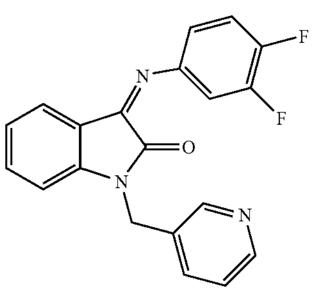 | 192 |
| 277 | 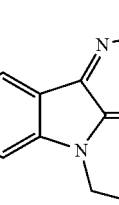 | 198 |
| 278 | 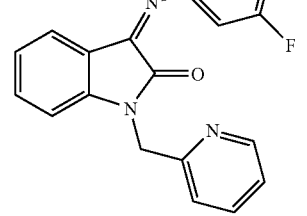 | 340 |
| 279 | 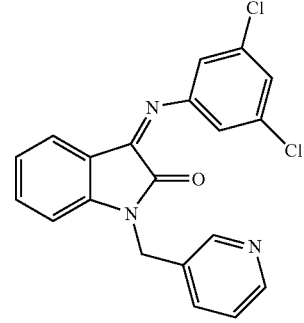 | 81 |
| 280 | 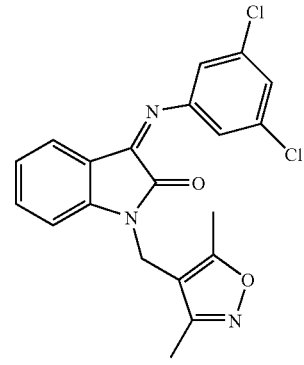 | 521 |
| 281 | 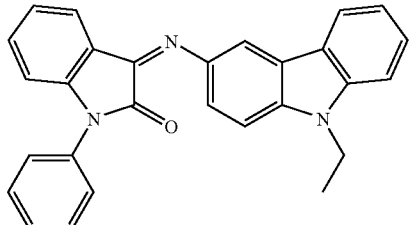 | 150 |
| 282 | 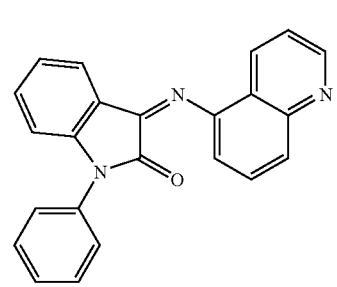 | 333 |

TABLE 4a-continued

| Example | Structure | Ki (nM) Gal3 |
|---|---|---|
| 283 | 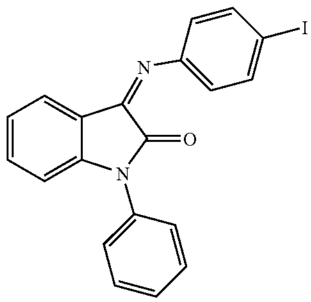 | 33 |
| 285 | 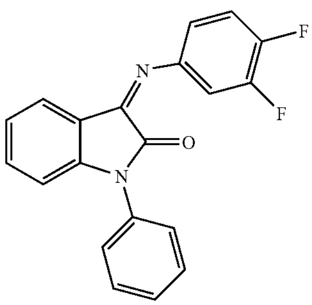 | 26 |
| 286 | 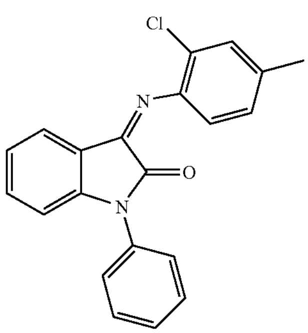 | 38 |
| 287 | | 260 |ара

TABLE 4a-continued

| Example | Structure | Ki (nM) Gal3 |
|---|---|---|
| 288 | 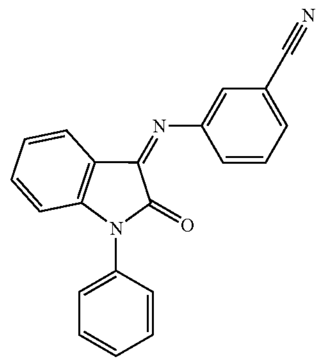 | 39 |
| 289 | 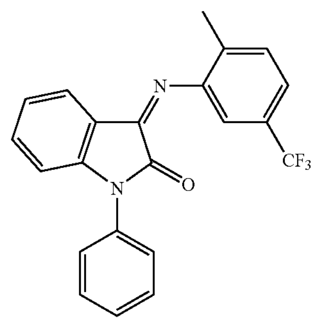 | 59 |
| 290 | 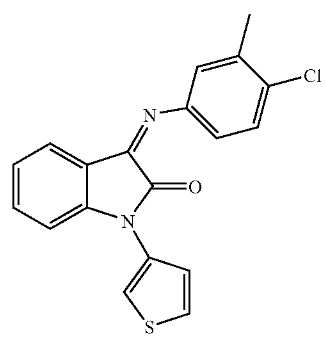 | 55 |
| 291 | 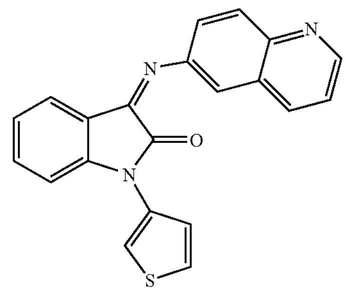 | 271 |

TABLE 4a-continued
| Example | Structure | Ki (nM) Gal3 |
|---|---|---|
| 292 | 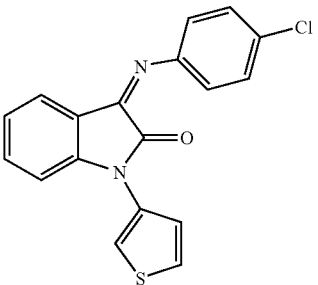 | 34 |
| 295 | 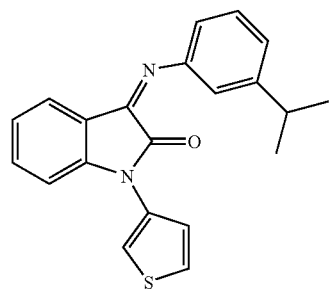 | 242 |
| 296 | 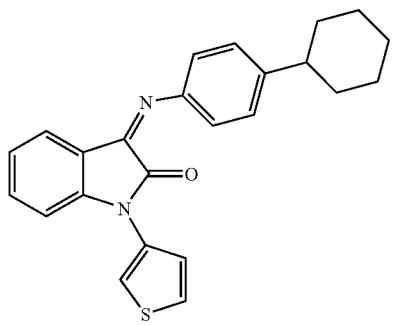 | 82 |
| 297 | 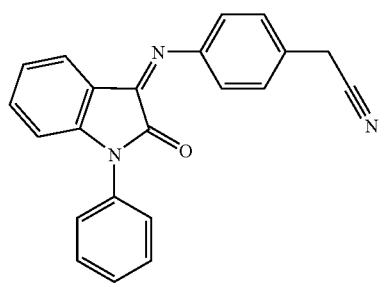 | 226 |
TABLE 4a-continued
| Example | Structure | Ki (nM) Gal3 |
|---|---|---|
| 298 | 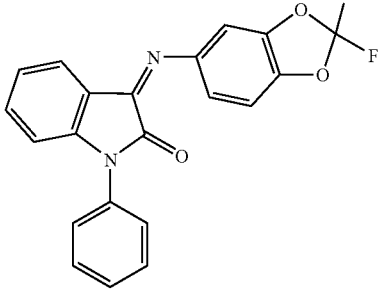 | 22 |
| 299 | 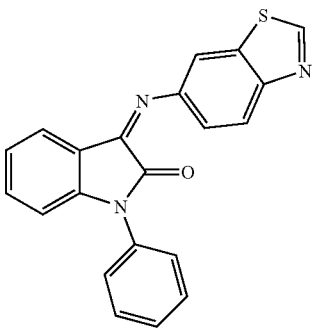 | 377 |
| 300 | 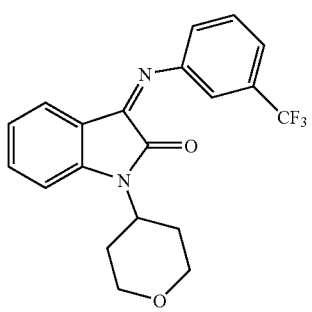 | 742 |
| 301 | 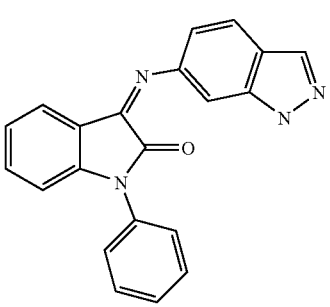 | 875 |

TABLE 4a-continued

| Example | Structure | Ki (nM) Gal3 |
|---|---|---|
| 302 | 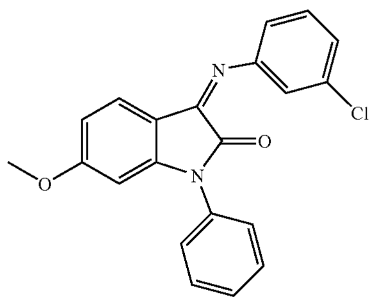 | 150 |
| 303 | 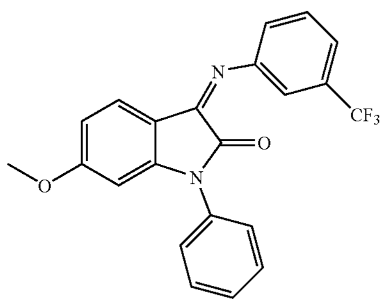 | 214 |
| 304 | 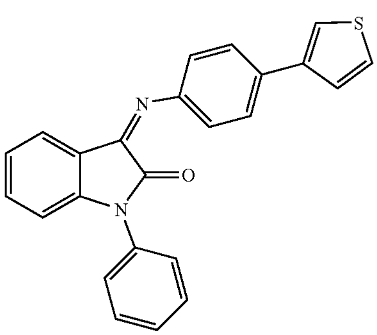 | 728 |
| 305 | 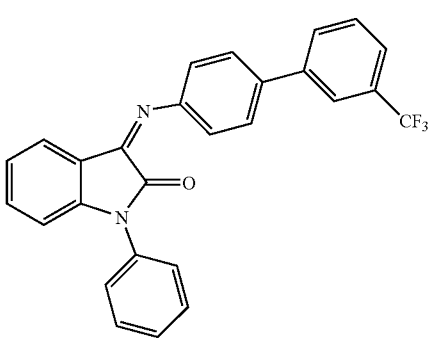 | 638 |
| 306 | | 160 |
| 307 | | 41 |
| 308 | | 98 |
| 309 | | 224 |

TABLE 4a-continued

| Example | Structure | Ki (nM) Gal3 |
|---|---|---|
| 310 | (3-CF3-phenyl-N=)indolin-2-one, N-(4-hydroxyphenyl) | 126 |
| 311 | (3,4-dichlorophenyl-N=)indolin-2-one, N-(pyridin-3-ylmethyl) | 32 |

Oral Compositions

As a specific embodiment of an oral composition of a compound of this invention, 100 mg of one of the compounds described herein is formulated with sufficient finely divided lactose to provide a total amount of 580 to 590 mg to fill a size O hard gel capsule.

I. In-Vivo Models

A. Materials and Methods

1. Forced Swim Test (FST)

The procedure used in this study was similar to that previously described (Porsolt, et al., 1978), except the water depth (30 cm in this procedure). The greater depth in this test prevented the rats from supporting themselves by touching the bottom of the cylinder with their feet. Swim sessions were conducted by placing rats in individual plexiglass cylinders (46 cm tall×20 cm in diameter) containing 23-25° C. water 30 cm deep (Porsolt, et al. used a depth of only 15 cm; also, see Detke, et al., 1995). Two swim tests were conducted always between 1200 and 1800 hours: an initial 15-min pretest followed 24 h later by a 5-minute test. Drug treatments were administered 60 minutes before the 5-minute test period. All other test sessions were conducted between 1300 to 1700 hours. Following all swim sessions, rats were removed from the cylinders, dried with paper towels and placed in a heated cage for 15 minutes and returned to their home cages. All test sessions were videotaped using a Panasonic color video camera and recorder for scoring later.

Animals

Male Sprague-Dawley rats (Taconic Farms, N.Y.) were used in all experiments. Rats were housed in pairs and maintained on a 12:12 h light-dark cycle. Rats were handled for 5 minutes each day for 5 days prior to behavioral testing.

Behavioral Scoring

The rat's behavior was rated at 5 second intervals during the 5 minute test as one of the following:
1. Immobility—rat remained floating in the water without struggling and was only making those movements necessary to keep its head above water;
2. Climbing—rat was making active movements with its forepaws in and out of the water, usually directed against the walls;
3. Swimming—rat was making active swimming motions, more than necessary to merely maintain its head above water, e.g. moving around in the cylinder; and
4. Diving—entire body of the rat was submerged.

All of the behavior scoring was done by a single rater, who was blind to the treatment condition. The rater was also present in the room throughout the entire test period.

Drug Administration

Animals were randomly assigned to receive a single i.p. administration of Example 92 (1, 3, 10 or 30 mg/kg, dissolved in 100% DMSO), fluoxetine (10 mg/kg, dissolved in distilled water) or vehicle (equal mixture of DMSO and distilled water) 30 minutes before the start of the 5 minute test period. All injections were given using 1 cc tuberculin syringe with 26 3/8 gauge needles (Becton-Dickinson, VWR Scientific, Bridgeport, N.J.). The volume of injection was 1 ml/kg.

In another set of experiments, animals were randomly assigned to receive a single p.o. administration of one of the following treatments: Example 151 (1, 3 or 10 mg/kg), fluoxetine (5 or 10 mg/kg) or vehicle (1 ml/kg of 100% N,N-dimethylacetamide) 60 minutes before the start of the 5 minute test period. The drugs were dissolved in 100% N,N-dimethylacetamide. All administrations were given using 1 cc tuberculin syringes, to which a 3 inch, curved, stainless steel gavage needle was attached. The volume of administration was 1 ml/kg.

In other sets of experiments, animals were randomly assigned to receive a single p.o. administration of one of the following treatments: Example 103 (3, 10 and 30 mg/kg), fluoxetine (10 mg/kg) or vehicle, (1 ml/kg of 100% N,N-dimethylacetamide) 60 minutes before the start of the 5 minute test period; or Example 272 (3 mg/kg), fluoxetine (10 mg/kg) or vehicle (1 ml/kg of 100% N,N-dimethylacetamide) 24 hours before the start of the 5 minute test period; or Example 98 (3, 10 and 30 mg/kg), fluoxetine (10 mg/kg) or vehicle (1 ml/kg of 100% N,N-dimethylacetamide) 60 minutes before the start of the 5 minute test period; or Example 34 (0.3, 1, 3 and 10 mg/kg), fluoxetine (10 mg/kg) or vehicle (1 ml/kg of a 100% solution of dimethylacetamide) 60 minutes before the start of the 5 minute test period; or Example 49 (3, 10 and 30 mg/kg), fluoxetine (10 mg/kg) or vehicle (1 ml/kg of 100% N,N-dimethylacetamide) 60 minutes before the start of the 5 minute test period; or Example 22 (3, 10 and 30 mg/kg), fluoxetine (10 mg/kg) or vehicle (1 ml/kg of 100% N,N-dimethylacetamide) 60 minutes before the start of the 5 minute test period. The compounds were dissolved in 100% N,N-dimethylacetamide. All administrations were given using 1 cc tuberculin syringes, to which a 3 inch, curved, stainless steel gavage needle was attached. The volume of administration was 1 ml/kg.

The effect of 5 or 10 mg/kg of fluoxetine was utilized in the FST as a positive control.

Data Analysis

The forced swim test data (immobility, swimming, climbing, diving) were subjected to a randomized, one-way ANOVA and post hoc tests conducted using the Student-Newman-Keuls test. The data were analyzed using the GBSTAT program, version 6.5 (Dynamics Microsystems, Inc., Silver Spring, Md., 1997). All data are presented as means±S.E.M.

2. Social Interaction Test (SIT)

Rats were allowed to acclimate to the animal care facility for 5 days and were housed singly for 5 days prior to testing. Animals were handled for 5 minutes per day. The design and procedure for the Social Interaction Test was carried out as previously described by Kennett, et al. (1997). On the test day, weight matched pairs of rats (±5%), unfamiliar to each other, were given identical treatments and returned to their home cages. Animals were randomly divided into 5 treatment groups, with 5 pairs per group, and were given one of the following i.p. treatments: Example 92 (10, 30 or 100 mg/kg), vehicle (1 ml/kg) or chlordiazepoxide (5 mg/kg). Dosing was 1 hour prior to testing. Rats were subsequently placed in a white perspex test box or arena (54×37×26 cm), whose floor was divided up into 24 equal squares, for 15 minutes. An air conditioner was used to generate background noise and to keep the room at approximately 74° F. All sessions were videotaped using a JVC camcorder (model GR-SZ1, Elmwood Park, N.J.) with either TDK (HG ultimate brand) or Sony 30 minute videocassettes. All sessions were conducted between 1:00-4:30 P.M. Active social interaction, defined as grooming, sniffing, biting, boxing, wrestling, following and crawling over or under, was scored using a stopwatch (Sportsline model no. 226, 1/100 sec. discriminability) The number of episodes of rearing (animal completely raises up its body on its hind limbs), grooming (licking, biting, scratching of body), and face washing (i.e. hands are moved repeatedly over face), and number of squares crossed were scored. Passive social interaction (animals are lying beside or on top of each other) was not scored. All behaviors were assessed later by an observer who was blind as to the treatment of each pair. At the end of each test, the box was thoroughly wiped with moistened paper towels.

Animals

Male albino Sprague-Dawley rats (Taconic Farms, N.Y.) were housed in pairs under a 12 hr light dark cycle (lights on at 0700 hrs.) with free access to food and water.

Drug Administration

Example 92 was dissolved in 100% DMSO (Sigma Chemical Co., St. Louis, Mo.). Chlordiazepoxide (purchased from Sigma Chemical Co., St. Louis, Mo.) was dissolved in double distilled water. The vehicle consisted of 50% DMSO (v/v). All drug solutions were made up 10 minutes prior to injection and the solutions were discarded.

Example 34 was dissolved in 5% lactic acid, v/v. The vehicle consisted of 100% dimethylacetamide (DMA) and this was used to make up all drug solutions. All drug solutions were made up fresh each day and any unused solutions were discarded at the end of the test day. The volume of drug solution administered was 1 ml/kg.

Data Analysis

The social interaction data (time interacting, rearing and squares crossed) were subjected to a randomized, one-way ANOVA and post hoc tests conducted using the Student-Newman-Keuls test. The data were subjected to a test of normality (Shapiro-Wilk test). The data were analyzed using the GBSTAT program, version 6.5 (Dynamics Microsystems, Inc., Silver Spring, Md., 1997). All data are presented as means±S.E.M.

B. Results

1. Forced Swim Test

Figure 1:
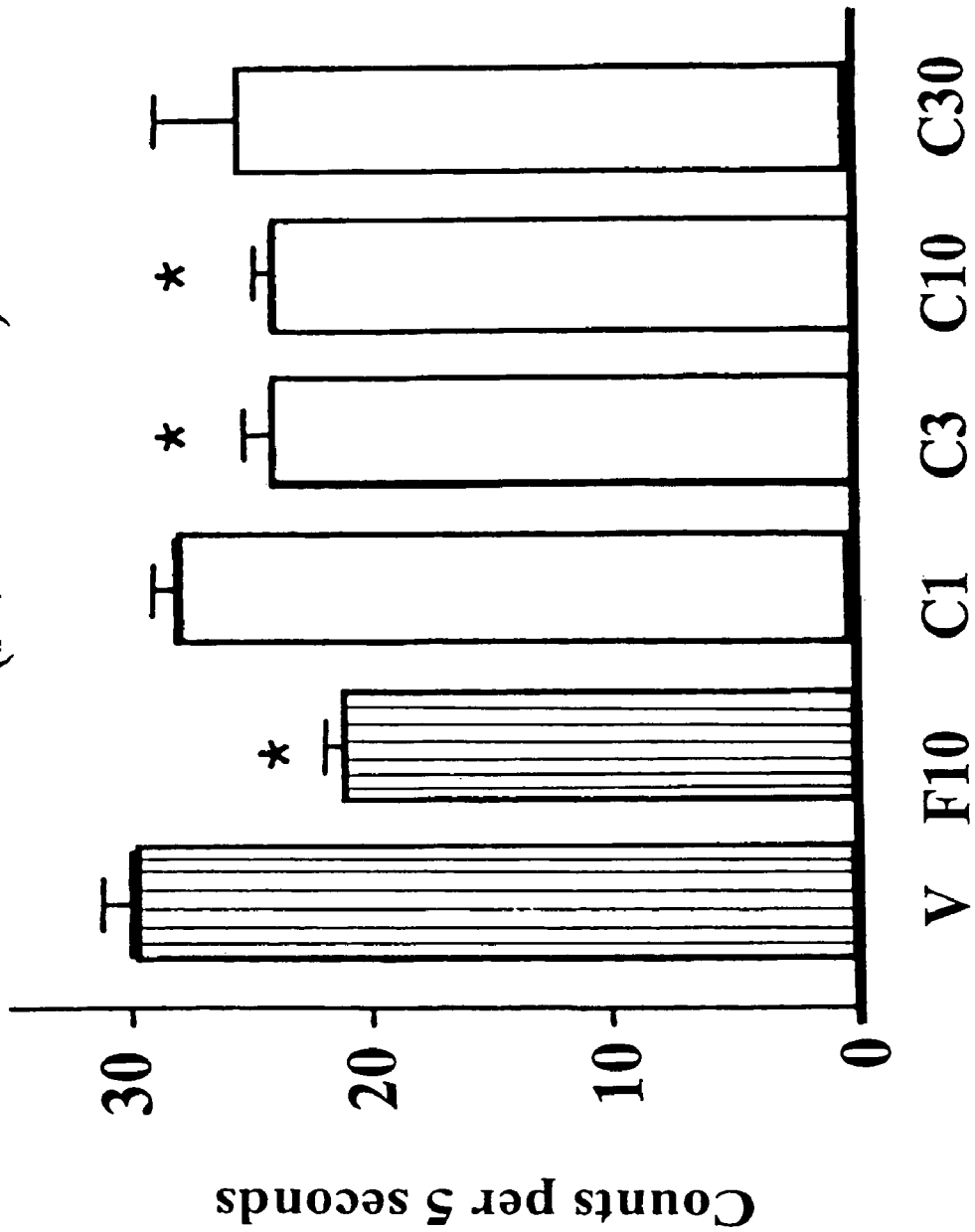
FIG. 1: Rat Forced Swim Test Results (Immobility: Normal Rats)

A. The Effect of Vehicle, Fluoxetine and Example 92 on Immobility, Climbing and Swimming in the Forced Swim Test Immobility Statistical analysis indicated that there was a significant drug effect [$F(4,45)=12.1$, $p<0.0001$] on immobility. Subsequent post hoc analysis revealed that a single injection of 10 mg/kg i.p. of fluoxetine significantly decreased immobility to 21.0±0.9 (Student-Newman-Keuls value was 36.5, $p<0.01$) compared to vehicle-treated controls (Table 5 and FIG. 1). In addition, a single injection of either 3 or 10 mg/kg i.p. of Example 92 significantly decreased immobility (24±1.1 & 24±0.8 counts at each dose, respectively) compared to vehicle-treated controls 30±1.2 (Student-Newman-Keuls values of 16.8 and 15.7, respectively) (Table 5 and FIG. 1). No significant effects on immobility were observed with Example 92 at 30 mg/kg i.p. (Table 5 and FIG. 1).

Climbing

The statistical analysis of the climbing counts indicated that there was a significant drug effect [$F(4,45)=4.4$, $p=0.004$]. Post hoc analysis indicated that a single injection of 10 mg/kg of fluoxetine did not significantly alter climbing counts compared to vehicle-treated animals (Table 5 and FIG. 2). In contrast, a single injection of 10 mg/kg of Example 92 produced a significant increase (16.8±0.6) in climbing counts (Student-Newman-Keuls value=11.6, $p<0.01$) compared to vehicle-treated animals (12±0.8). Example 92 dosed at 1, 3 & 30 mg/kg did not significantly alter climbing.

Swimming

The statistical analysis of the swimming data indicated that there was a significant drug effect [$F(4,45)=6.6$, $p<0.0001$] (Table 5 and FIG. 3). The post hoc test showed that a single injection of 10 mg/kg i.p. of fluoxetine produced a significant increase (25±1.2) in swimming counts over the vehicle treated animals, 18±1 (Student-Newman-Keuls value of 19.9, $p<0.01$). In contrast, a single injection of 1, 3 or 10 mg/kg i.p. of Example 92 did not significantly alter swimming counts 20±1.1, 21±0.9,& 18±0.9, respectively (Table 5 and FIG. 3). (However, at 30 mg/kg i.p. Example 92 significantly increased swim behavior in the rat, comparable to fluoxetine at 10 mg/kg i.p. (27±2.5 vs. 25±1.2, Table 5 and FIG. 3).

Diving

This behavior was rarely observed following a single injection of vehicle (0.1±0.1, one animal dove once), fluoxetine (0.1±0.1, one animal out of 10 dove once), 1 mg/kg of Example 92 (0.6±0.2; 5 animals had counts of 2, 1, 1, 1, and 1), 3 mg/kg of Example 92 (0.6±0.3; 3 animals had counts of 3, 2 and 1) or 10 mg/kg of Example 92 (0.5±0.5; note: only one animal at this dose showed diving behavior and the score was 5). At 30 mg/kg i.p. of Example 92 diving behavior was only observed in two, animals (mean=0.2±0.2). Thus there was no significant drug effect on diving [$F(4,45)=0.77$, $p=0.55$].

TABLE 5

The effect of a single injection of vehicle, fluoxetine and Example 92 on immobility, climbing and swimming in the rat Forced Swim Test.

| Treatment  | Dose (mg/kg) | Immobility       | Climbing          | Swimming          |
|------------|--------------|------------------|-------------------|-------------------|
| Vehicle    | —            | 30 ± 1.2         | 12.0 ± 0.8        | 18 ± 1            |
| Fluoxetine | 10           | 21 ± 0.9[a]      | 14.3 ± 0.9        | 25 ± 1.2[b]       |
| Example 92 | 1            | 28 ± 1.0         | 11.7 ± 1.1        | 20 ± 1.1          |
| Example 92 | 3            | 24 ± 1.1[a]      | 14.6 ± 1.5        | 21 ± 0.9          |
| Example 92 | 10           | 24 ± 0.8[a]      | 16.8 ± 0.6[c]     | 18 ± 0.9          |
| Example 92 | 30           | 25 ± 3.5         | 8.6 ± 1.7         | 27 ± 2.5[d]       |

Each value represents the mean number of counts per 5 seconds ± S.E.M in a 5 minute observation period.
[a]Significantly less than Vehicle on immobility scores, p < 0.01, ANOVA and Student-Newman-Keuls test.
[b]Significantly greater than Vehicle and 1, 3 & 10 of Example 92, on swim scores, p < 0.01, ANOVA and Student-Newman-Keuls.
[c]Significantly greater than vehicle and 1, 3 & 30 mg/kg dose of Example 92 on climbing scores, p < 0.01, ANOVA and Student-Newman-Keuls
[d]Significantly greater than Vehicle, 1, 3 and 10 mg/kg i.p. of Example 92 on swim scores, p < 0.01, ANOVA and Student-Newman-Keuls test.

The results of the Forced Swim Test indicate that using a modified version of the Lucki forced swim test, a single injection of 10 mg/kg i.p. of fluoxetine produced a significant decrease in immobility and an increase in swimming in male Sprague-Dawley rats. This is consistent with findings from previous studies using the Lucki version (Detke, et al., 1995; Kirby and Lucki, 1997; Lucki, 1997; Page, et al., 1999; Reneric and Lucki, 1998). In addition, the results obtained using fluoxetine are consistent with those using other SSRIs (Detke, et al., 1995). Thus; a modified version of the Lucki forced swim test can consistently detect the antidepressant action of SSRIs such as fluoxetine.

Interestingly, at doses of 3 and 10 mg/kg i.p., Example 92, significantly decreased immobility compared to vehicle-treated animals. The magnitude of the decrease was not significantly different than that of fluoxetine. Thus, based on past interpretations of the Forced Swim Test, our results suggest that Example 92 has antidepressant-like properties.

A single injection of either 1, 3 or 10 mg/kg i.p. of Example 92 did not significantly alter swimming behavior. This is in contrast to the results obtained with fluoxetine, which increased swimming at 10 mg/kg i.p. Previously, it has been reported that compounds which selectively block serotonin uptake significantly increase swimming but not climbing whereas selective NE uptake blockers significantly increase climbing but not swimming behavior (Reneric and Lucki, 1998). Thus, the present findings suggest that Example 92 exhibits a profile similar to NE and selective serotonin reuptake inhibitors (SSRIs) depending on the dose tested.

Finally, as previously reported by Lucki, diving behavior was rarely observed in vehicle or fluoxetine-treated animals (1 dive in one rat for each group). Example 92 at all doses tested did not produce a significant effect on diving behavior. It is possible that antidepressant drugs do not induce diving behavior.

In conclusion, compared to vehicle-treated animals, Example 92, at doses of 3 and 10 mg/kg, produced a significant decrease in immobility and a significant increase in climbing at the 10 mg/kg dose. At 30 mg/kg i.p. Example 92 produced a significant increase in swimming behavior comparable with that observed with the antidepressant fluoxetine, thus supporting the antidepressant-like profile of Example 92.

B. The Effect of Example 151, Fluoxetine, and Vehicle on Swimming, Climbing, Immobility, and Diving in the Forced Swim Test.

Immobility

Statistical analysis indicated a significant effect of treatment on immobility (ANOVA, $F(5,46)=3.5$, $p=0.0095$). Post hoc analyses revealed that a single p.o. administration of 10 mg/kg of fluoxetine significantly decreased immobility (Fisher's LSD value of 2.9) compared to vehicle-treated animals (Table 5a). In contrast, a single p.o. administration of 5 mg/kg of fluoxetine did not significantly alter immobility compared to vehicle-treated animals.

A single p.o. administration of 1 mg/kg of Example 151 did not significantly alter immobility compared to vehicle-treated animals (Table 5a). In contrast, a single p.o. administration of either 3 or 10 mg/kg of Example 151 significantly decreased immobility compared to animals treated with vehicle (Fisher's LSD values of 2.8 and 2.6, respectively) or 5 mg/kg p.o. of fluoxetine (Fisher's LSD values of 2.6 and 2.4, respectively). There was no significant difference in the reduction in immobility between 10 mg/kg of fluoxetine and 3 and 10 mg/kg of Example 151.

Swimming

Statistical analysis indicated a significant treatment effect on swimming behavior (ANOVA, $F(5,46)=5.5$, $p=0.0005$). Post hoc analyses revealed that a single p.o. administration of 10 mg/kg of fluoxetine produced a significant increase in swimming behavior compared to vehicle-treated animals (Student-Newman-Keuls value of 16.8 (Table 5a). In contrast, a single p.o. administration of 5 mg/kg of fluoxetine did not significantly alter swimming compared to vehicle-treated animals.

A single p.o. administration of either 1, 3 or 10 mg/kg of Example 151 significantly increased swimming (Student-Newman-Keuls values of 6.9, 14.8 and 13.4, respectively) compared to vehicle-treated animals. There was no significant difference in the magnitude of the increase in swimming between the doses of Example 151. The 3 and 10 mg/kg doses of Example 151 produced a significantly greater increase in swimming compared to animals treated with 5 mg/kg p.o. of fluoxetine. There was no significant difference in the increase in swimming between animals treated with 10 mg/kg of fluoxetine and those treated with Example 51.

Climbing Behavior

Statistical analysis revealed that climbing was not significantly altered by a single p.o. administration of 1, 3 or 10 mg/kg of Example 151 or 5 or 10 mg/kg of fluoxetine compared to vehicle-treated animals (ANOVA, $F(5,46)=0.81$, $p=0.55$) (Table 5a).

Diving

Statistical analysis revealed that diving was not significantly altered by a single p.o. administration of 1, 3 or 10 mg/kg of Example 151 or 5 or 10 mg/kg of fluoxetine compared to vehicle-treated animals (ANOVA, $F(5,46)=0.36$, $p=0.87$) (Table 5a).

TABLE 5a

The effect of a single p.o. administration of
vehicle, 1, 3 and 10 mg/kg of Example 151 and 5 and 10 mg/kg
of fluoxetine on immobility, climbing, diving and
swimming in the forced swim t st in male Sprague-Dawley
rats.

| Treatment | Immobility | Climbing | Swimming | Diving |
|---|---|---|---|---|
| Vehicle | 46 ± 1.8 | 2.7 ± 0.7 | 11.4 ± 1.2 | 0.4 ± 0.4 |
| 1 mg/kg EX151 | 41 ± 2.0 | 2.3 ± 0.6 | 16.8 ± 1.4$^d$ | 0.2 ± 0.2 |
| 3 mg/kg EX151 | 38 ± 2.0$^a$ | 2.4 ± 0.5 | 19.5 ± 1.5$^e$ | 0.3 ± 0.2 |
| 10 mg/kg EX151 | 39 ± 1.8$^b$ | 2.2 ± 0.5 | 18.9 ± 1.5$^e$ | 0.3 ± 0.2 |
| 5 mg/kg Fluox | 45 ± 1.3$^c$ | 1.2 ± 0.4 | 13.9 ± 1.0 | 0.0 ± 0.0 |
| 10 mg/kg Fluox | 38 ± 2.3$^a$ | 2.0 ± 0.6 | 19.8 ± 1.8$^e$ | 0.6 ± 0.6 |

Each value represents the mean ± S.E.M. A total of 8-9 animals were examined for each treatment group.
Fluox = Fluoxetine, EX151 = Example 151. Experiments were conducted 1 hr. after the appropriate treatment.
$^a$Significantly less than Vehicle ($p < 0.01$), ANOVA and Fisher's protected t test.
$^b$Significantly less than Vehicle ($p < 0.05$), ANOVA and Fisher's protected t test.
$^c$Significantly greater than 3 and 10 mg/kg of Example 151 and 10 mg/kg of fluoxetine, ANOVA and ANOVA and Fisher's protected t test.
$^d$Significantly greater than Vehicle ($p < 0.05$) and 5 mg/kg of fluoxetine ($p < 0.05$), ANOVA and Student-Newman-Keuls test.
$^e$Significantly greater than Vehicle ($p < 0.01$) and 5 mg/kg of fluoxetine ($p < 0.05$), ANOVA and Student-Newman-Keuls test.

The results of this study indicate that a single p.o. administration of Example 151, at doses of 1, 3 and 10 mg/kg, produces a significant increase in swimming behavior. There was no significant difference in the magnitude of the increase in swimming between the doses of Example 151, although the 1 mg/kg dose produced a lower increase. In contrast, only the 3 and 10 mg/kg doses of Example 151 significantly decreased immobility compared to vehicle-treated animals. Thus, it appears that a single p.o. administration of either 3 or 10 mg/kg, compared to 1 mg/kg of Example 151, produce a more robust antidepressant profile in the FST in male Sprague-Dawley rats. Our results also indicate that Example 151 produced changes in swimming and immobility that were not significantly different from that of 10 mg/kg p.o. of fluoxetine. This suggests that Example 151 produces behavioral effects similar to that of 10 mg/kg of fluoxetine in the FST.

A single p.o. administration of 5 mg/kg of fluoxetine did not significantly alter swimming, climbing, diving or immobility compared to vehicle treated animals. This finding, together with the data indicating that 10 mg/kg of fluoxetine produces a significant effect on swimming and immobility in the FST, suggest that the threshold dose of fluoxetine is greater than 5, but less than 10 mg/kg. This is consistent with ex vivo data indicating that a p.o. dose of 7 mg/kg of fluoxetine is required to inhibit 5-HT uptake in the CNS by 50% (Leonard, 1996).

In conclusion, the results of this study indicate that a single p.o. administration of Example 151 (particularly the 3 and 10 mg/kg doses) produces behavioral effects in the FST in rats that resemble those of antidepressants.

C. The Effect of a Single P.O. Administration of Example 103, Fluoxetine and Vehicle on Swimming, Immobility, Climbing and Diving in the Forced Swim Test Immobility Statistical analysis indicated a significant effect of treatment on immobility (ANOVA, $F(4,40)=6.3$, $p=0.0005$). Post hoc analyses revealed that a single p.o. administration of 10 mg/kg of fluoxetine significantly decreased immobility (Student-Newman-Keuls value of 8.3) compared to vehicle-treated animals (Table 5b). The decrease in immobility produced by fluoxetine was significantly greater than that of either 3 or 10 mg/kg p.o. of Example 103 (Student-Newman-Keuls values of 9.1 and 6.1, respectively).

A single p.o. administration of either 3 or 10 mg/kg of Example 103 did not significantly alter immobility compared to vehicle-treated animals. However, the 30 mg/kg dose of Example 103 produced a significant decrease in immobility (Student-Newman-Keuls values of 13.9) compared to vehicle-treated animals. In addition, the decrease in immobility produced by 30 mg/kg of Example 103 was significantly greater than that of 3 and 10 mg/kg of Example 103 (Student-Newman-Keuls values of 14.4 and 10.6, respectively). There was no significant difference between fluoxetine and 30 mg/kg of Example 103 in the reduction of immobility.

Swimming

Statistical analysis indicated a significant treatment effect on swimming behavior (ANOVA, $F(4,40)=9.2$, $p<0.0001$). Post hoc analyses revealed that a single p.o. administration of 10 mg/kg of fluoxetine produced a significant increase in swimming behavior compared to animals treated with vehicle, 3 or 10 mg/kg p.o. of Example 103 (Student-Newman-Keuls values of 14.9, 15.3 and 11.6, respectively) (Table 5b).

A single p.o. administration of either 3 or 10 mg/kg of Example 103 did not significantly alter swimming behavior compared to vehicle-treated animals. A single p.o. administration of 30 mg/kg of Example 103 produced a significantly greater increase in swimming behavior compared to animals treated with either vehicle, 3 or 10 mg/kg of Example 103 (Student-Newman-Keuls values of 18, 18.6 and 14.5 respectively).

Climbing Behavior

Statistical analysis revealed that diving was not significantly altered by a single p.o. administration of 3, 10 or 30 mg/kg of Example 103 or 10 mg/kg of fluoxetine compared to vehicle-treated animals (ANOVA, $F(4,40)=1.2$, $p=0.31$) (Table 5b).

Diving

Statistical analysis revealed that diving was not significantly altered by a single p.o. administration of 3, 10 or 30 mg/kg of Example 103 or 10 mg/kg of fluoxetine compared to vehicle-treated animals (ANOVA, $F(4,40)=1.1$, $p=0.36$) (Table 5b).

TABLE 5b

The effect of a single p.o. administration of
vehicle, 10 mg/kg of fluoxetine and 3, 10 or 30 mg/kg of
Example 103 on immobility, climbing, diving and swimming
in the forced swim test in male Sprague-Dawley rats.

| Treatment | Immobility | Climbing | Swimming | Diving |
|---|---|---|---|---|
| Vehicle | 44 ± 1.7 | 2.9 ± 0.7 | 13.1 ± 1.2 | 0.4 ± 0.2 |
| 3 mg/kg EX103 | 44 ± 2.7 | 2.8 ± 0.6 | 13.2 ± 1.9 | 0.5 ± 0.4 |
| 10 mg/kg EX103 | 42 ± 2.2 | 3.5 ± 0.6 | 14.3 ± 1.6 | 0.4 ± 0.2 |
| 30 mg/kg EX103 | 32 ± 1.8$^a$ | 4.8 ± 0.7 | 22.7 ± 1.1$^c$ | 1.1 ± 0.5 |
| 10 mg/kg Fluox | 34 ± 2.3$^b$ | 3.8 ± 0.8 | 21.8 ± 1.4$^c$ | 0.1 ± 0.1 |

Each value represents the mean ± S.E.M. A total of 8-10 animals were examined for each treatment group.
Fluox = Fluoxetine, EX103 = Example 103. Experiments were conducted 1 hr. after the appropriate treatment.
$^a$Significantly less than Vehicle, 3 and 10 mg/kg of Example 103, $p < 0.01$, ANOVA and Student-Newman-Keuls test.
$^b$Signficantly less than Vehicle, 3 and 10 mg/kg of Example 103, $p < 0.05$, ANOVA and Student-Newman-Keuls test.
$^c$Signficantly greater than Vehicle, 3 and 10 mg/kg of Example 103, $P < 0.01$, ANOVA and Student-Newman-Keuls test.

The results of this study indicated that as previously reported, a single p.o. administration of 10 mg/kg of fluoxetine produced a significant increase in swimming and a significant decrease in immobility in male rats in the FST compared to vehicle-treated animals. The magnitude of these changes are similar to those reported of our past studies with 10 mg/kg p.o. of fluoxetine. In contrast, neither climbing nor diving behavior was significantly altered by a single p.o. administration of 10 mg/kg of fluoxetine.

A single p.o. administration of either 3 or 10 mg/kg of Example 103 did not significantly alter swimming, climbing, immobility or diving in male rats in the FST, indicating that at these doses using the p.o. route, Example 103 does not exhibit antidepressant action in the FST. In contrast, a single p.o. administration of 30 mg/kg of Example 103 produced a significant increase in swimming and a significant decrease in immobility compared to animals treated with vehicle or 10 mg/kg of Example 103. However, the 30 mg/kg p.o. dose of Example 103 did not significantly alter diving or climbing counts compared to vehicle-treated animals. The increase in swimming counts produced by 30 mg/kg p.o. of Example 103 was comparable to that for 10 mg/kg of fluoxetine.

In conclusion, a single p.o. administration of 30 mg/kg of Example 103 (one hour before the last swim test) increases swimming and decreases immobility counts in the FST, suggesting that Example 103 has antidepressant properties.

D. Effect of a Single P.O. Administration of Example 272, Fluoxetine and Vehicle on Swimming, Climbing, Immobility and Diving in the Forced Swim Test Immobility Statistical analysis indicated a significant effect of treatment on immobility (ANOVA, $F(2,27)=5.2$, $p=0.0126$). Post hoc analyses revealed that a single p.o. administration of 10 mg/kg of fluoxetine and 3 mg/kg of Example 272 significantly decreased immobility (Student-Newman-Keuls values of 5.4 and 9.8, respectively) compared to vehicle-treated animals (Table 5c). There was no significant difference between fluoxetine and 3 mg/kg of Example 272 in the reduction of immobility (Student-Newman-Keuls value of 0.53).

Swimming

Statistical analysis indicated a significant treatment effect on swimming behavior (ANOVA, $F(2,27)=9.9$, $p<0.0007$). Post hoc analyses revealed that a single p.o. administration of 10 mg/kg of fluoxetine and Example 272 produced a significant increase in swimming behavior compared to animals treated with vehicle (Student-Newman-Keuls values of 11.9 and 17.5, respectively) (Table 5c). There was no significant difference in the increase in swimming between 10 mg/kg of fluoxetine and 3 mg/kg of Example 272 (Student-Newman-Keuls value of 0.42).

Climbing Behavior

Statistical analysis revealed that diving was not significantly altered by a single p.o. administration of either 3 mg/kg of Example 272 or 10 mg/kg of fluoxetine compared to vehicle-treated animals (ANOVA, $F(2,27)=1.8$, $p=0.19$) (Table 5c).

Diving

Statistical analysis revealed that diving was not significantly altered by a single p.o. administration of 3 mg/kg of Example 272 or 10 mg/kg of fluoxetine compared to vehicle-treated animals (ANOVA, $F(2,27)=0.65$, $p=0.53$) (Table 5c).

TABLE 5c

The effect of a single p.o. administration of vehicle, fluoxetine and Example 272 on immobility, climbing, diving and swimming in the forced swim test in male Sprague-Dawley rats.

| Treatment | Immobility | Climbing | Swimming | Diving |
|---|---|---|---|---|
| Vehicle | 43 ± 3.3 | 2.4 ± 0.4 | 13.4 ± 2.2 | 0.2 ± 0.1 |
| 3 mg/kg EX272 | 33 ± 1.8[a] | 3.9 ± 0.6 | 22.9 ± 1.3[b] | 0.6 ± 0.4 |
| 10 mg/kg FLUOX | 35 ± 1.7[a] | 3.3 ± 0.6 | 21.4 ± 1.0[b] | 0.2 ± 0.1 |

Each value represents the mean ± S.E.M. A total of 9-10 animals were examined for each treatment group.
Abbreviations:
FLUOX = Fluoxetine,
EX272 = Example 272.
Animals received 1 p.o. administration of the appropriate treatment 24 hours before the test day.
[a]Significantly less than Vehicle, $p < 0.05$, ANOVA and Student-Newman-Keuls test.
[b]Significantly less than Vehicle, $p < 0.01$, ANOVA and Student-Newman-Keuls test.

The finding of this study indicate that a single p.o. administration of 3 mg/kg of the compound Example 272 produced a significant increase in swimming and a significant decrease in immobility 24 hours after administration compared to vehicle-treated animals. However, the administration of Example 272 did not significantly alter climbing or diving compared to vehicle-treated animals. These results are similar to those of a single p.o. administration of 10 mg/kg of fluoxetine. Our finding suggest that a single p.o. administration of 3 mg/kg of Example 272 has the profile of an antidepressant in male Sprague-Dawley rats in the Lucki version of the FST.

E. Effect of a Single P.O. Administration of Example 98, Fluoxetine and Vehicle on Swimming, Climbing, Immobility and Diving in the Forced Swim Test.

Immobility

Statistical analysis indicated a significant effect of treatment on immobility (ANOVA, $F(4,43)=7.5$, $p=0.0001$). Post hoc analyses revealed that a single p.o. administration of 10 mg/kg of fluoxetine significantly decreased immobility (Student-Newman-Keuls value of 23.8) compared to vehicle-treated animals (Table 5d).

A single p.o. administration of 3, 10 or 30 mg/kg of Example 98 significantly decreased immobility compared to vehicle-treated animals (Student-Newman-Keuls values of 19.3, 9.7 and 13.7, respectively). There was no significant difference between fluoxetine and 3, 10 or 30 mg/kg of Example 98 in the magnitude of the reduction of immobility. There were no significant differences between the doses of Example 98 regarding the magnitude of the decrease in immobility.

Swimming

Statistical analysis indicated a significant treatment effect on swimming behavior (ANOVA, $F(4,43)=11$, $p<0.0001$). Post hoc analyses revealed that a single p.o. administration of 10 mg/kg of fluoxetine produced a significant increase in swimming behavior compared to vehicle-treated animals (Student-Newman-Keuls value of 35.1) (Table 5d).

A single p.o. administration of 3, 10 or 30 mg/kg of Example 98 significantly increased swimming compared to vehicle-treated animals (Student-Newman-Keuls values of 24.4, 14.7 and 25.1, respectively) (Table 5d). There was no significant difference between fluoxetine and 3, 10 or 30 mg/kg of Example 98 in the magnitude of the increase in swimming. There were no significant differences between the doses of Example 98 regarding the magnitude of the increase in immobility.

Climbing Behavior

There was a significant treatment effect on climbing behavior (ANOVA, $F(4,43)=2.8$, $p=0.04$) (Table 5d). Post hoc tests indicated that this was the result of the 3 mg/kg dose of, Example 98 producing a significantly greater increase in climbing compared to 30 mg/kg of Example 98 (Table 5d; Student-Newman-Keuls value of 8.6). There was no significant difference in the number of climbing counts between animals treated with vehicle and Example 98.

Diving

Statistical analysis revealed that diving was not significantly altered by a single p.o. administration of 3, 10 or 30 mg/kg of Example 98 or 10 mg/kg of fluoxetine compared to vehicle-treated animals (ANOVA, $F(4,43)=1.29$, $p=0.29$) (Table 5d).

TABLE 5d

The effect of a single p.o. administration of vehicle, 10 mg/kg of fluoxetine and 3, 10 or 30 mg/kg of Example 98 on immobility, climbing, diving and swimming in the forced swim test in male Sprague-Dawley rats.

| Treatment | Immobility | Climbing | Swimming | Diving |
|---|---|---|---|---|
| Vehicle | 48 ± 1.2 | 2.5 ± 0.5 | 8.8 ± 0.9 | 0.4 ± 0.3 |
| 3 mg/kg EX98 | 35 ± 2.6[a] | 4.3 ± 0.9[b] | 20.4 ± 1.9[c] | 0.1 ± 0.1 |
| 10 mg/kg EX98 | 39 ± 1.1[a] | 2.4 ± 0.3 | 17.6 ± 1.0[c] | 0.8 ± 0.4 |
| 30 mg/kg EX98 | 38 ± 2.3[a] | 2.0 ± 0.3 | 20.3 ± 2.1[c] | 0.2 ± 0.2 |
| 10 mg/kg Fluox | 34 ± 3.0[a] | 3.4 ± 0.8 | 22.8 ± 2.2[c] | 0.1 ± 0.1 |

Each value represents the mean ± S.E.M. A total of 10 animals were examined for each treatment group, except for the fluoxetine and 3 mg/kg groups, where a total of 9 animals were examined. Vehicle = 100% DMA.
Fluox = Fluoxetine, EX98 = Example 98. Experiments were conducted 1 hr. after the appropriate treatment.
[a]Significantly less than Vehicle, $p < 0.01$, ANOVA and Student-Newman-Keuls test.
[b]Significantly greater than 30 mg/kg of Example 98, $p < 0.05$, ANOVA and Student-Newman-Keuls test.
[c]Significantly greater than Vehicle, $p < 0.01$, ANOVA and Student-Newman-Keuls test.

The results of this study clearly indicate that in male Sprague-Dawley rats, a single p.o. administration of 3, 10 or 30 mg/kg of Example 98 produces a significant increase in swimming and a significant decrease in immobility compared to vehicle-treated animals in the FST. In addition, the Example 98 induced alterations were similar in magnitude to that of a single p.o. administration of 10 mg/kg p.o. of fluoxetine. However, neither fluoxetine nor Example 98 produced a significant alteration in climbing or diving compared to vehicle-treated animals.

In conclusion, these results indicate that a single p.o. administration of Example 98 produces a profile in the modified Lucki version of the FST resembling that of the clinically established antidepressant fluoxetine.

F. Effect of a Single P.O. Administration of Example 34, Fluoxetine And Vehicle on Swimming, Climbing, Immobility and Diving in the Forced Swim Test.

Immobility

Statistical analysis indicated a significant effect of treatment on immobility (ANOVA, $F(5,44)=18.1$, $p<0.0001$). Post hoc analyses revealed that a single p.o. administration of 10 mg/kg of fluoxetine significantly decreased immobility (Student-Newman-Keuls value of 39.6) compared to vehicle-treated animals (Table 5e). Fluoxetine also produced a significantly greater decrease in immobility compared to the 0.3 and 10 mg/kg doses of Example 34 (Student-Newman-Keuls values of 15.3 and 29.8, respectively). There was no significant difference in the magnitude of the decrease in immobility between fluoxetine and the 1 and 3 mg/doses of Example 34.

A single p.o. administration of 0.3, 1 and 3 mg/kg of Example 34 significantly decreased immobility compared to vehicle-treated animals (Student-Newman-Keuls values of 7.03, 41.6 and 42.0, respectively) (Table 5e). However, a single p.o. administration of 10 mg/kg of Example 34 did, not significantly decrease in immobility compared to vehicle-treated animals. The magnitude of the decrease in immobility produced by 1 and 3 mg/kg doses of Example 34 was significantly greater than that for the 0.3 (Student-Newman-Keuls values of 14.5 and 15.3) and 10 mg/kg (Student-Newman-Keuls of 30.6 and 31.3, respectively) doses of Example 34 (Student-Newman-Keuls of 21.3 and 10.8, respectively).

Swimming

Statistical analysis indicated a significant treatment effect on swimming behavior (ANOVA, $F(5,44)=33.0$, $p<0.0001$). Post hoc analyses revealed that a single p.o. administration of 10 mg/kg of fluoxetine produced a significant increase in swimming compared to animals treated with vehicle, 0.3 or 10 mg/kg of Example 34 (Student-Newman-Keuls values of 73.7, 30.0 and 53.9, respectively) (Table 5e). There was no significant difference in swimming behavior between fluoxetine and the 1 and 3 mg/kg p.o. of Example 34.

A single p.o. administration of either 0.3, 1 or 3 mg/kg of Example 34 produced a significant increase in swimming behavior compared to vehicle-treated animals (Student-Newman-Keuls values of 12.1, 72.1 and 80.3, respectively) (Table 5e). In addition, the magnitude of the increase in swimming was greater for the 1 and 3 mg/kg doses (Student-Newman-Keuls values of 50.4 and 57.9, respectively) compared to 0.3 mg/kg of Example 34.

Climbing Behavior

Statistical analysis indicated a significant treatment effect on swimming behavior (ANOVA, $F(5,44)=3.2.$, $p=0.014$) (Table 5e). Post hoc analyses revealed that a single p.o. administration of 1 mg/kg of Example 34 produced a significant increase in climbing compared to vehicle-treated animals (Student-Newman-Keuls value of 9.2) (Table 5e).

Diving

Statistical analysis revealed that diving was not significantly altered by a single p.o. administration of 0.3, 1, 3 or 10 mg/kg of Example 34 or 10 mg/kg of fluoxetine compared to vehicle-treated animals (ANOVA, $F(5,44)=0.75$, $p=0.59$) (Table 5e).

TABLE 5e

The effect of a single p.o. administration of vehicle, 10 mg/kg of fluoxetine and Example 34 on immobility, climbing, diving and swimming in the forced swim test in male Sprague-Dawley rats.

| Treatment | Immobility | Climbing | Swimming | Diving |
|---|---|---|---|---|
| Vehicle | 52 ± 1.3 | 2.1 ± 0.6 | 6.0 ± 0.6 | 0.8 ± 0.7 |
| 0.3 mg/kg EX34 | 45 ± 1.5[a] | 3.3 ± 0.7 | 11.6 ± 0.9[d] | 0.2 ± 0.1 |
| 1 mg/kg EX34 | 35 ± 1.9[b] | 5.0 ± 0.8[c] | 19.6 ± 1.3[d,e] | 0.3 ± 0.2 |

TABLE 5e-continued

The effect of a single p.o. administration of vehicle, 10 mg/kg of fluoxetine and Example 34 on immobility, climbing, diving and swimming in the forced swim test in male Sprague-Dawley rats.

| Treatment | Immobility | Climbing | Swimming | Diving |
|---|---|---|---|---|
| 3 mg/kg EX34 | 35 ± 2.0[b] | 4.3 ± 0.8 | 20.8 ± 1.3[d,e] | 0.3 ± 0.3 |
| 10 mg/kg EX34 | 49 ± 1.4 | 2.0 ± 0.4 | 8.2 ± 1.2 | 0.4 ± 0.3 |
| 10 mg/kg Fluox | 34 ± 3.3[b] | 4.5 ± 1.2 | 21.3 ± 1.8[d,e] | 1.0 ± 0.8 |

Each value represents the mean ± S.E.M. A total of 9 animals were examined for each treatment group, except for the 3 mg/kg Example 34 and fluoxetine groups, were a total of 8 and 6 animals were examined, respectively. Fluox = Fluoxetine, EX34 = Example 34. Experiments were conducted 1 hr. after the appropriate treatment.
[a]Significantly less than Vehicle, p < 0.05, ANOVA and Student-Newman-Keuls test.
[b]Significantly less than Vehicle, 0.3 and 10 mg/kg of Example 34, ANOVA and Student-Newman-Keuls test.
[c]Significantly greater than Vehicle, p < 0.05, ANOVA and Student-Newman-Keuls test.
[d]Significantly greater than Vehicle (p < 0.01) and 10 mg/kg Example 34 (all p < 0.01 except for 0.3 mg/kg of Example 34, p < 0.05), ANOVA and Student-Newman-Keuls test.
[e]Significantly greater 0.3 mg/kg of Example 34, p < 0.05, ANOVA and Student-Newman-Keuls test.

The results of this study indicate that a single p.o. administration (one hour before the final swim test) of either 0.3, 1 or 3 mg/kg of Example 34 produced a significant increase in swimming and a significant decrease in immobility compared to vehicle-treated animals. However, a single p.o. administration of 10 mg/kg of Example 34 did not significantly alter swimming or climbing compared to vehicle-treated animals. Currently, the explanation for the lack of effect of 10 mg/kg p.o. of Example 34 is unknown. The 1 mg/kg dose of Example 34 produced a significant increase in climbing compared to vehicle-treated animals. The magnitude of the alterations in swimming and immobility produced by 1 and 3 mg/kg p.o. of Example 34 was significantly greater than that for the 0.3 and 10 mg/kg doses of Example 34. Finally, none of the doses of Example 34 significantly altered diving behavior compared to vehicle-treated controls.

As previously reported, a single p.o. administration of 10 mg/kg of fluoxetine produced a significant increase in swimming and a significant decrease in immobility compared to vehicle-treated controls. The effect of fluoxetine on swimming and immobility was similar to that for the 1 and 3 mg/kg doses of Example 34 but was significantly greater than that of 0.3 and 10 mg/kg of Example 34. A single p.o. administration of 10 mg/kg of fluoxetine did not significantly alter climbing or diving behavior compared to vehicle-treated controls.

In conclusion, these results indicate that a single p.o. administration of 0.3, 1 or 3 mg/kg Example 34 produces an effect in the FST that resembles that of antidepressants in male Sprague-Dawley rats.

G. Effect of a Single P.O. Administration of Example 49, Fluoxetine and Vehicle on Swimming, Climbing, Immobility and Diving in the Forced Swim Test.

Immobility

Statistical analysis indicated a significant effect of treatment on immobility (ANOVA, $F(4,41)=6.5$, $p=0.0004$). Post hoc analyses revealed that a single p.o. administration of 10 mg/kg of fluoxetine significantly decreased immobility (Student-Newman-Keuls value of 15.6) compared to vehicle-treated animals (Table 5f).

A single p.o. administration of either 3 or 10 mg/kg of Example 49 did not significantly alter immobility compared to vehicle-treated animals. However, the 30 mg/kg dose of Example 49 produced a significant decrease in immobility (Student-Newman-Keuls values of 8.0) compared to vehicle-treated animals. In addition, the decrease in immobility produced by either fluoxetine or 30 mg/kg of Example 49 was significantly greater than that of the 10 mg/kg dose of Example 49. There was no significant difference between fluoxetine and 30 mg/kg of Example 49 in the reduction of immobility.

Swimming

Statistical analysis indicated a significant treatment effect on swimming behavior (ANOVA, $F(4,41)=16.2$, $p<0.0001$). Post hoc analyses revealed that a single p.o. administration of 10 mg/kg of fluoxetine produced a significant increase in swimming behavior compared to animals treated with vehicle, 3, 10 or 30 mg/kg p.o. of Example 49 (Student-Newman-Keuls values of 42.7, 20.9, 47.5 and 8.4, respectively) (Table 5f).

A single p.o. administration of either 3 or 10 mg/kg of Example 49 did not significantly alter swimming behavior compared to vehicle-treated animals. A single p.o. administration of 30 mg/kg of Example 49 produced a significantly greater increase in swimming behavior compared to animals treated with vehicle, 3 or 10 mg/kg of Example 49 (Student-Newman-Keuls values of 14 and 16.9, respectively).

Climbing Behavior

There was a significant treatment effect on climbing behavior (ANOVA, $F(4,42)=5.9$, $p=0.007$). Post hoc tests indicated that this was the results of the vehicle, 3, 10 and 30 mg/kg doses of Example 49 producing a significantly greater increase in climbing counts compared to fluoxetine-treated animals (Table 5f; Student-Newman-Keuls values of 7.9, 18.1, 14.05 and 12.9, respectively). There was no significant difference in the number of climbing counts between animals treated with vehicle and Example 49.

Diving

Statistical analysis revealed that diving was not significantly altered by a single p.o. administration of 3, 10 or 30 mg/kg of Example 49 or 10 mg/kg of fluoxetine compared to vehicle-treated animals (ANOVA, $F(4,41)=1.06$, $p=0.38$) (Table 5f).

TABLE 5f

The effect of a single p.o. administration of vehicle, 10 mg/kg of fluoxetine and 3, 10 or 30 mg/kg of Example 49 on immobility, climbing, diving and swimming in the forced swim test in male Sprague-Dawley rats.

| Treatment | Immobility | Climbing | Swimming | Diving |
|---|---|---|---|---|
| Vehicle | 47 ± 1.2 | 1.8 ± 0.3 | 10.6 ± 1.1 | 0.2 ± 0.2 |
| 3 mg/kg EX 49 | 43 ± 1.9 | 3.0 ± 0.7 | 13.1 ± 1.4 | 1.0 ± 0.7 |
| 10 mg/kg EX49 | 48 ± 1.7 | 2.4 ± 0.7 | 10.0 ± 1.0 | 0.0 ± 0.0 |
| 30 mg/kg EX49 | 41 ± 2.0[a] | 2.3 ± 0.4 | 16.7 ± 1.3[d] | 0.4 ± 0.4 |
| 10 mg/kg Fluox | 38 ± 1.3[b] | 0.0 ± 0.0[c] | 21.6 ± 1.1[e] | 0.8 ± 0.5 |

Each value represents the mean ± S.E.M. A total of 10 animals were examined for each treatment group, except for the fluoxetine and 3 mg/kg groups, where a total of 9 and 7 animals were examined, respectively.
Fluox = Fluoxetine, EX49 = Example 49. Experiments were conducted 1 hr. after the appropriate treatment.

TABLE 5f-continued

The effect of a single p.o. administration of
vehicle, 10 mg/kg of fluoxetine and 3, 10 or 30 mg/kg of
Example 49 on immobility, climbing, diving and swimming
in the forced swim test in male Sprague-Dawley rats.

| Treatment | Immobility | Climbing | Swimming | Diving |
|---|---|---|---|---|

[a]Significantly less than Vehicle and 10 mg/kg of Example 49, p < 0.05, ANOVA and Student-Newman-Keuls test.
[b]Signficantly less than Vehicle and 10 mg/kg of Example 49, p < 0.01, ANOVA and Student-Newman-Keuls test.
[c]Signficantly less than all other treatment groups, p < 0.01, ANOVA and Student-Newman-Keuls test.
[d]Significantly greater than vehicle and 10 mg/kg of Example 49, p < 0.01, ANOVA and Student-Newman-Keuls test.
[e]Signficantly greater than all other treatment groups, p < 0.01, ANOVA and Student-Newman-Keuls test.

The results of this study indicated that as previously reported, a single p.o. administration of 10 mg/kg of fluoxetine produced a significant increase in swimming and a significant decrease in immobility in male rats in the FST compared to vehicle-treated animals. The magnitude of these changes are similar to those reported of our past studies with 10 mg/kg p.o. of fluoxetine. In contrast, climbing behavior was significantly decreased by a single p.o. administration of 10 mg/kg of fluoxetine compared to all other treatment groups. However, this could be related to the fact that fluoxetine has a much greater effect on swimming than climbing and it is likely that fluoxetine is not producing climbing as opposed to actually decreasing climbing. Finally, fluoxetine, as previously reported, does not significantly alter diving compared to vehicle-treated behavior.

A single p.o. administration of either 3 or 10 mg/kg of Example 49 did not significantly alter swimming, climbing, immobility or diving in male rats in the FST, indicating that at these doses using the p.o. route, Example 49 does not exhibit antidepressant action in the FST. In contrast, a single p.o. administration of 30 mg/kg of Example 49 produced a significant increase in swimming and a significant decrease in immobility compared to animals treated with vehicle, or 3 and 10 mg/kg of Example 49. However, the 30 mg/kg p.o. dose of Example 49 did not significantly alter diving or climbing counts compared to vehicle-treated animals. The increase in swimming counts produced by 30 mg/kg p.o. of Example 49 was comparable to that of 10 mg/kg of fluoxetine, although Example 49 was less effective than fluoxetine in reducing immobility.

In conclusion, a single p.o. administration of 30 mg/kg of Example 49 (one hour before the last swim test) increases swimming and decreases immobility counts in the FST, suggesting that Example 49 may have antidepressant properties in this model.

H. Effect of a Single P.O. Administration of Example 22, Fluoxetine and Vehicle on Swimming, Climbing, Immobility and Diving in the Forced Swim Test Immobility Statistical analysis indicated a significant effect of treatment on immobility (ANOVA, $F(4,44)=20.2$, $p<0.0001$). Post hoc analyses revealed that a single p.o. administration of 10 mg/kg of fluoxetine significantly decreased immobility (Student-Newman-Keuls value of 20.1) compared to vehicle-treated animals (Table 5g).

A single p.o. administration of 10 or 30 mg/kg doses of Example 22 produced a significant decrease in immobility compared to vehicle-treated animals (Student-Newman-Keuls values of 12.2 and 55.0, respectively). In addition, the decrease in immobility produced the either fluoxetine or the 10 and 30 mg/kg doses of Example 22 (Student-Newman-Keuls values of 21.2, 13.0 and 56.8, respectively) was significantly greater than that of the 3 mg/kg dose of Example 22. The decrease in immobility produced by 30 mg/kg i.p. of Example 22 was significantly greater than that of the 10 mg/kg dose (Student-Newman-Keuls value 16.2). In addition, the magnitude of the decrease in immobility produced by 30 mg/kg of Example 22 was significantly greater than that of fluoxetine (Student-Newman-Keuls value of 9.3).

Swimming

Statistical analysis indicated a significant treatment effect on swimming behavior (ANOVA, $F(4,44)=35.00$, $p<0.0001$). Post hoc analyses revealed that a single i.p. administration of 10 mg/kg of fluoxetine produced a significant increase in swimming compared to animals treated with vehicle, 3 or 10 mg/kg of Example 22 (Student-Newman-Keuls values of 49.6, 51.3 and 5.8, respectively) (Table 5g).

A single p.o. administration of 3 mg/kg did not significant alter swimming behavior compared to vehicle-treated animals (Table 5g). However, a single p.o. administration of 30 mg/kg of Example 22 produced a significantly greater increase in swimming behavior compared to animals treated with vehicle, 3 or 10 mg/kg of Example 22 and fluoxetine (Student-Newman-Keuls values of 85.9, 88.1, 22.7 and 5.84, respectively).

Climbing Behavior

There was a significant treatment effect on climbing behavior (ANOVA, $F(4,44)=4.1$, $p=0.0066$). Post hoc tests indicated that a single p.o. administration of 30 mg/kg dose of Example 22 produced a significant increase in climbing compared to animals treated with vehicle, 3 or 10 mg/kg of Example 22 and fluoxetine (Student-Newman-Keuls values of 10.5, 11.1, 5.8 and 11.8, respectively).

Diving

Statistical analysis revealed that diving was not significantly altered by a single i.p. administration of 3, 10 or 30 mg/kg of Example 22 or 10 mg/kg of fluoxetine compared to vehicle-treated animals (ANOVA, $F(4,44)=0.58$, $p=0.68$) (Table 5g).

TABLE 5g

The effect of a single p.o. administration of
vehicle, 10 mg/kg of fluoxetine and Example 22 on
immobility, climbing, diving and swimming in the forced
swim test in male Sprague-Dawley rats.

| Treatment | Immobility | Climbing | Swimming | Diving |
|---|---|---|---|---|
| Vehicle | 50 ± 1.6 | 2.1 ± 0.7 | 7.8 ± 1.0 | 0.3 ± 0.3 |
| 3 mg/kg EX22 | 50 ± 0.9 | 2.0 ± 0.6 | 7.6 ± 0.5 | 0.4 ± 0.4 |
| 10 mg/kg EX22 | 41 ± 1.3[c] | 2.9 ± 0.5 | 15.3 ± 0.8[g] | 0.4 ± 0.3 |
| 30 mg/kg EX22 | 31 ± 2.8[b] | 5.2 ± 1.0[a] | 23.2 ± 2.0[f] | 0.0 ± 0.0 |
| 10 mg/kg Flux | 39 ± 1.7[d] | 1.9 ± 0.5 | 19.2 ± 1.2[e] | 0.0 ± 0.0 |

Each value represents the mean ± S.E.M. A total of 10 animals were examined for each treatment group, except for the 30 mg/kg dose of Example 22, where a total of 9 animals were examined.
Flux = Fluoxetine, EX22 = Example 22. Experiments were conducted 1 hr. after the appropriate treatment.
[a]Significantly greater than the vehicle (p < 0.01), 3 mg/kg Example 22 (p < 0.01), 10 mg/kg Example 22 (p < 0.05) and 10 mg/kg of fluoxetine (p < 0.05), ANOVA and Student-Newman-Keuls test.
[b]Significantly less than all other treatment groups, p < 0.01, ANOVA and Student-Newman-Keuls test.
[c]Significantly less than vehicle, 3 and 30 mg/kg of Example 22 (p < 0.01) and 10 mg/kg of fluoxetine (p < 0.05), ANOVA and Student-Newman-Keuls.
[d]Significantly less than vehicle, 3 and 30 mg/kg of Example 22, p < 0.01, ANOVA and Student-Newman-Keuls test.

TABLE 5g-continued

The effect of a single p.o. administration of vehicle, 10 mg/kg of fluoxetine and Example 22 on immobility, climbing, diving and swimming in the forced swim test in male Sprague-Dawley rats.

| Treatment | Immobility | Climbing | Swimming | Diving |
| --- | --- | --- | --- | --- |

[e]Significantly greater than the vehicle, 3 and 10 mg/kg of Example 22, p < 0.01, ANOVA and Student-Newman-Keuls test.
[f]Significantly greater than the vehicle, 3 and 10 mg/kg of Example 22, p < 0.01 and fluoxetine, p < 0.05, ANOVA and Student-Newman-Keuls test.
[g]Significantly greater than the vehicle and 3 mg/kg of Example 22, p < 0.05, ANOVA and Student-Newman-Keuls test.

The results of this study indicated that as previously reported, a single p.o. administration of 10 mg/kg of fluoxetine produced a significant increase in swimming and a significant decrease in immobility in male Sprague-Dawley rats in the FST compared to vehicle-treated animals. The magnitude of these changes are similar to those reported of our past studies with 10 mg/kg p.o. of fluoxetine. In contrast, neither climbing nor diving behavior was significantly altered by a single i.p. administration of 10 mg/kg of fluoxetine.

A single p.o. administration of 3 mg/kg of Example 22 did not significantly alter swimming in male rats in the FST. In contrast, a single p.o. administration of 10 or 30 mg/kg of Example 22 produced a significant increase in swimming and a significant decrease in immobility compared to animals treated with vehicle or 3 mg/kg of Example 22. In addition, the magnitude of the increase in swimming behavior produced by 30 mg/kg p.o. of Example 22 was significantly greater than that of 10 mg/kg of Example 22 and 10 mg/kg of fluoxetine. The rank order of the treatments for increasing swimming is: 30 mg/kg Example 22>fluoxetine >10 mg/kg Example 22>3 mg/kg Example 22

Climbing behavior was significantly greater in animals treated with 30 mg/kg p.o. of Example 22 compared to animals treated p.o. with either vehicle, 3 or 10 mg/kg of Example 22 or 10 mg/kg of fluoxetine. None of the other treatments besides 30 mg/kg of Example 22 significantly altered climbing behavior compared to vehicle-treated animals. The rank order of the treatments for increasing climbing is: 30 mg/kg Example 22>>3 Mg/kg Example 22=10 mg/kg Example 22=fluoxetine.

A single p.o. administration of 3 mg/kg of Example 22 did not significantly alter swimming compared to vehicle-treated animals. However, the 10 and 30 mg/kg doses produced a significantly greater decrease in immobility compared to vehicle-treated animals, with the effect at 30 mg/kg being greater then that of 10 mg/kg. Furthermore, 30 mg/kg p.o. of Example 22 produced a significantly greater decrease in immobility than 10 mg/kg p.o. of fluoxetine. The rank order of the treatments for decreasing immobility is 30 mg/kg Example 22>10 mg/kg Example 22=fluoxetine>3 mg/kg Example 22.

In conclusion, a single p.o. administration of 10 or 30 mg/kg of Example 22 significantly increases swimming and significantly decreases immobility in vehicle-treated male Sprague-Dawley rats. This suggests that at these doses, Example 22 has antidepressant properties.

I. Effect of a Single P.O. Administration of Example 95, Fluoxetine and Vehicle on Swimming, Climbing, Immobility and Diving in the Forced Swim Test Statistical analysis indicated that a single p.o. administration of 10 or 30 mg/kg Example 95 significantly increased rat immobility and significantly decreased swim behavior in the rat forced swim test at both doses (Table 5h, p<0.01, ANOVA and Student-Newman-Keuls, respectively).

TABLE 5h

The effect of a single p.o. administration of vehicle, 10 mg/kg of fluoxetine and 3, 10 or 30 mg/kg of Example 95 on immobility, climbing, diving and swimming in the forced swim test in male Sprague-Dawley rats.

| Treatment | Immobility | Climbing | Swimming | Diving |
| --- | --- | --- | --- | --- |
| Vehicle | 42 ± 1.7 | 2.3 ± 0.5 | 14.7 ± 1.0 | 0.1 ± 0.1 |
| 3 mg/kg EX95 | 40 ± 3.3 | 2.6 ± 0.8 | 17.1 ± 2.5 | 0.0 ± 0.0 |
| 10 mg/kg EX95 | 52 ± 1.2[a] | 1.3 ± 0.5 | 6.9 ± 0.9[b] | 0.1 ± 0.1 |
| 30 mg/kg EX95 | 54 ± 0.9[a] | 1.0 ± 0.3 | 4.8 ± 0.7[b] | 0.0 ± 0.0 |
| 10 mg/kg Flux | 38 ± 2.2 | 1.9 ± 0.6 | 20.0 ± 1.5[c] | 0.1 ± 0.1 |

Each value represents the mean ± S.E.M. A total of 8 animals were examined for each treatment group, except for the vehicle, where a total of 10 animals were examined. Fluox = Fluoxetine; EX95 = Example 95. Experiments were conducted 1 hr. after the appropriate treatment.
[a]Significantly less than Vehicle, 3 mg/kg of Example 95 and 10 mg/kg of fluoxetine, p < 0.01, ANOVA and Student-Newman-Keuls test.
[b]Signficantly less than Vehicle, 3 mg/kg of Example 95 and 10 mg/kg of fluoxetine, p < 0.01, ANOVA and Student-Newman-Keuls test.
[c]Signficantly greater than Vehicle (p < 0.05), 10 and 30 mg/kg of Example 95 (p < 0.01), ANOVA and Student-Newman-Keuls test.

A single p.o. administration of 10 mg/kg of fluoxetine produced a significant increase in swimming behavior compared to vehicle-treated animals. In addition, fluoxetine significantly decreased immobility compared to vehicle-treated animals. A single p.o. administration of 3 mg/kg of Example 95 did not significantly alter swimming, climbing, immobility or diving behavior compared to vehicle-treated animals. In contrast, a single p.o. administration of either 10 or 30 mg/kg of Example 95 produced a significant increase in immobility and a significant decrease in swimming, behavior compared to vehicle-treated animals. There was no significant difference in the magnitude of change in swimming and immobility between the 10 and 30 mg/kg doses of Example 95.

These data indicate that at a doses of 10 and 30 mg/kg p.o., Example 95 produced effects opposite of that seen with antidepressants in the rat forced swim test, suggesting that Example 95 does not produce antidepressant-like actions in the forced swim test in male Sprague-Dawley rats.

2. Social Interaction Test

A. The Effect of Example 92 And Chlordiazepoxide On Behavior in the Rat Social Interaction Test A single i.p. administration of either, 10 or 30 mg/kg of Example 92 significantly increased social interaction (Table 6 and FIG. 4), as did the benzodiazepine anxiolytic, chlordiazepoxide (Student-Newman-Keuls value of 31.3) compared to vehicle-treated animals (ANOVA, F(4,45)=10.3, p<0.0001; Student-Newman-Keuls values for the 10 and 30 mg/kg doses were 8.61 and 19.55, respectively). However, the 100 mg/kg i.p. dose of Example 92 did not significantly alter social interaction time compared to vehicle-treated animals (Table 6 and FIG. 4). The degree of social interaction was greater in the chlordiazepoxide-treated animals compared to those that received either the 10 or 30 mg/kg doses of Example 92.

TABLE 6

The Effect Of A Single Injection Of Vehicle,
Chlordiazepoxide And Example 92 On The Social Interaction
And Rearing Of Unfamiliar Cage Mates In A Familiar Arena

| Drug Social Treatment (i.p.) | Interaction (sec)[a] |
|---|---|
| Vehicle, 1 ml/kg | 96 ± 12 |
| Chlordiazepoxide, 5 mg/kg | 188 ± 15[b] |
| Example 92, 10 mg/kg | 144 ± 12[b] |
| Example 92, 30 mg/kg | 169 ± 13[c] |
| Example 92, 100 mg/kg | 117 ± 6[d] |

[a]Each value represents the mean seconds of social interaction ± S.E.M.
[b]Significantly greater than Vehicle, $p < 0.05$, ANOVA and Student-Newman-Keuls test.
[c]Significantly greater than Vehicle, $p < 0.01$, ANOVA and Student-Newman-Keuls test.
[d]Significantly less than 30 mg/kg dose and chlordiazepoxide, $p < 0.01$, ANOVA and Student-Newman-Keuls.

B. The Effect of Example 92 And Chlordiazepoxide on Rearing Behavior, Locomotor Activity And Grooming in the Rat Social Interaction Test The administration of 10 and 30 mg/kg, but not 100 mg/kg of Example 92, significantly increased rearing behavior compared to either vehicle or chlordiazepoxide [ANOVA, $F(4,45) = 2.6$, $p=0.046$; See Table 13]. In addition, the number of rearings at the 10 mg/kg dose of Example 92 was significantly greater than that produced by chlordiazepoxide (Table 13).

The administration of either Example 92 or chlordiazepoxide did not significantly alter the number of grooming bouts compared to vehicle-treated animals [$F(4,45)=0.67$, $p=0.62$].

A single injection of either 10 or 30 mg/kg i.p. of Example 92 or 5 mg/kg i.p. of chlordiazepoxide did not significantly alter the number of squares crossed (Table 13). However, the number of squares crossed following the 100 mg/kg dose of Example 92 was significantly lower than animals treated with either vehicle, 10 mg/kp i.p. of Example 92, 30 mg/kg i.p. of Example 92 or 5 mg/kg i.p. of chlordiazepoxide. [ANOVA, $F(4,43)=6.94$, $p=0.0002$].

TABLE 13

The Effect of a Single Injection of Vehicle,
Chlordiazepoxide and Example 92 on the Number of
Rearings, Squares Crossed and Grooming Bouts in the Rat
Social Interaction Test.

| Drug Treatment (i.p.) | Rearings | Squares Crossed | Grooming Bouts |
|---|---|---|---|
| Vehicle, 1 ml/kg | 33 ± 4 | 393 ± 26 | 5.1 ± 1.1 |
| Chlordiazepoxide, 5 mg/kg | 30 ± 2 | 287 ± 28 | 7.3 ± 1.3 |
| Example 92, 10 mg/kg | 47 ± 8[a] | 298 ± 40 | 6.1 ± 0.5 |
| Example 92, 30 mg/kg | 45 ± 5[b] | 368 ± 36 | 6.2 ± 0.7 |
| Example 92, 100 mg/kg | 31 ± 4 | 195 ± 19[c] | 6.8 ± 1.3 |

All values represent the mean ± S.E.M.
[a]Significantly greater than chlordiazepoxide, $p < 0.05$, ANOVA and Student-Newman-Keuls test
[b]Significantly greater than vehicle and chlordiazepoxide, $p < 0.05$, ANOVA and Student-Newman-Keuls test.
[c]Significantly less than 10 & 30 mg/kg of Example 92 ($p < 0.01$), vehicle ($p < 0.01$) and chlordiazepoxide ($p < 0.05$), ANOVA and Student-Newman-Keuls test.

At doses of 10 and 30 mg/kg i.p., Example 92 produced a significant increase in social interaction time in male rats compared to vehicle-treated animals. Also, the anxiolytic agent (5 mg/kg i.p. chlordiazepoxide) produced a significant increase in social interaction time compared to vehicle-treated animals. The response produced by the 30 mg/kg dose of Example 92 was comparable to that of the positive control, chlordiazepoxide. The 30 mg/kg dose of Example 92 produced a significant increase in rearing compared to vehicle and chlordiazepoxide-treated animals. Previously, it has been shown that in the Social Interaction Test, psychostimulants such as amphetamine and caffeine, increase social interaction and locomotor activity, whereas anxiolytics increase social interaction time. (File, 1985; File and Hyde, 1979; Guy and Gardner, 1985). Consistent with an increase in social interaction, Example 92 increased rearing behavior. However, it did not produce an increase in horizontal locomotor activity or grooming bouts. In addition, Example 92 did not elicit stereotypes or produce aggressive behaviors. In fact, locomotor activity as measured by squares crossed was significantly reduced at the 100 mg/kg i.p. dose of Example 92 compared to vehicle-treated animals. This decrease in locomotor activity did not appear to be accompanied by ataxia or sedation. Thus, it is unlikely that Example 92 is producing a non-specific effect on social interaction through motor stimulation. In order to justify this claim, in another study (not reported), the effect of Example 92 was dosed to familiar cage mates in the social interaction test and no significant increase in interaction in this variation of the Social Interaction Test was observed. In this test, the anxiogenic stimulus of a novel partner is removed and therefore only locomotor activity and normal behavior are observed (Guy and Gardner, 1985) In conclusion, the results of this study indicate that Example 92, at doses of 10 and 30 mg/kg i.p., significantly increases social interaction time without producing an increase in horizontal locomotor activity or grooming bouts. Furthermore, the effect produced by the 30 mg/kg of Example 92 was comparable to that observed for 5 mg/kg of chlordiazepoxide, the active control. No increase in social interaction was observed at the 100 mg/kg dose of Example 92. However, a decrease in the number of squares crossed was observed. In summary, Example 92 has the profile of an anxiolytic, drug in the Social Interaction Test.

C. The Effect of a Single P.O. Administration of Example 34, Vehicle and Chlordiazepoxide on the Duration of Social Interaction in the Rat Social Interaction Test.

There was a significant treatment effect on the duration of social interaction (ANOVA, $F(5,40)=11.8$, $p<0.001$). Subsequent post hoc analyses indicated that a single p.o. administration of either 0.03, 0.1, 0.3 and 1 mg/kg of Example 34 (Student-Newman-Keuls test values of 8.0, 10.6, 4.3 and 13.2, respectively) significantly increased social interaction, as did chlordiazepoxide (Student-Newman-Keuls value of 57.1), compare to vehicle-treated animals (Table 6a). The duration of social interaction produced by chlordiazepoxide was significantly greater than that of 0.03, 0.1, 0.3 and 1 mg/kg p.o. of Example 34 (Student-Newman-Keuls values of 19.6, 18.6, 26.2 and 17.6, respectively). There was no significant difference in the duration of social interaction between the various doses of Example 34 (Table 6a).

TABLE 6a

The effect of a single p.o. administration of
vehicle, chlordiazepoxide and Example 34 on social
interaction time in unfamiliar cage mates in a familiar
arena

| Drug Treatment (p.o.) | Social Interaction (sec) |
|---|---|
| Vehicle, 1 ml/kg | 27 ± 1.4[A] |
| Chlordiazepoxide, 5 mg/kg | 122 ± 18[S] |

TABLE 6a-continued

The effect of a single p.o. administration of
vehicle, chlordiazepoxide and Example 34 on social
interaction time in unfamiliar cage mates in a familiar
arena

| Drug Treatment (p.o.) | Social Interaction (sec) |
|---|---|
| Example 34, 0.03 mg/kg | 62 ± 11* |
| Example 34, 0.1 mg/kg | 66 ± 7* |
| Example 34, 0.3 mg/kg | 53 ± 6* |
| Example 34, 1 mg/kg | 69 ± 6# |

Animals received one p.o administration of the appropriate treatment and all experiments were conducted one hour after the last injection.
[A]Each value represents the mean seconds of social interaction ± S.E.M. A total of 6-8 animals were examined for each treatment group.
*Significantly greater than Vehicle, $p < 0.05$, ANOVA and Student-Newman-Keuls test.
Significantly greater than Vehicle, $p < 0.01$, ANOVA and Student-Newman-Keuls test.
[S]Significantly greater than all other treatment groups, $p < 0.01$, ANOVA and Student-Newman-Keuls test.

D. The Effect of a Single P.O. Administration of Example 34, Vehicle and Chlordiazepoxide on Rearing Behavior, Locomotor Activity and Grooming in the Social Interaction Test.

Statistical analysis indicated a significant effect of treatment on rearing behavior (ANOVA, $F(5,40)=3.5$, $p=0.01$; Table 14). Post hoc analyses revealed that the number of rears following 0.3 mg/kg of Example 34 was significantly lower than that of 0.1 and 1 mg/kg p.o. of Example 34 (Student-Newman-Keuls values of 8.8 and 9.4, respectively).

Statistical analysis indicated a significant effect of treatment on number of squares crossed ($F(5,40)=2.9$, $p=0.03$). Post hoc analyses indicated that a single p.o. administration of 0.3 mg/kg of Example 34 produced a significantly greater effect on the number of squares crossed compared to vehicle-treated animals (Student-Newman-Keuls values of 10.4).

Statistical analysis indicated a significant effect of treatment on grooming behavior ($F(5,40)=4.3$, $p=0.004$). Post hoc analyses indicated that the number of grooming episodes was significantly lower in the 0.03 mg/kg group compared to animals treated with 0.1, 0.3 or 1 mg/kg p.o. of Example 34 (Student-Newman-Keuls values of 11, 8 and 9.7, respectively (Table 14). In addition, the number of grooming episodes was significantly greater in animals treated with 0.1 mg/kg p.o. of Example 34 compared to those treated with vehicle (Table 14).

TABLE 14

The effect of a single p.o. administration of
vehicle, chlordiazepoxide and Example 34 on the number of
rearings, grooming episodes and squares crossed in the
social interaction test in unfamiliar cage mates in a
familiar arena

| Drug Treatment (p.o.) | Rearing | Squares Crossed | Grooming bouts |
|---|---|---|---|
| Vehicle, 1 ml/kg | 34 ± 3 | 250 ± 31 | 4.6 ± 0.7 |
| Chlordiazepoxide, 5 mg/kg | 35 ± 2 | 265 ± 30 | 5.3 ± 0.7 |
| Example 34, 0.03 mg/kg | 27 ± 3* | 312 ± 23 | 4.0 ± 0.4& |
| Example 34, 0.1 mg/kg | 40 ± 5 | 295 ± 40 | 7.6 ± 0.5+ |
| Example 34, 0.3 mg/kg | 27 ± 2S | 363 ± 17 | 7.2 ± 1.1 |
| Example 34, 1 mg/kg | 40 ± 1 | 343 ± 15@ | 7.3 ± 0.8 |

Animals received one p.o administration of the appropriate treatment and all experiments were conducted one hour after the last injection. All values represent the mean ± S.E.M. A total of 6-8 animals were examined for each treatment group.

TABLE 14-continued

The effect of a single p.o. administration of
vehicle, chlordiazepoxide and Example 34 on the number of
rearings, grooming episodes and squares crossed in the
social interaction test in unfamiliar cage mates in a
familiar arena

| Drug Treatment (p.o.) | Rearing | Squares Crossed | Grooming bouts |
|---|---|---|---|

*Significantly less than 0.1 mg/kg of Example 34, $p < 0.05$, ANOVA and Student-Newman-Keuls test.
[S]Significantly less than 0.1 and 1 mg/kg of Example 34, $p < 0.05$, ANOVA and Student-Newman-Keuls test.
@Significantly greater than Vehicle, $p < 0.05$, ANOVA and Student-Newman-Keuls test.
&Significantly less than 0.1, 0.3 and 1 mg/kg of Example 34, $p < 0.05$, ANOVA and Student-Newman-Keuls test.
+Significantly greater than Vehicle, $p < 0.05$, ANOVA and Student-Newman-Keuls test.

One of the main findings of this study was that in paired, unfamiliar male Sprague-Dawley rats, a single p.o. administration of either 0.03, 0.1, 0.3 or 1 mg/kg p.o. of Example 34 produced a significant increase (2-2.6 fold) in the duration of social interaction compared to animals treated with vehicle. In addition, there was no significant difference in the magnitude of increase in social interaction between the various doses of Example 34, i.e. there was no dose-response relationship. As previously reported, a single p.o. administration of 5 mg/kg of chlordiazepoxide produced a significant increase in the duration of social interaction compared to vehicle-treated animals.

Rearing behavior was not significantly altered by any of the doses of Example 34 or by chlordiazepoxide compared to vehicle-treated animals, although there were differences between the doses of Example 34. The number of squares crossed was significantly greater following a single p.o. administration of 1 mg/kg of Example 34 compared to vehicle-treated animals, whereas there were no significant differences between the other doses of Example 34 and vehicle. Thus, overall, Example 34 does not significantly alter locomotor activity, suggesting that it does not produce locomotor activation or stimulation.

Grooming behavior following a single p.o. administration tended to be greater after 0.1, 0.3 and 1 mg/kg of Example 34 compared to animals that had received vehicle, although this was only statistically significant for the 0.1 mg/kg dose. Furthermore, the number of grooming episodes was significantly lower after a single p.o. administration of 0.03 mg/kg of Example 34 compared to 0.1, 0.3 and 1 mg/kg of Example 34.

In conclusion, the above results suggest that a single p.o. administration of 0.03, 0.1, 0.3 or 1 mg/kg of Example 34 produces an anxioltyic action in the social interaction test in male Sprague-Dawley rats.

III Binding Properties of Compounds at Cloned Receptors

A. Materials and Methods

The binding properties of the compounds of the present invention were evaluated at one or more cloned receptors or native, tissue-derived transporters, using protocols described below.

Cell Culture

COS-7 cells were grown on 150 mm plates in D-MEM with supplements (Dulbecco's. Modified Eagle Medium with 10% bovine calf serum, 4 mM glutamine, 100 units/ml penicillin, 100 µg/ml streptomycin) at 37° C. with 5% $CO_2$. Stock plates of COS-7 cells were trypsinized and split 1:6 every 3-4 days. Human embryonic kidney 293 cells were grown on 150 mm plates in D-MEM with supplements (minimal essential medium) with Hanks' salts and supplements (Dulbecco's Modified Eagle Medium with 10% bovine calf serum, 4 mM glutamine, 100 units/ml penicillin, 100 µg/ml streptomycin) at 37° C. with 5% $CO_2$. Stock plates of 293 cells were trypsinized and split 1:6 every 3-4 days. Mouse fibroblast LM(tk-) cells were grown on 150 mm plates in D-MEM with supplements (Dulbecco's Modified Eagle Medium with 10% bovine calf serum, 4 mM glutamine, 100 units/mL penicillin, 100 µg/mL streptomycin) at 37° C. with 5% $CO_2$. Stock plates of LM(tk-) cells were trypsinized and split 1:10 every 3-4 days. Chinese Hamster Ovary (CHO) cells were grown on 150 mm plates in HAM's F12 medium with (HAM's F-12 with 10% bovine calf serum, 4 mM glutamine, 100 units/mL penicillin, 100 µg/mL streptomycin) at 37° C. with 5% $CO_2$. Stock plates of CHO cells were trypsinized and split 1:8 every 3-4 days.

LM(tk-) cells were stably transfected with the human GAL1 or GAL3 receptor. CHO cells were stably transfected with the human GAL2 receptor.

Stable Transfection cDNAs for the human and rat GAL1, and human and rat GAL3 receptors were transfected with a G-418 resistant gene into the mouse fibroblast LM(tk-) cell line by a calcium phosphate transfection method (Cullen, 1987). Stably transfected cells were selected with G-418. Human and rat GAL2 receptors were similarly transfected into CHO cells.

Membrane Harvest

Membranes were harvested from stably transfected LM(tk-) cells. Adherent cells were washed twice in ice-cold phosphate buffered saline (138 mM NaCl, 8.1 mM Na2HPO4, 2.5 mM KCl, 1.2 mM $KH_2PO_4$, 0.9 mM CaCl2, 0.5 mM MgCl2, pH 7.4) and lysed by sonication in ice-cold sonication buffer (20 mM Tris-HCl, 5 mM EDTA, pH 7.7). Large particles and debris were cleared by low speed centrifugation (200×g, 5 min, 4° C.). Membranes were collected from the supernatant fraction by centrifugation (32,000×g, 18 min, 4° C.), washed with ice-cold hypotonic buffer, and collected again by centrifugation (32,000×g, 18 min, 4° C.). The final membrane pellet was resuspended by sonication into a small volume of ice-cold binding buffer (~1 ml for every 5 plates: 10 mM NaCl, 20 mM HEPES, 0.22 mM $KH_2PO_4$, 1.26 mM CaCl2, 0.81 mM MgSO4, pH 7.4). Protein concentration was measured by the Bradford method (Bradford, 1976) using Bio-Rad Reagent, with bovine serum albumin as a standard. Membranes were held on ice for up to one hour and used fresh, or flash frozen and stored in liquid nitrogen. Membranes were prepared similarly from CHO cells.

As described in the Background of the Invention, compounds that block the effects of galanin on the GAL3 receptor subtype can potentially be used for the treatment of depression and anxiety. Biogenic amine transmitter molecules that mediate neuronal signals are currently known in the art and include among others serotonin (5HT), norepinephrine (NE), and dopamine (DA). Recent advances in the molecular studies of the mechanisms for these transmitter molecules, together with the characterization of their pharmacological properties, has enabled the identification of numerous potential targets for therapeutic intervention. Inhibitors of the 5HT, NE and DA transporter systems, and inhibitors of the enzyme, monoamine oxidase, have been widely studied and are known to enhance the action of biogenic amine neurotransmitters. The resultant clinically effective antidepressant drugs are known today as TCAs, SSRIs and MAOIs. (Tatsumi et al., 1997; Iversen, 2000).

In the case of galanin, the evidence presented in this invention suggests that GPCR-targeted molecules that bind to and antagonize the GAL3 receptor may be used for the treatment of depression and/or anxiety disorders. Another approach could involve the administration of an antagonist of the GAL3 receptor, such as those described herein, which also possesses $5HT_4$ receptor antagonist properties (Kennett et al., 1997). A further approach could involve the administration of a GAL3 antagonist, such as those described herein, which also possesses $5HT_{1A}$ receptor binding properties (Razani et al., 1997). However, in any case the GAL3 antagonist(s) should be free of activity at the human GAL1 receptor and the 5HT, NE and DA transporters. Furthermore, the GAL3 antagonist(s) should not inhibit the enzymatic activity of monoamine oxidase A ($MAO_A$) or monoamine oxidase B ($MAO_B$) present in the brain (i.e. central MAO). The design of such compounds can be optimized by determining their binding affinity at the recombinant GAL3, GAL1, $5HT_4$, and $5HT_{1A}$ receptors; and the native 5HT, NE and DA transporters. The design of such compounds can be further optimized by determining their interaction with central $MAO_A$ and central $MAO_B$.

Additionally, the GAL3 antagonist(s) would optimally not bind at the following receptors due to possible side effects: human GAL2; human $H_1$ histamine; human $\alpha_{1A}$ adrenergic, human $\alpha_{1B}$ adrenergic, human $\alpha_{1D}$ adrenergic, human $\alpha_{2A}$ adrenergic, human $\alpha_{2B}$ adrenergic, and human $\alpha_{2C}$ adrenergic; human dopamine $D_1$, $D_2$, $D_3$, $D_4$, and $D_5$; and the human $5HT_{1B}$, human $5HT_{1D}$, human $5HT_{1E}$, human $5HT_{1F}$, human $5HT_{2A}$, rat $5HT_{2C}$, human $5HT_6$, and human $5HT_7$ receptors.

Radioligand Binding Assays and Enzymatic Assays

The methods to obtain the cDNA of the receptors, express said receptors in heterologous systems, and carry out assays to determine binding affinity are described as follows.

Galanin Receptors Binding assays were performed according to the following published methods: human GAL3 (PCT International Publication No. WO 98/15570), human GAL1 (PCT International Publication No. WO 95/2260), human GAL2 (PCT International Publication No. WO 97/26853).

Human $5HT_{1B}$, $5HT_{1D}$, $5HT_{1E}$, $5HT_{1F}$, and $5HT_7$ Receptors: The cell lysates of LM(tk-) clonal cell line stably transfected with the genes encoding each of these 5HT receptor-subtypes were prepared as described above. Cell membranes were suspended in 50 mM Tris-HCl buffer (pH 7.4 at 37° C.) containing 10 mM MgCl2, 0.2 mM EDTA, 10 M pargyline, and 0.1% ascorbate. The affinities of compounds were determined in equilibrium competition binding assays by incubation for 30 minutes at 37° C. in the presence of 5 nM [$^3$H]-serotonin. Nonspecific binding was determined in the presence of 10 µM serotonin. The bound radioligand was separated by filtration through GF/B filters using a cell harvester.

Human $5HT_{2A}$ Receptor: The coding sequence of the human $5HT_{2A}$ receptor was obtained from a human brain cortex cDNA library, and cloned into the cloning site of pCEXV-3 eukaryotic expression vector. This construct was transfected into COS-7 cells by the DEAE-dextran method (Cullen, 1987). Cells were harvested after 72 hours and lysed by sonication in 5 mM Tris-HCl, 5 mM EDTA, pH 7.5. The cell lysates were subjected to centrifugation at 1000 rpm for 5 minutes at 4° C., and the supernatant was subjected to centrifugation at 30,000×g for 20 minutes at 4° C. The pellet was suspended in 50 mM Tris-HCl buffer (pH 7.7 at room temperature) containing 10 mM MgSO4, 0.5 mM EDTA, and 0.1% ascorbate. The affinity of compounds at $5HT_{2A}$ receptors were determined in equilibrium competition binding assays using [$^3$H]ketanserin (1 nM). Nonspecific binding was defined by the addition of 10 μM mianserin. The bound radioligand was separated by filtration through GF/B filters using a cell harvester.

$5-HT_{1A}$ Receptor: The cDNA corresponding to the $5-HT_{1A}$ receptor open reading frames and variable non-coding 5'- and 3'-regions, was cloned into the eukaryotic expression vector pCEXV-3. These constructs were transfected transiently into COS-7 cells by the DEAE-dextran method (Cullen, 1987), and harvested after 72 hours. Radioligand binding assays were performed as described above for the $5-HT_{2A}$ receptor, except that $^3$H-8-OH-DPAT was used as the radioligand and nonspecific binding was determined by the addition of 10 μM mianserin.

Other 5-HT Receptors: Other serotonin receptor binding assays were performed according to published methods: rat $5HT_{2C}$ receptor (Julius et al., 1988); and $5-HT_6$ (Monsma, et al., 1993). The binding assays using the $5-HT_4$ receptor were performed according to the procedures described in U.S. Pat. No. 5,766,879, the disclosure of which is hereby incorporated by reference in its entirety into this application.

Other receptors: Cell membranes expressing human dopamine $D_1$, $D_2$, $D_4$ and rat $D_3$ receptors were purchased through BioSignal, Inc. (Montreal, Canada). Binding assays using the histamine $H_1$ receptor; dopamine receptors; and $\alpha_{1A}$, $\alpha_{1B}$, and $\alpha_2$ adrenergic receptors may be carried out according to the procedures described in U.S. Pat. No. 5,780,485, the disclosure of which is hereby incorporated by reference in its entirety into this application. Binding assays using the dopamine $D_5$ receptor may be carried out according to the procedures described in U.S. Pat. No. 5,882,855, the disclosure of which is hereby incorporated by reference in its entirety into this application. Binding assays for the human $\alpha_{1D}$ adrenergic receptor may be carried out according to the procedures described in U.S. Pat. No. 6,156,518, the disclosure of which is hereby incorporated by reference in its entirety into this application.

The methods to determine binding affinity at native transporters are described in the following publications: 5HT transporter and NE transporter (Owens et al., 1997), and DA transporter (Javitch et al, 1984).

The methods to determine activity at monoamine oxidase enzymes (for example, central $MAO_A$ and $MAO_B$) are described by Otsuka and Kobayashi, 1964, and were performed by NovaScreen (Hanover, Md.) with the following modifications.

Central Monoamine Oxidase A Enzyme Assay: Rat brain was used as the enzyme source. The enzyme source was pre-incubated with reference compound (RO 41-1049), test compound (Example 92), and subtype selective blocker (100 nM deprenyl) for 60 minutes at 37° C. in 50 mM $KPO_4$ containing 50 μM EDTA and 10 μM dithiothreitol (pH 7.2 at 25° C.). Substrate ([$^{14}$C]Serotonin, 45-60 Ci/mmol) was then added and incubated for 30 minutes. The reaction was stopped by the addition of 0.5 ml of 1-2M citric acid. Radioactive product was extracted into xylene/ethyl acetate fluor and compared to control values by scintillation spectrophotometry in order to ascertain any interactions of test compound with central $MAO_A$.

Central Monoamine Oxidase B Enzyme Assay: Rat brain was used as the enzyme source. The assay was performed as described above for central $MAO_A$, except the reference compound was RO 166491 and the subtype selective blocker was 100 nM clorgyline. Also, the substrate ([$^{14}$C]Phenylethylamine, 0.056 Ci/mmol) was added and incubated for 10 minutes.

Materials

Cell culture media and supplements were from Specialty Media (Lavallette, N.J.). Cell culture plates (150 mm and 96-well microtiter) were from Corning (Corning, N.Y.). Polypropylene 96-well microtiter plates were from Co-star (Cambridge, Mass.). Bovine serum albumin (ultra-fat free, A-7511) was from Sigma (St. Louis, Mo.). All radioligands were from New England Nuclear (Boston, Mass.). Commercially available peptides and peptide analogs were either from Bachem California (Torrance, Calif.) or Peninsula (Belmont, Calif.). All other materials were reagent grade.

Data Analysis

Binding data were analyzed using nonlinear regression and statistical techniques available in the GraphPAD Prism package (San Diego, Calif.). Enzymatic assay data were derived from a standard curve of reference compound data.

The selectivity ratios for compounds of the claimed invention were calculated from the binding data presented in Tables 1-4, Table 7 and Table 9 of the subject application. More specifically, these ratios were calculated by dividing (a) the binding affinity ($K_i$ value) of said compound to a particular receptor or transporter by (b) the binding affinity ($K_i$ value) of said compound to the human GAL3 receptor. The data presented in Table 8 and Table 10, hereinafter, were calculated using the above described method.

For example, the GAL3/GAL1 selectivity ratio of 10-fold recited in claim 110 of the subject application is characteristic of Example 34. This binding ratio was calculated by dividing (a) the $K_i$ value of 912 for the binding of Example 34 to the GAL1 receptor (see Table 1) by (b) the $K_i$ value of 23 for the binding of Example 34 to the human GAL3 receptor, thus obtaining the result of 39. Therefore the GAL3/GAL1 binding ratio for Example 34 was determined to be greater than 10-fold.

B. Results

The compounds described in the claimed invention were assayed using a panel of cloned receptors and native transporters. The preferred compounds were found to be selective GAL3 antagonists. The binding affinities and selectivity ratios of several compounds are illustrated in Tables 7-10.

TABLE 7

Antagonist binding affinity (Ki) at the human GAL3 receptor vs. serotonin receptors and several transporters.

| Example | hGAL3 Ki (nM) | h5HT$_{1A}$ Ki (nM) | h5HT$_{1B}$ Ki (nM) | h5HT$_{1D}$ Ki (nM) | h5HT$_{1E}$ Ki (nM) | h5HT$_{1F}$ Ki (nM) | h5HT$_{2A}$ Ki (nM) | r5HT$_{2C}$ Ki (nM) | h5HT$_4$ Ki (nM) | h5HT$_6$ Ki (nM) | h5HT$_7$ Ki (nM) | r5HT Uptk Ki (nM) | rNE Uptk Ki (nM) | rDA Uptk Ki (nM) |
|---|---|---|---|---|---|---|---|---|---|---|---|---|---|---|
| 11 | 91 | 4682 | 101 | 102 | 9174 | 1780 | 6708 | 802 | 1308 | 800 | 1012 | 1595 | * | 5430 |
| 15 | 73 | 5098 | 487 | 1272 | 11038 | 4192 | 11270 | 572 | 2301 | 1457 | 2527 | 1737 | * | 24500 |
| 17 | 87 | 3477 | 407 | 1032 | 33523 | 10271 | 7157 | 562 | 2606 | 711 | 1797 | 719 | 18325 | 27200 |
| 22 | 28 | 9714 | 1981 | 1852 | 13230 | 5773 | 20689 | 1717 | 2457 | 2264 | 2672 | 8483 | 13085 | 7480 |
| 34 | 23 | * | 1059 | 2976 | 28282 | 4803 | * | 2076 | 20762 | 38921 | 4439 | 37462 | * | 3900 |
| 49 | 211 | 29187 | 8447 | 16872 | 23886 | 8894 | * | 6687 | 13230 | 13 | 12268 | 40666 | 37585 | 2010 |
| 60 | 86 | 33666 | 5461 | 9198 | 1180 | 2124 | 26118 | 1781 | 1180 | 47536 | 3235 | 25274 | 46108 | 14500 |
| 77 | 79 | 5472 | 365 | 716 | 5888 | 3237 | 2242 | 456 | 1324 | 503 | 1547 | 821 | 28083 | 2790 |
| 92 | 38 | * | 11323 | 32139 | 18934 | 5290 | * | ND | 72 | * | ND | 45111 | 33879 | 17800 |
| 94 | 49 | * | 3349 | 10764 | 25227 | 5683 | * | 4099 | 4120 | 3647 | 8018 | 12961 | 4876 | 2200 |
| 95 | 29 | 28288 | 5226 | 16018 | 27211 | 4446 | * | 3471 | 3031 | 21507 | 11638 | * | 6101 | 12000 |
| 97 | 51 | * | 5057 | 14235 | 22692 | 4157 | * | 1950 | 2550 | 29131 | 11283 | 36308 | 4412 | 8440 |
| 98 | 38 | 24576 | 2419 | 9118 | 16240 | 3359 | * | 2260 | 1210 | 14018 | 8464 | 36329 | 5496 | 7430 |

* = >50000
ND = Not determined

TABLE 8

Antagonist selectivity ratios determined for the human GAL3 receptor vs. serotonin receptors and several transporters.

| Example | hGAL3 | h5HT$_{1A}$ | h5HT$_{1B}$ | h5HT$_{1D}$ | h5HT$_{1E}$ | h5HT$_{1F}$ | h5HT$_{2A}$ | r5HT$_{2C}$ | h5HT$_4$ | h5HT$_6$ | h5HT$_7$ | r5HT Uptk | rNE Uptk | rDA Uptk |
|---|---|---|---|---|---|---|---|---|---|---|---|---|---|---|
| 11 | 1 | >30 | 1 | 1 | >100 | 20 | >30 | 9 | 14 | 9 | 11 | 18 | >100 | >30 |
| 15 | 1 | >30 | 7 | 17 | >100 | >30 | >100 | 8 | >30 | 20 | >30 | 24 | >100 | >100 |
| 17 | 1 | >30 | 5 | 12 | >100 | >100 | >100 | 6 | 30 | 8 | 21 | 8 | >100 | >100 |
| 22 | 1 | >100 | >30 | >30 | >100 | >100 | >100 | >30 | >30 | >30 | >30 | >100 | >100 | >100 |
| 34 | 1 | >100 | >30 | >100 | >100 | >100 | >100 | >30 | >100 | >100 | >100 | >100 | >100 | >100 |
| 49 | 1 | >100 | >30 | >30 | >100 | >30 | >100 | >30 | >30 | 0 | >30 | >100 | >100 | 10 |
| 60 | 1 | >100 | >30 | >100 | 14 | 25 | >100 | 21 | 14 | >100 | >30 | >100 | >100 | >100 |
| 77 | 1 | >30 | 5 | 9 | >30 | >30 | 28 | 6 | 17 | 6 | 20 | 10 | >100 | >30 |
| 92 | 1 | >100 | >100 | >100 | >100 | >100 | >100 | ND | 2 | >100 | ND | >100 | >100 | >100 |
| 94 | 1 | >100 | >30 | >100 | >100 | >100 | >100 | >30 | >30 | >30 | >100 | >100 | >30 | >130 |
| 95 | 1 | >100 | >100 | >100 | >100 | >100 | >100 | >100 | >100 | >100 | >100 | >100 | >100 | >100 |
| 97 | 1 | >100 | >30 | >100 | >100 | >100 | >30 | >100 | >30 | >30 | >100 | >100 | >30 | >100 |
| 98 | 1 | >100 | >30 | >100 | >100 | >30 | >100 | >30 | >30 | >100 | >100 | >100 | >100 | >100 |

ND = Not determined

TABLE 9

Antagonist binding affinity (Ki) at the human GAL3 receptor vs. alpha-adrenergic, dopamine, and histamine receptors.

| Example | hGAL3 Ki (nM) | hα$_{1A}$ Ki (nM) | hα$_{1B}$ Ki (nM) | hα$_{1D}$ Ki (nM) | hα$_{2A}$ Ki (nM) | hα$_{2B}$ Ki (nM) | hα$_{2C}$ Ki (nM) | hD$_1$ Ki (nM) | hD$_2$ Ki (nM) | rD$_3$ Ki (nM) | hD$_4$ Ki (nM) | hD$_5$ Ki (nM) | hH$_1$ Ki (nM) |
|---|---|---|---|---|---|---|---|---|---|---|---|---|---|
| 11 | 91 | 926 | 1436 | 264 | 1819 | 10235 | 3004 | 79 | 782 | 2139 | 4828 | 64 | ND |
| 15 | 73 | 3392 | 853 | 480 | 14413 | 24515 | 8202 | 344 | 2184 | 8809 | 13151 | 78 | ND |
| 17 | 87 | 996 | 1167 | 221 | 3523 | 38732 | 10269 | 516 | 1808 | 2477 | 22227 | 89 | ND |
| 22 | 28 | 1278 | 1582 | 368 | 906 | 5757 | 2737 | 128 | 1501 | 5664 | 11621 | 63 | ND |
| 34 | 23 | 3756 | 15004 | 1240 | 3679 | 15488 | 8832 | 290 | 2500 | 9922 | 18716 | 111 | ND |
| 49 | 211 | 6646 | 18852 | 678 | 4731 | 25374 | 9244 | 3781 | 5940 | 13964 | 45824 | 328 | ND |
| 60 | 86 | 13604 | 40615 | 4231 | 10838 | * | 7200 | 600 | 26815 | 15295 | 48756 | 538 | 39909 |
| 77 | 79 | 834 | 452 | 217 | 315 | 7783 | 634 | 60 | 910 | 2716 | 504 | 122 | ND |
| 92 | 38 | ND | * | 17175 | 21943 | * | * | * | 41369 | 48180 | 41369 | 29290 | 39909 |
| 94 | 49 | 12715 | 31135 | 4027 | 12718 | 45378 | 47863 | 2145 | 6249 | 423 | * | 727 | ND |
| 95 | 29 | 13137 | 32494 | 3468 | 30072 | * | 48552 | 4394 | 9716 | 466 | * | 2590 | ND |
| 97 | 51 | 16921 | 45845 | 6454 | 13569 | * | * | 25115 | * | 9716 | * | 10069 | ND |
| 98 | 38 | 14500 | 31693 | 1891 | 23236 | * | * | 2524 | 3788 | 592 | * | 1199 | ND |

* = >50000
ND = Not determined

TABLE 10

Antagonist selectivity ratios determined for the human GAL3 receptor vs. alpha-adrenergic, dopamine, and histamine receptors.

| Example | hGAL3 | hα$_{1A}$ | hα$_{1B}$ | hα$_{1D}$ | hα$_{2A}$ | hα$_{2B}$ | hα$_{2C}$ | hD$_1$ | hD$_2$ | rD$_3$ | hD$_4$ | hD$_5$ | hH$_1$ |
|---|---|---|---|---|---|---|---|---|---|---|---|---|---|
| 11 | 1 | 10   | 16   | 3    | 20   | >100 | >30  | 0.9  | 9    | 24   | >30  | 0.7  | ND |
| 15 | 1 | 46   | 12   | 7    | >100 | >100 | >100 | 5    | 30   | >100 | >30  | 1    | ND |
| 17 | 1 | 11   | 13   | 3    | >30  | >100 | >100 | 6    | 21   | 28   | >100 | 1    | ND |
| 22 | 1 | >30  | >30  | 13   | >30  | >100 | >100 | 5    | >30  | >100 | >100 | 2    | ND |
| 34 | 1 | >100 | >100 | >30  | >100 | >100 | >100 | 13   | >100 | >100 | >100 | 5    | ND |
| 49 | 1 | >30  | >30  | 3    | 22   | >100 | >30  | 18   | 28   | >30  | >100 | 2    | ND |
| 60 | 1 | >100 | >100 | >30  | >100 | >100 | >30  | 7    | >100 | >100 | >100 | 6    | >100 |
| 77 | 1 | 11   | 6    | 3    | 4    | >30  | 8    | 0.8  | 11   | >30  | 6    | 2    | ND |
| 92 | 1 | ND   | >100 | >100 | >100 | >100 | >100 | >100 | >100 | >100 | >100 | >100 | >100 |
| 94 | 1 | >100 | >100 | >30  | >100 | >100 | >100 | >30  | >100 | 9    | >100 | 15   | ND |
| 95 | 1 | >100 | >100 | >100 | >100 | >100 | >100 | >100 | >100 | 16   | >100 | >30  | ND |
| 97 | 1 | >100 | >100 | >100 | >100 | >100 | >100 | >100 | >100 | >100 | >100 | >100 | ND |
| 98 | 1 | >100 | >100 | >30  | >100 | >100 | >100 | >30  | >100 | 16   | >100 | >30  | ND |

ND = Not determined

The activity of Example 92 was determined for central MAO$_A$ and central MAO$_B$ using the methods described hereinabove.

The results, expressed as percent inhibition, are illustrated in Table 11.

TABLE 11

Percent inhibition of Example 92 in the central monoamine oxidase enzyme assay

| TARGET | SPECIES | % INHIBITION |
|---|---|---|
| Monoamine Oxidase A (central) | Rat | 10 |
| Monoamine Oxidase B (central) | Rat | 1 |

IV. GAL3 Receptor Localization

A. Materials And Methods

Preparation of the Anti-GAL3 Antiserum

BioSource International, Hopkinton, Mass. performed the immunization and maintenance of rabbits. Following a preimmune bleed, one peptide for each GAL receptor was injected into a pair of New Zealand white rabbits. The peptide sequences was chosen based on sequence specificity and immunogenicity. The rabbit anti-GAL3 antiserum were raised against C-terminal epitopes corresponding to amino acids 357-370 (Genbank accession number AF073798). The peptides were conjugated to the carrier KLH (keyhole limpet hemocyanin) by a cross linker and subcutaneously injected into the rabbits. The generation of the anti-GAL3 antiserum required OVA followed by a third series of injections with the GAL3 peptide conjugated to tetanus toxoid (TTOX). All injections were done using the Freund's Adjuvant System. Once immunoreactivity was established (see below) the antiserum was affinity purified by passing it over an agarose based column thiol coupled to its antigenic peptide. The column washed and the antiserum was eluted using a low pH glycine buffer. The purified material was dialyzed, the optical density is taken at 280λ and the purified antiserum was frozen.

Characterization of the Anti-GAL3 Antiserum

Recombinant GAL1, GAL2, and GAL3 Receptor Transfected Cells

To determine the ability of the GAL3 antiserum to recognize only the GAL3 receptor protein in vitro, COS-7 cells were grown on poly-L-lysine-coated plastic chamber slides (Nalge Nunc International, Naperville, Ill.) and transfected with recombinant rat GAL receptors (Genbank accession numbers U30290, AF010318, AF073798, respectively) or expression vector only (for mock-transfected cells) as previously described by Borowsky et al. (1999). Receptor expression was confirmed by radioligand binding. Briefly, a subset of slides was washed three times in binding buffer (50 mM Tris, pH 7.5, 5 mM MgCl$_2$, 1 mM EDTA, 0.1% bovine serum albumin, and 0.1% bacitracin) and incubated in 500 µl binding buffer containing porcine $^{125}$I-galanin (625,000 dpm) plus or minus 10 µM porcine galanin. After incubation at room temperature for 1 hour, the binding buffer was aspirated and slides were rinsed three times in ice cold 50 mM Tris, pH 7.5. Cells were solubilized in 1 ml of 0.1 N NaOH and 0.05% sodium deoxycholate for 30 minutes then transferred to test tubes for gamma counting of $^{125}$I. To evaluate antibody activity another subset of slides were washed with phosphate buffered saline (PBS) (Sigma, St. Louis, Mo.) to remove the medium and fixed with 4% paraformaldehyde (PFA) (Sigma, St. Louis, Mo.) then permeabilized using 0.2% Triton X-100/PBS and incubated in 3% normal goat serum for 30 minutes to minimize nonspecific binding of the primary antibody. Cells were incubated overnight at 4° C. with the anti-GAL3 antiserum (1:1000 dilution). The cells were rinsed three times with PBS, incubated for 30 minutes at 25° C. with goat anti-rabbit IgG (1:200 dilution) (Santa Cruz Biotechnology, Santa Cruz, Calif.), rinsed and processed using the peroxidase-antiperoxidase (PAP) reaction of Sternberger et al. (1982). Control experiments for antibody specificity were (1) incubation of the cells in primary antiserum that had been preabsorbed with the respective antigenic peptide (20 µg/ml), (2) incubation without the primary antiserum, or (3) incubation with the primary antiserum replaced by normal goat serum.

Western Blotting

Membranes were prepared from COS-7 cells transiently transfected with the rat recombinant receptors GAL1, GAL2, and GAL3 as previously described (Borowsky et al., 1999). Transfected cells were lysed by sonication in ice-cold sonication buffer (20 mM Tris-HCl, pH 7.7, 5 mM EDTA). Cell lysates were subjected to centrifugation at 4° C. for 10 minutes at 200 g. The supernatant was then fractionated by centrifugation at 4° C. for 18 minutes at 32,000 g. The resulting membrane pellet was suspended into 50 mM Tris, pH 7.5, 5 mM $MgCl_2$, 1 mM EDTA. Protein samples (1-10 µg) were solubilized in 2× Laemmli buffer (Bio-Rad, Hercules, Calif.) and fractionated by SDS-PAGE in 10% polyacrylamide gels. Proteins were transferred to polyvinylidine difluoride membranes for immunoblot analysis in ice-cold 25 mM Tris, pH 8, 192 mM glycine, 20% methanol as previously described by Harlow and Lane (1999). Blots were incubated for 1 hour at 25° C. in blocking buffer composed of 5% non-fat dried milk in TTBS (0.1% Tween-20, 500 mM NaCl, 20 mM Tris, pH 7.5) then for 16 hours at 25° C. with the receptor-specific polyclonal antibody (1:1000 dilution in blocking buffer) (0.25 mg/ml for GAL2 or 1.5 mg/ml for GAL3). Immunoreactive bands were detected with the Phototope-HRP Detection Kit for Western Blotting (New England BioLab, Beverly, Mass.) according to the protocol. Briefly, the blots were incubated with horseradish peroxidase-conjugated goat anti-rabbit IgG then developed with a mixture of LumiGLO plus hydrogen peroxide and recorded by chemiluminescence on Kodak Biomax-ML film (Kodak, Rochester, N.Y.).

Immunohistochemistry

Male Sprague-Dawley rats, (200-250 g; Charles Rivers, Rochester, N.Y.) were anesthetized by intraperitoneal injection of ketamine 20 mg/kg (RBI, Natick, Mass.) and xylazine 0.2 mg/kg (Bayer, Shawnee Mission, Kans.) then transcardially perfused with 200 ml PBS, pH 7.4 followed by 200 ml 4% PFA in PBS. The brains and spinal cords were removed, blocked, and postfixed in the same fixative for 4 hours at 4° C. then cryoprotected in 30% sucrose in PBS at 4° C. for 48 hours before freezing on dry ice. Coronal brain sections and transverse spinal cord sections were cut at 30 µm using a freezing microtome. Tissue sections were immediately immersed in PBS and stored at 4° C. until use. Sections were processed free-floating according to the protocol outlined in NEN Life Science Products TSA (Tyramide Signal Amplification) Indirect Kit. Briefly, tissue sections were permeabilized in 0.2% Triton X-100 (Sigma, St. Louis, Mo.)/PBS, incubated in 1% hydrogen peroxide (Sigma, St. Louis, Mo.)/PBS to remove endogenous peroxidase activity then blocked in TNB Buffer (0.1 M Tris-HCl, pH 7.5, 0.15 M NaCl, and 0.5% Blocking Reagent. Sections were incubated for 24 hours at 4° C. in either the anti-GAL2 or anti-GAL3 antiserum (1:100). Following incubation with the primary antiserum, the tissue sections were washed in TNT Buffer (0.1 M Tris-HCl, pH 7.4, 0.15 M NaCl, 0.05% Tween 20) followed by incubation at 25° C. for 30 minutes with horseradish peroxidase (HRP)-conjugated goat anti-rabbit immunoglobulin (1:200) (Sternberger Monoclonals Inc., Lutherville, Md.). Tissue sections were rinsed in TNT Buffer and incubated in a solution containing biotinylated tyramide to amplify the signal then rinsed in TNT buffer and incubated with HRP-conjugated to streptavidin at 25° C. for 30 minutes. An immunoperoxidase reaction was done by incubating the section in 3,3'-diaminobenzidine (DAB) (0.05%) in 0.1 mM Tris, pH 7.4 and adding hydrogen peroxide to 0.006% immediately before use. The reaction was stopped in water and the sections mounted on microscopic slide with mounting medium (40% ethanol:gelatin) and counterstained with Cresyl violet then coverslipped for light microscopy.

Optimal GAL3 antibody concentrations (1:200) for rat brain sections were determined in preliminary titration experiments. Experimental controls in the tissue sections included (1) incubation in normal rabbit serum or (2) omission of the primary antiserum.

Analysis

COS-7 cells and tissue sections were examined using a Zeiss Axioscope. A total of 6 male rats were examined with the anti-GAL3 antiserum. The identification of GAL3-LI in the transfected cells and brain regions was based on the presence of immunoreactivity appearing as a brownish precipitate in individual cells and their projections or in the neuropil of the tissue by light microscopy. The descriptions of neuroanatomic boundaries are based on the atlas of Paxinos and Watson (1998).

B. Results

Characterization of the GAL3 Antiserum

Recombinant GAL1, GAL2, and GAL3 Receptor Transfected Cells

The ability of the anti-GAL3 antiserum to recognize only the GAL3 receptor protein in vitro was established by performing immunocytochemistry on COS-7 cells transiently transfected with the recombinant receptor proteins for the rat GAL1, GAL2, and GAL3, or mock-transfected with vector only. Specific porcine $^{125}$I-galanin binding was detected for all transfectants except mock-transfected cells. An immune response was detected only in the COS-7 cells incubated with the antiserum generated for the particular recombinant receptor. Specifically, no immune reaction was observed with the anti-GAL3 antiserum (1:1000) in GAL1 or GAL2 transfected cells. Furthermore, no visible immune reaction was detected in the mock-transfected cells. Incubation of the cells in primary antiserum that had been preabsorbed with the antigenic peptide (20 µg/ml) or without the primary antiserum or with the primary replaced by normal goat serum did not result in an immune response.

Taken together, these data demonstrate that the anti-GAL3 antiserum recognizes the receptor against which it was generated and does not show cross reactivity with other known GAL receptors.

Western Blots

To determine the specificity of the anti-GAL3 antiserum, COS-7 cells were transiently transfected either with recombinant rat GAL2 or GAL3 receptors or with expression vector only; membranes were then isolated for evaluation by immunoblotting (see FIG. 5). The anti-GAL3 antiserum labeled proteins in membranes only from rat GAL3-transfected cells; a predominant band was evident with an apparent molecular weight of approximately 56 kDa (FIG. 5), somewhat higher than the amino acid-derived value of 40.4 kDa. (For comparison, apparent molecular weights determined by SDS-PAGE are 56 kDa (Servin et al., 1987) or 54 kDa (Chen et al., 1992) for native GAL receptors purified from rat brain and 54 kDa (Amiranoff et al., 1989) for native GAL receptors purified from Rin m SF cells. These values are all higher than the amino acid-derived value any known GAL receptor subtype, including the value of 38.9 kDa for rat GAL1 (Parker et al., 1995). The apparently high molecular weight observed for rat GAL3 very likely reflects post-translational processing such as glycosylation; note that rat GAL3 contains multiple N-terminal glycosylation sites (Smith et al., 1998). Relative to the predominant band, additional species of higher molecular weight as well as lower molecular weight were labeled by the corresponding antiserum (FIG. 5). These are presumably receptor-related species composed of protein aggregates of C-terminal fragments, as they are absent in mock-transfected cells.

Immunohistochemical Distribution of GAL3-LI in the CNS

GAL3-like immunoreactivity (GAL3-LI) was observed in many regions of the brain, specifically, the neocortex, septum, hippocampus, amygdala, and brainstem (see Table 12). Throughout the brain and spinal cord GAL3-LI was found to be associated with neuronal profiles however, there was neuropil staining observed in several brain regions. Several regions of the CNS almost exclusively expressed GAL3-LI, specifically the accumbens nucleus, dorsal raphe, ventral tegmental area (Table 12). There was no observable staining of the fiber tracts.

The specificity of the anti-GAL3 antiserum was determined in tissue sections by (1) omission of the primary antiserum or (2) incubation with normal rabbit serum. No specific staining was observed in either condition. Preabsorption of the GAL3 primary antiserum with the antigenic peptide (10 μg/ml) decreased but did not completely block staining in the tissue sections as in the transfected cells. This was most likely related to the different localization approaches. In the transiently transfected COS-7 cells the expression of GAL3 receptor protein was relatively high therefore, indirect immunocytochemistry with no amplification was used. In contrast, GAL3 receptor protein expression is presumed to be relatively lower in the tissue sections and for that reason the TSA (amplification) technique was employed. It is possible that because of the amplification (1000-fold) in the TSA technique even small amounts of unabsorbed antiserum may result in a signal.

Distribution of GAL3-LI in the Rat CNS

Cerebral Cortex

GAL3-LI was widespread in the cerebral cortex and the distribution pattern extended rostrocaudally. A weak to moderate GAL3-LI was seen in numerous cell bodies in the anterior cingulate cortex.

Septal Region

An extensive and densely stained fiber network was seen throughout the entire lateral, intermediate and medial septal nuclei. The dorsal division of the lateral septum contained scarce moderately GAL3-like immunoreactive somata.

Basal Ganglia

Numerous moderately GAL3-like immunoreactive cell bodies and fibers were present in the shell and core of the accumbens nucleus. The cell bodies of the subthalamic nucleus, a relay nucleus in the basal ganglia, contained weak GAL3-LI.

Amygdala and Extended Amygdala

In general, GAL3-LI was weak throughout the amygdala. Scattered cell bodies and fibers exhibited weak staining in several nuclei. Very fine GAL3-like immunoreactive fibers with scattered moderately labeled cells were detected in the central amygdaloid nucleus.

Midbrain/Mesencephalon

Labeled cells were detected within the dorsal raphe and projections from these cells were seen converging toward the midline of the raphe. Moderately immunoreactive scattered cells were evident in the ventral tegmental area.

Brain Stem

Intense staining was observed in cell bodies in the locus coeruleus.

The distribution of rat GAL3 protein in the CNS using receptor subtype selective polyclonal antibodies and tyramide signal amplification (TSA) immunocytochemistry is illustrated in Table 12. These were qualitative evaluations for the rat GAL3 receptor protein distribution based on the relative intensity of the chromogen (3,3'-diaminobenzidine) observed in individual cells at the microscopic level.

A total of 4 rat brains were analyzed for this study. As shown in Table 12, the strength of the signal obtained in various regions of the rat brain was graded as weak (+) or moderate (++) or intense (+++).

TABLE 12

| REGION | cells | fibers | Potential Therapeutic Application |
|---|---|---|---|
| Telencephalon | | | |
| Frontal cortex | ++ | | Anxiety/Depression |
| Cingulate cortex | ++ | | Anxiety/Depression |
| Basal ganglia | | | |
| Accumbens nucleus | ++ | − | Treatment of the positive symptoms of schizophrenia Treatment of drug addiction. This region is particularly sensitive to psychoactive drugs. Anxiety/depression Relief of fear |
| Septal Region | | | |
| Lateral septal nucleus, dorsal | + | ++ | |
| Lateral septal nucleus, ventral | + | ++ | |
| Intermediate septal nucleus | − | ++ | |
| Medial septal nucleus | | ++ | |
| Amygdala and extended Amygdala | | | Treatment of anxiety, panic attack, and depression. Treatment of disorders of integrated behaviors such as defense, ingestion, reproduction, and learning. |
| Central nucleus | ++ | ++ | Fear and anxiety |
| Mesencephalon | | | |
| Dorsal raphe | ++ | − | Depression/Analgesia |
| Ventral tegmental area | ++ | − | Depression |
| Brainstem/Pons/Medulla | | | |
| Locus coeruleus | +++ | − | Modulation of noradrenergic transmission. Treatment of depression |

The GAL3 antiserum was characterized using recombinant GAL receptors in transiently transfected COS-7 cells and, western blot analysis and the specificity of the GAL3 antiserum to recognize only the cognate receptor in vitro was established. The anatomical distribution of the GAL3 receptor protein in the rat CNS was determined using a modified immunohistochemical technique to enhance sensitivity and delectability via tyramide signal amplification (Toda et al., 1999).

The results indicate that the expression GAL3-LI was primarily found in neuronal profiles with neuropil labeling detectable in several areas. In general, the distribution of GAL3-LI is in good agreement with the reported distribution for galanin-LI, galanin binding sites, and GAL3 mRNA in the rat brain (for recent review, Branchek et al., 2000). Overall, GAL3-LI was extensively distributed throughout the brain. Paralleling the distribution of galanin binding sites GAL3-LI was observed in ventral regions of the brain.

The localization of the GAL3 protein in the dorsal raphe and locus coeruleus suggests a potential therapeutic application of galanin receptor antagonists in the treatment of depression by attenuating galanin's inhibitory tone on both of these regions.

A decrease in central serotonin (5-HT) neurotransmission has been implicated in depression. GAL3 antagonists could possibly act via GAL3 receptors on the cell bodies of dorsal raphe neurons to increase firing rate of raphe neurons thus increasing 5-HT release in the telencephalon and diencephalon. Another possible site of action for a GAL3 antagonist could be on postsynaptic GAL3 receptors in the limbic forebrain to block the putative ability of galanin to negatively regulate $5\text{-HT}_{1A}$ receptor transmission (Misane et al, 1998).

Unlike the dorsal raphe cells, the cells of the locus coeruleus express abundant galanin under normal conditions and it has been proposed that galanin may be released from dendrites and soma of the noradrenergic cell bodies (for review, Hökfelt et al., 1998). The ascending afferent projections of the locus coeruleus are extensive throughout the brain. Changes in the noradrenergic system have been hypothesized to be involved in depression-related behaviors and symptoms (for review, Weiss et al., 1998). The ventral tegmental area (VTA) receives projections from the locus coeruleus that have been reported to co-localize galanin and noradrenaline. It has been proposed that in certain pathological states (ex. stress induced depression) galanin released from noradrenergic terminals in the VTA inhibits dopaminergic neurons in the region that results in decreased dopamine release in the forebrain regions, particularly the accumbens nucleus and prefrontal cortex. This decrease in dopamine release produces a decreased motor activation and anhedonia. GAL3 has been identified in all of these regions and thus presents itself as a potential therapeutic target in the treatment of depression. Drugs that would effectively decrease galanin's release in the VTA whether at the level of the locus coeruleus (somatodendritic GAL3 receptors to decrease the activity of LC cells) or in the VTA itself (presynaptically on NE/GAL terminals in the VTA or via GAL3 receptors on VTA-DA neurons to prevent the hyperpolarization VTA-DA cells by released galanin) would produce an antidepressant effect.

REFERENCES

American Psychiatric Association (1994) Diagnostic and Statistical Manual of Mental Disorders, Fourth Edition. American Psychiatric Association, Washington, D.C.

Amiranoff, B., et al., (1989) Galanin receptor in the rat pancreatic beta cell line Rin m 5F. Molecular characterization by chemical cross-linking. *J. Biol. Chem.*, 264(34): 20714-20717.

*Asymmetric Synthesis* (1983) Vol: 2-5, Academic Press, Editor Morrison, J.

Bakker, R. A., et al., (2000) Constitutive activity of the histamine H1 receptor reveals inverse agonism of histamine H1 receptor antagonists. *Eur. J. Pharmacol.*, 387: R5-R7.

Borowsky, B., et al., (1999) Cloning and characterization of the human galanin GALR2 receptor. *Peptides*, 19: 1771-1781.

Bradford, M. M. (1976) A rapid and sensitive method for the quantitation of microgram quantities of protein utilizing the principle of the protein-dye binding. *Anal. Biochem.*, 72: 248-254.

Branchek, T. A., et al., (2000) Galanin receptor subtypes. *Trends in Pharm. Sci.*, 21: 109-116.

Bryant, W. M. III, et al., (1993) *Synthetic Communications*, 23: 1617-1625.

Chen, Y., et al., (1992) Solubilization and molecular characterization of active galanin receptors from rat brain. *Biochemistry*, 31(8): 2415-2422.

Coppola, G. M. (1987) *Journal of Heterocyclic Chemistry*, 24: 1249.

Cullen, B. (1987) Use of eukaryotic expression technology in the functional analysis of cloned genes. *Methods Enzymol.*, 152: 685-704.

deLigt, R. A., et al., (2000) Inverse agonism at G protein-coupled receptors: (patho)physiological relevance and implications for drug discovery. *Br. J. Pharmacol.*, 130(1): 1-12.

De Weille, J. R., et al., (1989) Galanin inhibits dopamine secretion and activates a potassium channel in pheochromocytoma cells. *Brain Res.*, 485: 199-203.

Detke, M. J., et al., (1995) Active behaviors in the rat forced swim test differentially produced by serotonergic and noradrenergic antidepressants. *Psychopharmacology*, 121: 66-72.

Ennis, M. D. and Ghazal, N. B., (1992) The synthesis of (+) and (−)-flesinoxan: Application of enzymatic resolution methodology. *Tetrahedron Lett.*, 33: 6287-6290.

File, S. E. (1985) Animal models for predicting clinical efficacy of anxiolytic drugs: social behaviour. *Neuropsychobiology*, 13: 55-62.

File, S. E. and Pellow, S. (1984) The anxiogenic action of FG 7142 in the social interaction test is reversed by chlordiazepoxide and Ro-15-1788 but not by CGS 8216. *Archs. Int. Pharmacodyn. Ther.*, 271: 198-205.

File, S. E. and Pellow, S. (1983) The anxiogenic action of a convulsant benzodiazepine: reversal by chlordiazepoxide. *Brain Res.*, 278: 370-372.

File, S. E., et al., (1982) The anxiogenic action of benzodiazepine-like antagonists. *Neuropharmacology*, 21: 1033-1037.

File, S. E. (1980) The use of social interaction as a method for detecting anxiolytic activity of chlordiazepoxide-like drugs. *J. Neurosci. Methods*, 2: 219-238.

File, S. E. and Hyde, J. R. G. (1979) A test of anxiety that distinguishes between the actions of benzodiazepines and those of other minor tranquilisers and of stimulants. *Pharmacol. Behav. Biochem.*, 11: 65-69.

File, S. E. and Hyde, J. R. G. (1978) Can social interaction be used to measure anxiety? *Br. J. Pharmacol.*, 62: 19-24.

Garden, S. J., et al., (1998). *Synthetic Communications*, 28: 1679-1689.

Glover, V. (1998) Function of endogenous monoamine oxidase inhibitors (tribulin). *J. Neural. Transm. Suppl.*, 52: 307-13.

Gopalan, C., et al., (1993) Neurochemical evidence that the inhibitory effect of galanin on tuberoinfundibular dopamine neurons is activity dependent. *Neuroendocrinology*, 58: 287-293.

Green, T. W. and Wuts, P. G. M. (1991) *Protection groups in Organic Synthesis*, second Edition John Wiley & Sons, New York.

Guy, A. P. and Gardner, C. R. (1985) Pharmacological characterisation of a modified social interaction model of anxiety. *Neuropsychobiology*, 13: 194-200.

Harlow, E. and Lane, D. (1999) *Immunoblotting*. In: Barker, P. editor. Using Antibodies: A Laboratory Manual. New York: Cold Spring Harbor Laboratory Press. p 267-309.

Herrick-Davis, K., et al., (2000) Inverse agonist activity of atypical antipsychotic drugs at human 5-Hydroxytryptamine-2C receptors. *J. Pharmacol. Exp. Ther.*, 295 (1): 226-32.

Hess, B. A. Jr. and Corbino, S. (1971) *Journal of Heterocyclic Chemistry*, 8: 161.

Hökfelt, T., et al., (1998) Galanin in Ascending Systems. *Annals of the N.Y. Acad. Sci.*, Ed. T. Hökfelt, Tamas Bartfai and J. Crawley p. 252-263.

Iversen, L. (2000) Neurotransmitter transporters: fruitful targets for CNS drug discovery. *Mol. Psychiatry*, 5(4): 357-62.

Jansson, A., et al., (1989) Centrally administered galanin reduces dopamine utilization in the median eminence and increases dopamine utilization in the medial neostriatum of the male rat. *Acta Physiol. Scand.*, 135: 199-200.

Javitch, J. A., et al, (1984) $^3$H-Mazindol binding associated with neuronal dopamine and norepinephrine uptake sites. *Molecular Pharmacology*, 26: 35-44.

Jaques, J., et al., (1981) *Eriantiomer, Racemates and Resolutions*. John Wiley & Sons.

Julius, D., et al., (1988) Molecular characterization of a functional cDNA encoding the serotonin 1c receptor. *Science*, 241: 558-564.

Kenakin, T. (1996) The classification of seven transmembrane receptors in recombinant expression systems. *Pharmacol. Rev.*, 48(3): 413-63.

Kennett, G. A., et al., (1997) Anxiolytic-like actions of the selective 5-HT$_4$ receptor antagonist SB-20470-A and SB-20766-A in rats. *Neuropharmacology*, 36 (4-5): 707-712.

Kirby, L. G. and Lucki, I. (1997) Interaction between the forced swimming test and fluoxetine treatment on extracellular 5-hydroxytryptamine and 5-hydroxyindoleacetic acid in the rat. *Stress*, 2(4): 251-263.

Leonard B E. (1996) New approaches to the treatment of depression. *J Clin Psychiatry.* 57(4): 26-33.

Lightowler, S., et al., (1994) Anxiolytic-like effect of paroxetine in a rat social interaction test. *Pharmacol. Behav. Biochem.*, 49: 281-285.

Lucki, I. (1997) The forced swimming test as a model for core and component behavioral effects of antidepressant drugs. *Behav. Pharmacol.*, 8: 523-528.

Lutz, M. and Kenakin, T. (1999) *Quantitative Molecular Pharmacology and Informatics in Drug Discovery*, John Wiley & Sons, LTD, West Sussex, England. p. 153.

Misane, I., et al., (1998) Modulation of a 5-HT1A receptor-mediated behavioral response by the neuropeptide galanin. *Ann. N.Y. Acad. Sci.*, 863: 442-444.

Monsma, F. J. Jr., et al., (1993) Cloning and expression of a novel serotonin receptor with high affinity for tricyclic psychotropic drugs. *Mol. Pharmacol.*, 43: 320-327.

Nógrádi, M. (1987) *Stereoselective Synthesis*, VCH, Editor Ebel, H.

Nordstrom, O., et al., (1987) Evidence for an inhibitory effect of the peptide galanin on dopamine release from the rat median eminence. *Neurosci. Lett.*, 73: 21-26.

Owens, M. J. (1997) Neurotransmitter receptor and transporter binding profile of antidepressants and their metabolites. *J. Pharm. Exp. Ther.*, 283: 1305-1322.

Otsuka, S. and Kobayashi, Y. (1964) A radioisotopic assay for monoamine oxidase determinations in human plasma. *Biochem. Pharmacol.*, 13: 995-1006.

Page, M. E., et al., (1999) Serotonergic mediation of the effects of fluoxetine, but not desipramine, in the rat forced swim test. *Psychopharmacology*, 147: 162-167.

Parker, E. M., et al., (1995) Cloning and characterization of the rat GALR1 galanin receptor from Rin14B insulinoma cells. *Mol. Brain. Res.*, 34: 179-189.

Paxinos, G. and Watson, C. (1986) The Rat Brain in Stereotaxic Coordinates. San Diego: Academic Press, Inc.

Porsolt, R. D. (1981) Behavioral despair. In Enna, S J (ed) *Antidepressants: neurochemical, behavioral and clinical perspectives*. Raven Press, New York, pp. 121-139.

Porsolt, R. D., et al., (1978) Behavioral despair in rats: a new model sensitive to antidepressant treatments. *Eur. J. Pharmacol.*, 47: 379-391.

Porsolt, R. D., et al., (1977) Depression: a new animal model sensitive to antidepressant treatments. *Nature*, 266: 730-732.

Razani, H., et al., (1997) 5-HT1A receptor activation: short-term effects on the mRNA expression of the 5-HT1A receptor and galanin in the raphe nuclei. *Neuroreport*, 8 (16): 3565-3570

Reneric, J. P. and Lucki, I. (1998) Antidepressant behavioral effects by dual inhibition of monoamine reuptake in the rat forced swim test. *Psychopharmacology*, 136: 190-197.

Rodgers, R. J., et al., (1997) Animal models of anxiety: an ethological perspective. *Braz. J. Med. Biol. Res.*, 30: 289-304.

Servin, A. L., et al., (1987) Identification and molecular characterization of galanin receptor sites in rat brain. *Biochem. Biophys. Res. Commun.*, 144(1); 298-306.

Seutin, V., et al., (1989) Galanin decreases the activity of locus coeruleus neurons in vitro. *Euro. J. Pharmacol.* 164: 373-376.

Smith, K. E., et al., (1998) Cloned human and rat galanin GALR3 receptors Pharmacology and activation of G-protein inwardly rectifying K+ channels. *J. Biol. Chem.*, 273 (36): 23321-223326.

Sternberger, L. A. (1982) Neurotypy: regional individuality in rat brain detected by immunocytochemistry with monoclonal antibodies. *Proc. Natl. Acad. Sci. USA*, 79: 1326-1330.

Tatsumi, M., et al., (1997) Pharmacological profile of antidepressants and related compounds at human monoamine transporters. *Eur. J. Pharmacol.*, 340 (2-3): 249-258.

Toda, Y., et al., (1999) Application of tyramide signal amplification system to immunohistochemistry: a potent method to localize antigens that are not detectable by ordinary method. *Pathol. Int.*, 49(5): 479-483.

Treit, D. (1985) Animal models for the study of anti-anxiety agents: a review. *Neurosci. Biobehav. Rev.*, 9: 203-222.

Weiss, J. M., et al., (1998) *Annals of the N.Y. Acad. Sci.*, (Ed. T. Hökfelt, Tamas Bartfai and J. Crawley) p. 364-382.

Xu, Z., et al., (1998) Galanin-5-hydroxytryptamine interactions: Electrophysiological, immunohistochemical and in situ hybridization studies on rat dorsal raphe neurons with a note on galanin R1 and R2 receptors. *Neuroscience*, 87: 79-94.

What is claimed:

1. A compound having the structure:

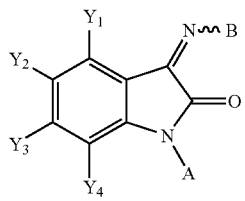

wherein B is phenyl and the phenyl is optionally substituted with one or more of the following: —F, —Cl, —Br, —CF$_3$, straight chained or branched C$_1$-C$_7$ alkyl, C$_3$-C$_7$ cycloalkyl, —N(R$_4$)$_2$, —OR$_4$, —COR$_4$, —NHCOR$_4$, —CO$_2$R$_4$, or —CON(R$_4$)$_2$;

wherein each R$_4$ is independently —H, straight chained or branched C$_1$-C$_7$ alkyl, —CF$_3$, or phenyl;

wherein A is heteroaryl, where the heteroaryl is furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl;

wherein the heteroaryl may be substituted with one or more of the following: —F, —Cl, —Br, —I, —NO$_2$, —CN, straight chained or branched C$_1$-C$_7$ alkyl, straight chained or branched C$_1$-C$_7$ monofluoroalkyl or polyfluoroalkyl;

wherein each of Y$_1$, Y$_2$, Y$_3$, and Y$_4$ is independently —H; straight chained or branched C$_1$-C$_7$ alkyl, —CF$_3$, —F, —Cl, —Br, —I, —OR$_4$, —N(R$_4$)$_2$, or —CON(R$_4$)$_2$; or a pharmaceutically acceptable salt thereof.

2. The compound of claim 1, wherein the compound has the structure:

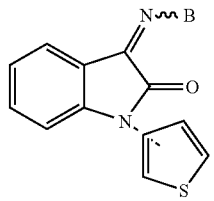

wherein B is defined as in claim 1; and wherein the thienyl may be substituted with one or more of the following: —F, —Cl, —Br, —I, —NO$_2$, —CN, straight chained or branched C$_1$-C$_7$ alkyl, straight chained or branched C$_1$-C$_7$ monofluoroalkyl or polyfluoroalkyl.

3. The compound of claim 2, wherein the compound has the structure:

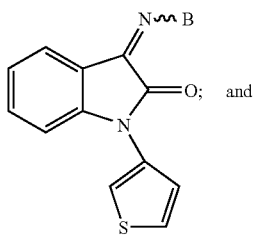

wherein B is phenyl and the phenyl is substituted with one or more of the following: —F, —Cl, —Br, —CF$_3$, straight chained or branched C$_1$-C$_7$ alkyl, CO$_2$R$_4$; and wherein R$_4$ is independently selected from —H, straight chained or branched C$_1$-C$_7$ alkyl, —CF$_3$, or phenyl.

4. The compound of claim 3, wherein the compound has the structure:

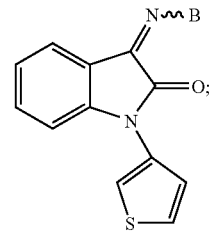

wherein B is phenyl and the phenyl is substituted with one of the following: —F, —Cl, —Br, —CF$_3$, straight chained or branched C$_1$-C$_7$ alkyl, CO$_2$R$_4$; and wherein R$_4$ is independently selected from —H, straight chained or branched C$_1$-C$_7$ alkyl, —CF$_3$, or phenyl.

5. The compound of claim 4, wherein the compound has the structure:

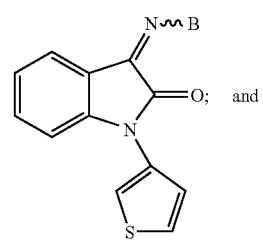

wherein B is phenyl and the phenyl is substituted with two of the following: —F, —Cl, —Br, —CF$_3$, or straight chained or branched C$_1$-C$_7$ alkyl.

6. The compound of claim 5, wherein the compound is selected from the group consisting of:

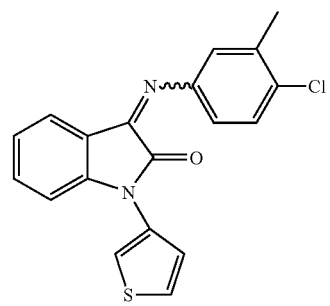

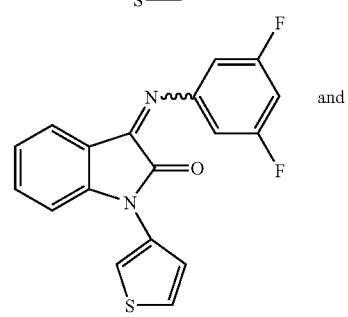

-continued
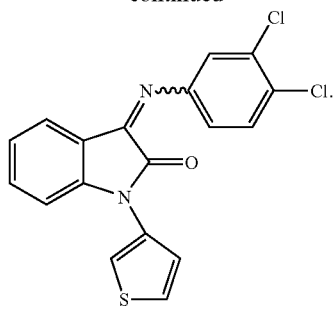
7. The compound of claim 4, wherein the compound is selected from the group consisting of:
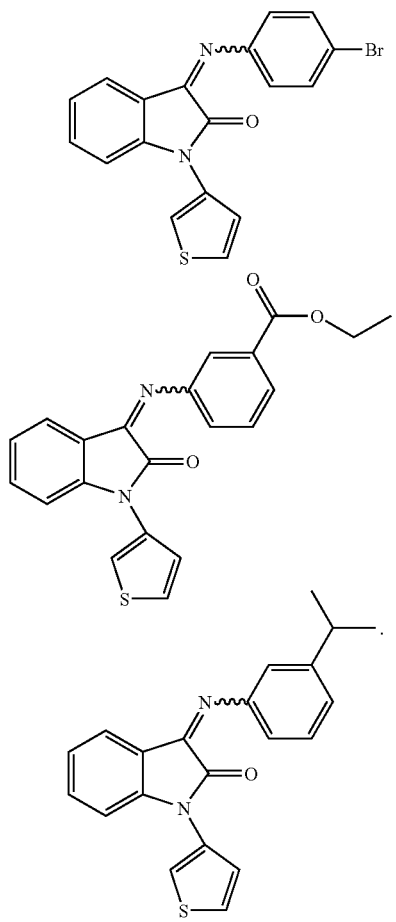
8. The compound of claim 4, wherein the compound is
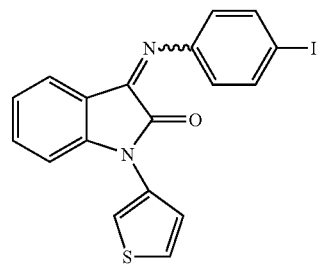 or
-continued
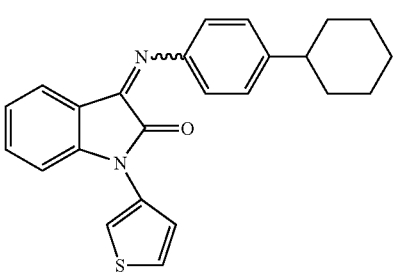
9. A compound selected form the group consisting of:
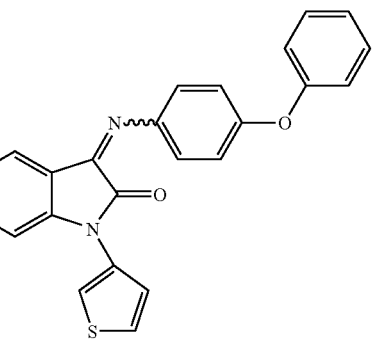
and
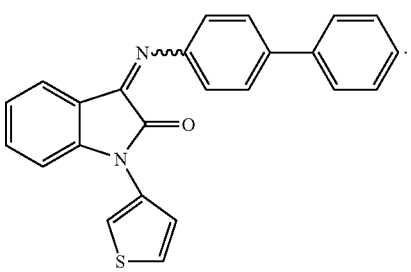
10. A pure Z imine isomer of the compound of claim 1.
11. A pure E imine isomer of the compound of claim 1.

12. A pharmaceutical composition comprising a therapeutically effective amount of the compound of claim 1 and a pharmaceutically acceptable carrier.

13. A process for making a pharmaceutical composition comprising combining a therapeutically effective amount of the compound of claim 1 and a pharmaceutically acceptable carrier.

14. A method of treating a subject suffering from depression which comprises administering to the subject an amount of the compound of claim 1 effective to treat the subject's depression.

15. A method of treating a subject suffering from anxiety which comprises administering to the subject an amount of the compound of claim 1 effective to treat the subject's anxiety.

16. A method of treating a subject suffering from anxiety and depression which comprises administering to the subject an amount of the compound of claim 1 effective to treat the subject's anxiety and depression.

* * * * *